United States Patent
Siegel et al.

(10) Patent No.: US 9,890,147 B2
(45) Date of Patent: Feb. 13, 2018

(54) 2,3-BENZODIAZEPINES

(71) Applicant: BAYER PHARMA AKTIENGESELLSCHAFT, Berlin (DE)

(72) Inventors: Stephan Siegel, Berlin (DE); Stefan Bäurle, Berlin (DE); Arwed Cleve, Berlin (DE); Bernard Haendler, Berlin (DE); Amaury Ernesto Fernandez-Montalvan, Berlin (DE); Ursula Mönning, Woltersdorf (DE); Sabine Krause, Berlin (DE); Pascale Lejeune, Berlin (DE); Norbert Schmees, Berlin (DE); Matthias Busemann, Berlin (DE); Simon Holton, Berlin (DE); Joachim Kuhnke, Potsdam (DE)

(73) Assignee: Bayer Pharma Aktiengesellshaft, Berlin (DE)

( * ) Notice: Subject to any disclaimer, the term of this patent is extended or adjusted under 35 U.S.C. 154(b) by 0 days.

(21) Appl. No.: 14/421,994

(22) PCT Filed: Aug. 13, 2013

(86) PCT No.: PCT/EP2013/066931
§ 371 (c)(1),
(2) Date: Feb. 16, 2015

(87) PCT Pub. No.: WO2014/026997
PCT Pub. Date: Feb. 20, 2014

(65) Prior Publication Data
US 2015/0203483 A1 Jul. 23, 2015

(30) Foreign Application Priority Data

Aug. 16, 2012 (DE) ......... 10 2012 214 602
Feb. 8, 2013 (DE) ......... 10 2013 202 104

(51) Int. Cl.
*A61K 31/551* (2006.01)
*C07D 243/02* (2006.01)
(Continued)

(52) U.S. Cl.
CPC .......... *C07D 417/10* (2013.01); *A61K 31/551* (2013.01); *A61K 31/5513* (2013.01); *C07D 243/02* (2013.01); *C07D 401/04* (2013.01); *C07D 401/10* (2013.01); *C07D 401/12* (2013.01); *C07D 401/14* (2013.01); *C07D 403/10* (2013.01); *C07D 403/14* (2013.01); *C07D 409/10* (2013.01); *C07D 413/04* (2013.01); *C07D 413/10* (2013.01); *C07D 413/14* (2013.01)

(58) Field of Classification Search
CPC .. A61K 31/551; C07D 243/02; C07D 401/04; C07D 403/04

USPC .......................................... 514/221; 540/567
See application file for complete search history.

(56) References Cited

U.S. PATENT DOCUMENTS

| 5,712,274 A | 1/1998 | Sueoka | |
|---|---|---|---|
| 7,189,711 B2* | 3/2007 | Ling ............... | C07D 243/02 514/221 |
| 2008/0269202 A1* | 10/2008 | Csuzdi ............ | C07D 243/02 514/221 |

FOREIGN PATENT DOCUMENTS

| CN | 1227555 | 9/1999 |
|---|---|---|
| EP | 0638560 A1 | 2/1995 |

(Continued)

OTHER PUBLICATIONS

P. Filippakopoulos et al., Nature 2010, vol. 468, 1067-1073 Need.
(Continued)

*Primary Examiner* — Brenda Coleman

(57) ABSTRACT

What is described are BET protein-inhibitory, in particular BRD4-inhibitory 2,3-benzodiazepines of the general formula (I)

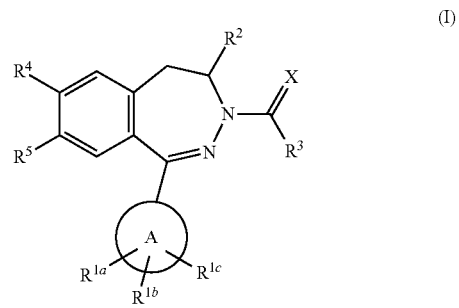

in which $R^{1a}$, $R^{1b}$, $R^{1c}$, $R^2$, $R^3$, $R^4$, $R^5$, A and X have the meanings given in the description, intermediates for preparing the compounds according to the invention, pharmaceutical compositions comprising the compounds according to the invention and their prophylactic and therapeutic use for hyperproliferative disorders, in particular for tumor disorders. Also described is the use of BET protein inhibitors for benign hyperplasias, atherosclerotic disorders, sepsis, autoimmune disorders, vascular disorders, viral infections, for neurodegenerative disorders, for inflammatory disorders, for atherosclerotic disorders and for the control of male fertility.

19 Claims, No Drawings

(51) Int. Cl.

| | |
|---|---|
| *C07D 401/04* | (2006.01) |
| *C07D 403/04* | (2006.01) |
| *C07D 417/10* | (2006.01) |
| *C07D 401/14* | (2006.01) |
| *C07D 413/14* | (2006.01) |
| *C07D 401/10* | (2006.01) |
| *C07D 401/12* | (2006.01) |
| *C07D 403/10* | (2006.01) |
| *C07D 403/14* | (2006.01) |
| *C07D 409/10* | (2006.01) |
| *C07D 413/04* | (2006.01) |
| *C07D 413/10* | (2006.01) |
| *A61K 31/5513* | (2006.01) |

(56) References Cited

FOREIGN PATENT DOCUMENTS

| | | | |
|---|---|---|---|
| EP | 0934940 | A1 | 8/1999 |
| EP | 0989131 | A1 | 3/2000 |
| EP | 1887008 | A1 | 2/2008 |
| EP | 2239264 | A1 | 10/2010 |
| WO | 1994/26718 | A1 | 11/1994 |
| WO | 2009/084693 | A1 | 7/2009 |
| WO | 2011/054553 | A1 | 5/2011 |
| WO | 2011/054843 | A1 | 5/2011 |
| WO | 2011/054844 | A1 | 5/2011 |
| WO | 2011/054845 | A1 | 5/2011 |
| WO | 2012/075456 | A1 | 6/2011 |
| WO | 2011/143669 | A2 | 11/2011 |
| WO | 2012/075383 | A2 | 6/2012 |

OTHER PUBLICATIONS

Vu and Chiang, J. Biol. Chem., 2007, 282:13141-13145 Need
Kuo and Allis, Bioessays, 1998, 20:615-626.
Huang et al., Mol. Cell. Biol., 2009, 29:1375-1387.
Rahman et al., Mol. Cell. Biol., 2011, 31:2641-2652.
Dey et al., Mol. Biol. Cell, 2009, 20:4899-4909.
Yang et al., Mol. Cell. Biol., 2008, 28:967-976.
Yang et al., Mol. Cell, 2005, 19:535-545.
You et al., Mol. Cell. Biol., 2009, 29:5094-5103.
Zuber et al., Nature, 2011, doi:10.1038.
LeRoy et al., Mol. Cell, 2008, 30:51-60.
Mochizuki et al., J. Biol. Chem., 2008, 283:9040-9048.
Nicodeme et al., Nature, 2010, 468:1119-1123.
Gyuris et al., Biochim. Biophys. Acta, 2009, 1789:413-421.
Houzelstein et al., Mol. Cell. Biol., 2002, 22:3794-3802.
French, Cancer Genet. Cytogenet., 2010, 203:16-20.
Yan et al., J. Biol. Chem., 2011, 286:27663-27675.
Kadota et al., Cancer Res, 2009, 69:7357-7365.
Greenwald et al., Blood, 2005, 103:1475-1484.
Wu et al., Genes Dev., 2006, 20:2383-2396.
Viejo-Borbolla et al., J. Virol., 2005, 79:13618-13629.
You et al., J. Virol., 2006, 80:8909-8919.
Bisgrove et al., Proc. Natl Acad. Sci. USA, 2007, 104:13690-13695.
Wang et al., Biochem. J., 2009, 425:71-83.
Co-pending U.S. Appl. No. 14/342,519, filed Mar. 3, 2014, Examiner: Brenda Libby Coleman.
Co-pending U.S. Appl. No. 14/432,158, filed Feb. 16, 2015, Examiner: Brenda Libby Coleman.
Co-pending U.S. Appl. No. 14/769,921, filed Aug. 24, 2015.
Co-pending U.S. Appl. No. 14/770,000, filed Aug. 24, 2015.
Mirguet et al., Bioorg. Med. Chem. Lett., 2012, 22:2963-2967.
Smith, Arterioscler. Thromb. Vasc. Biol., 2010, 30:151-155.
Shang et al., Development, 2007, 134:3507-3515.
Matzuk et al., Cell, 2012, 150:673-684.
Dhar et al., J. Biol. Chem., 2012, 287:6387-6405.
Chun-Wa Chung et al., Progress in Medicinal Chemistry 2012, 51, 1-55.
J. Med. Chem. 2011, 54, 3827-3838.

* cited by examiner

2,3-BENZODIAZEPINES

The present invention relates to BET protein-inhibitory, in particular BRD4-inhibitory substituted phenyl-2,3-benzodiazepines, to pharmaceutical compositions comprising the compounds according to the invention and to their prophylactic and therapeutic use for hyperproliferative disorders, in particular for tumour disorders. The present invention furthermore relates to the use of BET protein inhibitors for benign hyperplasias, atherosclerotic disorders, sepsis, autoimmune disorders, vascular disorders, viral infections, for neurodegenerative disorders, for inflammatory disorders, for atherosclerotic disorders and for the control of male fertility.

The human BET family (bromodomain and extra C-terminal domain family) has four members (BRD2, BRD3, BRD4 and BRDT), which contain two related bromodomains and one extraterminal domain (Wu and Chiang, J. Biol. Chem., 2007 282:13141-13145). The bromodomains are protein regions that recognize acetylated lysine residues. These acetylated lysines are often found at the N-terminal end of histones (e.g. histone 3 or histone 4) and are characteristic features of an open chromatin structure and active gene transcription (Kuo and Allis, Bioessays, 1998, 20:615-626). The various acetylation patterns recognized by BET proteins in histones were studied in detail (Umehara et al., J. Biol. Chem., 2010, 285:7610-7618; Filippakopoulos et al., Cell, 2012, 149:214-231). In addition, bromodomains can recognize other acetylated proteins. For example, BRD4 binds to RelA, which leads to stimulation of NF-κB and transcriptional activity of inflammatory genes (Huang et al., Mol. Cell. Biol., 2009, 29:1375-1387; Zhang et al., J. Biol. Chem., 2012, 287: 28840-28851; Zou el al., Oncogene, 2013, doi: 10.1038/onc.2013.179). The extraterminal domain of BRD2, BRD3 and BRD4 interacts with several proteins having a role in chromatin modulation and regulation of gene expression (Rahman et al., Mol. Cell. Biol., 2011, 31:2641-2652).

Mechanistically BET proteins play an important role in cell growth and in the cell cycle. They are associated with mitotic chromosomes, suggesting a role in epigenetic memory (Dey et al., Mol. Biol. Cell, 2009, 20:4899-4909; Yang et al., Mol. Cell. Biol., 2008, 28:967-976). BRD4 is important for the post-mitotic reactivation of gene transcription (Zhao et al., Nat. Cell. Biol., 2011, 13:1295-1304). It has been shown that BRD4 is essential for transcription elongation and for recruting the elongation complex P-TEFb, which consists of CDK9 and cyclin T1, resulting in activation of RNA polymerase II (Yang et al., Mol. Cell, 2005, 19:535-545; Schroder et al., J. Biol. Chem., 2012, 287:1090-1099). As a consequence, the expression of genes involved in cell proliferation such as, for example, c-Myc and aurora B, is stimulated (You et al., Mol. Cell. Biol., 2009, 29:5094-5103; Zuber et al., Nature, 2011, 478:524-528). BRD2 and BRD3 bind to transcribed genes in hyperacetylated chromatin regions and promote transcription by RNA polymerase II (LeRoy et al., Mol. Cell, 2008, 30:51-60).

The knock-down of BRD4 or the inhibition of the interaction with acetylated histones in various cell lines leads to G1 arrest and to cell death by apoptosis (Mochizuki et al., J. Biol. Chem., 2008, 283:9040-9048; Mertz et al., Proc. Natl. Acad. Sci. USA, 2011, 108:16669-16674). It has also been shown that BRD4 binds to promoter regions of several genes that are activated in the G1 phase, for example cyclin D1 and D2 (Mochizuki et al., J. Biol. Chem., 2008, 283:9040-9048). In addition, after BRD4 inhibition, inhibition of the expression of c-Myc, an essential factor in cell proliferation, was demonstrated (Dawson et al., Nature, 2011, 478:529-533; Delmore et al., Cell, 2011, 146:1-14; Mertz et al., Proc. Natl. Acad. Sci. USA, 2011, 108:16669-16674).

BRD2 and BRD4 knockout mice die early during embryogenesis (Gyuris et al., Biochim. Biophys. Acta, 2009, 1789:413-421; Houzelstein et al., Mol. Cell. Biol., 2002, 22:3794-3802). Heterozygous BRD4 mice have various growth defects, which can be attributed to reduced cellular proliferation (Houzelstein et al., Mol. Cell. Biol., 2002, 22:3794-3802).

BET proteins play an important role in various types of tumours. Fusion between the BET proteins BRD3 or BRD4 and NUT, a protein that normally is only expressed in the testis, leads to an aggressive form of squamous cell carcinoma, called NUT midline carcinoma (French, Cancer Genet. Cytogenet., 2010, 203:16-20). The fusion protein prevents cellular differentiation and promotes proliferation (Yan et al., J. Biol. Chem., 2011, 286:27663-27675; Grayson et al., 2013, doi: 10-1038/onc.2013.126). The growth of in vivo models derived therefrom is inhibited by a BRD4-inhibitor (Filippakopoulos et al., Nature, 2010, 468:1067-1073). Screening for therapeutic targets in an acute myeloid leukaemia cell line (AML) showed that BRD4 plays an important role in this tumour (Zuber et al., Nature, 2011, doi:10.1038). The reduction of BRD4 expression leads to selective arrest of the cell cycle and to apoptosis. Treatment with a BRD4-inhibitor prevents the proliferation of an AML xenograft in vivo. Amplification of the DNA region that contains the BRD4 gene was detected in primary breast tumours (Kadota et al., Cancer Res, 2009, 69:7357-7365). There are also data for BRD2 regarding a role in tumours. A transgenic mouse that overexpresses BRD2 selectively in B cells develops B cell lymphomas and leukaemias (Greenwall et al., Blood, 2005, 103:1475-1484).

BET proteins are also involved in viral infections. BRD4 binds to the E2 protein of various papilloma viruses and is important for the survival of the viruses in latently infected cells (Wu et al., Genes Dev., 2006, 20:2383-2396; Vosa et al., J. Virol., 2012, 86:348-357; McBride and Jang, Viruses, 2013, 5:1374-1394). The herpes virus that is responsible for Kaposi's sarcoma also interacts with various BET proteins, which is important for disease resistance (Viejo-Borbolla et al., J. Virol., 2005, 79:13618-13629; You et al., J. Virol., 2006, 80:8909-8919). By binding to P-TEFb, BRD4 also plays an important role in HIV replication (Bisgrove et al., Proc. Natl Acad. Sci. USA, 2007, 104:13690-13695).

BET proteins are in addition involved in inflammatory processes. BRD2-hypomorphic mice display reduced inflammation in fat tissue (Wang et al., Biochem. J., 2009, 425:71-83). The infiltration of macrophages in white fat tissue is also reduced in BRD2-deficient mice (Wang et al., Biochem. J., 2009, 425:71-83). It has also been shown that BRD4 regulates a number of genes that are involved in inflammation. In LPS-stimulated macrophages, a BRD4-inhibitor prevents the expression of inflammatory genes, for example IL-1 or IL-6 (Nicodeme et al., Nature, 2010, 468:1119-1123).

BET proteins also regulate the expression of the ApoA1 gene which plays an important role in atherosclerosis and in inflammatory processes (Chung et al., J. Med. Chem, 2011, 54:3827-3838). Apolipoprotein A1 (ApoA1) is a main component of high density lipoproteins (HDL), and an elevated expression of ApoA1 leads to increased blood cholesterol levels (Degoma and Rader, Nat. Rev. Cardiol., 2011, 8:266-277). Increased HDL levels are associated with a reduced risk of atherosclerosis (Chapman et al., Eur. Heart J., 2011, 32:1345-1361).

PRIOR ART

The nomenclature used for looking at the structural prior art is illustrated by the figure below:

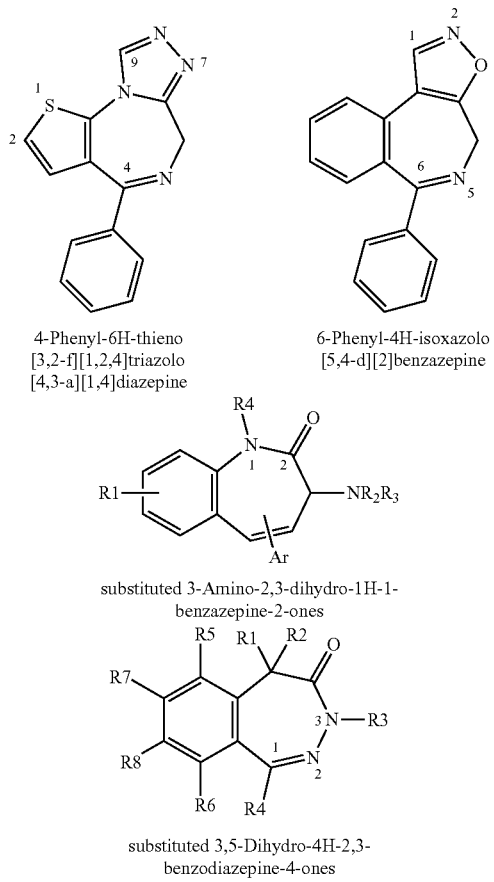

4-Phenyl-6H-thieno
[3,2-f][1,2,4]triazolo
[4,3-a][1,4]diazepine

6-Phenyl-4H-isoxazolo
[5,4-d][2]benzazepine substituted 3-Amino-2,3-dihydro-1H-1-
benzazepine-2-ones substituted 3,5-Dihydro-4H-2,3-
benzodiazepine-4-ones Based on the chemical structure, only very few types of BRD4 inhibitors have been described to date (Chun-Wa Chung et al., Progress in Medicinal Chemistry 2012, 51, 1-55).

The first BRD4 inhibitors published were phenylthieno-triazolo-1,4-diazepines (4-phenyl-6H-thieno[3,2-f][1,2,4]triazolo[4,3-a][1,4]diazepines) as described in WO2009/084693 (Mitsubishi Tanabe Pharma Corporation) and with the compound JQ1 in WO2011/143669 (Dana Farber Cancer Institute). Replacement of the thieno moiety by a benzo moiety also led to activated inhibitors (J. Med. Chem. 2011, 54, 3827-3838; E. Nicodeme et al., Nature 2010, 468, 1119). These and one further publication show that the pyrazole moiety condensed to the 1,4-benzodiazepine or thieno-1,4-diazepine ring system is actively involved in the binding of the target protein BRD4 (P. Filippakopoulos et al., Nature 2010, 468, 1067). Further 4-phenyl-6H-thieno[3,2-f][1,2,4]triazolo[4,3-a][1,4]diazepines and related compounds having alternative rings as fusion partners instead of the benzo moiety are addressed in a general manner or directly described in WO2012/075456 (Constellation Pharmaceuticals). WO2012/075383 (Constellation Pharmaceuticals) describes 6-substituted 4H-isoxazolo[5,4-d][2]benzazepines and 4H-isoxazolo[3,4-d][2]benzazepines including compounds having an optionally substituted phenyl in position 6 as BRD4 inhibitors, and also analogues having alternative heterocyclic fusion partners instead of the benzo moiety, e.g. thieno- or pyridoazepines.

7-Isoxazolochinolines and related chinolone derivatives are described as another structural class of BRD4 inhibitors (WO2011/054843, Bioorganic & Medicinal Chemistry Letters 22 (2012) 2963-2967, GlaxoSmithKline).

WO94/26718 and EP0703222A1 (Yoshitomi Pharmaceutical Industries) described substituted 3-amino-2,3-dihydro-1H-1-benzazepin-2-ones or the corresponding 2-thiones and analogues in which the benzo unit is replaced by alternative monocyclic systems and in which the 2-ketone or the 2-thione may, together with the substituted nitrogen atom of the azepine ring, form a heterocycle, as CCK and gastrin antagonists for the therapy of disorders of the CNS such as anxiety and depressions, and also of disorders of the pancreas and of gastrointestinal ulcers. Ligands of the gastrin and the cholecystokinin receptor are described in WO2006/051312 (James Black Foundation). They also include substituted 3,5-dihydro-4H-2,3-benzodiazepin-4-ones which differ from the compounds according to the invention mainly by the obligatory oxo group in position 4 and by an obligatory carbonyl group-carrying alkyl chain in position 5. Finally, substituted 3,5-dihydro-4H-2,3-benzodiazepin-4-ones are likewise described as AMPA antagonists in WO97/34878 (Cocensys Inc.). In spite of a very broad general claim with respect to the possible substitution patterns at the benzodiazepine skeleton, the working examples are limited to a very narrow section.

Accordingly, it would be desirable to provide novel compounds having prophylactic and therapeutic properties.

It is therefore an object of the present invention to provide compounds and pharmaceutical compositions comprising these compounds for prophylactic and therapeutic use for hyperproliferative disorders, in particular for tumour disorders, and also as BET protein inhibitors for viral infections, for neurodegenerative disorders, for inflammatory disorders, for atherosclerotic disorders and for the control of male fertility.

The compounds according to the invention are novel phenyl-2,3-benzodiazepines (1-phenyl-4,5-dihydro-3H-2,3-benzodiazepines) and heteroaryl-2,3-benzodiazepines (1-heteroaryl-4,5-dihydro-3H-2,3-benzodiazepines) which, at the benzodiazepine skeleton, are not condensed with a second heterocyclic unit, specifically an isoxazole or triazole, and, surprisingly, are still BRD4 inhibitors. Furthermore, the compounds according to the invention differ from known 2,3-benzodiazepines such as the numerous published AMPA antagonists (WO0198280, Annovis Inc.; WO 9728135, Schering AG; for a review see Med. Res. Rev. 2007, 27(2), 239-278) or from analogous diazepines where the benzo moiety is replaced by another monocyclic moiety, by their substitution pattern at the phenyl group or at the benzo moiety or another monocyclic moiety: at least one substituent at the phenyl group or at the benzo group is cyclic ((hetero)aromatic, (hetero)cyclic) or is novel at the position in question, such as trifluoromethoxy or alkylaminosulphonylphenyl at the benzo moiety. The compounds according to the invention also differ from the known psychopharmacological 2,3-benzodiazepine derivatives which are inhibitors of the adenosine transporter and the MT2 receptor (WO2008/124075, Teva Pharm).

The prior art compounds which are closest in terms of structure have not been disclosed in connection with the prophylaxis and therapy of tumour disorders.

Using the prior art described above as a starting point, there was no reason to modify the structures of the prior art in a manner to obtain structures suitable for the prophylaxis and therapy of tumour disorders.

It has now been found that compounds of the general formula (I-A)

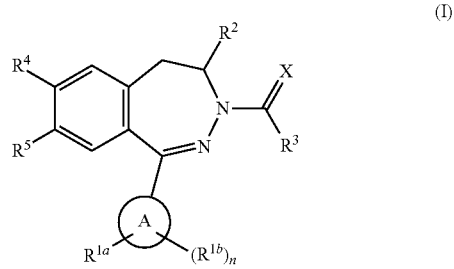

in which

X represents an oxygen or sulphur atom, and

A represents a monocyclic heteroaryl ring which has 5 or 6 ring atoms or represents a phenyl ring, and $R^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, or represents a monocyclic heterocyclyl radical which has 3 to 8 ring atoms and may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or a monocyclic heterocyclyl radical which has 3 to 8 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or by a monocyclic heterocyclyl radical which has 3 to 8 ring atoms, and/or by a monocyclic heteroaryl radical which has 5 or 6 ring atoms, and/or by a rhenyl radical which for its part may optionally be mono- or polysubstituted by halogen, $C_1$-$C_3$-alkyl and/or $C_1$-$C_3$-alkoxy, or represents a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, $C_1$-$C_3$-alkylcarbonyl, —C(=O)NH$_2$, $C_1$-$C_3$-alkylaminocarbonyl, $C_3$-$C_6$-cycloalkylaminocarbonyl, $C_1$-$C_3$-alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl, and/or a monocyclic heterocyclyl radical which has 3 to 8 ring atoms, and/or a monocyclic heteroaryl radical which has 5 or 6 ring atoms and which for its part may optionally be mono- or polysubstituted by identical or different substituents from the group consisting of halogen, $C_1$-$C_3$-alkyl and $C_1$-$C_3$-alkoxy, and n represents 0, 1 or 2, and $R^{1b}$ represents halogen, hydroxy, cyano, nitro and/or represents a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl radical and/or a monocyclic heterocyclyl radical which has 3 to 8 ring atoms, and $R^2$ represents a $C_1$-$C_3$-alkyl or trifluoromethyl or a $C_3$- or $C_4$-cycloalkyl radical, and $R^3$ represents cyclopropyl, $C_1$-$C_3$-alkyl, $C_1$-$C_3$-alkoxy, amino, cyclopropylamino or $C_1$-$C_3$-alkylamino, and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, monocyclic heterocyclyl which has 3 to 8 ring atoms and/or monocyclic heteroaryl which has 5 or 6 ring atoms, where the monocyclic heterocyclyl and heteroaryl radicals mentioned for their part may optionally be monosubstituted by $C_1$-$C_3$-alkyl, or represent $C_3$-$C_{10}$-cycloalkyl which may optionally be mono- or polysubstituted by identical or different substituents from the group consisting of halogen, amino, hydroxy, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical which has 3 to 8 ring atoms, or represent monocyclic heteroaryl which has 5 or 6 ring atoms which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 3 to 8 ring atoms, or represent monocyclic heterocyclyl which has 3 to 8 ring atoms and which may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 3 to 8 ring atoms, or represent phenyl which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms, and $R^6$ and $R^7$ independently of one another represent hydrogen, $C_1$-$C_3$-alkyl-, cyclopropyl or di-$C_1$-$C_3$-alkyl-amino-$C_1$-$C_3$-alkyl, and $R^8$ represents hydroxy, $C_1$-$C_6$-alkyl, halo-$C_1$-$C_3$-alkyl, hydroxy-$C_1$-$C_3$-alkyl, $C_1$-$C_3$-alkoxy-$C_1$-$C_3$-alkyl, $C_3$-$C_8$-cycloalkyl, phenyl, monocyclic heterocyclyl which has 3 to 8 ring atoms or monocyclic heteroaryl which has 5 or 6 ring atoms, where phenyl, heteroaryl and heterocyclyl may optionally be mono- or disubstituted by halogen, $C_1$-$C_3$-alkoxy or $C_1$-$C_3$-alkyl, and $R^9$ represents $C_1$-$C_6$-alkyl, and their polymorphs, enantiomers, diastereomers, racemates, tautomers, solvates, physiologically acceptable salts and solvates of these salts are particularly suitable for numerous prophylactic and therapeutic uses, in particular for hyperproliferative disorders, for tumour disorders and also as BET protein inhibitors for viral infections, for neurodegenerative disorders, for inflammatory disorders, for atherosclerotic disorders and for the control of male fertility.

The present invention therefore relates to compounds of the general formula (I-A), as described above, with the proviso that, if A represents a phenyl ring and $R^4$ and $R^5$ independently of one another represent hydrogen, hydroxy, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino or $C_1$-$C_6$-alkylaminocarbonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, monocyclic heterocyclyl which has 3 to 8 ring atoms and/or monocyclic heteroaryl which has 5 or 6 ring atoms, where the monocyclic heterocyclyl and heteroaryl radicals mentioned for their part may optionally be monosubstituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical.

Surprisingly, the compounds according to the invention inhibit the interaction between BET proteins, in particular BRD4 and an acetylated histone 4 peptide and inhibit the growth of cancer cells. Thus, they represent novel structures for the therapy of human and animal disorders, in particular of cancerous disorders.

The invention is based on the following definitions:

Alkyl:

Alkyl represents a straight-chain or branched saturated monovalent hydrocarbon radical having generally 1 to 6 ($C_1$-$C_6$-alkyl), preferably 1 to 3 carbon atoms ($C_1$-$C_3$-alkyl).

The following may be mentioned by way of example: methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, 1,2-dimethylbutyl.

Preference is given to a methyl, ethyl, propyl, isopropyl or tert-butyl radical.

Cycloalkyl:

Cycloalkyl represents a mono- or bicyclic saturated monovalent hydrocarbon radical having generally 3 to 10 ($C_3$-$C_{10}$-cycloalkyl), preferably 3 to 8 ($C_3$-$C_8$-cycloalkyl), and particularly preferably 3 to 7 ($C_3$-$C_7$-cycloalkyl) carbon atoms.

The following may be mentioned by way of example and by way of preference for monocyclic cycloalkyl radicals: cyclopropyl, cyclobutyl, cyclopentyl, cyclohexyl and cycloheptyl.

Particular preference is given to a cyclopropyl, cylopentyl or a cyclohexyl radical.

The following may be mentioned by way of example for bicyclic cycloalkyl radicals: perhydropentalenyl, decalinyl.

Phenylalkyl:

Phenyl-$C_1$-$C_6$-alkyl is to be understood as meaning a group composed of an optionally substituted phenyl radical and a $C_1$-$C_6$-alkyl group, which is attached via the $C_1$-$C_6$-alkyl group to the remainder of the molecule. Here, the alkyl radical has the meanings given above under alkyl. Preference is given to phenyl-$C_1$-$C_3$-alkyl.

The following may be mentioned by way of example: benzyl, phenethyl, phenylpropyl, phenylpentyl, with benzyl being particularly preferred.

Alkoxy:

Alkoxy represents a straight-chain or branched saturated alkyl ether radical of the formula —O-alkyl having generally 1 to 6 ($C_1$-$C_6$-alkoxy), preferably 1 to 3 ($C_1$-$C_3$-alkoxy) carbon atoms.

The following may be mentioned by way of example and by way of preference:

methoxy, ethoxy, n-propoxy, isopropoxy, tert-butoxy, n-pentyloxy and n-hexyloxy.

Alkoxyalkyl

Alkoxyalkyl represents an alkoxy-substituted alkyl radical.

Here, $C_1$-$C_3$-alkoxy-$C_1$-$C_3$-alkyl means that the binding to the rest of the molecule is via the alkyl moiety.

Alkoxyalkoxy

Alkoxyalkoxy represents an alkoxy-substituted alkoxy radical.

Here, $C_1$-$C_3$-alkoxy-$C_2$-$C_3$-alkoxy means that the binding to the rest of the molecule is via the inner $C_2$-$C_3$-alkoxy moiety.

Oxo

Oxo, an oxo group or an oxo substituent is to be understood as meaning a doubly attached oxygen atom =O. Oxo may be attached to atoms of suitable valency, for example to a saturated carbon atom or to sulphur.

Preference is given to binding to carbon with formation of a carbonyl group —C(=O)—. Preference is furthermore given to binding two doubly attached oxygen atoms to a sulphur atom with formation of a sulphonyl group —S(=O)$_2$—.

Alkylamino

Alkylamino represents an amino radical having one or two alkyl substituents (chosen independently of one another) having generally 1 to 6 ($C_1$-$C_6$-alkylamino), preferably 1 to 3 carbon atoms ($C_1$-$C_3$-alkylamino).

($C_1$-$C_3$)-alkylamino represents, for example, a monoalkylamino radical having 1 to 3 carbon atoms or represents a dialkylamino radical having in each case 1 to 3 carbon atoms per alkyl substituent.

The following may be mentioned by way of example: methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

Alkylaminocarbonyl

Alkylaminocarbonyl represents the group alkylamino-C(=O)— having one or two alkyl substituents (chosen independently of one another) having generally 1 to 6 ($C_1$-$C_6$-alkylaminocarbonyl), preferably 1 to 3 carbon atoms ($C_1$-$C_3$-alkylaminocarbonyl).

Cycloalkylaminocarbonyl

Cycloalkylaminocarbonyl represents the group cycloalkyl-NH—C(=O)— having a cycloalkyl substituent, generally consisting of 3 to 6 ($C_3$-$C_6$-cycloalkylaminocarbonyl) carbon atoms.

The following may be mentioned by way of example and by way of preference: cyclopropylaminocarbonyl and cyclopentylaminocarbonyl.

Alkylcarbonyl

Alkylcarbonyl represents the group —C(=O)-alkyl having generally 1 to 6 ($C_1$-$C_6$-alkylcarbonyl), preferably 1 to 4, and particularly preferably 1 to 3 carbon atoms in the alkyl moiety.

The following are mentioned by way of example: acetyl and propanoyl.

Alkylcarbonylamino

Alkylcarbonylamino represents the group alkyl-C(=O)—NH— having generally 1 to 6 ($C_1$-$C_6$-alkylcarbonylamino), preferably 1 to 4, and particularly preferably 1 to 3 carbon atoms in the alkyl moiety.

Alkoxycarbonyl

Alkoxycarbonyl represents the group —C(=O)—O-alkyl having generally 1 to 6 ($C_1$-$C_6$-alkoxycarbonyl), preferably 1 to 4, and particularly preferably 1 to 3 carbon atoms in the alkyl moiety.

The following may be mentioned by way of example: methoxycarbonyl, ethoxycarbonyl, propoxycarbonyl, isopropoxycarbonyl, tert-butoxycarbonyl, n-pentyloxycarbonyl and n-hexyloxycarbonyl.

Alkylsulphonyl

Alkylsulphonyl represents a straight-chain or branched saturated radical of the formula —S(=O)$_2$-alkyl having generally 1 to 6 ($C_1$-$C_6$-alkylsulphonyl), preferably 1 to 3 ($C_1$-$C_3$-alkylsulphonyl) carbon atoms.

The following may be mentioned by way of example and by way of preference: methylsulphonyl, ethylsulphonyl, propylsulphonyl.

Alkylsulphinyl

Alkylsulphinyl represents a straight-chain or branched saturated radical of the formula —S(=O)-alkyl having generally 1 to 6 ($C_1$-$C_6$-alkylsulphinyl), preferably 1 to 3 ($C_1$-$C_3$-alkylsulphinyl) carbon atoms.

The following may be mentioned by way of example and by way of preference: methylsulphinyl, ethylsulphinyl, propylsulphinyl.

Alkylsulphonylamino Alkylsulphonylamino represents a straight-chain or branched saturated radical of the formula —NH—S(=O)$_2$-alkyl having 1 to 3 ($C_1$-$C_3$-alkylsulphonyl) carbon atoms in the alkyl group.

The following may be mentioned by way of example and by way of preference: methylsulphonylamino, ethylsulphonylamino, propylsulphonylamino.

Alkylaminosulphonyl

Alkylaminosulphonyl represents the group alkylamino-S(=O)$_2$— having one or two alkyl substituents (chosen independently of one another) having generally 1 to 6 ($C_1$-$C_6$-alkylaminosulphonyl), preferably 1 to 3 carbon atoms.

The following may be mentioned by way of example and by way of preference: methylaminosulphonyl, ethylaminosulphonyl, dimethylaminosulphonyl.

Cycloalkylaminosulphonyl Cycloalkylaminosulphonyl represents the group cycloalkyl-NH—S(=O)$_2$— having a cycloalkyl substituent, generally consisting of 3 to 6 ($C_3$-$C_6$-cycloalkylaminosulphonyl) carbon atoms.

The following may be mentioned by way of example and by way of preference: cyclopropylaminosulphonyl.

Heteroatoms

Heteroatoms are to be understood as meaning oxygen, nitrogen and sulphur atoms.

Heteroaryl

Heteroaryl denotes a monovalent monocyclic aromatic ring system having 5 or 6 ring atoms, of which at least one is a heteroatom. Heteroatoms present may be nitrogen atoms, oxygen atoms and/or sulphur atoms. The binding valency may be located at any aromatic carbon atom or at an oxygen atom.

A monocyclischer heteroaryl radical in accordance with the present invention has 5 or 6 ring atoms. Heteroaryl radicals having 5 ring atoms include, for example, the following rings: thienyl, thiazolyl, furyl, pyrrolyl, oxazolyl, imidazolyl, pyrazolyl, isoxazolyl, isothiazolyl, oxadiazolyl, triazolyl, tetrazolyl and thiadiazolyl.

Heteroaryl radicals having 6 ring atoms include, for example, the following rings: pyridyl, pyridazinyl, pyrimidinyl, pyrazinyl and triazinyl.

Heterocyclyl

Heterocyclyl means a non-aromatic monocyclic ring system having at least one heteroatom or a heterogroup. Heteroatoms which may be present are nitrogen atoms, oxygen atoms and/or sulphur atoms. Heterogroups which may be present are —S(=O), —S(=O)$_2$— or —N$^+$(O$^-$)—.

A monocyclic heterocyclyl ring in accordance with the present invention may have 3 to 8, preferably 5 to 8 or 4 to 7, particularly preferably 5 or 6, ring atoms.

The following may be mentioned in an exemplary and preferred manner for monocyclic heterocyclyl radicals having 3 ring atoms:
aziridinyl.

The following may be mentioned in an exemplary and preferred manner for monocyclic heterocyclyl radicals having 4 ring atoms:
azetidinyl, oxetanyl.

The following may be mentioned in an exemplary and preferred manner for monocyclic heterocyclyl radicals having 5 ring atoms:
pyrrolidinyl, imidazolidinyl, pyrazolidinyl, pyrrolinyl, dioxolanyl and tetrahydrofuranyl.

The following may be mentioned in an exemplary and preferred manner for monocyclic heterocyclyl radicals having 6 ring atoms:
piperidinyl, piperazinyl, morpholinyl, dioxanyl, tetrahydropyranyl and thiomorpholinyl.

The following may be mentioned in an exemplary and preferred manner for monocyclic heterocyclyl radicals having 7 ring atoms:
azepanyl, oxepanyl, 1,3-diazepanyl, 1,4-diazepanyl.

The following may be mentioned in an exemplary and preferred manner for monocyclic heterocyclyl radicals having 8 ring atoms:
oxocanyl, azocanyl.

Preference is given to 5- to 8- and 4 to 7-membered monocyclic saturated heterocyclyl radicals having up to two heteroatoms from the group consisting of O, N and S.

Particular preference is given to morpholinyl, piperidinyl, piperazinyl and pyrrolidinyl.
N-Heterocyclyl N-Heterocyclyl means a non-aromatic cyclic ring system having at least one nitrogen atom as heteroatom, which is attached to the remainder of the molecule via the nitrogen atom.
Halogen The term halogen comprises fluorine, chlorine, bromine and iodine.

Preference is given to fluorine and chlorine.
Halo

Halo represents halogen and comprises fluorine, chlorine and bromine and refers to a radical substituted by fluorine, chlorine or bromine such as, for example, halophenyl, which is a phenyl radical which is mono- or polysubstituted by identical or different fluorine, chlorine and/or bromine substituents.
Haloalkyl Haloalkyl represents an alkyl radical having at least one halogen substituent.

A halo-$C_1$-$C_6$-alkyl radical is an alkyl radical having 1-6 carbon atoms and at least one halogen substituent. If a plurality of halogen substituents are present, these may also be different from one another. Preference is given to fluoro-$C_1$-$C_3$-alkyl radicals.

The following may be mentioned by way of example and by way of further preference: the trifluoromethyl, 2,2,2-trifluoroethyl, pentafluoroethyl, 4,4,5,5,5-pentafluoropentyl or 3,3,4,4,5,5,5-heptafluoropentyl group.

Particular preference is given to trifluoromethyl, 2,2-difluoroethyl and 2,2,2-trifluoroethyl.
Haloalkoxy Haloalkoxy represents an alkoxy radical having at least one halogen substituent.

A halo-$C_1$-$C_6$-alkoxy radical is an alkoxy radical having 1-6 carbon atoms and at least one halogen substituent. If a plurality of halogen substituents are present, these may also be different from one another. Preference is given to fluoro-$C_1$-$C_3$-alkoxy radicals.

The following may be mentioned by way of example and by way of particular preference: difluoromethoxy, trifluoromethoxy or 2,2,2-trifluoroethoxy.
Hydroxyalkyl Hydroxyalkyl represents an alkyl radical having at least one hydroxy substituent.

A hydroxy-$C_1$-$C_6$-alkyl radical is an alkyl radical having 1-6 carbon atoms and at least one hydroxy substituent. Preference is given to hydroxy-$C_1$-$C_3$-alkyl.

Preference is given to compounds of the general formula (I-A) in which
X represents an oxygen atom,
A represents a phenyl or pyridyl ring,
$R^{1a}$ represents hydrogen, halogen, cyano, carboxyl, amino or aminosulphonyl,
or
represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical,
or
represents a monocyclic heterocyclyl radical which has 3 to 8 ring atoms and may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical which has 3 to 8 ring atoms,
or
represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical which has 3 to 8 ring atoms and/or by a monocyclic heteroaryl radical which has 5 or 6 ring atoms and/or by a phenyl radical which for its part may optionally be mono- or polysubstituted by halogen, $C_1$-$C_3$-alkyl and/or $C_1$-$C_3$-alkoxy,
or
represents a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, $C_1$-$C_3$-alkylcarbonyl, —C(=O)NH$_2$, $C_1$-$C_3$-alkylaminocarbonyl, $C_3$-$C_6$-cycloalkylaminocarbonyl, $C_1$-$C_3$- alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl, and/or a monocyclic heterocyclyl radical which has 3 to 8 ring atoms and/or a monocyclic heteroaryl radical which has 5 or 6 ring atoms and which for its part may optionally be mono- or polysubstituted by identical or different substituents from the group consisting of halogen, $C_1$-$C_3$-alkyl and $C_1$-$C_3$-alkoxy, and n represents 0, 1 or 2, and $R^{1b}$ represents halogen, hydroxy, cyano, nitro and/or represents a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl radical and/or a monocyclic heterocyclyl radical which has 3 to 8 ring atoms, and $R^2$ represents methyl, and $R^3$ represents cyclopropyl, $C_1$-$C_3$-alkyl, $C_1$-$C_3$-alkoxy, amino, cyclopropylamino or $C_1$-$C_3$-alkylamino, and $R^4$ and $R^5$ independently of one another represent hydrogen, hydroxy, cyano, nitro, amino, aminocarbonyl-, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino or amino-$C_1$-$C_6$-alkyl, a monocyclic heterocyclyl radical which has 3 to 8 ring atoms and/or a monocyclic heteroaryl radical which has 5 or 6 ring atoms, where the monocyclic heterocyclyl and heteroaryl radicals mentioned for their part may optionally be monosubstituted by $C_1$-$C_3$-alkyl, or represent a $C_3$-$C_{10}$-cycloalkyl radical which may optionally be mono- or polysubstituted by identical or different substituents from the group consisting of halogen, amino, hydroxy, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical which has 3 to 8 ring atoms, or represent a monocyclic heteroaryl radical which has 5 or 6 ring atoms and which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 3 to 8 ring atoms, or represent a monocyclic heterocyclyl radical which has 3 to 8 ring atoms and which may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 3 to 8 ring atoms, or represent a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 3 to 8 ring atoms, and $R^6$ and $R^7$ independently of one another represent hydrogen, $C_1$-$C_3$-alkyl, cyclopropyl, or di-$C_1$-$C_3$-alkyl-amino-$C_1$-$C_3$-alkyl, and $R^8$ represents hydroxy, $C_1$-$C_6$-alkyl, halo-$C_1$-$C_3$-alkyl, hydroxy-$C_1$-$C_3$-alkyl, $C_1$-$C_3$-alkoxy-$C_1$-$C_3$-alkyl, $C_3$-$C_8$-cycloalkyl, phenyl, monocyclic heterocyclyl having 3 to 8 ring atoms or monocyclic heteroaryl having 5 or 6 ring atoms, and $R^9$ represents $C_1$-$C_6$-alkyl, with the proviso that, if A represents a phenyl ring and $R^4$ and $R^5$ independently of one another represent hydrogen, hydroxy, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino and amino-$C_1$-$C_6$-alkyl, a monocyclic heterocyclyl radical which has 3 to 8 ring atoms and/or a monocyclic heteroaryl radical which has 5 or 6 ring atoms, where the monocyclic heterocyclyl and heteroaryl radicals mentioned for their part may optionally be monosubstituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, and to their polymorphs, enantiomers, diastereomers, racemates, tautomers, solvates, physiologically acceptable salts and solvates of these salts.

More preference is given to compounds of the general formula (I-A) in which

X represents an oxygen atom,

A represents a phenyl or pyridyl ring, $R^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, or represents a monocyclic heterocyclyl radical which has 4 to 7 ring atoms and may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or by a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or by a monocyclic heterocyclyl radical which has 4 to 7 ring atoms and/or by a monocyclic heteroaryl radical which has 5 or 6 ring atoms and/or by a phenyl radical which for its part may be mono- or polysubstituted by identical or different substituents from the group consisting of halogen, $C_1$-$C_3$-alkyl and/or $C_1$-$C_3$-alkoxy, or represents a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, $C_1$-$C_3$-alkylcarbonyl, —C(=O)$NH_2$, $C_1$-$C_3$-alkylaminocarbonyl, $C_3$-$C_6$-cycloalkylaminocarbonyl, $C_1$-$C_3$-alkylsulphinyl, $C_1$-$C_3$-alkylsulphonyl, —S(=O)$_2NH_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl, and/or a monocyclic heterocyclyl radical which has 4 to 7 ring atoms and/or a monocyclic heteroaryl radical which has 5 or 6 ring atoms and which for its part may optionally be mono- or polysubstituted by identical or different substituents from the group consisting of halogen, $C_1$-$C_3$-alkyl and/or $C_1$-$C_3$-alkoxy, and n represents 0 or 1, and $R^{1b}$ represents halogen, hydroxy, cyano, nitro or represents a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl radical, and/or a monocyclic heterocyclyl radical which has 4 to 7 ring atoms, and $R^2$ represents methyl, and $R^3$ represents cyclopropyl, $C_1$-$C_3$-alkyl, $C_1$-$C_3$-alkoxy, amino, cyclopropylamino or $C_1$-$C_3$-alkylamino, and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, a monocyclic heterocyclyl radical which has 4 to 7 ring atoms, and/or a monocyclic heteroaryl radical which has 5 or 6 ring atoms, where the monocyclic heterocyclyl and heteroaryl radicals mentioned for their part may optionally be monosubstituted by $C_1$-$C_3$-alkyl, or represent a $C_3$-$C_{10}$-cycloalkyl radical which may optionally be mono- or polysubstituted by identical or different substituents from the group consisting of halogen, amino, hydroxy, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical which has 4 to 7 ring atoms, or represent a monocyclic heteroaryl radical which has 5 or 6 ring atoms and which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, or represent a monocyclic heterocyclyl radical which has 4 to 7 ring atoms and which may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, or represent a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, and $R^6$ and $R^7$ independently of one another represent hydrogen, $C_1$-$C_3$-alkyl, cyclopropyl, or di-$C_1$-$C_3$-alkyl-amino-$C_1$-$C_3$-alkyl, and $R^8$ represents hydroxy, $C_1$-$C_6$-alkyl, halo-$C_1$-$C_3$-alkyl, hydroxy-$C_1$-$C_3$-alkyl, $C_1$-$C_3$-alkoxy-$C_1$-$C_3$-alkyl, $C_3$-$C_8$-cycloalkyl, phenyl, monocyclic heterocyclyl which has 5 or 6 ring atoms, and $R^9$ represents $C_1$-$C_6$-alkyl, with the proviso that, if A represents a phenyl ring and $R^4$ and $R^5$ independently of one another represent hydrogen, hydroxy, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino and amino-$C_1$-$C_6$-alkyl, a monocyclic heterocyclyl radical which has 4 to 7 ring atoms and/or a monocyclic heteroaryl radical which has 5 or 6 ring atoms, where the monocyclic heterocyclyl and heteroaryl radicals mentioned for their part may optionally be monosubstituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, and to their polymorphs, enantiomers, diastereomers, racemates, tautomers, solvates, physiologically acceptable salts and solvates of these salts.

Even more preference is given to those compounds of the general formula (I-A) in which X represents an oxygen atom, A represents a phenyl or pyridyl ring, $R^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl- or $C_1$-$C_6$-alkoxycarbonyl radical, or represents a monocyclic heterocyclyl radical which has 4 to 7 ring atoms and may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or by a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or by a monocyclic heterocyclyl radical which has 4 to 7 ring atoms, and/or by a monocyclic heteroaryl radical which has 5 or 6 ring atoms, and/or by a phenyl radical which for its part may be mono- or polysubstituted by identical or different substituents from the group consisting of halogen, $C_1$-$C_3$-alkyl and/or $C_1$-$C_3$-alkoxy, or represents a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, $C_1$-$C_3$-alkylcarbonyl, —C(=O)$NH_2$, $C_1$-$C_3$-alkylaminocarbonyl, $C_3$-$C_6$-cycloalkylaminocarbonyl, $C_1$-$C_3$-alkylsulphinyl, $C_1$-$C_3$-alkylsulphonyl, —S(=O)$_2NH_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl, and/or a monocyclic heterocyclyl radical which has 4 to 7 ring atoms, and/or a monocyclic heteroaryl radical which has 5 or 6 ring atoms which for its part may optionally be mono- or polysubstituted by identical or different substituents from the group consisting of halogen, $C_1$-$C_3$-alkyl and/or $C_1$-$C_3$-alkoxy, and n represents 0 or 1, and $R^{1b}$ represents halogen, hydroxy, cyano, nitro or represents a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl radical and/or a monocyclic heterocyclyl radical which has 4 to 7 ring atoms, and $R^2$ represents methyl, and $R^3$ represents methyl or $C_1$-$C_3$-alkylamino, and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, a monocyclic heterocyclyl radical which has 4 to 7 ring atoms, and/or a monocyclic heteroaryl radical which has 5 or 6 ring atoms, where the monocyclic heterocyclyl and heteroaryl radicals mentioned for their part may optionally be monosubstituted by $C_1$-$C_3$-alkyl, or represent a $C_3$-$C_{10}$-cycloalkyl radical which may optionally be mono- or polysubstituted by identical or different substituents from the group consisting of halogen, amino, hydroxy, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical which has 4 to 7 ring atoms, or represent a monocyclic heteroaryl radical which has 5 or 6 ring atoms and may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, or represent a monocyclic heterocyclyl radical which has 4 to 7 ring atoms and may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, or represent a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, and $R^6$ and $R^7$ independently of one another represent hydrogen, $C_1$-$C_3$-alkyl, cyclopropyl, or di-$C_1$-$C_3$-alkyl-amino-$C_1$-$C_3$-alkyl, and $R^8$ represents hydroxy, $C_1$-$C_6$-alkyl, halo-$C_1$-$C_3$-alkyl, hydroxy-$C_1$-$C_3$-alkyl, $C_1$-$C_3$-alkoxy-$C_1$-$C_3$-alkyl, $C_3$-$C_8$-cycloalkyl, monocyclic heterocyclyl which has 5 or 6 ring atoms, and $R^9$ represents $C_1$-$C_6$-alkyl, with the proviso that, if A represents a phenyl ring and $R^4$ and $R^5$ independently of one another represent hydrogen, hydroxy, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino and amino-$C_1$-$C_6$-alkyl, a monocyclic heterocyclyl radical which has 4 to 7 ring atoms and/or a monocyclic heteroaryl radical which has 5 or 6 ring atoms, where the monocyclic heterocyclyl and heteroaryl radicals mentioned for their part may optionally be monosubstituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, and to their polymorphs, enantiomers, diastereomers, racemates, tautomers, solvates, physiologically acceptable salts and solvates of these salts.

Particular preference is given to compounds of the general formula (I-A) in which X represents an oxygen atom, A represents a phenyl or pyridyl ring, $R^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl- or $C_1$-$C_6$-alkoxycarbonyl radical, or represents a monocyclic heterocyclyl radical which has 4 to 7 ring atoms and may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical which has 4 to 7 ring atoms, and/or by a monocyclic heteroaryl radical which has 5 or 6 ring atoms, and/or by a phenyl radical which for its part may be mono- or polysubstituted by identical or different substituents from the group consisting of halogen, $C_1$-$C_3$-alkyl and/or $C_1$-$C_3$-alkoxy, or represents a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, $C_1$-$C_3$-alkylcarbonyl, —C(=O)NH$_2$, $C_1$-$C_3$-alkylaminocarbonyl, $C_3$-$C_6$-cycloalkylaminocarbonyl, $C_1$-$C_3$- alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl, and/or a monocyclic heterocyclyl radical which has 4 to 7 ring atoms, and/or a monocyclic heteroaryl radical which has 5 or 6 ring atoms which for its part may optionally be mono- or polysubstituted by identical or different substituents from the group consisting of halogen, $C_1$-$C_3$-alkyl and/or $C_1$-$C_3$-alkoxy, and n represents 0 or 1, and $R^{1b}$ represents halogen, hydroxy, cyano, nitro or represents a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl radical and/or a monocyclic heterocyclyl radical which has 4 to 7 ring atoms, and $R^2$ represents methyl, and $R^3$ represents methyl or $C_1$-$C_3$-alkylamino, and $R^4$ represents hydrogen, chlorine, cyano, methoxy, ethoxy or difluoromethoxy, and $R^5$ represents hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represents $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, a monocyclic heterocyclyl radical which has 4 to 7 ring atoms, and/or a monocyclic heteroaryl radical which has 5 or 6 ring atoms, where the monocyclic heterocyclyl and heteroaryl radicals mentioned for their part may optionally be monosubstituted by $C_1$-$C_3$-alkyl, or represents a $C_3$-$C_{10}$-cycloalkyl radical which may optionally be mono- or polysubstituted by identical or different substituents from the group consisting of halogen, amino, hydroxy, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, or represents a monocyclic heterocyclyl radical which has 4 to 7 ring atoms and may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, or represents a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, and $R^6$ and $R^7$ independently of one another represent hydrogen, $C_1$-$C_3$-alkyl, cyclopropyl, or di-$C_1$-$C_3$-alkyl-amino-$C_1$-$C_3$-alkyl, and $R^8$ represents hydroxy, $C_1$-$C_6$-alkyl, hydroxy-$C_1$-$C_3$-alkyl, trifluoromethyl, pyrrolidinyl, morpholinyl or piperidinyl, and $R^9$ represents $C_1$-$C_6$-alkyl, with the proviso that, if A represents phenyl, $R^4$ represents hydrogen, chlorine, methoxy, ethoxy or difluoromethoxy and $R^5$ represents hydrogen, hydroxy, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represents $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, a monocyclic heterocyclyl radical which has 4 to 7 ring atoms, and/or a monocyclic heteroaryl radical which has 5 or 6 ring atoms, where the monocyclic heterocyclyl and heteroaryl radicals mentioned for their part may optionally be monosubstituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, and to their polymorphs, enantiomers, diastereomers, racemates, tautomers, solvates, physiologically acceptable salts and solvates of these salts.

Very particular preference is given to compounds of the general formula (I-A) in which X represents an oxygen atom, A represents a phenyl or pyridyl ring, $R^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, or represents a monocyclic heterocyclyl radical which has 4 to 7 ring atoms and may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or by a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl-, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or by a monocyclic heterocyclyl radical which has 4 to 7 ring atoms, and/or by a monocyclic heteroaryl radical which has 5 or 6 ring atoms, and/or by a phenyl radical which for its part may be mono- or polysubstituted by identical or different substituents from the group consisting of halogen, $C_1$-$C_3$-alkyl and $C_1$-$C_3$-alkoxy, or represents a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, $C_1$-$C_3$-alkylcarbonyl, —C(=O)$NH_2$, $C_1$-$C_3$-alkylaminocarbonyl, $C_3$-$C_6$-cycloalkylaminocarbonyl, $C_1$-$C_3$-alkylsulphinyl, $C_1$-$C_3$-alkylsulphonyl, —S(=O)$_2NH_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl, and/or a monocyclic heterocyclyl radical which has 4 to 7 ring atoms, and/or a monocyclic heteroaryl radical which has 5 or 6 ring atoms which for its part may optionally be mono- or polysubstituted by identical or different substituents from the group consisting of halogen, $C_1$-$C_3$-alkyl and/or $C_1$-$C_3$-alkoxy, and n represents 0 or 1, and $R^{1b}$ represents fluorine, and $R^2$ represents methyl, and $R^3$ represents methyl or $C_1$-$C_3$-alkylamino, and $R^4$ represents hydrogen, chlorine, cyano, methoxy, ethoxy or difluoromethoxy, and $R^5$ represents hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represents $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, a monocyclic heterocyclyl radical which has 4 to 7 ring atoms, or a monocyclic heteroaryl radical which has 5 or 6 ring atoms, where the monocyclic heterocyclyl and heteroaryl radicals mentioned for their part may optionally be substituted by $C_1$-$C_3$-alkyl, represents a $C_3$-$C_{10}$-cycloalkyl radical and may optionally be mono- or polysubstituted by identical or different substituents from the group consisting of halogen, amino, hydroxy, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, or represents a monocyclic heterocyclyl radical which has 4 to 7 ring atoms and may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, or represents a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, and $R^6$ and $R^7$ independently of one another represent hydrogen, $C_1$-$C_3$-alkyl, cyclopropyl, or di-$C_1$-$C_3$-alkyl-amino-$C_1$-$C_3$-alkyl, and $R^8$ represents hydroxy, $C_1$-$C_3$-alkyl, hydroxy-$C_1$-$C_3$-alkyl, trifluoromethyl, pyrrolidinyl, morpholinyl or piperidinyl, and $R^9$ represents $C_1$-$C_3$-alkyl, with the proviso that if A represents phenyl, $R^4$ represents hydrogen, chlorine, methoxy, ethoxy or difluoromethoxy and $R^5$ represents hydrogen, hydroxy, amino, aminocarbonyl, fluorine, chlorine, bromine, $C_1$-$C_6$-alkyl, $C_1$-$C_6$-alkoxy, $C_1$-$C_6$- alkylamino, $C_1$-$C_6$-alkylcarbonylamino, $C_1$-$C_6$-alkylaminocarbonyl or $C_1$-$C_6$-alkylaminosulphonyl, or represents $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, a monocyclic heterocyclyl radical which has 4 to 7 ring atoms, or a monocyclic heteroaryl radical which has 5 or 6 ring atoms, where the monocyclic heterocyclyl and heteroaryl radicals mentioned for their part may optionally be monosubstituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, and to their polymorphs, enantiomers, diastereomers, racemates, tautomers, solvates, physiologically acceptable salts and solvates of these salts.

Very particular preference is likewise given to compounds of the general formula (I-A) in which X represents an oxygen atom, A represents a phenyl or pyridyl ring, $R^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, or represents a monocyclic heterocyclyl radical which has 4 to 7 ring atoms and may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl-, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or by a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O)—$NR^6R^7$, —C(=O)—$R^8$, —S(=O)$_2$—$NR^6R^7$, —S(=O)—$R^9$, —S(=O)$_2$—$R^9$ or —NH—S(=O)$_2$—$R^9$, and/or by a monocyclic heterocyclyl radical which has 4 to 7 ring atoms, and/or by a monocyclic heteroaryl radical which has 5 or 6 ring atoms, and/or by a phenyl radical which for its part may be mono- or polysubstituted by identical or different substituents from the group consisting of halogen, $C_1$-$C_3$-alkyl- and $C_1$-$C_3$-alkoxy, or represents a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, $C_1$-$C_3$-alkylcarbonyl, —C(=O)$NH_2$, $C_1$-$C_3$-alkylaminocarbonyl, $C_3$-$C_6$-cycloalkylaminocarbonyl, $C_1$-$C_3$-alkylsulphinyl, $C_1$-$C_3$-alkylsulphonyl, —S(=O)$_2NH_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl, and/or a monocyclic heterocyclyl radical which has 4 to 7 ring atoms, and/or a monocyclic heteroaryl radical which has 5 or 6 ring atoms which for its part may optionally be mono- or polysubstituted by identical or different substituents from the group consisting of halogen, $C_1$-$C_3$-alkyl and $C_1$-$C_3$-alkoxy, and n represents 0 or 1, and $R^{1b}$ represents fluorine, and $R^2$ represents methyl, and $R^3$ represents methyl or $C_1$-$C_3$-alkylamino, and $R^4$ represents hydrogen, chlorine, cyano, methoxy, ethoxy or difluoromethoxy, and $R^5$ represents chlorine, hydroxy, amino, $C_1$-$C_6$-alkyl, methoxy, ethoxy, difluoromethoxy, trifluoromethoxy, $C_1$-$C_3$-alkylcarbonylamino, cyclopropyl, pyridinyl, morpholinyl, piperidinyl, piperazinyl which is optionally mono- or polysubstituted by methyl, pyrazolyl, or represents phenyl which is optionally substituted by $C_1$-$C_3$-alkylaminosulphonyl, or represents $C_1$-$C_3$-alkoxy which may be substituted by morpholinyl, pyrrolidinyl, piperazinyl or pyridinyl, where the piperazinyl or pyridinyl for its part may be substituted by $C_1$-$C_3$-alkyl, and $R^6$ and $R^7$ independently of one another represent hydrogen, $C_1$-$C_3$-alkyl, cyclopropyl, or di-$C_1$-$C_3$-alkyl-amino-$C_1$-$C_3$-alkyl, and $R^8$ represents hydroxy, $C_1$-$C_3$-alkyl, hydroxy-$C_1$-$C_3$-alkyl, trifluoromethyl, pyrrolidinyl, morpholinyl or piperidinyl, and $R^9$ represents $C_1$-$C_3$-alkyl, with the proviso that, if A represents phenyl, $R^4$ represents hydrogen, chlorine, methoxy, ethoxy or difluoromethoxy and $R^5$ represents chlorine, hydroxy, amino, $C_1$-$C_6$-alkyl, methoxy, ethoxy, difluoromethoxy, trifluoromethoxy, $C_1$-$C_3$-alkylcarbonylamino, or represents $C_1$-$C_3$-alkoxy which may be substituted by morpholinyl, pyrrolidinyl, piperazinyl or pyridinyl where the piperazinyl or pyridinyl for its part may be substituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, and to their polymorphs, enantiomers, diastereomers, racemates, tautomers, solvates, physiologically acceptable salts and solvates of these salts.

Extraordinary preference is given to compounds of the general formula (I-A) in which X represents an oxygen atom, A represents a phenyl or pyridyl ring, $R^{1a}$ represents hydrogen or chlorine, or represents a monocyclic heterocyclyl radical which has 4 to 7 ring atoms and may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, $C_1$-$C_6$-alkylcarbonyl, $C_1$-$C_6$-alkylsulphonyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_3$-alkyl, pyridinyl, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or by a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or by a monocyclic heterocyclyl radical which has 4 to 7 ring atoms, and/or by a monocyclic heteroaryl radical which has 5 or 6 ring atoms, and/or by a phenyl radical which for its part may be mono- or polysubstituted by identical or different substituents from the group consisting of halogen, $C_1$-$C_3$-alkyl and $C_1$-$C_3$-alkoxy, or represents a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, $C_1$-$C_3$-alkylcarbonyl, —C(=O)$NH_2$, $C_1$-$C_3$-alkylaminocarbonyl, $C_3$-$C_6$-cycloalkylaminocarbonyl, $C_1$-$C_3$-alkylsulphinyl, $C_1$-$C_3$-alkylsulphonyl, —S(=O)$_2NH_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl, and/or a monocyclic heterocyclyl radical which has 4 to 7 ring atoms, and/or a monocyclic heteroaryl radical which has 5 or 6 ring atoms which for its part may optionally be mono- or polysubstituted by identical or different substituents from the group consisting of halogen, $C_1$-$C_3$-alkyl and $C_1$-$C_3$-alkoxy, and n represents 0 or 1, and $R^{1b}$ represents fluorine, and $R^2$ represents methyl, $R^3$ represents methyl or $C_1$-$C_3$-alkylamino, and $R^4$ represents hydrogen, chlorine, cyano, methoxy, ethoxy or difluoromethoxy, and $R^5$ represents chlorine, hydroxy, amino, $C_1$-$C_6$-alkyl, methoxy, ethoxy, difluoromethoxy, trifluoromethoxy, $C_1$-$C_3$-alkylcarbonylamino, cyclopropyl, pyridinyl, morpholinyl, piperidinyl, piperazinyl which is optionally mono- or polysubstituted by methyl, pyrazolyl, or represents phenyl which is optionally substituted by $C_1$-$C_3$-alkylaminosulphonyl, or represents $C_1$-$C_3$-alkoxy which may be substituted by morpholinyl, pyrrolidinyl, piperazinyl or pyridinyl, where the piperazinyl or pyridinyl for its part may be substituted by $C_1$-$C_3$-alkyl, and $R^6$ and $R^7$ independently of one another represent hydrogen, $C_1$-$C_3$-alkyl, cyclopropyl, or di-$C_1$-$C_3$-alkyl-amino-$C_1$-$C_3$-alkyl, and $R^8$ represents hydroxy, $C_1$-$C_3$-alkyl, hydroxy-$C_1$-$C_3$-alkyl, trifluoromethyl, pyrrolidinyl, morpholinyl or piperidinyl, and $R^9$ represents $C_1$-$C_3$-alkyl, with the proviso that, if A represents phenyl, $R^4$ represents hydrogen, chlorine, methoxy, ethoxy or difluoromethoxy, and $R^5$ represents chlorine, hydroxy, amino, $C_1$-$C_6$-alkyl, methoxy, ethoxy, difluoromethoxy, trifluoromethoxy, $C_1$-$C_3$-alkylcarbonylamino, or represents $C_1$-$C_3$-alkoxy which may be substituted by morpholinyl, pyrrolidinyl, piperazinyl or pyridinyl, where the piperazinyl or pyridinyl for its part may be substituted by $C_1$-$C_3$-alkyl, $R^{1a}$ does not represent hydrogen or chlorine, and to their polymorphs, enantiomers, diastereomers, racemates, tautomers, solvates, physiologically acceptable salts and solvates of these salts.

Particularly interesting compounds of the general formula (I-A) are those in which X represents an oxygen atom, A represents a phenyl or 3-pyridyl ring, $R^{1a}$ represents hydrogen, chlorine, morpholinyl, dioxidothiomorpholinyl or tetrazolyl, or represents isoxazolyl, pyrazolyl, thienyl, thiazolyl, imidazolyl, triazolyl, azinanyl, piperazinyl, pyrrolyl, pyrrolidinyl, piperidinyl, piperazinyl, diazepanyl, oxazinanyl, oxazolidinyl, morpholinyl, azolidinyl, azetidinyl, phenyl, pyridinyl or pyrimidinyl, optionally mono- or polysubstituted by identical or different substituents from the group consisting of fluorine, chlorine, oxo, hydroxy, cyano, nitro, $C_1$-$C_3$-alkyl, $C_1$-$C_3$-alkoxy, $C_1$-$C_3$-alkoxy-$C_1$-$C_3$-alkyl, hydroxy-$C_1$-$C_3$-alkyl, $C_3$-$C_6$-cycloalkyl, phenyl-$C_1$-$C_3$-alkyl, trifluoromethyl, trifluoromethoxy, phenyl, fluorophenyl, pyridinyl, —C(=O)—$NR^6R^7$, —C(=O)—$R^8$, —S(=O)$_2$—$NR^6R^7$, —S(=O)—$R^9$, —S(=O)$_2$—$R^9$ and —NH—S(=O)$_2$—$R^9$, or represents phenyl which is substituted by morpholinyl or halothienyl, n represents 0 or 1, $R^{1b}$ represents fluorine, $R^2$ represents methyl, $R^3$ represents methyl or $C_1$-$C_3$-alkylamino, and $R^4$ represents hydrogen, chlorine, cyano, methoxy, ethoxy or difluoromethoxy, and $R^5$ represents chlorine, hydroxy, amino, $C_1$-$C_6$-alkyl, methoxy, ethoxy, difluoromethoxy, trifluoromethoxy, $C_1$-$C_3$-alkylcarbonylamino, cyclopropyl, pyridinyl, morpholinyl, piperidinyl, piperazinyl which is optionally mono- or polysubstituted by methyl, pyrazolyl, or represents phenyl which is optionally substituted by $C_1$-$C_3$-alkylaminosulphonyl, or represents $C_1$-$C_3$-alkoxy which may be substituted by morpholinyl, pyrrolidinyl, piperazinyl or pyridinyl, where the piperazinyl or pyridinyl for its part may be substituted by $C_1$-$C_3$-alkyl, and $R^6$ and $R^7$ independently of one another represent hydrogen, $C_1$-$C_3$-alkyl, cyclopropyl or di-$C_1$-$C_3$-alkyl-amino-$C_1$-$C_3$-alkyl, and $R^8$ represents hydroxy, $C_1$-$C_3$-alkyl, hydroxy-$C_1$-$C_3$-alkyl, trifluoromethyl, pyrrolidinyl, morpholinyl or piperidinyl, and $R^9$ represents $C_1$-$C_3$-alkyl, with the proviso that, if A represents phenyl, $R^4$ represents hydrogen, chlorine, methoxy, ethoxy or difluoromethoxy and $R^5$ represents chlorine, hydroxy, amino, $C_1$-$C_6$-alkyl, methoxy, ethoxy, difluoromethoxy, trifluoromethoxy, $C_1$-$C_3$-alkylcarbonylamino, or represents $C_1$-$C_3$-alkoxy which may be substituted by morpholinyl, pyrrolidinyl, piperazinyl or pyridinyl, where the piperazinyl or pyridinyl for its part may be substituted by $C_1$-$C_3$-alkyl, $R^{1a}$ does not represent hydrogen or chlorine, and their polymorphs, enantiomers, diastereomers, racemates, tautomers, solvates, physiologically acceptable salts and solvates of these salts.

Very particularly interesting are compounds of the general formula (I-A)

in which

X represents an oxygen atom,

A represents a phenyl or 3-pyridyl ring, $R^{1a}$ represents hydrogen, chlorine, morpholinyl, dioxidothiomorpholinyl or tetrazolyl, or represents isoxazolyl, pyrazolyl, thienyl, thiazolyl, imidazolyl, triazolyl, azinanyl, piperazinyl, pyrrolyl, pyrrolidinyl, piperidinyl, piperazinyl, diazepanyl, oxazinanyl, oxazolidinyl, morpholinyl, azolidinyl, azetidinyl, phenyl, pyridinyl or pyrimidinyl, optionally mono- or polysubstituted by identical or different substituents from the group consisting of fluorine, chlorine, oxo, hydroxy, cyano, nitro, $C_1$-$C_3$-alkyl, $C_1$-$C_3$-alkoxy, $C_1$-$C_3$-alkoxy-$C_1$-$C_3$-alkyl, hydroxy-$C_1$-$C_3$-alkyl, cyclopropyl, phenyl-$C_1$-$C_3$-alkyl, trifluoromethoxy, trifluoromethyl, phenyl, fluorophenyl, pyridinyl, —C(=O)—NR$^6$R$^7$, —C(=O)—R$^8$, —S(=O)$_2$—NR$^6$R$^7$, —S(=O)—R$^9$, —S(=O)$_2$—R$^9$ and/or —NH—S(=O)$_2$—R$^9$, or represents phenyl which is substituted by morpholinyl or halothienyl, n represents 0 or 1, $R^{1b}$ represents fluorine, $R^2$ represents methyl, $R^3$ represents methylamino, $R^4$ represents hydrogen, chlorine, cyano, methoxy, ethoxy or difluoromethoxy, and $R^5$ represents chlorine, hydroxy, amino, $C_1$-$C_6$-alkyl, methoxy, ethoxy, difluoromethoxy, trifluoromethoxy, $C_1$-$C_3$-alkylcarbonylamino, cyclopropyl, pyridinyl, morpholinyl, piperidinyl, piperazinyl which is optionally mono- or polysubstituted by methyl, pyrazolyl, or represents phenyl which is optionally substituted by $C_1$-$C_3$-alkylaminosulphonyl, or represents $C_1$-$C_3$-alkoxy which may be substituted by morpholinyl, pyrrolidinyl, piperazinyl or pyridinyl, where the piperazinyl or pyridinyl for its part may be substituted by $C_1$-$C_3$-alkyl, and $R^6$ and $R^7$ independently of one another represent hydrogen, $C_1$-$C_3$-alkyl, cyclopropyl- or di-$C_1$-$C_3$-alkyl-amino-$C_1$-$C_3$-alkyl, and $R^8$ represents hydroxy, $C_1$-$C_3$-alkyl, hydroxy-$C_1$-$C_3$-alkyl, trifluoromethyl, pyrrolidinyl, morpholinyl or piperidinyl, and $R^9$ represents $C_1$-$C_3$-alkyl, with the proviso that, if A represents phenyl, $R^4$ represents hydrogen, chlorine, methoxy, ethoxy or difluoromethoxy and $R^5$ represents chlorine, hydroxy, amino, $C_1$-$C_6$-alkyl, methoxy, ethoxy, difluoromethoxy, trifluoromethoxy, $C_1$-$C_3$-alkylcarbonylamino, or represents $C_1$-$C_3$-alkoxy which may be substituted by morpholinyl, pyrrolidinyl, piperazinyl or pyridinyl, where the piperazinyl or pyridinyl for its part may be substituted by $C_1$-$C_3$-alkyl, $R^{1a}$ does not represent hydrogen or chlorine, and their polymorphs, enantiomers, diastereomers, racemates, tautomers, solvates, physiologically acceptable salts and solvates of these salts.

However, the proviso does not include compounds of the general formula (I-A) in which A represents phenyl and $R^4$ represents hydrogen or chlorine and $R^5$ represents trifluoromethoxy and $R^{1a}$ represents chlorine, and compounds of the general formula (I-A) in which A represents phenyl and $R^4$ represents hydrogen and $R^5$ represents $C_1$-$C_3$-alkoxy which may be substituted by morpholinyl, pyrrolidinyl, piperazinyl or pyridyl, where the piperazinyl or pyridinyl for its part may be substituted by $C_1$-$C_3$-alkyl, and $R^{1a}$ represents chlorine.

These are to be understood as meaning, for example, compounds of the synthesized Working Examples Nos. 1; 15; 32; 33; 164; 164.1; 164.2; 165; 166 and 167.

Likewise of interest are compounds of the general formula (I-A)

in which

X represents an oxygen or sulphur atom, and

A represents a monocyclic heteroaryl ring which has 5 or 6 ring atoms or represents a phenyl ring, and $R^{1a}$ a) represents hydrogen, halogen, cyano, carboxyl, amino or aminosulphonyl, or b) represents a $C_1$-$C_6$-alkoxy, $C_1$-$C_3$-alkoxy-$C_1$-$C_3$-alkyl, $C_1$-$C_3$-alkoxy-$C_1$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-heterocyclyl-$C_1$-$C_6$-alkyl, N-heterocyclyl-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, or c) represents a monocyclic heterocyclyl radical which has 3 to 8 ring atoms and which may be mono- or polysubstituted by identical or different substituents from the group consisting of hydroxy, halogen, amino, oxo, carboxyl and a $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms, or d) represents a monocyclic heteroaryl radical which has 5 or 6 ring atoms and which may be mono- or polysubstituted by identical or different substituents from the group consisting of halogen, hydroxy, amino, cyano, nitro, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms and/or a monocyclic heteroaryl radical which has 5 or 6 ring atoms, or e) represents a phenyl radical which may be mono- or polysubstituted by identical or different substituents from the group consisting of halogen, amino, hydroxy, cyano, nitro, carboxyl and a $C_1$-$C_6$-alkyl, $C_1$-$C_6$- alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, hydroxy-$C_1$-$C_6$-alkyl, $C_3$-$C_{10}$-cycloalkyl- and/or a monocyclic heterocyclyl radical which has 3 to 8 ring atoms, and $R^{1b}$ represents halogen, hydroxy, cyano, nitro and/or represents a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms, and n represents 0-2, and $R^2$ represents a $C_1$-$C_3$-alkyl or trifluoromethyl or a $C_3$- or $C_4$-cycloalkyl radical, and $R^3$ represents a cyclopropyl, $C_1$-$C_3$-alkyl, $C_1$-$C_3$-alkoxy, amino, cyclopropylamino or a $C_1$-$C_3$-alkylamino radical, and $R^4$, $R^5$ independently of one another
  i) represent hydrogen, hydroxy, amino, aminocarbonyl, fluorine, chlorine, bromine or a trifluoromethyl, $C_1$-$C_6$-alkyl, $C_1$-$C_6$-alkoxy, $C_1$-$C_6$-alkylamino, $C_1$-$C_6$-alkylcarbonylamino or $C_1$-$C_6$-alkylaminocarbonyl radical, where the alkyl moiety of a radical listed under i) may be mono- or polysubstituted by identical or different radicals from the group consisting of amino, fluorine, hydroxy, carboxyl and a hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, or a monocyclic heterocyclyl radical which has 3 to 6 ring atoms, or
  ii) represent cyano or nitro or
  iii) represent a $C_1$-$C_6$-alkylaminosulphonyl, halo-$C_1$-$C_6$-alkyl- or halo-$C_1$-$C_6$-alkoxy radical, where the alkyl moiety of a radical listed under iii) may be mono- or polysubstituted by identical or different radicals from the group consisting of amino, fluorine, hydroxy, carboxyl and a hydroxy-$C_1$-$C_6$-alkyl, $C_1$-$C_6$-alkoxy, $C_1$-$C_6$-alkylamino, amino-$C_1$-$C_6$-alkyl, $C_1$-$C_6$-alkoxy-$C_1$-$C_6$-alkyl- or a monocyclic heterocyclyl radical which has 3 to 6 ring atoms, or
  iv) represent a $C_3$-$C_{10}$-cycloalkyl radical which may optionally be mono- or polysubstituted by identical or different substituents from the group consisting of halogen, amino, hydroxy, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl or halo-$C_1$-$C_6$-alkoxy radical, or
  v) represent a monocyclic heteroaryl radical which has 5 or 6 ring atoms and which may be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl or halo-$C_1$-$C_6$-alkoxy, $C_3$-$C_{10}$-cycloalkyl and/or a monocyclic heterocyclyl radical which has 3 to 8 ring atoms, or
  vi) represent a monocyclic heterocyclyl radical which has 3 to 8 ring atoms and which may optionally be mono- or polysubstituted by identical or different substituents from the group consisting of halogen, amino, hydroxy, cyano, oxo, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl or halo-$C_1$-$C_6$-alkoxy, $C_3$-$C_{10}$-cycloalkyl and/or a monocyclic heterocyclyl radical which has 3 to 8 ring atoms, or
  vii) represent a phenyl radical which may optionally be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-Alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl or halo-$C_1$-$C_6$-alkoxy, $C_3$-$C_{10}$-cycloalkyl and/or a monocyclic heterocyclyl radical which has 3 to 8 ring atoms, with the proviso that, if A represents a phenyl radical and $R^4$ and $R^5$ represent a radical listed under i), $R^{1a}$ represents a radical listed under c), d) or e), and their enantiomers, diastereomers, racemates, tautomers, solvates, physiologically acceptable salts and solvates of these salts.

A preferred subgroup thereof are compounds of the formula (I-A)

in which

X represents an oxygen or sulphur atom, and

A represents a monocyclic heteroaryl ring which has 5 or 6 ring atoms or represents a phenyl ring, and $R^{1a}$ a) represents a monocyclic heterocyclyl radical which has 3 to 8 ring atoms and which may be mono- or polysubstituted by identical or different substituents from the group consisting of hydroxy, halogen, amino, oxo, carboxyl and a $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms, or b) represents a monocyclic heteroaryl radical which has 5 or 6 ring atoms and which may be mono- or polysubstituted by identical or different substituents from the group consisting of halogen, hydroxy, amino, cyano, nitro, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms and/or a monocyclic heteroaryl radical which has 5 or 6 ring atoms, or c) represents a phenyl radical which may be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, hydroxy-$C_1$-$C_6$-alkyl, $C_3$-$C_{10}$-cycloalkyl and/or a monocyclic heterocyclyl radical which has 3 to 8 ring atoms, and $R^{1b}$ represents halogen, hydroxy, cyano, nitro and/or represents a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms, and n represents 0-2, and $R^2$ represents a $C_1$-$C_3$-alkyl or trifluoromethyl or a $C_3$- or $C_4$-cycloalkyl radical, and $R^3$ represents a cyclopropyl, $C_1$-$C_3$-alkyl, $C_1$-$C_3$-alkoxy, amino, cyclopropylamino or a $C_1$-$C_3$-alkylamino radical, and $R^4$, $R^5$ independently of one another
  i) represent hydrogen, hydroxy, amino, aminocarbonyl, fluorine, chlorine, bromine or a trifluoromethyl, $C_1$-$C_6$-alkyl, $C_1$-$C_6$-alkoxy, $C_1$-$C_6$-alkylamino, $C_1$-$C_6$-alkylcarbonylamino or $C_1$-$C_6$-alkylaminocarbonyl radical, where the alkyl moiety of a radical listed under i) may be mono- or polysubstituted by identical or different radicals from the group consisting of amino, fluorine, hydroxy, carboxyl and a hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, or a monocyclic heterocyclyl radical which has 3 to 6 ring atoms, or
ii) represent cyano or nitro or
iii) represent a $C_1$-$C_6$-alkylaminosulphonyl, halo-$C_1$-$C_6$-alkyl- or halo-$C_1$-$C_6$-alkoxy radical, where the alkyl moiety of a radical listed under iii) may be mono- or polysubstituted by identical or different radicals from the group consisting of amino, fluorine, hydroxy, carboxyl and a hydroxy-$C_1$-$C_6$-alkyl, $C_1$-$C_6$-alkoxy, $C_1$-$C_6$-alkylamino, amino-$C_1$-$C_6$-alkyl, $C_1$-$C_6$-alkoxy-$C_1$-$C_6$-alkyl or a monocyclic heterocyclyl radical which has 3 to 6 ring atoms, or
iv) represent a $C_3$-$C_{10}$-cycloalkyl radical which may be mono- or polysubstituted by identical or different substituents from the group consisting of halogen, amino, hydroxy, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl or halo-$C_1$-$C_6$-alkoxy radical, or
v) represent a monocyclic heteroaryl radical which has 5 or 6 ring atoms and which may be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl- or halo-$C_1$-$C_6$-alkoxy, $C_3$-$C_{10}$-cycloalkyl and/or a monocyclic heterocyclyl radical which has 3 to 8 ring atoms, or
vi) represent a monocyclic heterocyclyl radical which has 3 to 8 ring atoms and which may be mono- or polysubstituted by identical or different substituents from the group consisting of halogen, amino, hydroxy, cyano, oxo, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl or halo-$C_1$-$C_6$-alkoxy, $C_3$-$C_{10}$-cycloalkyl and/or a monocyclic heterocyclyl radical which has 3 to 8 ring atoms, or
vii) represent a phenyl radical which may be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl or halo-$C_1$-$C_6$-alkoxy, $C_3$-$C_{10}$-cycloalkyl and/or a monocyclic heterocyclyl radical which has 3 to 8 ring atoms, and their enantiomers, diastereomers, racemates, tautomers, solvates, physiologically acceptable salts and solvates of these salts.

A further subgroup thereof are compounds of the formula (I-A),
in which
X represents an oxygen or sulphur atom, and
A represents a monocyclic heteroaryl ring which has 5 or 6 ring atoms or represents a phenyl ring, and
$R^{1a}$ a) represents hydrogen, halogen, cyano, carboxyl, amino or aminosulphonyl, or b) represents a $C_1$-$C_6$-alkoxy, $C_1$-$C_3$-alkoxy-$C_1$-$C_3$-alkyl, $C_1$-$C_3$-alkoxy-$C_1$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-heterocyclyl-$C_1$-$C_6$-alkyl, N-heterocyclyl-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, or
c) represents a monocyclic heterocyclyl radical which has 3 to 8 ring atoms and which may be mono- or polysubstituted by identical or different substituents from the group consisting of hydroxy, halogen, amino, oxo, carboxyl and a $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms, or
d) represents a monocyclic heteroaryl radical which has 5 or 6 ring atoms and which may be mono- or polysubstituted by identical or different substituents from the group consisting of halogen, hydroxy, amino, cyano, nitro, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms and/or a monocyclic heteroaryl radical which has 5 or 6 ring atoms, or
e) represents a phenyl radical which may be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, hydroxy-$C_1$-$C_6$-alkyl, $C_3$-$C_{10}$-cycloalkyl and/or a monocyclic heterocyclyl radical which has 3 to 8 ring atoms, and $R^{1b}$ represents halogen, hydroxy, cyano, nitro and/or represents a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms, and n represents 0-2, and $R^2$ represents a $C_1$-$C_3$-alkyl or trifluoromethyl or a $C_3$- or $C_4$-cycloalkyl radical, and $R^3$ represents a cyclopropyl, $C_1$-$C_3$-alkyl, $C_1$-$C_3$-alkoxy, amino, cyclopropylamino or a $C_1$-$C_3$-alkylamino radical, and $R^4$, $R^5$ independently of one another
i) represent cyano or nitro or
ii) represent a $C_1$-$C_6$-alkylaminosulphonyl, halo-$C_1$-$C_6$-alkyl- or halo-$C_1$-$C_6$-alkoxy radical, where the alkyl moiety of a radical listed under ii) may be mono- or polysubstituted by identical or different radicals from the group consisting of amino, fluorine, hydroxy, carboxyl and a hydroxy-$C_1$-$C_6$-alkyl, $C_1$-$C_6$-alkoxy, $C_1$-$C_6$-alkylamino, amino-$C_1$-$C_6$-alkyl, $C_1$-$C_6$-alkoxy-$C_1$-$C_6$-alkyl or a monocyclic heterocyclyl radical which has 3 to 6 ring atoms, or
iii) represent a $C_3$-$C_{10}$-cycloalkyl radical which may be mono- or polysubstituted by identical or different substituents from the group consisting of halogen, amino, hydroxy, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl or halo-$C_1$-$C_6$-alkoxy radical, or iv) represent a monocyclic heteroaryl radical which has 5 or 6 ring atoms and which may be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl or halo-$C_1$-$C_6$-alkoxy, $C_3$-$C_{10}$-cycloalkyl and/or a monocyclic heterocyclyl radical which has 3 to 8 ring atoms, or v) represent a monocyclic heterocyclyl radical which has 3 to 8 ring atoms and which may be mono- or polysubstituted by identical or different substituents from the group consisting of halogen, amino, hydroxy, cyano, oxo, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl or halo-$C_1$-$C_6$-alkoxy, $C_3$-$C_{10}$-cycloalkyl and/or a monocyclic heterocyclyl radical which has 3 to 8 ring atoms, or vi) represent a phenyl radical which may be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl or halo-$C_1$-$C_6$-alkoxy, $C_3$-$C_{10}$-cycloalkyl and/or a monocyclic heterocyclyl radical which has 3 to 8 ring atoms, and their enantiomers, diastereomers, racemates, tautomers, solvates, physiologically acceptable salts and solvates of these salts.

A further subgroup thereof are compounds of the formula (I-A), in which

X represents an oxygen atom, and

A represents a monocyclic heteroaryl ring having 5 or 6 ring atoms or represents a phenyl ring, and $R^{1a}$ a) represents hydrogen or halogen, or b) represents a monocyclic heterocyclyl radical which has 3 to 8 ring atoms and which may be mono- or polysubstituted by identical or different substituents from the group consisting of hydroxy, fluorine, oxo, carboxyl and a $C_1$-$C_6$-alkyl, hydroxy-$C_1$-$C_6$-alkyl, halo-$C_1$-$C_6$-alkyl or halo-$C_1$-$C_6$-alkoxy radical, or c) represents a monocyclic heteroaryl radical which has 5 or 6 ring atoms and which may be mono- or polysubstituted by identical or different substituents from the group consisting of halogen, hydroxy, carboxyl and a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heteroaryl radical which has 5 or 6 ring atoms, or d) represents a phenyl radical which may be mono- or polysubstituted by identical or different substituents from the group consisting of halogen, hydroxy, carboxyl and a $C_1$-$C_6$-alkyl, $C_1$-$C_6$-alkoxy, halo-$C_1$-$C_6$-alkyl or halo-$C_1$-$C_6$-alkoxy radical, and $R^{1b}$ represents halogen, cyano and/or represents a $C_1$-$C_6$-alkyl, $C_1$-$C_6$-alkoxy, halo-$C_1$-$C_6$-alkyl or halo-$C_1$-$C_6$-alkoxy radical, and n represents 0-2, and $R^2$ represents a $C_1$-$C_3$-alkyl or trifluoromethyl radical, and $R^3$ represents a $C_1$-$C_3$-alkyl or a $C_1$-$C_3$-alkylamino radical, and $R^4$, $R^5$ independently of one another i) represent hydrogen or fluorine, chlorine, bromine or represent a $C_1$-$C_6$-alkoxy radical, where the alkyl moiety of the $C_1$-$C_6$-alkoxy radical may be mono- or polysubstituted by identical or different radicals from the group consisting of a monocyclic heterocyclyl radical which has 3 to 6 ring atoms, or ii) represent a halo-$C_1$-$C_6$-alkyl or halo-$C_1$-$C_6$-alkoxy radical, or iii) represent a $C_3$-$C_{10}$-cycloalkyl radical which may be mono- or polysubstituted by identical or different substituents from the group consisting of halogen, hydroxy, carboxyl and a $C_1$-$C_6$-alkyl radical, or iv) represent a monocyclic heteroaryl radical which has 5 or 6 ring atoms and which may be mono- or polysubstituted by identical or different substituents from the group consisting of halogen, hydroxy, and a $C_1$-$C_6$-alkyl, $C_1$-$C_6$-alkoxy or hydroxy-$C_1$-$C_6$-alkyl radical, or v) represent a monocyclic heterocyclyl radical which has 3 to 8 ring atoms and which may be mono- or polysubstituted by identical or different substituents from the group consisting of halogen, hydroxy, carboxyl and a $C_1$-$C_6$-alkyl radical, or vi) represent a phenyl radical which may be mono- or polysubstituted by identical or different substituents from the group consisting of halogen, cyano, carboxyl and a $C_1$-$C_6$-alkyl, $C_1$-$C_6$-alkoxy, hydroxy-$C_1$-$C_6$-alkyl or $C_1$-$C_6$-alkylaminosulphonyl radical, with the proviso that, if A represents a phenyl radical and $R^4$ and $R^5$ represent a radical listed under i), $R^{1a}$ represents a radical listed under b), c) or d), and their enantiomers, diastereomers, racemates, tautomers, solvates, physiologically acceptable salts and solvates of these salts.

A further subgroup thereof are compounds of the formula (I-A)

in which

X represents an oxygen atom, and

A represents a monocyclic heteroaryl ring which has 5 or 6 ring atoms or represents a phenyl ring, and $R^{1a}$ a) represents a monocyclic heterocyclyl radical which has 3 to 8 ring atoms and which may be mono- or polysubstituted by identical or different substituents from the group consisting of hydroxy, fluorine, oxo, carboxyl and/or a $C_1$-$C_6$-alkyl, hydroxy-$C_1$-$C_6$-alkyl, halo-$C_1$-$C_6$-alkyl or halo-$C_1$-$C_6$-alkoxy radical, or c) represents a monocyclic heteroaryl radical which has 5 or 6 ring atoms and which may be mono- or polysubstituted by identical or different substituents from the group consisting of halogen, hydroxy, carboxyl and a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl or a monocyclic heteroaryl radical which has 5 or 6 ring atoms, or d) represents a phenyl radical which may be mono- or polysubstituted by identical or different substituents from the group consisting of halogen, hydroxy, carboxyl and a $C_1$-$C_6$-alkyl, $C_1$-$C_6$-alkoxy, halo-$C_1$-$C_6$-alkyl- or halo-$C_1$-$C_6$-alkoxy radical, and $R^{1b}$ represents halogen, cyano and/or represents a $C_1$-$C_6$-alkyl, $C_1$-$C_6$-alkoxy, halo-$C_1$-$C_6$-alkyl or halo-$C_1$-$C_6$-alkoxy radical, and n represents 0-2, and $R^2$ represents a $C_1$-$C_3$-alkyl or trifluoromethyl radical, and $R^3$ represents a $C_1$-$C_3$-alkyl or a $C_1$-$C_3$-alkylamino radical, and $R^4$, $R^5$ independently of one another
  i) represent hydrogen or fluorine, chlorine, bromine or represents a $C_1$-$C_6$-alkoxy radical, where the alkyl moiety of the $C_1$-$C_6$-alkoxy radical may be mono- or polysubstituted by identical or different radicals from the group consisting of a monocyclic heterocyclyl radical which has 3 to 6 ring atoms, or
  ii) represent a halo-$C_1$-$C_6$-alkyl- or halo-$C_1$-$C_6$-alkoxy radical, or
  iii) represent a $C_3$-$C_{10}$-cycloalkyl radical which may be mono- or polysubstituted by identical or different substituents from the group consisting of halogen, hydroxy, carboxyl and a $C_1$-$C_6$-alkyl radical, or
  iv) represent a monocyclic heteroaryl radical which has 5 or 6 ring atoms and which may be mono- or polysubstituted by identical or different substituents from the group consisting of halogen, hydroxy and a $C_1$-$C_6$-alkyl, $C_1$-$C_6$-alkoxy or hydroxy-$C_1$-$C_6$-alkyl radical, or
  v) represent a monocyclic heterocyclyl radical which has 3 to 8 ring atoms and which may be mono- or polysubstituted by identical or different substituents from the group consisting of halogen, hydroxy, carboxyl and a $C_1$-$C_6$-alkyl radical, or
  vi) represent a phenyl radical which may be mono- or polysubstituted by identical or different substituents from the group consisting of halogen, cyano, carboxyl and a $C_1$-$C_6$-alkyl, $C_1$-$C_6$-alkoxy, hydroxy-$C_1$-$C_6$-alkyl or $C_1$-$C_6$-alkylaminosulphonyl radical, and their enantiomers, diastereomers, racemates, tautomers, solvates, physiologically acceptable salts and solvates of these salts.

A further subgroup thereof are compounds of the formula (I-A)
in which
X represents an oxygen atom, and
A represents a monocyclic heteroaryl ring which has 5 or 6 ring atoms or represents a phenyl ring, and
$R^{1a}$ a) represents hydrogen or halogen, or
  b) represents a monocyclic heterocyclyl radical which has 3 to 8 ring atoms and which may be mono- or polysubstituted by identical or different substituents from the group consisting of hydroxy, fluorine, oxo, carboxyl and/or a $C_1$-$C_6$-alkyl, hydroxy-$C_1$-$C_6$-alkyl, halo-$C_1$-$C_6$-alkyl or halo-$C_1$-$C_6$-alkoxy radical, or
  c) represents a monocyclic heteroaryl radical which has 5 or 6 ring atoms and which may be mono- or polysubstituted by identical or different substituents from the group consisting of halogen, hydroxy, carboxyl and/or a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heteroaryl radical which has 5 or 6 ring atoms, or
  d) represents a phenyl radical which may be mono- or polysubstituted by identical or different substituents from the group consisting of halogen, hydroxy, carboxyl and/or a $C_1$-$C_6$-alkyl, $C_1$-$C_6$-alkoxy, halo-$C_1$-$C_6$-alkyl or halo-$C_1$-$C_6$-alkoxy radical, and $R^{1b}$ represents halogen, cyano and/or represents a $C_1$-$C_6$-alkyl, $C_1$-$C_6$-alkoxy, halo-$C_1$-$C_6$-alkyl or halo-$C_1$-$C_6$-alkoxy radical, and
n represents 0-2, and
$R^2$ represents a $C_1$-$C_3$-alkyl or trifluoromethyl radical, and $R^3$ represents a $C_1$-$C_3$-alkyl or a $C_1$-$C_3$-alkylamino radical, and $R^4$, $R^5$ independently of one another
  i) represent a halo-$C_1$-$C_6$-alkyl or halo-$C_1$-$C_6$-alkoxy radical, or
  ii) represent a $C_3$-$C_{10}$-cycloalkyl radical which may be mono- or polysubstituted by identical or different substituents from the group consisting of halogen, hydroxy, carboxyl and a $C_1$-$C_6$-alkyl radical, or
  iii) represent a monocyclic heteroaryl radical which has 5 or 6 ring atoms and which may be mono- or polysubstituted by identical or different substituents from the group consisting of halogen, hydroxy and a $C_1$-$C_6$-alkyl, $C_1$-$C_6$-alkoxy or hydroxy-$C_1$-$C_6$-alkyl radical, or
  iv) represent a monocyclic heterocyclyl radical which has 3 to 8 ring atoms and which may be mono- or polysubstituted by identical or different substituents from the group consisting of halogen, hydroxy, carboxyl and a $C_1$-$C_6$-alkyl radical, or
  v) represent a phenyl radical which may be mono- or polysubstituted by identical or different substituents from the group consisting of halogen, cyano, carboxyl and a $C_1$-$C_6$-alkyl, $C_1$-$C_6$-alkoxy, hydroxy-$C_1$-$C_6$-alkyl or $C_1$-$C_6$-alkylaminosulphonyl radical, and their enantiomers, diastereomers, racemates, tautomers, solvates, physiologically acceptable salts and solvates of these salts.

A further subgroup thereof are compounds of the formula (I-A)
in which
X represent an oxygen atom, and
A represents a monocyclic heteroaryl ring which has 6 ring atoms or represents a phenyl ring, and
$R^{1a}$ a) represents hydrogen or halogen, or
  b) represents a monocyclic heterocyclyl radical which has 4 to 6 ring atoms, or
  c) represents a monocyclic heteroaryl radical which has 5 or 6 ring atoms and which may be mono- or polysubstituted by identical or different substituents from the group consisting of halogen, carboxyl and a $C_1$-$C_6$-alkyl, $C_1$-$C_6$-alkoxy-$C_1$-$C_6$-alkyl, $C_3$-$C_{10}$-cycloalkyl or a monocyclic heteroaryl radical which has 6 ring atoms, or
  d) represents a phenyl radical which may be mono- or polysubstituted by carboxyl and
n represents 0, and
$R^2$ represents a $C_1$-$C_3$-alkyl radical, and
$R^3$ represents a $C_1$-$C_3$-alkylamino radical, and
$R^4$, $R^5$ independently of one another
  i) represent hydrogen, chlorine or a $C_1$-$C_6$-alkoxy radical, where the alkyl moiety of the $C_1$-$C_6$-alkoxy radical may be mono- or polysubstituted by identical or different radicals from the group consisting of a monocyclic heterocyclyl radical which has 3 to 6 ring atoms, or
  ii) represent a halo-$C_1$-$C_6$-alkoxy radical, or
  iii) represent a $C_3$-$C_{10}$-cycloalkyl radical, or
  iv) represent a monocyclic heteroaryl radical which has 6 ring atoms, or
  v) represent a monocyclic heterocyclyl radical which has 3 to 6 ring atoms and which may be mono- or polysubstituted by identical or different substituents from the group consisting of a $C_1$-$C_6$-alkyl radical, or
  vi) represent a phenyl radical which may be mono- or polysubstituted by identical or different substituents from the group consisting of a $C_1$-$C_6$-alkylaminosulphonyl radical,
with the proviso that, if A represents a phenyl radical and $R^4$ and $R^5$ represent a radical listed under i), $R^{1a}$ represents a radical listed under b), c) or d), and their enantiomers, diastereomers, racemates, tautomers, solvates, physiologically acceptable salts and solvates of these salts.

A further subgroup thereof are compounds of the formula (I-A)
in which
X represents an oxygen atom, and
A represents a pyridyl or a phenyl ring, and
$R^{1a}$ a) represents hydrogen or chlorine, or
  b) represents a morpholinyl radical, or
  c) represents an isoxazolyl, pyrazolyl, tetrazolyl, thienyl or pyridinyl radical which may be mono- or polysubstituted by identical or different radicals from the group consisting of chlorine, carboxyl and a $C_1$-$C_3$-alkyl, $C_1$-$C_3$-alkoxy-$C_1$-$C_3$-alkyl, $C_3$-$C_6$-cycloalkyl and/or a pyridinyl radical, or
  d) represent a phenyl radical which may be substituted by carboxyl, and
n represents 0, and
$R^2$ represents a methyl radical, and
$R^3$ represents a methylamino radical, and
$R^4$ represents hydrogen, chlorine or a $C_1$-$C_3$-alkyoxy radical, and
$R^5$ i) represents hydrogen, chlorine or a $C_1$-$C_3$-alkoxy radical, where the alkyl moiety of the $C_1$-$C_3$-alkoxy radical may be mono- or polysubstituted by identical or different radicals from the group consisting of a morpholinyl or pyrrolidinyl radical, or
  ii) represents a trifluoromethoxy radical, or
  iii) represents a cyclopropyl radical, or
  iv) represents a pyridinyl radical, or
  v) represents a morpholinyl, piperazinyl or piperidinyl radical which may be mono- or polysubstituted by identical or different substituents from the group consisting of a $C_1$-$C_3$-alkyl radical,
with the proviso that, if A represents a phenyl radical and $R^4$ and $R^5$ represent hydrogen, chlorine or a $C_1$-$C_3$-alkoxy radical, $R^{1a}$ represents a radical listed under b), c) or d),
and their enantiomers, diastereomers, racemates, tautomers, solvates, physiologically acceptable salts and solvates of these salts.

A further subgroup thereof are compounds of the formula (I-A)
in which
X represents an oxygen atom, and
A represents a phenyl ring, and
$R^{1a}$ a) represents chlorine, or
  b) represents a morpholinyl radical, or
  c) represents an isoxazolyl, pyrazolyl, thienyl or pyridinyl radical which may be mono- or polysubstituted by identical or different substituents from the group consisting of chlorine, carboxyl and a $C_1$-$C_3$-alkyl, $C_1$-$C_3$-alkoxy-$C_1$-$C_3$-alkyl, $C_3$-$C_6$-cycloalkyl and/or a pyridinyl radical, and
n represents 0, and
$R^2$ represents a $C_1$-$C_3$-alkyl radical, and
$R^3$ represents a $C_1$-$C_3$-alkylamino radical, and
$R^4$ represents hydrogen or a methoxy radical, and
$R^5$ i) represents a methoxy radical, or
  ii) represents a trifluoromethoxy radical, or
  iii) represents a cyclopropyl radical, or
  iv) represents a pyridinyl radical, or
  v) represents a morpholinyl radical,
with the proviso that, if $R^4$ represents hydrogen or a methoxy radical and $R^5$ represents a methoxy radical, $R^{1a}$ represents a radical listed under b) or c), and their enantiomers, diastereomers, racemates, tautomers, solvates, physiologically acceptable salts and solvates of these salts.

In the general formula I-A, n may represent 0, 1 or 2, and $(R^{1b})_n$ may also synonymously represent $R^{1b}$ and $R^{1c}$, with $R^{1b}$ and $R^{1c}$ then independently of one another being able to represent hydrogen, halogen, hydroxy, cyano, nitro and/or a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl radical and/or a monocyclic heterocyclyl radical having 3 to 8 ring atoms.

The present invention therefore relates to compounds of the general formula (I)

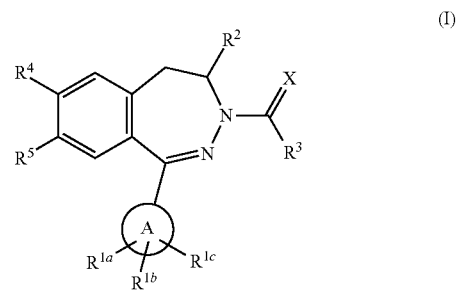

in which
X represents an oxygen or sulphur atom
A represents a monocyclic heteroaryl ring which has 5 or 6 ring atoms or represents a phenyl ring, and
$R^{1a}$ represents hydrogen, halogen, cyano, carboxyl, amino or aminosulphonyl,
or
represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical,
or
represents a monocyclic heterocyclyl radical having 3 to 8 ring atoms, which may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl, —$NR^6C(\!=\!O)$—$R^9$, —$C(\!=\!O)$—$NR^6R^7$, —$C(\!=\!O)$—$R^8$, —$S(\!=\!O)_2$—$NR^6R^7$, —$S(\!=\!O)$—$R^9$, —$S(\!=\!O)_2$—$R^9$, —$NH$—$S(\!=\!O)_2$—$R^9$, and/or a monocyclic heterocyclyl radical having 3 to 8 ring atoms,
or
represents a monocyclic heteroaryl radical having 5 or 6 ring atoms, which may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-

$C_6$-alkyl, halo-$C_1$-$C_6$-alkyl, halo-$C_1$-$C_6$-alkoxy, $C_3$-$C_{10}$-cycloalkyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical having 3 to 8 ring atoms, and/or by a monocyclic heteroaryl radical having 5 or 6 ring atoms, and/or by a phenyl radical which for its part may optionally be mono- or polysubstituted by halogen, $C_1$-$C_3$-alkyl and/or $C_1$-$C_3$-alkoxy, or represents a phenyl radical, which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, —C(=O)NR$^6$R$^7$, —C(=O) R$^8$, $C_1$-$C_3$-alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl, and/or a monocyclic heterocyclyl radical having 3 to 8 ring atoms, and/or a monocyclic heteroaryl radical having 5 or 6 ring atoms and which for its part may optionally be mono- or polysubstituted by identical or different substituents from the group consisting of halogen, $C_1$-$C_3$-alkyl and $C_1$-$C_3$-alkoxy, and $R^{1b}$ and $R^{1c}$ independently of one another being able to represent hydrogen, halogen, hydroxy, cyano, nitro and/or a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl radical and/or a monocyclic heterocyclyl radical having 3 to 8 ring atoms, and $R^2$ represents a $C_1$-$C_3$-alkyl or trifluoromethyl or a $C_3$- or $C_4$-cycloalkyl radical, and $R^3$ represents cyclopropyl, $C_1$-$C_3$-alkyl, $C_1$-$C_3$-alkoxy, amino, cyclopropylamino or $C_1$-$C_3$-alkylamino, and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, monocyclic heterocyclyl having 3 to 8 ring atoms and/or monocyclic heteroaryl having 5 or 6 ring atoms, where the monocyclic heterocyclyl and heteroaryl radicals mentioned for their part may optionally be monosubstituted by $C_1$-$C_3$-alkyl, or represent $C_3$-$C_{10}$-cycloalkyl which may optionally be mono- or polysubstituted by identical or different substituents from the group consisting of halogen, amino, hydroxy, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical having 3 to 8 ring atoms, or represent monocyclic heteroaryl which has 5 or 6 ring atoms and which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O) R$^8$, —S(=O)$_2$ R$^9$, —NR$^6$R$^7$, and/or a monocyclic heterocyclyl radical having 3 to 8 ring atoms, or represent monocyclic heterocyclyl having 3 to 8 ring atoms and which may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, —C(=O) R$^8$, —S(=O)$_2$R$^9$, —NR$^6$R$^7$, and/or a monocyclic heterocyclyl radical having 3 to 8 ring atoms, or represent phenyl which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical having 3 to 8 ring atoms, and $R^6$ and $R^7$ independently of one another represent hydrogen, $C_1$-$C_3$-alkyl, cyclopropyl or di-$C_1$-$C_3$-alkylamino-$C_1$-$C_3$-alkyl or fluoropyridyl, and $R^8$ represents hydroxy, $C_1$-$C_6$-alkyl, halo-$C_1$-$C_3$-alkyl, hydroxy-$C_1$-$C_3$-alkyl, $C_1$-$C_3$-alkoxy-$C_1$-$C_3$-alkyl, $C_3$-$C_8$-cycloalkyl, phenyl, monocyclic heterocyclyl having 3 to 8 ring atoms or monocyclic heteroaryl having 5 or 6 ring atoms, where phenyl, heteroaryl and heterocyclyl may optionally be mono- or disubstituted by halogen, $C_1$-$C_3$-alkoxy or $C_1$-$C_3$-alkyl, and $R^9$ represents hydrogen, $C_1$-$C_6$-alkyl or $C_1$-$C_4$-alkoxy, and their polymorphs, enantiomers, diastereomers, racemates, tautomers, solvates, physiologically acceptable salts and solvates of these salts, with the proviso that if A represents a phenyl ring and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$- alkyl, monocyclic heterocyclyl having 3 to 8 ring atoms and/or monocyclic heteroaryl which has 5 or 6 ring atoms, where the monocyclic heterocyclyl and heteroaryl radicals mentioned for their part may optionally be monosubstituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical.

The proviso, however, does not encompass those compounds of the general formula (I) in which A is phenyl and $R^4$ is hydrogen, fluorine, chlorine or bromine and $R^5$ is $C_1$-$C_6$-alkoxy which is substituted one or more times by identical or different halogens, and $R^{1a}$ is halogen, and also not those compounds of the general formula (I) in which A is phenyl and $R^4$ is hydrogen and $R^5$ is $C_1$-$C_6$-alkoxy which is substituted one or more times by an identical or different monocyclic heterocyclyl radical having 3 to 8 ring atoms and/or a monocyclic heteroaryl radical having 5 or 6 ring atoms, it being possible for the stated monocyclic heterocyclyl and heteroaryl radicals in turn to be optionally monosubstituted by $C_1$-$C_3$-alkyl, and $R^{1a}$ is halogen.

Accordingly, for example, the present invention also encompasses compounds of the prepared working examples No. 1; 15; 32; 33; 164; 164.2; 165; 166 and 167.

Preference is given to those compounds of the general formula I in which

X represents an oxygen atom, and

A represents a phenyl or pyridyl ring, and $R^{1a}$ represents hydrogen, halogen, cyano, carboxyl, amino or amino sulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, or represents a monocyclic heterocyclyl radical having 4 to 7 ring atoms, which may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl, —$NR^6C(=O) R^9$, —$C(=O)$—$NR^6R^7$, —$C(=O)$—$R^8$, —$S(=O)_2$—$NR^6R^7$, —$S(=O)$—$R^9$, —$S(=O)_2$—$R^9$, —NH—S$(=O)_2$—$R^9$, and/or by a monocyclic heterocyclyl radical having 4 to 7 ring atoms or represents a monocyclic heteroaryl radical having 5 or 6 ring atoms, which may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —$C(=O)$—$NR^6R^7$, —$C(=O)$—$R^8$, —$S(=O)_2$—$NR^6R^7$, —$S(=O)$—$R^9$, —$S(=O)_2$—$R^9$, —NH—$S(=O)_2$—$R^9$, and/or by a monocyclic heterocyclyl radical having 4 to 7 ring atoms and/or by a monocyclic heteroaryl radical having 5 or 6 ring atoms and/or by a phenyl radical which for its part may optionally be mono- or polysubstituted by identical or different substituents from the group consisting of halogen, $C_1$-$C_3$-alkyl and/or $C_1$-$C_3$-alkoxy, or represents a phenyl radical, which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, —$C(=O)NR^6R^7$, $C(=O) R^8$, $C_1$-$C_3$-alkylsulphinyl, $C_1$-$C_3$-alkylsulphonyl, —$S(=O)_2NH_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl, and/or a monocyclic heterocyclyl radical having 4 to 7 ring atoms and/or a monocyclic heteroaryl radical having 5 or 6 ring atoms and which for its part may optionally be mono- or polysubstituted by identical or different substituents from the group consisting of halogen, $C_1$-$C_3$-alkyl and $C_1$-$C_3$-alkoxy, and $R^{1b}$ and $R^{1c}$ independently of one another represent hydrogen, halogen, hydroxy, cyano, nitro or a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl radical and/or a monocyclic heterocyclyl radical having 4 to 7 ring atoms, and $R^2$ represents methyl, ethyl or isopropyl, and $R^3$ represents cyclopropyl, $C_1$-$C_3$-alkyl, $C_1$-$C_3$-alkoxy, amino, cyclopropylamino or $C_1$-$C_3$-alkylamino, and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, a monocyclic heterocyclyl having 4 to 7 ring atoms and/or a monocyclic heteroaryl having 5 or 6 ring atoms, where the monocyclic heterocyclyl and heteroaryl radicals mentioned for their part may optionally be monosubstituted by $C_1$-$C_3$-alkyl, or represent a $C_3$-$C_{10}$-cycloalkyl radical, which may optionally be mono- or polysubstituted by identical or different substituents from the group consisting of halogen, amino, hydroxy, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical having 4 to 7 ring atoms, or represent monocyclic heteroaryl having 5 or 6 ring atoms and which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O) $R^8$, —S(=O)$_2$ $R^9$, —NR$^6$R$^7$, and/or a monocyclic heterocyclyl radical having 4 to 7 ring atoms, or represent monocyclic heterocyclyl having 4 to 7 ring atoms and which may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, —C(=O) $R^8$, —S(=O)$_2$R$^9$, —NR$^6$R$^7$, and/or a monocyclic heterocyclyl radical having 4 to 7 ring atoms, or represent a phenyl radical, which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical having 4 to 7 ring atoms, and $R^6$ and $R^7$ independently of one another represent hydrogen, $C_1$-$C_3$-alkyl, cyclopropyl, di-$C_1$-$C_3$-alkyl-amino-$C_1$-$C_3$-alkyl or fluoropyridyl, and $R^8$ represents hydroxy, $C_1$-$C_6$-alkyl, halo-$C_1$-$C_3$-alkyl, hydroxy-$C_1$-$C_3$-alkyl, $C_1$-$C_3$-alkoxy-$C_1$-$C_3$-alkyl, $C_3$-$C_8$-cycloalkyl, phenyl, monocyclic heterocyclyl having 5 or 6 ring atoms, and $R^9$ represents hydrogen, $C_1$-$C_6$-alkyl or $C_1$-$C_4$-alkoxy, and their polymorphs, enantiomers, diastereomers, racemates, tautomers, solvates, physiologically acceptable salts and solvates of these salts, with the proviso that if A represents a phenyl ring and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino or $C_1$-$C_6$-alkylaminocarbonyl, or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, monocyclic heterocyclyl having 4 to 7 ring atoms and/or monocyclic heteroaryl having 5 or 6 ring atoms, where the monocyclic heterocyclyl and heteroaryl radicals mentioned for their part may optionally be monosubstituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical.

The proviso, however, does not encompass those compounds of the general formula (I), in which A is phenyl and $R^4$ is hydrogen, fluorine, chlorine or bromine and $R^5$ is $C_1$-$C_6$-alkoxy which is substituted one or more times by identical or different halogens, and $R^{1a}$ is halogen, and also not those compounds of the general formula (I) in which A is phenyl and $R^4$ is hydrogen and $R^5$ is $C_1$-$C_6$-alkoxy which is substituted one or more times by an identical or different monocyclic heterocyclyl radical having 4 to 7 ring atoms and/or a monocyclic heteroaryl radical having 5 or 6 ring atoms, it being possible for the stated monocyclic heterocyclyl and heteroaryl radicals in turn to be optionally monosubstituted by $C_1$-$C_3$-alkyl, and $R^{1a}$ is halogen.

The present invention therefore, for example, also encompasses compounds of the prepared working examples No. 1; 15; 32; 33; 164; 164.2; 165; 166 and 167.

Particular preference is given to those compounds of the general formula (I) in which X represents an oxygen atom, and A represents a phenyl or pyridyl ring, and $R^{1a}$ represents hydrogen, halogen, cyano, carboxyl, amino or aminosulphonyl, or represents a $C_1$-$C_6$-alkoxy, $C_1$-$C_6$-alkoxy-$C_1$-$C_3$-alkyl, $C_1$-$C_3$-alkoxy-$C_2$-$C_3$-alkoxy, $C_1$-$C_3$-alkylamino, $C_1$-$C_3$-alkylcarbonylamino, $C_1$-$C_3$-alkylamino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_1$-$C_3$-alkylcarbonyl or $C_1$-$C_4$-alkoxycarbonyl radical, or represents a monocyclic heterocyclyl radical having 4 to 7 ring atoms, which may optionally be mono- or polysubstituted by identical or different substituents from the group consisting of halogen, cyano, nitro, hydroxy, amino, oxo, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, phenyl, halophenyl, phenyl-$C_1$-$C_3$-alkyl, pyridinyl, —NR$^6$C(=O)—R$^9$, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, hydroxy, amino, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical having 4 to 7 ring atoms and/or by a monocyclic heteroaryl radical having 5 or 6 ring atoms and/or by a phenyl radical which for its part may optionally be mono- or polysubstituted by identical or different substituents from the group consisting of fluorine, chlorine, bromine, methyl and/or methoxy, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, —C(=O)NR$^6$R$^7$, —C(=O) R$^8$, $C_1$-$C_3$-alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, fluoro-$C_1$-$C_3$-alkyl, fluoro-$C_1$-$C_3$-alkoxy, hydroxy-$C_1$-$C_3$-alkyl, $C_3$-$C_6$-cycloalkyl and/or a monocyclic heterocyclyl radical having 4 to 7 ring atoms and/or a monocyclic heteroaryl radical having 5 or 6 ring atoms and which for its part may optionally be mono- or polysubstituted by identical or different substituents from the group consisting of fluorine, chlorine, bromine, methyl and/or methoxy, and $R^{1b}$ represents hydrogen, halogen, hydroxy, cyano, nitro or represents a $C_1$-$C_3$-alkyl, $C_1$-$C_3$-alkoxy, fluoro-$C_1$-$C_3$-alkyl or fluoro-$C_1$-$C_3$-alkoxy radical, and $R^{1c}$ represents hydrogen, fluorine, chlorine, bromine or cyano, and $R^2$ represents methyl, ethyl or isopropyl, and $R^3$ represents cyclopropyl, $C_1$-$C_3$-alkyl, $C_1$-$C_3$-alkoxy, cyclopropylamino or $C_1$-$C_3$-alkylamino, and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_3$-alkyl, $C_1$-$C_3$-alkoxy, $C_1$-$C_3$-alkylamino, which may be mono- or polysubstituted by identical or different substituents from the group consisting of halogen, amino, hydroxy, carboxyl, hydroxy-$C_1$-$C_3$-alkyl, $C_1$-$C_3$-alkoxy, $C_1$-$C_3$-alkylamino, amino-$C_1$-$C_3$-alkyl, monocyclic heterocyclyl having 4 to 7 ring atoms, and/or monocyclic heteroaryl having 5 or 6 ring atoms, where the monocyclic heterocyclyl and heteroaryl radicals mentioned for their part may optionally be monosubstituted by $C_1$-$C_3$-alkyl, or represent a $C_3$-$C_7$-cycloalkyl radical, which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical having 4 to 7 ring atoms, or represent monocyclic heterocyclyl having 5 or 6 ring atoms and which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O) R$^8$, —S(=O)$_2$R$^9$, —NR$^6$R$^7$, and/or a monocyclic heterocyclyl radical having 4 to 7 ring atoms, or represent monocyclic heterocyclyl having 4 to 7 ring atoms and which may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O) R$^8$, —S(=O)$_2$R$^9$, —NR$^6$R$^7$ and/or a monocyclic heterocyclyl radical having 4 to 7 ring atoms, or represent a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl and/or a monocyclic heterocyclyl radical having 4 to 7 ring atoms, and $R^6$ and $R^7$ independently of one another represent hydrogen, $C_1$-$C_3$-alkyl, cyclopropyl, di-$C_1$-$C_3$-alkylamino-$C_1$-$C_3$-alkyl or fluoropyridyl, and $R^8$ represents hydroxy, $C_1$-$C_6$-alkyl, hydroxy-$C_1$-$C_3$-alkyl, fluoro-$C_1$-$C_3$-alkyl, $C_1$-$C_3$-alkoxy-$C_1$-$C_3$-alkyl, $C_3$-$C_8$-cycloalkyl or monocyclic heterocyclyl which has 5 or 6 ring atoms, and $R^9$ represents hydrogen, $C_1$-$C_6$-alkyl or $C_1$-$C_4$-alkoxy, and their polymorphs, enantiomers, diastereomers, racemates, tautomers, solvates, physiologically acceptable salts and solvates of these salts, with the proviso that if A represents a phenyl ring and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or $C_1$-$C_3$-alkyl, $C_1$-$C_3$-alkoxy-, $C_1$-$C_3$-alkylamino which may be mono- or polysubstituted by identical or different substituents from the group consisting of halogen, amino, hydroxy, carboxyl, hydroxy-$C_1$-$C_3$-alkyl, $C_1$-$C_3$-alkoxy, $C_1$-$C_3$-alkylamino, amino-$C_1$-$C_3$-alkyl, monocyclic heterocyclyl having 4 to 7 ring atoms and/or monocyclic heteroaryl having 5 or 6 ring atoms, where the monocyclic heterocyclyl and heteroaryl radicals mentioned for their part may optionally be monosubstituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_3$-alkylamino, $C_1$-$C_3$-alkylcarbonylamino, $C_1$-$C_3$-alkylamino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_1$-$C_3$-alkylcarbonyl or $C_1$-$C_4$-alkoxycarbonyl radical.

The proviso, however, does not encompass those compounds of the general formula (I) in which A is phenyl and $R^4$ is hydrogen, fluorine, chlorine or bromine and $R^5$ is $C_1$-$C_3$-alkoxy which is substituted one or more times by identical or different halogens, and $R^{1a}$ is halogen, and also not those compounds of the general formula (I) in which A is phenyl and $R^4$ is hydrogen and $R^5$ is $C_1$-$C_3$-alkoxy which is substituted one or more times by an identical or different monocyclic heterocyclyl radical having 4 to 7 ring atoms and/or a monocyclic heteroaryl radical having 5 or 6 ring atoms, it being possible for the stated monocyclic heterocyclyl and heteroaryl radicals in turn to be optionally monosubstituted by $C_1$-$C_3$-alkyl, and $R^{1a}$ is halogen.

The present invention therefore also, for example, encompasses compounds of the prepared working examples No. 1; 15; 32; 33; 164; 164.2; 165; 166 and 167.

Particular preference is further given to those compounds of the general formula (I) in which X represents an oxygen atom, and A represents a phenyl or pyridyl ring, and $R^{1a}$ represents a monocyclic heterocycyl radical having 4 to 7 ring atoms, which may optionally be mono- or polysubstituted by identical or different substituents from the group consisting of halogen, cyano, nitro, hydroxy, amino, oxo, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, phenyl, halophenyl, phenyl-$C_1$-$C_3$-alkyl, pyridinyl, —NR$^6$C(=O)—R$^9$, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$ and/or by a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, hydroxy, amino, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical having 4 to 7 ring atoms, and/or by a monocyclic heteroaryl radical having 5 or 6 ring atoms, and/or by a phenyl radical which for its part may be mono- or polysubstituted by identical or different substituents from the group consisting of fluorine, chlorine, bromine, methyl or methoxy, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, —C(=O)NR$^6$R$^7$, —C(=O)R$^8$, $C_1$-$C_3$-alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, fluoro-$C_1$-$C_3$-alkyl, fluoro-$C_1$-$C_3$-alkoxy, hydroxy-$C_1$-$C_3$-alkyl, $C_3$-$C_6$-cycloalkyl and/or a monocyclic heterocyclyl radical having 4 to 7 ring atoms, and/or a monocyclic heteroaryl radical having 5 or 6 ring atoms which for its part may optionally be mono- or polysubstituted by identical or different substituents from the group consisting of fluorine, chlorine, bromine, methyl or methoxy, and $R^{1b}$ represents hydrogen, halogen, hydroxy, cyano, nitro or represents a $C_1$-$C_3$-alkyl, $C_1$-$C_3$-alkoxy, fluoro-$C_1$-$C_3$-alkyl or fluoro-$C_1$-$C_3$-alkoxy radical, and $R^{1c}$ represents hydrogen, fluorine, chlorine, bromine or cyano, and $R^2$ represents methyl, ethyl or isopropyl, and $R^3$ represents cyclopropyl, $C_1$-$C_3$-alkyl, $C_1$-$C_3$-alkoxy, cyclopropylamino or $C_1$-$C_3$-alkylamino, and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_3$-alkyl, $C_1$-$C_3$-alkoxy, $C_1$-$C_3$-alkylamino, which may be mono- or polysubstituted by identical or different substituents from the group consisting of halogen, amino, hydroxy, carboxyl, hydroxy-$C_1$-$C_3$-alkyl, $C_1$-$C_3$-alkoxy, $C_1$-$C_3$-alkylamino, amino-$C_1$-$C_3$-alkyl, monocyclic heterocyclyl having 4 to 7 ring atoms, and/or monocyclic heteroaryl having 5 or 6 ring atoms, where the monocyclic heterocyclyl and heteroaryl radicals mentioned for their part may optionally be monosubstituted by $C_1$-$C_3$-alkyl, or represent a $C_3$-$C_7$-cycloalkyl radical, which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical having 4 to 7 ring atoms, or represent monocyclic heteroaryl having 5 or 6 ring atoms, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)R$^8$, —S(=O)$_2$R$^9$, —NR$^6$R$^7$, and/or a monocyclic heterocyclyl radical having 4 to 7 ring atoms, or represent monocyclic heterocyclyl having 4 to 7 ring atoms, which may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O)R$^8$, —S(=O)$_2$R$^9$, —NR$^6$R$^7$, and/or a monocyclic heterocyclyl radical having 4 to 7 ring atoms, or represent a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical having 4 to 7 ring atoms, and $R^6$ and $R^7$ independently of one another represent hydrogen, $C_1$-$C_3$-alkyl, cyclopropyl, di-$C_1$-$C_3$-alkylamino-$C_1$-$C_3$-alkyl or fluoropyridyl, and $R^8$ represents hydroxy, $C_1$-$C_6$-alkyl, hydroxy-$C_1$-$C_3$-alkyl, fluoro-$C_1$-$C_3$-alkyl, $C_1$-$C_3$-alkoxy-$C_1$-$C_3$-alkyl, $C_3$-$C_8$-cycloalkyl or monocyclic heterocyclyl which has 5 or 6 ring atoms, and $R^9$ represents hydrogen, $C_1$-$C_6$-alkyl or $C_1$-$C_4$-alkoxy, and their polymorphs, enantiomers, diastereomers, racemates, tautomers, solvates, physiologically acceptable salts and solvates of these salts.

Particular preference is further given to those compounds of the general formula (I) in which X represents an oxygen atom, and A represents a phenyl or pyridyl ring, and $R^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_3$-alkylamino, $C_1$-$C_3$-alkylcarbonylamino, $C_1$-$C_3$-alkylamino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_1$-$C_3$-alkylcarbonyl or $C_1$-$C_4$-alkoxycarbonyl radical, or represents a monocyclic heterocyclyl radical having 4 to 7 ring atoms, which may optionally be mono- or polysubstituted by identical or different substituents from the group consisting of halogen, cyano, nitro, hydroxy, amino, oxo, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, phenyl, halophenyl, phenyl-$C_1$-$C_3$-alkyl, pyridinyl, —NR$^6$C(=O)—R$^9$, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, hydroxy, amino, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical having 4 to 7 ring atoms, and/or by a monocyclic heteroaryl radical having 5 or 6 ring atoms, and/or by a phenyl radical which for its part may be mono- or polysubstituted by identical or different substituents from the group consisting of fluorine, chlorine, bromine, methyl and/or methoxy, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, —C(=O)NR$^6$R$^7$, C(=O) R$^8$, $C_1$-$C_3$-alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, fluoro-$C_1$-$C_3$-alkyl, fluoro-$C_1$-$C_3$-alkoxy, hydroxy-$C_1$-$C_3$-alkyl, $C_3$-$C_6$-cycloalkyl and/or a monocyclic heterocyclyl radical having 4 to 7 ring atoms, and/or a monocyclic heteroaryl radical having 5 or 6 ring atoms which for its part may optionally be mono- or polysubstituted by identical or different substituents from the group consisting of fluorine, chlorine, bromine, methyl and/or methoxy, and $R^{1b}$ represents hydrogen, halogen, hydroxy, cyano, nitro or represents a $C_1$-$C_3$-alkyl, $C_1$-$C_3$-alkoxy, fluoro-$C_1$-$C_3$-alkyl or fluoro-$C_1$-$C_3$-alkoxy radical, and $R^{1c}$ represents hydrogen, fluorine, chlorine, bromine or cyano, and $R^2$ represents methyl, ethyl or isopropyl, and $R^3$ represents cyclopropyl, $C_1$-$C_3$-alkyl, $C_1$-$C_3$-alkoxy, cyclopropylamino or $C_1$-$C_3$-alkylamino, and $R^4$ represents a $C_3$-$C_7$-cycloalkyl radical, which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical having 4 to 7 ring atoms, or represents monocyclic heteroaryl having 5 or 6 ring atoms, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O) R$^8$, —S(=O)$_2$R$^9$, —NR$^6$R$^7$, and/or a monocyclic heterocyclyl radical having 4 to 7 ring atoms, or represents monocyclic heterocyclyl having 4 to 7 ring atoms, which may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O) R$^8$, —S(=O)$_2$R$^9$, —NR$^6$R$^7$, and/or a monocyclic heterocyclyl radical having 4 to 7 ring atoms, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical having 4 to 7 ring atoms, and $R^5$ represents hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, and $R^6$ and $R^7$ independently of one another represent hydrogen, $C_1$-$C_3$-alkyl, cyclopropyl, di-$C_1$-$C_3$-alkylamino-$C_1$-$C_3$-alkyl or fluoropyridyl, and $R^8$ represents hydroxy, $C_1$-$C_6$-alkyl, hydroxy-$C_1$-$C_3$-alkyl, fluoro-$C_1$-$C_3$-alkyl, $C_1$-$C_3$-alkoxy-$C_1$-$C_3$-alkyl, $C_3$-$C_8$-cycloalkyl or monocyclic heterocyclyl which has 5 or 6 ring atoms, and $R^9$ represents hydrogen, $C_1$-$C_6$-alkyl or $C_1$-$C_4$-alkoxy, and their polymorphs, enantiomers, diastereomers, racemates, tautomers, solvates, physiologically acceptable salts and solvates of these salts.

Particular preference is further given to those compounds of the general formula (I) in which X represents an oxygen atom, and A represents a phenyl or pyridyl ring, and $R^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_3$-alkylamino, $C_1$-$C_3$-alkylcarbonylamino, $C_1$-$C_3$-alkylamino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_1$-$C_3$-alkylcarbonyl or $C_1$-$C_4$-alkoxycarbonyl radical, or represents a monocyclic heterocyclyl radical having 4 to 7 ring atoms, which may optionally be mono- or polysubstituted by identical or different substituents from the group consisting of halogen, cyano, nitro, hydroxy, amino, oxo, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, phenyl, halophenyl, phenyl-$C_1$-$C_3$-alkyl, pyridinyl, —NR$^6$C(=O)—R$^9$, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, hydroxy, amino, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical having 4 to 7 ring atoms, and/or by a monocyclic heteroaryl radical having 5 or 6 ring atoms, and/or by a phenyl radical which for its part may be mono- or polysubstituted by identical or different substituents from the group consisting of fluorine, chlorine, bromine, methyl and/or methoxy, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, —C(=O)NR$^6$R$^7$, —C(=O)R$^8$, $C_1$-$C_3$-alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, fluoro-$C_1$-$C_3$-alkyl, fluoro-$C_1$-$C_3$-alkoxy, hydroxy-$C_1$-$C_3$-alkyl, $C_3$-$C_6$-cycloalkyl and/or a monocyclic heterocyclyl radical having 4 to 7 ring atoms, and/or a monocyclic heteroaryl radical having 5 or 6 ring atoms which for its part may optionally be mono- or polysubstituted by identical or different substituents from the group consisting of fluorine, chlorine, bromine, methyl and/or methoxy, and $R^{1b}$ represents hydrogen, halogen, hydroxy, cyano, nitro or represents a $C_1$-$C_3$-alkyl, $C_1$-$C_3$-alkoxy, fluoro-$C_1$-$C_3$-alkyl or fluoro-$C_1$-$C_3$-alkoxy radical, and $R^{1c}$ represents hydrogen, fluorine, chlorine, bromine or cyano, and $R^2$ represents methyl, ethyl or isopropyl, and $R^3$ represents cyclopropyl, $C_1$-$C_3$-alkyl, $C_1$-$C_3$-alkoxy, cyclopropylamino or $C_1$-$C_3$-alkylamino, and $R^4$ represents hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, and $R^5$ represents a $C_3$-$C_7$-cycloalkyl radical, which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical having 4 to 7 ring atoms, or represents monocyclic heteroaryl having 5 or 6 ring atoms, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)R$^8$, —S(=O)$_2$R$^9$, —NR$^6$R$^7$, and/or a monocyclic heterocyclyl radical having 4 to 7 ring atoms, or represents monocyclic heterocyclyl having 4 to 7 ring atoms, which may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O)R$^8$, —S(=O)$_2$R$^9$, —NR$^6$R$^7$, and/or a monocyclic heterocyclyl radical having 4 to 7 ring atoms, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical having 4 to 7 ring atoms, and $R^6$ and $R^7$ independently of one another represent hydrogen, $C_1$-$C_3$-alkyl, cyclopropyl, di-$C_1$-$C_3$-alkylamino-$C_1$-$C_3$-alkyl or fluoropyridyl, and $R^8$ represents hydroxy, $C_1$-$C_6$-alkyl, hydroxy-$C_1$-$C_3$-alkyl, fluoro-$C_1$-$C_3$-alkyl, $C_1$-$C_3$-alkoxy-$C_1$-$C_3$-alkyl, $C_3$-$C_8$-cycloalkyl or monocyclic heterocyclyl which has 5 or 6 ring atoms, and $R^9$ represents hydrogen, $C_1$-$C_6$-alkyl or $C_1$-$C_4$-alkoxy, and their polymorphs, enantiomers, diastereomers, racemates, tautomers, solvates, physiologically acceptable salts and solvates of these salts.

Particular preference is further given to those compounds of the general formula (I) in which X represents an oxygen atom, and A represents a phenyl or 3-pyridyl ring, and $R^{1a}$ represents hydrogen or chlorine, or represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, chlorine, cyano, nitro, hydroxy, oxo, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, dimethylamino, trifluoromethyl, difluoroethyl, trifluoroethyl, trifluoromethoxy, cyclopropyl, phenyl, fluorophenyl, phenyl, $C_1$-$C_3$-alkyl, pyridinyl, —$NR^6C(=O)$—$R^9$, —$C(=O)$—$NR^6R^7$, —$C(=O)$—$R^8$, —$S(=O)_2$—$NR^6R^7$, —$S(=O)$—$R^9$, —$S(=O)_2$—$R^9$ and/or —NH—$S(=O)_2$—$R^9$, or represents tetrazolyl, or represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, amino, cyano, nitro, $C_1$-$C_3$-alkyl, $C_1$-$C_3$-alkoxy, $C_1$-$C_2$-alkoxy-$C_1$-$C_2$-alkyl, dimethylamino, trifluoromethyl, difluoroethyl, trifluoroethyl, trifluoromethoxy, cyclopropyl, pyridinyl, phenyl, fluorophenyl, —$C(=O)$—$NR^6R^7$, —$C(=O)$—$R^8$, —$S(=O)_2$—$NR^6R^7$, —$S(=O)$—$R^9$, —$S(=O)_2$—$R^9$ and/or —NH—$S(=O)_2$—$R^9$, or represents a phenyl radical, which may optionally be mono- or polysubstituted by identical or different substituents from the group consisting of fluorine, chlorine, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, dimethylamino, —$C(=O)NR^6R^7$, —$C(=O)R^8$, $C_1$-$C_3$-alkylsulphinyl, $C_1$-$C_3$-alkylsulphonyl, —$S(=O)_2NH_2$, $C_1$-$C_3$-alkylsulphonylamino, $C_1$-$C_3$-alkylaminosulphonyl, $C_3$-$C_6$-cycloalkylaminosulphonyl, trifluoromethyl, difluoroethyl, trifluoroethyl, trifluoromethoxy, hydroxy-$C_1$-$C_3$-alkyl, cyclopropyl, chlorothienyl, morpholino and/or pyridinyl, and $R^{1b}$ represents hydrogen, fluorine, bromine or cyano, $R^{1c}$ represents hydrogen or bromine, and $R^2$ represents methyl, ethyl or isopropyl, and $R^3$ represents cyclopropyl, methyl, ethyl, methoxy, ethoxy, cyclopropylamino, methylamino or ethylamino, and $R^4$ and $R^5$ independently of one another represent hydrogen, hydroxy, cyano, amino, chlorine, $C_1$-$C_6$-alkyl, methoxy, ethoxy or $C_1$-$C_3$-alkylcarbonylamino, or represent difluoromethoxy or trifluoromethoxy, or represent $C_1$-$C_3$-alkoxy, which may be substituted by pyridinyl, morpholinyl, pyrrolidinyl or piperazinyl, in which pyridinyl and piperazinyl in turn may be optionally substituted by $C_1$-$C_3$-alkyl, or represent cyclopropyl, or represent pyridinyl, pyrazolyl, triazolyl or isoxazolyl, which may be optionally mono- or polysubstituted by identical or different substituents from the group consisting of hydroxy and/or methyl, or represent pyrrolidinyl, morpholinyl, piperidinyl, piperazinyl, oxazolidinyl, thiomorpholinyl, which may optionally be mono- or polysubstituted by oxo, methyl and/or —$S(=O)_2R^9$, or represent phenyl optionally substituted by $C_1$-$C_3$-alkylaminosulphonyl or fluorine, and $R^6$ and $R^7$ independently of one another represent hydrogen, $C_1$-$C_3$-alkyl, cyclopropyl, di-$C_1$-$C_3$-alkylamino-$C_1$-$C_3$-alkyl or fluoropyridyl, and $R^8$ represents hydroxy, $C_1$-$C_3$-alkyl, hydroxy-$C_1$-$C_3$-alkyl, trifluoromethyl, pyrrolidinyl, morpholinyl or piperidinyl, and $R^9$ represents $C_1$-$C_4$-alkyl or $C_1$-$C_4$-alkoxy, and their polymorphs, enantiomers, diastereomers, racemates, tautomers, solvates, physiologically acceptable salts and solvates of these salts, with the proviso that, if A represents a phenyl ring and $R^4$ and $R^5$ independently of one another represent hydrogen, hydroxy, cyano, amino, chlorine, $C_1$-$C_6$-alkyl, methoxy, ethoxy or $C_1$-$C_3$-alkylcarbonylamino, or represent difluoromethoxy or trifluoromethoxy, or represent $C_1$-$C_3$-alkoxy, which may be substituted by pyridinyl, morpholinyl, pyrrolidinyl or piperazinyl, in which pyridinyl and piperazinyl in turn may be optionally substituted by $C_1$-$C_3$-alkyl, $R^{1a}$ does not represent hydrogen or chlorine.

The proviso, however, does not encompass those compounds of the general formula (I) in which A is phenyl and $R^4$ represents hydrogen or chlorine and $R^5$ represents trifluoromethoxy, and $R^{1a}$ represents chlorine, and also not those compounds of the general formula (I) in which A is phenyl and $R^4$ represents hydrogen and $R^5$ represents $C_1$-$C_3$-alkoxy, which is substituted by morpholinyl, pyrrolidinyl, piperazinyl or pyridyl, in which the piperazinyl and pyridinyl itself may be substituted by $C_1$-$C_3$-alkyl, and $R^{1a}$ represents chlorine.

The present invention therefore also, for example, encompasses compounds of the prepared working examples No. 1; 15; 32; 33; 164; 164.2; 165; 166 and 167.

Of very particular interest, furthermore, are those compounds of the general formula (I) in which X represents an oxygen atom, and A represents a phenyl or 3-pyridyl ring, and $R^{1a}$ represents hydrogen or chlorine, or represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, hydroxy, oxo, $C_1$-$C_3$-alkyl, methoxy, hydroxy-$C_1$-$C_3$-alkyl, dimethylamino, difluoroethyl, trifluoroethyl, benzyl, —$NR^6C(=O)$—$R^9$, —$C(=O)$—$NR^6R^7$, —$C(=O)$—$R^8$, and/or —$S(=O)_2$—$R^9$, or represents tetrazolyl, or represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, cyano, $C_1$-$C_2$-alkyl, methoxy, methoxymethyl, trifluoromethyl, cyclopropyl, pyridinyl, phenyl, fluorophenyl and/or —$C(=O)$—$R^8$, or represents a phenyl radical, which may optionally be mono- or polysubstituted by identical or different substituents from the group consisting of fluorine, chlorine, hydroxy, cyano, nitro, carboxyl, $C_1$-$C_3$-alkyl, methoxy, —$C(=O)NR^6R^7$, —$C(=O)$ $R^8$, $C_1$-$C_3$-alkylsulphinyl, $C_1$-$C_3$-alkylsulphonyl, —$S(=O)_2NH_2$, $C_1$-$C_3$-alkylsulphonylamino, $C_1$-$C_3$-alkylaminosulphonyl, $C_3$-$C_6$-cycloalkylaminosulphonyl, trifluoromethyl, trifluoromethoxy, hydroxy-$C_1$-$C_3$-alkyl, cyclopropyl, chlorothienyl and/or morpholino, and $R^{1b}$ represents hydrogen, fluorine, bromine or cyano, and $R^{1c}$ represents hydrogen or bromine, and $R^2$ represents methyl, ethyl or isopropyl, and $R^3$ represents cyclopropyl, methyl, ethyl, methoxy, ethoxy, cyclopropylamino, methylamino or ethylamino, and $R^4$ and $R^5$ independently of one another represent hydrogen, hydroxy, cyano, amino, chlorine, $C_1$-$C_6$-alkyl, methoxy, ethoxy or $C_1$-$C_3$-alkylcarbonylamino, or represent difluoromethoxy or trifluoromethoxy, or represent $C_1$-$C_3$-alkoxy, which may be substituted by pyridinyl, morpholinyl, pyrrolidinyl or piperazinyl, in which pyridinyl and piperazinyl in turn may be optionally substituted by $C_1$-$C_3$-alkyl, or represent cyclopropyl, or represent pyridinyl, pyrazolyl, triazolyl or isoxazolyl, optionally mono- or polysubstituted by identical or different substituents from the group consisting of hydroxy and/or methyl, or represent pyrrolidinyl, morpholinyl, piperidinyl, piperazinyl, oxazolidinyl, thiomorpholinyl, which may optionally be mono- or polysubstituted by methyl, oxo and/or —$S(=O)_2R^9$, or represent phenyl optionally substituted by $C_1$-$C_3$-alkylaminosulphonyl or fluorine, and $R^6$ and $R^7$ independently of one another represent hydrogen, $C_1$-$C_3$-alkyl, cyclopropyl, di-$C_1$-$C_3$-alkylamino-$C_1$-$C_3$-alkyl or fluoropyridyl, and $R^8$ represents hydroxy, $C_1$-$C_3$-alkyl, hydroxy-$C_1$-$C_3$-alkyl, trifluoromethyl, pyrrolidinyl, morpholinyl or piperidinyl, and $R^9$ represents $C_1$-$C_4$-alkyl or $C_1$-$C_4$-alkoxy, and their polymorphs, enantiomers, diastereomers, racemates, tautomers, solvates, physiologically acceptable salts and solvates of these salts, with the proviso that, if A represents a phenyl ring and $R^4$ and $R^5$ independently of one another represent hydrogen, hydroxy, cyano, amino, chlorine, $C_1$-$C_6$-alkyl, methoxy, ethoxy or $C_1$-$C_3$-alkylcarbonylamino, or represent difluoromethoxy or trifluoromethoxy, or represent $C_1$-$C_3$-alkoxy, which may be substituted by pyridinyl, morpholinyl, pyrrolidinyl or piperazinyl, in which pyridinyl and piperazinyl in turn may be optionally substituted by $C_1$-$C_3$-alkyl, $R^{1a}$ does not represent hydrogen or chlorine.

The proviso, however, does not encompass those compounds of the general formula (I) in which A is phenyl and $R^4$ represents hydrogen or chlorine and $R^5$ represents trifluoromethoxy, and $R^{1a}$ represents chlorine, and also not those compounds of the general formula (I) in which A is phenyl and $R^4$ represents hydrogen and $R^5$ represents $C_1$-$C_3$-alkoxy, which is substituted by morpholinyl, pyrrolidinyl, piperazinyl or pyridyl, in which the piperazinyl and pyridinyl itself may be substituted by $C_1$-$C_3$-alkyl, and $R^{1a}$ represents chlorine.

The present invention therefore also, for example, encompasses compounds of the prepared working examples No. 1; 15; 32; 33; 164; 164.2; 165; 166 and 167.

Of exceptional interest are those compounds of the general formula (I) in which

X represents an oxygen atom, and

A represents a phenyl ring, and $R^{1a}$ represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, hydroxy, oxo, $C_1$-$C_3$-alkyl, methoxy, hydroxy-$C_1$-$C_3$-alkyl, dimethylamino, difluoroethyl, trifluoroethyl, benzyl, —$NR^6C(=O)$—$R^9$, —$C(=O)$—$NR^6R^7$, —$C(=O)$—$R^8$, and/or —$S(=O)_2$—$R^9$, or represents tetrazolyl, or represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, cyano, $C_1$-$C_2$-alkyl, methoxy, methoxymethyl, trifluoromethyl, cyclopropyl, pyridinyl, phenyl, fluorophenyl and/or —$C(=O)$—$R^8$, or represents a phenyl radical, which may optionally be mono- or polysubstituted by identical or different substituents from the group consisting of fluorine, chlorine, hydroxy, cyano, nitro, carboxyl, $C_1$-$C_3$-alkyl, methoxy, —$C(=O)NR^6R^7$, $C(=O)$ $R^8$, $C_1$-$C_3$-alkylsulphinyl, $C_1$-$C_3$-alkylsulphonyl, —$S(=O)_2NH_2$, $C_1$-$C_3$-alkylsulphonylamino, $C_1$-$C_3$-alkylaminosulphonyl, $C_3$-$C_6$-cycloalkylaminosulphonyl, trifluoromethyl, trifluoromethoxy, hydroxy-$C_1$-$C_3$-alkyl, cyclopropyl, chlorothienyl and/or morpholino, $R^{1b}$ represents hydrogen, fluorine, bromine or cyano, and
$R^{1c}$ represents hydrogen, and
$R^2$ represents methyl or ethyl, and
$R^3$ represents methylamino, and
$R^4$ and $R^5$ independently of one another represent hydrogen, hydroxy, cyano, chlorine, $C_1$-$C_6$-alkyl, methoxy, ethoxy or $C_1$-$C_3$-alkylcarbonylamino,
or
represent difluoromethoxy or trifluoromethoxy, and
$R^6$ and $R^7$ independently of one another represent hydrogen, $C_1$-$C_3$-alkyl, cyclopropyl or di-$C_1$-$C_3$-alkylamino-$C_1$-$C_3$-alkyl, and
$R^8$ represents hydroxy, $C_1$-$C_3$-alkyl, hydroxy-$C_1$-$C_3$-alkyl, trifluoromethyl, pyrrolidinyl, morpholinyl or piperidinyl, and
$R^9$ represents $C_1$-$C_4$-alkyl or $C_1$-$C_4$-alkoxy,
and their polymorphs, tautomers, solvates, physiologically acceptable salts and solvates of these salts, and
where the stereocentre, which is represented by the carbon atom of the benzodiazepine skeleton which is bound to $R^2$, is present either in racemic form or predominantly or completely in the (S) configuration.

Of exceptional interest, furthermore, are those compounds of the general formula (I) in which
X represents an oxygen atom, and
A represents a phenyl ring, and
$R^{1a}$ represents hydrogen or chlorine, and
$R^{1b}$ represents hydrogen, fluorine, bromine or cyano, and
$R^{1c}$ represents hydrogen, and
$R^2$ represents methyl or ethyl, and
$R^3$ represents methylamino, and
$R^4$ represents cyclopropyl,
or
represents pyridinyl, pyrazolyl, triazolyl or isoxazolyl, which may optionally be mono- or polysubstituted by identical or different substituents from the group consisting of hydroxy and/or methyl,
or
represents pyrrolidinyl, morpholinyl, piperidinyl, piperazinyl, oxazolidinyl or thiomorpholinyl, which may optionally be mono- or polysubstituted by methyl, oxo and/or —S(=O)$_2$R$^9$,
or
represents phenyl optionally substituted by $C_1$-$C_3$-alkylaminosulphonyl or fluorine, and
$R^5$ represents hydrogen, hydroxy, cyano, chlorine, $C_1$-$C_6$-alkyl, methoxy, ethoxy or $C_1$-$C_3$-alkylcarbonylamino,
or
represents difluoromethoxy or trifluoromethoxy, and
$R^6$ and $R^7$ independently of one another represent hydrogen, $C_1$-$C_3$-alkyl, cyclopropyl or di-$C_1$-$C_3$-alkylamino-$C_1$-$C_3$-alkyl, and
$R^8$ represents hydroxy, $C_1$-$C_3$-alkyl, hydroxy-$C_1$-$C_3$-alkyl, trifluoromethyl, pyrrolidinyl, morpholinyl or piperidinyl, and
$R^9$ represents $C_1$-$C_4$-alkyl or $C_1$-$C_4$-alkoxy,
and their polymorphs, tautomers, solvates, physiologically acceptable salts and solvates of these salts, and
where the stereocentre, which is represented by the carbon atom of the benzodiazepine skeleton which is bound to $R^2$, is present either in racemic form or predominantly or completely in the (S) configuration.

Of exceptional interest, furthermore, are those compounds of the general formula (I) in which
X represents an oxygen atom, and
A represents a phenyl ring, and
$R^{1a}$ represents hydrogen or chlorine, and
$R^{1b}$ represents hydrogen, fluorine, bromine or cyano, and
$R^{1c}$ represents hydrogen, and
$R^2$ represents methyl or ethyl, and
$R^3$ represents methylamino, and
$R^4$ represents hydrogen, chlorine, methoxy or ethoxy,
or
represents difluoromethoxy or trifluoromethoxy, and
$R^5$ represents cyclopropyl,
or
represents pyridinyl or pyrazolyl, which may optionally be substituted one or more times by methyl,
or
represents morpholinyl, piperidinyl, piperazinyl or thiomorpholinyl, which may optionally be mono- or polysubstituted by methyl, oxo and/or —S(=O)$_2$R$^9$,
or
represents phenyl which is substituted by $C_1$-$C_3$-alkylaminosulphonyl, and
$R^6$ and $R^7$ independently of one another represent hydrogen, $C_1$-$C_3$-alkyl, cyclopropyl or di-$C_1$-$C_3$-alkylamino-$C_1$-$C_3$-alkyl, and
$R^8$ represents hydroxy, $C_1$-$C_3$-alkyl, hydroxy-$C_1$-$C_3$-alkyl, trifluoromethyl, pyrrolidinyl, morpholinyl or piperidinyl, and
$R^9$ represents $C_1$-$C_4$-alkyl or $C_1$-$C_4$-alkoxy,
and their polymorphs, tautomers, solvates, physiologically acceptable salts and solvates of these salts, and
where the stereocentre, which is represented by the carbon atom of the benzodiazepine skeleton which is bound to $R^2$, is present either in racemic form or predominantly or completely in the (S) configuration.

Of exceptional interest, furthermore, are those compounds of the general formula (I) in which
X represents an oxygen atom, and
A represents a phenyl ring, and
$R^{1a}$ represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, hydroxy, oxo, $C_1$-$C_3$-alkyl, methoxy, hydroxy-$C_1$-$C_3$-alkyl, dimethylamino, difluoroethyl, trifluoroethyl, benzyl, —NR$^6$C(=O)—R$^9$, —C(=O)—NR$^6$R$^7$, —C(=O)—R$^8$ and/or —S(=O)$_2$—R$^9$,
or
represents isoxazolyl or pyrazolyl, which may optionally be substituted one or more times by identical or different $C_1$-$C_2$-alkyls, and
$R^{1b}$ represents hydrogen, fluorine, bromine or cyano, and
$R^{1c}$ represents hydrogen, and
$R^2$ represents methyl, and
$R^3$ represents methylamino, and
$R^4$ and $R^5$ independently of one another represent hydrogen, hydroxy, cyano, chlorine, $C_1$-$C_6$-alkyl, methoxy, ethoxy or $C_1$-$C_3$-alkylcarbonylamino,
or
represent difluoromethoxy or trifluoromethoxy, and
$R^6$ and $R^7$ independently of one another represent hydrogen, $C_1$-$C_3$-alkyl, cyclopropyl or di-$C_1$-$C_3$-alkylamino-$C_1$-$C_3$-alkyl, and
$R^8$ represents hydroxy, $C_1$-$C_3$-alkyl, hydroxy-$C_1$-$C_3$-alkyl, trifluoromethyl, pyrrolidinyl, morpholinyl or piperidinyl, and
$R^9$ represents $C_1$-$C_4$-alkyl or $C_1$-$C_4$-alkoxy,
and their polymorphs, tautomers, solvates, physiologically acceptable salts and solvates of these salts, and where the stereocentre, which is represented by the carbon atom of the benzodiazepine skeleton which is bound to $R^2$, is present either in racemic form or predominantly or completely in the (S) configuration.

Of exceptional interest, furthermore, are those compounds of the general formula (I) in which X represents an oxygen atom, and A represents a phenyl ring, and $R^{1a}$ represents piperazinyl, pyrrolidinyl, piperidinyl, morpholinyl, thiomorpholinyl or azetidinyl, which may optionally be mono- or polysubstituted by identical or different substituents from the group consisting of hydroxy, oxo, $C_1$-$C_3$-alkyl, methoxy, dimethylamino, difluoroethyl, trifluoroethyl, —$NR^6C(=O)$—$R^9$, —$C(=O)$—$NR^6R^7$ and/or —$C(=O)$—$R^8$, and $R^{1b}$ represents hydrogen, fluorine, bromine or cyano, and $R^{1c}$ represents hydrogen, and $R^2$ represents methyl, and $R^3$ represents methylamino, and $R^4$ and $R^5$ independently of one another represent hydrogen, chlorine, methoxy or ethoxy, or represent difluoromethoxy or trifluoromethoxy, and $R^6$ and $R^7$ independently of one another represent hydrogen or $C_1$-$C_3$-alkyl, and $R^8$ represents methyl, and $R^9$ represents methyl, and their polymorphs, tautomers, solvates, physiologically acceptable salts and solvates of these salts, and where the stereocentre, which is represented by the carbon atom of the benzodiazepine skeleton which is bound to $R^2$, is present either in racemic form or predominantly or completely in the (S) configuration.

Most preference is given to the following compounds:

(±)-1-(4-chlorophenyl)-N,4-dimethyl-8-(trifluoromethoxy)-4,5-dihydro-3H-2,3-benzodiazepine-3-carboxamide (4S)-1-(4-chlorophenyl)-N,4-dimethyl-8-(trifluoromethoxy)-4,5-dihydro-3H-2,3-benzodiazepine-3-carboxamide (4R)-1-(4-chlorophenyl)-N,4-dimethyl-8-(trifluoromethoxy)-4,5-dihydro-3H-2,3-benzodiazepine-3-carboxamide (±)-1-[4-(3,5-dimethyl-4-isoxazolyl)phenyl]-7,8-dimethoxy-N,4-dimethyl-4,5-dihydro-3H-2,3-benzodiazepine-3-carboxamide (4R)-1-[4-(3,5-dimethyl-4-isoxazolyl)phenyl]-7,8-dimethoxy-N,4-dimethyl-4,5-dihydro-3H-2,3-benzodiazepine-3-carboxamide (4S)-1-[4-(3,5-dimethyl-4-isoxazolyl)phenyl]-7,8-dimethoxy-N,4-dimethyl-4,5-dihydro-3H-2,3-benzodiazepine-3-carboxamide (±)-7,8-dimethoxy-N,4-dimethyl-1-[4-(1H-pyrazol-3-yl)phenyl]-4,5-dihydro-3H-2,3-benzodiazepine-3-carboxamide (±)-1-[4-(2-chloropyridin-3-yl)phenyl]-7,8-dimethoxy-N,4-dimethyl-4,5-dihydro-3H-2,3-benzodiazepine-3-carboxamide (±)-5-(4-{7,8-dimethoxy-4-methyl-3-[(methylamino)carbonyl]-4,5-dihydro-3H-2,3-benzodiazepin-1-yl}phenyl)thiophene-2-carboxylic acid (±)-4'-{7,8-dimethoxy-4-methyl-3-[(methylamino)carbonyl]-4,5-dihydro-3H-2,3-benzodiazepin-1-yl}biphenyl-2-carboxylic acid (±)-7,8-dimethoxy-N,4-dimethyl-1-[4-(morpholin-4-yl)phenyl]-4,5-dihydro-3H-2,3-benzodiazepine-3-carboxamide (±)-1-(4-chlorophenyl)-N,4-dimethyl-8-(pyridin-4-yl)-4,5-dihydro-3H-2,3-benzodiazepine-3-carboxamide (±)-1-(4-chlorophenyl)-8-cyclopropyl-N,4-dimethyl-4,5-dihydro-3H-2,3-benzodiazepine-3-carboxamide (±)-1-(4-chlorophenyl)-N,4-dimethyl-8-{4-[(methylamino)sulphonyl]phenyl}-4,5-dihydro-3H-2,3-benzodiazepine-3-carboxamide (±)-1-(4-chlorophenyl)-N,4-dimethyl-8-(morpholin-4-yl)-4,5-dihydro-3H-2,3-benzodiazepine-3-carboxamide (4S)-1-(4-chlorophenyl)-N,4-dimethyl-8-(morpholin-4-yl)-4,5-dihydro-3H-2,3-benzodiazepine-3-carboxamide (4R)-1-(4-chlorophenyl)-N,4-dimethyl-8-(morpholin-4-yl)-4,5-dihydro-3H-2,3-benzodiazepine-3-carboxamide (±)-1-(4-chlorophenyl)-N,4-dimethyl-8-(4-methylpiperazin-1-yl)-4,5-dihydro-3H-2,3-benzodiazepine-3-carboxamide (±)-1-(4-chlorophenyl)-N,4-dimethyl-8-(piperidin-1-yl)-4,5-dihydro-3H-2,3-benzodiazepine-3-carboxamide (±)-8-methoxy-N,4-dimethyl-1-(pyridin-3-yl)-4,5-dihydro-3H-2,3-benzodiazepine-3-carboxamide (±)-7-chloro-1-(4-chlorophenyl)-N,4-dimethyl-8-(trifluoromethoxy)-4,5-dihydro-3H-2,3-benzodiazepine-3-carboxamide 7-chloro-1-(4-chlorophenyl)-N,4-dimethyl-8-(trifluoromethoxy)-4,5-dihydro-3H-2,3-benzodiazepine-3-carboxamide, enantiomer 1

(4S)-1-[4-(3,5-dimethyl-1H-pyrazol-1-yl)phenyl]-8-methoxy-N,4-dimethyl-4,5-dihydro-3H-2,3-benzodiazepine-3-carboxamide (4S)-8-methoxy-N,4-dimethyl-1-[4-(morpholin-4-yl)phenyl]-4,5-dihydro-3H-2,3-benzodiazepine-3-carboxamide (4S)-1-[4-(4-isoxazolyl)phenyl]-8-methoxy-N,4-dimethyl-4,5-dihydro-3H-2,3-benzodiazepine-3-carboxamide (4S)-8-methoxy-N,4-dimethyl-1-[4-(1-methyl-1H-pyrazol-5-yl)phenyl]-4,5-dihydro-3H-2,3-benzodiazepine-3-carboxamide (4S)-1-[4-(3,5-dimethyl-4-isoxazolyl)phenyl]-8-methoxy-N,4-dimethyl-4,5-dihydro-3H-2,3-benzodiazepine-3-carboxamide (4S)-8-methoxy-N,4-dimethyl-1-[4-(1-methyl-1H-pyrazol-4-yl)phenyl]-4,5-dihydro-3H-2,3-benzodiazepine-3-carboxamide (4S)-8-methoxy-N,4-dimethyl-1-[4-(1,3,5-trimethyl-1H-pyrazol-4-yl)phenyl]-4,5-dihydro-3H-2,3-benzodiazepine-3-carboxamide (4S)-8-methoxy-N,4-dimethyl-1-[4-(1H-pyrazol-5-yl)phenyl]-4,5-dihydro-3H-2,3-benzodiazepine-3-carboxamide (4S)-1-[4-(3-cyclopropyl-5-ethyl-1H-pyrazol-1-yl)phenyl]-8-methoxy-N,4-dimethyl-4,5-dihydro-3H-2,3-benzodiazepine-3-carboxamide (4S)-1-[4-(5-cyclopropyl-3-ethyl-1H-pyrazol-1-yl)phenyl]-8-methoxy-N,4-dimethyl-4,5-dihydro-3H-2,3-benzodiazepine-3-carboxamide (4S)-8-methoxy-1-{4-[3-(methoxymethyl)-5-methyl-1H-pyrazol-1-yl]phenyl}-N,4-dimethyl-4,5-dihydro-3H-2,3-benzodiazepine-3-carboxamide (4S)-8-methoxy-1-{4-[5-(methoxymethyl)-3-methyl-1H-pyrazol-1-yl]phenyl}-N,4-dimethyl-4,5-dihydro-3H-2,3-benzodiazepine-3-carboxamide (4S)-1-{4-[5-cyclopropyl-3-(pyridin-2-yl)-1H-pyrazol-1-yl]phenyl}-8-methoxy-N,4-dimethyl-4,5-dihydro-3H-2,3-benzodiazepine-3-carboxamide (4S)-1-{4-[3-cyclopropyl-5-(pyridin-2-yl)-1H-pyrazol-1-yl]phenyl}-8-methoxy-N,4-dimethyl-4,5-dihydro-3H-2,3-benzodiazepine-3-carboxamide (4S)-8-methoxy-N,4-dimethyl-1-[4-(1H-tetrazol-1-yl)phenyl]-4,5-dihydro-3H-2,3-benzodiazepine-3-carboxamide (±)-1-[3-(3,5-dimethylisoxazol-4-yl)phenyl]-7,8-dimethoxy-N,4-dimethyl-4,5-dihydro-3H-2,3-benzodiazepine-3-carboxamide (±)-1-(4-chlorophenyl)-N,4-dimethyl-8-[2-(morpholin-4-yl)ethoxy]-4,5-dihydro-3H-2,3-benzodiazepine-3-carboxamide (±)-1-(4-chlorophenyl)-N,4-dimethyl-8-[2-(pyrrolidin-1-yl)ethoxy]-4,5-dihydro-3H-2,3-benzodiazepine-3-carboxamide (±)-7,8-dimethoxy-N,4-dimethyl-1-[4-(2-oxooxazolidin-3-yl)phenyl]-4,5-dihydro-3H-2,3-benzodiazepine-3-carboxamide (4S)-7,8-dimethoxy-N,4-dimethyl-1-[4-(2-oxooxazolidin-3-yl)phenyl]-4,5-dihydro-3H-2,3-benzodiazepine-3-carboxamide (±)-7,8-dimethoxy-N,4-dimethyl-1-[4-(2-oxopiperidin-1-yl)phenyl]-4,5-dihydro-3H-2,3-benzodiazepine-3-carboxamide (±)-1-[4-(4-benzyl-2-oxopiperazin-1-yl)phenyl]-7,8-dimethoxy-N,4-dimethyl-4,5-dihydro-3H-2,3-benzodiazepine-3-carboxamide (±)-7,8-dimethoxy-N,4-dimethyl-1-[4-(4-methyl-2-oxo-1,4-diazepan-1-yl)phenyl]-4,5-dihydro-3H-2,3-benzodiazepine-3-carboxamide (±)-7,8-dimethoxy-N,4-dimethyl-1-[4-(2-oxo-1,3-oxazinan-3-yl)phenyl]-4,5-dihydro-3H-2,3-benzodiazepine-3-carboxamide (±)-7,8-dimethoxy-N,4-dimethyl-1-[4-(2-oxopyrrolidin-1-yl)phenyl]-4,5-dihydro-3H-2,3-benzodiazepine-3-carboxamide (±)-7,8-dimethoxy-N,4-dimethyl-1-[4-(3-oxomorpholin-4-yl)phenyl]-4,5-dihydro-3H-2,3-benzodiazepine-3-carboxamide (4S)-7,8-dimethoxy-N,4-dimethyl-1-[4-(3-oxomorpholin-4-yl)phenyl]-4,5-dihydro-3H-2,3-benzodiazepine-3-carboxamide (±)-7,8-dimethoxy-N,4-dimethyl-1-[4-(2-methyl-5-oxomorpholin-4-yl)phenyl]-4,5-dihydro-3H-2,3-benzodiazepine-3-carboxamide (stereoisomer mixture)

(±)-7,8-dimethoxy-N,4-dimethyl-1-[4-(2-methyl-3-oxomorpholin-4-yl)phenyl]-4,5-dihydro-3H-2,3-benzodiazepine-3-carboxamide (stereoisomer mixture)

(±)-7,8-dimethoxy-N,4-dimethyl-1-[4-(4-methyl-2-oxopiperazin-1-yl)phenyl]-4,5-dihydro-3H-2,3-benzodiazepine-3-carboxamide (4S)-7,8-dimethoxy-N,4-dimethyl-1-[4-(4-methyl-2-oxopiperazin-1-yl)phenyl]-4,5-dihydro-3H-2,3-benzodiazepine-3-carboxamide (4R)-7,8-dimethoxy-N,4-dimethyl-1-[4-(4-methyl-2-oxopiperazin-1-yl)phenyl]-4,5-dihydro-3H-2,3-benzodiazepine-3-carboxamide (±)-7,8-dimethoxy-N,4-dimethyl-1-[4-(2-oxopiperazin-1-yl)phenyl]-4,5-dihydro-3H-2,3-benzodiazepine-3-carboxamide (±)-7,8-dimethoxy-N,4-dimethyl-1-[4-(1-methyl-1H-1,2,3-triazol-4-yl)phenyl]-4,5-dihydro-3H-2,3-benzodiazepine-3-carboxamide (4S)-7,8-dimethoxy-N,4-dimethyl-1-[4-(1-methyl-1H-1,2,3-triazol-4-yl)phenyl]-4,5-dihydro-3H-2,3-benzodiazepine-3-carboxamide (±)-1-[4-(2,4-dimethylthiazol-5-yl)phenyl]-7,8-dimethoxy-N,4-dimethyl-4,5-dihydro-3H-2,3-benzodiazepine-3-carboxamide (4S)-1-[4-(2,4-dimethylthiazol-5-yl)phenyl]-7,8-dimethoxy-N,4-dimethyl-4,5-dihydro-3H-2,3-benzodiazepine-3-carboxamide (4R)-1-[4-(2,4-dimethylthiazol-5-yl)phenyl]-7,8-dimethoxy-N,4-dimethyl-4,5-dihydro-3H-2,3-benzodiazepine-3-carboxamide (±)-1-[4-(1,2-dimethyl-1H-imidazol-5-yl)phenyl]-7,8-dimethoxy-N,4-dimethyl-4,5-dihydro-3H-2,3-benzodiazepine-3-carboxamide (±)-7,8-dimethoxy-N,4-dimethyl-1-{4-[2-(trifluoromethyl)pyridin-3-yl]phenyl}-4,5-dihydro-3H-2,3-benzodiazepine-3-carboxamide (±)-1-[4-(6-hydroxypyridin-3-yl)phenyl]-7,8-dimethoxy-N,4-dimethyl-4,5-dihydro-3H-2,3-benzodiazepine-3-carboxamide (4S)-1-[4-(6-hydroxypyridin-3-yl)phenyl]-7,8-dimethoxy-N,4-dimethyl-4,5-dihydro-3H-2,3-benzodiazepine-3-carboxamide (±)-7,8-dimethoxy-N,4-dimethyl-1-{4-[6-(trifluoromethyl)pyridin-3-yl]phenyl}-4,5-dihydro-3H-2,3-benzodiazepine-3-carboxamide (±)-7,8-dimethoxy-N,4-dimethyl-1-[4-(1,3,5-trimethyl-1H-pyrazol-4-yl)phenyl]-4,5-dihydro-3H-2,3-benzodiazepine-3-carboxamide (4R)-7,8-dimethoxy-N,4-dimethyl-1-[4-(1,3,5-trimethyl-1H-pyrazol-4-yl)phenyl]-4,5-dihydro-3H-2,3-benzodiazepine-3-carboxamide (4S)-7,8-dimethoxy-N,4-dimethyl-1-[4-(1,3,5-trimethyl-1H-pyrazol-4-yl)phenyl]-4,5-dihydro-3H-2,3-benzodiazepine-3-carboxamide (±)-1-[4-(isoxazol-4-yl)phenyl]-7,8-dimethoxy-N,4-dimethyl-4,5-dihydro-3H-2,3-benzodiazepine-3-carboxamide (±)-7,8-dimethoxy-N,4-dimethyl-1-[3-(1,3,5-trimethyl-1H-pyrazol-4-yl)phenyl]-4,5-dihydro-3H-2,3-benzodiazepine-3-carboxamide (±)-7,8-dimethoxy-N,4-dimethyl-1-[3-(1-methyl-1H-pyrazol-4-yl)phenyl]-4,5-dihydro-3H-2,3-benzodiazepine-3-carboxamide (±)-7,8-dimethoxy-N,4-dimethyl-1-[3-(1-methyl-1H-pyrazol-5-yl)phenyl]-4,5-dihydro-3H-2,3-benzodiazepine-3-carboxamide (±)-1-[4-fluoro-3-(1,3,5-trimethyl-1H-pyrazol-4-yl)phenyl]-7,8-dimethoxy-N,4-dimethyl-4,5-dihydro-3H-2,3-benzodiazepine-3-carboxamide (±)-1-[4-fluoro-3-(1-methyl-1H-pyrazol-4-yl)phenyl]-7,8-dimethoxy-N,4-dimethyl-4,5-dihydro-3H-2,3-benzodiazepine-3-carboxamide (±)-1-[3-(3,5-dimethylisoxazol-4-yl)-4-fluorophenyl]-7,8-dimethoxy-N,4-dimethyl-4,5-dihydro-3H-2,3-benzodiazepine-3-carboxamide (±)-7,8-dimethoxy-N,4-dimethyl-1-(3'-nitrobiphenyl-4-yl)-4,5-dihydro-3H-2,3-benzodiazepine-3-carboxamide (±)-1-(biphenyl-4-yl)-7,8-dimethoxy-N,4-dimethyl-4,5-dihydro-3H-2,3-benzodiazepine-3-carboxamide (±)-1-(2',4'-dichlorobiphenyl-4-yl)-7,8-dimethoxy-N,4-dimethyl-4,5-dihydro-3H-2,3-benzodiazepine-3-carboxamide (±)-1-(4'-fluorobiphenyl-4-yl)-7,8-dimethoxy-N,4-dimethyl-4,5-dihydro-3H-2,3-benzodiazepine-3-carboxamide (±)-1-(4'-chlorobiphenyl-4-yl)-7,8-dimethoxy-N,4-dimethyl-4,5-dihydro-3H-2,3-benzodiazepine-3-carboxamide (±)-7,8-dimethoxy-N,4-dimethyl-1-(4'-methylbiphenyl-4-yl)-4,5-dihydro-3H-2,3-benzodiazepine-3-carboxamide (±)-7,8-dimethoxy-1-(4'-methoxybiphenyl-4-yl)-N,4-dimethyl-4,5-dihydro-3H-2,3-benzodiazepine-3-carboxamide (±)-7,8-dimethoxy-1-[4-(6-methoxypyridin-3-yl)phenyl]-N,4-dimethyl-4,5-dihydro-3H-2,3-benzodiazepine-3-carboxamide (±)-7,8-dimethoxy-N,4-dimethyl-1-[4'-(methylsulphinyl)biphenyl-4-yl]-4,5-dihydro-3H-2,3-benzodiazepine-3-carboxamide (±)-7,8-dimethoxy-N,4-dimethyl-1-{2'-[(methylsulphonyl)amino]biphenyl-4-yl}-4,5-dihydro-3H-2,3-benzodiazepine-3-carboxamide (±)-7,8-dimethoxy-N,4-dimethyl-1-[2'-(methylsulphonyl)biphenyl-4-yl]-4,5-dihydro-3H-2,3-benzodiazepine-3-carboxamide (±)-7,8-dimethoxy-N,4-dimethyl-1-{4'-[(methylsulphonyl)amino]biphenyl-4-yl}-4,5-dihydro-3H-2,3-benzodiazepine-3-carboxamide (±)-7,8-dimethoxy-N,4-dimethyl-1-{3'-[(methylsulphonyl)amino]biphenyl-4-yl}-4,5-dihydro-3H-2,3-benzodiazepine-3-carboxamide (±)-7,8-dimethoxy-N,4-dimethyl-1-(2'-methylbiphenyl-4-yl)-4,5-dihydro-3H-2,3-benzodiazepine-3-carboxamide (±)-7,8-dimethoxy-N,4-dimethyl-1-[3'-(methylsulphonyl)biphenyl-4-yl]-4,5-dihydro-3H-2,3-benzodiazepine-3-carboxamide (±)-7,8-dimethoxy-1-[4-(2-methoxypyrimidin-5-yl)phenyl]-N,4-dimethyl-4,5-dihydro-3H-2,3-benzodiazepine-3-carboxamide (±)-1-(3'-cyano-4'-fluorobiphenyl-4-yl)-7,8-dimethoxy-N,4-dimethyl-4,5-dihydro-3H-2,3-benzodiazepine-3-carboxamide (±)-7,8-dimethoxy-1-[4-(2-methoxypyridin-3-yl)phenyl]-N,4-dimethyl-4,5-dihydro-3H-2,3-benzodiazepine-3-carboxamide (±)-1-(3'-carbamoylbiphenyl-4-yl)-7,8-dimethoxy-N,4-dimethyl-4,5-dihydro-3H-2,3-benzodiazepine-3-carboxamide (±)-7,8-dimethoxy-N,4-dimethyl-1-[4'-(pyrrolidin-1-ylcarbonyl)biphenyl-4-yl]-4,5-dihydro-3H-2,3-benzodiazepine-3-carboxamide (±)-7,8-dimethoxy-N,4-dimethyl-1-[4'-(morpholin-4-ylcarbonyl)biphenyl-4-yl]-4,5-dihydro-3H-2,3-benzodiazepine-3-carboxamide (±)-7,8-dimethoxy-1-[4-(5-methoxypyridin-3-yl)phenyl]-N,4-dimethyl-4,5-dihydro-3H-2,3-benzodiazepine-3-carboxamide (±)-7,8-dimethoxy-N,4-dimethyl-1-[4-(5-methylpyridin-3-yl)phenyl]-4,5-dihydro-3H-2,3-benzodiazepine-3-carboxamide (±)-7,8-dimethoxy-N,4-dimethyl-1-[4-(4-methylpyridin-3-yl)phenyl]-4,5-dihydro-3H-2,3-benzodiazepine-3-carboxamide (±)-1-[4'-(cyclopropylcarbamoyl)biphenyl-4-yl]-7,8-dimethoxy-N,4-dimethyl-4,5-dihydro-3H-2,3-benzodiazepine-3-carboxamide (±)-1-[4-(3-fluoropyridin-4-yl)phenyl]-7,8-dimethoxy-N,4-dimethyl-4,5-dihydro-3H-2,3-benzodiazepine-3-carboxamide (±)-7,8-dimethoxy-N,4-dimethyl-1-[3'-(trifluoromethyl)biphenyl-4-yl]-4,5-dihydro-3H-2,3-benzodiazepine-3-carboxamide (±)-7,8-dimethoxy-N,4-dimethyl-1-[4'-(trifluoromethyl)biphenyl-4-yl]-4,5-dihydro-3H-2,3-benzodiazepine-3-carboxamide (±)-7,8-dimethoxy-1-(3'-methoxybiphenyl-4-yl)-N,4-dimethyl-4,5-dihydro-3H-2,3-benzodiazepine-3-carboxamide (±)-1-[4'-(5-chlorothien-2-yl)biphenyl-4-yl]-7,8-dimethoxy-N,4-dimethyl-4,5-dihydro-3H-2,3-benzodiazepine-3-carboxamide (±)-1-(3'-fluorobiphenyl-4-yl)-7,8-dimethoxy-N,4-dimethyl-4,5-dihydro-3H-2,3-benzodiazepine-3-carboxamide (±)-7,8-dimethoxy-1-(2'-methoxybiphenyl-4-yl)-N,4-40dimethyl-4,5-dihydro-3H-2,3-benzodiazepine-3-carboxamide (±)-7,8-dimethoxy-N,4-dimethyl-1-[2'-(trifluoromethyl)biphenyl-4-yl]-4,5-dihydro-3H-2,3-benzodiazepine-3-carboxamide (±)-1-(2'-chlorobiphenyl-4-yl)-7,8-dimethoxy-N,4-dimethyl-4,5-dihydro-3H-2,3-benzodiazepine-3-carboxamide (±)-1-(2'-fluorobiphenyl-4-yl)-7,8-dimethoxy-N,4-dimethyl-4,5-dihydro-3H-2,3-benzodiazepine-3-carboxamide (±)-1-[4'-(hydroxymethyl)biphenyl-4-yl]-7,8-dimethoxy-N,4-dimethyl-4,5-dihydro-3H-2,3-benzodiazepine-3-carboxamide (±)-7,8-dimethoxy-N,4-dimethyl-1-[4'-(trifluoromethoxy)biphenyl-4-yl]-4,5-dihydro-3H-2,3-benzodiazepine-3-carboxamide (±)-7,8-dimethoxy-N,4-dimethyl-1-[3'-(pyrrolidin-1-ylcarbonyl)biphenyl-4-yl]-4,5-dihydro-3H-2,3-benzodiazepine-3-carboxamide (±)-7,8-dimethoxy-N,4-dimethyl-1-[3'-(piperidin-1-ylcarbonyl)biphenyl-4-yl]-4,5-dihydro-3H-2,3-benzodiazepine-3-carboxamide (±)-7,8-dimethoxy-N,4-dimethyl-1-[3'-(morpholin-4-ylcarbonyl)biphenyl-4-yl]-4,5-dihydro-3H-2,3-benzodiazepine-3-carboxamide (±)-1-[3'-(cyclopropylcarbamoyl)biphenyl-4-yl]-7,8-dimethoxy-N,4-dimethyl-4,5-dihydro-3H-2,3-benzodiazepine-3-carboxamide (±)-1-(2',4'-difluorobiphenyl-4-yl)-7,8-dimethoxy-N,4-dimethyl-4,5-dihydro-3H-2,3-benzodiazepine-3-carboxamide (±)-7,8-dimethoxy-N,4-dimethyl-1-[4-(1-methyl-1H-pyrazol-5-yl)phenyl]-4,5-dihydro-3H-2,3-benzodiazepine-3-carboxamide (±)-7,8-dimethoxy-N,4-dimethyl-1-(4'-nitrobiphenyl-4-yl)-4,5-dihydro-3H-2,3-benzodiazepine-3-carboxamide (±)-7,8-dimethoxy-N,4-dimethyl-1-[4-(pyridin-3-yl)phenyl]-4,5-dihydro-3H-2,3-benzodiazepine-3-carboxamide (±)-7,8-dimethoxy-1-[4-(4-methoxypyridin-3-yl)phenyl]-N,4-dimethyl-4,5-dihydro-3H-2,3-benzodiazepine-3-carboxamide (±)-1-(3'-cyanobiphenyl-4-yl)-7,8-dimethoxy-N,4-dimethyl-4,5-dihydro-3H-2,3-benzodiazepine-3-carboxamide (±)-1-(4'-cyanobiphenyl-4-yl)-7,8-dimethoxy-N,4-dimethyl-4,5-dihydro-3H-2,3-benzodiazepine-3-carboxamide (±)-7,8-dimethoxy-N,4-dimethyl-1-[2'-(trifluoromethoxy)biphenyl-4-yl]-4,5-dihydro-3H-2,3-benzodiazepine-3-carboxamide (±)-7,8-dimethoxy-N,4-dimethyl-1-[4'-(methylsulphonyl)biphenyl-4-yl]-4,5-dihydro-3H-2,3-benzodiazepine-3-carboxamide (±)-1-(2'-cyanobiphenyl-4-yl)-7,8-dimethoxy-N,4-dimethyl-4,5-dihydro-3H-2,3-benzodiazepine-3-carboxamide (±)-7,8-dimethoxy-N,4-dimethyl-1-[4'-(morpholin-4-yl)biphenyl-4-yl]-4,5-dihydro-3H-2,3-benzodiazepine-3-carboxamide (±)-7,8-dimethoxy-N,4-dimethyl-1-[4-(pyrimidin-5-yl)phenyl]-4,5-dihydro-3H-2,3-benzodiazepine-3-carboxamide (±)-1-[2'-(hydroxymethyl)biphenyl-4-yl]-7,8-dimethoxy-N,4-dimethyl-4,5-dihydro-3H-2,3-benzodiazepine-3-carboxamide (±)-1-(3'-{[2-(dimethylamino)ethyl]carbamoyl}biphenyl-4-yl)-7,8-dimethoxy-N,4-dimethyl-4,5-dihydro-3H-2,3-benzodiazepine-3-carboxamide (±)-7,8-dimethoxy-N,4-dimethyl-1-(3'-sulphamoylbiphenyl-4-yl)-4,5-dihydro-3H-2,3-benzodiazepine-3-carboxamide (±)-7,8-dimethoxy-N,4-dimethyl-1-[4'-(methylsulphamoyl)biphenyl-4-yl]-4,5-dihydro-3H-2,3-benzodiazepine-3-carboxamide (±)-7,8-dimethoxy-N,4-dimethyl-1-[4-(1-methyl-1H-pyrrol-2-yl)phenyl]-4,5-dihydro-3H-2,3-benzodiazepine-3-carboxamide (±)-7,8-dimethoxy-N,4-dimethyl-1-[4-(6-methylpyridin-3-yl)phenyl]-4,5-dihydro-3H-2,3-benzodiazepine-3-carboxamide (±)-1-[4'-(cyclopropylsulphamoyl)biphenyl-4-yl]-7,8-dimethoxy-N,4-dimethyl-4,5-dihydro-3H-2,3-benzodiazepine-3-carboxamide (±)-1-(3'-fluoro-5'-hydroxybiphenyl-4-yl)-7,8-dimethoxy-N,4-dimethyl-4,5-dihydro-3H-2,3-benzodiazepine-3-carboxamide (±)-1-(3'-fluoro-5'-methylbiphenyl-4-yl)-7,8-dimethoxy-N,4-dimethyl-4,5-dihydro-3H-2,3-benzodiazepine-3-carboxamide (±)-7,8-dimethoxy-N,4-dimethyl-1-[3'-(methylsulphamoyl)biphenyl-4-yl]-4,5-dihydro-3H-2,3-benzodiazepine-3-carboxamide (±)-1-[4-(5-fluoropyridin-3-yl)phenyl]-7,8-dimethoxy-N,4-dimethyl-4,5-dihydro-3H-2,3-benzodiazepine-3-carboxamide (±)-1-[4-(4-fluoropyridin-3-yl)phenyl]-7,8-dimethoxy-N,4-dimethyl-4,5-dihydro-3H-2,3-benzodiazepine-3-carboxamide (±)-7,8-dimethoxy-N,4-dimethyl-1-[4-(2-methylpyridin-3-yl)phenyl]-4,5-dihydro-3H-2,3-benzodiazepine-3-carboxamide (±)-7,8-dimethoxy-1-[4-(2-methoxypyridin-4-yl)phenyl]-N,4-dimethyl-4,5-dihydro-3H-2,3-benzodiazepine-3-carboxamide (±)-1-[4-(5-cyanopyridin-3-yl)phenyl]-7,8-dimethoxy-N,4-dimethyl-4,5-dihydro-3H-2,3-benzodiazepine-3-carboxamide (4R)-7,8-dimethoxy-N,4-dimethyl-1-[4-(morpholin-4-yl)phenyl]-4,5-dihydro-3H-2,3-benzodiazepine-3-carboxamide (4S)-7,8-dimethoxy-N,4-dimethyl-1-[4-(morpholin-4-yl)phenyl]-4,5-dihydro-3H-2,3-benzodiazepine-3-carboxamide (4S)-7,8-dimethoxy-N,4-dimethyl-1-[4-(4-methylpiperazin-1-yl)phenyl]-4,5-dihydro-3H-2,3-benzodiazepine-3-carboxamide (±)-1-[4-(azetidin-1-yl)phenyl]-7,8-dimethoxy-N,4-dimethyl-4,5-dihydro-3H-2,3-benzodiazepine-3-carboxamide (4R)-1-[4-(azetidin-1-yl)phenyl]-7,8-dimethoxy-N,4-dimethyl-4,5-dihydro-3H-2,3-benzodiazepine-3-carboxamide (4S)-1-[4-(azetidin-1-yl)phenyl]-7,8-dimethoxy-N,4-dimethyl-4,5-dihydro-3H-2,3-benzodiazepine-3-carboxamide (±)-1-[4-(3-fluoroazetidin-1-yl)phenyl]-7,8-dimethoxy-N,4-dimethyl-4,5-dihydro-3H-2,3-benzodiazepine-3-carboxamide (4R)-1-[4-(3-fluoroazetidin-1-yl)phenyl]-7,8-dimethoxy-N,4-dimethyl-4,5-dihydro-3H-2,3-benzodiazepine-3-carboxamide (4S)-1-[4-(3-fluoroazetidin-1-yl)phenyl]-7,8-dimethoxy-N,4-dimethyl-4,5-dihydro-3H-2,3-benzodiazepine-3-carboxamide (±)-1-[4-(4-hydroxypiperidin-1-yl)phenyl]-7,8-dimethoxy-N,4-dimethyl-4,5-dihydro-3H-2,3-benzodiazepine-3-carboxamide (4S)-1-[4-(4-hydroxypiperidin-1-yl)phenyl]-7,8-dimethoxy-N,4-dimethyl-4,5-dihydro-3H-2,3-benzodiazepine-3-carboxamide (±)-7,8-dimethoxy-N,4-dimethyl-1-[4-(piperazin-1-yl)phenyl]-4,5-dihydro-3H-2,3-benzodiazepine-3-carboxamide (4S)-7,8-dimethoxy-N,4-dimethyl-1-[4-(piperazin-1-yl)phenyl]-4,5-dihydro-3H-2,3-benzodiazepine-3-carboxamide (±)-7,8-dimethoxy-N,4-dimethyl-1-[4-(4-methylpiperazin-1-yl)phenyl]-4,5-dihydro-3H-2,3-benzodiazepine-3-carboxamide (±)-1-[4-(4-acetylpiperazin-1-yl)phenyl]-7,8-dimethoxy-N,4-dimethyl-4,5-dihydro-3H-2,3-benzodiazepine-3-carboxamide (4R)-1-[4-(4-acetylpiperazin-1-yl)phenyl]-7,8-dimethoxy-N,4-dimethyl-4,5-dihydro-3H-2,3-benzodiazepine-3-carboxamide (4S)-1-[4-(4-acetylpiperazin-1-yl)phenyl]-7,8-dimethoxy-N,4-dimethyl-4,5-dihydro-3H-2,3-benzodiazepine-3-carboxamide (±)-7,8-dimethoxy-N,4-dimethyl-1-{4-[4-(trifluoroacetyl)piperazin-1-yl]phenyl}-4,5-dihydro-3H-2,3-benzodiazepine-3-carboxamide (±)-1-{4-[4-(2-hydroxy-2-methylpropanoyl)piperazin-1-yl]phenyl}-7,8-dimethoxy-N,4-dimethyl-4,5-dihydro-3H-2,3-benzodiazepine-3-carboxamide (±)-7,8-dimethoxy-N,4-dimethyl-1-{4-[4-(methylsulphonyl)piperazin-1-yl]phenyl}-4,5-dihydro-3H-2,3-benzodiazepine-3-carboxamide (4S)-1-[4-(1,1-dioxidothiomorpholin-4-yl)phenyl]-7,8-dimethoxy-N,4-dimethyl-4,5-dihydro-3H-2,3-benzodiazepine-3-carboxamide (±)-7,8-dimethoxy-N,4-dimethyl-1-[4-(3-oxopiperazin-1-yl)phenyl]-4,5-dihydro-3H-2,3-benzodiazepine-3-carboxamide (±)-7,8-dimethoxy-N,4-dimethyl-1-[4-(4-methyl-3-oxopiperazin-1-yl)phenyl]-4,5-dihydro-3H-2,3-benzodiazepine-3-carboxamide (±)-7,8-dimethoxy-N,4-dimethyl-1-[4-(piperidin-1-yl)phenyl]-4,5-dihydro-3H-2,3-benzodiazepine-3-carboxamide (±)-7,8-dimethoxy-N,4-dimethyl-1-[3-(morpholin-4-yl)phenyl]-4,5-dihydro-3H-2,3-benzodiazepine-3-carboxamide (±)-1-[3-(3,3-difluoroazetidin-1-yl)phenyl]-7,8-dimethoxy-N,4-dimethyl-4,5-dihydro-3H-2,3-benzodiazepine-3-carboxamide (±)-1-[3-(azetidin-1-yl)phenyl]-7,8-dimethoxy-N,4-dimethyl-4,5-dihydro-3H-2,3-benzodiazepine-3-carboxamide (±)-7,8-dimethoxy-N,4-dimethyl-1-[3-(4-methylpiperazin-1-yl)phenyl]-4,5-dihydro-3H-2,3-benzodiazepine-3-carboxamide (±)-1-[4-fluoro-3-(morpholin-4-yl)phenyl]-7,8-dimethoxy-N,4-dimethyl-4,5-dihydro-3H-2,3-benzodiazepine-3-carboxamide (±)-1-[3-(3,3-difluoroazetidin-1-yl)-4-fluorophenyl]-7,8-dimethoxy-N,4-dimethyl-4,5-dihydro-3H-2,3-benzodiazepine-3-carboxamide (±)-1-[4-fluoro-3-(4-hydroxypiperidin-1-yl)phenyl]-7,8-dimethoxy-N,4-dimethyl-4,5-dihydro-3H-2,3-benzodiazepine-3-carboxamide (±)-7,8-dimethoxy-N,4-dimethyl-1-[4-(5-methyl-3-phenyl-1H-pyrazol-1-yl)phenyl]-4,5-dihydro-3H-2,3-benzodiazepine-3-carboxamide (4S)-7,8-dimethoxy-N,4-dimethyl-1-[4-(5-methyl-3-phenyl-1H-pyrazol-1-yl)phenyl]-4,5-dihydro-3H-2,3-benzodiazepine-3-carboxamide (±)-1-[4-(5-cyclopropyl-3-phenyl-1H-pyrazol-1-yl)phenyl]-7,8-dimethoxy-N,4-dimethyl-4,5-dihydro-3H-2,3-benzodiazepine-3-carboxamide (4S)-1-[4-(5-cyclopropyl-3-phenyl-1H-pyrazol-1-yl)phenyl]-7,8-dimethoxy-N,4-dimethyl-4,5-dihydro-3H-2,3-benzodiazepine-3-carboxamide (±)-7,8-dimethoxy-N,4-dimethyl-1-{4-[3-phenyl-5-(trifluoromethyl)-1H-pyrazol-1-yl]phenyl}-4,5-dihydro-3H-2,3-benzodiazepine-3-carboxamide (±)-1-{4-[3-(4-fluorophenyl)-1H-pyrazol-1-yl]phenyl}-7,8-dimethoxy-N,4-dimethyl-4,5-dihydro-3H-2,3-benzodiazepine-3-carboxamide (4S)-1-{4-[3-(4-fluorophenyl)-1H-pyrazol-1-yl]phenyl}-7,8-dimethoxy-N,4-dimethyl-4,5-dihydro-3H-2,3-benzodiazepine-3-carboxamide (4R)-1-{4-[3-(4-fluorophenyl)-1H-pyrazol-1-yl]phenyl}-7,8-dimethoxy-N,4-dimethyl-4,5-dihydro-3H-2,3-benzodiazepine-3-carboxamide (±)-7,8-dimethoxy-N,4-dimethyl-1-{4-[5-methyl-3-(trifluoromethyl)-1H-pyrazol-1-yl]phenyl}-4,5-dihydro-3H-2,3-benzodiazepine-3-carboxamide (±)-7,8-dimethoxy-N,4-dimethyl-1-[4-(1H-1,2,4-triazol-1-yl)phenyl]-4,5-dihydro-3H-2,3-benzodiazepine-3-carboxamide (±)-7,8-dimethoxy-N,4-dimethyl-1-[4-(5-methyl-1H-1,2,4-triazol-1-yl)phenyl]-4,5-dihydro-3H-2,3-benzodiazepine-3-carboxamide (±)-1-[4-(3,5-dimethyl-1H-1,2,4-triazol-1-yl)phenyl]-7,8-dimethoxy-N,4-dimethyl-4,5-dihydro-3H-2,3-benzodiazepine-3-carboxamide (±)-8-tert-butyl-1-[4-(3,5-dimethylisoxazol-4-yl)phenyl]-N,4-dimethyl-4,5-dihydro-3H-2,3-benzodiazepine-3-carboxamide (±)-7-chloro-1-[4-(3,5-dimethylisoxazol-4-yl)phenyl]-N,4-dimethyl-8-(trifluoromethoxy)-4,5-dihydro-3H-2,3-benzodiazepine-3-carboxamide (4S)-7-chloro-1-[4-(3,5-dimethylisoxazol-4-yl)phenyl]-N,4-dimethyl-8-(trifluoromethoxy)-4,5-dihydro-3H-2,3-benzodiazepine-3-carboxamide (4R)-7-chloro-1-[4-(3,5-dimethylisoxazol-4-yl)phenyl]-N,4-dimethyl-8-(trifluoromethoxy)-4,5-dihydro-3H-2,3-benzodiazepine-3-carboxamide (±)-8-chloro-1-[4-(3,5-dimethylisoxazol-4-yl)phenyl]-7-methoxy-N,4-dimethyl-4,5-dihydro-3H-2,3-benzodiazepine-3-carboxamide (4S)-8-chloro-1-[4-(3,5-dimethylisoxazol-4-yl)phenyl]-7-methoxy-N,4-dimethyl-4,5-dihydro-3H-2,3-benzodiazepine-3-carboxamide (4R)-8-chloro-1-[4-(3,5-dimethylisoxazol-4-yl)phenyl]-7-methoxy-N,4-dimethyl-4,5-dihydro-3H-2,3-benzodiazepine-3-carboxamide (±)-1-[4-(3,5-dimethylisoxazol-4-yl)phenyl]-N,4,8-trimethyl-4,5-dihydro-3H-2,3-benzodiazepine-3-carboxamide (±)-7,8-bis(difluoromethoxy)-1-[4-(3,5-dimethylisoxazol-4-yl)phenyl]-N,4-dimethyl-4,5-dihydro-3H-2,3-benzodiazepine-3-carboxamide (±)-1-[4-(3,5-dimethylisoxazol-4-yl)phenyl]-7,8-diethoxy-N,4-dimethyl-4,5-dihydro-3H-2,3-benzodiazepine-3-carboxamide (±)-7-(difluoromethoxy)-1-[4-(3,5-dimethylisoxazol-4-yl)phenyl]-8-methoxy-N,4-dimethyl-4,5-dihydro-3H-2,3-benzodiazepine-3-carboxamide (4S)-7-(difluoromethoxy)-1-[4-(3,5-dimethylisoxazol-4-yl)phenyl]-8-methoxy-N,4-dimethyl-4,5-dihydro-3H-2,3-benzodiazepine-3-carboxamide (4R)-7-(difluoromethoxy)-1-[4-(3,5-dimethylisoxazol-4-yl)phenyl]-8-methoxy-N,4-dimethyl-4,5-dihydro-3H-2,3-benzodiazepine-3-carboxamide (±)-7-(difluoromethoxy)-8-methoxy-N,4-dimethyl-1-[4-(4-methylpiperazin-1-yl)phenyl]-4,5-dihydro-3H-2,3-benzodiazepine-3-carboxamide (4R)-7-(difluoromethoxy)-8-methoxy-N,4-dimethyl-1-[4-(4-methylpiperazin-1-yl)phenyl]-4,5-dihydro-3H-2,3-benzodiazepine-3-carboxamide (4S)-7-(difluoromethoxy)-8-methoxy-N,4-dimethyl-1-[4-(4-methylpiperazin-1-yl)phenyl]-4,5-dihydro-3H-2,3-benzodiazepine-3-carboxamide (±)-1-(4-chlorophenyl)-N,4-dimethyl-8-[3-(4-methylpiperazin-1-yl)propoxy]-4,5-dihydro-3H-2,3-benzodiazepine-3-carboxamide (4S)-1-(4-chlorophenyl)-N,4-dimethyl-8-[3-(4-methylpiperazin-1-yl)propoxy]-4,5-dihydro-3H-2,3-benzodiazepine-3-carboxamide (±)-1-(4-chlorophenyl)-N,4-dimethyl-8-[3-(morpholin-4-yl)propoxy]-4,5-dihydro-3H-2,3-benzodiazepine-3-carboxamide (±)-1-(4-chlorophenyl)-N,4-dimethyl-8-[2-(4-methylpiperazin-1-yl)ethoxy]-4,5-dihydro-3H-2,3-benzodiazepine-3-carboxamide (±)-1-(4-chlorophenyl)-N,4-dimethyl-8-[(6-methylpyridin-2-yl)methoxy]-4,5-dihydro-3H-2,3-benzodiazepine-3-carboxamide (±)-1-[4-(3,5-dimethylisoxazol-4-yl)phenyl]-8-hydroxy-N,4-dimethyl-4,5-dihydro-3H-2,3-benzodiazepine-3-carboxamide (±)-1-[4-(3,5-dimethylisoxazol-4-yl)phenyl]-N,4-dimethyl-8-[3-(morpholin-4-yl)propoxy]-4,5-dihydro-3H-2,3-benzodiazepine-3-carboxamide (±)-7-cyano-1-[4-(3,5-dimethylisoxazol-4-yl)phenyl]-8-methoxy-N,4-dimethyl-4,5-dihydro-3H-2,3-benzodiazepine-3-carboxamide (±)-8-acetamido-N,4-dimethyl-1-[4-(morpholin-4-yl)phenyl]-4,5-dihydro-3H-2,3-benzodiazepine-3-carboxamide (±)-8-acetamido-N,4-dimethyl-1-[4-(4-methylpiperazin-1-yl)phenyl]-4,5-dihydro-3H-2,3-benzodiazepine-3-carboxamide (±)-8-acetamido-1-[4-(3,5-dimethylisoxazol-4-yl)phenyl]-N,4-dimethyl-4,5-dihydro-3H-2,3-benzodiazepine-3-carboxamide (±)-1-(4-chlorophenyl)-8-(3,5-dimethyl-1H-pyrazol-1-yl)-N,4-dimethyl-4,5-dihydro-3H-2,3-benzodiazepine-3-carboxamide (±)-1-[4-(3,5-dimethylisoxazol-4-yl)phenyl]-8-(3,5-dimethyl-1H-pyrazol-1-yl)-N,4-dimethyl-4,5-dihydro-3H-2,3-benzodiazepine-3-carboxamide (±)-1-[4-(3,5-dimethylisoxazol-4-yl)phenyl]-N,4-dimethyl-8-(morpholin-4-yl)-4,5-dihydro-3H-2,3-benzodiazepine-3-carboxamide (4R)-1-[4-(3,5-dimethylisoxazol-4-yl)phenyl]-N,4-dimethyl-8-(morpholin-4-yl)-4,5-dihydro-3H-2,3-benzodiazepine-3-carboxamide (4S)-1-[4-(3,5-dimethylisoxazol-4-yl)phenyl]-N,4-dimethyl-8-(morpholin-4-yl)-4,5-dihydro-3H-2,3-benzodiazepine-3-carboxamide (4S)-8-methoxy-N,4-dimethyl-1-[4-(3-oxomorpholin-4-yl)phenyl]-4,5-dihydro-3H-2,3-benzodiazepine-3-carboxamide.

(±)-1-{4-[4-(2-hydroxyethyl)piperazin-1-yl]phenyl}-7,8-dimethoxy-N,4-dimethyl-4,5-dihydro-3H-2,3-benzodiazepine-3-carboxamide (±)-7,8-dimethoxy-1-[4-(4-methoxypiperidin-1-yl)phenyl]-N,4-dimethyl-4,5-dihydro-3H-2,3-benzodiazepine-3-carboxamide (4R)-7,8-dimethoxy-1-[4-(4-methoxypiperidin-1-yl)phenyl]-N,4-dimethyl-4,5-dihydro-3H-2,3-benzodiazepine-3-carboxamide (4S)-7,8-dimethoxy-1-[4-(4-methoxypiperidin-1-yl)phenyl]-N,4-dimethyl-4,5-dihydro-3H-2,3-benzodiazepine-3-carboxamide (±)-1-{4-[4-(dimethylamino)piperidin-1-yl]phenyl}-7,8-dimethoxy-N,4-dimethyl-4,5-dihydro-3H-2,3-benzodiazepine-3-carboxamide (4R)-1-{4-[4-(dimethylamino)piperidin-1-yl]phenyl}-7,8-dimethoxy-N,4-dimethyl-4,5-dihydro-3H-2,3-benzodiazepine-3-carboxamide (4S)-1-{4-[4-(dimethylamino)piperidin-1-yl]phenyl}-7,8-dimethoxy-N,4-dimethyl-4,5-dihydro-3H-2,3-benzodiazepine-3-carboxamide (±)-1-[4-(3,3-difluoroazetidin-1-yl)phenyl]-7,8-dimethoxy-N,4-dimethyl-4,5-dihydro-3H-2,3-benzodiazepine-3-carboxamide (±)-1-[4-(4-acetamidopiperidin-1-yl)phenyl]-7,8-dimethoxy-N,4-dimethyl-4,5-dihydro-3H-2,3-benzodiazepine-3-carboxamide (±)-1-{4-[4-(2-hydroxyethyl)piperidin-1-yl]phenyl}-7,8-dimethoxy-N,4-dimethyl-4,5-dihydro-3H-2,3-benzodiazepine-3-carboxamide (±)-1-[4-(3-hydroxyazetidin-1-yl)phenyl]-7,8-dimethoxy-N,4-dimethyl-4,5-dihydro-3H-2,3-benzodiazepine-3-carboxamide (±)-1-[4-(3-hydroxy-3-methylazetidin-1-yl)phenyl]-7,8-dimethoxy-N,4-dimethyl-4,5-dihydro-3H-2,3-benzodiazepine-3-carboxamide (4R)-1-[4-(3-hydroxy-3-methylazetidin-1-yl)phenyl]-7,8-dimethoxy-N,4-dimethyl-4,5-dihydro-3H-2,3-benzodiazepine-3-carboxamide (4S)-1-[4-(3-hydroxy-3-methylazetidin-1-yl)phenyl]-7,8-dimethoxy-N,4-dimethyl-4,5-dihydro-3H-2,3-benzodiazepine-3-carboxamide (±)-1-[4-(4-Isopropylpiperazin-1-yl)phenyl]-7,8-dimethoxy-N,4-dimethyl-4,5-dihydro-3H-2,3-benzodiazepine-3-carboxamide (±)-7,8-dimethoxy-1-[4-(3-methoxyazetidin-1-yl)phenyl]-N,4-dimethyl-4,5-dihydro-3H-2,3-benzodiazepine-3-carboxamide (±)-1-[4-(4-hydroxy-4-methylpiperidin-1-yl)phenyl]-7,8-dimethoxy-N,4-dimethyl-4,5-dihydro-3H-2,3-benzodiazepine-3-carboxamide (4R)-1-[4-(4-hydroxy-4-methylpiperidin-1-yl)phenyl]-7,8-dimethoxy-N,4-dimethyl-4,5-dihydro-3H-2,3-benzodiazepine-3-carboxamide (4S)-1-[4-(4-hydroxy-4-methylpiperidin-1-yl)phenyl]-7,8-dimethoxy-N,4-dimethyl-4,5-dihydro-3H-2,3-benzodiazepine-3-carboxamide (±)-1-[4-(4-isopropylpiperazin-1-yl)phenyl]-7,8-dimethoxy-N,4-dimethyl-4,5-dihydro-3H-2,3-benzodiazepine-3-carboxamide (±)-7,8-dimethoxy-1-[4-(3-methoxyazetidin-1-yl)phenyl]-N,4-dimethyl-4,5-dihydro-3H-2,3-benzodiazepine-3-carboxamide (±)-1-[4-(4-hydroxy-4-methylpiperidin-1-yl)phenyl]-7,8-dimethoxy-N,4-dimethyl-4,5-dihydro-3H-2,3-benzodiazepine-3-carboxamide (4R)-1-[4-(4-hydroxy-4-methylpiperidin-1-yl)phenyl]-7,8-dimethoxy-N,4-dimethyl-4,5-dihydro-3H-2,3-benzodiazepine-3-carboxamide (4S)-1-[4-(4-hydroxy-4-methylpiperidin-1-yl)phenyl]-7,8-dimethoxy-N,4-dimethyl-4,5-dihydro-3H-2,3-benzodiazepine-3-carboxamide (±)-7,8-dimethoxy-N,4-dimethyl-1-{4-[4-(methylcarbamoyl)piperidin-1-yl]phenyl}-4,5-dihydro-3H-2,3-benzodiazepine-3-carboxamide (±)-7,8-dimethoxy-N,4-dimethyl-1-{4-[4-(methylcarbamoyl)piperidin-1-yl]phenyl}-4,5-dihydro-3H-2,3-benzodiazepine-3-carboxamide (4R)-7,8-dimethoxy-N,4-dimethyl-1-{4-[4-(methylcarbamoyl)piperidin-1-yl]phenyl}-4,5-dihydro-3H-2,3-benzodiazepine-3-carboxamide (±)-1-{4-[(3S)-3-hydroxypyrrolidin-1-yl]phenyl}-7,8-dimethoxy-N,4-dimethyl-4,5-dihydro-3H-2,3-benzodiazepine-3-carboxamide (4S)-1-{4-[(3S)-3-hydroxypyrrolidin-1-yl]phenyl}-7,8-dimethoxy-N,4-dimethyl-4,5-dihydro-3H-2,3-benzodiazepine-3-carboxamide (±)-tert-butyl(1-{4-[7,8-dimethoxy-4-methyl-3-(methylcarbamoyl)-4,5-dihydro-3H-2,3-benzodiazepin-1-yl]phenyl}-4-methylpiperidin-4-yl)carbamate (±)-1-{4-[(2S,5R)-2,5-dimethylpiperazin-1-yl]phenyl}-7,8-dimethoxy-N,4-dimethyl-4,5-dihydro-3H-2,3-benzodiazepine-3-carboxamide (±)-1-{4-[4-(2,2-difluoroethyl)piperazin-1-yl]phenyl}-7,8-dimethoxy-N,4-dimethyl-4,5-dihydro-3H-2,3-benzodiazepine-3-carboxamide (4S)-7,8-dimethoxy-N,4-dimethyl-1-[4-(3-oxopiperazin-1-yl)phenyl]-4,5-dihydro-3H-2,3-benzodiazepine-3-carboxamide (4S)-1-{4-[(2R,6S)-2,6-dimethylmorpholin-4-yl]phenyl}-7,8-dimethoxy-N,4-dimethyl-4,5-dihydro-3H-2,3-benzodiazepine-3-carboxamide (±)-7,8-dimethoxy-N,4-dimethyl-1-[4-(4-oxopiperidin-1-yl)phenyl]-4,5-dihydro-3H-2,3-benzodiazepine-3-carboxamide (±)-7,8-dimethoxy-N,4-dimethyl-1-{4-[4-(2,2,2-trifluoroethyl)piperazin-1-yl]phenyl}-4,5-dihydro-3H-2,3-benzodiazepine-3-carboxamide (4S)-1-{4-[(3R,5S)-3,5-dimethylpiperazin-1-yl]phenyl}-7,8-dimethoxy-N,4-dimethyl-4,5-dihydro-3H-2,3-benzodiazepine-3-carboxamide (±)-7,8-dihydroxy-N,4-dimethyl-1-[4-(4-methylpiperazin-1-yl)phenyl]-4,5-dihydro-3H-2,3-benzodiazepine-3-carboxamide (±)-7,8-diethoxy-N,4-dimethyl-1-[4-(4-methylpiperazin-1-yl)phenyl]-4,5-dihydro-3H-2,3-benzodiazepine-3-carboxamide (±)-4-ethyl-7,8-dimethoxy-N-methyl-1-[4-(4-methylpiperazin-1-yl)phenyl]-4,5-dihydro-3H-2,3-benzodiazepine-3-carboxamide (4S)-4-ethyl-7,8-dimethoxy-N-methyl-1-[4-(4-methylpiperazin-1-yl)phenyl]-4,5-dihydro-3H-2,3-benzodiazepine-3-carboxamide (±)-4-ethyl-7,8-dimethoxy-N-methyl-1-[4-(piperazin-1-yl)phenyl]-4,5-dihydro-3H-2,3-benzodiazepine-3-carboxamide (4S)-4-ethyl-7,8-dimethoxy-N-methyl-1-[4-(piperazin-1-yl)phenyl]-4,5-dihydro-3H-2,3-benzodiazepine-3-carboxamide (4R)-4-ethyl-7,8-dimethoxy-N-methyl-1-[4-(piperazin-1-yl)phenyl]-4,5-dihydro-3H-2,3-benzodiazepine-3-carboxamide (±)-4-ethyl-7,8-dimethoxy-N-methyl-1-{4-[4-(methylsulphonyl)piperazin-1-yl]phenyl}-4,5-dihydro-3H-2,3-benzodiazepine-3-carboxamide (4S)-4-ethyl-7,8-dimethoxy-N-methyl-1-{4-[4-(methylsulphonyl)piperazin-1-yl]phenyl}-4,5-dihydro-3H-2,3-benzodiazepine-3-carboxamide (4R)-4-ethyl-7,8-dimethoxy-N-methyl-1-{4-[4-(methylsulphonyl)piperazin-1-yl]phenyl}-4,5-dihydro-3H-2,3-benzodiazepine-3-carboxamide (±)-4-ethyl-1-[4-(3-fluorazetidin-1-yl)phenyl]-7,8-dimethoxy-N-methyl-4,5-dihydro-3H-2,3-benzodiazepine-3-carboxamide (±)-1-[4-(4-acetylpiperazin-1-yl)phenyl]-4-ethyl-7,8-dimethoxy-N-methyl-4,5-dihydro-3H-2,3-benzodiazepine-3-carboxamide (±)-1-[4-(1,1-dioxidothiomorpholin-4-yl)phenyl]-4-ethyl-7,8-dimethoxy-N-methyl-4,5-dihydro-3H-2,3-benzodiazepine-3-carboxamide (±)-4-ethyl-1-[4-(4-hydroxypiperidin-1-yl)phenyl]-7,8-dimethoxy-N-methyl-4,5-dihydro-3H-2,3-benzodiazepine-3-carboxamide (±)-4-ethyl-7,8-dimethoxy-N-methyl-1-[4-(morpholin-4-yl)phenyl]-4,5-dihydro-3H-2,3-benzodiazepine-3-carboxamide (4S)-4-ethyl-7,8-dimethoxy-N-methyl-1-[4-(morpholin-4-yl)phenyl]-4,5-dihydro-3H-2,3-benzodiazepine-3-carboxamide (±)-8-chloro-1-[4-(1,1-dioxidothiomorpholin-4-yl)phenyl]-N,4-dimethyl-7-(trifluoromethoxy)-4,5-dihydro-3H-2,3-benzodiazepine-3-carboxamide (±)-8-chloro-N,4-dimethyl-1-[4-(piperazin-1-yl)phenyl]-7-(trifluoromethoxy)-4,5-dihydro-3H-2,3-benzodiazepine-3-carboxamide (±)-8-chloro-1-[4-(4-hydroxypiperidin-1-yl)phenyl]-N,4-dimethyl-7-(trifluoromethoxy)-4,5-dihydro-3H-2,3-benzodiazepine-3-carboxamide (±)-8-chloro-N,4-dimethyl-1-[4-(4-methylpiperazin-1-yl)phenyl]-7-(trifluoromethoxy)-4,5-dihydro-3H-2,3-benzodiazepine-3-carboxamide (±)-8-chloro-N,4-dimethyl-1-{4-[4-(methylsulphonyl)piperazin-1-yl]phenyl}-7-(trifluoromethoxy)-4,5-dihydro-3H-2,3-benzodiazepine-3-carboxamide (±)-8-(1,1-dioxidothiomorpholin-4-yl)-1-[4-(1,1-dioxidothiomorpholin-4-yl)phenyl]-N,4-dimethyl-7-(trifluoromethoxy)-4,5-dihydro-3H-2,3-benzodiazepine-3-carboxamide (±)-1-(4-chlorophenyl)-8-(1,1-dioxidothiomorpholin-4-yl)-N,4-dimethyl-7-(trifluoromethoxy)-4,5-dihydro-3H-2,3-benzodiazepine-3-carboxamide (±)-1-[4-(4-acetylpiperazin-1-yl)phenyl]-N,4-dimethyl-7-(trifluoromethoxy)-4,5-dihydro-3H-2,3-benzodiazepine-3-carboxamide (±)-1-{4-[4-(2-hydroxyethyl)piperazin-1-yl]phenyl}-N,4-dimethyl-7-(trifluoromethoxy)-4,5-dihydro-3H-2,3-benzodiazepine-3-carboxamide (±)-8-methoxy-N,4-dimethyl-1-[4-(4-methylpiperazin-1-yl)phenyl]-7-(trifluoromethoxy)-4,5-dihydro-3H-2,3-benzodiazepine-3-carboxamide (±)-4-ethyl-7,8-dimethoxy-N-methyl-1-[4-(1,3,5-trimethyl-1H-pyrazol-4-yl)phenyl]-4,5-dihydro-3H-2,3-benzodiazepine-3-carboxamide (±)-4-ethyl-1-(4'-fluorobiphenyl-4-yl)-7,8-dimethoxy-N-methyl-4,5-dihydro-3H-2,3-benzodiazepine-3-carboxamide (±)-4-ethyl-7,8-dimethoxy-N-methyl-1-[4-(1-methyl-1H-1,2,3-triazol-4-yl)phenyl]-4,5-dihydro-3H-2,3-benzodiazepine-3-carboxamide (±)-1-[4-(3,5-dimethyl-1,2-oxazol-4-yl)phenyl]-4-ethyl-7,8-dimethoxy-N-methyl-4,5-dihydro-3H-2,3-benzodiazepine-3-carboxamide (±)-4-isopropyl-7,8-dimethoxy-N-methyl-1-[4-(1,3,5-trimethyl-1H-pyrazol-4-yl)phenyl]-4,5-dihydro-3H-2,3-benzodiazepine-3-carboxamide (±)-4-ethyl-7,8-dimethoxy-N-methyl-1-[4-(2-oxopyrrolidin-1-yl)phenyl]-4,5-dihydro-3H-2,3-benzodiazepine-3-carboxamide (±)-4-ethyl-7,8-dimethoxy-N-methyl-1-[4-(3-oxomorpholin-4-yl)phenyl]-4,5-dihydro-3H-2,3-benzodiazepine-3-carboxamide (±)-4-ethyl-7,8-dimethoxy-N-methyl-1-[4-(2-oxopiperidin-1-yl)phenyl]-4,5-dihydro-3H-2,3-benzodiazepine-3-carboxamide (±)-4-ethyl-7,8-dimethoxy-N-methyl-1-[4-(2-oxo-1,3-oxazolidin-3-yl)phenyl]-4,5-dihydro-3H-2,3-benzodiazepine-3-carboxamide (4S)-7,8-dimethoxy-N,4-dimethyl-1-[4-(4-methyl-2-oxo-1,4-diazepan-1-yl)phenyl]-4,5-dihydro-3H-2,3-benzodiazepine-3-carboxamide (±)-1-(4-chlorophenyl)-N,4-dimethyl-7-(2-oxo-1,3-oxazolidin-3-yl)-4,5-dihydro-3H-2,3-benzodiazepine-3-carboxamide (4S)-1-(4-chlorophenyl)-N,4-dimethyl-7-(2-oxo-1,3-oxazolidin-3-yl)-4,5-dihydro-3H-2,3-benzodiazepine-3-carboxamide (±)-1-(4-chlorophenyl)-N,4-dimethyl-7-(2-oxopiperidin-1-yl)-4,5-dihydro-3H-2,3-benzodiazepine-3-carboxamide (±)-1-(4-chlorophenyl)-N,4-dimethyl-7-(3-oxomorpholin-4-yl)-4,5-dihydro-3H-2,3-benzodiazepine-3-carboxamide (±)-1-(4-chlorophenyl)-N,4-dimethyl-7-(morpholin-4-yl)-4,5-dihydro-3H-2,3-benzodiazepine-3-carboxamide (±)-1-(4-chlorophenyl)-N,4-dimethyl-7-(pyrrolidin-1-yl)-4,5-dihydro-3H-2,3-benzodiazepine-3-carboxamide (±)-1-(4-chlorophenyl)-7-(1,1-dioxidothiomorpholin-4-yl)-N,4-dimethyl-4,5-dihydro-3H-2,3-benzodiazepine-3-carboxamide (±)-1-(4-chlorophenyl)-N,4-dimethyl-7-(4-methylpiperazin-1-yl)-4,5-dihydro-3H-2,3-benzodiazepine-3-carboxamide (±)-N,4-dimethyl-7-(4-methylpiperazin-1-yl)-1-[4-(4-methylpiperazin-1-yl)phenyl]-4,5-dihydro-3H-2,3-benzodiazepine-3-carboxamide (±)-N,4-dimethyl-7-(4-methyl-3-oxopiperazin-1-yl)-1-[4-(4-methyl-3-oxopiperazin-1-yl)phenyl]-4,5-dihydro-3H-2,3-benzodiazepine-3-carboxamide (±)-1-(4-chlorophenyl)-7-(4-fluorophenyl)-N,4-dimethyl-4,5-dihydro-3H-2,3-benzodiazepine-3-carboxamide (±)-1-(4-chlorophenyl)-N,4-dimethyl-7-(pyridin-4-yl)-4,5-dihydro-3H-2,3-benzodiazepine-3-carboxamide (±)-1-(4-chlorophenyl)-7-(6-hydroxypyridin-3-yl)-N,4-dimethyl-4,5-dihydro-3H-2,3-benzodiazepine-3-carboxamide (±)-1-(4-chlorophenyl)-7-(3,5-dimethyl-1,2-oxazol-4-yl)-N,4-dimethyl-4,5-dihydro-3H-2,3-benzodiazepine-3-carboxamide (±)-1-(4-chlorophenyl)-N,4-dimethyl-7-(1-methyl-1H-1,2,3-triazol-4-yl)-4,5-dihydro-3H-2,3-benzodiazepine-3-carboxamide (4R)-1-[4-(4-hydroxypiperidin-1-yl)phenyl]-7,8-dimethoxy-N,4-dimethyl-4,5-dihydro-3H-2,3-benzodiazepine-3-carboxamide (4R)-7,8-dimethoxy-N,4-dimethyl-1-[4-(4-methylpiperazin-1-yl)phenyl]-4,5-dihydro-3H-2,3-benzodiazepine-3-carboxamide (±)-1-[4-(1,1-dioxido-1,2-thiazolidin-2-yl)phenyl]-7,8-dimethoxy-N,4-dimethyl-4,5-dihydro-3H-2,3-benzodiazepine-3-carboxamide (±)-1-{7,8-dimethoxy-4-methyl-1-[4-(4-methylpiperazin-1-yl)phenyl]-4,5-dihydro-3H-2,3-benzodiazepin-3-yl}ethanone 1-{(4S)-7,8-dimethoxy-4-methyl-1-[4-(4-methylpiperazin-1-yl)phenyl]-4,5-dihydro-3H-2,3-benzodiazepin-3-yl}ethanone (±)-1-{1-[4-(3,5-dimethyl-1,2-oxazol-4-yl)phenyl]-7,8-dimethoxy-4-methyl-4,5-dihydro-3H-2,3-benzodiazepin-3-yl}ethanone (±)-7,8-dimethoxy-N,4-dimethyl-1-[4-(5-methyl-1,3,4-oxadiazol-2-yl)phenyl]-4,5-dihydro-3H-2,3-benzodiazepine-3-carboxamide (±)-7,8-dimethoxy-N,4-dimethyl-1-[4-(3-methyl-1,2,4-oxadiazol-5-yl)phenyl]-4,5-dihydro-3H-2,3-benzodiazepine-3-carboxamide (±)-N,4-dimethyl-8-(trifluoromethoxy)-1-[4-(1,3,5-trimethyl-1H-pyrazol-4-yl)phenyl]-4,5-dihydro-3H-2,3-benzodiazepine-3-carboxamide (4S)—N,4-dimethyl-8-(trifluoromethoxy)-1-[4-(1,3,5-trimethyl-1H-pyrazol-4-yl)phenyl]-4,5-dihydro-3H-2,3-benzodiazepine-3-carboxamide (4R)—N,4-dimethyl-8-(trifluoromethoxy)-1-[4-(1,3,5-trimethyl-1H-pyrazol-4-yl)phenyl]-4,5-dihydro-3H-2,3-benzodiazepine-3-carboxamide (±)-N,4-dimethyl-1-[4-(4-methyl-1-piperazinyl)phenyl]-8-(trifluoromethoxy)-4,5-dihydro-3H-2,3-benzodiazepine-3-carboxamide (4R)—N,4-dimethyl-1-[4-(4-methyl-1-piperazinyl)phenyl]-8-(trifluoromethoxy)-4,5-dihydro-3H-2,3-benzodiazepine-3-carboxamide (4S)—N,4-dimethyl-1-[4-(4-methyl-1-piperazinyl)phenyl]-8-(trifluoromethoxy)-4,5-dihydro-3H-2,3-benzodiazepine-3-carboxamide (±)-1-[4-(4-hydroxy-1-piperidinyl)phenyl]-N,4-dimethyl-8-(trifluoromethoxy)-4,5-dihydro-3H-2,3-benzodiazepine-3-carboxamide (±)-1-[2,4-dibromo-5-(4-methylpiperazin-1-yl)phenyl]-7,8-dimethoxy-N,4-dimethyl-4,5-dihydro-3H-2,3-benzodiazepine-3-carboxamide (4S)-1-[3-bromo-4-(4-methylpiperazin-1-yl)phenyl]-7,8-dimethoxy-N,4-dimethyl-4,5-dihydro-3H-2,3-benzodiazepine-3-carboxamide (4S)-1-[3-cyano-4-(4-methylpiperazin-1-yl)phenyl]-7,8-dimethoxy-N,4-dimethyl-4,5-dihydro-3H-2,3-benzodiazepine-3-carboxamide (±)-7,8-dimethoxy-4-methyl-1-[4-(4-methylpiperazin-1-yl)phenyl]-3-(1-oxopropyl)-4,5-dihydro-3H-2,3-benzodiazepine (±)-3-(cyclopropylcarbonyl)-7,8-dimethoxy-4-methyl-1-[4-(4-methylpiperazin-1-yl)phenyl]-4,5-dihydro-3H-2,3-benzodiazepine (±)-N-cyclopropyl-7,8-dimethoxy-4-methyl-1-[4-(4-methylpiperazin-1-yl)phenyl]-4,5-dihydro-3H-2,3-benzodiazepine (±)-7,8-dimethoxy-N,4-dimethyl-1-[4-(4-methylpiperazin-1-yl)phenyl]-4,5-dihydro-3H-2,3-benzodiazepin-3-carbothioamide methyl(±)-7,8-dimethoxy-4-methyl-1-[4-(4-methylpiperazin-1-yl)phenyl]-4,5-dihydro-3H-2,3-benzodiazepine-3-carboxylate ethyl(±)-7,8-dimethoxy-4-methyl-1-[4-(4-methylpiperazin-1-yl)phenyl]-4,5-dihydro-3H-2,3-benzodiazepine-3-carboxylate (±)-N-ethyl-7,8-dimethoxy-4-methyl-1-[4-(4-methylpiperazin-1-yl)phenyl]-4,5-dihydro-3H-2,3-benzodiazepine-3-carboxamide (4S)—N-ethyl-7,8-dimethoxy-4-methyl-1-[4-(4-methylpiperazin-1-yl)phenyl]-4,5-dihydro-3H-2,3-benzodiazepine-3-carboxamide.

In the general formula (I-A), X may represent an oxygen or sulphur atom.

In the general formula (I-A), X preferably represents an oxygen atom.

In the general formula (I-A), A may represent a monocyclic heteroaryl ring which has 5 or 6 ring atoms or a phenyl ring.

In the general formula (I-A), A preferably represents a monocyclic heteroaryl ring which has 6 ring atoms or a phenyl ring.

In the general formula (I-A), A more preferably represents a pyridyl or a phenyl ring.

In the general formula (I-A), A particularly preferably represents a phenyl ring.

In the general formula (I-A), $R^{1a}$ may also a) represent hydrogen, halogen, cyano, carboxyl, amino or aminosulphonyl, or b) represent a $C_1$-$C_6$-alkoxy, $C_1$-$C_3$-alkoxy-$C_1$-$C_3$-alkyl, $C_1$-$C_3$-alkoxy-$C_1$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-heterocyclyl-$C_1$-$C_6$-alkyl, N-heterocyclyl-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl- or $C_1$-$C_6$-alkoxycarbonyl radical, or c) represent a monocyclic heterocyclyl radical which has 3 to 8 ring atoms and which may be mono- or polysubstituted by identical or different substituents from the group consisting of hydroxy, halogen, amino, oxo, carboxyl and a $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms, or d) represent a monocyclic heteroaryl radical which has 5 or 6 ring atoms and which may be mono- or polysubstituted by identical or different substituents from the group consisting of halogen, hydroxy, amino, cyano, nitro, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms and/or a monocyclic heteroaryl radical which has 5 or 6 ring atoms, or e) represent a phenyl radical which may be mono- or polysubstituted by identical or different substituents from the group consisting of halogen, amino, hydroxy, cyano, nitro, carboxyl and/or a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$- alkyl, halo-$C_1$-$C_6$-alkoxy, hydroxy-$C_1$-$C_6$-alkyl, $C_3$-$C_{10}$-cycloalkyl and a monocyclic heterocyclyl radical which has 3 to 8 ring atoms.

In the general formula (I-A), $R^{1a}$ preferably
a) represents a monocyclic heterocyclyl radical which has 3 to 8 ring atoms and which may be mono- or polysubstituted by identical or different substituents from the group consisting of hydroxy, halogen, amino, oxo, carboxyl and a $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms, or
b) represents a monocyclic heteroaryl radical which has 5 or 6 ring atoms and which may be mono- or polysubstituted by identical or different substituents from the group consisting of halogen, hydroxy, amino, cyano, nitro, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms and/or a monocyclic heteroaryl radical which has 5 or 6 ring atoms, or
c) represents a phenyl radical which may be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, hydroxy-$C_1$-$C_6$-alkyl, $C_3$-$C_{10}$-cycloalkyl and/or a monocyclic heterocyclyl radical which has 3 to 8 ring atoms.

In the general formula (I-A), $R^{1a}$ also preferably
a) represents hydrogen or halogen, or
b) represents a monocyclic heterocyclyl radical which has 3 to 8 ring atoms and which may be mono- or polysubstituted by identical or different substituents from the group consisting of hydroxy, fluorine, oxo, carboxyl and a $C_1$-$C_6$-alkyl, hydroxy-$C_1$-$C_6$-alkyl, halo-$C_1$-$C_6$-alkyl or halo-$C_1$-$C_6$-alkoxy radical, or
c) represents a monocyclic heteroaryl radical which has 5 or 6 ring atoms and which may be mono- or polysubstituted by identical or different substituents from the group consisting of halogen, hydroxy, carboxyl and a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heteroaryl radical which has 5 or 6 ring atoms, or
d) represents a phenyl radical which may be mono- or polysubstituted by identical or different substituents from the group consisting of halogen, hydroxy, carboxyl and a $C_1$-$C_6$-alkyl, $C_1$-$C_6$-alkoxy, halo-$C_1$-$C_6$-alkyl or halo-$C_1$-$C_6$-alkoxy radical.

In the general formula (I-A), $R^{1a}$ more preferably
a) represents hydrogen or halogen, or
b) represents a monocyclic heterocyclyl radical which has 4 to 6 ring atoms, or
c) represents a monocyclic heteroaryl radical which has 5 or 6 ring atoms and which may be mono- or polysubstituted by identical or different substituents from the group consisting of halogen, carboxyl and a $C_1$-$C_6$-alkyl, $C_1$-$C_6$-alkoxy-$C_1$-$C_6$-alkyl, $C_3$-$C_{10}$-cycloalkyl and/or a monocyclic heteroaryl radical which has 6 ring atoms, or
d) represents a phenyl radical which may be mono- or polysubstituted by carboxyl.

In the general formula (I-A), $R^{1a}$ very preferably
a) represents hydrogen or chlorine, or
b) represents a morpholinyl radical, or
c) represents an isoxazolyl, pyrazolyl, tetrazolyl, thienyl or pyridinyl radical which may be mono- or polysubstituted by identical or different substituents from the group consisting of chlorine, carboxyl and/or a $C_1$-$C_3$-alkyl, $C_1$-$C_3$-alkoxy-$C_1$-$C_3$-alkyl, $C_3$-$C_6$-cycloalkyl and/or a pyridinyl radical, or
d) represents a phenyl radical which may be substituted by carboxyl.

In the general formula (I-A), $R^{1a}$ particularly preferably
a) represents chlorine, or
b) represents a morpholinyl radical, or
c) represents an isoxazolyl, pyrazolyl, thienyl or pyridinyl radical which may be mono- or polysubstituted by identical or different substituents from the group consisting of chlorine, carboxyl and a $C_1$-$C_3$-alkyl, $C_1$-$C_3$-alkoxy-$C_1$-$C_3$-alkyl, $C_3$-$C_6$-cycloalkyl- and/or a pyridinyl radical.

In the general formula (I-A), $R^{1b}$ may represent halogen, hydroxy, cyano, nitro and/or represents a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical which has 3 to 8 ring atoms, and n in the general formula (I-A) may represent 0-2.

In the general formula (I-A), $R^{1b}$ preferably represents halogen, cyano and/or represents a $C_1$-$C_6$-alkyl, $C_1$-$C_6$-alkoxy, halo-$C_1$-$C_6$-alkyl or halo-$C_1$-$C_6$-alkoxy radical, and n in the general formula (I-A) may represent 0-2.

In the general formula (I-A), n preferably represents 0.

In the general formula (I-A), $R^2$ may represent a $C_1$-$C_3$-alkyl or trifluoromethyl or a $C_3$- or $C_4$-cycloalkyl radical.

In the general formula (I-A), $R^2$ preferably represents a $C_1$-$C_3$-alkyl or trifluoromethyl radical.

In the general formula (I-A), $R^2$ more preferably represents a $C_1$-$C_3$-alkyl radical.

In the general formula (I-A), $R^2$ particularly preferably represents a methyl radical.

In the general formula (I-A), $R^3$ may represent a cyclopropyl, $C_1$-$C_3$-alkyl, $C_1$-$C_3$-alkoxy, amino, cyclopropylamino or a $C_1$-$C_3$-alkylamino radical.

In the general formula (I-A), $R^3$ preferably represents a $C_1$-$C_3$-alkyl or a $C_1$-$C_3$-alkylamino radical.

In the general formula (I-A), $R^3$ preferably represents a methyl or a $C_1$-$C_3$-alkylamino radical.

In the general formula (I-A), $R^3$ preferably represents a methyl radical.

In the general formula (I-A), $R^3$ more preferably represents a $C_1$-$C_3$-alkylamino radical.

In the general formula (I-A), $R^3$ particularly preferably represents a methylamino radical.

In the general formula (I-A), $R^4$ and $R^5$ independently of one another may
i) represent hydrogen, hydroxy, amino, aminocarbonyl, fluorine, chlorine, bromine or a trifluoromethyl, $C_1$-$C_6$-alkyl, $C_1$-$C_6$-alkoxy, $C_1$-$C_6$-alkylamino, $C_1$-$C_6$-alkylcarbonylamino or $C_1$-$C_6$-alkylaminocarbonyl radical, where the alkyl moiety of a radical listed under i) may be mono- or polysubstituted by identical or different radicals from the group consisting of amino, fluorine, hydroxy, carboxyl and a hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, or a monocyclic heterocyclyl radical which has 3 to 6 ring atoms, or
ii) represent cyano or nitro or
iii) represent a $C_1$-$C_6$-alkylaminosulphonyl, halo-$C_1$-$C_6$-alkyl or halo-$C_1$-$C_6$-alkoxy radical, where the alkyl moiety of a radical listed under iii) may be mono- or polysubstituted by identical or different radicals from the group consisting of amino, fluorine, hydroxy, carboxyl and a hydroxy-$C_1$-$C_6$-alkyl, $C_1$-$C_6$-alkoxy, $C_1$-$C_6$-alkylamino, amino-$C_1$-$C_6$-alkyl, $C_1$-$C_6$-alkoxy-$C_1$-$C_6$-alkyl or a monocyclic heterocyclyl radical which has 3 to 6 ring atoms,
or iv) represent a $C_3$-$C_{10}$-cycloalkyl radical which may be mono- or polysubstituted by identical or different substituents from the group consisting of halogen, amino, hydroxy, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl or halo-$C_1$-$C_6$-alkoxy radical, or v) represent a monocyclic heteroaryl radical which has 5 or 6 ring atoms and which may be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl or halo-$C_1$-$C_6$-alkoxy, $C_3$-$C_{10}$-cycloalkyl and/or a monocyclic heterocyclyl radical which has 3 to 8 ring atoms, or vi) represent a monocyclic heterocyclyl radical which has 3 to 8 ring atoms and which may be mono- or polysubstituted by identical or different substituents from the group consisting of halogen, amino, hydroxy, cyano, oxo, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl or halo-$C_1$-$C_6$-alkoxy, $C_3$-$C_{10}$-cycloalkyl and/or a monocyclic heterocyclyl radical which has 3 to 8 ring atoms, or vii) represent a phenyl radical which may be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl or halo-$C_1$-$C_6$-alkoxy, $C_3$-$C_{10}$-cycloalkyl and/or a monocyclic heterocyclyl radical which has 3 to 8 ring atoms.

In the general formula (I-A), $R^4$ and $R^5$ independently of one another preferably i) represent cyano or nitro or ii) represent a $C_1$-$C_6$-alkylaminosulphonyl, halo-$C_1$-$C_6$-alkyl or halo-$C_1$-$C_6$-alkoxy radical, where the alkyl moiety of a radical listed under iii) may be mono- or polysubstituted by identical or different radicals from the group consisting of amino, fluorine, hydroxy, carboxyl and a hydroxy-$C_1$-$C_6$-alkyl, $C_1$-$C_6$-alkoxy, $C_1$-$C_6$-alkylamino, amino-$C_1$-$C_6$-alkyl, $C_1$-$C_6$-alkoxy-$C_1$-$C_6$-alkyl or a monocyclic heterocyclyl radical which has 3 to 6 ring atoms, or iii) represent a $C_3$-$C_{10}$-cycloalkyl radical which may be mono- or polysubstituted by identical or different substituents from the group consisting of halogen, amino, hydroxy, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl or halo-$C_1$-$C_6$-alkoxy radical, or iv) represent a monocyclic heteroaryl radical which has 5 or 6 ring atoms and which may be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl or halo-$C_1$-$C_6$-alkoxy, $C_3$-$C_{10}$-cycloalkyl and/or a monocyclic heterocyclyl radical which has 3 to 8 ring atoms, or v) represent a monocyclic heterocyclyl radical which has 3 to 8 ring atoms and which may be mono- or polysubstituted by identical or different substituents from the group consisting of halogen, amino, hydroxy, cyano, oxo, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl or halo-$C_1$-$C_6$-alkoxy, $C_3$-$C_{10}$-cycloalkyl- and/or a monocyclic heterocyclyl radical which has 3 to 8 ring atoms, or vi) represent a phenyl radical which may be mono- or polysubstituted by identical or different substituents from the group consisting of halogen, amino, hydroxy, cyano, nitro, carboxyl and a $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl- or halo-$C_1$-$C_6$-alkoxy, $C_3$-$C_{10}$-cycloalkyl and/or a monocyclic heterocyclyl radical which has 3 to 8 ring atoms.

In the general formula (I-A), $R^4$ and $R^5$ independently of one another more preferably i) represent hydrogen or fluorine, chlorine, bromine or represent a $C_1$-$C_6$-alkoxy radical, where the alkyl moiety of the $C_1$-$C_6$-alkoxy radical may be mono- or polysubstituted by identical or different radicals from the group consisting of a monocyclic heterocyclyl radical which has 3 to 6 ring atoms, or ii) represent a halo-$C_1$-$C_6$-alkyl or halo-$C_1$-$C_6$-alkoxy radical, or iii) represent a $C_3$-$C_{10}$-cycloalkyl radical which may be mono- or polysubstituted by identical or different substituents from the group consisting of halogen, hydroxy, carboxyl and/or a $C_1$-$C_6$-alkyl radical, or iv) represent a monocyclic heteroaryl radical which has 5 or 6 ring atoms and which may be mono- or polysubstituted by identical or different substituents from the group consisting of halogen, hydroxy and a $C_1$-$C_6$-alkyl, $C_1$-$C_6$-alkoxy or hydroxy-$C_1$-$C_6$-alkyl radical, or v) represent a monocyclic heterocyclyl radical which has 3 to 8 ring atoms and which may be mono- or polysubstituted by identical or different substituents from the group consisting of halogen, hydroxy, carboxyl and a $C_1$-$C_6$-alkyl radical, or vi) represent a phenyl radical which may be mono- or polysubstituted by identical or different substituents from the group consisting of halogen, cyano, carboxyl and a $C_1$-$C_6$-alkyl, $C_1$-$C_6$-alkoxy, hydroxy-$C_1$-$C_6$-alkyl, or $C_1$-$C_6$-alkylaminosulphonyl radical.

In the general formula (I-A), $R^4$ and $R^5$ independently of one another more preferably i) represent hydrogen, chlorine or a $C_1$-$C_6$-alkoxy radical, where the alkyl moiety of the $C_1$-$C_6$-alkoxy radical may be mono- or polysubstituted by identical or different radicals from the group consisting of a monocyclic heterocyclyl radical which has 3 to 6 ring atoms, or ii) represent a halo-$C_1$-$C_6$-alkoxy radical, or iii) represent a $C_3$-$C_{10}$-cycloalkyl radical, or iv) represent a monocyclic heteroaryl radical which has 6 ring atoms, or v) represent a monocyclic heterocyclyl radical which has 3 to 6 ring atoms and which may be mono- or polysubstituted by identical or different substituents from the group consisting of a $C_1$-$C_6$-alkyl radical, or vi) represent a phenyl radical which may be mono- or polysubstituted by identical or different substituents from the group consisting of a $C_1$-$C_6$-alkylaminosulphonyl radical.

In the general formula (I-A), $R^4$ particularly preferably represents hydrogen, chlorine or a $C_1$-$C_3$-alkyoxy radical.

In the general formula (I-A), $R^4$ with extraordinary preference represents hydrogen or a methoxy radical.

In the general formula (I-A), $R^5$ particularly preferably i) represents hydrogen, chlorine or a $C_1$-$C_3$-alkoxy radical, where the alkyl moiety of the $C_1$-$C_3$-alkoxy radical may be mono- or polysubstituted by identical or different radicals from the group consisting of a morpholinyl or pyrrolidinyl radical, or ii) represents a trifluoromethoxy radical, or iii) represents a cyclopropyl radical, or iv) represents a pyridinyl radical, or v) represents a morpholinyl, piperazinyl or piperidinyl radical which may be mono- or polysubstituted by identical or different substituents from the group consisting of a $C_1$-$C_3$-alkyl radical.

In the general formula (I-A), $R^5$ with extraordinary preference i) represents a methoxy radical, or ii) represents a trifluoromethoxy radical, or iii) represents a cyclopropyl radical, or iv) represents a pyridinyl radical, or v) represents a morpholinyl radical.

$R^4$ and $R^5$ independently of one another may represent a monocyclic heterocyclyl radical. Preference is given here to heterocyclyl radicals having at least two heteroatoms.

In the general formula (I-A), $R^6$ and $R^7$ very particularly preferably represent hydrogen, $C_1$-$C_3$-alkyl, cyclopropyl, or di-$C_1$-$C_3$-alkyl-amino-$C_1$-$C_3$-alkyl.

In the general formula (I-A), $R^8$ very particularly preferably
represents hydroxy, $C_1$-$C_3$-alkyl, hydroxy-$C_1$-$C_3$-alkyl, trifluoromethyl, pyrrolidinyl, morpholinyl or piperidinyl.

In the general formula (I-A), $R^9$ very particularly preferably
represents $C_1$-$C_3$-alkyl.

In the general formula (I) it is possible that X represents an oxygen or sulphur atom.

In the general formula (I) X preferably represents an oxygen atom.

In the general formula (I) it is possible that A represents a monocyclic heteroaryl ring having 5 or 6 ring atoms or represents a phenyl ring.

In the general formula (I) A preferably represents a monocyclic heteroaryl ring having 6 ring atoms or represents a phenyl ring.

In the general formula (I) A more preferably represents a pyridyl ring or a phenyl ring.

In the general formula (I) A very preferably represents pyrid-3-yl.

In the general formula (I) A very preferably represents a phenyl ring.

In the general formula (I) it is possible that $R^{1a}$ represents hydrogen, halogen, cyano, carboxyl, amino or aminosulphonyl,
or
represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical,
or
represents a monocyclic heterocyclyl radical having 3 to 8 ring atoms, which may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl, —$NR^6C(=O)$—$R^9$, —$C(=O)$—$NR^6R^7$, —$C(=O)$—$R^8$, —$S(=O)_2$—$NR^6R^7$, —$S(=O)$—$R^9$, —$S(=O)_2$—$R^9$, —$NH$—$S(=O)_2$—$R^9$, and/or a monocyclic heterocyclyl radical having 3 to 8 ring atoms,
or
represents a monocyclic heteroaryl radical having 5 or 6 ring atoms, which may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —$C(=O)$—$NR^6R^7$, —$C(=O)$—$R^8$, —$S(=O)_2$—$NR^6R^7$, —$S(=O)$—$R^9$, —$S(=O)_2$—$R^9$, —$NH$—$S(=O)_2$—$R^9$, and/or by a monocyclic heterocyclyl radical having 3 to 8 ring atoms, and/or by a monocyclic heteroaryl radical having 5 or 6 ring atoms, and/or by a phenyl radical which for its part may optionally be mono- or polysubstituted by identical or different substituents from the group consisting of halogen, $C_1$-$C_3$-alkyl and/or $C_1$-$C_3$-alkoxy,
or
represents a phenyl radical, which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, —$C(=O)NR^6R^7$, —$C(=O)$ $R^8$, $C_1$-$C_3$-alkylsulphinyl, $C_1$-$C_3$-alkylsulphonyl, —$S(=O)_2$ $NH_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl and/or a monocyclic heterocyclyl radical having 3 to 8 ring atoms, and/or a monocyclic heteroaryl radical having 5 or 6 ring atoms and which for its part may optionally be mono- or polysubstituted by identical or different substituents from the group consisting of halogen, $C_1$-$C_3$-alkyl and/or $C_1$-$C_3$-alkoxy.

In the general formula (I) $R^{1a}$ preferably represents hydrogen, halogen, cyano, carboxyl, amino or aminosulphonyl,
or
represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical,
or
represents a monocyclic heterocyclyl radical having 4 to 7 ring atoms, which may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl, —$NR^6C(=O)$—$R^9$, —$C(=O)$—$NR^6R^7$, —$C(=O)$—$R^8$, —$S(=O)_2$—$NR^6R^7$, —$S(=O)$—$R^9$, —$S(=O)_2$—$R^9$, —NH—$S(=O)_2$—$R^9$, and by a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —$C(=O)$—$NR^6R^7$, —$C(=O)$—$R^8$, —$S(=O)_2$—$NR^6R^7$, —$S(=O)$—$R^9$, —$S(=O)_2$—$R^9$, —NH—$S(=O)_2$—$R^9$, and by a monocyclic heterocyclyl radical having 4 to 7 ring atoms and/or by a monocyclic heteroaryl radical having 5 or 6 ring atoms and/or by a phenyl radical which for its part may optionally be mono- or polysubstituted by identical or different substituents from the group consisting of halogen, $C_1$-$C_3$-alkyl and/or $C_1$-$C_3$-alkoxy, or represents a phenyl radical, which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, —$C(=O)NR^6R^7$, $C(=O)$ $R^8$, $C_1$-$C_3$-alkylsulphinyl, $C_1$-$C_3$-alkylsulphonyl, —$S(=O)_2NH_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl and/or a monocyclic heterocyclyl radical having 4 to 7 ring atoms and/or a monocyclic heteroaryl radical having 5 or 6 ring atoms and which for its part may optionally be mono- or polysubstituted by identical or different substituents from the group consisting of halogen, $C_1$-$C_3$-alkyl and/or $C_1$-$C_3$-alkoxy.

In the general formula (I) $R^{1a}$ very preferably represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_3$-alkylamino, $C_1$-$C_3$-alkylcarbonylamino, $C_1$-$C_3$-alkylamino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_1$-$C_3$-alkylcarbonyl or $C_1$-$C_4$-alkoxycarbonyl radical, or represents a monocyclic heterocyclyl radical having 4 to 7 ring atoms, which may optionally be mono- or polysubstituted by identical or different substituents from the group consisting of halogen, cyano, nitro, hydroxy, amino, oxo, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, phenyl, halophenyl, phenyl-$C_1$-$C_3$-alkyl, pyridinyl, —$NR^6C(=O)$—$R^9$, —$C(=O)$—$NR^6R^7$, —$C(=O)$—$R^8$, —$S(=O)_2$—$NR^6R^7$, —$S(=O)$—$R^9$, —$S(=O)_2$—$R^9$, —NH—$S(=O)_2$—$R^9$, and/or by a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, hydroxy, amino, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —$C(=O)$—$NR^6R^7$, —$C(=O)$—$R^8$, —$S(=O)_2$—$NR^6R^7$, —$S(=O)$—$R^9$, —$S(=O)_2$—$R^9$, —NH—$S(=O)_2$—$R^9$, and/or by a monocyclic heterocyclyl radical having 4 to 7 ring atoms, and/or by a monocyclic heteroaryl radical having 5 or 6 ring atoms, and/or by a phenyl radical which for its part may optionally be mono- or polysubstituted by identical or different substituents from the group consisting of fluorine, chlorine, bromine, methyl or methoxy, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, —$C(=O)NR^6R^7$, $C(=O)$ $R^8$, $C_1$-$C_3$-alkylsulphinyl, $C_1$-$C_3$-alkylsulphonyl, —$S(=O)_2NH_2$, $C_1$-$C_3$-alkylsulphonylamino, $C_1$-$C_3$-alkylaminosulphonyl, $C_3$-$C_6$-cycloalkylaminosulphonyl, fluoro-$C_1$-$C_3$-alkyl, fluoro-$C_1$-$C_3$-alkoxy, hydroxy-$C_1$-$C_3$-alkyl, $C_3$-$C_6$-cycloalkyl and/or a monocyclic heterocyclyl radical having 4 to 7 ring atoms, and/or a monocyclic heteroaryl radical having 5 or 6 ring atoms and which for its part may optionally be mono- or polysubstituted by identical or different substituents from the group consisting of fluorine, chlorine, bromine, methyl or methoxy.

In the general formula (I) $R^{1a}$ particularly preferably represents a monocyclic heterocyclyl radical having 4 to 7 ring atoms, which may optionally be mono- or polysubstituted by identical or different substituents from the group consisting of halogen, cyano, nitro, hydroxy, amino, oxo, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, phenyl, halophenyl, phenyl-$C_1$-$C_3$-alkyl, pyridinyl, —$NR^6C(=O)$—$R^9$, —$C(=O)$—$NR^6R^7$, —$C(=O)$—$R^8$, —$S(=O)_2$—$NR^6R^7$, —$S(=O)$—$R^9$, —$S(=O)_2$—$R^9$, —NH—$S(=O)_2$—$R^9$, and/or by a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, hydroxy, amino, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —$C(=O)$—$NR^6R^7$, —$C(=O)$—$R^8$, —$S(=O)_2$—$NR^6R^7$, —$S(=O)$—$R^9$, —$S(=O)_2$—$R^9$, —NH—$S(=O)_2$—$R^9$, and/or by a monocyclic heterocyclyl radical having 4 to 7 ring atoms, and/or by a monocyclic heteroaryl radical having 5 or 6 ring atoms, and/or by a phenyl radical which for its part may optionally be mono- or polysubstituted by identical or different substituents from the group consisting of fluorine, chlorine, bromine, methyl or methoxy, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, —C(=O)NR$^6$R$^7$, C(=O) R$^8$, C$_1$-C$_3$-alkylsulphinyl, C$_1$-C$_3$-alkylsulphonyl, —S(=O)$_2$NH$_2$, C$_1$-C$_3$-alkylsulphonylamino, C$_1$-C$_3$-alkylaminosulphonyl, C$_3$-C$_6$-cycloalkylaminosulphonyl, fluoro-C$_1$-C$_3$-alkyl, fluoro-C$_1$-C$_3$-alkoxy, hydroxy-C$_1$-C$_3$-alkyl, C$_3$-C$_6$-cycloalkyl and/or a monocyclic heterocyclyl radical having 4 to 7 ring atoms, and/or a monocyclic heteroaryl radical having 5 or 6 ring atoms and which for its part may optionally be mono- or polysubstituted by identical or different substituents from the group consisting of fluorine, chlorine, bromine, methyl or methoxy.

In the general formula (I) R$^{1a}$ further particularly preferably represents hydrogen, halogen, cyano, carboxyl, amino or aminosulphonyl, or represents a C$_1$-C$_6$-alkoxy, C$_1$-C$_3$-alkoxy-C$_1$-C$_3$-alkyl, C$_1$-C$_3$-alkoxy-C$_2$-C$_3$-alkoxy, C$_1$-C$_3$-alkylamino, C$_1$-C$_3$-alkylcarbonylamino, C$_1$-C$_3$-alkylamino-C$_1$-C$_3$-alkyl, hydroxy-C$_1$-C$_3$-alkyl, fluoro-C$_1$-C$_3$-alkyl, fluoro-C$_1$-C$_3$-alkoxy, C$_1$-C$_3$-alkylcarbonyl or C$_1$-C$_4$-alkoxycarbonyl radical.

In the general formula (I) R$^{1a}$ further particularly preferably represents a monocyclic heterocyclyl radical having 4 to 7 ring atoms, which may optionally be mono- or polysubstituted by identical or different substituents from the group consisting of halogen, cyano, nitro, hydroxy, amino, oxo, carboxyl, C$_1$-C$_3$-alkyl, C$_1$-C$_3$-alkoxy, C$_1$-C$_2$-alkoxy-C$_1$-C$_2$-alkyl, hydroxy-C$_1$-C$_3$-alkyl, C$_1$-C$_3$-alkylamino, amino-C$_1$-C$_3$-alkyl, fluoro-C$_1$-C$_3$-alkyl, fluoro-C$_1$-C$_3$-alkoxy, C$_3$-C$_6$-cycloalkyl, phenyl, halophenyl, phenyl-C$_1$-C$_3$-alkyl, pyridinyl, —NR$^6$C(=O)—R$^9$, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical having 4 to 7 ring atoms.

In the general formula (I) R$^{1a}$ further particularly preferably represents a monocyclic heteroaryl radical having 5 or 6 ring atoms, which may optionally be mono- or polysubstituted by identical or different substituents from the group consisting of halogen, hydroxy, amino, cyano, nitro, carboxyl, C$_1$-C$_3$-alkyl, C$_1$-C$_3$-alkoxy, C$_1$-C$_2$-alkoxy-C$_1$-C$_2$-alkyl, C$_1$-C$_3$-alkylamino, amino-C$_1$-C$_3$-alkyl, fluoro-C$_1$-C$_3$-alkyl, fluoro-C$_1$-C$_3$-alkoxy, C$_3$-C$_6$-cycloalkyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical having 4 to 7 ring atoms, and/or by a monocyclic heteroaryl radical having 5 or 6 ring atoms, and/or by a phenyl radical which for its part may optionally be mono- or polysubstituted by identical or different substituents from the group consisting of fluorine, chlorine, bromine, methyl or methoxy.

In the general formula (I) R$^{1a}$ further particularly preferably represents a phenyl radical, which may optionally be mono- or polysubstituted by identical or different substituents from the group consisting of halogen, amino, hydroxy, cyano, nitro, carboxyl, C$_1$-C$_3$-alkyl, C$_1$-C$_3$-alkoxy, C$_1$-C$_2$-alkoxy-C$_1$-C$_2$-alkyl, C$_1$-C$_3$-alkylamino, amino-C$_1$-C$_3$-alkyl, —C(=O)NR$^6$R$^7$, C(=O) R$^8$, C$_1$-C$_3$-alkylsulphinyl, C$_1$-C$_3$-alkylsulphonyl, —S(=O)$_2$NH$_2$, C$_1$-C$_3$-alkylsulphonylamino, C$_1$-C$_3$-alkylaminosulphonyl, C$_3$-C$_6$-cycloalkylaminosulphonyl, fluoro-C$_1$-C$_3$-alkyl, fluoro-C$_1$-C$_3$-alkoxy, hydroxy-C$_1$-C$_3$-alkyl, C$_3$-C$_6$-cycloalkyl and/or a monocyclic heterocyclyl radical having 4 to 7 ring atoms, and/or a monocyclic heteroaryl radical having 5 or 6 ring atoms and which for its part may optionally be mono- or polysubstituted by identical or different substituents from the group consisting of fluorine, chlorine, bromine, methyl or methoxy.

In the general formula (I) R$^{1a}$ very preferably represents hydrogen or chlorine, or represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, chlorine, cyano, nitro, hydroxy, oxo, C$_1$-C$_3$-alkyl, C$_1$-C$_3$-alkoxy, C$_1$-C$_2$-alkoxy-C$_1$-C$_2$-alkyl, hydroxy-C$_1$-C$_3$-alkyl, dimethylamino, trifluoromethyl, difluoroethyl, trifluoroethyl, trifluoromethoxy, cyclopropyl, phenyl, fluorophenyl, phenyl-C$_1$-C$_3$-alkyl, pyridinyl, —NR$^6$C(=O)—R$^9$, —C(=O)—NR$^6$R$^7$, —C(=O)—R$^8$, —S(=O)$_2$—NR$^6$R$^7$, —S(=O)—R$^9$, —S(=O)$_2$—R$^9$ and/or —NH—S(=O)$_2$—R$^9$, or represents tetrazolyl, or represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, amino, cyano, nitro, C$_1$-C$_3$-alkyl, C$_1$-C$_3$-alkoxy, C$_1$-C$_2$-alkoxy-C$_1$-C$_2$-alkyl, dimethylamino, trifluoromethyl, difluoroethyl, trifluoroethyl, trifluoromethoxy, cyclopropyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, pyridinyl, phenyl, and/or fluorophenyl, or represents phenyl, which may optionally be mono- or polysubstituted by identical or different substituents from the group consisting of fluorine, chlorine, amino, hydroxy, cyano, nitro, carboxyl, C$_1$-C$_3$-alkyl, C$_1$-C$_3$-alkoxy, C$_1$-C$_2$-alkoxy-C$_1$-C$_2$-alkyl, dimethylamino, —C(=O)NR$^6$R$^7$, C(=O) R$^8$, C$_1$-C$_3$-alkylsulphinyl, C$_1$-C$_3$-alkylsulphonyl, —S(=O)$_2$NH$_2$, C$_1$-C$_3$-alkylsulphonylamino, C$_1$-C$_3$-alkylaminosulphonyl, C$_3$-C$_6$-cycloalkylaminosulphonyl, trifluoromethyl, difluoroethyl, trifluoroethyl, trifluoromethoxy, hydroxy-C$_1$-C$_3$-alkyl, cyclopropyl, morpholino and/or pyridinyl.

In the general formula (I) R$^{1a}$ further very particularly preferably represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, chlorine, cyano, nitro, hydroxy, oxo, C$_1$-C$_3$-alkyl, C$_1$-C$_3$-alkoxy, C$_1$-C$_2$-alkoxy-C$_1$-C$_2$-alkyl, hydroxy-C$_1$-C$_3$-alkyl, dimethylamino, trifluoromethyl, difluoroethyl, trifluoroethyl, trifluoromethoxy, cyclopropyl, phenyl, fluorophenyl, phenyl-C$_1$-C$_3$-alkyl, pyridinyl, —NR$^6$C(=O)—R$^9$, —C(=O)—NR$^6$R$^7$, —C(=O)—R$^8$, —S(=O)$_2$—NR$^6$R$^7$, —S(=O)—R$^9$, —S(=O)$_2$—R$^9$ and/or —NH—S(=O)$_2$—R$^9$, or represents tetrazolyl, or represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, amino, cyano, nitro, C$_1$-C$_3$-alkyl, C$_1$-C$_3$-alkoxy, C$_1$-C$_2$-alkoxy-C$_1$-C$_2$-alkyl, dimethylamino, trifluoromethyl, difluoroethyl, trifluoroethyl, trifluoromethoxy, cyclopropyl, —C(=O)—NR$^6$R$^7$, —C(=O)—

$R^8$, —S(═O)$_2$—NR$^6$R$^7$, —S(═O)—R$^9$, —S(═O)$_2$—R$^9$, —NH—S(═O)$_2$—R$^9$, pyridinyl, phenyl, and/or fluorophenyl, or represents phenyl which may optionally be mono- or polysubstituted by identical or different substituents from the group consisting of fluorine, chlorine, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, dimethylamino, —C(═O)NR$^6$R$^7$, C(═O) R$^8$, $C_1$-$C_3$-alkylsulphinyl, $C_1$-$C_3$-alkylsulphonyl, —S(═O)$_2$NH$_2$, $C_1$-$C_3$-alkylsulphonylamino, $C_1$-$C_3$-alkylaminosulphonyl, $C_3$-$C_6$-cycloalkylaminosulphonyl, trifluoromethyl, difluoroethyl, trifluoroethyl, trifluoromethoxy, hydroxy-$C_1$-$C_3$-alkyl, cyclopropyl, morpholino and/or pyridinyl.

In the general formula (I) $R^{1a}$ further very particularly preferably represents hydrogen or chlorine.

In the general formula (I) $R^{1a}$ further very particularly preferably represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, chlorine, cyano, nitro, hydroxy, oxo, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, dimethylamino, trifluoromethyl, difluoroethyl, trifluoroethyl, trifluoromethoxy, cyclopropyl, phenyl, fluorophenyl, phenyl-$C_1$-$C_3$-alkyl, pyridinyl, —NR$^6$C(═O)—R$^9$, —C(═O)—NR$^6$R$^7$, —C(═O)—R$^8$, —S(═O)$_2$—NR$^6$R$^7$, —S(═O)—R$^9$, —S(═O)$_2$—R$^9$ and/or —NH—S(═O)$_2$—R$^9$.

In the general formula (I) $R^{1a}$ further very particularly preferably represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, amino, cyano, nitro, $C_1$-$C_3$-alkyl, $C_1$-$C_3$-alkoxy, $C_1$-$C_2$-alkoxy-$C_1$-$C_2$-alkyl, dimethylamino, trifluoromethyl, difluoroethyl, trifluoroethyl, trifluoromethoxy, cyclopropyl, —C(═O)—NR$^6$R$^7$, —C(═O)—R$^8$, —S(═O)$_2$—NR$^6$R$^7$, —S(═O)—R$^9$, —S(═O)$_2$—R$^9$, —NH—S(═O)$_2$—R$^9$, pyridinyl, phenyl, and/or fluorophenyl.

In the general formula (I) $R^{1a}$ further very particularly preferably represents phenyl, which may optionally be mono- or polysubstituted by identical or different substituents from the group consisting of fluorine, chlorine, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, dimethylamino, —C(═O)NR$^6$R$^7$, C(═O) R$^8$, $C_1$-$C_3$-alkylsulphinyl, $C_1$-$C_3$-alkylsulphonyl, —S(═O)$_2$NH$_2$, $C_1$-$C_3$-alkylsulphonylamino, $C_1$-$C_3$-alkylaminosulphonyl, $C_3$-$C_6$-cycloalkylaminosulphonyl, trifluoromethyl, difluoroethyl, trifluoroethyl, trifluoromethoxy, hydroxy-$C_1$-$C_3$-alkyl, cyclopropyl, morpholino and/or pyridinyl.

In the general formula (I) $R^{1a}$ very particularly preferably represents hydrogen or chlorine, or represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, hydroxy, oxo, $C_1$-$C_3$-alkyl, methoxy, hydroxy-$C_1$-$C_3$-alkyl, dimethylamino, difluoroethyl, trifluoroethyl, benzyl, —NR$^6$C(═O)—R$^9$, —C(═O)—NR$^6$R$^7$, —C(═O)—R$^8$, and/or —S(═O)$_2$—R$^9$, or represents tetrazolyl, or represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, cyano, $C_1$-$C_2$-alkyl, methoxy, methoxymethyl, trifluoromethyl, cyclopropyl, —C(═O)—R$^8$, pyridinyl, phenyl, and/or fluorophenyl, or represents phenyl which may optionally be mono- or polysubstituted by identical or different substituents from the group consisting of fluorine, chlorine, hydroxy, cyano, nitro, carboxyl, $C_1$-$C_3$-alkyl, methoxy, —C(═O)NR$^6$R$^7$, C(═O) R$^8$, $C_1$-$C_3$-alkylsulphinyl, $C_1$-$C_3$-alkylsulphonyl, —S(═O)$_2$NH$_2$, $C_1$-$C_3$-alkylsulphonylamino, $C_1$-$C_3$-alkylaminosulphonyl, $C_3$-$C_6$-cycloalkylaminosulphonyl, trifluoromethyl, trifluoromethoxy, hydroxy-$C_1$-$C_3$-alkyl, cyclopropyl, and/or morpholino.

In the general formula (I) $R^{1a}$ further very particularly preferably represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, hydroxy, oxo, $C_1$-$C_3$-alkyl, methoxy, hydroxy-$C_1$-$C_3$-alkyl, dimethylamino, difluoroethyl, trifluoroethyl, benzyl, —NR$^6$C(═O)—R$^9$, —C(═O)—NR$^6$R$^7$, —C(═O)—R$^8$, and/or —S(═O)$_2$—R$^9$, or represents tetrazolyl, or represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, cyano, $C_1$-$C_2$-alkyl, methoxy, methoxymethyl, trifluoromethyl, cyclopropyl, —C(═O)—R$^8$, pyridinyl, phenyl, and/or fluorophenyl, or represents phenyl, which may optionally be mono- or polysubstituted by identical or different substituents from the group consisting of fluorine, chlorine, hydroxy, cyano, nitro, carboxyl, $C_1$-$C_3$-alkyl, methoxy, —C(═O)NR$^6$R$^7$, C(═O) R$^8$, $C_1$-$C_3$-alkylsulphinyl, $C_1$-$C_3$-alkylsulphonyl, —S(═O)$_2$NH$_2$, $C_1$-$C_3$-alkylsulphonylamino, $C_1$-$C_3$-alkylaminosulphonyl, $C_3$-$C_6$-cycloalkylaminosulphonyl, trifluoromethyl, trifluoromethoxy, hydroxy-$C_1$-$C_3$-alkyl, cyclopropyl, and/or morpholino.

In the general formula (I) $R^{1a}$ further very particularly preferably represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, hydroxy, oxo, $C_1$-$C_3$-alkyl, methoxy, hydroxy-$C_1$-$C_3$-alkyl, dimethylamino, difluoroethyl, trifluoroethyl, benzyl, —NR$^6$C(═O)—R$^9$, —C(═O)—NR$^6$R$^7$, —C(═O)—R$^8$, and/or —S(═O)$_2$—R$^9$, or represents tetrazolyl, or represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, cyano, $C_1$-$C_2$-alkyl, methoxy, methoxymethyl, trifluoromethyl, cyclopropyl, —C(=O)—R$^8$, pyridinyl, phenyl, and/or fluorophenyl, or represents phenyl, which may optionally be mono- or polysubstituted by identical or different substituents from the group consisting of fluorine, chlorine, hydroxy, cyano, nitro, carboxyl, C$_1$-C$_3$-alkyl, C$_1$-C$_3$-methoxy, —C(=O)NR$^6$R$^7$, C(=O) R$^8$, C$_1$-C$_3$-alkylsulphinyl, C$_1$-C$_3$-alkylsulphonyl, —S(=O)$_2$NH$_2$, C$_1$-C$_3$-alkylsulphonylamino, C$_1$-C$_3$-alkylaminosulphonyl, C$_3$-C$_6$-cycloalkylaminosulphonyl, trifluoromethyl, trifluoromethoxy, hydroxy-C$_1$-C$_3$-alkyl, cyclopropyl, and/or morpholino.

In the general formula (I) R$^{1a}$ further exceptionally preferably represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, hydroxy, oxo, C$_1$-C$_3$-alkyl, methoxy, hydroxy-C$_1$-C$_3$-alkyl, dimethylamino, difluoroethyl, trifluoroethyl, benzyl, —NR$^6$C(=O)—R$^9$, —C(=O)—NR$^6$R$^7$, —C(=O)—R$^8$, and/or —S(=O)$_2$—R$^9$.

In the general formula (I) R$^{1a}$ further exceptionally preferably represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, cyano, C$_1$-C$_2$-alkyl, methoxy, methoxymethyl, trifluoromethyl, cyclopropyl, —C(=O)—R$^8$, pyridinyl, phenyl, and/or fluorophenyl.

In the general formula (I) R$^{1a}$ further exceptionally preferably represents phenyl, which may optionally be mono- or polysubstituted by identical or different substituents from the group consisting of fluorine, chlorine, hydroxy, cyano, nitro, carboxyl, C$_1$-C$_3$-alkyl, C$_1$-C$_3$-methoxy, —C(=O)NR$^6$R$^7$, C(=O) R$^8$, C$_1$-C$_3$-alkylsulphinyl, C$_1$-C$_3$-alkylsulphonyl, —S(=O)$_2$NH$_2$, C$_1$-C$_3$-alkylsulphonylamino, C$_1$-C$_3$-alkylaminosulphonyl, C$_3$-C$_6$-cycloalkylaminosulphonyl, trifluoromethyl, trifluoromethoxy, hydroxy-C$_1$-C$_3$-alkyl, cyclopropyl, and/or morpholino.

In the general formula (I) R$^{1a}$ further exceptionally preferably represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, hydroxy, oxo, C$_1$-C$_3$-alkyl, methoxy, hydroxy-C$_1$-C$_3$-alkyl, dimethylamino, difluoroethyl, trifluoroethyl, benzyl, —NR$^6$C(=O)—R$^9$, —C(=O)—NR$^6$R$^7$, —C(=O)—R$^8$, and/or —S(=O)$_2$—R$^9$, or represents isoxazolyl or pyrazolyl, which may optionally be mono- or polysubstituted by identical or different C$_1$-C$_2$-alkyl substituents.

In the general formula (I) R$^{1a}$ further exceptionally preferably represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, hydroxy, oxo, C$_1$-C$_3$-alkyl, methoxy, hydroxy-C$_1$-C$_3$-alkyl, dimethylamino, difluoroethyl, trifluoroethyl, benzyl, —NR$^6$C(=O)—R$^9$, —C(=O)—NR$^6$R$^7$, —C(=O)—R$^8$, and/or —S(=O)$_2$—R$^9$.

In the general formula (I) R$^{1a}$ further exceptionally preferably represents isoxazolyl or pyrazolyl, which may optionally be mono- or polysubstituted by identical or different C$_1$-C$_2$-alkyl substituents.

In the general formula (I) R$^{1a}$ further exceptionally preferably represents piperazinyl, pyrrolidinyl, piperidinyl, morpholinyl, thiomorpholinyl or azetidinyl, which may optionally be mono- or polysubstituted by identical or different substituents from the group consisting of hydroxy, oxo, C$_1$-C$_3$-alkyl, methoxy, dimethylamino, difluoroethyl, trifluoroethyl, —NR$^6$C(=O)—R$^9$, —C(=O)—NR$^6$R$^7$, and/or —C(=O)—R$^8$.

In the general formula (I) R$^{1a}$ further exceptionally preferably represents piperazinyl, pyrrolidinyl, piperidinyl, morpholinyl, thiomorpholinyl or azetidinyl, which may optionally be monosubstituted by C$_1$-C$_3$-alkyl.

In the general formula (I) R$^{1a}$ further exceptionally preferably represents piperazinyl, pyrrolidinyl, piperidinyl, morpholinyl, thiomorpholinyl or azetidinyl, which may optionally be monosubstituted by methyl.

In the general formula (I) R$^{1a}$ further exceptionally preferably represents piperazinyl which may optionally be mono- or polysubstituted by identical or different substituents from the group consisting of hydroxy, oxo, C$_1$-C$_3$-alkyl, methoxy, dimethylamino, difluoroethyl, trifluoroethyl, —NR$^6$C(=O)—R$^9$, —C(=O)—NR$^6$R$^7$, and/or —C(=O)—R$^8$.

In the general formula (I) R$^{1b}$ and R$^{1c}$ preferably and independently of one another represent hydrogen, halogen, hydroxy, cyano, nitro or represent a C$_1$-C$_6$-alkyl, C$_1$-C$_6$-alkoxy, C$_1$-C$_6$-alkoxy-C$_1$-C$_6$-alkyl, halo-C$_1$-C$_6$-alkyl, halo-C$_1$-C$_6$-alkoxy, C$_3$-C$_{10}$-cycloalkyl radical, and/or a monocyclic heterocycyl radical having 4 to 7 ring atoms.

In the general formula (I) R$^{1b}$ preferably represents hydrogen, halogen, hydroxy, cyano, nitro or represents a C$_1$-C$_6$-alkyl, C$_1$-C$_6$-alkoxy, C$_1$-C$_6$-alkoxy-C$_1$-C$_6$-alkyl, halo-C$_1$-C$_6$-alkyl, halo-C$_1$-C$_6$-alkoxy, C$_3$-C$_{10}$-cycloalkyl radical, or a monocyclic heterocycyl radical having 4 to 7 ring atoms.

In the general formula (I) R$^{1b}$ very preferably represents hydrogen, halogen, hydroxy, cyano, nitro or represents a C$_1$-C$_3$-alkyl, C$_1$-C$_3$-alkoxy, fluoro-C$_1$-C$_3$-alkyl or fluoro-C$_1$-C$_3$-alkoxy radical.

In the general formula (I) R$^{1c}$ very preferably represents hydrogen, fluorine, chlorine, bromine or cyano.

In the general formula (I) R$^{1b}$ very preferably represents hydrogen, fluorine, bromine or cyano.

In the general formula (I) R$^{1c}$ very preferably represents hydrogen or bromine.

In the general formula (I) R$^{1c}$ very preferably represents hydrogen.

In the general formula (I) R$^{1b}$ very preferably represents hydrogen, fluorine, bromine or cyano and R$^{1c}$ represents hydrogen.

In the general formula (I) it is possible that R$^2$ represents a C$_1$-C$_3$-alkyl or trifluoromethyl or a C$_3$- or C$_4$-cycloalkyl radical.

In the general formula (I) R$^2$ preferably represents methyl, ethyl or isopropyl.

In the general formula (I) R$^2$ very preferably represents methyl or ethyl.

In the general formula (I) R$^2$ exceptionally preferably represents methyl.

In the general formula (I) R$^3$ preferably represents cyclopropyl, C$_1$-C$_3$-alkyl, C$_1$-C$_3$-alkoxy, amino, cyclopropylamino or C$_1$-C$_3$-alkylamino.

In the general formula (I) $R^3$ very preferably represents cyclopropyl, $C_1$-$C_3$-alkyl, $C_1$-$C_3$-alkoxy, cyclopropylamino or $C_1$-$C_3$-alkylamino.

In the general formula (I) $R^3$ very preferably represents cyclopropyl, methyl, ethyl, methoxy, ethoxy, cyclopropylamino, methylamino or ethylamino In the general formula (I) $R^3$ exceptionally preferably represents methylamino.

In the general formula (I) it is possible that $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, monocyclic heterocyclyl having 3 to 8 ring atoms and/or monocyclic heteroaryl having 5 or 6 ring atoms, where the monocyclic heterocyclyl and heteroaryl radicals mentioned for their part may optionally be monosubstituted by $C_1$-$C_3$-alkyl, or represent $C_3$-$C_{10}$-cycloalkyl which may optionally be mono- or polysubstituted by identical or different substituents from the group consisting of halogen, amino, hydroxy, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical having 3 to 8 ring atoms, or represent monocyclic heteroaryl which has 5 or 6 ring atoms which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O) $R^8$, —S(=O)$_2$$R^9$, —NR$^6$R$^7$, and/or a monocyclic heterocyclyl radical having 3 to 8 ring atoms, or represent monocyclic heterocyclyl having 3 to 8 ring atoms which may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, —C(=O) $R^8$, —S(=O)$_2$$R^9$, —NR$^6$R$^7$, and/or a monocyclic heterocyclyl radical having 3 to 8 ring atoms, or represent phenyl which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl and/or a monocyclic heterocyclyl radical having 3 to 8 ring atoms.

In the general formula (I) $R^4$ and $R^5$ preferably and independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, a monocyclic heterocyclyl radical having 4 to 7 ring atoms, and/or a monocyclic heteroaryl radical having 5 or 6 ring atoms, where the monocyclic heterocyclyl and heteroaryl radicals mentioned for their part may optionally be monosubstituted by $C_1$-$C_3$-alkyl, or represents a $C_3$-$C_{10}$-cycloalkyl radical, which may optionally be mono- or polysubstituted by identical or different substituents from the group consisting of halogen, amino, hydroxy, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O) $R^8$, —S(=O)$_2$$R^9$, —NR$^6$R$^7$, and/or a monocyclic heterocyclyl radical having 4 to 7 ring atoms, or represents a monocyclic heterocyclyl radical having 4 to 7 ring atoms, which may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, —C(=O) $R^8$, —S(=O)$_2$$R^9$, —NR$^6$R$^7$, and/or a monocyclic heterocyclyl radical having 4 to 7 ring atoms.

In the general formula (I) $R^4$ preferably represents a $C_3$-$C_{10}$-cycloalkyl radical, which may optionally be mono- or polysubstituted by identical or different substituents from the group consisting of halogen, amino, hydroxy, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical having 4 to 7 ring atoms, or represents a monocyclic heteraryl radical having 5 or 6 ring atoms, which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$- alkoxy, $C_3$-$C_{10}$-cycloalkyl, —C(=O) $R^8$, —S(=O)$_2R^9$, —NR$^6R^7$, and/or a monocyclic heterocyclyl radical having 4 to 7 ring atoms, or represents a monocyclic heterocyclyl radical having 4 to 7 ring atoms, which may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, —C(=O) $R^8$, —S(=O)$_2R^9$, —NR$^6R^7$, and/or a monocyclic heterocyclyl radical having 4 to 7 ring atoms, and $R^5$ preferably represents hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represents $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, a monocyclic heterocyclyl radical having 4 to 7 ring atoms, and/or a monocyclic heteroaryl radical having 5 or 6 ring atoms, where the monocyclic heterocyclyl and heteroaryl radicals mentioned for their part may optionally be mono-substituted by $C_1$-$C_3$-alkyl.

In the general formula (I) $R^4$ preferably represents hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represents $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, a monocyclic heterocyclyl radical having 4 to 7 ring atoms, and/or a monocyclic heteroaryl radical having 5 or 6 ring atoms, where the monocyclic heterocyclyl and heteroaryl radicals mentioned for their part may optionally be mono-substituted by $C_1$-$C_3$-alkyl, and $R^5$ preferably represents a $C_3$-$C_{10}$-cycloalkyl radical, which may optionally be mono- or polysubstituted by identical or different substituents from the group consisting of halogen, amino, hydroxy, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O) $R^8$, —S(=O)$_2R^9$, —NR$^6R^7$, and/or a monocyclic heterocyclyl radical having 4 to 7 ring atoms, or represents a monocyclic heterocyclyl radical having 4 to 7 ring atoms, which may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, —C(=O) $R^8$, —S(=O)$_2R^9$, —NR$^6R^7$, and/or a monocyclic heterocyclyl radical having 4 to 7 ring atoms.

In the general formula (I) $R^4$ and $R^5$ particularly preferably and independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_3$-alkyl, $C_1$-$C_3$-alkoxy, $C_1$-$C_3$-alkylamino, which may optionally be mono- or polysubstituted by identical or different substituents from the group consisting of halogen, amino, hydroxy, carboxyl, hydroxy-$C_1$-$C_3$-alkyl, $C_1$-$C_3$-alkoxy, $C_1$-$C_3$-alkylamino, amino-$C_1$-$C_3$-alkyl, a monocyclic heterocyclyl radical having 4 to 7 ring atoms, and/or a monocyclic heteroaryl radical having 5 or 6 ring atoms, where the monocyclic heterocyclyl and heteroaryl radicals mentioned for their part may optionally be mono-substituted by $C_1$-$C_3$-alkyl, or represents a $C_3$-$C_7$-cycloalkyl radical, which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O) $R^8$, —S(=O)$_2R^9$, —NR$^6R^7$, and/or a monocyclic heterocyclyl radical having 4 to 7 ring atoms, or represents a monocyclic heterocyclyl radical having 4 to 7 ring atoms, which may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O) $R^8$, —S(=O)$_2R^9$, —NR$^6R^7$, and/or a monocyclic heterocyclyl radical having 4 to 7 ring atoms, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy- $C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical having 4 to 7 ring atoms.

In the general formula (I) $R^4$ very preferably represents hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represents $C_1$-$C_3$-alkyl, $C_1$-$C_3$-alkoxy, $C_1$-$C_3$-alkylamino, which may optionally be mono- or polysubstituted by identical or different substituents from the group consisting of halogen, amino, hydroxy, carboxyl, hydroxy-$C_1$-$C_3$-alkyl, $C_1$-$C_3$-alkoxy, $C_1$-$C_3$-alkylamino, amino-$C_1$-$C_3$-alkyl, a monocyclic heterocyclyl radical having 4 to 7 ring atoms, and/or a monocyclic heteroaryl radical having 5 or 6 ring atoms, where the monocyclic heterocyclyl and heteroaryl radicals mentioned for their part may optionally be monosubstituted by $C_1$-$C_3$-alkyl, and $R^5$ very preferably represents a $C_3$-$C_7$-cycloalkyl radical, which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O) $R^8$, —S(=O)$_2R^9$, —NR$^6R^7$, and/or a monocyclic heterocyclyl radical having 4 to 7 ring atoms, or represents a monocyclic heterocyclyl radical having 4 to 7 ring atoms, which may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O) $R^8$, —S(=O)$_2R^9$, —NR$^6R^7$, and/or a monocyclic heterocyclyl radical having 4 to 7 ring atoms, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical having 4 to 7 ring atoms.

In the general formula (I) $R^4$ very preferably represents a $C_3$-$C_7$-cycloalkyl radical, which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O) $R^8$, —S(=O)$_2R^9$, —NR$^6R^7$, and/or a monocyclic heterocyclyl radical having 4 to 7 ring atoms, or represents a monocyclic heterocyclyl radical having 4 to 7 ring atoms, which may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O) $R^8$, —S(=O)$_2R^9$, —NR$^6R^7$, and/or a monocyclic heterocyclyl radical having 4 to 7 ring atoms, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical having 4 to 7 ring atoms, and $R^5$ very preferably represents hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represents $C_1$-$C_3$-alkyl, $C_1$-$C_3$-alkoxy, $C_1$-$C_3$-alkylamino, which may optionally be mono- or polysubstituted by identical or different substituents from the group consisting of halogen, amino, hydroxy, carboxyl, hydroxy-$C_1$-$C_3$-alkyl, $C_1$-$C_3$-alkoxy, $C_1$-$C_3$-alkylamino, amino-$C_1$-$C_3$-alkyl, a monocyclic heterocyclyl radical having 4 to 7 ring atoms, and/or a monocyclic heteroaryl radical having 5 or 6 ring atoms, where the monocyclic heterocyclyl and heteroaryl radicals mentioned for their part may optionally be monosubstituted by $C_1$-$C_3$-alkyl.

In the general formula (I) $R^4$ very preferably represents a $C_3$-$C_7$-cycloalkyl radical, which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O) $R^8$, —S(=O)$_2R^9$, —NR$^6R^7$, and/or a monocyclic heterocyclyl radical having 4 to 7 ring atoms, or represents a monocyclic heterocyclyl radical having 4 to 7 ring atoms, which may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O) $R^8$, —S(=O)$_2R^9$, —$NR^6R^7$, and/or a monocyclic heterocyclyl radical having 4 to 7 ring atoms, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical having 4 to 7 ring atoms.

In the general formula (I) $R^4$ very preferably represents a $C_3$-$C_7$-cycloalkyl radical, which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical having 4 to 7 ring atoms.

In the general formula (I) $R^4$ very preferably represents a monocyclic heteroaryl radical having 5 or 6 ring atoms, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O) $R^8$, —S(=O)$_2R^9$, —$NR^6R^7$, and/or a monocyclic heterocyclyl radical having 4 to 7 ring atoms.

In the general formula (I) $R^4$ very preferably represents a monocyclic heterocyclyl radical having 4 to 7 ring atoms, which may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O) $R^8$, —S(=O)$_2R^9$, —$NR^6R^7$, and/or a monocyclic heterocyclyl radical having 4 to 7 ring atoms.

In the general formula (I) $R^4$ very preferably represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical having 4 to 7 ring atoms.

In the general formula (I) $R^5$ very preferably represents a $C_3$-$C_7$-cycloalkyl radical, which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical having 4 to 7 ring atoms, or represents a monocyclic heteroaryl radical having 5 or 6 ring atoms, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O) $R^8$, —S(=O)$_2R^9$, —$NR^6R^7$, and/or a monocyclic heterocyclyl radical having 4 to 7 ring atoms, or represents a monocyclic heterocyclyl radical having 4 to 7 ring atoms, which may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O) $R^8$, —S(=O)$_2R^9$, —$NR^6R^7$, and/or a monocyclic heterocyclyl radical having 4 to 7 ring atoms, or represents a phenyl radical, which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical having 4 to 7 ring atoms.

In the general formula (I) $R^4$ and $R^5$ very preferably and independently of one another represent hydrogen, hydroxy, cyano, amino, chlorine, $C_1$-$C_6$-alkyl, methoxy, ethoxy or $C_1$-$C_3$-alkylcarbonylamino, or represent difluoromethoxy or trifluoromethoxy, or represent $C_1$-$C_3$-alkoxy, which may be substituted by pyridinyl, morpholinyl, pyrrolidinyl or piperazinyl, in which the pyridinyl and piperazinyl may in turn optionally be substituted by $C_1$-$C_3$-alkyl, or represent cyclopropyl, or represent pyridinyl, pyrazolyl, triazolyl or isoxazolyl, which may optionally be mono- or polysubstituted by identical or different substituents from the group consisting of hydroxy and methyl, or represent pyrrolidinyl, morpholinyl, piperidinyl, piperazinyl, oxazolidinyl, thiomorpholinyl, which may optionally be mono- or polysubstituted by methyl, oxo, —S(=O)$_2$R$^9$, or represent phenyl optionally substituted by $C_1$-$C_3$-alkylaminosulphonyl or fluorine.

In the general formula (I) R$^4$ very preferably represents hydrogen, hydroxy, cyano, amino, chlorine, $C_1$-$C_6$-alkyl, methoxy, ethoxy or $C_1$-$C_3$-alkylcarbonylamino, or represents difluoromethoxy or trifluoromethoxy, or represents $C_1$-$C_3$-alkoxy, which may be substituted by pyridinyl, morpholinyl, pyrrolidinyl or piperazinyl, in which the pyridinyl and piperazinyl may in turn optionally be substituted by $C_1$-$C_3$-alkyl, or represents cyclopropyl, or represents pyridinyl, pyrazolyl, triazolyl or isoxazolyl, which may optionally be mono- or polysubstituted by identical or different substituents from the group consisting of hydroxy and methyl, or represents pyrrolidinyl, morpholinyl, piperidinyl, piperazinyl, oxazolidinyl, thiomorpholinyl, which may optionally be mono- or polysubstituted by methyl, oxo, —S(=O)$_2$R$^9$, or represents phenyl optionally substituted by $C_1$-$C_3$-alkylaminosulphonyl or fluorine.

In the general formula (I) R$^5$ very preferably represents hydrogen, hydroxy, cyano, amino, chlorine, $C_1$-$C_6$-alkyl, methoxy, ethoxy or $C_1$-$C_3$-alkylcarbonylamino, or represents difluoromethoxy or trifluoromethoxy, or represents $C_1$-$C_3$-alkoxy, which may be substituted by pyridinyl, morpholinyl, pyrrolidinyl or piperazinyl, in which the pyridinyl and piperazinyl may in turn optionally be substituted by $C_1$-$C_3$-alkyl, or represents cyclopropyl, or represents pyridinyl, pyrazolyl, triazolyl or isoxazolyl, which may optionally be mono- or polysubstituted by identical or different substituents from the group consisting of hydroxy and methyl, or represents pyrrolidinyl, morpholinyl, piperidinyl, piperazinyl, oxazolidinyl, thiomorpholinyl, which may optionally be mono- or polysubstituted by methyl, oxo, —S(=O)$_2$R$^9$, or represents phenyl optionally substituted by $C_1$-$C_3$-alkylaminosulphonyl or fluorine.

In the general formula (I) R$^4$ very preferably represents cyclopropyl, or represents pyridinyl, pyrazolyl, triazolyl or isoxazolyl, which may optionally be mono- or polysubstituted by identical or different substituents from the group consisting of hydroxy and methyl, or represents pyrrolidinyl, morpholinyl, piperidinyl, piperazinyl, oxazolidinyl, thiomorpholinyl, which may optionally be mono- or polysubstituted by methyl, oxo, —S(=O)$_2$R$^9$, or represents phenyl optionally substituted by $C_1$-$C_3$-alkylaminosulphonyl or fluorine.

In the general formula (I) R$^5$ very preferably represents cyclopropyl, or represents pyridinyl, pyrazolyl, triazolyl or isoxazolyl, which may optionally be mono- or polysubstituted by identical or different substituents from the group consisting of hydroxy and methyl, or represents pyrrolidinyl, morpholinyl, piperidinyl, piperazinyl, oxazolidinyl, thiomorpholinyl, which may optionally be mono- or polysubstituted by methyl, oxo, —S(=O)$_2$R$^9$, or represents phenyl optionally substituted by $C_1$-$C_3$-alkylaminosulphonyl or fluorine.

In the general formula (I) R$^4$ very particularly preferably represents $C_1$-$C_3$-alkoxy, which may be substituted by pyridinyl, morpholinyl, pyrrolidinyl or piperazinyl, in which the pyridinyl and piperazinyl may in turn optionally be substituted by $C_1$-$C_3$-alkyl.

In the general formula (I) R$^5$ very particularly preferably represents $C_1$-$C_3$-alkoxy, which may be substituted by pyridinyl, morpholinyl, pyrrolidinyl or piperazinyl, in which the pyridinyl and piperazinyl may in turn optionally be substituted by $C_1$-$C_3$-alkyl.

In the general formula (I) R$^4$ very particularly preferably represents difluoromethoxy or trifluoromethoxy.

In the general formula (I) R$^5$ very particularly preferably represents difluoromethoxy or trifluoromethoxy.

In the general formula (I) R$^5$ exceptionally preferably represents trifluoromethoxy.

In the general formula (I) R$^4$ very preferably represents cyclopropyl, or represents pyridinyl, pyrazolyl, triazolyl or isoxazolyl, which may optionally be mono- or polysubstituted by identical or different substituents from the group consisting of hydroxy and methyl, or represents pyrrolidinyl, morpholinyl, piperidinyl, piperazinyl, oxazolidinyl or thiomorpholinyl, which may optionally be mono- or polysubstituted by oxo, methyl, —S(=O)$_2$R$^9$, or represents phenyl optionally substituted by $C_1$-$C_3$-alkylaminosulphonyl or fluorine, and R$^5$ exceptionally preferably represents hydrogen, hydroxy, cyano, chlorine, $C_1$-$C_6$-alkyl, methoxy, ethoxy, $C_1$-$C_3$-alkylcarbonylamino, difluoromethoxy or trifluoromethoxy.

In the general formula (I) $R^4$ exceptionally preferably represents hydrogen, chlorine, methoxy, ethoxy, difluoromethoxy or trifluoromethoxy, and $R^5$ exceptionally preferably represents cyclopropyl, or represents pyridinyl or pyrazolyl, which may optionally be mono- or polysubstituted by methyl, or represents morpholinyl, piperidinyl, piperazinyl, or thiomorpholinyl, which may optionally be mono- or polysubstituted by oxo, methyl, —S(=O)$_2$R$^9$, or represents phenyl substituted by $C_1$-$C_3$-alkylaminosulphonyl.

In the general formula (I) $R^4$ and $R^5$ exceptionally preferably and independently of one another represent hydrogen, hydroxy, cyano, chlorine, $C_1$-$C_6$-alkyl, methoxy, ethoxy, $C_1$-$C_3$-alkylcarbonylamino, difluoromethoxy or trifluoromethoxy.

In the general formula (I) $R^4$ and $R^5$ exceptionally preferably and independently of one another represent hydrogen, chlorine, methoxy, ethoxy, difluoromethoxy or trifluoromethoxy.

In the general formula (I) $R^6$ and $R^7$ preferably and independently of one another represent hydrogen, $C_1$-$C_3$-alkyl, cyclopropyl, di-$C_1$-$C_3$-alkyl-amino-$C_1$-$C_3$-alkyl or fluoropyridyl.

In the general formula (I) $R^6$ and $R^7$ particularly preferably and independently of one another represent hydrogen, $C_1$-$C_3$-alkyl, cyclopropyl, di-$C_1$-$C_3$-alkyl-amino-$C_1$-$C_3$-alkyl.

In the general formula (I) $R^6$ and $R^7$ very preferably and independently of one another represent hydrogen or $C_1$-$C_3$-alkyl.

In the general formula (I) it is possible that $R^8$ represents hydroxy, $C_1$-$C_6$-alkyl, halo-$C_1$-$C_3$-alkyl, hydroxy-$C_1$-$C_3$-alkyl, $C_1$-$C_3$-alkoxy-$C_1$-$C_3$-alkyl, $C_3$-$C_8$-cycloalkyl, phenyl, monocyclic heterocyclyl having 3 to 8 ring atoms or monocyclic heteroaryl having 5 or 6 ring atoms, in which phenyl, heteroaryl and heterocyclyl may optionally be mono- or disubstituted by halogen, $C_1$-$C_3$-alkoxy- or $C_1$-$C_3$-alkyl.

In the general formula (I) $R^8$ preferably represents hydroxy, $C_1$-$C_6$-alkyl, halo-$C_1$-$C_3$-alkyl, hydroxy-$C_1$-$C_3$-alkyl, $C_1$-$C_3$-alkoxy-$C_1$-$C_3$-alkyl, $C_3$-$C_8$-cycloalkyl, phenyl, monocyclic heterocyclyl having 5 or 6 ring atoms.

In the general formula (I) $R^8$ very preferably represents hydroxy, $C_1$-$C_3$-alkyl, hydroxy-$C_1$-$C_3$-alkyl, trifluoromethyl, pyrrolidinyl, morpholinyl or piperidinyl.

In the general formula (I) $R^8$ very preferably represents $C_1$-$C_3$-alkyl.

In the general formula (I) $R^8$ very preferably represents methyl.

In the general formula (I) $R^9$ preferably represents hydrogen, $C_1$-$C_6$-alkyl or $C_1$-$C_4$-alkoxy.

In the general formula (I) $R^9$ very preferably represents $C_1$-$C_4$-alkyl or $C_1$-$C_4$-alkoxy.

In the general formula (I) $R^9$ very preferably represents methyl.

In the general formula (I) $R^9$ very preferably represents tert-butoxy.

In the general formula (I) the stereocentre, which is represented by the carbon atom of the benzodiazepine skeleton which is bound to $R^2$, is preferably present either in racemic form or predominantly or completely in the (S) configuration.

In the general formula (I) the stereocentre, which is represented by the carbon atom of the benzodiazepine skeleton which is bound to $R^2$, is preferably present in racemic form.

In the general formula (I) the stereocentre, which is represented by the carbon atom of the benzodiazepine skeleton which is bound to $R^2$, is more preferably present predominantly or completely in the (S) configuration.

In the general formula (I) the stereocentre, which is represented by the carbon atom of the benzodiazepine skeleton which is bound to $R^2$, is more preferably present predominantly in the (S) configuration.

In the general formula (I) the stereocentre, which is represented by the carbon atom of the benzodiazepine skeleton which is bound to $R^2$, is more preferably present completely in the (S) configuration.

The invention additionally relates to compounds of the general formula (I) in which A represents phenyl and $R^4$ represents hydrogen, fluorine, chlorine or bromine and $R^5$ represents $C_1$-$C_6$-alkoxy which is mono- or polysubstituted by identical or different halogen substituents, and $R^{1a}$ represents halogen.

The invention additionally relates to compounds of the general formula (I) in which A represents phenyl and $R^4$ represents hydrogen and $R^5$ represents $C_1$-$C_6$-alkoxy which is mono- or polysubstituted by identical or different substituents from the group consisting of a monocyclic heterocyclyl radical having 3 to 8 ring atoms, and/or a monocyclic heteroaryl radical having 5 or 6 ring atoms, in which the stated monocyclic heterocyclyl and heteroaryl radicals may in turn optionally be monosubstituted by $C_1$-$C_3$-alkyl, and $R^{1a}$ represents halogen.

The invention additionally relates to compounds of the general formula (I) in which A represents phenyl and $R^4$ represents hydrogen and $R^5$ represents $C_1$-$C_6$-alkoxy which is mono- or polysubstituted by identical or different substituents from the group consisting of a monocyclic heterocyclyl radical having 4 to 7 ring atoms, and/or a monocyclic heteroaryl radical having 5 or 6 ring atoms, in which the stated monocyclic heterocyclyl and heteroaryl radicals may in turn optionally be monosubstituted by $C_1$-$C_3$-alkyl, and $R^{1a}$ represents halogen.

Preferred compounds of the general formula (I) are those in which A represents phenyl and $R^4$ represents hydrogen, fluorine, chlorine or bromine and $R^5$ represents $C_1$-$C_3$-alkoxy which is mono- or polysubstituted by identical or different halogen substituents, and $R^{1a}$ represents halogen.

Preferred compounds of the general formula (I), furthermore, are those in which A represents phenyl and $R^4$ represents hydrogen and $R^5$ represents $C_1$-$C_3$-alkoxy which is mono- or polysubstituted by identical or different substituents from the group consisting of a monocyclic heterocyclyl radical having 4 to 7 ring atoms, and/or a monocyclic heteroaryl radical having 5 or 6 ring atoms, in which the stated monocyclic heterocyclyl and heteroaryl radicals may in turn optionally be monosubstituted by $C_1$-$C_3$-alkyl, and $R^{1a}$ represents halogen.

Of very particular interest are compounds of the general formula (I) in which A represents a phenyl ring and $R^4$ represents hydrogen or chlorine and $R^5$ represents trifluoromethoxy, and $R^{1a}$ represents chlorine.

Of very particular interest, furthermore, are compounds of the general formula (I) in which A represents a phenyl ring and $R^4$ represents hydrogen and $R^5$ represents $C_1$-$C_3$-alkoxy which is substituted by morpholinyl, pyrrolidinyl, piperazinyl or pyridyl, it being possible for the piperazinyl and pyridinyl itself to be substituted by $C_1$-$C_3$-alkyl, and $R^{1a}$ represents chlorine.

Of very particular interest, moreover, are the compounds of the prepared working examples No. 1; 15; 32; 33; 164; 164.2; 165; 166 and 167.

Also of interest are those compounds of the general formula (I) in which A represents phenyl and $R^{1a}$ represents a phenyl radical which may optionally be mono- or poly-substituted by identical or different substituents from the group consisting of fluorine, chlorine, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, dimethylamino, —C(=O)$NR^6R^7$, —C(=O) $R^8$, $C_1$-$C_3$-alkylsulphinyl, $C_1$-$C_3$-alkylsulphonyl, —S(=O)$_2NH_2$, $C_1$-$C_3$-alkylsulphonylamino, $C_1$-$C_3$-alkylaminosulphonyl, $C_3$-$C_6$-cycloalkylaminosulphonyl, trifluoromethyl, difluoroethyl, trifluoroethyl, trifluoromethoxy, hydroxy-$C_1$-$C_3$-alkyl, cyclopropyl, chlorothienyl, morpholino and/or pyridinyl.

The specific radical definitions given in the respective combinations or preferred combinations of radicals are, independently of the combinations of radicals given in each case, also replaced by radical definitions of other combinations.

Very particular preference is given to combinations of two or more of the preferred ranges mentioned above.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

The present invention likewise embraces the use of the salts of the compounds according to the invention.

In the context of the present invention, preferred salts are physiologically acceptable salts of the compounds according to the invention. However, salts which for their part are not suitable for pharmaceutical applications but which can be used, for example, for isolating and purifying the compounds according to the invention are also included.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluorooacetic acid, propionic acid, lactic acid, tartaric acid, malic acid, citric acid, fumaric acid, maleic acid, and benzoic acid.

Physiologically acceptable salts of the compounds according to the invention furthermore embrace, for example, base addition salts, for example of alkali metals such as sodium or potassium, of alkaline earth metals such as calcium or magnesium, or of ammonium salts derived from ammonia or organic amines containing 1 to 16 carbon atoms, such as, for example, methylamine, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and/or 1-amino-2,3,4-butanetriol. Furthermore, the compounds according to the invention can form base addition salts with quarternary ammonium ions which can be obtained, for example, by quarternization of appropriate amines with agents such as lower alkyl halides, for example methyl, ethyl, propyl and butyl chlorides, bromides and iodides, dialkyl sulphates such as dimethyl, diethyl, dibutyl and diamyl sulphate, long-chain halides such as decyl, lauryl, myristyl and stearyl chlorides, bromides and iodides, or arylalkyl halides such as benzyl bromide or phenethyl bromide. Examples of such quarternary ammonium ions are tetramethylammonium, tetraethylammonium, tetra(n-propyl)ammonium, tetra(n-butyl) ammonium, and also benzyltrimethylammonium.

The present invention furthermore provides all possible crystalline and polymorphic forms of the compounds according to the invention, the polymorphs being present either as individual polymorphs or as a mixture of a plurality of polymorphs in any concentration ranges.

The present invention furthermore provides medicaments comprising the compounds according to the invention and at least one or more other active compounds, in particular for the prophylaxis and/or therapy of tumour disorders.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The compounds according to the invention can exist in different stereoisomeric forms depending on their structure, i.e. in the form of configuration isomers or optionally also as conformation isomers. At position 4, the compounds according to the invention have a centre of asymmetry. They can therefore be present as pure enantiomers, racemates or else as diastereomers or mixtures thereof if one or more of the substituents described in formula (I) comprises a further asymmetric element, for example an achiral carbon atom. The present invention therefore also includes the enantiomers and diastereomers and their particular mixtures. The stereoisomerically uniform constituents can be isolated from such mixtures of enantiomers and/or diastereomers in a known manner; chromatography processes are preferably used for this, in particular HPLC chromatography on an achiral or chiral phase.

In general, the enantiomers according to the invention inhibit the target with different potency and have different activity in the cancer cell lines investigated. The more active enantiomer, which is frequently the 4S enantiomer, is preferred.

Where the compounds according to the invention can occur in tautomeric forms, the present invention includes all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2H$ (deuterium), $^3H$ (tritium), $^{14}C$, $^{15}N$, $^{17}O$, $18O$, $^{32}F$, $^{33}F$, $^{33}S$, $^{34}S$, $^{35}S$, $^{36}S$, $^{18}F$, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by generally used processes known to those skilled in the art, for example by the methods described below and the methods described in the working examples, by using corresponding isotopic modifications of the particular reagents and/or starting compounds therein.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

The compounds according to the invention can act systemically and/or locally. For this purpose, they can be administered in a suitable manner, such as, for example, orally, parenterally, pulmonarily, nasally, sublingually, lingually, buccally, rectally, dermally, transdermally, conjunctivally, otically, as or as an implant or stent.

For these administration routes, the compounds according to the invention can be administered in suitable administration forms.

Suitable for oral administration are administration forms working according to the prior art, which release the compounds according to the invention rapidly and/or in modified form and comprise the compounds according to the invention in crystalline and/or amorphized and/or dissolved form, such as, for example, tablets (non-coated or coated tablets, for example coated with enteric, slowly dissolving or insoluble coats which control the release of the compound according to the invention), tablets which decompose rapidly in the oral cavity or films/wafers, films/lyophylizates, capsules (for example hard gelatin capsules or soft gelatin capsules), sugar-coated tablets, granules, pellets, powders, emulsions, suspensions, aerosols or solutions.

Parenteral administration can take place with circumvention of an absorption step (for example intravenous, intraarterial, intracardiac, intraspinal or intralumbar) or with involvement of an absorption (for example intramuscular, subcutaneous, intracutaneous, percutaneous or intraperitoneal). For parenteral administration, suitable administration forms are, inter alia, injection and infusion preparations in the form of solutions, suspensions, emulsions, lyophilizates or sterile powders.

Suitable for the other administration routes are, for example, pharmaceutical forms for inhalation (inter alia powder inhalers, nebulizers), nasal drops, nasal solutions, nasal sprays; tablets, films/wafers or capsules to be applied lingually, sublingually or buccally, suppositories, ear or eye preparations, vaginal capsules, aqueous suspensions (lotions, shake lotions), lipophilic suspensions, ointments, creams, transdermal therapeutic systems (such as, for example, patches), milk, pastes, foams, dusting powders, implants or stents.

The compounds according to the invention can be converted into the administration forms mentioned. This may take place in a manner known per se by mixing with inert non-toxic, pharmaceutically acceptable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and taste and/or odour corrigents.

The present invention furthermore provides medicaments comprising the compounds according to the invention, usually together with one or more inert non-toxic, pharmaceutically suitable auxiliaries, and their use for the purposes mentioned above.

Formulation of the compounds according to the invention to give pharmaceutical products takes place in a manner known per se by converting the active compound(s) with the excipients customary in pharmaceutical technology into the desired administration form.

Auxiliaries which can be employed in this connection are, for example, carrier substances, fillers, disintegrants, binders, humectants, lubricants, absorbents and adsorbents, diluents, solvents, cosolvents, emulsifiers, solubilizers, masking flavours, colorants, preservatives, stabilizers, wetting agents, salts to alter the osmotic pressure or buffers. Reference should be made in this connection to Remington's Pharmaceutical Science, 15th ed. Mack Publishing Company, East Pennsylvania (1980).

The pharmaceutical formulations may be in solid form, for example as tablets, coated tablets, pills, suppositories, capsules, transdermal systems or in semisolid form, for example as ointments, creams, gels, suppositories, emulsions or in liquid form, for example as solutions, tinctures, suspensions or emulsions.

Auxiliaries in the context of the invention may be, for example, salts, saccharides (mono-, di-, tri-, oligo-, and/or polysaccharides), proteins, amino acids, peptides, fats, waxes, oils, hydrocarbons and derivatives thereof, where the auxiliaries may be of natural origin or may be obtained by synthesis or partial synthesis.

Suitable for Oral or Peroral Administration are in Particular Tablets, Coated Tablets, Capsules, Pills, Powders, Granules, Pastilles, Suspensions, Emulsions or Solutions.

Suitable for parenteral administration are in particular suspensions, emulsions and especially solutions.

The present invention relates to the use of the compounds according to the invention.

They can be used for the prophylaxis and therapy of human disorders, in particular tumour disorders.

The compounds according to the invention can be used in particular for inhibiting or reducing cell proliferation and/or cell division and/or to induce apoptosis.

The compounds according to the invention are suitable in particular for the treatment of hyperproliferative disorders such as, for example, psoriasis, keloids and other skin hyperplasias, benign prostate hyperplasias (BPH), solid tumours and
haematological tumours.

Solid tumours which can be treated in accordance with the invention are, for example, tumours of the breast, the respiratory tract, the brain, the reproductive organs, the gastrointestinal tract, the urogenital tract, the eye, the liver, the skin, the head and the neck, the thyroid gland, the parathyroid gland, the bones and the connective tissue and metastases of these tumours. Haematological tumours which can be treated are, for example,
- multiple myelomas,
- lymphomas or
- leukaemias.

Breast tumours which can be treated are, for example:
- breast carcinomas with positive hormone receptor status
- breast carcinomas with negative hormone receptor status
- Her-2 positive breast carcinomas
- hormone receptor and Her-2 negative breast carcinomas
- BRCA-associated breast carcinomas
- inflammatory breast carcinomas.

Tumours of the respiratory tract which can be treated are, for example,
- non-small-cell bronchial carcinomas such as squamous-cell carcinoma, adenocarcinoma, large-cell carcinoma and
- small-cell bronchial carcinomas.

Tumours of the brain which can be treated are, for example,
- gliomas,
- glioblastomas,
- astrocytomas,
- meningiomas and
- medulloblastomas.

Tumours of the male reproductive organs which can be treated are, for example:
- prostate carcinomas,
- malignant tumours of the epididymis,
- malignant testicular tumours and
- penis carcinomas.

Tumours of the female reproductive organs which can be treated are, for example:
- endometrial carcinomas
- cervix carcinomas
- ovarial carcinomas
- vaginal carcinomas
- vulvar carcinomas Tumours of the gastrointestinal tract which can be treated are, for example:
- colorectal carcinomas
- anal carcinomas
- stomach carcinomas
- pancreas carcinomas
- oesophagus carcinomas
- gall bladder carcinomas
- carcinomas of the small intestine
- salivary gland carcinomas
- neuroendocrine tumours
- gastrointestinal stroma tumours Tumours of the urogenital tract which can be treated are, for example:
- urinary bladder carcinomas
- kidney cell carcinomas
- carcinomas of the renal pelvis and lower urinary tract Tumours of the eye which can be treated are, for example:
- retinoblastomas
- intraocular melanomas Tumours of the liver which can be treated are, for example:
- hepatocellular carcinomas
- cholangiocellular carcinomas Tumours of the skin which can be treated are, for example:
- malignant melanomas
- basaliomas
- spinaliomas
- Kaposi sarcomas
- Merkel cell carcinomas Tumours of the head and neck which can be treated are, for example:
- larynx carcinomas
- carcinomas of the pharynx and the oral cavity
- carcinomas of midline structures (e.g. NMC, C. A. French, Annu. Rev. Pathol. 2012, 7:247-265)

Sarcomas which can be treated are, for example:
- soft tissue sarcomas
- osteosarcomas Lymphomas which can be treated are, for example:
- non-Hodgkin lymphomas
- Hodgkin lymphomas
- cutaneous lymphomas
- lymphomas of the central nervous system
- AIDS-associated lymphomas Leukaemias which can be treated are, for example:
- acute myeloid leukaemias
- chronic myeloid leukaemias
- acute lymphatic leukaemias
- chronic lymphatic leukaemias
- hairy cell leukaemias Advantageously, the compounds according to the invention can be used for the prophylaxis and/or therapy of leukaemias, in particular acute myeloid leukaemias, prostate carcinomas, in particular androgen receptor-positive prostate carcinomas, cervix carcinomas, breast carcinomas, in particular of hormone receptor negative, hormone receptor positive or BRCA-associated breast carcinomas, pancreas carcinomas, kidney cell carcinomas, hepatocellular carcinomas, melanomas and other skin tumours, non-small-cell bronchial carcinomas, endometrial carcinomas and colorectal carcinomas.

Particularly advantageously, the compounds according to the invention can be employed for the prophylaxis and/or therapy of leukaemias, in particular acute myeloid leukaemias, prostate carcinomas, in particular androgen receptor-positive prostate carcinomas, breast carcinomas, in particular oestrogen receptor alpha-negative breast carcinomas, melanomas or multiple myelomas.

The compounds according to the invention are also suitable for the prophylaxis and/or therapy of benign hyperproliferative diseases such as endometriosis, leiomyoma and benign prostate hyperplasia.

The compounds according to the invention are also suitable for controlling male fertility.

The compounds according to the invention are also suitable for the prophylaxis and/or therapy of systemic inflammatory diseases, in particular LPS-induced endotoxic shock and/or bacteria-induced sepsis.

The compounds according to the invention are also suitable for the prophylaxis and/or therapy of inflammatory or autoimmune disorders such as:
- pulmonary disorders associated with inflammatory, allergic and/or proliferative processes: chronic obstructive pulmonary disorders of any origin, especially bronchial asthma; bronchitis of varying origin; all types of restrictive pulmonary disorders, especially allergic alveolitis; all types of pulmonary oedema, especially toxic pulmonary oedema; sarcoidoses and granulomatoses, especially Boeck's disease rheumatic disorders/autoimmune diseases/joint disorders associated with inflammatory, allergic and/or proliferative processes: all types of rheumatic disorders, especially rheumatoid arthritis, acute rheumatic fever, polymyalgia rheumatica; reactive arthritis;

inflammatory soft tissue disorders of other origin; arthritic symptoms associated with degenerative joint disorders (arthroses); traumatic arthritides; collagenoses of any origin, e.g. systemic lupus erythematosus, *scleroderma*, polymyositis, dermatomyositis, Sjögren's syndrome, Still's syndrome, Felty's syndrome allergies associated with inflammatory and/or proliferative processes: all types of allergic reactions, e.g. angioedema, hay fever, insect bite, allergic reactions to drugs, blood derivatives, contrast media etc., anaphylactic shock, urticaria, contact dermatitis vessel inflammations (vasculitides): panarteriitis nodosa, arteriitis temporalis, erythema nodosum dermatological disorders associated with inflammatory, allergic and/or proliferative processes: atopic dermatitis; psoriasis; *pityriasis rubra* pilaris; erythematous disorders induced by various noxae, e.g. radiation, chemicals, burns etc.; bullous dermatoses; lichenoid disorders; pruritus; seborrheic eczema; rosacea; *pemphigus vulgaris*; erythema exsudativum multiforme; balanitis; vulvitis; hair loss such as alopecia areata; cutaneous T-cell lymphomas renal disorders associated with inflammatory, allergic and/or proliferative processes: nephrotic syndrome; all nephritides hepatic disorders associated with inflammatory, allergic and/or proliferative processes: acute liver cell necrosis; acute hepatitis of varying origin, e.g. viral, toxic, drug-induced; chronic aggressive and/or chronic intermittent hepatitis gastrointestinal disorders associated with inflammatory, allergic and/or proliferative processes: regional enteritis (Crohn's disease); ulcerative colitis; gastritis; reflux oesophagitis; gastroenteritides of other origin, e.g. indigenous sprue proctological disorders associated with inflammatory, allergic and/or proliferative processes: anal eczema; fissures; haemorrhoids; idiopatic proctitis ocular disorders associated with inflammatory, allergic and/or proliferative processes: allergic keratitis, uveitis, iritis; conjunctivitis; blepharitis; optic neuritis; chlorioditis; sympathetic ophthalmia ear-nose-throat disorders associated with inflammatory, allergic and/or proliferative processes: allergic rhinitis, hay fever; otitis externa, e.g. caused by contact eczema, infection etc.; otitis media neurological disorders associated with inflammatory, allergic and/or proliferative processes: cerebral oedema, especially tumour-induced cerebral oedema; multiple sclerosis; acute encephalomyelitis; meningitis; various types of spasms, e.g. West syndrome haematological disorders associated with inflammatory, allergic and/or proliferative processes: acquired haemolytic anaemia; idiopathic thrombocytopenia tumour disorders associated with inflammatory, allergic and/or proliferative processes: acute lymphatic leukaemia; malignant lymphomas; lymphogranulomatoses; lymphosarcomas; extensive metastasization, especially in cases of breast, bronchial and prostate carcinomas endocrine disorders associated with inflammatory, allergic and/or proliferative processes: endocrine orbitopathy; thyreotoxic crisis; de Quervain thyroiditis; Hashimoto thyroiditis; Basedow's disease organ and tissue transplantations, graft-versus-host disease severe states of shock, e.g. anaphylactic shock, systemic inflammatory response syndrome (SIRS)

substitution therapy in cases of: congenital primary adrenal insufficiency, e.g. congenital adrenogenital syndrome; acquired primary adrenal insufficiency, e.g. Addison's disease, autoimmune adrenalitis, postinfectious tumours, metastases, etc; congenital secondary adrenal insufficiency, e.g. congenitaler hypopituitarism; acquired secondary adrenal insufficiency, e.g. postinfectious, tumours, etc emesis associated with inflammatory, allergic and/or proliferative processes, e.g. in combination with a 5-HT3 antagonist for emesis induced by cytostatic drugs pain of inflammatory origin, e.g. lumbago The compounds according to the invention are also suitable for the treatment of viral disorders such as, for example, infections caused by papilloma viruses, herpes viruses, Epstein-Barr viruses, hepatitis B or C viruses and human immunodeficiency viruses.

The compounds according to the invention are also suitable for the treatment of atherosklerosis, dyslipidaemia, hypercholesterolaemia, hypertriglyceridaemia, peripheral vascular disorders, cardiovascular disorders, angina pectoris, ischaemia, stroke, myocardial infarction, angioplastic restenosis, hypertension, thrombosis, adiposity, endotoxemia.

The compounds according to the invention are also suitable for the treatment of neurodegenerative diseases such as, for example, multiple sclerosis, Alzheimer's disease and Parkinson's disease.

These disorders are well characterized in man but also exist in other mammals.

The present application furthermore provides the compounds according to the invention for use as medicaments, in particular for the prophylaxis and/or therapy of tumour disorders.

The present application furthermore provides the compounds according to the invention for the prophylaxis and/or therapy of leukaemias, in particular acute myeloid leukaemias, prostate carcinomas, in particular androgen receptor-positive prostate carcinomas, cervix carcinomas, breast carcinomas, in particular hormone receptor-negative, hormone receptor-positive or BRCA-associated breast carcinomas, pancreas carcinomas, kidney cell carcinomas, hepatocellular carcinomas, melanomas and other skin tumours, non-small-cell bronchial carcinomas, endometrial carcinomas and colorectal carcinomas.

The present application furthermore provides the compounds according to the invention for the prophylaxis and/or therapy of leukaemias, in particular acute myeloid leukaemias, prostate carcinomas, in particular androgen receptor-positive prostate carcinomas, breast carcinomas, in particular oestrogen receptor alpha-negative breast carcinomas, melanomas or multiple myelomas.

The invention furthermore provides the use of the compounds according to the invention for preparing a medicament.

The present application furthermore provides the use of the compounds according to the invention for preparing a medicament for the prophylaxis and/or therapy of tumour disorders.

The present application furthermore provides the use of the compounds according to the invention for preparing a medicament for the prophylaxis and/or therapy of leukaemias, in particular acute myeloid leukaemias, prostate carcinomas, in particular androgen receptor-positive prostate carcinomas, cervix carcinomas, breast carcinomas, in particular of hormone receptor-negative, hormone receptor-positive or BRCA-associated breast carcinomas, pancreas carcinomas, kidney cell carcinomas, hepatocellular carcinomas, melanomas and other skin tumours, non-small-cell bronchial carcinomas, endometrial carcinomas and colorectal carcinomas.

The present application furthermore provides the use of the compounds according to the invention for preparing a medicament for the prophylaxis and/or therapy of leukaemias, in particular acute myeloid leukaemias, prostate carcinomas, in particular androgen receptor-positive prostate carcinomas, breast carcinomas, in particular oestrogen receptor alpha-negative breast carcinomas, melanomas or multiple myelomas.

The present application furthermore provides the use of the compounds according to the invention for the prophylaxis and/or therapy of tumour disorders.

The present application furthermore provides the use of the compounds according to the invention for the prophylaxis and/or therapy of leukaemias, in particular acute myeloid leukaemias, prostate carcinomas, in particular androgen receptor-positive prostate carcinomas, cervix carcinomas, breast carcinomas, in particular hormone receptor-negative, hormone receptor-positive or BRCA-associated breast carcinomas, pancreas carcinomas, kidney cell carcinomas, hepatocellular carcinomas, melanomas and other skin tumours, non-small-cell bronchial carcinomas, endometrial carcinomas and colorectal carcinomas.

The present application furthermore provides the use of the compounds according to the invention for the prophylaxis and/or therapy of leukaemias, in particular acute myeloid leukaemias, prostate carcinomas, in particular androgen receptor-positive prostate carcinomas, breast carcinomas, in particular oestrogen receptor alpha-negative breast carcinomas, melanomas or multiple myelomas.

The present application furthermore provides pharmaceutical formulations in the form of tablets comprising one of the compounds according to the invention for the prophylaxis and/or therapy of leukaemias, in particular acute myeloid leukaemias, prostate carcinomas, in particular androgen receptor-positive prostate carcinomas, cervix carcinomas, breast carcinomas, in particular of hormone receptor-negative, hormone receptor-positive or BRCA-associated breast carcinomas, pancreas carcinomas, kidney cell carcinomas, hepatocellular carcinomas, melanomas and other skin tumours, non-small-cell bronchial carcinomas, endometrial carcinomas and colorectal carcinomas.

The present application furthermore provides pharmaceutical formulations in the form of tablets comprising one of the compounds according to the invention for the prophylaxis and/or therapy of leukaemias, in particular acute myeloid leukaemias, prostate carcinomas, in particular androgen receptor-positive prostate carcinomas, breast carcinomas, in particular oestrogen receptor-alpha-negative breast carcinomas, melanomas or multiple myelomas.

The invention furthermore provides the use of the compounds according to the invention for treating disorders associated with proliferative processes.

The invention furthermore provides the use of the compounds according to the invention for treating benign hyperplasias, inflammatory disorders, autoimmune disorders, sepsis, viral infections, vascular disorders and neurodegenerative disorders.

The compounds according to the invention can be employed by themselves or, if required, in combination with one or more other pharmacologically active substances, as long as this combination does not lead to unwanted and unacceptable side effects. Accordingly, the present invention furthermore provides medicaments comprising a compound according to the invention and one or more further active compounds, in particular for the prophylaxis and/or therapy of the disorders mentioned above.

For example, the compounds of the present invention can be combined with known antihyperproliferative, cytostatic or cytotoxic substances for treatment of cancer disorders. The combination of the compounds according to the invention with other substances customary for cancer therapy or else with radiotherapy is indicated in particular.

Suitable active compounds for combinations which may be mentioned by way of example, without this list being exclusive, are:

abiraterone acetate, Abraxane, acolbifene, Actimmune, actinomycin D (dactinomycin), afatinib, Affinitak, Afinitor, aldesleukin, alendronic acid, Alfaferone, alitretinoin, allopurinol, Aloprim, Aloxi, Alpharadin, altretamine, aminoglutethimide, aminopterin, amifostine, amrubicin, amsacrine, anastrozole, Anzmet, apatinib, Aranesp, arglabin, arsenic trioxide, Aromasin, arzoxifene, asoprisnil, L-asparaginase, atamestane, atrasentan, Avastin, axitinib, 5-azacytidine, azathioprine, BCG or tice-BCG, bendamustine, bestatin, betamethasone acetate, betamethasone sodium phosphate, bexarotene, bicalutamide, bleomycin sulphate, broxuridine, bortezomib, bosutinib, busulfan, cabazitaxel, calcitonin, Campath, camptothecin, capecitabin, carboplatin, carfilzomib, carmustine, Casodex, CCI-779, CDC-501, cediranib, Cefeson, Celebrex, celmoleukin, Cerubidine, cediranib, chlorambucil, cisplatin, cladribine, clodronic acid, clofarabine, colaspase, Corixa, crisnatol, crizotinib, cyclophosphamide, cyproterone acetate, cytarabine, dacarbazine, dactinomycin, dasatinib, daunorubicin, DaunoXome, Decadron, Decadron phosphate, decitabine, degarelix, Delestrogen, denileukin diftitox, Depo-Medrol, deslorelin, dexrazoxane, diethylstilbestrol, Diflucan, 2',2'-difluorodeoxycytidine, DN-101, docetaxel, doxifluridine, doxorubicin (Adriamycin), dronabinol, dSLIM, dutasteride, DW-166HC, edotecarin, eflornithine, Eligard, Elitek, Ellence, Emend, enzalutamide, epirubicin, epoetin-alfa, Epogen, epothilone and its derivatives, eptaplatin, Ergamisol, erlotinib, erythrohydroxynonyladenine, Estrace, estradiol, estramustine sodium phosphate, ethynylestradiol, Ethyol, etidronic acid, Etopophos, etoposide, everolimus, exatecan, exemestan, fadrozole, Fareston, fenretinide, filgrastim, finasteride, fligrastim, floxuridine, fluconazole, fludarabine, 5-fluordeoxyuridine monophosphate, 5-fluorouracil (5-FU), fluoxymesterone, flutamide, Folotyn, formestane, fosteabine, fotemustin, fulvestrant, Gammagard, gefitinib, gemcitabine, gemtuzumab, Gleevec, Gliadel, goserelin, gossypol, granisetron-hydrochloride, hexamethylmelamine, histamine dihydrochloride, histrelin, holmium-166-DOTPM, Hycamtin, Hydrocortone, erythro-hydroxynonyladenine, hydroxyurea, hydroxyprogesterone caproate, ibandronic acid, ibritumomab tiuxetan, idarubicin, ifosfamide, imatinib, iniparib, interferon alpha, interferon alpha 2, interferon alpha-2α, interferon alpha 2β, interferon alpha n1, interferon alpha n3, interferon beta, interferon gamma 1α, interleukin 2, Intron A, Iressa, irinotecan, ixabepilone, keyhole limpet haemocyanin, Kytril, lanreotide, lapatinib, lasofoxifene, lentinan sulphate, lestaurtinib, letrozole, leucovorin, leuprolide, leuprolide acetate, levamisole, levofolinic acid calcium salt, Levothroid, Levoxyl, Libra, liposomal MTP-PE, lomustine, lonafarnib, lonidamine, Marinol, mechlorethamine, mecobalamin, medroxyprogesterone acetate, megestrol acetate, melphalan, Menest, 6-mercaptopurine, mesna, methotrexate, Metvix, miltefosine, minocycline, minodronate, miproxifene, mitomycin C, mitotane, mitoxantrone, Modrenal, MS-209, MX-6, Myocet, nafarelin, nedaplatin, nelarabine, nemorubicin, Neovastat, neratinib, Neulasta, Neumega, Neupogen, nilotimib, nilutamide, nimustine, nolatrexed, Nolvadex, NSC-631570, obatoclax, oblimersen, OCT-43, octreotide, olaparib, ondansetron hydrochloride, Onco-TCS, Oraprolide, Osidem, oxaliplatin, paclitaxel, pamidronate disodium, pazopanib, Pediapred, pegaspargase, Pegasys, pemetrexed, pentostatin, N-phosphonoacetyl-L-aspartate, picibanil, pilocarpine hydrochloride, pirarubicin, plerixafor, plicamycin, PN-401, porfimer sodium, prednimustine, prednisolone, prednisone, Premarin, procarbazine, Procrit, QS-21, quazepam, R-1589, raloxifene, raltitrexed, ranpirnase, RDEA119, Rebif, regorafenib, 13-cis-retinoic acid, rhenium-186 etidronate, rituximab, Roferon-A, romidepsin, romurtide, ruxolitinib, Salagen, salinomycin, Sandostatin, sargramostim, satraplatin, semaxatinib, semustine, seocalcitol, sipuleucel-T, sizofiran, sobuzoxane, Solu-Medrol, sorafenib, streptozocin, strontium-89 chloride, sunitinib, Synthroid, T-138067, tamoxifen, tamsulosin, Tarceva, tasonermin, testolactone, Taxoprexin, Taxotere, teceleukin, temozolomide, temsirolimus, teniposide, testosterone propionate, Testred, thalidomide, thymosin alpha 1, thioguanine, thiotepa, thyrotropin, tiazofurin, tiludronic acid, tipifarnib, tirapazamine, TLK-286, toceranib, topotecan, toremifene, tositumomab, tastuzumab, treosulfan, TransMID-107R, tretinoin, Trexall, trimethylmelamine, trimetrexate, triptorelin acetate, triptorelin pamoate, trofosfamide, UFT, uridine, valrubicin, valspodar, vandetanib, vapreotid, vatalanib, vemurafinib, verteporfin, vesnarinon, vinblastine, vincristine, vindesine, vinflunine, vinorelbine, Virulizin, vismodegib, Xeloda, Z-100, Zinecard, zinostatin stimalamer, Zofran, zoledronic acid.

Also indicated is, in particular, a combination of the compounds according to the invention with a P-TEFb or CDK9 inhibitor.

The compounds according to the invention can also be combined in a very promising manner with biological therapeutics, such as antibodies (e.g. aflibercept, alemtuzumab, bevacizumab, brentuximumab, catumaxomab, cetuximab, denosumab, edrecolomab, gemtuzumab, ibritumomab, ipilimumab, ofatumumab, panitumumab, pertuzumab, rituximab, tositumumab, trastuzumab) and recombinant proteins.

The compounds according to the invention may also achieve positive effects in combination with other therapies directed against angiogenesis, such as, for example, with bevacizumab, axitinib, regorafenib, cediranib, sorafenib, sunitinib or thalidomide. Combinations with antihormones and steroidal metabolic enzyme inhibitors are particularly suitable because of their favourable profile of side effects.

Generally, the following aims can be pursued with the combination of compounds of the present invention with other agents having a cytostatic or cytotoxic action:

an improved activity in slowing down the growth of a tumour, in reducing its size or even in its complete elimination compared with treatment with an individual active compound;

the possibility of employing the chemotherapeutics used in a lower dosage than in monotherapy;

the possibility of a more tolerable therapy with few side effects compared with individual administration;

the possibility of treatment of a broader spectrum of tumour disorders;

achievement of a higher rate of response to the therapy;

a longer survival time of the patient compared with present-day standard therapy.

The compounds according to the invention can moreover also be employed in combination with radiotherapy and/or surgical intervention.

Synthesis Routes for Preparing the Compounds of the General Formula (I)

The schemes and general operating procedures below illustrate the general synthetic access to the compounds of the formula (I) according to the invention, without the synthesis of the compounds according to the invention being limited to these.

4,5-Dihydro-3H-2,3-benzodiazepines of the general formula (I) can be prepared analogously to processes described in the literature. Depending on the substituents present, protective group strategies may be required; however, these are generally known to the person skilled in the art. Scheme 1 describes the synthesis of 4,5-dihydro-3H-2,3-benzodiazepines employing a 3,4-dihydro-1H-2-benzopyran intermediate (III), where A, n and the radicals $R^{1a}$, $R^{1b}$, $R^2$, $R^4$ and $R^5$ have the meanings given in general formula (I), where $(R^{1b})_n$ can also synonymously represent $R^{1b}$ and $R^{1c}$. Corresponding approaches are described, for example, in F. Gatta et al. Il Farmaco—Ed. Sc. 1985, 40, 942 and in WO2008124075 or WO200198280.

The aldehydes used are commercially available, and/or their preparation is known to the person skilled in the art. $R^{1a}$ and $R^{1b}$ can also be introduced at a later stage of the synthesis, as described, for example, in Schemes 5a, 6, 7, 8, 9 and 11.

The 1-aryl-2-propanols (II) are either commercially available or are prepared in a manner generally known to the person skilled in the art by reduction of the corresponding ketones (IIa), e.g. by reduction with lithium aluminium hydride in THF.

This synthesis route is preferably used for electron-rich substituted arylpropanols (II) (e.g. with alkoxy).

3,4-Dihydro-1H-2-benzopyrans (III) are obtained by condensation of the 1-aryl-2-propanols (II) with aromatic or heteroaromatic aldeydes under acidic conditions. The reaction is preferably carried out at elevated temperature (about 100° C.) in hydrogen chloride-containing dioxane in the presence of anhydrous zinc chloride. Further conversion of the 3,4-dihydro-1H-2-benzopyrans (III) can be by various routes:

Oxidative ring opening using chromium(VI) oxide/sulphuric acid affords the diketone (IV), which can be cyclized with hydrazine to give the 4-methyl-1-aryl-5H-2,3-benzodiazepine or 4-methyl-1-heteroaryl-5H-2,3-benzodiazepine (V) (cf. U.S. Pat. No. 5,288,863). Reduction, e.g. with sodium cyanoborohydride (Synthetic Communications, 2002, 32, 527), then yield the desired 4,5-dihydro-3H-2,3-benzodiazepine derivative (VI).

Oxidation with atmospheric oxygen affords the 1-aryl-3,4-dihydro-1H-2-benzopyran-1-ol or 1-heteroaryl-3,4-dihydro-1H-2-benzopyran-1-ol (VII) which can be reacted with elimination of water using H₂NNHBoc to give the corresponding hydrazone derivative (VIII). This can be cyclized by mesylation and subsequent treatment with base to give the Boc-protected 4,5-dihydro-3H-2,3-benzodiaz- epine derivative (IX), which for its part can be converted by acidic deprotection in a generally known manner into the corresponding 4,5-dihydro-3H-2,3-benzodiazepine derivative (VI).

Scheme 1: 4,5-Dihydro-3H-2,3-benzodiazepines via 3,4-dihydro-1H-2-benzopyrans

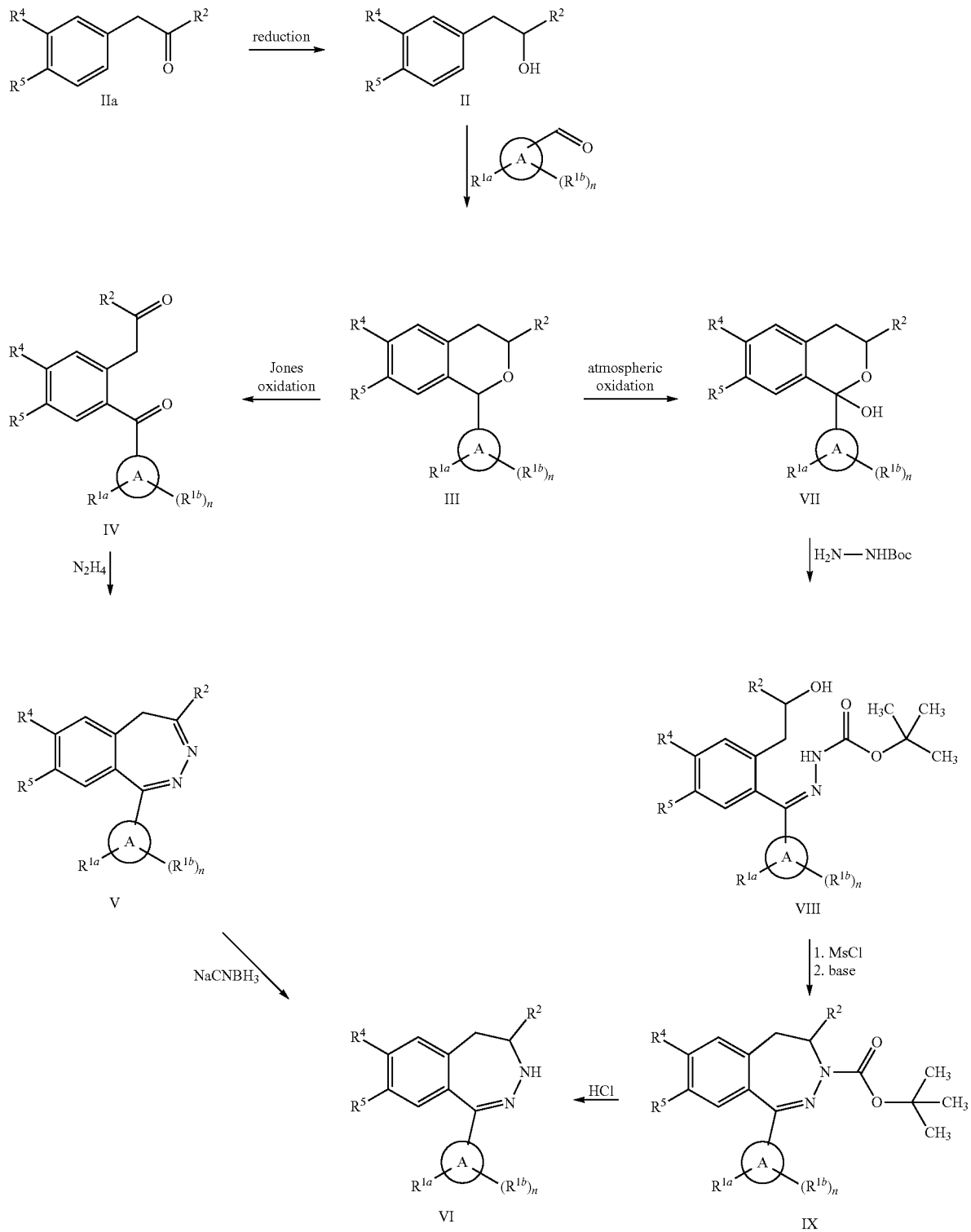

Scheme 2 describes the synthesis of 4,5-dihydro-3H-2,3-benzodiazepines from indanones (X).

The indanone derivative (X) can be converted by addition of organomagnesium reagents in a generally known

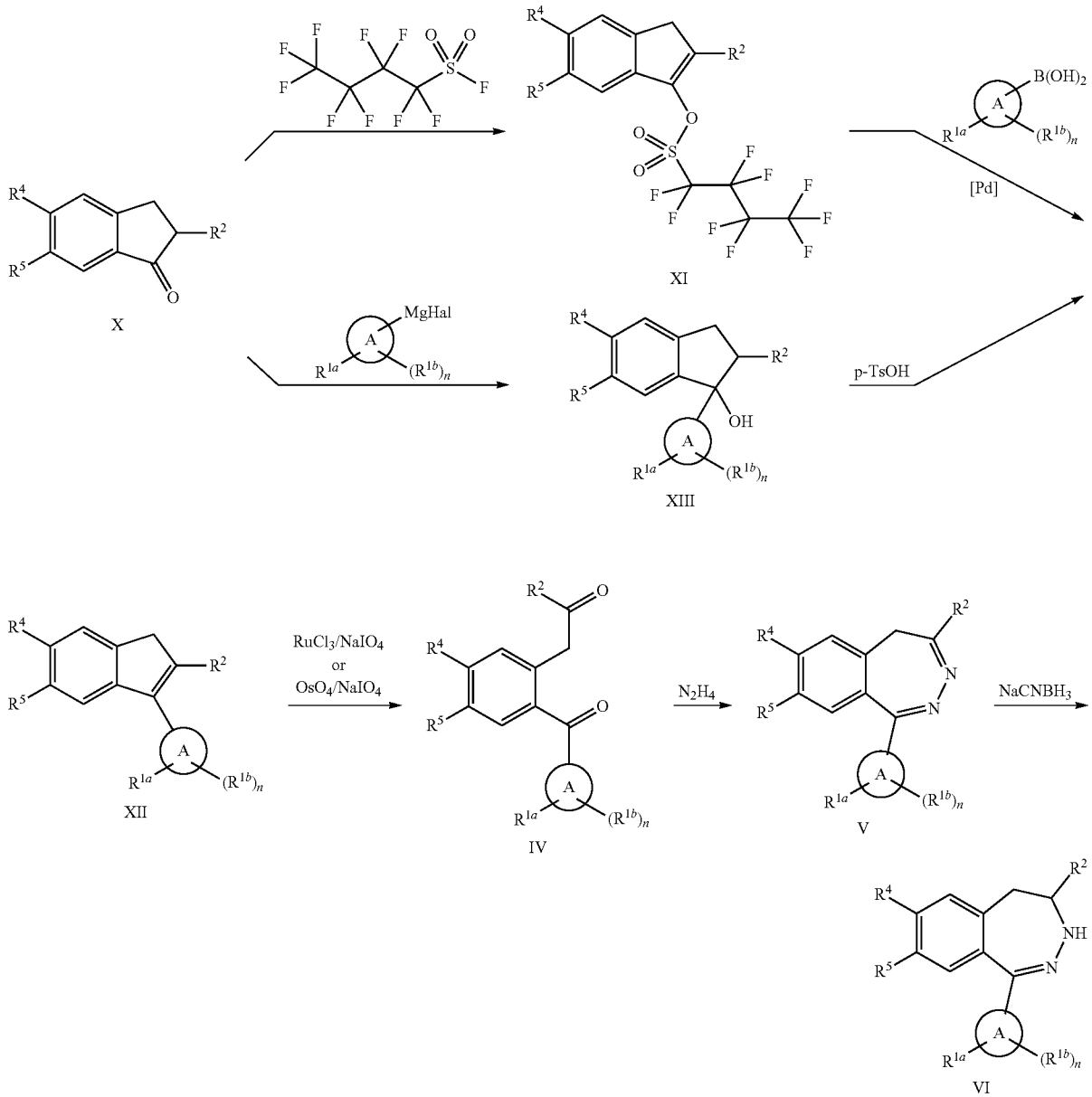

Scheme 2: 4,5-Dihydro-3H-2,3-benzodiazepines from indanones

A, n and the radicals $R^{1a}$, $R^{1b}$, $R^2$, $R^4$ and $R^5$ in Scheme 2 have the meanings given for the general formula (I), where $(R^{1b})_n$ can also synonymously represent $R^{1b}$ and $R^{1e}$.

The indanone (X) can be converted into the corresponding 3-aryl-1H-indene or 3-heteroaryl-1H-indene (XII). To this end, use may be made of the following processes:

The indanone derivative (X) can, for example, be converted in a generally known manner into the corresponding enol nonaflate (XI), and then be converted by palladium-catalyzed Suzuki coupling with the appropriate boronic acid derivatives into indene (XII).

manner into the corresponding indanols (XIII) which, by acid-catalyzed elimination, readily form the corresponding indenes (XII).

The 3-aryl-1H-indenes or 3-heteroaryl-1H-indenes (XII) can be converted by oxidative methods, e.g. with ruthenium (III) chloride/sodium periodate (Bioorganic and Medicinal Chemistry Letters, 2011, 21, 2554), into the corresponding diketones (IV). These can be converted analogously to Scheme 1 into the corresponding 4,5-dihydro-3H-2,3-benzodiazepine derivatives (VI).

The indanones (X) used for preparing the working examples are either commercially available or can be prepared as shown, for example, in Scheme 3, where the radicals $R^2$, $R^4$ and $R^5$ have the meanings given for general formula (I).

Scheme 3: Synthesis of indanones

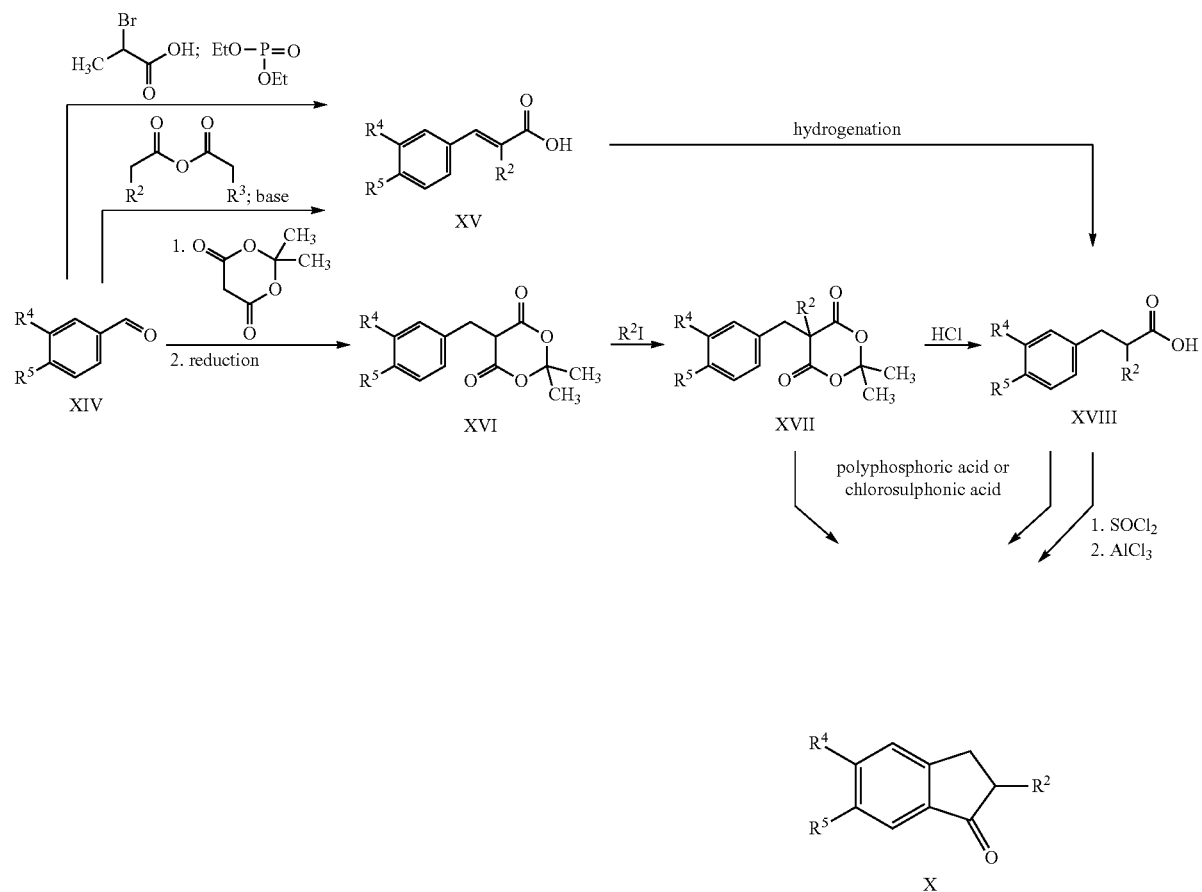

From the appropriate aromatic aldehydes (XIV), using processes known from the literature e.g. via Perkin reaction (Medicinal Chemistry Research, 2004, Vol. 13, 660) or Wittig reaction (Journal of Organic Chemistry, 2001, Vol. 66, 3682), it is possible to prepare the 2-methyl-3-arylpropanoic acids (XVIII). These can be cyclized for example with chlorosulphonic acid or polyphosphoric acid to give the corresponding indanones (X) (cf. Synthesis 2009, 627 and Org. Process Res. Dev. 2011, 15, 570-580, J. Org. Chem. 2005, 70, 1316 and Bioorg. Med. Chem. Lett. 2011, 21, 2554-2558). Scheme 4 illustrates the preparation of the exemplary compounds according to the invention starting from 4,5-dihydro-3H-2,3-benzodiazepines (VI) by means of generally known reactions, e.g. with acid chlorides, anhydrides, chloroformates or isocyanates or isothiocyanates, where A, n and the radicals $R^{1a}$, $R^{1b}$, $R^2$, $R^3$, $R^4$ and $R^5$ have the meanings given for general formula (I), where $(R^{1b})_n$ can also synonymously represent $R^{1b}$ and $R^{1c}$. The corresponding alkylureas (XIX) can also be obtained by reacting a reactive intermediate such as the 4-nitrophenyl carbamate with alkylamines.

Scheme 4: Synthesis of 4,5-dihydro-3H-2,3-benzodiazepine-3-carbonyl compounds

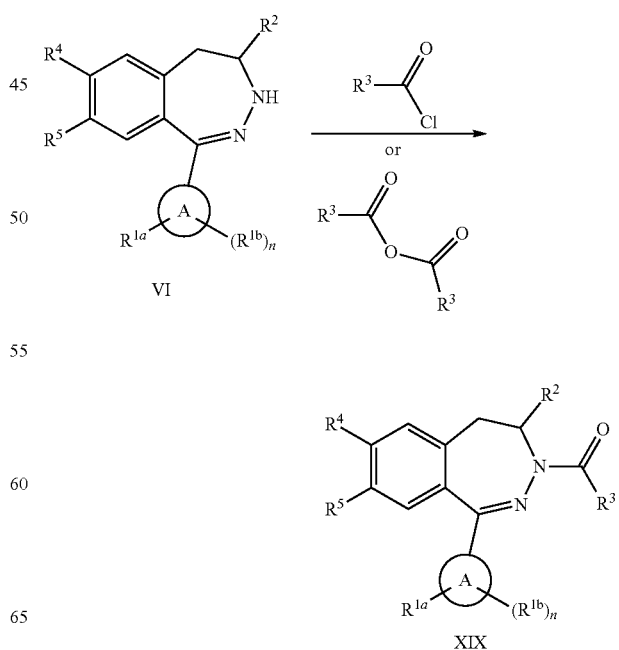

-continued

1.

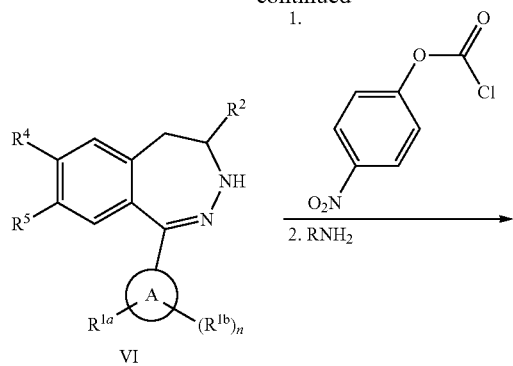

Scheme 5a:

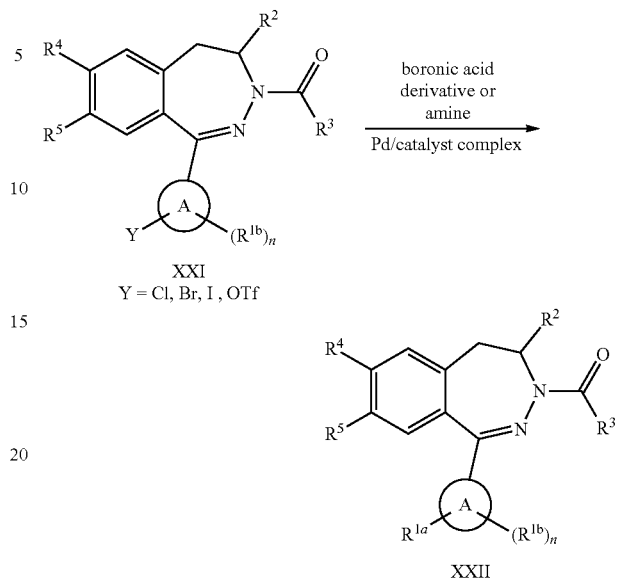

The radicals $R^{1b}$, $R^2$, $R^3$, $R^4$, $R^5$, and A and n in Scheme 5a have the meanings given for general formula (I), where $(R^{1b})_n$ can also synonymously represent $R^{1b}$ and $R^{1c}$.

In scheme 5a, $R^{1a}$ represents, for example, a phenyl radical or a monocyclic heteroaryl radical which has 5 or 6 ring atoms as defined for $R^{1a}$ in general formula (I), or represents an amino radical, in particular represents a monocyclic heterocyclyl radical which has 3 to 8 ring atoms, as defined for $R^{1a}$ in general formula (I), with the proviso that it is attached to the remainder of the molecule via a nitrogen atom located in the heterocycle.

Scheme 5b:

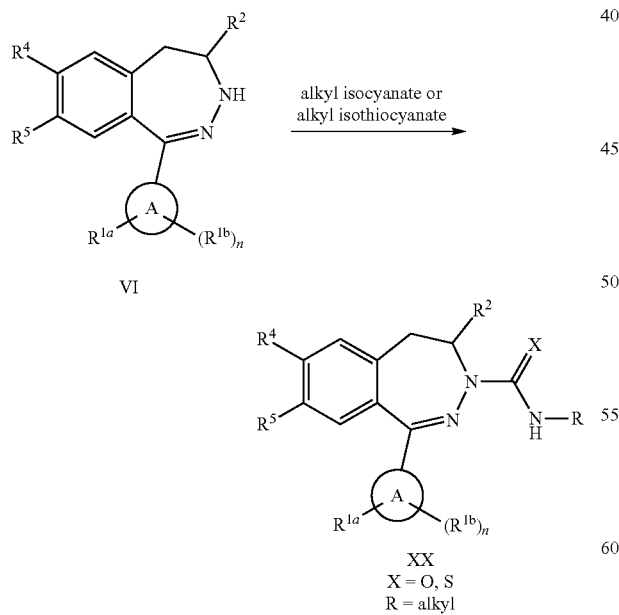

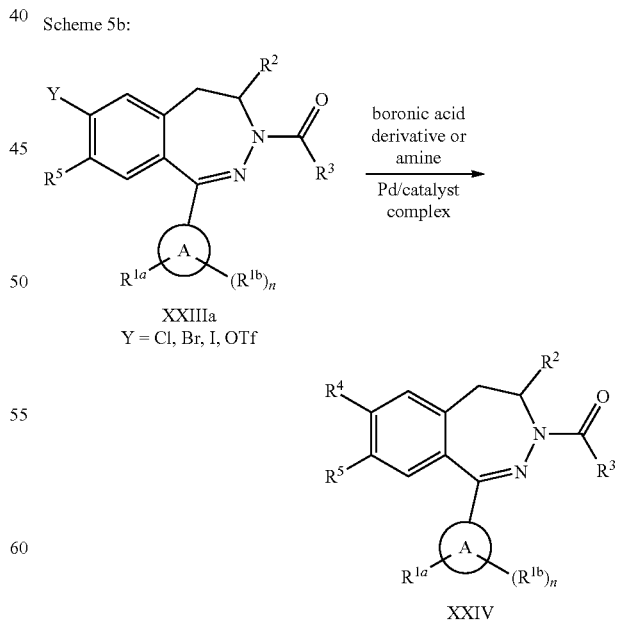

$R^{1a}$, $R^4$ and $R^5$ can also be introduced at a later stage of the synthesis, for example as described in Schemes 5a, 5b, 5c, 6, 8, 9 and 11.

The radicals $R^{1a}$, $R^{1b}$, $R^2$, $R^3$, $R^5$, and A and n in Scheme 5b have the meanings given for general formula (I), where $(R^{1b})_n$ can also synonymously represent $R^{1b}$ and $R^{1c}$.

In Scheme 5b, $R^4$ represents, for example, a phenyl radical or a monocyclic heteroaryl radical which has 5 or 6 ring atoms as defined for $R^4$ in general formula (I), or represents an amino radical, in particular represents a monocyclic heterocyclyl radical which has 3 to 8 ring atoms, as defined for $R^4$ in general formula (I), with the proviso that it is attached to the remainder of the molecule via a nitrogen atom located in the heterocycle.

Scheme 5c:

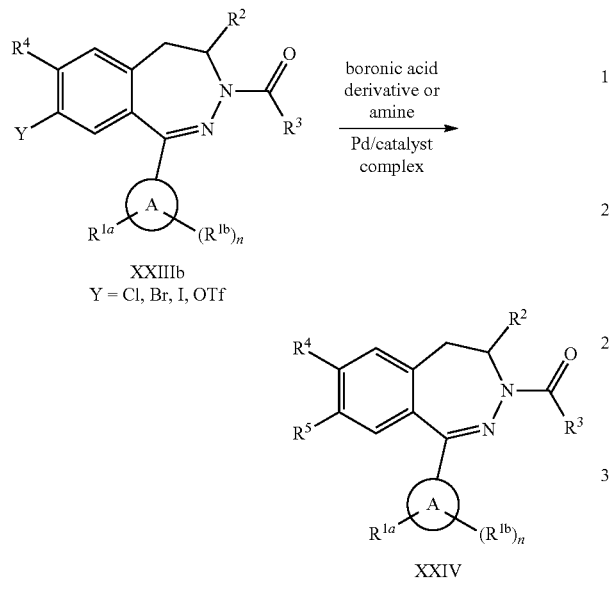

XXIIIb
Y = Cl, Br, I, OTf

XXIV

The radicals $R^{1a}$, $R^{1b}$, $R^2$, $R^3$, $R^4$, and A and n in Scheme 5c have the meanings given for general formula (I), where $(R^{1b})_n$ can also synonymously represent $R^{1b}$ and $R^{1c}$.

In Scheme 5c, $R^5$ represents, for example, a phenyl radical or a monocyclic heteroaryl radical which has 5 or 6 ring atoms as defined for $R^5$ in general formula (I), or represents an amino radical, in particular represents a monocyclic heterocyclyl radical which has 3 to 8 ring atoms, as defined for $R^5$ in general formula (I), with the proviso that it is attached to the remainder of the molecule via a nitrogen atom located in the heterocycle.

Schemes 5a, 5b and 5c illustrate the preparation of working examples which can be prepared by palladium-catalyzed coupling reactions known to the person skilled in the art, for example from bromine-substituted aryl- or heteroaryl derivatives (XXI, XXIIIa and XXIIIb) by reaction with the appropriate boronic acid derivatives (Chem. Rev. 1995, 95, 2457-2483; Angewandte Chemie, International Edition (2002), 41(22), 4176-4211) or amines. The intermediates XXI, XXIIIa and XXIIIb can be prepared analogously to the synthesis routes shown.

Boronic acid derivatives are commercially available or can be prepared in a generally known manner. The preparation of the exemplary compounds according to the invention by reaction with amines is carried out, for example, by reaction under Buchwald-Hartwig conditions (Journal of Organometallic Chemistry (1999), 576(1-2), 125-146).

Alternatively and for example for A=phenyl, corresponding pyrazole derivatives (XXVI) (cf. US200419045) or morpholine derivatives (XXVII) (cf. US2006199804) can also be prepared from aniline derivatives by methods known from the literature, as shown in Scheme 6.

Scheme 6:

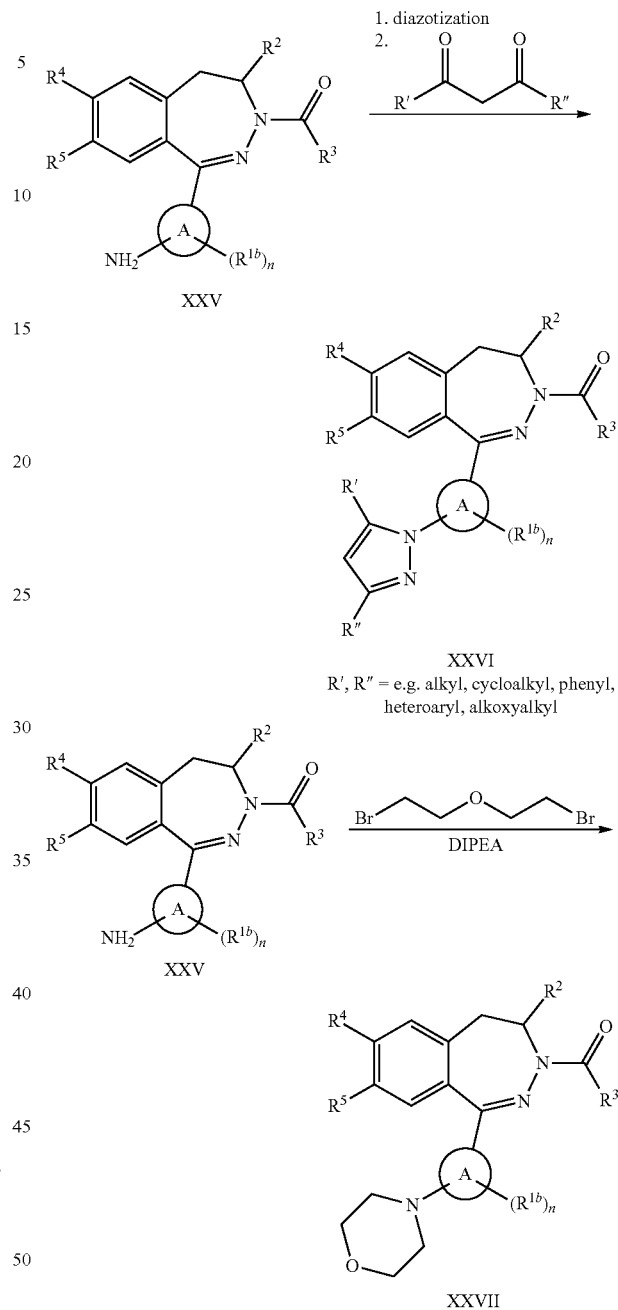

XXV

XXVI
R', R" = e.g. alkyl, cycloalkyl, phenyl, heteroaryl, alkoxyalkyl

XXV

XXVII

The radicals $R^{1b}$, $R^2$, $R^3$, $R^4$, $R^5$, and A and n in Scheme 6 have the meanings given for general formula (I), where $(R^{1b})_n$ can also synonymously represent $R^{1b}$ and $R^{1c}$.

Scheme 7 illustrates the synthesis of working examples which can be prepared by brominations, known in general to the person skilled in the art, of compounds of the formula XXVIII (Synth. Commun. 1993, 23, 855). In the stated compounds of the formula XXVIII, $R^2$, $R^3$, $R^4$, $R^5$, n and also A have the definitions indicated in the general formula (I), and Hetcyc represents a monocyclic heterocyclyl radical having 3 to 8 ring atoms, as defined in the general formula (I) for $R^{1a}$, with the proviso that this radical is bonded to the rest of the molecule via a nitrogen atom present in the heterocyclic structure. The resulting brominated working examples of the formula XXIX can be converted by methods known from the literature (Advanced Synthesis and Catalysis 2011, 777; Journal of the American Chemical Society 2003, 2890; US 2009/62541) into the corresponding cyano compounds of the formula XXX. The intermediates of the formula XXVIII that are used here can be prepared by the synthesis methods described above.

Scheme 7:

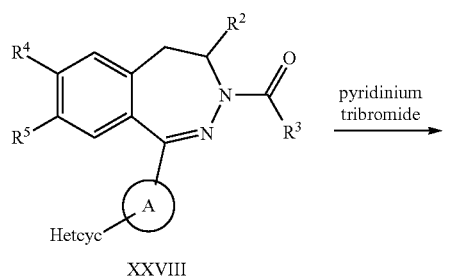

XXVIII

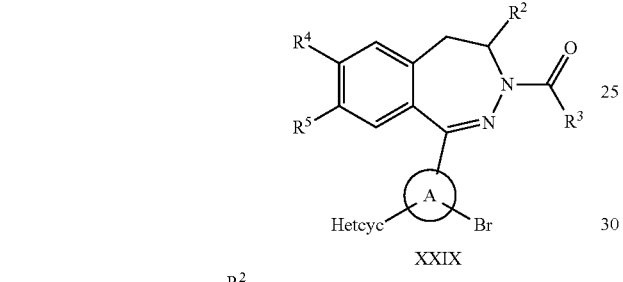

XXIX

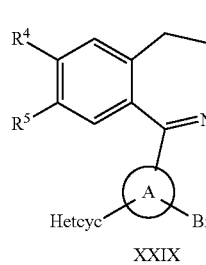

XXIX

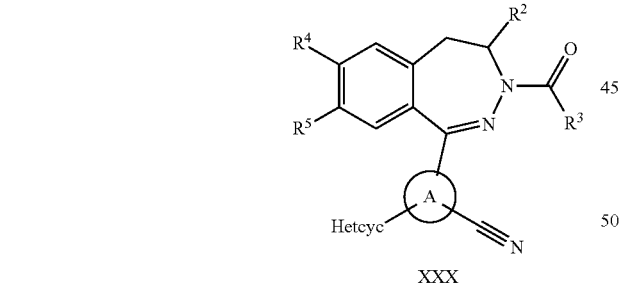

XXX

4827; Tetrahedron 2009, 9989). The intermediates of the formula XXIa that are used here can be prepared with the synthesis methods described above.

Scheme 8:

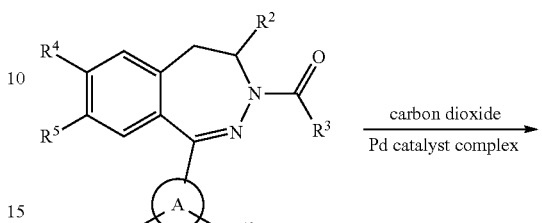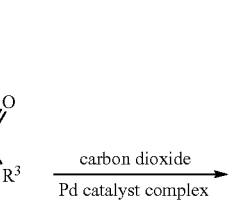

XXIa

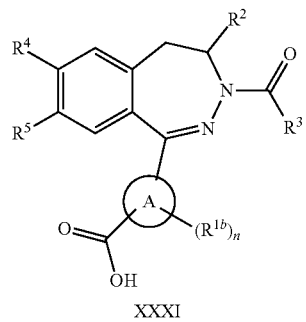

XXXI

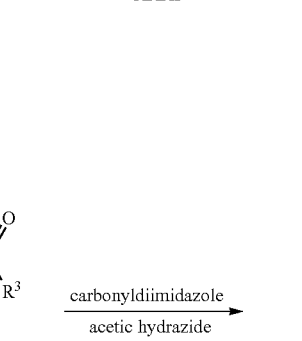

XXXI

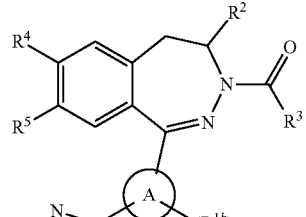

XXXII

Scheme 8 illustrates the preparation of working examples which, starting from brominated intermediates of the formula XXIa, in which $R^{1b}$, $R^2$, $R^3$, $R^4$, $R^5$, A and n have the definitions indicated in the general formula (I), it also being possible for $(R^{1b})_n$, synonymously, to represent $R^{1b}$ and $R^{1c}$, can be converted by methods known to the person skilled in the art, as for example by palladium-catalysed reaction with carbon dioxide (European Journal of Organic Chemistry 2000, 2253), to carboxylic acid derivatives of the formula XXXI. These in turn can then be converted in analogy to methods known from the literature into the corresponding oxadiazole derivatives of the formulae XXXII and XXXIII (Tetrahedron 2009, 65, 9989; Tetrahedron Letters 2006,

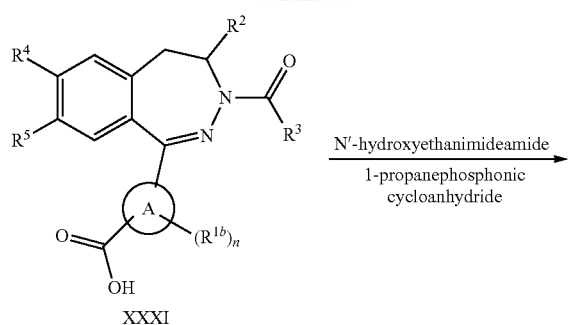

XXXI

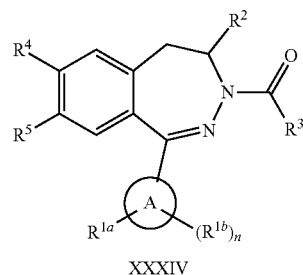

XXXIV

N'-hydroxyethanimideamide
1-propanephosphonic cycloanhydride

XXXIII amides or carbamates
Cu catalyst complex

XXXV

Scheme 9 illustrates the preparation of working examples which can be converted by copper-catalysed coupling reactions known in general to the person skilled in the art (see J. Am. Chem. Soc. 2001, 123, 7727; J. Am. Chem. Soc. 2002, 124, 7421), starting for example from brominated intermediates of the formula XXIIIc, in which $R^{1a}$, $R^{1b}$, $R^2$, $R^3$, $R^5$, A and also n have the definitions indicated in the general formula (I), it also being possible for $(R^{1b})_n$, synonymously, to represent $R^{1b}$ and $R^{1c}$, and also from compounds of the formula XXIa, in which $R^{1b}$, $R^2$, $R^3$, $R^4$, $R^5$, A and also n have the definitions indicated in the general formula (I), it also being possible for $(R^{1b})_n$, synonymously, to represent $R^{1b}$ and $R^{1c}$, by reaction with amides or carbamates, into the corresponding coupled derivatives of the formulae XXXIV, in which $R^4$ represents an optionally cyclic carboxamide or carbamate bonded via a nitrogen atom, and XXXV, in which, again, $R^{1a}$ represents an optionally cyclic carboxamide or carbamate bonded via a nitrogen atom. The intermediates of the formulae XXIIIc and XXIa that are used here can be prepared with the synthesis methods described above.

Scheme 10 illustrates the preparation of inventive example compounds, starting from dimethoxy-substituted 4,5-dihydro-3H-2,3-benzodiazepines of the formula XXXVI, in which $R^{1a}$, $R^{1b}$, $R^2$, $R^3$, A and n have the definitions indicated in the general formula (I), it also being possible for $(R^{1b})_n$, synonymously, to represent $R^{1b}$ and $R^{1c}$, by means of reactions that are general knowledge, for example with boron tribromide (Bioorganic and Medicinal Chemistry Letters 2012, 2827), to give the corresponding dihydroxy derivatives of the formula XXXVII, which can in turn be converted using suitable alkylating agents into the corresponding ether derivatives XXXVIII, in which $R^4$ and $R^5$ represent optionally substituted alkoxy radicals (Journal of Medicinal Chemistry 2000, 3244). The intermediates of the formula XXXVI that are used here can be prepared with the synthesis methods described above.

Scheme 9:

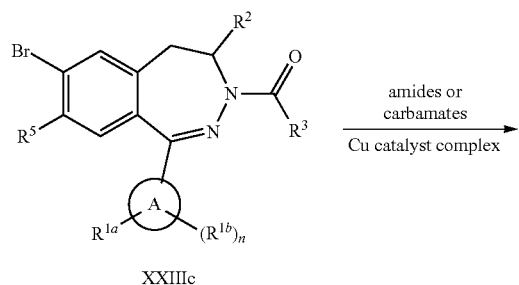

XXIIIc amides or carbamates
Cu catalyst complex

Scheme 10:

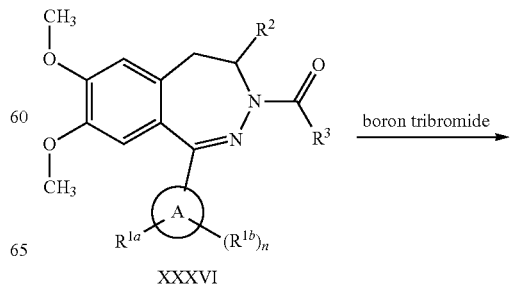

XXXVI boron tribromide

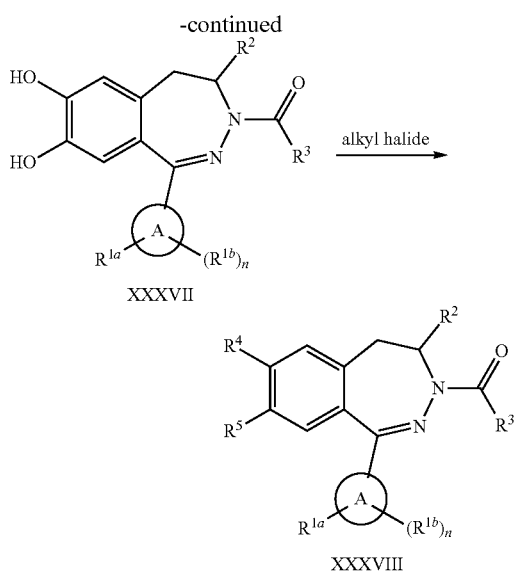

XXXVII

XXXVIII

As shown in Scheme 11, starting from brominated intermediates of the formula XXIa, in which $R^{1b}$, $R^2$, $R^3$, $R^4$, $R^5$, A and n have the definitions indicated in the general formula (I), it also being possible for $(R^1)_n$, synonymously, to represent $R^{1b}$ and $R^{1c}$, it is possible to prepare inventive compounds of the formula XL by palladium-catalysed reaction of XXIa with cyclic sulphonamides with a free NH group, of the formula XXXIX, in which p represents a number 1, 2, 3 or 4, so that the ring system has 5 to 8 ring members (Org. Lett. 2011, 2564).

Scheme 11:

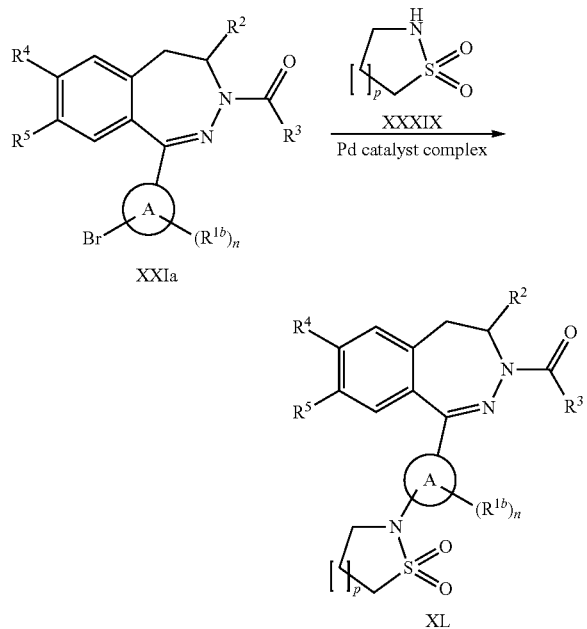

ABBREVIATIONS abs. absolute
ACN acetonitrile
AS formic acid
Boc tert-butoxycarbonyl
$CDCl_3$ deuterochloroform
$CO_2$ carbon dioxide
d day
DEA diethylamine
DIPEA N,N-diisopropylethylamine
DMAP 4-N,N-dimethylaminopyridine
DMF dimethylformamide
DMSO dimethyl sulphoxide
eq. equivalent
ESI electrospray ionization (in MS)
sat. saturated
h hour
HOBt 1-hydroxy-1H-benzotriazole×$H_2O$
HPLC high-pressure, high-performance liquid chromatography
IPA 2-propanol
conc. concentrated
LC-MS liquid chromatography-coupled mass spectrometry
min minutes
MS mass spectrometry
Ms methanesulphonyl
MW molecular weight [g/mol]
NMP N-methylpyrrolidone
NMR nuclear magnetic resonance spectroscopy
$R_f$ retention index (in TLC)
RP-HPLC reverse phase HPLC
RT room temperature
$R_t$ retention time (in HPLC)
SFC supercritical fluid chromatography
TFA trifluoroacetic acid
THF tetrahydrofuran Yields given in percentages (in % of theory) are purity-adjusted where appropriate.

LC-MS Methods:
Method 1: instrument: Waters Acquity LCT; column: Phenomenex Kinetex C18, 50 mm×2.1 mm, 2.4μ; mobile phase A: water/0.05% AS, mobile phase B: ACN/0.05% AS; gradient 0.0 min 98% A→0.2 min: 98% A→1.7 min: 10% A→1.9 min: 10% A→2 min: 98% A→2.5 min: 98% A; flow rate: 1.3 ml/min; column temperature: 60° C.; UV detection: 200-400 nm.

Method 2: instrument: Waters Acquity Platform ZQ4000; column: Waters BEHC 18, 50 mm×2.1 mm, 1.7μ; mobile phase A: water/0.05% AS, mobile phase B: ACN/0.05% AS; gradient 0.0 min 98% A→0.2 min: 98% A→1.7 min: 10% A→1.9 min: 10% A→2 min: 98% A→2.5 min: 98% A; flow rate: 1.3 ml/min; column temperature: 60° C.; UV detection: 200-400 nm.

Method 3: UPLC-SQD-HCOOH; instrument: Waters Acquity UPLC-MS SQD; column: Acquity UPLC BEH C18 1.7 50×2.1 mm; mobile phase A: water+0.1% by volume of formic acid (99%), mobile phase B: acetonitrile; gradient: 0-1.6 min 1-99% B, 1.6-2.0 min 99% B; flow rate 0.8 ml/min; temperature: 60° C.; injection: 2 μl; DAD scan: 210-400 nm.

Method 4: MS instrument: Waters ZQ; HPLC instrument: Waters Acquity; column: Acquity BEH C18 (Waters), 50 mm×2.1 mm, 1.7 μm; mobile phase A: water+0.1% formic acid, mobile phase B: acetonitrile (Lichrosolv Merck); gradient: 0.0 min 99% A—1.6 min 1% A—1.8 min 1% A—1.81 min 99% A—2.0 min 99% A; oven: 60° C.; flow rate 0.800 ml/min; UV detection PDA 210-400 nm. (AMC method)

Method 5: instrument: Agilent 1290-Platform, ESI-TOF 6224; column: Waters BEH C18, 50 mm×2.1 mm, 1.7μ; mobile phase A: water/0.05% AS, mobile phase B: ACN/0.05% AS; gradient: 0.0 min 98% A, up to 1.7 min linearly to 10% A, up to 2.0 min: 10% A, flow rate: 1.2 ml/min; column temperature: 60° C.; UV detection: 200-400 nm.

Analytical HPLC Methods:

Method A: system: Waters Alliance 2695, DAD 996, ESA Corona; column: Chiralpak IC 3 µm 100×4.6 mm; mobile phase: hexane/2-propanol 80:20 (v/v); flow rate: 1.0 ml/min; column temperature: 25° C.; detection: DAD 254 nm.

Method B: system: Waters Alliance 2695, DAD 996; column: Chiralpak ID 3 µm 100×4.6 mm; mobile phase hexane/2-propanol 70:30 (v/v); flow rate: 1.0 ml/min; column temperature: 25° C.; detection: DAD 280 nm.

Method C: system: Waters Alliance 2695, DAD 996; column: Chiralpak IC 3 µm 100×4.6 mm; mobile phase: hexane/ethanol 70:30 (v/v); flow rate: 1.0 ml/min; column temperature: 25° C.; detection: DAD 254 nm.

Method Ca: system: Waters Alliance 2695, DAD 996, ESA Corona; column: Chiralpak IC 3 µm 100×4.6 mm; mobile phase: hexane/ethanol 70:30 (v/v); flow rate: 1.0 ml/min; column temperature: 25° C.; detection: DAD 280 nm.

Method D: system: Agilent 1260 AS, MWD, Aurora SFC module; column: Chiralpak IA 3 µm 100×4.6 mm; mobile phase: $CO_2$/ethanol+0.2% by volume of diethylamine 90/10; flow rate: 4.0 ml/min; pressure (outlet): 120 bar; column temperature: 37.5° C.; detection: DAD 254 nm.

Method Da: system: Agilent 1260 AS, MWD, Aurora SFC module; column: Chiralpak IA 3 µm 100×4.6 mm; mobile phase: $CO_2$/methanol 97/3; flow rate: 4.0 ml/min; pressure (outlet): 100 bar; column temperature: 37.5° C.; detection: DAD 254 nm.

Method E: system: Waters Alliance 2695, DAD 996, ESA Corona; column: Chiralpak IC 3 µm 100×4.6 mm; mobile phase: ethanol/methanol 50:50 (v/v); flow rate: 1.0 ml/min; column temperature: 25° C.; detection: DAD 254 nm.

Method Ea: system: Waters Alliance 2695, DAD 996, ESA Corona; column: Chiralpak IC 3 µm 100×4.6 mm; mobile phase: ethanol/methanol/DEA 50:50:0.1 (v/v/v); flow rate: 1.0 ml/min; column temperature: 25° C.; detection: DAD 254 nm.

Method F: system: Agilent 1260 AS, MWD, Aurora SFC module; column: Chiralpak IC 3 µm 100×4.6 mm; mobile phase: $CO_2$/2-propanol+0.2% by volume of diethylamine 90/10; flow rate: 4.0 ml/min; pressure (outlet): 100 bar; column temperature: 37.5° C.; detection: DAD 254 nm.

Method Fa: system: Agilent 1260 AS, MWD, Aurora SFC module; column: Chiralpak IC 5 µm 100×4.6 mm; mobile phase: $CO_2$/ethanol 6/4; flow rate: 4.0 ml/min; pressure (outlet): 100 bar; column temperature: 37.5° C.; detection: DAD 254 nm.

Method G: system: Waters Alliance 2695, DAD 996, ESA Corona; column: Chiralpak ID 3 µm 100×4.6 mm; mobile phase: hexane/2-propanol 70:30 (v/v) +0.1% DEA; flow rate: 1.0 ml/min; column temperature: 25° C.; detection: DAD 254 nm.

Method H: system: Agilent: 1260 AS, MWD, Aurora SFC module; column: Chiralpak IA 5 µm 100×4.6 mm; mobile phase: $CO_2$/methanol 9:1; flow rate: 4.0 mL/min; pressure (outlet): 100 bar; column temperature: 37.5° C.; detection: DAD 254 nm.

Method J: system: Waters Alliance 2695, DAD 996, ESA: Corona; column: Chiralpak IC 3 µm 100×4.6 mm; mobile phase: ethanol/methanol/diethylamine 50:50:0.1 (v/v/v); flow rate: 1.0 ml/min; column temperature: 25° C.; detection: DAD 254 nm.

Method L: system: Waters Alliance 2695, DAD 996; column: Chiralpak ID-3 3 µm 100×4.6 mm; mobile phase: hexane/IPA 70:30 (v/v) +0.1% DEA; flow rate: 1.0 ml/min; column temperature: 25° C.; detection: DAD 280 nm.

Method M: system: Waters: Alliance 2695, DAD 996, ESA: Corona; column: Chiralpak IC 3 µm 100×4.6 mm; mobile phase: hexane/ethanol/diethylamine 80:20:0.1 (v/v/v); flow rate: 1.0 ml/min; column temperature: 25° C.; detection: DAD 254 nm.

Method N: system: Agilent: 1260 AS, MWD, Aurora SFC module; column: Chiralpak IA 5 µm 100×4.6 mm; mobile phase: $CO_2$/2-propanol 75:25; flow rate: 4.0 ml/min; pressure (outlet): 100 bar; column temperature: 37.5° C.; detection: DAD 254 nm.

Method O: system: Waters: Alliance 2695, DAD 996; column: Chiralpak ID 5 µm 150×4.6 mm; mobile phase: hexane/2-propanol/diethylamine 70:30:0.1 (v/v/v); flow rate: 1.0 ml/min; column temperature: 25° C.; detection: DAD 280 nm.

Method P: system: Waters: Alliance 2695, DAD 996, ESA: Corona; column: Chiralpak IC 3 µm 100×4.6 mm; mobile phase: methanol 100 (v); flow rate: 1.0 ml/min; column temperature: 25° C.; detection: DAD 280 nm.

Method Q: system: Waters: Alliance 2695, DAD 996, ESA: Corona; column: Chiralpak IC 3 µm 100×4.6 mm; mobile phase: hexane/ethanol/diethylamine 70:30:0.1 (v/v/v); flow rate: 1.0 ml/min; column temperature: 25° C.; detection: DAD 254 nm.

Method R: system: Waters: Alliance 2695, DAD 996, ESA: Corona; column: Chiralpak IA 3 µm 100×4.6 mm; mobile phase: hexane/2-propanol 70:30 (v/v); flow rate: 1.0 ml/min; column temperature: 25° C.; detection: DAD 254 nm.

Method Ra: system: Waters: Alliance 2695, DAD 996, ESA: Corona; column: Chiralpak IA 3 µm 100×4.6 mm; mobile phase: hexane/2-propanol DEA 70:30:0.1 (v/v); flow rate: 1.0 ml/min; column temperature: 25° C.; detection: DAD 254 nm.

Method S: system: Waters: Alliance 2695, DAD 996; column: Chiralpak ID 5 µm 150×4.6 mm; mobile phase: hexane/ethanol/diethylamine 70:30:0.1 (v/v/v); flow rate: 1.0 mL/min; column temperature: 25° C.; detection: DAD 254 nm.

Method T: system: SFC01; column: Chiralpak AZ-H 5 µm 250×4.6 mm; mobile phase: $CO_2$/2-propanol 70:30; flow rate: 3.0 ml/min; detection: DAD 254 nm.

Method U: system: Waters: Alliance 2695, DAD 996; ESA: Corona; column: Chiralpak ID 5 µm 150×4.6 mm; mobile phase: hexane/2-propanol 70:30 (v/v); flow rate: 1.0 ml/min; column temperature: 25° C.; detection: DAD 280 nm.

Method Ua: system: Waters: Alliance 2695, DAD 996; ESA: Corona; column: Chiralpak ID 3 µm 100×4.6 mm; mobile phase: hexane/2-propanol 70:30 (v/v) +0.1 DEA; flow rate: 1.0 ml/min; column temperature: 25° C.; detection: DAD 254 nm.

Method K: system: Waters: Alliance 2695, DAD 996, ESA: Corona; column: Chiralpak IA 5 µm 150×4.6 mm; mobile phase: hexane/ethanol/diethylamine 70:30:0.1 (v/v/v); flow rate: 1.0 ml/min; column temperature: 25° C.; detection: DAD 254 nm.

Method K1: system: Waters: Alliance 2695, DAD 996, ESA: Corona; column: Chiralpak IC 5 µm 150×4.6 mm; mobile phase: hexane/ethanol/diethylamine 70:30:0.1 (v/v/v); flow rate: 1.0 ml/min; column temperature: 25° C.; detection: DAD 280 nm.

Method W: system: Agilent: 1260 AS, MWD, Aurora SFC module; column: Chiralpak IC 5 µm 100×4.6 mm; mobile phase: $CO_2$/ethanol 75/25; flow rate: 4.0 ml/min; pressure (outlet): 150 bar; column temperature: 40° C.; detection: DAD 254 nm.

Method V: system: Waters: Alliance 2695, DAD 996, ESA: Corona; column: Chiralpak ID 3 µm 100×4.6 mm; mobile phase: hexane/ethanol/diethylamine 70:30:0.1 (v/v/v); flow rate: 1.0 ml/min; column temperature: 25° C.; detection: DAD 280 nm.

Method Y: system: Agilent: 1260 AS, MWD, Aurora SFC module; column: Chiralpak ID 5 µm 100×4.6 mm; mobile phase: $CO_2$/ethanol 70/30; flow rate: 4.0 mL/min; pressure (outlet): 100 bar.

Method Y1: system: Agilent: 1260 AS, MWD, Aurora SFC module; column: Chiralpak ID 3 µm 100×4.6 mm; mobile phase: $CO_2$/2-propanol 6/4; flow rate: 4.0 mL/min; pressure (outlet): 100 bar; detection: DAD 254 nm.

Method L1: system: Waters: Alliance 2695, DAD 996, ESA: Corona; column: Chiralpak IA 5 µm 150×4.6 mm; mobile phase: acetonitrile/MTBE 70:30 (v/v) +0.1% DEA; flow rate: 1.0 ml/min; column temperature: 25° C.; detection: DAD 254 nm.

Preparative HPLC Methods:

Method I: system: Agilent Prep 1200, 2× Prep Pump, DLA, MWD, Prep FC; column: Chiralpak IC 5 µm 250×30 mm; mobile phase: hexane/2-propanol 80:20 (v/v); flow rate: 60 ml/min; column temperature: 25° C.; detection: UV 254 nm.

Method II: system: Sepiatec Prep SFC100; column: Chiralpak IA 5 µm 250×20 mm; mobile phase: $CO_2$/ethanol+0.5% by volume of diethylamine 80/20; flow rate: 80 ml/min; pressure (outlet): 150 bar; column temperature: 40° C.; detection: UV 254 nm.

Method III: system: Dionex Pump P 580, Gilson Liquid Handler 215, Knauer UV-detector K-2501; column: Chiralpak IC 5 µm 250×30 mm; mobile phase: hexane/ethanol 70:30 (v/v); flow rate: 50 ml/min; column temperature: 25° C.; detection: UV 254 nm.

Method IIIa: system: Dionex Pump P 580, Gilson Liquid Handler 215, Knauer UV-detector K-2501; column: Chiralpak IC 5 µm 250×30 mm; mobile phase: hexane/ethanol/diethylamine 70:30:0.1 (v/v/v); flow rate: 50 ml/min; column temperature: 25° C.; detection: UV 280 nm.

Method IV: system: Sepiatec Prep SFC100; column: Chiralpak IC 5 µm 250×20 mm; mobile phase: $CO_2$/2-propanol+0.2% by volume of diethylamine 90/10; flow rate: 80 ml/min; pressure (outlet): 150 bar; column temperature: 40° C.; detection: UV 254 nm.

Method IVa: system: Sepiatec Prep SFC100; column: Chiralpak IC 5 µm 250×20 mm; mobile phase: $CO_2$/ethanol 6/4; flow rate: 60 mL/min; pressure (outlet): 100 bar; column temperature: 37° C.; detection: UV 254 nm.

Method V: system: Agilent: Prep 1200, 2× Prep Pump, DLA, MWD, Prep FC; column: Chiralpak ID 5 µm 250×20 mm; mobile phase: hexane/2-propanol 70:30 (v/v) +0.1% DEA; flow rate: 23.5 ml/min; temperature: RT; detection: UV 254 nm.

Method Va: system: Agilent: Prep 1200, 2× Prep Pump, DLA, MWD, Prep FC; column: Chiralpak ID 5 µm 250×30 mm; mobile phase: hexane/2-propanol 70:30 (v/v) +0.1% DEA; flow rate: 50 ml/min; temperature: RT; detection: UV 254 nm.

Method VI: system: Agilent: Prep 1200, 2× Prep Pump, DLA, MWD, Prep FC; column: Chiralpak IC 5 µm 250×20 mm; mobile phase: ethanol/methanol/diethylamine 50:50:0.1 (v/v/v); flow rate: 20 ml/min; temperature: RT; detection: UV 254 nm.

Method VIa: system: Agilent: Prep 1200, 2× Prep Pump, DLA, MWD, Prep FC; column: Chiralpak IC 5 µm 250×30 mm; mobile phase: ethanol/methanol/diethylamine 50:50:0.1 (v/v/v); flow rate: 35 ml/min; temperature: RT; detection: UV 254 nm.

Method VII: system: Dionex: Pump P 580, Gilson: Liquid Handler 215, Knauer: UV detector K-2501; column: Chiralpak IC 5 µm 250×30 mm; mobile phase: ethanol/methanol/diethylamine 50:50:0.1 (v/v/v); flow rate: 40 ml/min; temperature: RT; detection: UV 254 nm.

Method VIII: system: Sepiatec: Prep SFC100; column: Chiralpak IA 5 µm 250×20 mm; mobile phase: $CO_2$/methanol 8:2; flow rate: 80 ml/min; pressure (outlet): 150 bar; temperature: 40° C.; detection: UV 254 nm.

Method VIIIa: system: Sepiatec: Prep SFC100; column: Chiralpak IA 5 µm 250×20 mm; mobile phase: $CO_2$/methanol 97:3; flow rate: 80 ml/min; pressure (outlet): 100 bar; temperature: 40° C.; detection: UV 254 nm.

Method XI: system: Agilent: Prep 1200, 2× Prep Pump, DLA, MWD, Prep FC; column: Chiralpak IC 5 µm 250×20 mm; mobile phase: methanol 100 (v); flow rate: 50 ml/min; temperature: RT; detection: UV 280 nm.

Method XII: system: Agilent: Prep 1200, 2× Prep Pump, DLA, MWD, Prep FC; column: Chiralpak IC 5 µm 250×20 mm No.: 007; mobile phase: hexane/ethanol/diethylamine 70:30:0.1 (v/v/v); flow rate: 25 ml/min; temperature: RT; detection: UV 254 nm.

Method XIIa: system: Agilent: Prep 1200, 2× Prep Pump, DLA, MWD, Prep FC; column: Chiralpak IC 5 µm 250×30 mm No.: 009; mobile phase: hexane/ethanol/diethylamine 70:30:0.1 (v/v/v); flow rate: 50 ml/min; temperature: RT; detection: UV 254 nm.

Method XIII: system: Agilent: Prep 1200, 2× Prep Pump, DLA, MWD, Prep FC; column: Chiralpak IA 5 µm 250×30 mm No.: 010; mobile phase: hexane/2-propanol 70/30 (v/v); flow rate: 40 ml/min; temperature: RT; detection: UV 254 nm.

Method XIV: system: Agilent: Prep 1200, 2× Prep Pump, DLA, MWD, Prep FC; column: Chiralpak IA 5 µm 250×20 mm No.: 008; mobile phase: hexane/ethanol/diethylamine 70:30:0.1 (v/v/v); flow rate: 30 ml/min; temperature: RT; detection: UV 254 nm.

Method XV: system: Sepiatec Prep SFC100; column: Chiralpak IA 5 µm 250×20 mm; mobile phase: $CO_2$/methanol 9:1; flow rate: 60 mL/min; pressure (outlet): 150 bar; temperature: 40° C.; detection: UV 254 nm.

Method XVI: system: Agilent: Prep 1200, 2× Prep Pump, DLA, MWD, Prep FC; column: Chiralpak IA 5 µm 250×20 mm No.: 006; mobile phase: hexane/ethanol 70/30 (v/v); flow rate: 30 ml/min; temperature: RT; detection: UV 280 nm.

Method XVIa: system: Agilent: Prep 1200, 2× Prep Pump, DLA, MWD, Prep FC; column: Chiralpak IC 5 µm 250×20 mm No.: 021; mobile phase: hexane/ethanol 70/30 (v/v); flow rate: 50 ml/min; temperature: RT; detection: UV 280 nm.

Method XVII: system: Agilent: Prep 1200, 2× Prep Pump, DLA, MWD, Prep FC; column: Chiralpak IA 5 µm 250×20 mm No.: 001; mobile phase: hexane/ethanol 70/30 (v/v) +0.1% diethylamine; flow rate: 20 ml/min; temperature: RT; detection: UV 254 nm.

Method XVIII: system: Sepiatec Prep SFC100; column: Chiralpak IC 5 µm 250×20 mm; mobile phase: $CO_2$/ethanol 75/25; flow rate: 80 ml/min; pressure (outlet): 150 bar; column temperature: 40° C.; detection: UV 254 nm.

Method XIX: system: Agilent: Prep 1200, 2× Prep Pump, DLA, MWD, Prep FC; column: Chiralpak ID 5 µm 250×30 mm No.: 018; mobile phase: hexane/ethanol 70/30 (v/v) +0.1% diethylamine; flow rate: 50 ml/min; temperature: RT; detection: UV 280 nm.

Method XX: system: Agilent: Prep 1200, 2× Prep Pump, DLA, MWD, Prep FC; column: Chiralpak IA 5 µm 250×20 mm No.: 003; mobile phase: hexane/2-propanol 70/30 (v/v) +0.1% diethylamine; flow rate: 25 ml/min; temperature: RT; detection: UV 280 nm.
Method XXa: system: Agilent: Prep 1200, 2× Prep Pump, DLA, MWD, Prep FC; column: Chiralpak IA 5 μm 250×20 mm No.: 014; mobile phase: acetonitrile/MTBE 90/10 (v/v) +0.1% diethylamine; flow rate: 30 ml/min; temperature: RT; detection: UV 254 nm.
Method XXb: system: Agilent: Prep 1200, 2× Prep Pump, DLA, MWD, Prep FC; column: Chiralpak IA 5 μm 250×20 mm No.: 007; mobile phase: hexane/2-propanol 70/30 (v/v) +0.1% diethylamine; flow rate: 20 ml/min; temperature: RT; detection: UV 254 nm.
Method XXI: system: Sepiatec Prep SFC100; column: Chiralpak ID 5 μm 250×20 mm; mobile phase: $CO_2$/ethanol 78/22; flow rate: 60 mL/min; pressure (outlet): 150 bar; column temperature: 40° C.; detection: UV 254 nm
Method XXIa: system: Sepiatec Prep SFC100; column: Chiralpak ID 5 μm 250×20 mm; mobile phase: $CO_2$/2-propanol 6/4; flow rate: 80 mL/min; pressure (outlet): 150 bar; column temperature: 40° C.; detection: UV 254 nm
Method XXII: system: Agilent: Prep 1200, 2× Prep Pump, DLA, MWD, Prep FC; column: Chiralpak ID 5 μm 250×20 mm No.: 003; mobile phase: hexane/2-propanol 70/30 (v/v); flow rate: 30 ml/min; temperature: RT; detection: UV 280 nm.

The examples below describe the preparation of the intermediates preferably used for preparing the compounds according to the invention.

Accordingly, the present invention also provides intermediates of the general formula (I-A1),

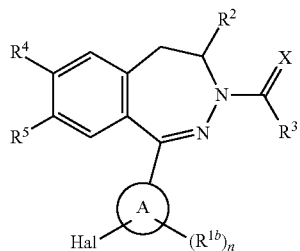

(I-A1)

in which X, A, $R^{1b}$, $R^2$, $R^3$, $R^4$, $R^5$ and n have the meanings given in the general formula (I), and where Hal represents fluorine, chlorine or bromine, and where $(R^{1b})_n$ can also synonymously represent $R^{1b}$ and $R^{1c}$, which may be used with preference for preparing the compounds of the general formula I.

Preferably, Hal represents chlorine or bromine.

Accordingly, the present invention further provides intermediates of the general formula (Ia)

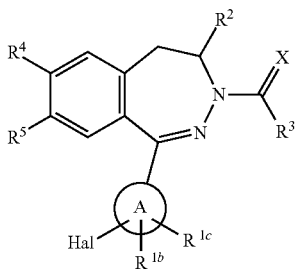

(Ia)

in which X, A, $R^{1b}$, $R^{1c}$, $R^2$, $R^3$, $R^4$ and $R^5$ have the meanings given in the general formula (I), and Hal represents fluorine, chlorine or bromine, and which may be used with preference for preparing the compounds of the general formula (I).

PREPARATION OF THE INTERMEDIATES

Example 1A 2,2-Dimethyl-5-[4-(trifluoromethoxy)benzyl]-1,3-dioxane-4,6-dione

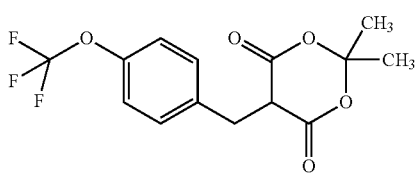 [SMILES: CC1(C)OC(=O)C(Cc2ccc(OC(F)(F)F)cc2)C(=O)O1]

25.4 g (134 mmol) of 4-(trifluoromethoxy)benzaldehyde (CAS [659-28-9]), 19.3 g (134 mmol) of Meldrum's acid (2,2-dimethyl-1,3-dioxane-4,6-dione, CAS [2033-24-1]) and 1.93 g (13.4 mmol) of piperidinium acetate (CAS [4540-33-4]) were dissolved in 500 ml of ethanol and stirred at RT for 30 min. The reaction solution was cooled to 0° C. using an ice bath and stirred for a further 10 min. 12.6 g (200 mmol) of sodium cyanoborhydride were introduced a little at a time, and the reaction was then allowed to warm to RT and stirred for a further 1.5 h. 250 ml of 2M hydrochloric acid were then added carefully and stirring was continued until the evolution of gas had ceased completely (about 30 min) The ethanol was removed on a rotary evaporator and the residue was taken up in 2M hydrochloric acid and extracted repeatedly with dichloromethane. The combined organic phases were dried with sodium sulphate and the solvent was removed on a rotary evaporator. This gave 32.7 g (41% of theory) of crude product as a white solid which was reacted without further purification.

LCMS (Method 1): $R_t$=1.33 min; m/z=319 (M+H)$^+$

Example 2A 5-(4-Bromobenzyl)-2,2-dimethyl-1,3-dioxane-4,6-dione

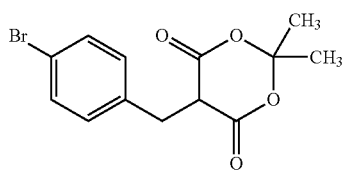 [SMILES: CC1(C)OC(=O)C(Cc2ccc(Br)cc2)C(=O)O1]

The compound was prepared analogously to Example 1A from 25.0 g (135 mmol) of 4-bromobenzaldehyde, 19.4 g (135 mmol) of Meldrum's acid, 1.95 g (13.5 mmol) of piperidinium acetate and 12.7 g (202 mmol) of sodium cyanoborohydride. This gave 27.1 g (64% of theory) of the desired product which was reacted further without purification.

LCMS (Method 2): $R_t$=1.23 min; m/z=313, 315 (Br isotope pattern, M+H)$^+$

Example 3A 5-(4-Methoxybenzyl)-2,2-dimethyl-1,3-dioxane-4,6-dione

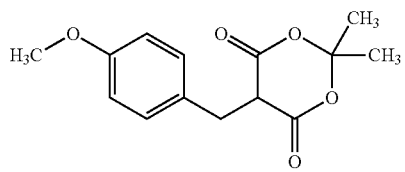

30.0 g (220 mmol) of 4-methoxybenzaldehyde were initially charged in 500 ml of water, and 33.3 g (231 mmol) of Meldrum's acid were suspended therein. The mixture was stirred mechanically at an internal temperature of 75° C. for 2 h. During this time, the yellowish emulsion turned into a yellow suspension. After cooling, the reaction mixture was extracted with dichloromethane and the extracts were dried with magnesium sulphate. This dichloromethane solution of the intermediate 5-(4-methoxybenzylidene)-2,2-dimethyl-1,3-dioxane-4,6-dione ($^1$H-NMR (300 MHz, CDCl$_3$): δ=1.78 (s, 6H), 3.90 (s, 3H), 6.98 (d, 2H), 8.23 (d, 2H), 8.37 (s, 1H)) was directly processed further. The solution (800 ml) was cooled to −3° C., and 110 ml of acetic acid were added. 20.8 g (155 mmol) of sodium borohydride were then introduced a little at a time over a period of 60 min (temperature at most 2° C.). The suspension formed was stirred at RT for another 15 min. The reaction mixture was quenched by careful dropwise addition of 300 ml of water and stirred at RT for another about 30 min. The phases were separated and the organic phase washed with sodium bicarbonate solution and water and dried with magnesium sulphate. The solvents were removed on a rotary evaporator. This gave 46.60 g (80% of theory) of the desired product as a yellowish oil which crystallized to give a slightly yellow solid and did not require any further purification.

$^1$H-NMR (300 MHz, CDCl$_3$): δ=1.48 (s, 3H), 1.72 (s, 3H), 3.44 (d, 2H), 3.72 (t, 1H), 3.77 (s, 3H), 6.82 (d, 2H), 7.24 (d, 2H).

Example 4A 2,2,5-Trimethyl-5-[4-(trifluoromethoxy)benzyl]-1,3-dioxane-4,6-dione

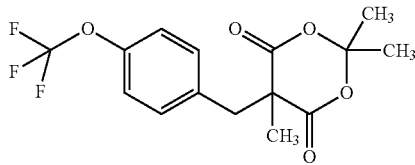 [SMILES: CC1(C)OC(=O)C(C)(Cc2ccc(OC(F)(F)F)cc2)C(=O)O1]

At RT, 32.7 g (103 mmol) of 2,2-dimethyl-5-[4-(trifluoromethoxy)benzyl]-1,3-dioxane-4,6-dione (Example 1A) and 21.3 g (154 mmol) of potassium carbonate were initially charged in 400 ml of DMF, and 72.9 g (514 mmol, 32.0 ml) of iodomethane were slowly added dropwise. The mixture was stirred vigorously at RT for 1.5 h and then added to water. The mixture was extracted 3× with ethyl acetate and the combined organic phases were washed with sat. sodium chloride solution and dried with sodium sulphate. The solvents were removed on a rotary evaporator and the crude product (32.5 g colourless oil) was purified by flash chromatography (SiO$_2$, hexane/ethyl acetate). This gave 20.0 g (55% of theory) of the desired product as a colourless oil.

$^1$H-NMR (300 MHz, DMSO-d$_6$): δ=0.99 (s, 3H), 1.57 (s, 3H), 1.63 (s, 3H), 3.22 (s, 2H), 7.12 (d, 2H), 7.31 (d, 2H).

Example 5A 5-(4-Bromobenzyl)-2,2,5-trimethyl-1,3-dioxane-4,6-dione

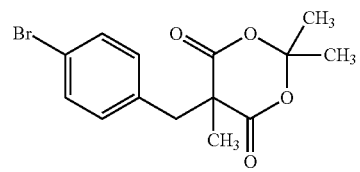 [SMILES: CC1(C)OC(=O)C(C)(Cc2ccc(Br)cc2)C(=O)O1]

The compound was prepared analogously to Example 4A from 7.37 g (23.5 mmol) of 5-(4-bromobenzyl)-2,2-dimethyl-1,3-dioxane-4,6-dione (Example 2A), 16.7 g (118 mmol) of iodomethane and 4.88 g (35.3 mmol) of potassium carbonate. This gave 8 g of crude product which was directly reacted further.

$^1$H-NMR (300 MHz, CDCl$_3$): δ=1.06 (s, 3H), 1.62 (s, 3H), 1.74 (s, 3H), 3.28 (s, 2H), 7.05 (d, 2H), 7.40 (s, 2H).

Example 6A 5-(4-Methoxybenzyl)-2,2,5-trimethyl-1,3-dioxane-4,6-dione

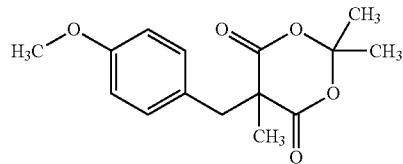

548 g (2.08 mol) of 5-(4-methoxybenzyl)-2,2-dimethyl-1,3-dioxane-4,6-dione (Example 3A) were initially charged in 3000 ml of dimethyl sulphoxide, and 295 g (2.08 mol) of iodomethane were added dropwise with stirring at RT. Using an ice bath, the solution was cooled to an internal temperature of about 15° C., and 231 g (2.28 mol) of triethylamine were added dropwise over a period of 30 min (internal temperature 15-22° C.). The mixture was stirred in the ice bath for 30 min and at RT for another 3 h. The mixture was added to dilute sodium chloride solution (2 portions of in each case 12 l water and in each case 500 g of sodium chloride) and extracted with methyl tert-butyl ether. The organic phases were combined, washed with semisaturated sodium chloride solution and dried with magnesium sulphate. The solvents were removed, which gave 497 g (86% of theory) of the desired product as a yellowish wax-like solid. Further purification was possible by crystallization (hexane/isopropanol) or chromatographically.

$^1$H-NMR (400 MHz, CDCl$_3$): δ=0.98 (s, 3H), 1.60 (s, 3H), 1.72 (s, 3H), 3.27 (s, 2H), 3.76 (s, 3H), 6.79 (d, 2H), 7.09 (s, 2H).

Example 7A

2-Methyl-3-[4-(trifluoromethoxy)phenyl]propanoic acid

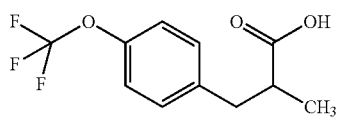 [SMILES: CC(Cc1ccc(OC(F)(F)F)cc1)C(=O)O]

19.0 g (57.2 mmol) of 2,2,5-trimethyl-5-[4-(trifluoromethoxy)benzyl]-1,3-dioxane-4,6-dione (Example 4A) were taken up in 90 ml of dioxane and 35 ml of conc. aqueous hydrochloric acid and heated at 125° C. under reflux for 2 h. The mixture was allowed to cool and the solvents were removed on a rotary evaporator. The residue (19.5 g colourless resin) was heated at 200° C. for 1 h. The crude product obtained was reacted further without further purification.

LCMS (Method 2): R$_t$=1.21 min; m/z [ES−]=247 (M−H)$^-$
$^1$H-NMR (300 MHz, DMSO-d$_6$): δ=1.12 (s, 3H), 3.06 (s, 2H), 7.21-7.27 (m, 4H).

Example 8A 3-(4-Fluoro-3-methoxyphenyl)-2-methylprop-2-enenoic acid

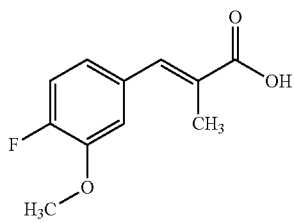

2.18 g (14.1 mmol) of 4-fluoro-3-methoxybenzaldehyde (CAS [128495-46-5]), 2.45 g (14.1 mmol) of sodium propoxide (CAS [137-40-6]) and 1.84 g (14.1 mmol) of propionic anhydride (CAS [123-62-6]) were stirred together at 150° C. for 3 h. During this time, the suspension, which was initially white, turned into a clear solution. The mixture was cooled, diluted with 2M aqueous sodium hydroxide solution and extracted 2× with diethyl ether. The aqueous phase was acidified with 6M hydrochloric acid (pH about 5) and extracted 3× with ethyl acetate. The combined organic phases were washed with sat. sodium chloride solution and dried with sodium sulphate, and the solvents were removed on a rotary evaporator. This gave 1.70 g (51% of theory) of the product as a yellow solid which was reacted further without further purification.

LCMS (Method 2): R$_t$=1.06 min; m/z [ES−]=209 (M−H)$^-$
$^1$H-NMR (300 MHz, DMSO-d$_6$): δ=2.01 (d, 3H), 3.85 (s, 3H), 7.00-7.03 (m, 1H), 7.19-7.25 (m, 2H), 7.51 (s, 1H).

The following compound was prepared analogously to Example 8A from the appropriate aldehyde:

| No | Structure | Name | Analytical data |
|---|---|---|---|
| 9A | 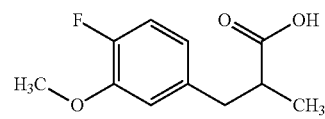 | 3-[3-chloro-4-(trifluoromethoxy)-phenyl]-2-methylprop-2-enenoic acid | $^1$H-NMR (300 MHz, DMSO-d$_6$): δ = 1.98 (d, 3H), 7.51-7.59 (m, 3H), 7.75 (d, 1H). LCMS (Method 2): R$_t$ = 1.32 min; m/z [ES$^-$] = 279/281 (M − H, Cl isotopes)$^-$ |

Example 10A 3-(4-Fluoro-3-methoxyphenyl)-2-methylpropanoic acid 1.55 g (7.34 mmol) of 3-(4-fluoro-3-methoxyphenyl)-2-methylprop-2-enoic acid (Example 8A) were hydrogenated (1 atm hydrogen atmosphere) in the presence of 780 mg of palladium catalyst (10% Pd on activated carbon, 0.73 mmol) in 70 ml of ethyl acetate with vigorous shaking at RT for 1 h. The catalyst was then filtered off and washed with dichloromethane, and the filtrate was concentrated on a rotary evaporator. This gave 1.34 g (60%) of 3-(4-fluoro-3-methoxyphenyl)-2-methylpropanoic acid as an oily product.

LCMS (Method 2): R$_t$=1.01 min; m/z [ES−]=211 (M−H)$^-$
$^1$H-NMR (300 MHz, DMSO-d$_6$): δ=1.00 (d, 3H), 2.49-2.66 (m, 2H), 2.84 (dd, 1H), 3.77 (s, 3H), 6.67-6.72 (m, 1H), 6.96 (dd, 1H), 7.04 (dd, 1H).

The following compound was prepared analogously to Example 10A from Example 9A:

| No | Structure | Name | Analytical data |
|---|---|---|---|
| 11A | 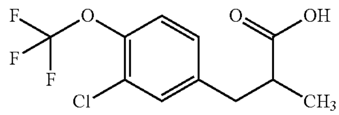 [SMILES: CC(Cc1ccc(OC(F)(F)F)c(Cl)c1)C(=O)O] | 3-[3-chloro-4-(trifluoromethoxy)-phenyl]-2-methylpropanoic acid | $^1$H-NMR (300 MHz, DMSO-d$_6$): δ = 1.02 (d, 3H), 2.61-2.71 (m, 2H), 2.82-2.91 (m, 1H), 7.27 (dd, 1H), 7.44 (dd, 1H), 7.50 (d, 1H). LCMS (Method 2): R$_t$ = 1.28 min; m/z [ES$^-$] = 281/283 (M − H, Cl isotopes)$^-$ |

Example 12A

2-Methyl-6-(trifluoromethoxy)indan-1-one

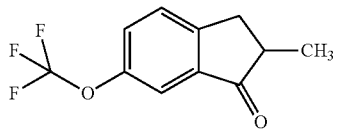 [SMILES: CC1Cc2ccc(OC(F)(F)F)cc2C1=O]

17.2 g (69.3 mmol) of crude 2-methyl-3-[4-(trifluoromethoxy)phenyl]propanoic acid (Example 7A) were dissolved in 100 ml of dichloromethane, and 12.1 ml (16.6 g, 166 mmol) of thionyl chloride and 0.16 ml of DMF were added dropwise at RT. The mixture was subsequently heated under reflux for about 30 min until the evaluation of gas had ceased. The solution was allowed to cool and the solvents were removed on a rotary evaporator. The residue (yellow solid) was taken up in 35 ml of dichloromethane and, at RT, added dropwise to a suspension of 10.2 g (76.2 mmol) of anhydrous aluminium chloride in 200 ml of dichloromethane. The dark-red solution was stirred for 30 min and then added to water, and the phases were separated. The aqueous phase was extracted 3× with dichloromethane, washed with water, sat. sodium bicarbonate solution and sat. sodium chloride solution and dried with sodium sulphate. The solvents were removed and the residue (10.0 g) was purified by flash chromatography (SiO$_2$, hexane/dioxane). This gave 5.84 g (14% of theory) of the product as a yellow oil.

LCMS (Method 2): R$_t$=1.27 min; m/z=231; 272 (M+H)$^+$/(M+ACN+H)$^+$

Example 13A

6-Bromo-2-methylindan-1-one

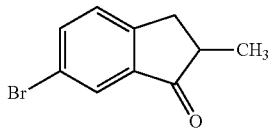

36 ml of polyphosphoric acid were added to 3.64 g (11.1 mmol) of 5-(4-bromobenzyl)-2,2,5-trimethyl-1,3-dioxane-4,6-dione (Example 5A), and the mixture was stirred at 100° C. for 10 h. After cooling, the mixture was added to ice-water and extracted with ethyl acetate. The combined organic phases were washed with sat. sodium bicarbonate solution and dried with sodium sulphate. The solvents were removed on a rotary evaporator and the residue was purified by flash chromatography (SiO$_2$, hexane/ethyl acetate). This gave 812 mg (32% of theory) of the product as a brown oil.

LCMS (Method 1): R$_t$=1.18 min; m/z=225; 227 (Br isotope pattern, M+H)$^+$ and 266; 268 (Br isotope pattern, M+ACN+H)$^+$ $^1$H-NMR (400 MHz, CDCl$_3$): δ=1.31 (d, 3H), 2.68 (dd, 1H), 2.72-2.79 (m, 1H), 3.35 (dd, 1H), 7.34 (d, 1H), 7.68 (dd, 1H), 7.88 (d, 1H).

Example 14A

6-Methoxy-2-methylindan-1-one

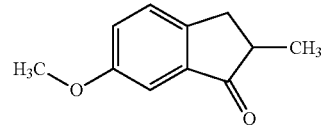

628 g (5.39 mol) of polyphosphoric acid (CAS [8017-16-1]) were initially charged and heated to about 100° C. With stirring, 100 g (359 mmol) of 5-(4-methoxybenzyl)-2,2,5-trimethyl-1,3-dioxane-4,6-dione (Example 6A), dissolved in 400 ml of toluene, were then added dropwise over a period of 15 min. The mixture was stirred for about 15 min, the reaction mixture was then added to water (about 3 l) and residual material was transferred using dichloromethane. The mixture was diluted with more dichloromethane and water and the phases were separated. The aqueous phase was re-extracted with dichloromethane and the combined organic phases were repeatedly washed carefully with semi-saturated sodium bicarbonate solution and with water and dried with magnesium sulphate. The solvents were removed on a rotary evaporator. This gave 58.2 g (92% of theory) the crude product as a brown oil, which was reacted further without purification. Purification can be carried out by kugelrohr distillation at 140° C., this gave a virtually colourless oil.

$^1$H-NMR (300 MHz, CDCl$_3$): δ=1.30 (d, 3H), 2.64 (dd, 1H), 2.70-2.78 (m, 1H), 3.32 (dd, 1H), 3.82 (s, 3H), 7.15-7.21 (m, 2H), 7.33 (d, 1H).

Example 15A

6-Fluoro-5-methoxy-2-methylindan-1-one

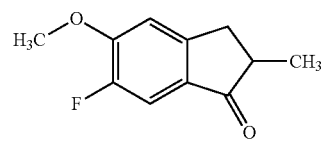

With ice-bath cooling, 13.5 g (116 mmol, 7.71 ml) of chlorosulphonic acid (CAS [7790-94-5]) were added carefully to 4.10 g (19.3 mmol) of 3-(4-fluoro-3-methoxyphenyl)-2-methylpropanoic acid (Example 10A), and the mixture was stirred in an ice bath for 2 h. The reaction was then terminated by carefully adding, at little at a time, crushed ice. The mixture was extracted with dichloromethane and the combined organic phases were washed with sat. sodium bicarbonate solution and sat. sodium chloride solution and dried with sodium sulphate. The solvents were removed on a rotary evaporator and the brown residue was purified by flash chromatography (SiO$_2$, dichloromethane/methanol 0-3%). This gave 2.15 g (57% of theory) of the product as a pale-yellow solid.

LCMS (Method 2): R$_t$=1.01 min; m/z=195 (M+H)$^+$ $^1$H-NMR (300 MHz, DMSO-d$_6$): δ=1.13 (d, 3H), 2.57-2.71 (m, 2H), 3.30 (dd, 1H), 3.90 (s, 3H), 7.29 (d, 1H), 7.37 (d, 1H).

The following indanone was prepared analogously to Example 15A from the appropriate carboxylic acid (Example 11A):

chloride solution, dried with sodium sulphate and the solvents were removed on a rotary evaporator.

The residue was taken up in 375 ml of dichloromethane, 55 mg of 4-toluenesulphonic acid monohydrate were added and the mixture was stirred at RT for 16 h. The reaction mixture was added to sat. sodium bicarbonate solution and extracted 3× with dichloromethane, the combined organic phases were washed with sat. sodium chloride solution and dried with sodium sulphate and the solvent was removed on a rotary evaporator. The residue was purified by flash chromatography (SiO$_2$, hexane/ethyl acetate). This gave 2.42 g (21% of theory) of the product as a colourless resin.

LCMS (Method 1): R$_t$=1.76 min; m/z=325 (M+H)$^+$ $^1$H-NMR (400 MHz, DMSO-d$_6$): δ=2.09 (s, 3H), 3.53 (s, 2H), 6.93 (s, br, 1H), 7.07-7.12 (m, 1H), 7.38 (d, 2H), 7.50-7.56 (m, 1H), 7.54 (d, 2H).

| No | Structure | Name | Analytical data |
|---|---|---|---|
| 16A | 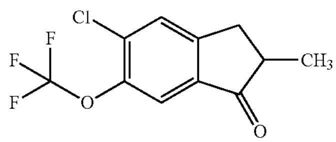 [SMILES: CC1Cc2cc(Cl)c(OC(F)(F)F)cc2C1=O] | 5-chloro-2-methyl-6-(trifluoromethoxy)-indan-1-one | $^1$H-NMR (300 MHz, DMSO-d$_6$): δ = 1.17 (d, 3H), 2.66-2.83 (m, 2H), 3.37 (dd, 1H), 7.66 (s, 1H), 7.94 (d, 1H). LCMS (Method 2): R$_t$ = 1.38 min; m/z = 265/267 (M + H, Cl isotopes)$^+$, 306/308 (M + H + ACN, Cl isotopes)$^+$ |

Example 17A 3-(4-Chlorophenyl)-2-methyl-5-(trifluoromethoxy)-1H-indene

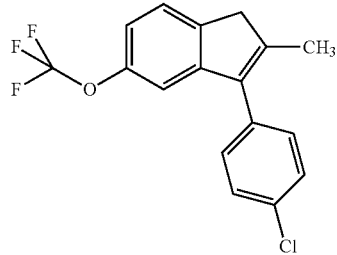 [SMILES: CC1=C(c2ccc(Cl)cc2)c2cc(OC(F)(F)F)ccc2C1]

Under argon, 38.1 ml of 4-chlorophenylmagnesium bromide (1M in diethyl ether, 38.1 mmol) were initially charged in 80 ml of THF, and 5.84 g (25.4 mmol) of 2-methyl-6-trifluoromethoxy-indan-1-one (Example 12A), dissolved in 20 ml of THF, were added dropwise at RT. The mixture was stirred at RT for 1 h and then added to sat ammonium chloride solution and extracted 3× with ethyl acetate, the combined organic phases were washed with sat. sodium Example 18A 5-Bromo-3-(4-chlorophenyl)-2-methyl-1H-indene

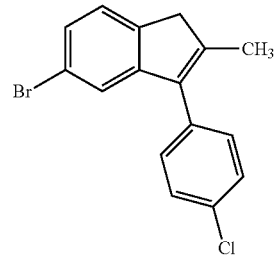 [SMILES: CC1=C(c2ccc(Cl)cc2)c2cc(Br)ccc2C1]

The preparation was carried out analogously to Example 17A from 800 mg (3.55 mmol) of 6-bromo-2-methylindan-1-one (Example 13A), 5.33 ml of 1M 4-chlorophenylmagnesium bromide solution in 8 ml of THF; the elimination of water from the tertiary alcohol formed in this reaction was carried out using 7 mg (0.04 mmol) of 4-toluenesulphonic acid monohydrate. The crude product was directly reacted further.

The following compounds were prepared analogously to Example 17A from the appropriate indanones by reaction with 4-chlorophenylmagnesium bromide and subsequent elimination of water using 4-toluenesulphonic acid:

| No | Structure | Name | Analytical data |
|---|---|---|---|
| 21A | ![structure] | 6-chloro-3-(4-chlorophenyl)-2-methyl-5-(trifluoromethoxy)-1H-indene | $^1$H-NMR (300 MHz, DMSO-$d_6$): δ = 2.08 (s, 3H), 3.57 (s, 2H), 7.07 (d, 1H), 7.38 (d, 2H), 7.55 (d, 2H), 7.73 (s, 1H). LCMS (Method 2): $R_t$ = 1.81 min; m/z [ES$^-$] = 357/359 (M − H, Cl isotopes)$^-$ |
| 22A | ![structure] | 3-(4-chlorophenyl)-5-methoxy-2-methyl-1H-indene | $^1$H-NMR (300 MHz, CDCl$_3$): δ = 2.11 (s, 3H), 3.40 (s, 2H), 3.78 (s, 3H), 6.72 (dd, 1H), 6.73 (sbr, 1H), 7.32 (d, 1H), 7.33 (d, 2H), 7.44 (d, 2H). |

Example 23A 3-(5-Methoxy-2-methyl-1H-inden-3-yl)pyridine

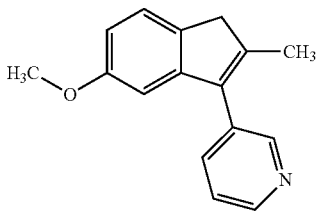

6.28 g (30.6 mmol) of 3-iodopyridine (CAS [1120-90-7]) were initially charged in 30 ml of THF, 24 ml of isopropylmagnesium chloride/lithium chloride complex solution (1.3 M in THF, CAS[807329-97-1]) were added dropwise at 0° C. and the mixture was stirred at 0° C. for 30 min. 2.0 g (11.4 mmol) of 6-methoxy-2-methylindan-1-one (Example 14A) dissolved in 30 ml of THF were then added dropwise at 0° C., and the mixture was stirred at 0° C. for 3 h. The reaction was terminated by addition of 100 ml of sat. ammonium chloride solution and stirred for another 10 min. The mixture was then extracted with ethyl acetate, and the combined organic phases were washed with water and sat. sodium chloride solution and dried with sodium sulphate. The solvents were removed on a rotary evaporator and the residue was taken up in 60 ml of dichloromethane. 4.8 g (25 mmol) of 4-toluenesulphonic acid were added in 2 portions and the mixture was heated to 35-45° C. for a total of 36 h. With ice-bath cooling, 100 ml of sat. sodium bicarbonate solution were then added, and the mixture was stirred for another 10 min and extracted with dichloromethane. The combined organic phases were washed with water and dried with sodium sulphate. The solvents were removed on a rotary evaporator and the residue was purified by flash chromatography (SiO$_2$, hexane/ethyl acetate). This gave 851 mg (30% of theory) of the desired product as a yellow oil.

LCMS (Method 2): $R_t$=0.98 min; m/z=238 (M+H)$^+$; 279 (M+ACN+H)$^+$ $^1$H-NMR (600 MHz, CDCl$_3$): δ=2.15 (s, 3H), 3.45 (s, 2H), 3.78 (s, 3H), 6.72 (d, 1H), 6.75 (dd, 1H), 7.34 (d, 1H), 7.41 (dd, 1H), 7.73 (dt, 1H), 8.62 (dd, 1H), 8.67 (d, 1H).

Example 24A

5-Methoxy-2-methyl-3-1H-inden-3-yl-1,1,2,2,3,3,4,4-nonafluorobutane-1-sulphonate

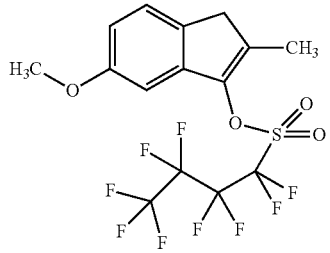 [SMILES: COc1ccc2c(c1)C(OS(=O)(=O)C(F)(F)C(F)(F)C(F)(F)C(F)(F)F)=C(C)C2]

12.6 g (71.5 mmol) of freshly kugelrohr-distilled 6-methoxy-2-methylindan-1-one (Example 14A) were initially charged in 400 ml of THF, and the mixture was stirred in an ice bath for 10 min. 17.1 g (85.8 mmol) of potassium hexamethyldisilazide (CAS [40949-94-8]) were then added a little at a time (internal temperature at most 5° C.). After a further 10 min in the ice bath, the mixture was cooled to −72° C., and 25.9 g (85.8 mmol) of 1,1,2,2,3,3,4,4,4-nonafluorobutan-1-sulphonyl fluoride (CAS [375-72-4]) were then added quickly. During the addition, the internal temperature temporarily rose to 10° C., and the colour of the solution changed to green-brown. The mixture was stirred at −72° C. for 30 min and at 0° C. for a further 30 min, and the reaction mixture was then added to water and extracted with dichloromethane. The organic phases were washed with water and dried with sodium sulphate and the solvents were removed. The crude product (25 g of an orange oil) was purified by flash chromatography (SiO$_2$, hexane/ethyl acetate). This gave 16.5 g (45% of theory) of the product as an orange resin.

LCMS (Method 2): $R_t$=1.69 min; m/z=459 (M+H)$^+$ $^1$H-NMR (300 MHz, DMSO-$d_6$): δ=2.09 (s, 3H), 3.47 (s, 2H), 3.73 (s, 3H), 6.68 (d, 1H), 6.82 (dd, 1H), 7.34 (d, 1H).

Example 25A

1-[2-(4-Chlorobenzoyl)-4-(trifluoromethoxy)phenyl]propan-2-one

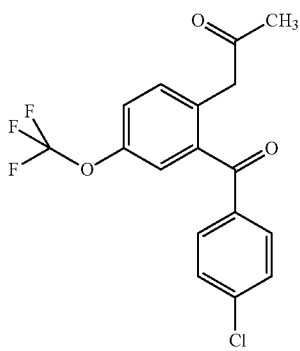 [SMILES: CC(=O)Cc1ccc(OC(F)(F)F)cc1C(=O)c1ccc(Cl)cc1]

2.42 g (7.45 mmol) of 3-(4-chlorophenyl)-2-methyl-5-trifluoromethoxy-1H-indene (Example 17A) were initially charged in 14 ml of hexane and 14 ml of acetonitrile, and 34 mg (0.15 mmol) of ruthenium(III) chloride hydrate (CAS [14898-67-0]) were added. The mixture was stirred at 0° C. for 10 min, and 3.19 g (14.9 mmol) of sodium periodate were then introduced a little at a time. The brown suspension was stirred for another 30 min and then added to 4M hydrochloric acid. The mixture was extracted 3× with ethyl acetate, the combined organic phases were washed with sat. sodium chloride solution, dried with sodium sulphate and the solvent was removed on a rotary evaporator. The residue was purified by flash chromatography (SiO$_2$, hexane/ethyl acetate). This gave 2.18 g (52% of theory) of the product as a colourless resin.

LCMS (Method 1): R$_t$=1. 45 min; m/z=357 (M+H)$^+$
$^1$H-NMR (400 MHz, DMSO-d$_6$): δ=2.05 (s, 3H), 3.98 (s, 2H), 7.31-7.33 (m, 1H), 7.46 (d, 1H), 7.50-7.56 (m, 1H), 7.60 (d, 2H), 7.68 (d, 2H).

Example 26A

1-[4-Bromo-2-(4-chlorobenzoyl)phenyl]propan-2-one

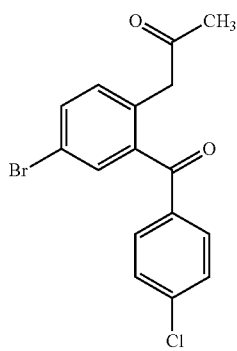 [SMILES: CC(=O)Cc1ccc(Br)cc1C(=O)c1ccc(Cl)cc1]

The preparation was carried out analogously to Example 25A from 1.14 g (3.57 mmol) of 5-bromo-3-(4-chlorophenyl)-2-methyl-1H-indene (Example 18A), 16 mg (0.07 mmol) of ruthenium(III) chloride hydrate and 1.53 g (7.13 mmol) of sodium periodate. This gave 347 mg (28% of theory) of the desired product as an orange oil.

LCMS (Method 1): R$_t$=1.41 min; m/z=351; 353; 355 (Br—Cl isotope pattern, M+H)$^+$
$^1$H-NMR (400 MHz, CDCl$_3$): δ=2.18 (s, 3H), 3.96 (s, 2H), 7.14 (d, 1H), 7.45-7.50 (m, 3H), 7.61 (dd, 1H), 7.76 (d, 2H).

Example 27A

1-[4-Methoxy-2-(pyridin-3-ylcarbonyl)phenyl]propan-2-one

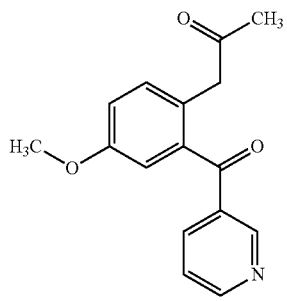 [SMILES: COc1ccc(CC(C)=O)c(C(=O)c2cccnc2)c1]

844 mg (3.56 mmol) of 3-(5-methoxy-2-methyl-1H-inden-3-yl)pyridine (Example 23A) were initially charged in 15 ml of dimethoxyethane and 5 ml of water, and 4.5 ml (0.36 mmol) of osmium tetroxide solution (CAS [20816-12-0], 2.5% in tert-butanol) were added. 1.52 g (7.11 mmol) of sodium periodate (CAS [7790-28-5]) were then added a little at a time, and the mixture was stirred at RT for 3 h. The reaction mixture was filtered through a few centimeters of silica gel 60, the silica gel washed with ethyl acetate and the filtrate washed with water and sat. sodium chloride solution and dried with sodium sulphate. The solvents were removed on a rotary evaporator. This gave 439 mg of a brown residue as a crude product (about 45% of theory) which was directly reacted further.

LCMS (Method 2): R$_t$=0.90 min; m/z=270 (M+H)$^+$

The following compounds were prepared analogously to Example 25A from the corresponding 1H-indenes:

| No | Structure | Name | Analytical data |
|---|---|---|---|
| 28A | (structure) | 1-[5-chloro-2-(4-chlorobenzoyl)-4-(trifluoromethoxy)-phenyl]propan-2-one | $^1$H-NMR (400 MHz, CDCl$_3$): δ = 2.06 (s, 3H), 3.99 (s, 2H), 7.54 (d, 1H), 7.60 (d, 2H), 7.69 (d, 2H), 7.72 (s, 1H). LCMS (Method 2): R$_t$ = 1.52 min; m/z = 391/393 (M + H, Cl isotopes)$^+$ |
| 29A | (structure) | 1-[2-(4-chlorobenzoyl)-4-methoxyphenyl]-propan-2-one | $^1$H-NMR (300 MHz, CDCl$_3$): δ = 2.15 (s, 3H), 3.89 (s, 2H), 3.78 (s, 3H), 6.89 (d, 1H), 7.02 (dd, 1H), 7.18 (d, 1H), 7.44 (d, 2H), 7.77 (d, 2H). |

Example 30A 1-(4-Chlorophenyl)-4-methyl-8-(trifluoromethoxy)-5H-2,3-benzodiazepine 2.18 g (6.11 mmol) of 1-[2-(4-chlorobenzyl)-4-trifluoromethoxyphenyl]propan-2-one (Example 25A) were initially charged in 25 ml of ethanol, and 920 mg (18.3 mmol) of hydrazine hydrate were added. The mixture was stirred at RT for 30 min, and the reaction mixture was then added to water and extracted 3× with ethyl acetate. The combined organic phases were washed with sat. sodium chloride solution and dried with sodium sulphate, and the solvent was removed on a rotary evaporator. The residue was purified by flash chromatography (SiO$_2$, hexane/ethyl acetate). This gave 1.53 g (65% of theory) of the product as a pale-yellow solid.

LCMS (Method 1): R$_t$=1.44 min; m/z=353 (M+H)$^+$ $^1$H-NMR (400 MHz, DMSO-d$_6$): δ=2.05 (s, 3H), 2.89 (d, 1H), 3.61 (d, 1H), 7.20 (s, br, 1H), 7.49-7.54 (m, 4H), 7.59-7.66 (m, 2H).

Example 31A

8-Bromo-1-(4-chlorophenyl)-4-methyl-5H-2,3-benzodiazepine

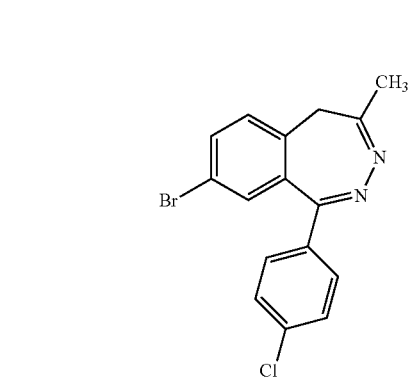

The preparation was carried out analogously to Example 30A from 340 mg (967 μmol) of 1-[4-bromo-2-(4-chlorobenzoyl)phenyl]propan-2-one (Example 26A) and 702 mg (14.0 mmol) of hydrazine hydrate in 34 ml of ethanol. This gave 376 mg of the crude product as an orange oil which was directly reacted further without purification.

LCMS (Method 1): R$_t$=1.41 min; m/z=347; 349; 351 (Br—Cl isotope pattern, M+H)$^+$ $^1$H-NMR (300 MHz, CDCl$_3$): δ=2.15 (s, 3H), 3.01 (d, 1H), 3.35 (d, 1H), 7.19 (d, 1H), 7.41 (d, 2H), 7.45 (d, 1H), 7.60 (d, 2H), 7.66 (dd, 1H).

Example 32A

8-Methoxy-4-methyl-1-(pyridin-3-yl)-5H-2,3-benzodiazepine

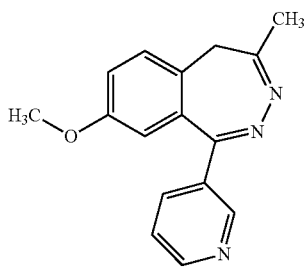

The preparation was carried out analogously to Example 30A from 430 mg (1.60 mmol) of crude 1-[4-methoxy-2-(pyridin-3-ylcarbonyl)phenyl]propan-2-one (Example 27A) and 888 mg (17.7 mmol) of hydrazine hydrate in 43 ml of ethanol. This gave 408 mg of the crude product as a brown resin which was directly reacted further without purification.

LCMS (Method 2): $R_t$=0.79 min; m/z=266 (M+H)$^+$

The following compounds were prepared analogously to Example 30A from the appropriate diketones:

Example 35A (±)-1-(4-Chlorophenyl)-4-methyl-8-(trifluoromethoxy)-4,5-dihydro-3H-2,3-benzodiazepine

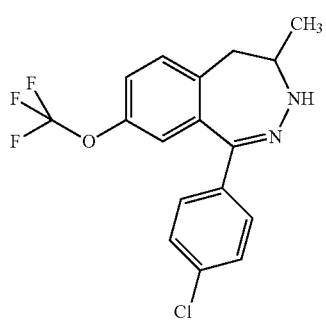

At RT, 1.53 g (4.34 mmol) of 1-(4-chlorophenyl)-4-methyl-8-(trifluoromethoxy)-5H-2,3-benzodiazepine (Example 30A) were initially charged in 160 ml of methanol, 2.5 ml of 2M hydrochloric acid were added and 1.36 g (21.7 mmol) of sodium cyanoborohydride were introduced. The mixture was stirred at RT for 1 h and then made alkaline using 2M aqueous sodium hydroxide solution (pH about 8).

| No | Structure | Name | Analytical data |
|---|---|---|---|
| 33A | 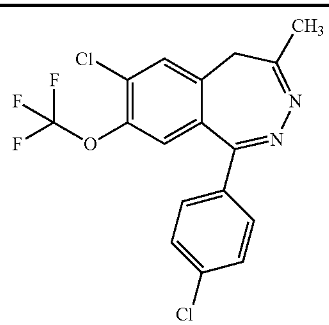 | 7-chloro-1-(4-chlorophenyl)-4-methyl-8-(trifluoromethoxy)-5H-2,3-benzodiazepine | $^1$H-NMR (300 MHz, DMSO-d$_6$): δ = 2.07 (s, 3H), 2.89 (d, 1H), 3.62 (d, 1H), 7.39 (d, 1H), 7.49-7.55 (m, 4H), 7.94 (s, 1H). LCMS (Method 1): R$_t$ = 1.51 min; m/z = 387/389/391 (M + H, Cl isotopes)$^+$ |
| 34A | 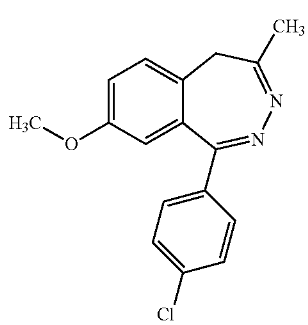 | 1-(4-chlorophenyl)-8-methoxy-4-methyl-5H-2,3-benzodiazepine | $^1$H-NMR (400 MHz, CDCl$_3$): δ = 2.12 (s, 3H), 3.00 (dd, 1H), 3.27 (dd, 1H), 3.72 (s, 3H), 6.78 (d, 1H), 7.08 (dd, 1H), 7.18 (d, 1H), 7.37 (d, 2H), 7.63 (d, 2H). LCMS (Method 3): R$_t$ = 1.03 min; m/z = 284; 286 (Cl isotope pattern, M + H)$^+$ |

Most of the methanol was removed on a rotary evaporator and the residue was partitioned between water and dichloromethane. The phases were separated and the aqueous phase was extracted with dichloromethane. The combined organic phases were washed with sat. sodium chloride solution, dried with sodium sulphate and the solvent was removed on a rotary evaporator. The residue was purified by flash chromatography (SiO$_2$, hexane/ethyl acetate). This gave 1.00 g (61% of theory) of the product as a yellow crystallizing resin.

LCMS (Method 2): R$_t$=1.50 min; m/z=355 (M+H)$^+$ $^1$H-NMR (400 MHz, DMSO-d$_6$): δ=1.10 (d, 3H), 2.75 (dd, 1H), 2.99 (dd, 1H), 3.76-3.83 (m, 1H), 6.84 (s, br, 1H), 7.21-7.24 (m, 1H), 7.32-7.38 (m, 5H), 7.64 (s, br, 1H).

Example 36A (±)-8-Bromo-1-(4-chlorophenyl)-4-methyl-4,5-dihydro-3H-2,3-benzodiazepine

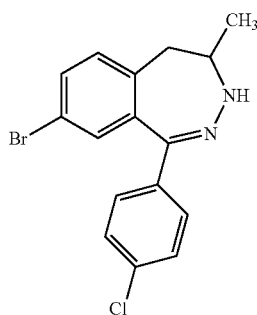 [SMILES: CC1Cc2ccc(Br)cc2C(c2ccc(Cl)cc2)=NN1]

The preparation was carried out analogously to Example 35A from 336 mg (966 μmol) of 8-bromo-1-(4-chlorophenyl)-4-methyl-5H-2,3-benzodiazepine (Example 31A) and 304 mg (4.83 mmol) of sodium cyanoborohydride in 33 ml of methanol and 0.5 ml of 2M hydrochloric acid. The crude product (282 mg) was purified by flash chromatography (SiO$_2$, hexane/ethyl acetate). This gave 141 mg (42% of theory) of the product as an orange foam.

LCMS (Method 1): R$_t$=1.39 min; m/z=349; 351; 353 (Br—Cl isotope pattern, M+H)$^+$ $^1$H-NMR (300 MHz, CDCl$_3$): δ=1.26 (d, 3H), 2.65 (dd, 1H), 2.92 (dd, 1H), 4.02-4.13 (m, 1H), 5.46 (s, br, 1H), 7.12 (d, 1H), 7.22 (d, 1H), 7.34 (d, 2H), 7.42-7.48 (m, 3H).

Example 37A (±)-8-Methoxy-4-methyl-1-(pyridin-3-yl)-4,5-dihydro-3H-2,3-benzodiazepine

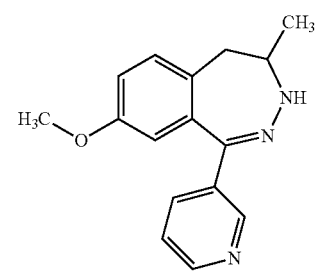

The preparation was carried out analogously to Example 35A from 400 mg (1.51 mmol) of crude 8-methoxy-4-methyl-1-(pyridin-3-yl)-5H-2,3-benzodiazepine (Example 32A) and 473 mg (7.54 mmol) of sodium cyanoborohydride in 20 ml of methanol and 0.6 ml of 2M hydrochloric acid. This gave 155 mg (about 38% of theory) of the crude product as a brown resin. It was directly reacted further.

LCMS (Method 2): R$_t$=0.77 min; m/z=268 (M+H)$^+$

The following compounds were prepared analogously to Example 35A from the appropriate 5H-2,3-benzodiazepines:

| No | Structure | Name | Analytical data |
|---|---|---|---|
| 38A | 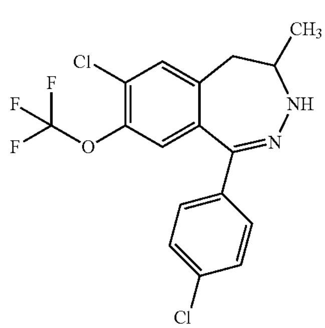 [SMILES: CC1Cc2cc(Cl)c(OC(F)(F)F)cc2C(c2ccc(Cl)cc2)=NN1] | (±)-7-chloro-1-(4-chlorophenyl)-4-methyl-8-(trifluoromethoxy)-4,5-dihydro-3H-2,3-benzodiazepine | $^1$H-NMR (300 MHz, DMSO-d$_6$): δ = 1.11 (d, 3H), 2.78 (dd, 1H), 3.02 (dd, 1H), 3.73-3.83 (m, 1H), 6.99 (d, 1H), 7.31-7.38 (m, 4H), 7.58 (s, 1H), 7.84 (d, 1H). LCMS (Method 2): R$_t$ = 1.26 min; m/z = 389/391 (M + H, Cl isotope pattern)$^+$ |

| No | Structure | Name | Analytical data |
|---|---|---|---|
| 39A | (structure) | (±)-1-(4-chlorophenyl)-4,5-dihydro-8-methoxy-4-methyl-3H-2,3-benzodiazepine | $^1$H-NMR (400 MHz, CDCl$_3$): δ = 1.24 (d, 3H), 2.60 (dd, 1H), 2.90 (dd, 1H), 3.70 (s, 3H), 4.07 (qdd, 1H), 6.61 (d, 1H), 6.89 (dd, 1H), 7.16 (d, 1H), 7.32 (d, 2H), 7.51 (d, 2H). LCMS (Method 3): R$_t$ = 1.09 min; m/z = 301; 303 (Cl isotope pattern, M + H)$^+$ |

Example 40A 1-(3,4-Dimethoxyphenyl)propan-2-ol

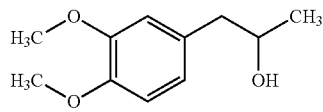

At 0° C., 147 mg (3.86 mmol) of lithium aluminium hydride were initially charged in 30 ml of THF, and 1.00 g (5.15 mmol) of 1-(3,4-dimethoxyphenyl)propan-2-one, dissolved in 10 ml of THF, were added dropwise. The mixture was stirred at 0° C. for another 2 h, and 0.1 ml of water, 0.1 ml of 2M aqueous sodium hydroxide solution and a further 0.3 ml of water were then added carefully in succession. After a further 30 min of stirring at RT, the mixture was filtered off through silica gel/sodium sulphate, the silica gel washed with ethyl acetate and the filtrate was concentrated on a rotary evaporator. This gave 950 mg of product (82% of theory) which was directly reacted further.

LCMS (Method 2): R$_t$=0.82 min; m/z=197 (M+H)$^+$; 179 (M−H$_2$O+H)$^+$ $^1$H-NMR (300 MHz, DMSO-d$_6$): δ=0.98 (d, 3H), 2.43 (dd, 1H), 2.59 (dd, 1H), 3.67 (s, 3H), 3.69 (s, 3H), 3.70-3.79 (m, 1H), 4.43 (d, 1H), 6.65 (dd, 1H), 6.75 (d, 1H), 6.79 (d, 1H).

Example 41A 1-(4-Bromophenyl)-3,4-dihydro-6,7-dimethoxy-3-methyl-1H-2-benzopyran

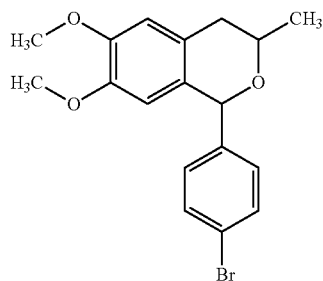

At RT, 950 mg (4.84 mmol) of 1-(3,4-dimethoxyphenyl) propan-2-ol (Example 40A) and 950 mg (5.14 mmol) of 4-bromobenzaldehyde (CAS [1122-91-4]) were initially charged in 4 ml of dioxane, and 7.70 ml of zinc chloride solution (0.7 M in THF, CAS [7646-85-7]) and 2.45 ml of hydrochloric acid (4 M in dioxane, CAS [7647-01-0]) were added. The mixture was then heated under reflux for 3 h and stirred at RT for a further 14 h. The mixture was added to water and extracted to ethyl acetate, and the combined organic phases were washed with sat. sodium bicarbonate solution and sat. sodium chloride solution and dried with sodium sulphate. The solvents were removed on a rotary evaporator. This gave 3.0 g of crude product as a light-brown oil which was directly reacted further without purification.

LCMS (Method 2): R$_t$=1.44 min; m/z=363; 365 (Br isotope pattern, M+H)$^+$

Alternative preparation procedure for Example 41A

At RT, 349.2 g (1.779 mol) of (±)-1-(3,4-dimethoxyphenyl)propan-2-ol (Example 40A) and 329.2 g (1.779 mol) of 4-bromobenzaldehyde (CAS [1122-91-4]) were initially charged in 3 l of toluene, and 140 ml of hydrochloric acid (36% aqueous solution) were added and the mixture was stirred at RT for 2 days. The mixture was then poured onto 2 l of water and extracted with 2×2 l of ethyl acetate, and the combined organic phases were washed 1× with saturated aqueous sodium hydrogencarbonate solution and 1× with 2 l of water, and dried using sodium sulphate. The solvent was reduced on a rotary evaporator. The product precipitated as a colourless solid. Shortly before dryness, 1 l of hexane was added and the mixture was cooled in an ice bath. The solid was isolated by suction filtration, washed with hexane and then dried under reduced pressure at 50° C. This gave 598.9 g (93% of theory) of the product (isomer mixture), which was directly reacted further without purification.

The following compound was prepared analogously to Example 41A from Example 40A and 3-bromobenzaldehyde:

| No | Structure | Name | Analytical data |
|---|---|---|---|
| 42A | ![structure] | 1-(3-bromophenyl)-3,4-dihydro-6,7-dimethoxy-3-methyl-1H-2-benzopyran | LCMS (Method 3): $R_t$ = 1.40 min; m/z = 363; 365 (M + H, Br isotope pattern)$^+$ |

Example 43A

1-[2-(4-Bromobenzoyl)-4,5-dimethoxyphenyl]propan-2-one

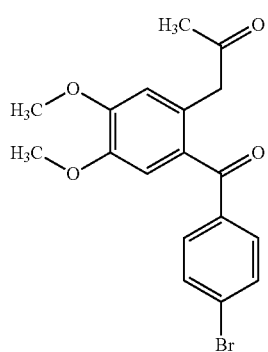 [SMILES: COc1cc(CC(C)=O)c(C(=O)c2ccc(Br)cc2)cc1OC]

At 0° C., 3.00 g (8.26 mmol) of 1-(4-bromophenyl)-3,4-dihydro-6,7-dimethoxy-3-methyl-1H-2-benzopyran (Example 41A) together with 3 g of silica gel were initially charged in 30 ml of acetone. A solution of 3.01 g (30.1 mmol) of chromium(VI) oxide (CAS [1333-82-0]) in 10 ml of conc. sulphuric acid and 20 ml of water was then slowly added dropwise, and the mixture was stirred at RT for 1 h. The mixture, which was now red-brown, was added to water and extracted with ethyl acetate. The organic phases were washed with sat. sodium chloride solution until neutral and dried with sodium sulphate, and the solvents were removed on a rotary evaporator. The residue (3 g) was purified by flash chromatography (SiO$_2$, hexane/ethyl acetate). This gave 1.03 g (33% of theory, 2 steps) of the product as a yellow solid.

LCMS (Method 2): $R_t$=1.26 min; m/z=377; 379 (Br isotope pattern, M+H)$^+$

Alternative Preparation Procedure for Example 43A

Preparation of Jones Reagent:

267 g of chromium(VI) oxide (CrO$_3$) were introduced cautiously into 230 ml of sulphuric acid (95-97%). Cooling took place with water/ice and water so that the internal temperature was 35-40° C. To start with an orange crystallisate was obtained, which slowly dissolved with the addition of water. Following addition of 500 ml of water, everything was in solution apart from a slight sediment. Stirring was carried out at RT for 30 minutes, after which the material was transferred to a bottle and made up to 1000 ml with water. This gave an approximately 2.6 M solution.

496.5 g (1.367 mol) of (±)-1-(4-bromophenyl)-3,4-dihydro-6,7-dimethoxy-3-methyl-1H-2-benzopyran (Example 13A) were initially charged in 5 l of acetone, cooled to 0° C. and admixed with 50 g of silica gel. Then 1.9 l of chromosulphuric acid (Jones reagent) were added dropwise over the course of 4 hours, followed by stirring at RT for 1 hour. After reaction had taken place, 4 l of water were added slowly to the reaction mixture. Extraction was carried out with 3×4 l of ethyl acetate. The combined organic phases were washed with 4 l of saturated aqueous sodium hydrogencarbonate solution and with 3×4 l of saturated aqueous sodium chloride solution, and dried using sodium sulphate. The solvent was reduced on a rotary evaporator. The product precipitated as a colourless solid. Shortly before dryness, 500 ml of hexane were added and the mixture was cooled in an ice bath. The solid was isolated by suction filtration, washed with hexane and then dried under reduced pressure at 50° C. This gave 334.1 g (65% of theory) of the product, which was directly reacted further without purification.

The following compound was prepared analogously to Example 43A from Example 42A:

| No | Structure | Name | Analytical data |
|---|---|---|---|
| 44A | 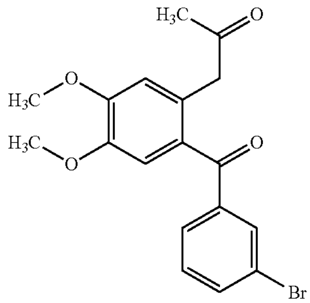 [SMILES: COc1cc(CC(C)=O)c(C(=O)c2cccc(Br)c2)cc1OC] | 1-[2-(3-bromobenzoyl)-4,5-dimethoxyphenyl]-propan-2-one | LCMS (Method 3): $R_t$ = 1.21 min; m/z = 377; 379 (M + H, Br isotope pattern)$^+$ |

Example 45A

1-(4-Bromophenyl)-7,8-dimethoxy-4-methyl-5H-2,3-benzodiazepine

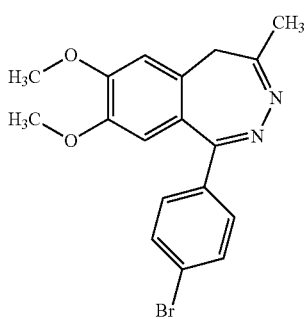

730 mg (1.94 mmol) of 1-[2-(4-bromobenzoyl)-4,5-dimethoxyphenyl]propan-2-one (Example 43A) were stirred with 513 mg (10.3 mmol) of hydrazine hydrate in 7 ml of ethanol at a bath temperature of 100° C. for 1 h. After cooling, the mixture was saturated with hydrogen chloride gas (introduced for about 5 min) The reaction solution was added to water, made alkaline with 1M aqueous sodium hydroxide solution and extracted with dichloromethane. The combined organic phases were dried with sodium sulphate and the solvent was removed on a rotary evaporator. The residue (1 g yellow solid) was purified by flash chromatography (SiO$_2$, dichloromethane/methanol 0-3%). This gave 390 mg (50% of theory) of the product as a yellow solid.

LCMS (Method 2): $R_t$=1.20 min; m/z=373; 375 (Br isotope pattern, M+H)$^+$ $^1$H-NMR (300 MHz, DMSO-d$_6$): δ=2.02 (s, 3H), 2.71 (d, 1H), 3.42 (d, 1H), 3.59 (s, 3H), 3.83 (s, 3H), 6.70 (s, 1H), 7.06 (s, 1H), 7.50 (d, 2H), 7.61 (d, 2H).

Alternative Preparation Procedure for Example 45a

At 0° C., 471 g (1.249 mol) of 1-[2-(4-bromobenzoyl)-4,5-dimethoxyphenyl]propan-2-one (Example 43A) were initially charged in 4.5 l of ethanol and admixed dropwise with 402 ml of hydrazine hydrate (6.62 mol). The mixture was allowed to come to RT and was stirred at this temperature for 2 days. It was decantered to remove the solid, and the clear supernatant was concentrated on a rotary evaporator. The concentrate was combined with the solid. Following addition of 8 l of ice-water, stirring took place for 2 days. The resulting precipitate was isolated by filtration with suction, washed with water and then dried under reduced pressure at 50° C. This gave 409.8 g (88% of theory) of the product, which was directly reacted further without purification.

The following compound was prepared analogously to Example 45A from Example 44A:

| No | Structure | Name | Analytical data |
|---|---|---|---|
| 46A | 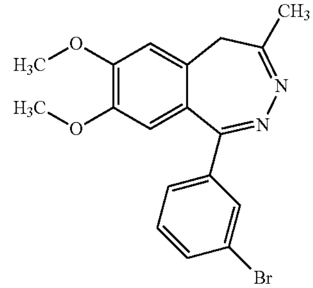 | 1-(3-bromophenyl)-7,8-dimethoxy-4-methyl-5H-2,3-benzodiazepine | $^1$H-NMR (300 MHz, CDCl$_3$): δ = 2.15 (s, 3H), 2.98 (d, 1H), 3.27 (d, 1H), 3.75 (s, 3H), 3.97 (s, 3H), 6.73 (s, 1H), 6.75 (s, 1H), 7.27 (dd, 1H), 7.55 (dbr, 1H), 7.61 (dbr, 1H), 7.86 (m, 1H). LCMS (Method 3): $R_t$ = 1.15 min; m/z = 373; 375 (M + H, Br isotope pattern)$^+$ |

Example 47A (±)-1-(4-Bromophenyl)-7,8-dimethoxy-4-methyl-4,5-dihydro-3H-2,3-benzodiazepine

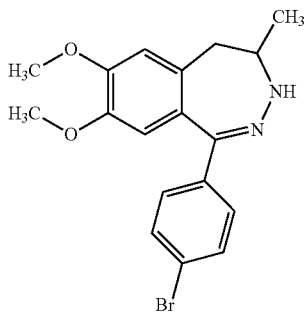

At RT, 1.99 g (5.33 mmol) of 1-(4-bromophenyl)-7,8-dimethoxy-4-methyl-5H-2,3-benzodiazepine (prepared according to the procedure in Example 45A) were initially charged in 200 ml of methanol, 3.0 ml of 2M hydrochloric acid were added and 1.68 g (26.6 mmol) of sodium cyanoborohydride were introduced. The mixture was stirred at RT for 1 h and then made alkaline with 2M aqueous sodium hydroxide solution (pH about 8). Most of the methanol was removed on a rotary evaporator, and the residue was partitioned between water and dichloromethane. The phases were separated and the aqueous phase was extracted with dichloromethane. The combined organic phases were washed with sat. sodium chloride solution and dried with sodium sulphate, and the solvent was removed on a rotary evaporator. The residue was purified by flash chromatography (SiO$_2$, hexane/ethyl acetate). This gave 1.56 g (78% of theory) of the product as a yellow crystallizing resin.

LCMS (Method 2): R$_t$=0.96 min; m/z=375; 377 (Br isotope pattern, M+H)$^+$ $^1$H-NMR (400 MHz, DMSO-d$_6$): δ=1.09 (d, 3H), 2.58 (dd, 1H), 2.83 (dd, 1H), 3.27 (s, 3H), 3.51 (s, 3H), 3.77-3.82 (m, 1H), 6.47 (s, 1H), 6.85 (s, 1H), 7.01 (d, 1H), 7.33 (d, 2H), 7.47 (d, 2H).

The following compound was prepared analogously to Example 47A from Example 46A:

Example 49A (±)-1-(4-Bromophenyl)-7,8-dimethoxy-N,4-dimethyl-4,5-dihydro-3H-2,3-benzodiazepine-3-carboxamide

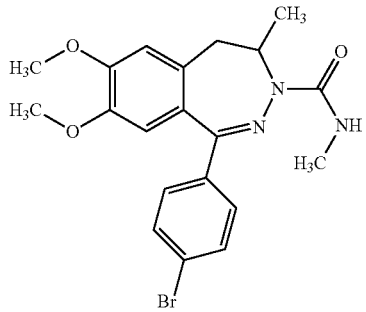 [SMILES: CNC(=O)N1N=C(c2ccc(Br)cc2)c2cc(OC)c(OC)cc2CC1C]

At RT, 1.56 g (4.16 mmol) of (±)-1-(4-bromophenyl)-7,8-dimethoxy-4-methyl-4,5-dihydro-3H-2,3-benzodiazepine (Example 47A) were dissolved in 50 ml of THF, 1.68 g (8.31 mmol) of 4-nitrophenyl chloroformate (CAS [7693-46-1]) were added dropwise and the mixture was stirred at RT for 1 h. During this time, the clear yellow solution slowly became turbid. 20.8 ml (41.6 mmol) of a 2M solution of methylamine in THF were added dropwise, and the mixture was stirred at 60° C. for 5 h. The mixture was allowed to warm slowly to RT and concentrated on a rotary evaporator, the mixture was partitioned between water and ethyl acetate and the phases were separated. The aqueous phase was extracted with ethyl acetate. The combined organic phases were washed with sat. sodium chloride solution and dried with sodium sulphate, and the solvent was removed on a rotary evaporator.

Since the reaction was incomplete (UPLC/MS control), the reaction with the resulting crude product/intermediate/starting material mixture was repeated in an analogous manner to achieve complete conversion. The crude product then obtained was purified by flash chromatography (SiO$_2$, hexane/ethyl acetate). This gave 1.90 g (100% of theory) of the desired product as a yellow foam.

LCMS (Method 2): R$_t$=1.33 min; m/z=432; 434 (Br isotope pattern, M+H)$^+$

| No | Structure | Name | Analytical data |
|---|---|---|---|
| 48A | ![structure] | (±)-1-(3-bromophenyl)-7,8-dimethoxy-4-methyl-4,5-dihydro-3H-2,3-benzodiazepine | $^1$H-NMR (300 MHz, CDCl$_3$): δ = 1.28 (d, 3H), 2.62 (dd, 1H), 2.89 (dd, 1H), 3.71 (s, 3H), 3.94 (s, 3H), 4.11 (m, 1H), 6.59 (s, 1H), 6.76 (s, 1H), 7.22 (dd, 1H), 7.45 (dbr, 1H), 7.48 (dbr, 1H), 7.75 (m, 1H). LCMS (Method 3): R$_t$ = 0.99 min; m/z = 375; 377 (M + H, Br isotope pattern)$^+$ |

¹H-NMR (400 MHz, DMSO-d$_6$): δ=0.92 (d, 3H), 2.64 (d, 3H), 2.67 (dd, 1H), 2.91 (dd, 1H), 3.53 (s, 3H), 3.80 (s, 3H), 5.03-5.11 (m, 1H), 6.47 (s, 1H), 6.60 (q, 1H), 6.98 (s, 1H), 7.56 (s, 4H).

Enantiomer Separation of Example 49A (±)-1-(4-Bromophenyl)-7,8-dimethoxy-N,4-dimethyl-4,5-dihydro-3H-2,3-benzodiazepine-3-carboxamide

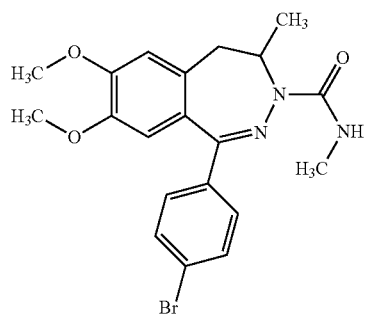 [SMILES: CNC(=O)N1N=C(c2ccc(Br)cc2)c2cc(OC)c(OC)cc2CC1C]

19.9 g of the compound prepared according to the procedure in Example 49A were separated into the enantiomers by chiral preparative HPLC under the following conditions: System: SFC Prep 400; column: Chiralpak AZ-H 5 μm 250×50 mm; mobile phase: CO$_2$/isopropanol 75:25 (v/v); flow rate: 300 ml/min; temperature: 38° C.; pressure 80 bar; solution: 5 g/100 ml of methanol/acetonitrile 50:50 (v/v); detection: UV 220 nm.

Example 49.1A: (4R)-1-(4-Bromophenyl)-7,8-dimethoxy-N,4-dimethyl-4,5-dihydro-3H-2,3-benzodiazepine-3-carboxamide 9.29 g, light-yellow solid, HPLC (Method T): R$_t$=3.29 min, purity>99%

Optical rotation: $[α]_D^{20}$=−89.3° (c=1.00; methanol)

Example 49.2A: (4S)-1-(4-Bromophenyl)-7,8-dimethoxy-N,4-dimethyl-4,5-dihydro-3H-2,3-benzodiazepine-3-carboxamide 9.9 g, light-yellow solid, HPLC (Method T): R$_t$=4.55 min, purity 96%

Optical rotation: $[α]_D^{20}$=+81.3° (c=1.00; methanol)

Alternative Preparation Procedure for Example 49a

At RT, 260 g (415.70 mmol) of (±)-1-(4-bromophenyl)-7,8-dimethoxy-4-methyl-4,5-dihydro-3H-2,3-benzodiazepine used in crude form (cf. Example 47A) were dissolved in 2000 ml of THF, 167.6 g (831.4 mmol) of 4-nitrophenyl chloroformate (CAS [7693-46-1]) were added, and subsequently 64.47 g (498.8 mmol) of diisopropylethylamine were added dropwise. Counter-cooling with an ice bath was carried out, owing to the development of heat. The batch was stirred at RT for 6 hours. Then 2078 ml (4157 mmol) of a 2-molar solution of methylamine in THF were added dropwise with ice-bath cooling, after which the batch was stirred at RT for 16 hours. The yellow suspension was admixed with 2-molar sodium hydroxide solution and thereafter extracted with three times 700 ml of ethyl acetate. The combined organic phases were washed with four times 200 ml of 2-molar sodium hydroxide solution, dried using sodium sulphate, and the solvent was removed on a rotary evaporator. The crude product obtained was purified by chromatography. This gave 147.5 g (51% of theory over 2 stages) of the desired product.

The following compounds were prepared analogously to Example 49A from the appropriate 4,5-dihydro-3H-2,3-benzodiazepines:

| No | Structure | Name | Analytical data |
|---|---|---|---|
| 50A | ![structure] | (±)-1-(4-chlorophenyl)-8-methoxy-N,4-dimethyl-4,5-dihydro-3H-2,3-benzodiazepine-3-carboxamide | ¹H-NMR (300 MHz, CDCl$_3$): δ = 0.92 (d, 3H), 2.86 (dd, 1H), 2.88 (d, 3H), 3.09 (dd, 1H), 3.69 (s, 3H), 5.43 (m, 1H), 6.59 (d, 1H), 6.88 (dd, 1H), 7.13 (d, 1H), 7.36 (d, 2H), 7.42 (d, 2H). LCMS (Method 3): R$_t$ = 1.35 min; m/z = 358; 360 (Cl isotope pattern, M + H)$^+$ |

-continued

| No | Structure | Name | Analytical data |
|---|---|---|---|
| 51A | 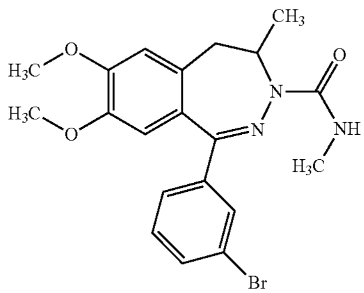 [SMILES: CNC(=O)N1N=C(c2cccc(Br)c2)c2cc(OC)c(OC)cc2CC1C] | (±)-1-(3-bromophenyl)-7,8-dimethoxy-N,4-dimethyl-4,5-dihydro-3H-2,3-benzodiazepine-3-carboxamide | $^1$H-NMR (500 MHz, CDCl$_3$): δ = 0.95 (d, 3H), 2.86 (dd, 1H), 2.90 (d, 3H), 3.12 (dd, 1H), 3.66 (s, 3H), 3.93 (s, 3H), 5.48 (m, 1H), 6.50 (m, 1H), 6.54 (s, 1H), 6.71 (s, 1H), 7.26 (dd, 1H), 7.39 (dbr, 1H), 7.52 (dbr, 1H), 7.64 (m, 1H).<br>LCMS (Method 3): R$_t$ = 1.27 min; m/z = 432; 434 (M + H, Br isotope pattern)$^+$ |

Example 52A (±)-8-Bromo-1-(4-chlorophenyl)-N,4-dimethyl-4,5-dihydro-3H-2,3-benzodiazepine-3-carboxamide

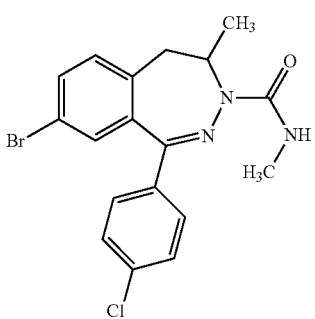 [SMILES: CNC(=O)N1N=C(c2ccc(Cl)cc2)c2cc(Br)ccc2CC1C]

At RT, 100 mg (286 μmol) of 8-bromo-1-(4-chlorophenyl)-4-methyl-4,5-dihydro-3H-2,3-benzodiazepine (Example 36A) were dissolved in 5 ml of THF, 58 mg (286 μmol) of 4-nitrophenyl chloroformate (CAS [7693-46-1]) were added and the mixture was stirred at RT for 2 h. 1.43 ml (2.86 mmol) of a 2M solution of methylamine in THF were added dropwise to the clear orange solution, and the mixture was stirred at 60° C. for 16 h. The mixture was allowed to warm to RT and partitioned between water and ethyl acetate, and the phases were separated. The aqueous phase was extracted with ethyl acetate. The combined organic phases were washed water and sat. sodium chloride solution and dried with sodium sulphate, and the solvent was removed on a rotary evaporator. The crude product was purified by flash chromatography (SiO$_2$, hexane/ethyl acetate). This gave 92 mg (79% of theory) of the desired product as an orange foam.

LCMS (Method 1): R$_t$=1.49 min; m/z=406; 408; 410 (Br—Cl isotope pattern, M+H)$^+$ $^1$H-NMR (300 MHz, CDCl$_3$): δ=0.91 (d, 3H), 2.89 (d, 3H), 2.90 (dd, 1H), 3.09 (dd, 1H), 5.43-5.53 (m, 1H), 6.43-6.51 (m, 1H), 7.11 (d, 1H), 7.21 (d, 1H), 7.39 (s, 4H), 7.45 (dd, 1H).

Enantiomer Separation

By chiral preparative HPLC, 320 mg of (±)-8-bromo-1-(4-chlorophenyl)-N,4-dimethyl-4,5-dihydro-3H-2,3-benzodiazepine-3-carboxamide were separated into the enantiomers under the following conditions:

System: Agilent: Prep 1200, 2× Prep Pump G1361A, DLA G2258A, MWD G1365D, Prep FC G1364B; column: Chiralpak IC 5 μm 250×20 mm; mobile phase: hexane/ethanol 95:05 (v/v); flow rate: 30 ml/min; temperature: RT; solution: 320 mg/3.4 ml of MeOH; injection: 2×200 ml, 5×400 ml; detection: UV 254 nm.

Example 52.1A 116 mg, colourless solid, HPLC (Method C): R$_t$=2.6 min, purity>99%

Optical rotation: [α]$_D^{20}$=−111.2°±0.08° (c=1.00; methanol)

Example 52.2A 123 mg, colourless solid, HPLC (Method C): R$_t$=3.1 min, purity 99.5%

Optical rotation: [α]$_D^{20}$=−111.2°±0.08° (c=1.00; methanol)

Example 53A (±)-1-(4-Aminophenyl)-8-methoxy-N,4-dimethyl-4,5-dihydro-3H-2,3-benzodiazepine-3-carboxamide

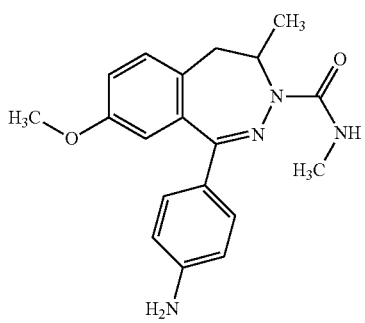 [SMILES: CNC(=O)N1N=C(c2ccc(N)cc2)c2cc(OC)ccc2CC1C]

The preparation of the title compound is described in WO97/28135 A1 (Schering AG) as Example 5.

UPLC/MS (Method 3): R$_t$=0.92 min; m/z=339 (M+H)$^+$ $^1$H-NMR (300 MHz, DMSO-d$_6$): δ=1.07 (d, 3H), 2.37 (dd, 1H), 2.60 (d, 3H), 2.81 (dd 1H), 3.69 (s, 3H), 4.74 (m, 1H), 5.70 (sbr, 2H), 6.19 (qbr, 1H), 6.53 (d, 1H), 6.57 (d, 2H), 6.98 (dd, 1H), 7.28 (d, 1H), 7.45 (d, 2H).

Enantiomer Separation (Preparative Method III)

Example 53.1A (4R)-1-(4-Aminophenyl)-8-methoxy-N,4-dimethyl-4,5-dihydro-3H-2,3-benzodiazepine-3-carboxamide 1.64 g, yellow solid, HPLC (Method C): $R_t$=5.05 min, purity 99%, $[\alpha]_D^{20}$=−637.8°±0.12° (c=1.040; MeOH)

Example 53.2A: (4S)-1-(4-Aminophenyl)-8-methoxy-N,4-dimethyl-4,5-dihydro-3H-2,3-benzodiazepine-3-carboxamide 1.71 g, yellow solid, HPLC (Method C): $R_t$=6.75 min, purity 95%, $[\alpha]_D^{20}$=+604.9°±0.10° (c=1.030; MeOH)

Example 54A (4S)-1-(4-Bromophenyl)-8-methoxy-N,4-dimethyl-4,5-dihydro-3H-2,3-benzodiazepine-3-carboxamide

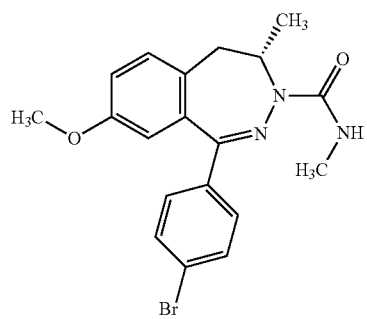 [SMILES: CNC(=O)N1N=C(c2ccc(Br)cc2)c2cc(OC)ccc2C[C@@H]1C]

1000 mg (2.96 mmol) of (4S)-1-(4-aminophenyl)-8-methoxy-N,4-dimethyl-4,5-dihydro-3H-2,3-benzodiazepine-3-carboxamide (Example 53.2A) were dissolved in 20 ml of acetonitrile, 528 mg (2.36 mmol) of copper(II) bromide and 351 µl (2.96 mmol) of tert-butyl nitrite were added and the mixture was stirred at room temperature for 2 hours. The mixture was poured into 1 M aqueous hydrochloric acid and extracted with ethyl acetate. The organic phase washed with saturated aqueous sodium chloride solution, dried over sodium sulphate, filtered and evaporated to dryness. The residue was purified by flash chromatography. This gave 505 mg (42% of theory) of the title compound.

UPLC/MS (Method 3): $R_t$=1.37 min; m/z=402; 404 (Br isotope pattern, M+H)+

1H-NMR (300 MHz, CDCl3): δ=0.91 (d, 3H), 2.85 (dd, 1H), 2.88 (d, 3H), 3.09 (dd, 1H), 3.69 (s, 3H), 5.44 (m, 1H), 6.48 (m, 1H), 6.59 (d, 1H), 6.87 (dd, 1H), 7.13 (d, 1H), 7.35 (d, 2H), 7.52 (d, 2H).

Example 55A (±)-1-(4-Chlorophenyl)-8-hydroxy-N,4-dimethyl-4,5-dihydro-3H-2,3-benzodiazepine-3-carboxamide

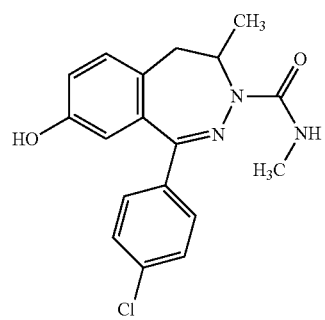 [SMILES: CNC(=O)N1N=C(c2ccc(Cl)cc2)c2cc(O)ccc2CC1C]

With ice-bath cooling, 38 ml (38.1 mmol) of boron tribromide were slowly added dropwise to a solution of 2.27 g (6.34 mmol) of (±)-1-(4-chlorophenyl)-8-methoxy-N,4-dimethyl-4,5-dihydro-3H-2,3-benzodiazepine-3-carboxamide (Example 50A) in 100 ml of dichloromethane. The mixture was stirred at room temperature for 16 hours. The reaction was poured onto ice-water and extracted with dichloromethane. The organic phase was dried over sodium sulphate, filtered and evaporated to dryness. This gave 2.16 g (99% of theory) of the title compound.

UPLC/MS (Method 3): $R_t$=1.12 min; m/z=344; 346 (Cl isotope pattern, M+H)+

1H-NMR (300 MHz, DMSO-$d_6$): δ=0.90 (d, 3H), 2.63 (dd, 1H), 2.65 (d, 3H), 2.89 (dd, 1H), 5.02 (m, 1H), 6.63 (m, 1H), 6.37 (d, 1H), 6.79 (dd, 1H), 7.16 (d, 1H), 7.47 (d, 2H), 7.61 (d, 2H), 9.53 (sbr, 1H).

Example 56A 1-(3-Bromo-4-fluorophenyl)-6,7-dimethoxy-3-methyl-3,4-dihydro-1H-2-benzopyran

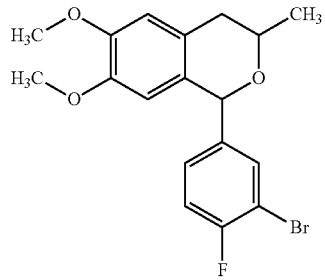 [SMILES: COc1cc2c(cc1OC)C(c1ccc(F)c(Br)c1)OC(C)C2]

The preparation was carried out analogously to Example 41A starting with commercially available 3-bromo-4-fluorobenzaldehyde (CAS [77771-02-9]).

LCMS (Method 3): $R_t$=1.44 min; m/z=381; 383 (Br isotope pattern, M+H)+

Example 57A

1-[2-(3-Bromo-4-fluorobenzoyl)-4,5-dimethoxyphenyl]propan-2-one

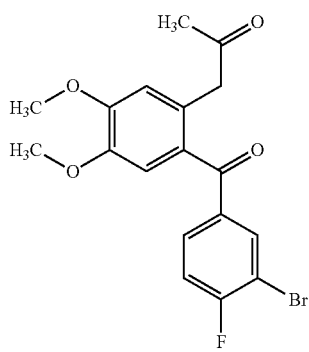 [SMILES: COc1cc(CC(C)=O)c(C(=O)c2ccc(F)c(Br)c2)cc1OC]

The preparation was carried out analogously to Example 43A.

LCMS (Method 3): $R_t$=1.25 min; m/z=395; 397 (Br isotope pattern, M+H)$^+$

Example 58A 1-(3-Bromo-4-fluorophenyl)-7,8-dimethoxy-4-methyl-5H-2,3-benzodiazepine

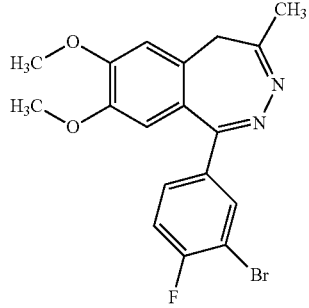

The preparation was carried out analogously to Example 45A.

LCMS (Method 3): $R_t$=1.21 min; m/z=381; 383 (Br isotope pattern, M+H)$^+$ $^1$H-NMR (400 MHz, CDCl$_3$): δ=2.16 (s, 3H), 2.99 (d, 1H), 3.29 (d, 1H), 3.77 (s, 3H), 3.98 (s, 3H), 6.74 (s, 2H), 7.16 (dd, 1H), 7.62 (ddd, 1H), 7.94 (dd, 1H).

Example 59A (±)-1-(3-Bromo-4-fluorophenyl)-7,8-dimethoxy-4-methyl-4,5-dihydro-3H-2,3-benzodiazepine

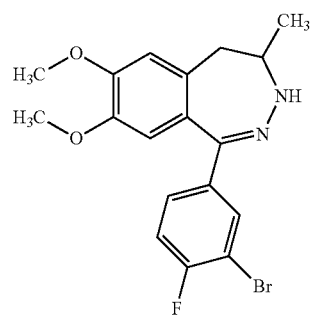

The preparation was carried out analogously to Example 47A.

LCMS (Method 3): $R_t$=1.03 min; m/z=393; 395 (Br isotope pattern, M+H)$^+$ $^1$H-NMR (400 MHz, CDCl$_3$): δ=1.29 (d, 3H), 2.61 (dd, 1H), 2.89 (dd, 1H), 3.72 (s, 3H), 3.95 (s, 3H), 4.12 (m, 1H), 6.57 (s, 1H), 6.77 (s, 1H), 7.10 (dd, 1H), 7.45 (ddd, 1H), 7.81 (dd, 1H).

Example 60A (±)-1-(3-Bromo-4-fluorophenyl)-7,8-dimethoxy-N,4-dimethyl-4,5-dihydro-3H-2,3-benzodiazepine-3-carboxamide

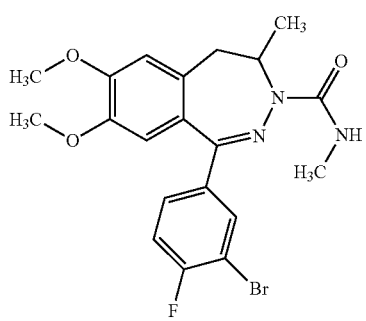 [SMILES: CNC(=O)N1N=C(c2ccc(F)c(Br)c2)c2cc(OC)c(OC)cc2CC1C]

The preparation was carried out analogously to Example 49A.

LCMS (Method 3): $R_t$=1.31 min; m/z=450; 452 (Br isotope pattern, M+H)$^+$ $^1$H-NMR (400 MHz, CDCl$_3$): δ=0.95 (d, 3H), 2.86 (dd, 1H), 2.90 (d, 3H), 3.10 (dd, 1H), 3.67 (s, 3H), 3.93 (s, 3H), 5.48 (m, 1H), 6.44 (m, 1H), 6.52 (s, 1H), 6.71 (s, 1H), 7.14 (dd, 1H), 7.39 (ddd, 1H), 7.69 (dd, 1H).

The following compound was prepared analogously to Example 8A from 4-nitrobenzaldehyde:

| No | Structure | Name | Analytical data |
|---|---|---|---|
| 61A | 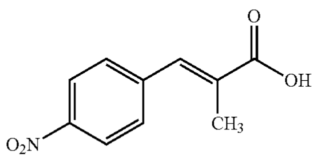 | 2-methyl-3-(4-nitrophenyl)acrylic acid | $^1$H-NMR (400 MHz, DMSO-d$_6$): δ = 2.01 (s, 3H), 7.62 (s, 1H), 7.70 (d, 2H), 8.23 (d, 2H), 12.8 (s, br, 1H). LCMS (Method 2): R$_t$ = 0.99 min; m/z [ES$^-$] = 206 (M − H)$^-$ |

Example 62A (±)-3-(4-Aminophenyl)-2-methylpropanoic acid

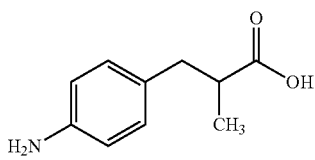

41 g (0.2 mol) of 2-methyl-3-(4-nitrophenyl)acrylic acid were reduced analogously to Example 10A. This gave 21 g (90%) of the desired compound as a yellow crystallizing oil.
LCMS (Method 2): R$_t$=0.48 min; m/z=180 (M+H)$^+$
$^1$H-NMR (400 MHz, CDCl$_3$): δ=0.95 (d, 3H), 2.36 (dd, 1H), 2.42-2.45 (m, 1H), 2.70 (dd, 1H), 6.43 (d, 2H), 6.78 (d, 2H).

Example 63A (±)-6-Amino-2-methylindan-1-one

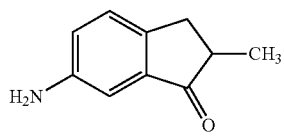

310 g of polyphosphoric acid were added to 38 g (11.1 mmol) of (±)-3-(4-aminophenyl)-2-methylpropanoic acid (Example 62A), and the mixture was stirred at 150° C. for 7 h using a pressurized air stirrer. After cooling, the mixture was carefully, a little at a time, diluted with water and then, with ice cooling, made alkaline using 32% strength aqueous sodium hydroxide solution (pH=10). The mixture was extracted with dichloromethane and the combined organic phases dried with sodium sulphate. The solvents were removed on a rotary evaporator and the crude product (26 g) was directly reacted further.

LCMS (Method 2): R$_t$=0.69 min; m/z=162; 203 (M+H; M+ACN+H)$^+$
$^1$H-NMR (300 MHz, DMSO-d$_6$): δ=1.11 (d, 3H), 2.53-2.60 (m, 1H), 2.68 (dd, 1H), 3.15 (dd, 1H), 5.25 (s, br, 2H), 6.71 (d, 1H), 6.88 (dd, 1H), 7.16 (d, 1H).

Example 64A (±)-tert-Butyl(2-methyl-3-oxo-2,3-dihydro-1H-inden-5-yl)carbamate

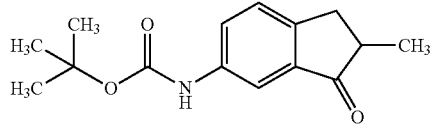 [SMILES: CC1Cc2ccc(NC(=O)OC(C)(C)C)cc2C1=O]

15.0 g (93.0 mmol) of (±)-6-amino-2-methylindan-1-one were dissolved in 450 ml of dichloromethane, the solution was stirred in an ice bath for 10 min, 21.3 g (97.7 mmol) of di-tert-butyl dicarbonate were then added and the mixture was stirred at RT for a further 16 h. The mixture was added to water and extracted with dichloromethane, the combined organic phases were washed with sat. sodium chloride solution and the solvents were removed on a rotary evaporator. The crude product was purified chromatographically (SiO$_2$, hexane/ethyl acetate 0-30%). This gave 13.3 g (50% of theory) as a yellow foam.

LCMS (Method 2): R$_t$=1.21 min; m/z=262; 303 (M+H)$^+$; (M+ACN+H)$^+$
$^1$H-NMR (400 MHz, DMSO-d$_6$): δ=1.14 (d, 3H), 1.45 (s, 9H), 2.58 (dd, 1H), 2.61-2.70 (m, 1H), 3.25 (dd, 1H), 7.40 (d, 1H), 7.63 (dd, 1H), 7.77 (d, 1H), 9.51 (s, 1H).

The following indanones were prepared analogously to Example 15A from the appropriate carboxylic acids:

| No | Structure | Name | Analytical data |
|---|---|---|---|
| 65A | 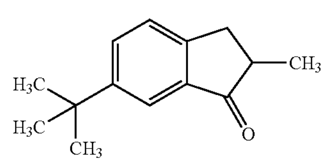 | (±)-6-tert-butyl-2-methylindan-1-one | $^1$H-NMR (400 MHz, CDCl$_3$): δ = 1.31 (d, 3H), 1.34 (s, 9H), 2.65-2.77 (m, 2H), 3.31-3.40 (m, 1H), 7.39 (d, 1H), 7.66 (dd, 1H), 7.78 (d, 1H). LCMS (Method 2): R$_t$ = 1.35 min; m/z = 244 (M + CH$_3$CN)$^+$. |

-continued

| No | Structure | Name | Analytical data |
|---|---|---|---|
| 66A | 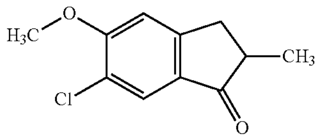 | (±)-6-chloro-5-methoxy-2-methylindan-1-one | $^1$H-NMR (300 MHz, CDCl$_3$): δ = 1.29 (d, 3H), 2.61-2.78 (m, 2H), 3.28-3.40 (m, 1H), 3.98 (s, 3H), 6.92 (s, 1H), 7.75 (s, 1H). LCMS (Method 2): R$_t$ = 1.10 min; m/z = 211 (M + H)$^+$. |

The following compounds were prepared analogously to Example 17A from the appropriate indanones by reaction with 4-chlorophenylmagnesium bromide and subsequent elimination of water using 4-toluenesulphonic acid:

| No | Structure | Name | Analytical data |
|---|---|---|---|
| 67A | 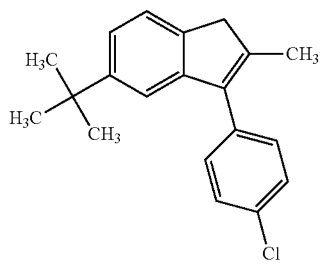 | 5-tert-butyl-3-(4-chlorophenyl)-2-methyl-1H-indene | $^1$H-NMR (300 MHz, CDCl$_3$): δ = 1.31 (s, 9H), 2.11 (s, 3H), 3.41 (s, 2H), 7.18-7.25 (m, 2H), 7.31-7.41 (m, 3H), 7.46 (d, 2H). LCMS (Method 3): R$_t$ = 1.0 min; m/z = 499 (M + H)$^+$. |
| 68A | 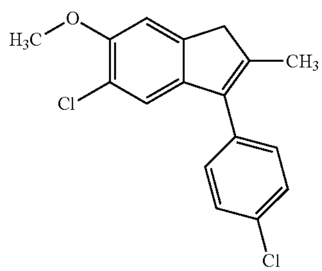 | 5-chloro-3-(4-chlorophenyl)-6-methoxy-2-methyl-1H-indene | $^1$H-NMR (400 MHz, CDCl$_3$): δ = 2.10 (s, 3H), 3.42 (s, 2H), 3.93 (s, 3H), 7.09 (s, 1H), 7.14 (s, 1H), 7.31 (d, 2H), 7.44 (d, 2H). LCMS (Method 2): R$_t$ = 1.68 min; m/z = 305 (M + H)$^+$. |
| 69A | 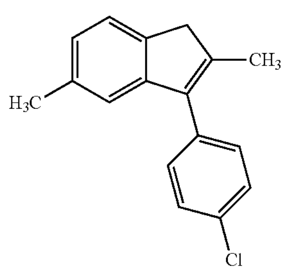 | 3-(4-chlorophenyl)-2,5-dimethyl-1H-indene | $^1$H-NMR (300 MHz, CDCl$_3$): δ = 2.11 (s, 3H), 2.35 (s, 3H), 3.42 (s, 2H), 6.96-7.02 (m, 2H), 7.31 (d, 1H), 7.33 (d, 2H), 7.45 (d, 2H). LCMS (Method 2): R$_t$ = 1.70 min; m/z = 255 (M + H)$^+$. |
| 70A | 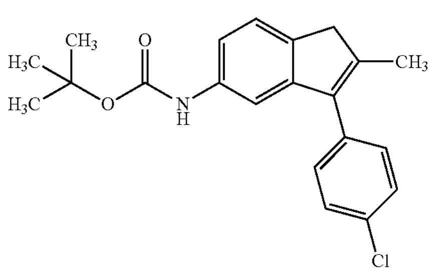 [SMILES: CC1=C(c2ccc(Cl)cc2)c2cc(NC(=O)OC(C)(C)C)ccc2C1] | tert-butyl [3-(4-chlorophenyl)-2-methyl-1H-inden-5-yl]carbamate | LCMS (Method 2): R$_t$ = 1.64 min; m/z = 256 (M + H)$^+$ |

The following compounds were prepared analogously to Example 25A from the appropriate 1H-indenes:

| No | Structure | Name | Analytical data |
|---|---|---|---|
| 71A | 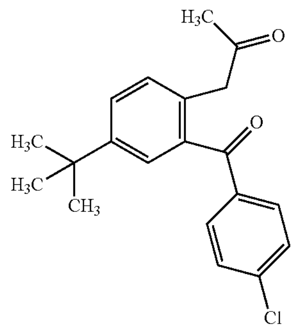 [SMILES: CC(=O)Cc1ccc(C(C)(C)C)cc1C(=O)c1ccc(Cl)cc1] | 1-[4-tert-butyl-2-(4-chlorobenzoyl)phenyl]-propan-2-one | $^1$H-NMR (400 MHz, CDCl$_3$): δ = 1.28 (s, 9H), 2.18 (s, 3H), 3.96 (s, 2H), 7.19 (d, 1H), 7.38 (d, 1H), 7.45 (d, 2H), 7.50 (dd, 1H), 7.77 (d, 2H). LCMS (Method 2): R$_t$ = 1.54 min; m/z = 329 (M + H)$^+$. |
| 72A | 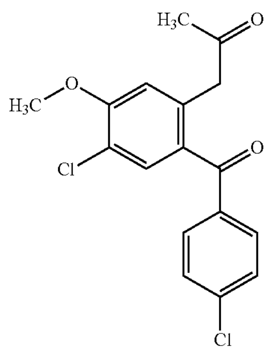 [SMILES: COc1cc(CC(C)=O)c(C(=O)c2ccc(Cl)cc2)cc1Cl] | 1-[4-chloro-2-(4-chlorobenzoyl)-5-methoxyphenyl]-propan-2-one | $^1$H-NMR (400 MHz, CDCl$_3$): δ = 2.24 (s, 3H), 3.98 (s, 3H), 4.01 (s, 2H), 6.80 (s, 1H), 7.43 (s, 1H), 7.45 (d, 2H), 7.70 (d, 2H). LCMS (Method 2): R$_t$ = 1.39 min; m/z = 337; 339 (Cl isotope pattern, M + H)$^+$. |
| 73A | 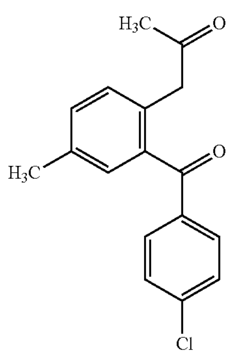 [SMILES: CC(=O)Cc1ccc(C)cc1C(=O)c1ccc(Cl)cc1] | 1-[2-(4-chlorobenzoyl)-4-methylphenyl]-propan-2-one | $^1$H-NMR (400 MHz, CDCl$_3$): δ = 2.17 (s, 3H), 2.34 (s, 3H), 3.93 (s, 2H), 7.15 (d, 1H), 7.17 (s, br, 1H), 7.29 (dd, 1H), 7.44 (d, 2H), 7.76 (d, 2H). LCMS (Method 2): R$_t$ = 1.37 min; m/z = 287 (M + H)$^+$. |
| 74A | 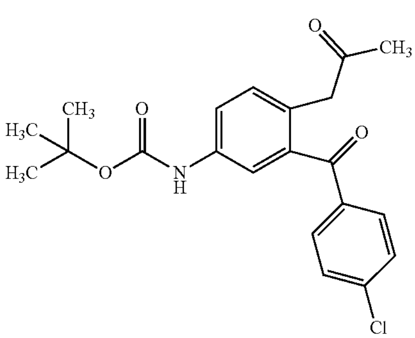 [SMILES: CC(=O)Cc1ccc(NC(=O)OC(C)(C)C)cc1C(=O)c1ccc(Cl)cc1] | tert-butyl [3-(4-chlorobenzoyl)-4-(2-oxopropyl)phenyl]-carbamate | $^1$H-NMR (300 MHz, DMSO-d$_6$): δ = 1.39 (s, 9H), 2.01 (s, 3H), 3.83 (s, 2H), 7.20 (d, 1H), 7.44 (d, 1H), 7.51-7.57 (m, 1H), 7.59 (d, 2H), 7.69 (d, 2H), 9.42 (s, 1H). LCMS (Method 2): R$_t$ = 1.39 min; m/z = 388 (M + H)$^+$ |

Example 75A 8-tert-Butyl-1-(4-chlorophenyl)-4-methyl-5H-2,3-benzodiazepine

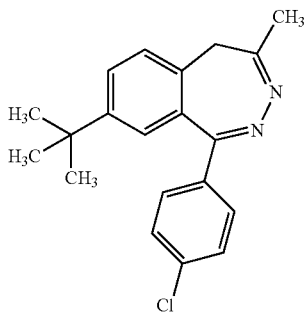 [SMILES: CC1=NN=C(c2ccc(Cl)cc2)c2cc(C(C)(C)C)ccc2C1]

7.0 g (21.29 mmol) of 1-[4-tert-butyl-2-(4-chlorobenzoyl)phenyl]propan-2-one (Example 71A) and 7.46 g (149 mmol) of hydrazine hydrate in 80.6 ml of ethanol were stirred at RT for 72 h. The reaction solution was added to water, made alkaline with 1M aqueous sodium hydroxide solution and extracted with dichloromethane. The combined organic phases were dried with sodium sulphate and the solvent was removed on a rotary evaporator. This gave 6.5 g (94% of theory) of the crude product which was reacted in the next reaction step without further purification. A portion of the residue was purified by preparative HPLC.

LCMS (Method 2): $R_t$=1.54 min; m/z=325 (M+H)$^+$.

$^1$H-NMR (300 MHz, CDCl$_3$): δ=1.26 (s, 9H), 2.15 (s, 3H), 3.04 (d, 1H), 3.33 (d, 1H), 7.21 (d, 1H), 7.31 (d, 1H), 7.38 (d, 2H), 7.55 (dd, 1H), 7.64 (d, 2H).

Example 76A tert-Butyl[1-(4-chlorophenyl)-4-methyl-5H-2,3-benzodiazepin-8-yl]carbamate

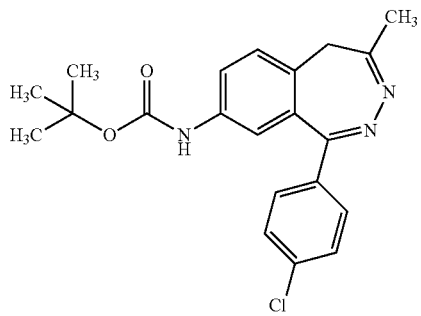 [SMILES: CC1=NN=C(c2ccc(Cl)cc2)c2cc(NC(=O)OC(C)(C)C)ccc2C1]

Together, 5.10 g (13.1 mmol) of tert-butyl[3-(4-chlorobenzoyl)-4-(2-oxopropyl)phenyl]carbamate (Example 74A) and 3.49 g (69.7 mmol) of hydrazine hydrate were heated in 100 ml of ethanol at 100° C. for 1.5 h. The mixture was then cooled, added to water and extracted with ethyl acetate. The combined organic phases were washed with water and sat. sodium chloride solution, dried with sodium sulphate and concentrated. This gave 5 g of crude product which was directly used further, without further purification.

LCMS (Method 1): $R_t$=1.37 min; m/z=384 (M+H)$^+$ $^1$H-NMR (400 MHz, CDCl$_3$): δ=1.48 (s, 9H), 2.13 (s, 3H), 3.03 (d, 1H), 3.30 (d, 1H), 6.48 (s, br, 1H), 7.11 (d, 1H), 7.22 (d, 1H), 7.37 (d, 2H), 7.62 (d, 2H), 7.73 (d, 1H).

The following compounds were prepared analogously to Example 75A from the appropriate diketo compounds:

| No | Structure | Name | Analytical data |
|---|---|---|---|
| 77A | 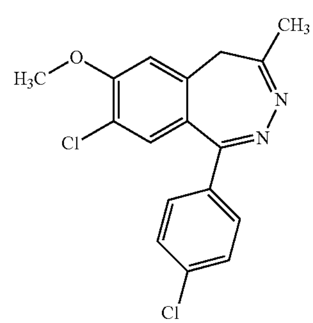 | 8-chloro-1-(4-chlorophenyl)-7-methoxy-4-methyl-5H-2,3-benzodiazepine | $^1$H-NMR (400 MHz, CDCl$_3$): δ = 2.25 (s, 3H), 3.12 (d, 1H), 3.41 (d, 1H), 4.01 (s, 3H), 6.82 (s, 1H), 7.32 (s, 1H), 7.42 (d, 2H), 7.62 (d, 2H). LCMS (Method 2): $R_t$ = 1.37 min; m/z = 333; 335 (Cl isotope pattern, M + H)$^+$. |
| 78A | 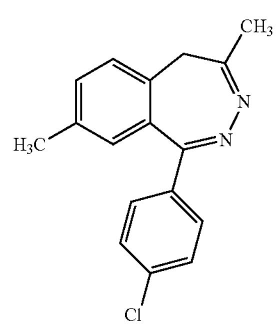 | 1-(4-chlorophenyl)-4,8-dimethyl-5H-2,3-benzodiazepine | $^1$H-NMR (300 MHz, CDCl$_3$): δ = 2.13 (s, 3H), 2.33 (s, 3H), 3.03 (d, 1H), 3.31 (d, 1H), 7.10 (s, br, 1H), 7.17 (d, 1H), 7.34 (dd, 1H), 7.38 (d, 2H), 7.62 (d, 2H). LCMS (Method 2): $R_t$ = 1.36 min; m/z = 283 (M + H)$^+$. |

The following compounds were prepared analogously to Example 47A:

| No | Structure | Name | Analytical data |
|---|---|---|---|
| 79A | 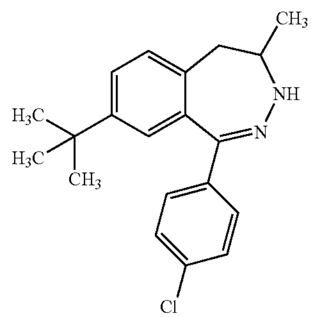 [SMILES: CC1Cc2ccc(C(C)(C)C)cc2C(c2ccc(Cl)cc2)=NN1] | (±)-8-tert-butyl-1-(4-chlorophenyl)-4-methyl-4,5-dihydro-3H-2,3-benzodiazepine | LCMS (Method 2): $R_t$ = 1.42 min; m/z = 327 (M + H)$^+$. |
| 80A | 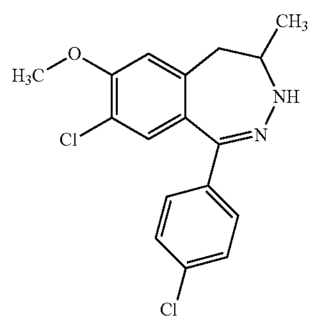 | (±)-8-chloro-1-(4-chlorophenyl)-7-methoxy-4-methyl-4,5-dihydro-3H-2,3-benzodiazepine | LCMS (Method 2): $R_t$ = 1.25 min; m/z = 335; 337 (Cl isotope pattern, M + H)$^+$. |
| 81A | 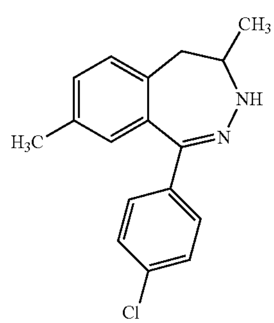 | (±)-1-(4-chlorophenyl)-4,8-dimethyl-4,5-dihydro-3H-2,3-benzodiazepine | $^1$H-NMR (300 MHz, CDCl$_3$): δ = 1.27 (d, 3H), 2.28 (s, 3H), 2.59 (dd, 1H), 2.92 (dd, 1H), 4.06-4.20 (m, 1H), 6.89 (s, 1H), 7.16 (s, br, 2H), 7.34 (d, 2H), 7.51 (d, 2H). LCMS (Method 2): $R_t$ = 1.17 min; m/z = 285 (M + H)$^+$. |
| 82A | 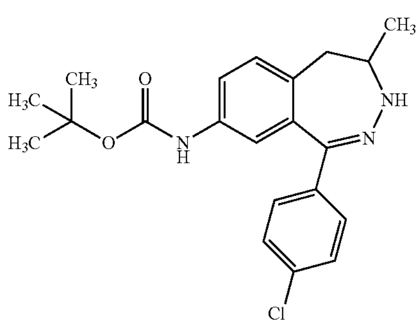 [SMILES: CC1Cc2ccc(NC(=O)OC(C)(C)C)cc2C(c2ccc(Cl)cc2)=NN1] | (±)-tert-butyl-[1-(4-chlorophenyl)-4-methyl-4,5-dihydro-3H-2,3-benzodiazepin-8-yl]carbamate | $^1$H-NMR (400 MHz, DMSO-d$_6$): δ = 1.60 (d, 3H), 1.37 (s, 9H), 2.58 (dd, 1H), 2.82 (dd, 1H), 3.75-3.81 (m, 1H), 7.07 (d, 1H), 7.09 (d, 1H), 7.14 (d, 1H), 7.33-7.38 (m, 4H), 9.16 (s, br, 1H). LCMS (Method 2): $R_t$ = 1.23 min; m/z = 386 (M + H)$^+$ |

The following compounds were prepared analogously to Example 49A from the appropriate 4,5-dihydro-3H-2,3-benzodiazepines:

| No | Structure | Name | Analytical data |
|---|---|---|---|
| 83A | 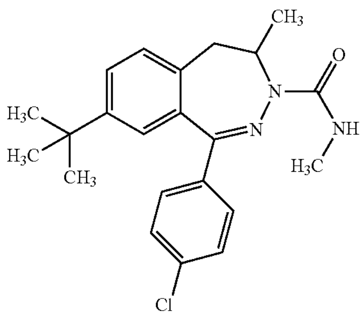 [SMILES: CNC(=O)N1N=C(c2ccc(Cl)cc2)c2cc(C(C)(C)C)ccc2CC1C] | (±)-8-tert-butyl-1-(4-chlorophenyl)-N,4-dimethyl-4,5-dihydro-3H-2,3-benzodiazepine-3-carboxamide | $^1$H-NMR (300 MHz, CDCl$_3$): δ = 0.95 (d, 3H), 1.21 (s, 9H), 2.86 (dd, 1H), 2.89 (d, 3H), 3.09 (dd, 1H), 5.36-5.49 (m, 1H), 6.43 (q, 1H), 7.08 (d, 1H), 7.15 (d, 1H), 7.32-7.40 (m, 3H), 7.41-7.47 (m, 2H). LCMS (Method 2): R$_t$ = 1.61 min; m/z = 384 (M + H)$^+$. |
| 83.1A | 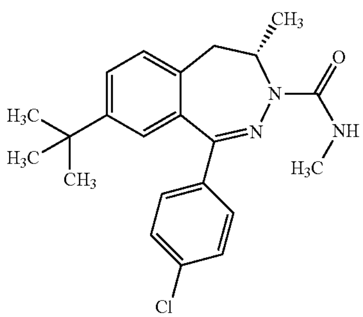 [SMILES: CNC(=O)N1N=C(c2ccc(Cl)cc2)c2cc(C(C)(C)C)ccc2C[C@@H]1C] | (4S)-8-tert-butyl-1-(4-chlorophenyl)-N,4-dimethyl-4,5-dihydro-3H-2,3-benzodiazepine-3-carboxamide | LCMS (Method 2): R$_t$ = 1.61 min; m/z = 384 (M + H)$^+$ HPLC (Method M): R$_t$ = 2.48 min [α]$_D^{20}$ = −133.8° (c = 1.00; chloroform) |
| 83.2A | 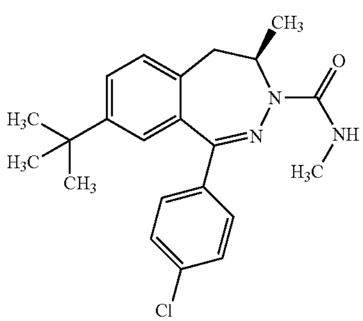 [SMILES: CNC(=O)N1N=C(c2ccc(Cl)cc2)c2cc(C(C)(C)C)ccc2C[C@H]1C] | (4R)-8-tert-butyl-1-(4-chlorophenyl)-N,4-dimethyl-4,5-dihydro-3H-2,3-benzodiazepine-3-carboxamide | LCMS (Method 2): R$_t$ = 1.61 min; m/z = 384 (M + H)$^+$ HPLC (Method M): R$_t$ = 2.84 min [α]$_D^{20}$ = 167.7° (c = 1.00; chloroform) |
| 84A | 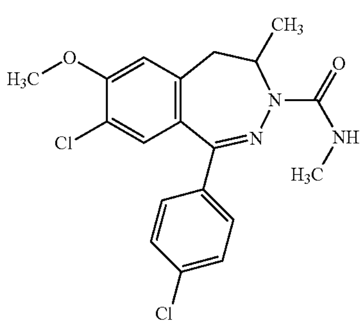 [SMILES: CNC(=O)N1N=C(c2ccc(Cl)cc2)c2cc(Cl)c(OC)cc2CC1C] | (±)-8-chloro-1-(4-chlorophenyl)-7-methoxy-N,4-dimethyl-4,5-dihydro-3H-2,3-benzodiazepine-3-carboxamide | $^1$H-NMR (400 MHz, CDCl$_3$): δ = 0.97 (d, 3H), 2.88 (s, br, 3H), 2.88-2.94 (m, 1H), 3.14 (dd, 1H), 3.96 (s, 3H), 5.45-5.54 (m, 1H), 6.46 (s, br, 1H), 6.77 (s, 1H), 7.08 (s, 1H), 7.38 (s, br, 4H). LCMS (Method 2): R$_t$ = 1.46 min; m/z = 392; 394 (Cl isotope pattern, M + H)$^+$. |

-continued

| No | Structure | Name | Analytical data |
|---|---|---|---|
| 84.1A | 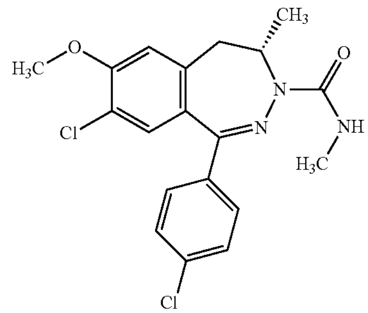 [SMILES: CNC(=O)N1N=C(c2ccc(Cl)cc2)c2cc(Cl)c(OC)cc2C[C@@H]1C] | (4S)-8-chloro-1-(4-chlorophenyl)-7-methoxy-N,4-dimethyl-4,5-dihydro-3H-2,3-benzodiazepine-3-carboxamide | LCMS (Method 2): $R_t$ = 1.46 min; m/z = 392; 394 (Cl isotope pattern, M + H)$^+$. HPLC (Method O): $R_t$ = 3.67 min [α]$_D^{20}$ = 70.5° (c = 1.00; methanol) |
| 84.2A | 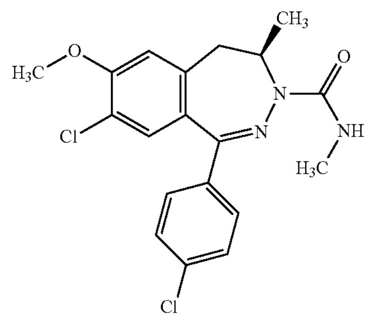 [SMILES: CNC(=O)N1N=C(c2ccc(Cl)cc2)c2cc(Cl)c(OC)cc2C[C@H]1C] | (4R)-8-chloro-1-(4-chlorophenyl)-7-methoxy-N,4-dimethyl-4,5-dihydro-3H-2,3-benzodiazepine-3-carboxamide | LCMS (Method 2): $R_t$ = 1.46 min; m/z = 392; 394 (Cl isotope pattern, M + H)$^+$. HPLC (Method O): $R_t$ = 2.47 min |
| 85A | 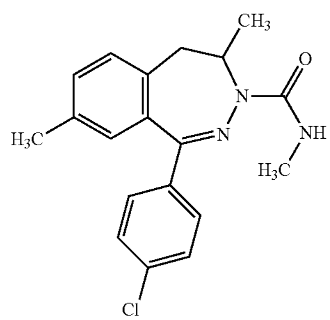 [SMILES: CNC(=O)N1N=C(c2ccc(Cl)cc2)c2cc(C)ccc2CC1C] | (±)-1-(4-chlorophenyl)-N,4,8-trimethyl-4,5-dihydro-3H-2,3-benzodiazepine-3-carboxamide | $^1$H-NMR (300 MHz, CDCl$_3$): δ = 0.93 (d, 3H), 2.25 (s, 3H), 2.86 (dd, 1H), 2.88 (s, br, 3H), 3.09 (dd, 1H), 5.36-5.48 (m, 1H), 6.44 (s, br, 1H), 6.86 (s, br, 1H), 7.08-7.18 (m, 2H), 7.36 (d, 2H), 7.42 (d, 2H). LCMS (Method 2): $R_t$ = 1.47 min; m/z = 342 (M + H)$^+$. |
| 85.1A | 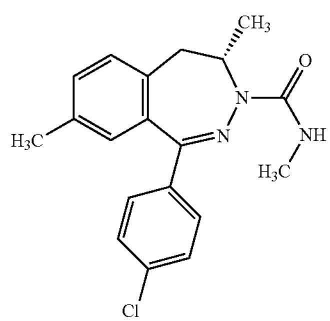 [SMILES: CNC(=O)N1N=C(c2ccc(Cl)cc2)c2cc(C)ccc2C[C@@H]1C] | (4S)-1-(4-chlorophenyl)-N,4,8-trimethyl-4,5-dihydro-3H-2,3-benzodiazepine-3-carboxamide | prep. HPLC: Method XV analyt. HPLC (Method H): $R_t$ = 1.82 min LCMS (Method 2): $R_t$ = 1.46 min; m/z = 342 (M + H)$^+$. [α]$_D^{20}$ = 213.9° (c = 1.00; methanol) |
| 85.2A | 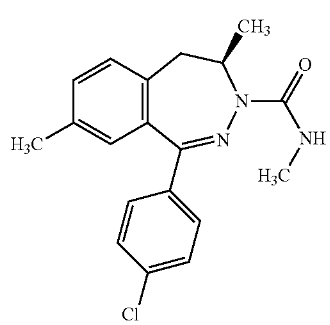 [SMILES: CNC(=O)N1N=C(c2ccc(Cl)cc2)c2cc(C)ccc2C[C@H]1C] | (4R)-1-(4-chlorophenyl)-N,4,8-trimethyl-4,5-dihydro-3H-2,3-benzodiazepine-3-carboxamide | prep. HPLC: Method XV analyt. HPLC (Method H): $R_t$ = 1.32 min LCMS (Method 2): $R_t$ = 1.46 min; m/z = 342 (M + H)$^+$. [α]$_D^{20}$ = −181.9° (c = 1.00; methanol) |

| No | Structure | Name | Analytical data |
|---|---|---|---|
| 86A | 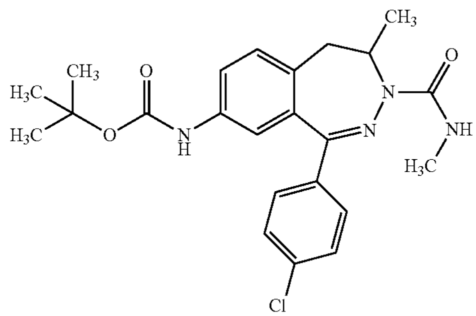 [SMILES: CNC(=O)N1N=C(c2ccc(Cl)cc2)c2cc(NC(=O)OC(C)(C)C)ccc2CC1C] | (±)-tert-butyl [1-(4-chlorophenyl)-4-methyl-3-(methylcarbamoyl)-4,5-dihydro-3H-2,3-benzodiazepin-8-yl]carbamate | $^1$H-NMR (400 MHz, DMSO-d$_6$): δ = 0.89 (d, 3H), 1.37 (s, 9H), 2.60-2.66 (m, 1H), 2.63 (d, 3H), 2.90 (dd, 1H), 4.97-5.05 (m, 1H), 6.61 (q, 1H), 7.14 (d, 1H), 7.21 (d, 1H), 7.43-7.47 (m, 1H), 7.45 (d, 2H), 7.62 (d, 2H), 9.30 (s, br, 1H). LCMS (Method 2): R$_t$ = 1.45 min; m/z = 443 (M + H)$^+$ |

Example 87A (±)-8-Amino-1-(4-chlorophenyl)-N,4-dimethyl-4,5-dihydro-3H-2,3-benzodiazepine-3-carboxamide

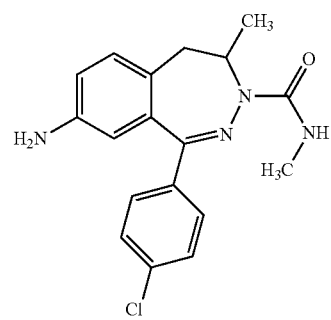 [SMILES: CNC(=O)N1N=C(c2ccc(Cl)cc2)c2cc(N)ccc2CC1C]

4.50 g (10.2 mmol) of (±)-tert-butyl 1-(4-chlorophenyl)-4-methyl-3-(methylcarbamoyl)-4,5-dihydro-3H-2,3-benzodiazepin-8-yl]carbamate (Example 86A) were initially charged in 100 ml of dichloromethane, 15 ml (20.3 mmol) of trifluoroacetic acid were added at 0° C. and the mixture was then stirred at RT for a further 4 h. The mixture was added carefully to 20% strength potassium carbonate solution and extracted with dichloromethane. The combined organic phases were dried with sodium sulphate and the solvents were removed on a rotary evaporator. This gave 3.40 g (97% of theory) of the desired product as a brownish solid.

LCMS (Method 2): R$_t$=1.12 min; m/z=343 (M+H)$^+$ $^1$H-NMR (300 MHz, DMSO-d$_6$): δ=0.88 (d, 3H), 2.52 (dd, 1H), 2.63 (d, 3H), 2.80 (dd, 1H), 4.89-5.05 (m, 1H), 5.01 (s, br, 2H), 6.19 (d, 1H), 6.52-6.59 (m, 2H), 6.96 (d, 1H), 7.44 (d, 1H), 7.61 (d, 2H).

Example 88A (±)-1-[8-tert-Butyl-1-(4-chlorophenyl)-4-methyl-4,5-dihydro-3H-2,3-benzodiazepin-3-yl]ethanone

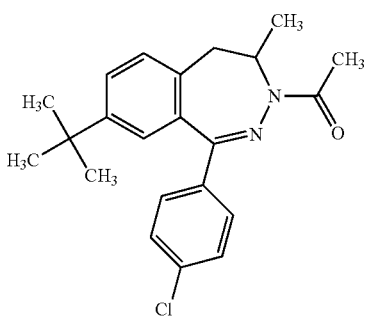 [SMILES: CC(=O)N1N=C(c2ccc(Cl)cc2)c2cc(C(C)(C)C)ccc2CC1C]

300 mg (0.918 mmol) of (±)-8-tert-butyl-1-(4-chlorophenyl)-4-methyl-4,5-dihydro-3H-2,3-benzodiazepine (Example 79A) were suspended in 3.5 ml of dichloromethane, and 281 mg (2.75 mmol) of acetic anhydride were added at RT. A clear, light-yellow solution was formed. The solution was stirred for 16 h, the pH was then adjusted to 6 by addition of saturated aqueous sodium bicarbonate solution and the mixture was extracted twice with dichloromethane. The combined organic phases were dried with sodium sulphate and the solvent was removed on a rotary evaporator. The residue was purified by preparative HPLC. This gave 210 mg (62% of theory) of the product as a solid.

LCMS (Method 2): R$_t$=1.61 min; m/z=369 (M+H)+.

$^1$H-NMR (300 MHz, CDCl$_3$): δ=1.18 (d, 3H), 1.24 (s, 9H), 2.17 (s, 3H), 2.72 (dd, 1H), 2.93 (dd, 1H), 5.24-5.37 (m, 1H), 7.06 (d, 1H), 7.21 (d, 1H), 7.36-7.45 (m, 3H), 7.59 (d, 2H).

Example 89A (±)-8-Acetamido-1-(4-chlorophenyl)-N,4-dimethyl-4,5-dihydro-3H-2,3-benzodiazepine-3-carboxamide

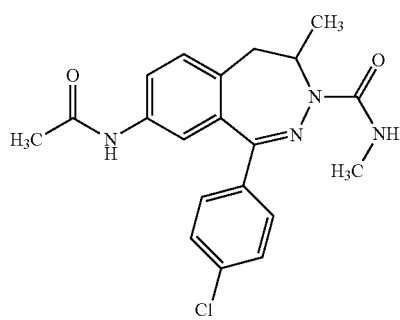 [SMILES: CNC(=O)N1N=C(c2ccc(Cl)cc2)c2cc(NC(C)=O)ccc2CC1C]

840 mg (2.45 mmol) of (±)-8-amino-1-(4-chlorophenyl)-N,4-dimethyl-4,5-dihydro-3H-2,3-benzodiazepine-3-carboxamide (Example 87A) were dissolved in dichloromethane and, at 0° C., 0.41 ml (2.94 mmol) of triethylamine and 0.21 ml (2.94 mmol) of acetyl chloride were added and the mixture was stirred for 1 h. The mixture was then added to water and extracted with dichloromethane, the combined organic phases dried with sodium sulphate and the solvents were removed on a rotary evaporator. This gave 940 mg (99%) of the desired product as a brownish solid foam.

LCMS (Method 2): $R_t$=1.15 min; m/z=385 (M+H)$^+$ $^1$H-NMR (400 MHz, DMSO-d$_6$): δ=0.87 (d, 3H), 1.93 (s, 3H), 2.64 (d, 3H), 2.69 (dd, 1H), 2.93 (dd, 1H), 5.02-5.10 (m, 1H), 6.66 (q, 1H), 7.22 (d, 1H), 7.25 (d, 1H), 7.45 (d, 2H), 7.60 (d, 2H), 7.60-7.63 (m, 1H), 9.88 (s, 1H).

Example 90A (±)-1-(4-Bromophenyl)-7-hydroxy-8-methoxy-N,4-dimethyl-4,5-dihydro-3H-2,3-benzodiazepine-3-carboxamide

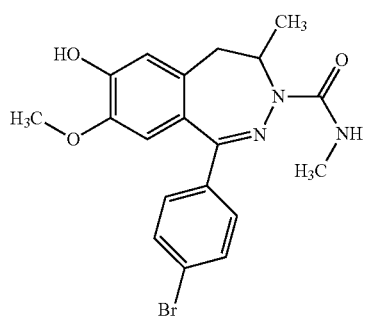

2.5 g (18.5 mmol) of aluminium trichloride were initially charged in 40 ml of dichloromethane, and a solution of 2.0 g (4.6 mmol) of (±)-1-(4-bromophenyl)-7,8-dimethoxy-N,4-dimethyl-4,5-dihydro-3H-2,3-benzodiazepine-3-carboxamide (Example 49A) in 20 ml of dichloromethane was added dropwise at RT. The suspension, which was yellow first and then orange, was stoned at RT for a further 2 h. The mixture was then added to water and extracted with dichloromethane, and the combined organic phases were washed with sat. sodium chloride solution and dried with sodium sulphate. The solvents were removed on a rotary evaporator and the crude product was purified chromatographically (SiO$_2$, hexane/ethyl acetate 0-70%). This gave 1.14 g (59% of theory) of the desired 7-hydroxy compound as a yellow solid. Also obtained was 0.63 g (32% of theory) of the regioisomeric (±)-1-(4-bromophenyl)-8-hydroxy-7-methoxy-N,4-dimethyl-4,5-dihydro-3H-2,3-benzodiazepine-3-carboxamide.

LCMS (Method 2): $R_t$=1.23 min; m/z=418/420 (M+H)$^+$, Br isotope pattern $^1$H-NMR (300 MHz, CDCl$_3$): δ=0.90 (d, 3H), 2.56 (dd, 1H), 2.63 (d, 3H), 2.82 (dd, 1H), 3.54 (s, 3H), 4.96-5.07 (m, 1H), 6.44 (s, 1H), 6.58 (q, 1H), 6.74 (s, 1H), 7.56 (s, 4H), 9.59 (s, 1H).

Example 91A (±)-1-(4-Bromophenyl)-7,8-dihydroxy-N,4-dimethyl-4,5-dihydro-3H-2,3-benzodiazepine-3-carboxamide

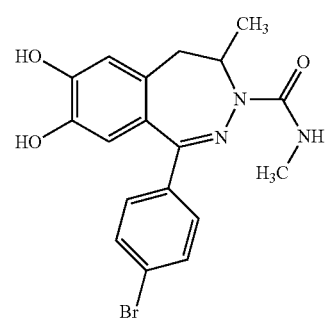 [SMILES: CNC(=O)N1N=C(c2ccc(Br)cc2)c2cc(O)c(O)cc2CC1C]

1.5 g (3.47 mmol) of (±)-1-(4-bromophenyl)-7,8-dimethoxy-N,4-dimethyl-4,5-dihydro-3H-2,3-benzodiazepine-3-carboxamide (Example 49A) were initially charged in 15 ml of dichloromethane, 6.94 ml of a 1M solution of boron tribromide in dichloromethane were slowly added dropwise at 0° C. and the mixture was stirred at RT for 16 h. A further 3.5 ml of boron tribromide solution were added, and the mixture was stirred for a further 20 h. 25 ml of 4M hydrochloric acid were added to the orange-brown solution, and the mixture was stirred for 10 min and then extracted with ethyl acetate. The combined organic phases were washed with water and sat. sodium chloride solution and dried with sodium sulphate. The solvents were removed on a rotary evaporator and the crude product was purified chromatographically. This gave 1.17 g (83% of theory) of the desired product.

LCMS (Method 2): $R_t$=1.12 min; m/z=404/406 (M+H)$^+$, Br isotope pattern $^1$H-NMR (400 MHz, DMSO-d$_6$): δ=0.87 (d, 3H), 2.58 (dd, 1H), 2.63 (d, 3H), 2.81 (dd, 1H), 5.01-5.09 (m, 1H), 6.34 (s, 1H), 6.58 (q, 1H), 6.66 (s, 1H), 7.49 (d, 2H), 7.56 (d, 2H).

Example 92A (±)-1-(4-Bromophenyl)-7,8-bis(difluoromethoxy)-N,4-dimethyl-4,5-dihydro-3H-2,3-benzodiazepine-3-carboxamide

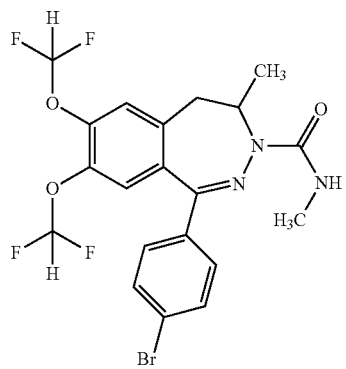 [SMILES: CNC(=O)N1N=C(c2ccc(Br)cc2)c2cc(OC(F)F)c(OC(F)F)cc2CC1C]

115 mg (2.28 mmol) of sodium hydroxide were suspended in 7.5 ml of DMF, 200 mg (495 µmol) of (±)-1-(4-bromophenyl)-7,8-dihydroxy-N,4-dimethyl-4,5-dihydro-3H-2,3-benzodiazepine-3-carboxamide were added at RT and the mixture was stirred for 15 min. The mixture was cooled to 0° C., and 0.63 ml (4.95 mmol) of chlorodifluoroacetate were added slowly. The mixture was allowed to warm to RT and then stirred at 70° C. for a further 5 h. After cooling, the mixture was added to water. The mixture was extracted with ethyl acetate, and the combined organic phases were washed with sat. sodium chloride solution and dried with sodium sulphate. The crude product was purified chromatographically (SiO$_2$, hexane/ethyl acetate 0-50-75%). This gave 113 mg (17% of theory) of the product.

LCMS (Method 2): R$_t$=1.44 min; m/z=504/506 (M+H)$^+$, Br isotope pattern

Example 93A (±)-1-(4-Bromophenyl)-7,8-diethoxy-N,4-dimethyl-4,5-dihydro-3H-2,3-benzodiazepine-3-carboxamide

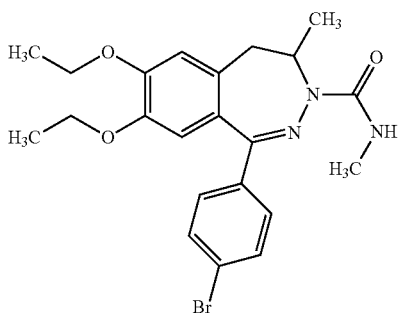 [SMILES: CCOc1cc2c(cc1OCC)C(c1ccc(Br)cc1)=NN(C(=O)NC)C(C)C2]

133 mg (329 µmol) of (±)-1-(4-bromophenyl)-7,8-dihydroxy-N,4-dimethyl-4,5-dihydro-3H-2,3-benzodiazepine-3-carboxamide (Example 91A) were initially charged in 5 ml of DMF, 236 mg (724 mol) of caesium carbonate and 54 µl (724 µmol) of bromoethane were added at RT and the mixture was stirred at RT for 16 h. The mixture was added to water and extracted with ethyl acetate. The combined organic phases were washed with water and sat. sodium chloride solution and dried with sodium sulphate. The solvents were removed on a rotary evaporator. This gave 152 mg (100% of theory) of the desired product.

LCMS (Method 2): R$_t$=1.47 min; m/z=460/462 (M+H)$^+$, Br isotope pattern $^1$H-NMR (400 MHz, DMSO-d$_6$): δ=0.90 (d, 3H), 1.18 (t, 3H), 1.32 (t, 3H), 2.64 (d, 3H), 2.66 (dd, 1H), 2.90 (dd, 1H), 3.72-3.80 (m, 2H), 4.08 (q, 2H), 5.03-5.11 (m, 1H), 6.45 (s, 1H), 6.62 (q, 1H), 6.96 (s, 1H), 7.52-7.58 (m, 4H).

Example 94A (4S)-1-(4-{[(2-Chloroethoxy)acetyl]amino}phenyl)-8-methoxy-N,4-dimethyl-4,5-dihydro-3H-2,3-benzodiazepine-3-carboxamide

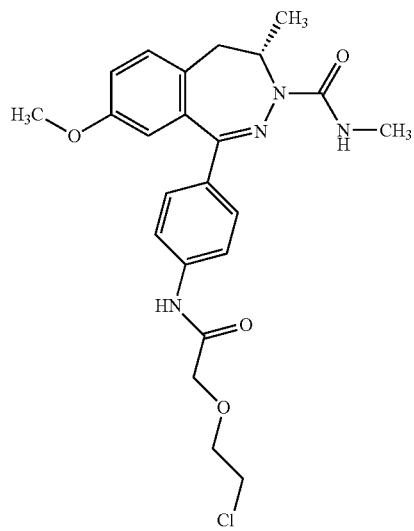

Under argon, 60 mg (0.177 mmol) of (4S)-1-(4-aminophenyl)-8-methoxy-N,4-dimethyl-4,5-dihydro-3H-2.3-benzodiazepine-3-carboxamide (Example 53.2A) were initially charged in 3 ml of toluene, and 33 mg (0.213 mmol) of (2-chloroethoxy)acetyl chloride were added. The mixture was heated at 100° C. for 5 h. After cooling, water was added, followed by a little saturated aqueous sodium bicarbonate solution, and the mixture was extracted three times with ethyl acetate. The combined organic phases were dried and freed from the solvent on a rotary evaporator. The crude product (112 mg) was used without further purification for the next reaction step.

UPLC/MS (Method 1): R$_t$=1.2 min; m/z=459 (M+H)$^+$

Example 95A (±)-7-Bromo-1-(4-chlorophenyl)-8-methoxy-N,4-dimethyl-4,5-dihydro-3H-2,3-benzodiazepine-3-carboxamide

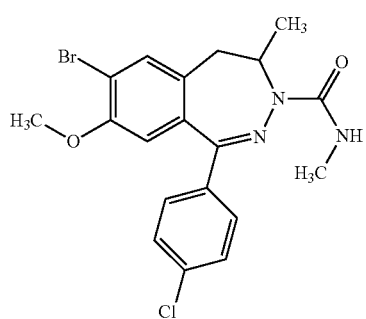 [SMILES: CNC(=O)N1N=C(c2ccc(Cl)cc2)c2cc(OC)c(Br)cc2CC1C]

At room temperature, 638 mg (1.69 mmol) of (±)-1-(4-chlorophenyl)-8-methoxy-N,4-dimethyl-4,5-dihydro-3H-2,3-benzodiazepine-3-carboxamide (Example 50A) were dissolved in 50 ml of dichloromethane, and 2.17 g (6.78 mmol) of pyridinium tribromide (CAS [39416-48-3]) were added. The orange solution was heated at reflux for 16.5 hours. A further 1.08 g (3.49 mmol) of pyridinium tribromide were added, and the mixture was heated at reflux for 2 days. The reaction mixture was added to saturated aqueous sodium thiosulphate solution and extracted three times with dichloromethane. The combined organic phases were washed with saturated aqueous sodium thiosulphate solution and dried with sodium sulphate, and the solvent was removed on a rotary evaporator. The crude product was purified by flash chromatography ($SiO_2$, hexane/ethyl acetate). This gave 642 mg (82% of theory) of the desired product as a yellow foam.

LCMS (Method 3): $R_t$=1.44 min; m/z=436; 438; 440 (Br—Cl isotope pattern; M+H)$^+$ $^1$H-NMR (300 MHz, CDCl$_3$): δ=0.93 (d, 3H), 2.83 (dd, 1H), 2.89 (d, 3H), 3.07 (dd, 1H), 3.67 (s, 3H), 5.46 (m, 1H), 6.49 (m, 1H), 6.57 (s, 1H), 7.38 (d, 2H), 7.40 (s, 1H), 7.41 (d, 2H).

Example 96A (±)-1-(4-Chlorophenyl)-7-cyan-8-methoxy-N,4-dimethyl-4,5-dihydro-3H-2,3-benzodiazepine-3-carboxamide

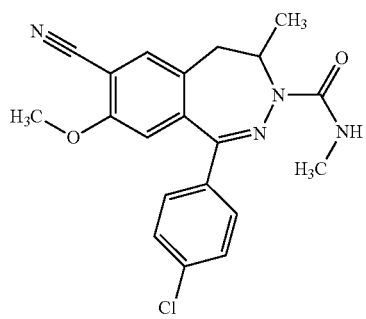 [SMILES: CNC(=O)N1N=C(c2ccc(Cl)cc2)c2cc(OC)c(C#N)cc2CC1C]

640 mg (1.39 mmol) of (±)-7-bromo-1-(4-chlorophenyl)-8-methoxy-N,4-dimethyl-4,5-dihydro-3H-2,3-benzodiazepine-3-carboxamide (Example 95A) were dissolved in 12 ml of toluene, and 173 mg (1.39 mmol) of 1-butyl-1H-imidazole, 118 mg (0.28 mmol) of potassium hexacyanoferrate(II), ground in a mortar and dried, and 26.5 mg (0.14 mmol) of copper(I) iodide were added. The reaction mixture was irradiated in a microwave reactor at 160° C. for 6 hours. For work-up, the reaction mixture was filtered through Celite®, the filter cake washed with ethyl acetate and the filtrate was concentrated under reduced pressure. The crude product was purified by flash chromatography ($SiO_2$, hexane/ethyl acetate). This gave 430 mg (79% of theory) of the desired product as a grey foam.

LCMS (Method 3): $R_t$=1.30 min; m/z=383; 385 (Cl isotope pattern; M+H)$^+$ $^1$H-NMR (400 MHz, CDCl$_3$): δ=0.89 (d, 3H), 2.90 (d, 3H), 2.91 (dd, 1H), 3.09 (dd, 1H), 3.71 (s, 3H), 5.50 (m, 1H), 6.52 (qbr, 1H), 6.66 (s, 1H), 7.38 (d, 2H), 7.39 (s, 1H), 7.41 (d, 2H).

Example 97A (±)-1-(4-Bromophenyl)-7-(difluoromethoxy)-8-methoxy-N,4-dimethyl-4,5-dihydro-3H-2,3-benzodiazepine-3-carboxamide

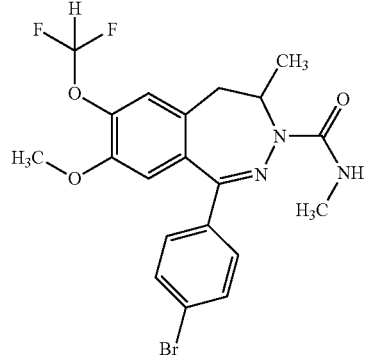 [SMILES: CNC(=O)N1N=C(c2ccc(Br)cc2)c2cc(OC)c(OC(F)F)cc2CC1C]

1.58 g (39.5 mmol) of sodium hydroxide were suspended in 42 ml of DMF. At RT, 1.14 g (2.73 mmol) of (±)-1-(4-bromophenyl)-7-hydroxy-8-methoxy-N,4-dimethyl-4,5-dihydro-3H-2,3-benzodiazepine-3-carboxamide (Example 90A) were added, and the mixture was stirred at RT for 15 min and then at 0° C. for 10 min. At 0° C., 4.32 g (27.3 mmol) of ethyl chloro-(difluoro)acetate (CAS [383-62-0]) were added, and the mixture was stirred at 70° C. for 5 h. After cooling, the mixture was added to water and extracted with ethyl acetate, and the combined organic phases were washed with sat. sodium chloride solution and dried with sodium sulphate. The solvents were removed on a rotary evaporator and the crude product was purified chromatographically ($SiO_2$, hexane/ethyl acetate 0-60%). This gave 370 mg (29% of theory) of the desired product as a pale-yellow foam.

LCMS (Method 2): $R_t$=1.42 min; m/z=468/470 (M+H)$^+$, Br isotope pattern $^1$H-NMR (400 MHz, CDCl$_3$): δ=0.91 (d, 3H), 2.64 (d, 3H), 2.65 (dd, 1H), 2.92 (dd, 1H), 3.61 (s, 3H), 4.99-5.08 (m, 1H), 6.65 (q, 1H), 6.67 (s, 1H), 7.13 (t, J=75 Hz, 1H), 7.20 (s, 1H), 7.59 (s, 4H).

The following compounds were prepared analogously to Example 8A from the appropriate commercially available aldehydes:

| No. | Structure | Name | Analytical data |
|---|---|---|---|
| 98A | (structure: 4-chloro-3-(trifluoromethoxy)phenyl methacrylic acid) | (2E)-3-[4-chloro-3-(trifluoromethoxy)phenyl]-2-methacrylic acid | $^1$H-NMR (300 MHz, CDCl$_3$): δ = 2.13 (s, 3H), 7.30 (d, 1H), 7.38 (s, br, 1H), 7.52 (d, 1H), 7.73 (s, br, 1H). LCMS (Method 2): R$_t$ = 1.31 min; m/z [ES$^-$] = 279/281 (M − H, Cl − isotopes)$^-$ |
| 99A | (structure: 4-methoxy-3-(trifluoromethoxy)phenyl methacrylic acid) | (2E)-3-[4-methoxy-3-(trifluoromethoxy)phenyl]-2-methacrylic acid | $^1$H-NMR (300 MHz, CDCl$_3$): δ = 2.15 (d, 3H), 3.93 (s, 3H), 7.03 (d, 1H), 7.33-7.40 (m, 2H), 7.72 (s, br, 1H). LCMS (Method 1): R$_t$ = 1.16 min; m/z [ES$^-$] = 277 (M + H)$^+$ |

The following compounds were prepared analogously to Example 10A from Example 98A and Example 99A respectively:

The following compounds were prepared analogously to Example 17A from the corresponding indanones, which are possibly available commercially, by reaction with 4-chloro-

| No. | Structure | Name | Analytical data |
|---|---|---|---|
| 100A | (structure) | 3-[4-chloro-3-(trifluoromethoxy)phenyl]-2-methylpropanoic acid | $^1$H-NMR (400 MHz, CDCl$_3$): δ = 1.21 (d, 3H), 2.67-2.81 (m, 2H), 2.98-3.08 (m, 1H), 7.08 (dd, 1H), 7.16 (t, 1H), 7.38 (d, 1H). LCMS (Method 2): R$_t$ = 1.27 min; m/z [ES$^-$] = 281/283 (M − H, Cl − isotopes)$^-$ |
| 101A | (structure) | 3-[4-methoxy-3-(trifluoromethoxy)phenyl]-2-methylpropanoic acid | $^1$H-NMR (300 MHz, CDCl$_3$): δ = 1.19 (d, 3H), 2.60-2.79 (m, 2H), 2.99 (dd, 1H), 3.85 (s, 3H), 6.91 (d, 1H), 7.03-7.10 (m, 2H). LCMS (Method 2): R$_t$ = 1.16 min; m/z [ES$^-$] = 278 (M − H)$^-$ |

The following indanones were prepared analogously to Example 15A from the corresponding carboxylic acid (Example 100A and Example 101A):

phenylmagnesium bromide and subsequent elimination of water using 4-toluenesulphonic acid:

| No. | Structure | Name | Analytical data |
|---|---|---|---|
| 102A | (structure) | 6-chloro-2-methyl-5-(trifluoromethoxy)indan-1-one | $^1$H-NMR (300 MHz, CDCl$_3$): δ = 1.32 (d, 3H), 2.68-2.84 (m, 2H), 3.40 (dd, 1H), 7.40 (s, br, 1H), 7.85 (s, 1H). LCMS (Method 2): R$_t$ = 1.36 min; m/z = 266 (M + H)$^+$ |
| 103A | (structure) | 6-methoxy-2-methyl-5-(trifluoromethoxy)indan-1-one | $^1$H-NMR (300 MHz, CDCl$_3$): δ = 1.31 (d, 3H), 2.63-2.81 (m, 2H), 3.35 (dd, 1H), 3.91 (s, 3H), 7.30 (s, br, 2H). LCMS (Method 2): R$_t$ = 1.27 min; m/z = 261 (M + H)$^+$ |

| No. | Structure | Name | Analytical data |
|---|---|---|---|
| 104A | 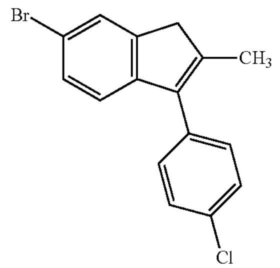 [SMILES: CC1=C(c2ccc(Cl)cc2)c2ccc(Br)cc2C1] | 6-bromo-3-(4-chlorophenyl)-2-methyl-1H-indene | $^1$H-NMR (400 MHz, CDCl$_3$): δ = 2.11 (s, 3H), 3.44 (s, 2H), 7.02 (d, 1H), 7.30 (d, 2H), 7.35 (dd, 1H), 7.44 (d, 2H), 7.56 (d, 1H). LCMS (Method 2): R$_t$ = 1.75 min; m/z = 319; 321 (Br isotope pattern, M + H)$^+$ |
| 105A | 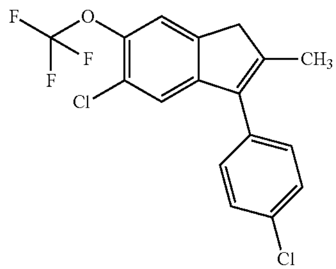 [SMILES: CC1=C(c2ccc(Cl)cc2)c2cc(Cl)c(OC(F)(F)F)cc2C1] | 5-chloro-3-(4-chlorophenyl)-2-methyl-1H-inden-6-yl trifluoromethyl ether | $^1$H-NMR (400 MHz, CDCl$_3$): δ = 2.13 (s, 3H), 3.46 (s, 2H), 7.20 (s, 1H), 7.29 (d, 2H), 7.38 (s, br, 1H), 7.46 (d, 2H). LCMS (Method 2): R$_t$ = 1.75 min; m/z = 357; 359 (Cl isotope pattern, M + H)$^+$ |
| 106A | 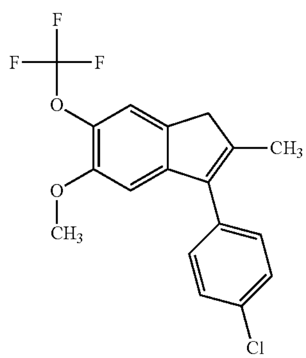 [SMILES: COc1cc2c(cc1OC(F)(F)F)CC(C)=C2c1ccc(Cl)cc1] | 3-(4-chlorophenyl)-5-methoxy-2-methyl-6-(trifluoromethoxy)-1H-indene | $^1$H-NMR (400 MHz, CDCl$_3$): δ = 2.11 (s, 3H), 3.41 (s, 2H), 3.81 (s, 3H), 6.76 (s, 1H), 7.30 (s, 1H), 7.31 (d, 2H), 7.47 (d, 2H). LCMS (Method 1): R$_t$ = 1.72 min; m/z = 355 (M + H)$^+$ |

Example 107A (3,4-Dimethoxyphenyl)acetaldehyde

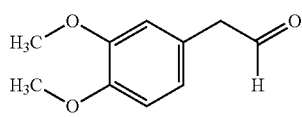

18 g (96.81 mmol) of 2-(3,4-dimethoxyphenyl)ethanol were initially charged in 395 ml of dichloromethane and 50.8 g (116.17 mmol) of Dess-Martin reagent were added in portions. The temperature was held at 20° C. The reaction mixture was stirred at RT for 3 h. The suspension was admixed with 200 ml of saturated aqueous sodium hydrogencarbonate solution and 200 ml of saturated aqueous sodium dithionite solution. It was stirred for 30 minutes and then the organic phase was separated off. The aqueous phase was extracted three times with dichloromethane and the combined organic phases were washed once with sodium hydrogencarbonate solution and once with water. After drying using sodium sulphate and removal of the solvent, 16.6 g of product were obtained (95% of theory), which was directly reacted further.

LCMS (Method 1): R$_t$=0.74 min; m/z=181 (M+H)$^+$ $^1$H-NMR (300 MHz, CDCl$_3$): δ=3.66 (d, 2H), 3.91 (s, 6H), 6.73 (d, 1H), 6.81 (t, 1H), 6.90 (d, 1H), 9.75 (t, 1H).

Example 108A (±)-1-(3,4-Dimethoxyphenyl)butan-2-ol

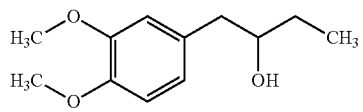

Under argon, 22.19 g (166.48 mmol) of ethylmagnesium bromide were initially charged and cooled to −40° C. 25 g (138.7 mmol) of (3,4-dimethoxyphenyl)acetaldehyde (Example 107A) were dissolved in 60 ml of THF and added slowly dropwise over the course of 30 minutes to the Grignard solution. An internal bath temperature of not more than −35° C. was maintained. Following the addition, the reaction mixture was stirred at RT for 2 h. It was worked up by adding 300 ml of cooled, saturated aqueous ammonium chloride solution, and the organic phase was separated off. The aqueous phase was extracted three times with ethyl acetate and the combined organic phases were washed once with water and once with saturated aqueous sodium chloride solution. Drying using sodium sulphate and removal of the solvent gave 21.53 g of product (64% of theory), which was further reacted directly.

LCMS (Method 1): $R_t$=0.92 min; m/z=211 (M+H)$^+$; 193 (M−H$_2$O+H)$^+$ $^1$H-NMR (400 MHz, CDCl$_3$): δ=1.03 (t, 3H), 1.52-1.66 (m, 2H), 2.59 (dd, 1H), 2.82 (dd, 1H), 3.69-3.80 (m, 1H), 3.84-3.96 (m, 1H), 3.89 (s, 3H), 3.90 (s, 3H), 6.77 (s, 1H), 6.78 (d, 1H), 6.85 (d, 1H).

Example 109A (±)-1-(3,4-Dimethoxyphenyl)-3-methylbutan-2-ol

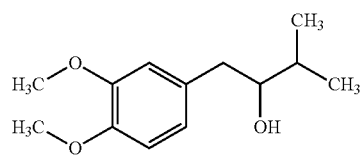 [SMILES: COc1ccc(CC(O)C(C)C)cc1OC]

Under argon, 6.16 g (59.93 mmol) of 2-propylmagnesium chloride were initially charged, and cooled to −40° C. 9 g (49.9 mmol) of (3,4-dimethoxyphenyl)acetaldehyde (Example 107A) were dissolved in 30 ml of THF and added slowly dropwise over the course of 30 minutes to the Grignard solution. Following the addition, the reaction mixture was stirred at RT for 2 h. It was worked up by adding 150 ml of cooled, saturated aqueous ammonium chloride solution, and the organic phase was separated off. The aqueous phase was extracted 3× with ethyl acetate and the combined organic phases were washed once with water and once with saturated aqueous sodium chloride solution. Drying using sodium sulphate and removal of the solvent gave 9.76 g or product (58% of theory), which was further reacted directly.

LCMS (Method 1): $R_t$=1.03 min; m/z=225 (M+H)$^+$; 207 (M−H$_2$O+H)$^+$ $^1$H-NMR (300 MHz, CDCl$_3$): δ=1.03 (d, 6H), 1.51 (s, br, 1H), 1.72-1.84 (m, 1H), 2.56 (dd, 1H), 2.84 (dd, 1H), 3.58 (m, 1H), 3.89 (s, 3H), 3.91 (s, 3H), 6.74-6.88 (m, 3H).

The following compounds were prepared analogously to Example 41A from Example 108A and Example 109A, respectively, and 4-bromobenzaldehyde:

| No. | Structure | Name | Analytical data |
|---|---|---|---|
| 110A | 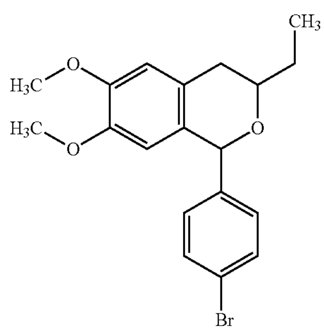 [SMILES: CCC1Cc2cc(OC)c(OC)cc2C(c2ccc(Br)cc2)O1] | 1-(4-bromophenyl)-3-ethyl-6,7-dimethoxy-3,4-dihydro-1H-isochromene | LCMS (Method 1): $R_t$ = 1.53 min; m/z = 377; 379 (Br isotope pattern, M + H)$^+$ |
| 111A | 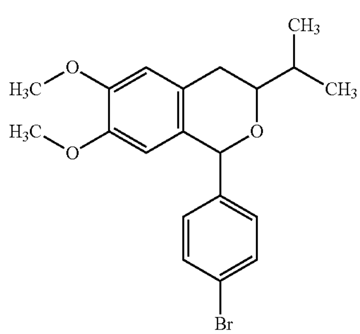 [SMILES: COc1cc2c(cc1OC)C(c1ccc(Br)cc1)OC(C(C)C)C2] | 1-(4-bromophenyl)-3-isopropyl-6,7-dimethoxy-3,4-dihydro-1H-isochromene | LCMS (Method 5): $R_t$ = 1.58 min; m/z = 391; 393 (Br isotope pattern, M + H)$^+$ |

The following diketones were prepared analogously to Example 43A:

| No. | Structure | Name | Analytical data |
|---|---|---|---|
| 112A | 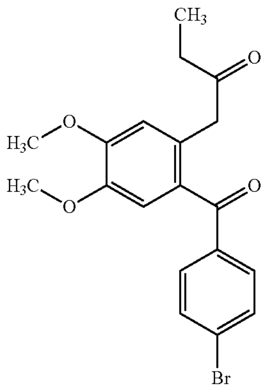 [SMILES: CCC(=O)Cc1cc(OC)c(OC)cc1C(=O)c1ccc(Br)cc1] | 1-[2-(4-bromobenzoyl)-4,5-dimethoxyphenyl]butan-2-one | $^1$H-NMR (300 MHz, CDCl$_3$): δ = 1.06 (t, 3H), 2.54 (q, 2H), 3.80 (s, 3H), 3.92 (s, 2H), 3.97 (s, 3H), 6.78 (s, 1H), 6.92 (s, 1H), 7.63 (d, 2H), 7.68 (d, 2H). LCMS (Method 1): R$_t$ = 1.33 min; m/z = 391; 393 (M + H, Br isotope pattern)$^+$ |
| 113A | 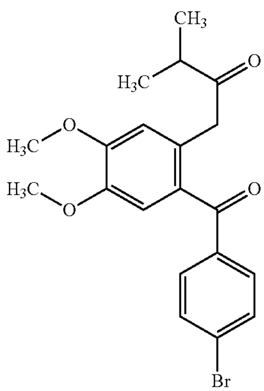 [SMILES: COc1cc(CC(=O)C(C)C)c(C(=O)c2ccc(Br)cc2)cc1OC] | 1-[2-(4-bromobenzoyl)-4,5-dimethoxyphenyl]-3-methylbutan-2-one | $^1$H-NMR (400 MHz, CDCl$_3$): δ = 1.12 (d, 6H), 2.69-2.80 (m, 1H), 3.80 (s, 3H), 3.97 (s, 3H), 4.02 (s, 2H), 6.77 (s, 1H), 6.91 (s, 1H), 7.62 (d, 2H), 7.68 (d, 2H). LCMS (Method 1): R$_t$ = 1.59 min; m/z = 407, 409 (M + H, Br isotope pattern)$^+$ |
| 114A | 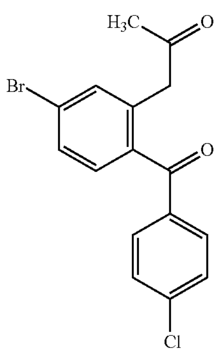 [SMILES: CC(=O)Cc1cc(Br)ccc1C(=O)c1ccc(Cl)cc1] | 1-[5-bromo-2-(4-chlorbenzoyl)phenyl]acetone | $^1$H-NMR (300 MHz, CDCl$_3$): δ = 2.19 (s, 3H), 4.00 (s, 2H), 7.24 (d, 1H), 7.40-7.51 (m, 4H), 7.73 (d, 2H). LCMS (Method 2): R$_t$ = 1.40 min; m/z = 351, 353 (M + H, Br isotope pattern)$^+$ |
| 115A | 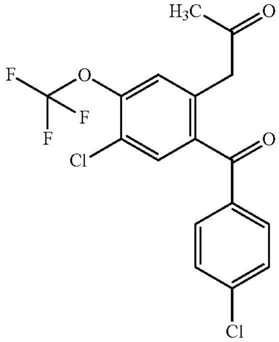 [SMILES: CC(=O)Cc1cc(OC(F)(F)F)c(Cl)cc1C(=O)c1ccc(Cl)cc1] | 1-[4-chloro-2-(4-chlorobenzoyl)-5-(trifluoromethoxy)phenyl]acetone | $^1$H-NMR (300 MHz, CDCl$_3$): δ = 2.20 (s, 3H), 4.04 (s, 2H), 7.21 (s, br, 1H), 7.45-7.52 (m, 3H), 7.77 (d, 2H). LCMS (Method 2): R$_t$ = 1.40 min; m/z = 391, 393 (M + H, Cl isotope pattern)$^+$ |

| No. | Structure | Name | Analytical data |
|---|---|---|---|
| 116A | 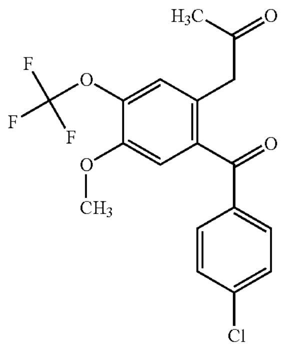 [SMILES: COc1cc(C(=O)c2ccc(Cl)cc2)c(CC(C)=O)cc1OC(F)(F)F] | 1-[2-(4-chlorobenzoyl)-4-methoxy-5-(trifluoromethoxy)phenyl]acetone | $^1$H-NMR (300 MHz, CDCl$_3$): δ = 2.19 (s, 3H), 3.83 (s, 3H), 3.95 (s, 2H), 6.99 (s, 1H), 7.15 (s, 1H), 7.49 (d, 2H), 7.81 (d, 2H). LCMS (Method 1): R$_t$ = 1.44 min; m/z = 387 (M + H)$^+$ |

The following benzodiazepines were prepared analogously to Example 45A, but at RT and without introduction of hydrogen chloride gas:

| No. | Structure | Name | Analytical data |
|---|---|---|---|
| 117A | 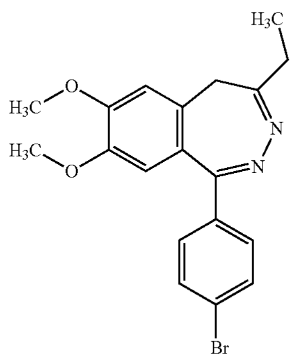 [SMILES: CCC1=NN=C(c2ccc(Br)cc2)c2cc(OC)c(OC)cc2C1] | 1-(4-bromophenyl)-4-ethyl-7,8-dimethoxy-5H-2,3-benzodiazepine | $^1$H-NMR (400 MHz, CDCl$_3$): δ = 1.20 (t, 3H), 2.40-2.58 (m, 2H), 2.99 (d, 1H), 3.32 (d, 1H), 3.77 (s, 3H), 3.99 (s, 3H), 6.74 (s, 1H), 6.77 (s, 1H), 7.56 (d, 2H), 7.62 (d, 2H). LCMS (Method 2): R$_t$ = 1.19 min; m/z = 387, 389 (Br isotope pattern, M + H)$^+$ |
| 118A | 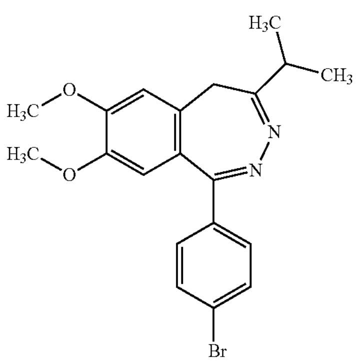 [SMILES: COc1cc2c(cc1OC)C(c1ccc(Br)cc1)=NN=C(C(C)C)C2] | 1-(4-bromophenyl)-4-isopropyl-7,8-dimethoxy-5H-2,3-benzodiazepine | $^1$H-NMR (300 MHz, CDCl$_3$): δ = 1.19 (d, 3H), 1.24 (d, 3H), 2.71 (m, 1H), 2.93 (d, 1H), 3.43 (d, 1H), 3.78 (s, 3H), 3.98 (s, 3H), 6.75 (s, 1H), 6.77 (s, 1H), 7.56 (d, 2H), 7.61 (d, 2H). LCMS (Method 5): R$_t$ = 1.28 min; m/z = 401, 403 (Br isotope pattern, M + H)$^+$ |
| 119A | 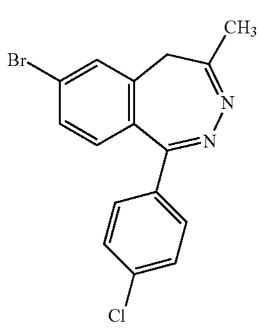 [SMILES: CC1=NN=C(c2ccc(Cl)cc2)c2ccc(Br)cc2C1] | 7-bromo-1-(4-chlorophenyl)-4-methyl-5H-2,3-benzodiazepine | $^1$H-NMR (300 MHz, CDCl$_3$): δ = 2.27 (s, 3H), 3.13 (d, 1H), 3.40 (d, 1H), 7.20 (d, 1H), 7.40 (d, 2H), 7.51 (s, 1H), 7.55 (d, 1H), 7.61 (d, 2H). LCMS (Method 2): R$_t$ = 1.41 min; m/z = 347, 349 (Br isotope pattern, M + H)$^+$ |

| No. | Structure | Name | Analytical data |
|---|---|---|---|
| 120A | 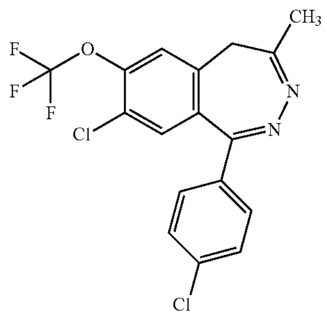 [SMILES: CC1=NN=C(c2ccc(Cl)cc2)c2cc(Cl)c(OC(F)(F)F)cc2C1] | 8-chloro-1-(4-chlorophenyl)-4-methyl-7-(trifluoromethoxy)-5H-2,3-benzodiazepine | $^1$H-NMR (300 MHz, CDCl$_3$): δ = 2.20 (s, 3H), 3.11 (d, 1H), 3.41 (d, 1H), 7.30 (s, 1H), 7.45 (d, 2H), 7.47 (s, 1H), 7.62 (d, 2H). LCMS (Method 1): R$_t$ = 1.55 min; m/z = 387, 389 (Cl isotope pattern, M + H)$^+$ |
| 121A | 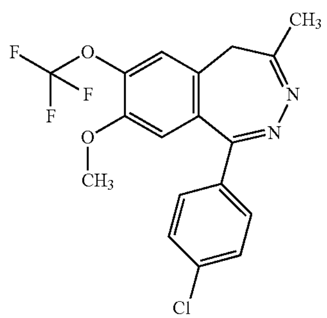 [SMILES: COc1cc2c(cc1OC(F)(F)F)CC(C)=NN=C2c1ccc(Cl)cc1] | 1-(4-chlorophenyl)-8-methoxy-4-methyl-7-(trifluoromethoxy)-5H-2,3-benzodiazepine | LCMS (Method 1): R$_t$ = 1.44 min; m/z = 383 (M + H)$^+$ |

The following amines were prepared analogously to Example 47A from the corresponding 5H-2,3-benzodiazepines:

| No. | Structure | Name | Analytical data |
|---|---|---|---|
| 122A | 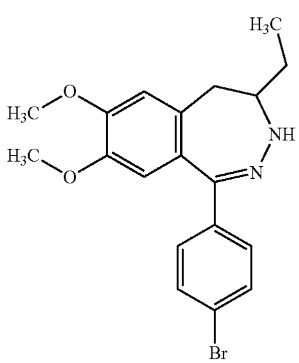 [SMILES: CCC1Cc2cc(OC)c(OC)cc2C(c2ccc(Br)cc2)=NN1] | (±)-1-(4-bromophenyl)-4-ethyl-7,8-dimethoxy-4,5-dihydro-3H-2,3-benzodiazepine | $^1$H-NMR (300 MHz, CDCl$_3$): δ = 1.04 (t, 3H), 1.56-1.71 (m, 2H), 2.66 (dd, 1H), 2.91 (dd, 1H), 3.73 (s, 3H), 3.87 (quin, 1H), 3.97 (s, 3H), 5.48 (s, br, 1H), 6.60 (s, 1H), 6.78 (s, 1H), 7.46 (d, 2H), 7.52 (d, 2H). LCMS (Method 2): R$_t$ = 0.96 min; m/z = 389, 391 (Br isotope pattern, M + H)$^+$ |
| 123A | 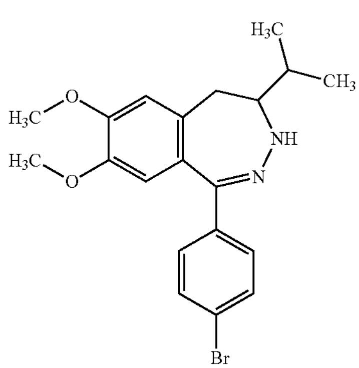 [SMILES: COc1cc2c(cc1OC)C(c1ccc(Br)cc1)=NNC(C(C)C)C2] | (±)-1-(4-bromophenyl)-4-isopropyl-7,8-dimethoxy-4,5-dihydro-3H-2,3-benzodiazepine | LCMS (Method 5): R$_t$ = 1.17 min; m/z = 403, 405 (Br isotope pattern, M + H)$^+$ |

-continued

| No. | Structure | Name | Analytical data |
|---|---|---|---|
| 124A | 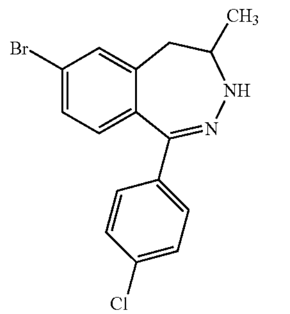 [SMILES: CC1Cc2cc(Br)ccc2C(c2ccc(Cl)cc2)=NN1] | (±)-7-bromo-1-(4-chlorophenyl)-4-methyl-4,5-dihydro-3H-2,3-benzodiazepine | $^1$H-NMR (300 MHz, CDCl$_3$): δ = 1.29 (d, 3H), 2.65 (dd, 1H), 2.93 (dd, 1H), 4.04-4.17 (m, 1H), 6.97 (d, 1H), 7.30-7.51 (m, 6H). LCMS (Method 2): R$_t$ = 1.43 min; m/z = 349, 351 (Br isotope pattern, M + H)$^+$ |
| 125A | 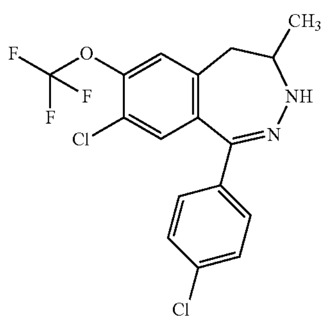 [SMILES: CC1Cc2cc(OC(F)(F)F)c(Cl)cc2C(c2ccc(Cl)cc2)=NN1] | (±)-8-chloro-1-(4-chlorophenyl)-4-methyl-7-(trifluoromethoxy)-4,5-dihydro-3H-2,3-benzodiazepine | $^1$H-NMR (300 MHz, CDCl$_3$): δ = 1.34 (d, 3H), 2.72 (dd, 1H), 2.99 (dd, 1H), 4.07-4.21 (m, 1H), 7.24 (s, 1H), 7.29 (s, 1H), 7.39 (d, 2H), 7.49 (d, 2H). LCMS (Method 2): R$_t$ = 1.63 min; m/z = 389, 391 (Cl isotope pattern, M + H)$^+$ |
| 126A | 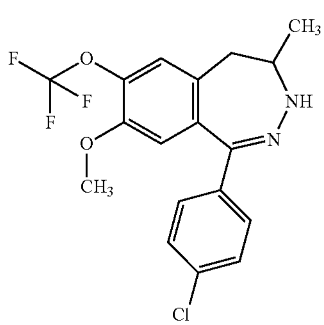 [SMILES: COc1cc2c(cc1OC(F)(F)F)CC(C)NN=C2c1ccc(Cl)cc1] | (±)-1-(4-chlorophenyl)-8-methoxy-4-methyl-7-(trifluoromethoxy)-4,5-dihydro-3H-2,3-benzodiazepine | LCMS (Method 3): R$_t$ = 1.63 min; m/z = 385 (M + H)$^+$ |

The following compounds were prepared analously to Example 49A from the corresponding 4,5-dihydro-3H-2,3-benzodiazepines:

| No. | Structure | Name | Analytical data |
|---|---|---|---|
| 127A | 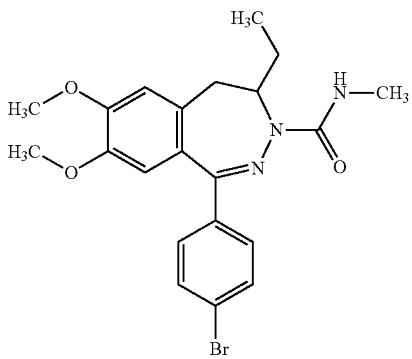 | (±)-1-(4-bromophenyl)-4-ethyl-7,8-dimethoxy-N-methyl-4,5-dihydro-3H-2,3-benzodiazepine-3-carboxamide | $^1$H-NMR (400 MHz, CDCl$_3$): δ = 0.86 (t, 3H), 1.04-1.17 (m, 1H), 1.32-1.44 (m, 1H), 2.91 (d, 3H), 3.01 (dd, 1H), 3.08 (dd, 1H), 3.68 (s, 3H), 3.95 (s, 3H), 5.27-5.36 (m, 1H), 6.58 (s, 1H), 6.68 (q, 1H), 6.73 (s, 1H), 7.37 (d, 2H), 7.54 (d, 2H). LCMS (Method 2): R$_t$ = 1.53 min; m/z = 446; 448 (Br isotope pattern, M + H)$^+$ |
| 128A | 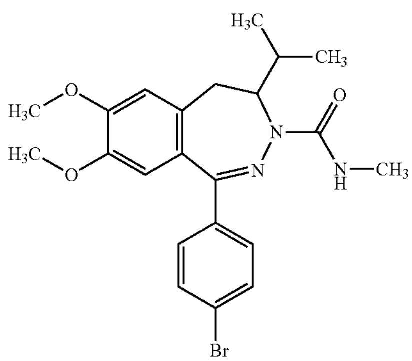 | (±)-1-(4-bromophenyl)-4-isopropyl-7,8-dimethoxy-N-methyl-4,5-dihydro-3H-2,3-benzodiazepine-3-carboxamide | $^1$H-NMR (400 MHz, CDCl$_3$): δ = 0.84 (d, 3H), 0.86 (d, 3H), 0.97 (t, 1H), 2.90 (d, 3H), 3.01 (dd, 1H), 3.15 (dd, 1H), 3.67 (s, 3H), 3.95 (s, 3H), 5.16-5.32 (m, 1H), 6.61 (s, 1H), 6.66 (q, 1H), 6.75 (s, 1H), 7.36 (d, 2H), 7.55 (d, 2H). LCMS (Method 5): R$_t$ = 1.40 min; m/z = 460; 462 (Br isotope pattern, M + H)$^+$ |
| 129A | 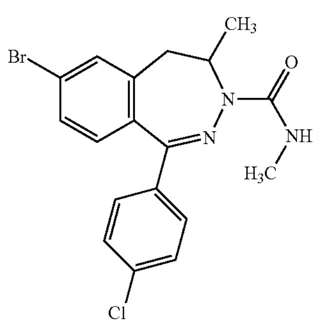 [SMILES: CNC(=O)N1N=C(c2ccc(Cl)cc2)c2ccc(Br)cc2CC1C] | (±)-7-bromo-1-(4-chlorophenyl)-N,4-dimethyl-4,5-dihydro-3H-2,3-benzodiazepine-3-carboxamide | $^1$H-NMR (300 MHz, CDCl$_3$): δ = 0.93 (d, 3H), 2.84-2.94 (m, 4H), 3.11 (d, 1H), 5.44-5.56 (m, 1H), 6.44-6.55 (m, 1H), 6.95 (d, 1H), 7.33 (dd, 1H), 7.36-7.42 (m, 5H). LCMS (Method 1): R$_t$ = 1.51 min; m/z = 406; 408 (Br isotope pattern, M + H)$^+$ |
| 130A | 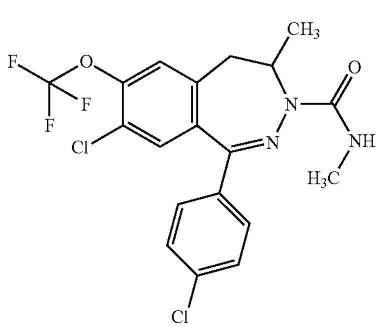 | (±)-8-chloro-1-(4-chlorophenyl)-N,4-dimethyl-7-(trifluoromethoxy)-4,5-dihydro-3H-2,3-benzodiazepine-3-carboxamide | $^1$H-NMR (400 MHz, CDCl$_3$): δ = 0.95 (d, 3H), 2.92 (d, 3H), 2.96 (dd, 1H), 3.16 (dd, 1H), 5.51-5.60 (m, 1H), 6.50 (q, 1H), 7.22 (dd, 1H), 7.23 (s, 1H), 7.40 (d, 2H), 7.43 (d, 2H). LCMS (Method 1): R$_t$ = 1.61 min; m/z = 446; 448 (Cl isotope pattern, M + H)$^+$ |

| No. | Structure | Name | Analytical data |
|---|---|---|---|
| 131A | 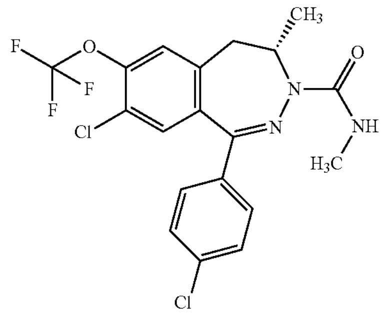 [SMILES: CNC(=O)N1N=C(c2ccc(Cl)cc2)c2cc(Cl)c(OC(F)(F)F)cc2C[C@@H]1C] | (4S)-8-chloro-1-(4-chlorophenyl)-N,4-dimethyl-7-(trifluoromethoxy)-4,5-dihydro-3H-2,3-benzodiazepine-3-carboxamide | Prep. HPLC: Method VIIIa<br>Analyt. HPLC (Method Da):<br>$R_t$ = 2.37 min<br>$[\alpha]_D^{20}$ = +73.0° (c = 1.00; MeOH)<br>LCMS (Method 2): $R_t$ = 1.64 min;<br>m/z = 446; 448 (Cl isotope pattern, M + H)$^+$ |
| 132A | 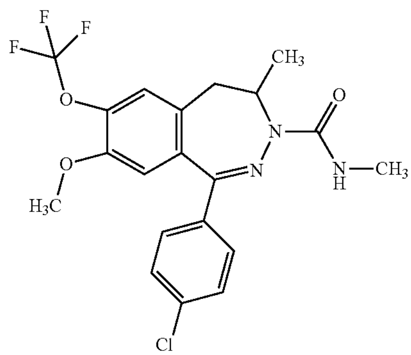 [SMILES: CNC(=O)N1N=C(c2ccc(Cl)cc2)c2cc(OC)c(OC(F)(F)F)cc2CC1C] | (±)-1-(4-chlorophenyl)-8-methoxy-N,4-dimethyl-7-(trifluoromethoxy)-4,5-dihydro-3H-2,3-benzodiazepine-3-carboxamide | $^1$H-NMR (400 MHz, CDCl$_3$): δ = 0.96 (d, 3H), 2.88 (dd, 1H), 2.92 (d, 3H), 3.12 (dd, 1H), 3.69 (s, 3H), 5.44-5.54 (m, 1H), 6.46-6.54 (m, 1H), 6.71 (s, 1H), 7.12 (s, 1H), 7.41 (d, 2H), 7.46 (d, 2H).<br>LCMS (Method 1): $R_t$ = 1.50 min; m/z = 442 (M + H)$^+$ |

Example 133A (±)-1-[1-(4-Bromophenyl)-7,8-dimethoxy-4-methyl-4,5-dihydro-3H-2,3-benzodiazepin-3-yl]ethanone

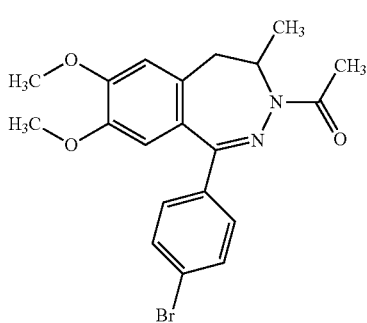 [SMILES: COc1cc2c(cc1OC)C(c1ccc(Br)cc1)=NN(C(C)=O)C(C)C2]

274 mg (0.73 mmol) of (±)-1-(4-bromophenyl)-7,8-dimethoxy-4-methyl-4,5-dihydro-3H-2,3-benzodiazepine (Example 47A) were admixed with 7 ml (73 mmol) of acetic anhydride and stirred at a jacket temperature of 140° C. for 1 hour. After this mixture had cooled, 25 ml of saturated sodium hydrogencarbonate solution were added. The mixture was extracted with ethyl acetate. The combined organic phases were washed with water and saturated sodium chloride solution, dried using sodium sulphate, and the solvent was removed on a rotary evaporator. The residue was purified by chromatography. This gave 195 mg (64% of theory) of the product as a brown oil.

LCMS (Method 1): $R_t$=1.29 min; m/z=417/419 (M+H)$^+$, Br isotope pattern.

$^1$H-NMR (300 MHz, CDCl$_3$): δ=1.19 (d, 3H), 2.22 (s, 3H), 2.76 (dd, 1H), 2.95 (dd, 1H), 3.74 (s, 3H), 3.97 (s, 3H), 5.33-5.42 (m, 1H), 6.57 (s, 1H), 6.80 (s, 1H), 7.53 (d, 2H), 7.59 (d, 2H).

Example 134A (±)-4-[7,8-Dimethoxy-4-methyl-3-[(methylamino)carbonyl]-4,5-dihydro-3H-2,3-benzodiazepin-1-yl]benzoic acid

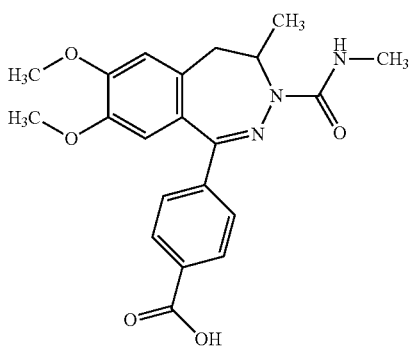

5.03 g (11.64 mmol) of (±)-1-(4-bromophenyl)-7,8-dimethoxy-N,4-dimethyl-4,5-dihydro-3H-2,3-benzodiazepine-3-carboxamide (Example 49A) were suspended in 65 ml of dimethyl sulphoxide and admixed with 1.33 g (2.33 mmol) of 1,1'-bis(diphenylphosphino)ferrocene (CAS [12150-46-8]), 130 mg (0.58 mmol) of palladium(II) acetate and 4.5 g (46.5 mmol) of potassium acetate. The mixture was exposed for half an hour at room temperature to a carbon monoxide pressure of 19 bar, with stirring. It was then let down, evacuated, and at 100° C. again stirred under a carbon monoxide pressure of 20 bar for 20 hours. It was worked up by filtration, washing with ethyl acetate, washing of the organic phase three times with saturated aqueous sodium chloride solution, drying using sodium sulphate, and removal of the solvent on a rotary evaporator. The residue was purified by chromatography. This gave 466 mg (10% of theory) of the product as a dark solid.

LCMS (Method 3): $R_t$=0.96 min; m/z=398 (M+H)$^+$.

$^1$H-NMR (400 MHz, CDCl$_3$): δ=0.96 (d, 3H), 2.89 (dd, 1H), 2.91 (d, 3H), 3.17 (dd, 1H), 3.64 (s, 3H), 3.94 (s, 3H), 5.52 (m, 1H), 6.53 (s, 1H), 6.58 (m, 1H), 6.72 (s, 1H), 7.58 (d, 2H), 8.13 (d, 2H).

Example 135A 7,8-Dimethoxy-4-methyl-1-[4-(4-methylpiperazin-1-yl)phenyl]-5H-2,3-benzodiazepine

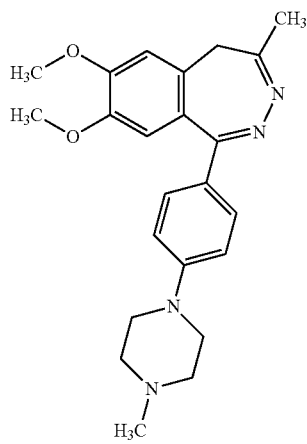

The compound was prepared analogously to Example 7 from 1-(4-bromophenyl)-7,8-dimethoxy-4-methyl-5H-2,3-benzodiazepine (Example 45A).

LCMS (Method 3): $R_t$=0.71 min; m/z=393 (M+H)

$^1$H-NMR (300 MHz, DMSO-d$_6$): δ=2.02 (s, 3H), 2.22 (s, 3H), 2.45 (m, 4H), 2.73 (d, 1H), 3.23 (m, 4H), 3.38 (d, 1H), 3.62 (s, 3H), 3.86 (s, 3H), 6.74 (s, 1H), 6.96 (d, 2H), 7.05 (s, 1H), 7.45 (d, 2H).

Example 136A (±)-7,8-Dimethoxy-4-methyl-1-[4-(4-methylpiperazin-1-yl)phenyl]-4,5-dihydro-3H-2,3-benzodiazepine

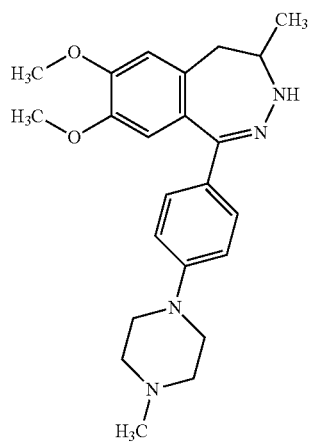

The compound was prepared analogously to Example 7 from 7,8-dimethoxy-4-methyl-1-[4-(4-methylpiperazin-1-yl)phenyl]-5H-2,3-benzodiazepine (Example 135A).

LCMS (Method 3): $R_t$=0.57 min; m/z=395 (M+H)

$^1$H-NMR (300 MHz, DMSO-d$_6$): δ=1.09 (s, 3H), 2.21 (s, 3H), 2.41 (m, 1H), 2.43 (m, 4H), 2.74 (dd, 1H), 3.17 (m, 4H), 3.58 (s, 3H), 3.81 (s, 3H), 3.88 (m, 1H), 6.18 (m, 1H), 6.53 (s, 1H), 6.89 (d, 2H), 6.90 (s, 1H), 7.34 (d, 2H).

Example 137A (±)-1-(4-Bromophenyl)-N-ethyl-7,8-dimethoxy-4-methyl-4,5-dihydro-3H-2,3-benzodiazepine-3-carboxamide

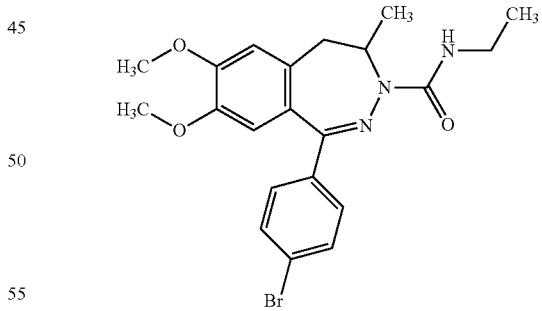

A solution of 150 mg (0.4 mmol) of (±)-1-(4-bromophenyl)-7,8-dimethoxy-4-methyl-4,5-dihydro-3H-2,3-benzodiazepine (Example 47A) in 6 ml of dichloromethane was admixed at RT with 56.8 mg (0.8 mmol) of ethyl isocyanate and stirred at this temperature for 16 h. The batch was freed from the solvent on a rotary evaporator and the residue was purified by means of preparative HPLC. This gave 120 mg (67% of theory) of the title compound as a solid.

LCMS (Method 5): $R_t$=1.35 min; m/z=446; 448 (Br isotope pattern, M+H)$^+$

¹H-NMR (400 MHz, CDCl₃): δ=0.96 (d, 3H), 1.18 (t, 3H), 2.84 (dd, 1H), 3.12 (dd, 1H), 3.29-3.39 (m, 2H), 3.66 (s, 3H), 3.93 (s, 3H), 5.40-5.50 (m, 1H), 6.53 (t, 1H), 6.55 (s, 1H), 6.71 (s, 1H), 7.36 (d, 2H), 7.53 (d, 2H).

The compounds 49.1A; 49.2A; 50A; 51A; 52A; 52.1A; 52.2A; 54A; 55A; 60A; 83A; 83.1A; 83.2A; 84A; 84.1A; 84.2A; 85A; 85.1A; 85.2A; 87A to 93A and 95A to 97A; 127A to 133A and 137A, mentioned in the examples above, are thus useful selected intermediates of the general formula (Ia), which are used with preference in the preparation of the compounds according to the invention.

The invention therefore also provides the intermediates of the general formula Ia according to the invention:
(4R)-1-(4-bromophenyl)-7,8-dimethoxy-N,4-dimethyl-4,5-dihydro-3H-2,3-benzodiazepine-3-carboxamide
(4S)-1-(4-bromophenyl)-7,8-dimethoxy-N,4-dimethyl-4,5-dihydro-3H-2,3-benzodiazepine-3-carboxamide
(±)-1-(4-bromophenyl)-7,8-dimethoxy-N,4-dimethyl-4,5-dihydro-3H-2,3-benzodiazepine-3-carboxamide
(±)-1-(4-chlorophenyl)-8-methoxy-N,4-dimethyl-4,5-dihydro-3H-2,3-benzodiazepine-3-carboxamide
(±)-1-(3-bromophenyl)-7,8-dimethoxy-N,4-dimethyl-4,5-dihydro-3H-2,3-benzodiazepine-3-carboxamide
(±)-8-bromo-1-(4-chlorophenyl)-N,4-dimethyl-4,5-dihydro-3H-2,3-benzodiazepine-3-carboxamide (4R)-8-bromo-1-(4-chlorophenyl)-N,4-dimethyl-4,5-dihydro-3H-2,3-benzodiazepine-3-carboxamide
(4S)-8-bromo-1-(4-chlorophenyl)-N,4-dimethyl-4,5-dihydro-3H-2,3-benzodiazepine-3-carboxamide
(4S)-1-(4-bromophenyl)-8-methoxy-N,4-dimethyl-4,5-dihydro-3H-2,3-benzodiazepine-3-carboxamide
(±)-1-(4-chlorophenyl)-8-hydroxy-N,4-dimethyl-4,5-dihydro-3H-2,3-benzodiazepine-3-carboxamide
(±)-1-(3-bromo-4-fluorophenyl)-7,8-dimethoxy-N,4-dimethyl-4,5-dihydro-3H-2,3-benzodiazepine-3-carboxamide
(±)-8-tert-butyl-1-(4-chlorophenyl)-N,4-dimethyl-4,5-dihydro-3H-2,3-benzodiazepine-3-carboxamide
(4S)-8-tert-butyl-1-(4-chlorophenyl)-N,4-dimethyl-4,5-dihydro-3H-2,3-benzodiazepine-3-carboxamide
(4R)-8-tert-butyl-1-(4-chlorophenyl)-N,4-dimethyl-4,5-dihydro-3H-2,3-benzodiazepine-3-carboxamide
(±)-8-chloro-1-(4-chlorophenyl)-7-methoxy-N,4-dimethyl-4,5-dihydro-3H-2,3-benzodiazepine-3-carboxamide
(4S)-8-chloro-1-(4-chlorophenyl)-7-methoxy-N,4-dimethyl-4,5-dihydro-3H-2,3-benzodiazepine-3-carboxamide
(4R)-8-chloro-1-(4-chlorophenyl)-7-methoxy-N,4-dimethyl-4,5-dihydro-3H-2,3-benzodiazepine-3-carboxamide
(±)-1-(4-chlorophenyl)-N,4,8-trimethyl-4,5-dihydro-3H-2,3-benzodiazepine-3-carboxamide
(4S)-1-(4-chlorophenyl)-N,4,8-trimethyl-4,5-dihydro-3H-2,3-benzodiazepine-3-carboxamide
(4R)-1-(4-chlorophenyl)-N,4,8-trimethyl-4,5-dihydro-3H-2,3-benzodiazepine-3-carboxamide
(±)-8-amino-1-(4-chlorophenyl)-N,4-dimethyl-4,5-dihydro-3H-2,3-benzodiazepine-3-carboxamide
(±)-1-[8-tert-butyl-1-(4-chlorophenyl)-4-methyl-4,5-dihydro-3H-2,3-benzodiazepin-3-yl]ethanone
(±)-8-acetamido-1-(4-chlorophenyl)-N,4-dimethyl-4,5-dihydro-3H-2,3-benzodiazepine-3-carboxamide
(±)-1-(4-bromophenyl)-7-hydroxy-8-methoxy-N,4-dimethyl-4,5-dihydro-3H-2,3-benzodiazepine-3-carboxamide
(±)-1-(4-bromophenyl)-7,8-dihydroxy-N,4-dimethyl-4,5-dihydro-3H-2,3-benzodiazepine-3-carboxamide
(±)-1-(4-bromophenyl)-7,8-bis(difluoromethoxy)-N,4-dimethyl-4,5-dihydro-3H-2,3-benzodiazepine-3-carboxamide
(±)-1-(4-bromophenyl)-7,8-diethoxy-N,4-dimethyl-4,5-dihydro-3H-2,3-benzodiazepine-3-carboxamide
(±)-7-bromo-1-(4-chlorophenyl)-8-methoxy-N,4-dimethyl-4,5-dihydro-3H-2,3-benzodiazepine-3-carboxamide
(±)-1-(4-chlorophenyl)-7-cyano-8-methoxy-N,4-dimethyl-4,5-dihydro-3H-2,3-benzodiazepine-3-carboxamide
(±)-1-(4-bromophenyl)-7-(difluoromethoxy)-8-methoxy-N,4-dimethyl-4,5-dihydro-3H-2,3-benzodiazepine-3-carboxamide
(±)-1-(4-bromophenyl)-4-ethyl-7,8-dimethoxy-N-methyl-4,5-dihydro-3H-2,3-benzodiazepine-3-carboxamide
(±)-1-(4-bromophenyl)-4-isopropyl-7,8-dimethoxy-N-methyl-4,5-dihydro-3H-2,3-benzodiazepine-3-carboxamide
(±)-7-bromo-1-(4-chlorophenyl)-N,4-dimethyl-4,5-dihydro-3H-2,3-benzodiazepine-3-carboxamide
(±)-8-chloro-1(4-chlorophenyl)-N,4-dimethyl-7-(trifluoromethoxy)-4,5-dihydro-3H-2,3-benzodiazepine-3-carboxamide
(4S)-8-chloro-1(4-chlorophenyl)-N,4-dimethyl-7-(trifluoromethoxy)-4,5-dihydro-3H-2,3-benzodiazepine-3-carboxamide
(±)-1-(4-chlorophenyl)-8-methoxy-N,4-dimethyl-7-(trifluoromethoxy)-4,5-dihydro-3H-2,3-benzodiazepine-3-carboxamide
(±)-1-[1-(4-bromophenyl)-7,8-dimethoxy-4-methyl-4,5-dihydro-3H-2,3-benzodiazepin-3-yl]ethanone
(±)-1-(4-bromophenyl)-N-ethyl-7,8-dimethoxy-4-methyl-4,5-dihydro-3H-2,3-benzodiazepine-3-carboxamide Preparation of the Compounds of the General Formula I According to the Invention Example 1

(±)-1-(4-Chlorophenyl)-N,4-dimethyl-8-(trifluoromethoxy)-4,5-dihydro-3H-2,3-benzodiazepine-3-carboxamide

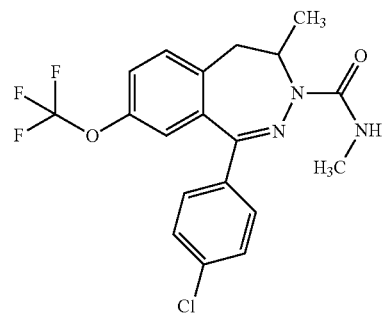 [SMILES: CNC(=O)N1N=C(c2ccc(Cl)cc2)c2cc(OC(F)(F)F)ccc2CC1C]

145 mg (3.64 mmol) of sodium hydroxide were dissolved in 8.7 ml of water, and a solution of 860 mg (2.42 mmol) of (±)-1-(4-chlorophenyl)-4-methyl-8-(trifluoromethoxy)-4,5-dihydro-3H-2,3-benzodiazepine (Example 35A) in 35 ml of ethyl acetate was added at 0° C. After 20 min of stirring at 0° C., 877 mg (7.27 mmol, 0.80 ml) of isopropenyl chloroformate (CAS [57933-83-2]) were added, and the mixture was stirred vigorously at 0° C. for 2.5 h. The phases were then separated, and the organic phase was dried with sodium sulphate and evaporated to dryness. The residue was dissolved in 35 ml of THF, and 2 mg (0.02 mmol) of 1-methylpyrrolidine and 6.1 ml (12.1 mmol) of a 2M solution of methylamine in THF were added. In a sealed pressure tube, the reaction mixture was stirred at 70° C. for a total of 10 h. After 5 h, the reaction was interrupted, the mixture was cooled and a further 6.1 ml of methylamine solution were added and the mixture was heated at 70° C. for another 5 h. At RT, the mixture was then partitioned between water and ethyl acetate, and the phases were separated. The aqueous phase was extracted with ethyl acetate. The combined organic phases were washed with sat. sodium chloride solution and dried with sodium sulphate, and the solvent was removed on a rotary evaporator. The residue was purified by flash chromatography (SiO$_2$, hexane/ethyl acetate). This gave 540 mg (54% of theory) of the desired product as a yellow oil which, after concentration from dichloromethane, was obtained as a solid foam. Also isolated were 428 mg (36% of theory) of the intermediate isopropenyl 1-(4-chlorophenyl)-4-methyl-8-(trifluoromethoxy)-4,5-dihydro-3H-2,3-benzodiazepine-3-carboxylate. (LCMS byproduct (Method 2): R$_t$=1.60 min; m/z=439 (M+H)$^+$).

Analysis of the title compound: LCMS (Method 2): R$_t$=1.53 min; m/z=412; 414 (Cl isotope pattern, M+H)$^+$ $^1$H-NMR (300 MHz, CDCl$_3$): δ=0.91 (d, 3H), 2.90 (d, 3H), 2.96 (dd, 1H), 3.14 (dd, 1H), 5.46-5.55 (m, 1H), 6.47-6.52 (m, 1H), 6.94 (s, br, 1H), 7.17-7.29 (m, 2H), 7.39 (s, 4H).

Enantiomer Separation

By chiral preparative HPLC, 488 mg of (±)-1-(4-chlorophenyl)-N,4-dimethyl-8-(trifluoromethoxy)-4,5-dihydro-3H-2,3-benzodiazepine-3-carboxamide (Example 1) were separated into the enantiomers under the following conditions:

System: Dionex: Pump P 580, Gilson: Liquid Handler 215, Knauer: UV detector K-2501; column: Chiralpak IC 5 μm 250×30 mm; mobile phase: hexane/2-propanol 80:20 (v/v); flow rate: 50 ml/min; temperature: RT; solution: 488 mg/8 ml of DCM/EtOH; injection: 16×0.5 ml; detection: UV 254 nm.

Example 1.1: (4S)-1-(4-Chlorophenyl)-N,4-dimethyl-8-(trifluoromethoxy)-4,5-dihydro-3H-2,3-benzodiazepine-3-carboxamide 224 mg, HPLC (Method A): R$_t$=3.31 min, purity>99.9%

Optical rotation: [α]$_D^{20}$=−265.9°±0.21° (c=1.00; chloroform)

Example 1.2: (4R)-1-(4-Chlorophenyl)-N,4-dimethyl-8-(trifluoromethoxy)-4,5-dihydro-3H-2,3-benzodiazepine-3-carboxamide 231 mg, HPLC (Method A): R$_t$=4.18 min, purity 99.5%

Optical rotation: [α]$_D^{20}$=+254.7°±0.16° (c=1.00; chloroform)

Example 2

(±)-1-[4-(3,5-Dimethyl-4-isoxazolyl)phenyl]-7,8-dimethoxy-N,4-dimethyl-4,5-dihydro-3H-2,3-benzodiazepine-3-carboxamide

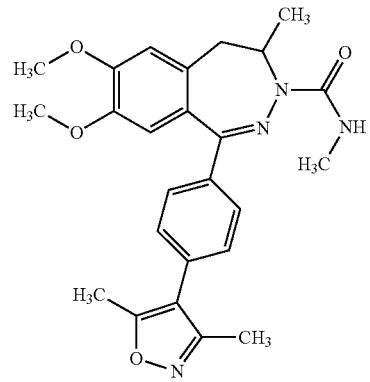 [SMILES: CNC(=O)N1N=C(c2ccc(-c3c(C)noc3C)cc2)c2cc(OC)c(OC)cc2CC1C]

1.13 g (2.61 mmol) of (±)-1-(4-bromophenyl)-7,8-dimethoxy-N,4-dimethyl-4,5-dihydro-3H-2,3-benzodiazepine-3-carboxamide (Example 49A) were dissolved in 18 ml of 1,4-dioxane, and 932 mg (6.61 mmol) of 3,5-dimethylisoxazole-4-boronic acid (CAS [16114-47-9]), 2.90 ml of 1.5 M aqueous potassium carbonate solution and 363 mg (0.44 mmol) of dichloro[1,1'-bis(diphenylphosphino)ferrocene] palladium(II) (complex with CH$_2$Cl$_2$, CAS [95464-05-4]) were added. The mixture was divided into 3 portions, and each portion was irradiated in a microwave reactor at 130° C. for in each case 15 min. The divided reactions were combined again and concentrated to dryness on a rotary evaporator. The residue was purified by flash chromatography (SiO$_2$, hexane/ethyl acetate). This gave 900 mg (73% of theory) of the desired product as a brown foam.

LCMS (Method 2): R$_t$=1.22 min; m/z=449 (M+H)$^+$ $^1$H-NMR (400 MHz, DMSO-d$_6$): δ=0.97 (d, 3H), 2.24 (s, 3H), 2.42 (s, 3H), 2.65 (d, 3H), 2.61-2.67 (m, 1H), 2.91 (dd, 1H), 3.56 (s, 3H), 3.81 (s, 3H), 4.99-5.08 (m, 1H), 6.54 (s, 1H), 6.56 (q, 1H), 7.01 (s, 1H), 7.41 (d, 2H), 7.74 (d, 2H).

Enantiomer Separation

By preparative chiral HPLC, 900 mg of (±)-1-[4-(3,5-dimethyl-4-isoxazolyl)phenyl]-7,8-dimethoxy-N,4-dimethyl-4,5-dihydro-3H-2,3-benzodiazepine-3-carboxamide (Example 2) were separated into the enantiomers under the following conditions:

System: Agilent: Prep 1200, 2× Prep Pump G1361A, DLA G2258A, MWD G1365D, Prep FC G1364B; column: Chiralpak ID 5 μm 250×20 mm; mobile phase: hexane/isopropanol 70:30 (v/v); flow rate: 40 ml/min; temperature: RT; solution: 900 mg/6 ml of MeOH/MeCl; injection: 12×0.1 ml, 13×0.2 ml; detection: UV 280 nm.

Example 2.1: (4R)-1-[4-(3,5-Dimethyl-4-isoxazolyl)phenyl]-7,8-dimethoxy-N,4-dimethyl-4,5-dihydro-3H-2,3-benzodiazepine-3-carboxamide 324 mg, colourless solid, HPLC (Method B): R$_t$=7.6 min, purity>99%

Optical rotation: [α]$_D^{20}$=−150.9°±0.08° (c=1.06; methanol)

Example 2.2: (4S)-1-[4-(3,5-Dimethyl-4-isoxazolyl)phenyl]-7,8-dimethoxy-N,4-dimethyl-4,5-dihydro-3H-2,3-benzodiazepine-3-carboxamide 321 mg, colourless solid, HPLC (Method B): R$_t$=9.0 min, purity 98.6%

Optical rotation: [α]$_D^{20}$=+148.0°±0.08° (c=1.03; methanol)

The absolute stereochemistry of Example 2.2 was determined by X-ray structural analysis of the complex from Example 2.2 and of the bromodomain 1 of BRD4.

Example 3

(±)-7,8-Dimethoxy-N,4-dimethyl-1-[4-(1H-pyrazol-3-yl)phenyl]-4,5-dihydro-3H-2,3-benzodiazepine-3-carboxamide

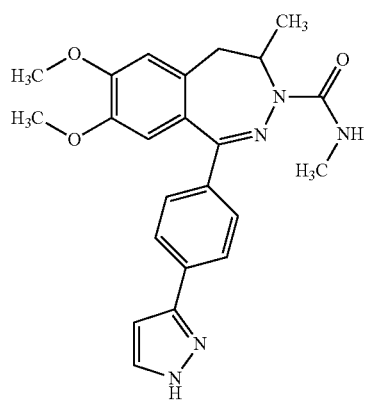 [SMILES: CNC(=O)N1N=C(c2ccc(-c3cc[nH]n3)cc2)c2cc(OC)c(OC)cc2CC1C]

Analogously to Example 2, the reaction was carried out using 100 mg (231 μmol) of (±)-1-(4-bromophenyl)-7,8-dimethoxy-N,4-dimethyl-4,5-dihydro-3H-2,3-benzodiazepine-3-carboxamide (Example 49A), 2 ml of 1,4-dioxane, 65 mg (585 μmol) of 1H-pyrazole-5-boronic acid (CAS [376584-63-3]), 0.25 ml of 1.5 M aqueous potassium carbonate solution and 32 mg (0.44 mmol) of dichloro[1,1'-bis(diphenylphosphino)ferrocene]palladium(II) (complex with $CH_2Cl_2$, CAS [95464-05-4]). This gave 55 mg (56% of theory) of the product.

LCMS (Method 2): $R_t$=1.04 min; m/z=420 $(M+H)^+$

1H-NMR (300 MHz, DMSO-$d_6$): δ=0.97 (d, 3H), 2.61-2.67 (m, 1H), 2.65 (d, 3H), 2.91 (dd, H), 3.54 (s, 3H), 3.81 (s, 3H), 4.99-5.08 (m, 1H), 6.50-6.53 (m, 2H), 7.76-7.78 (m, 1H), 7.00 (s, 1H), 7.66 (d, 2H), 7.73-7.75 (m, 1H), 7.84 (s, 2H), 12.92 (br, 1H).

The following exemplary compounds were prepared analogously to Example 2 from Example 49A and the appropriate commercially available boronic acid derivatives:

| No | Structure | Name | Analytical data |
|---|---|---|---|
| 4 | 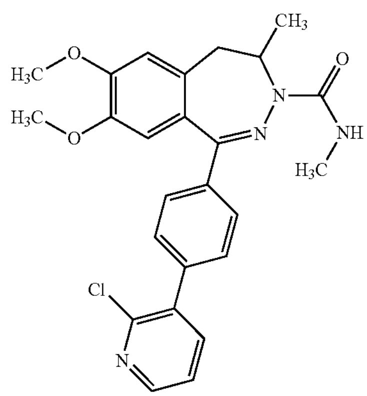 [SMILES: CNC(=O)N1N=C(c2ccc(-c3cccnc3Cl)cc2)c2cc(OC)c(OC)cc2CC1C] | (±)-1-[4-(2-chloropyridin-3-yl)phenyl]-7,8-dimethoxy-N,4-dimethyl-4,5-dihydro-3H-2,3-benzodiazepine-3-carboxamide | 1H-NMR (300 MHz, DMSO-d6): δ = 0.96 (d, 3H), 2.65 (d, 3H), 2.66-2.71 (m, 1H), 2.93 (dd, H), 3.55 (s, 3H), 3.81 (s, 3H), 5.00-5.11 (m, 1H), 6.54 (s, 1H), 6.60 (q, 1H), 7.01 (s, 1H), 7.52 (d, 2H), 7.51-7.55 (m, 1H), 7.76 (d, 2H), 7.92 (dd, 1H), 8.43 (dd, 1H).<br>LCMS (Method 2): $R_t$ = 1.24 min; m/z = 465 $(M + H)^+$ |
| 4.1 | 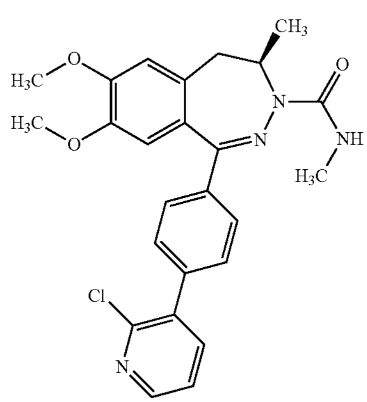 [SMILES: CNC(=O)N1N=C(c2ccc(-c3cccnc3Cl)cc2)c2cc(OC)c(OC)cc2C[C@H]1C] | (R)-1-[4-(2-chloropyridin-3-yl)phenyl]-7,8-dimethoxy-N,4-dimethyl-4,5-dihydro-3H-2,3-benzodiazepine-3-carboxamide | prep. HPLC: Method XXII<br>analyt. HPLC (Method B): $R_t$ = 7.75 min |

| No | Structure | Name | Analytical data |
|---|---|---|---|
| 4.2 | 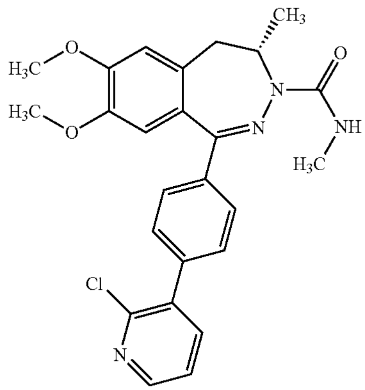 [SMILES: CNC(=O)N1N=C(c2ccc(-c3cccnc3Cl)cc2)c2cc(OC)c(OC)cc2C[C@@H]1C] | (S)-1-[4-(2-chloropyridin-3-yl)phenyl]-7,8-dimethoxy-N,4-dimethyl-4,5-dihydro-3H-2,3-benzodiazepine-3-carboxamide | prep. HPLC: Method XXII analyt. HPLC (Method B): $R_t$ = 8.89 min |
| 5 | 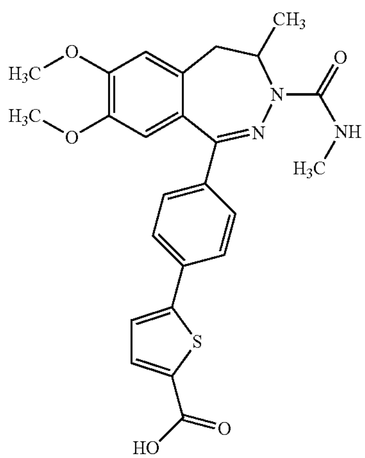 [SMILES: CNC(=O)N1N=C(c2ccc(-c3ccc(C(=O)O)s3)cc2)c2cc(OC)c(OC)cc2CC1C] | (±)-5-(4-{7,8-dimethoxy-4-methyl-3-[(methylamino)carbonyl]-4,5-dihydro-3H-2,3-benzodiazepin-1-yl}phenyl)thiophene-2-carboxylic acid | LCMS (Method 2): $R_t$ = 1.15 min; m/z = 480 (M + H)$^+$ |
| 6 | 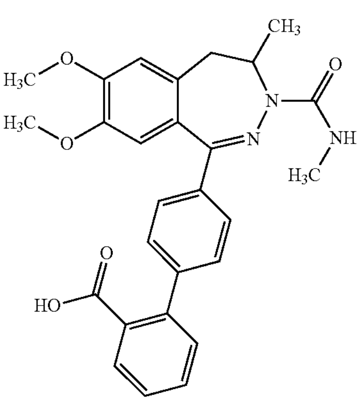 [SMILES: CNC(=O)N1N=C(c2ccc(-c3ccccc3C(=O)O)cc2)c2cc(OC)c(OC)cc2CC1C] | (±)-4'-{7,8-dimethoxy-4-methyl-3-[(methylamino)carbonyl]-4,5-dihydro-3H-2,3-benzodiazepin-1-yl}biphenyl-2-carboxylic acid | LCMS (Method 2): $R_t$ = 1.19 min; m/z = 474 (M + H)$^+$ |

Example 7

(±)-7,8-Dimethoxy-N,4-dimethyl-1-[4-(morpholin-4-yl)phenyl]-4,5-dihydro-3H-2,3-benzodiazepine-3-carboxamide

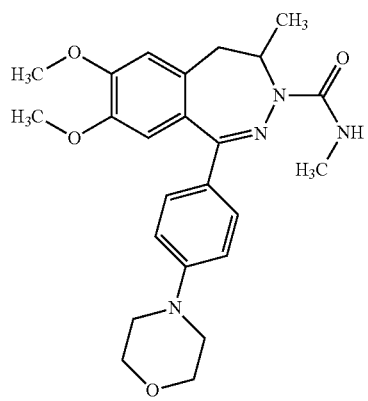 [SMILES: CNC(=O)N1N=C(c2ccc(N3CCOCC3)cc2)c2cc(OC)c(OC)cc2CC1C]

100 mg (231 mol) of (±)-1-(4-bromophenyl)-7,8-dimethoxy-N,4-dimethyl-4,5-dihydro-3H-2,3-benzodiazepine-3-carboxamide (Example 49A) were dissolved in 2 ml of toluene, and 24 mg (278 mol) of morpholine, 56 mg (578 mol) of sodium tert-butoxide, 2 mg (2 mol) of tris(dibenzylideneacetone)dipalladium(0) (CAS [51364-51-3]) and 5.5 mg (12 mol) of 2-(dicyclohexylphosphino)-2',4',6'-triisopropylbiphenyl (CAS [564483-18-7]) were added. The mixture was irradiated in a microwave reactor at 130° C. for 15 min. The catalyst was filtered off, the filtrate was evaporated to dryness on a rotary evaporator and the residue was purified by preparative HPLC. This gave 7 mg (9% of theory) of the desired product as a colourless solid.

LCMS (Method 2): $R_t$=1.09 min; m/z=439 (M+H)$^+$ $^1$H-NMR (300 MHz, DMSO-d$_6$): δ=1.02 (d, 3H), 2.39-2.44 (m, 1H), 2.60 (d, 3H), 2.81 (dd, H), 3.14-3.22 (m, 4H), 3.58 (s, 3H), 3.68-3.74 (m, 4H), 3.80 (s, 3H), 4.82-4.94 (m, 1H), 6.27 (q, 1H), 6.51 (s, 1H), 6.93 (d, 2H), 6.99 (s, 1H), 7.57 (s, 2H).

Example 8

(±)-1-(4-Chlorophenyl)-N,4-dimethyl-8-(pyridin-4-yl)-4,5-dihydro-3H-2,3-benzodiazepine-3-carboxamide

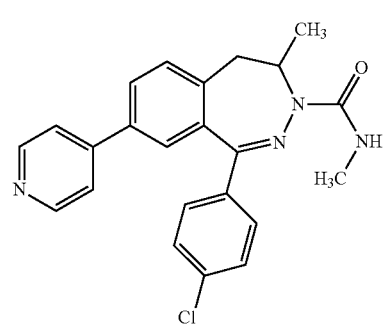 [SMILES: CNC(=O)N1N=C(c2ccc(Cl)cc2)c2cc(-c3ccncc3)ccc2CC1C]

100 mg (246 μmol) of 8-bromo-1-(4-chlorophenyl)-N,4-dimethyl-4,5-dihydro-3H-2,3-benzodiazepine-3-carboxamide (Example 52A) were dissolved in 1.3 ml of toluene and 0.2 ml of water, and 30 mg (246 μmol) of pyridine-4-boronic acid (CAS [1692-15-5]), 51 mg (369 μmol) of potassium carbonate and 18 mg (25 μmol) of dichloro[1,1'-bis(diphenylphosphino)ferrocene]palladium(II) (CAS [95464-05-4]) were added. The mixture was stirred at 70° C. for 16 h. Sat. sodium bicarbonate solution was added and the mixture was extracted with ethyl acetate. The combined organic phases were washed with water and sat. sodium chloride solution and dried with sodium sulphate. The solvents were removed on a rotary evaporator. The brown residue (88 mg) was purified by preparative HPLC. This gave 6.8 mg (7% of theory) of the desired product as a slightly yellowish solid.

UPLC/MS (Method 3): $R_t$=1.03 min; m/z=405 (M+H)$^+$ $^1$H-NMR (300 MHz, CDCl$_3$): δ=0.97 (d, 3H), 2.91 (d, 3H), 2.99 (dd, 1H), 3.19 (dd, 1H), 5.47-5.57 (m, 1H), 6.48 (q, 1H), 7.33-7.49 (m, 8H), 7.61 (dd, 1H), 8.62 (d, 2H).

The following exemplary compounds were prepared analogously to Example 8 from Example 52A and the appropriate commercially available boronic acid derivatives:

| No | Structure | Name | Analytical data |
|---|---|---|---|
| 9 | 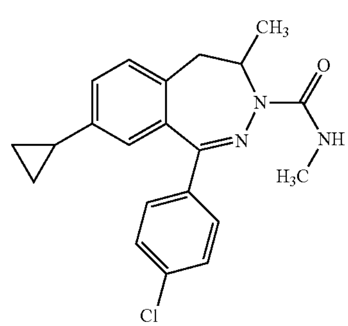 [SMILES: CNC(=O)N1N=C(c2ccc(Cl)cc2)c2cc(C3CC3)ccc2CC1C] | (±)-1-(4-chlorophenyl)-8-cyclopropyl-N,4-dimethyl-4,5-dihydro-3H-2,3-benzodiazepine-3-carboxamide | LCMS (Method 3): $R_t$ = 1.54 min; m/z = 368 (M + H)$^+$ $^1$H-NMR (300 MHz, CDCl$_3$): δ = 0.53-0.58 (m, 2H), 0.86-0.94 (m, 2H), 0.93 (d, 3H), 1.73-1.82 (m, 1H), 2.85 (dd, 1H), 2.88 (d, 3H), 3.09 (dd, 1H), 5.47-5.48 (m, 1H), 6.40-6.46 (m, br, 1H), 6.78 (d, 1H), 7.00 (dd, 1H), 7.11 (d, 1H), 7.35-7.44 (m, 4H). |

| No | Structure | Name | Analytical data |
|---|---|---|---|
| 10 | 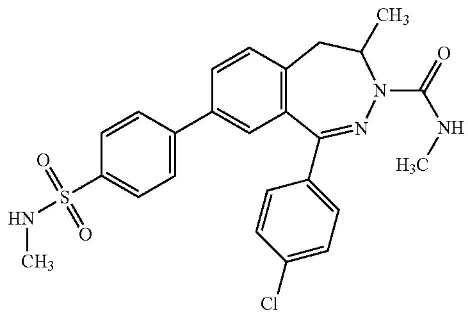 [SMILES: CNC(=O)N1N=C(c2ccc(Cl)cc2)c2cc(-c3ccc(S(=O)(=O)NC)cc3)ccc2CC1C] | (±)-1-(4-chlorophenyl)-N,4-dimethyl-8-{4-[(methylamino)sulphonyl]phenyl}-4,5-dihydro-3H-2,3-benzodiazepine-3-carboxamide | LCMS (Method 3): $R_t$ = 1.32 min; m/z = 497 (M + H)$^+$ $^1$H-NMR (300 MHz, CDCl$_3$): δ = 0.98 (d, 3H), 2.69 (d, 3H), 2.91 (d, 3H), 2.99 (dd, 1H), 3.19 (dd, 1H), 3.09 (dd, 1H), 4.26 (q, 1H), 5.47-5.56 (m, 1H), 6.48 (q, 1H), 7.30-7.48 (m, 6H), 7.55-7.61 (m, 3H), 7.88 (d, 2H). |

Example 11

(±)-1-(4-Chlorophenyl)-N,4-dimethyl-8-(morpholin-4-yl)-4,5-dihydro-3H-2,3-benzodiazepine-3-carboxamide

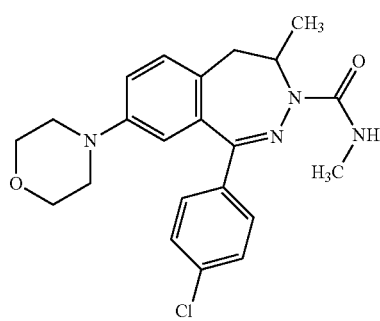 [SMILES: CNC(=O)N1N=C(c2ccc(Cl)cc2)c2cc(N3CCOCC3)ccc2CC1C]

200 mg (492 µmol) of 8-bromo-1-(4-chlorophenyl)-N,4-dimethyl-4,5-dihydro-3H-2,3-benzodiazepine-3-carboxamide (Example 52A) were dissolved in 4 ml of toluene, and 52 mg (590 µmol) of morpholine, 118 mg (1.23 mmol) of sodium tert-butoxide, 4.5 mg (5 µmol) of tris(dibenzylideneacetone)dipalladium(0) (CAS [51364-51-3]) and 15 mg (25 µmol) of (R)-(+)-2,2'-bis(diphenylphosphino)-1,1'-binaphthyl (CAS [98327-87-8]) were added. Sat. sodium bicarbonate solution was added, and the mixture was extracted with ethyl acetate. The combined organic phases were washed with water and sat. sodium chloride solution and dried with sodium sulphate. The solvents were removed on a rotary evaporator and the residue was purified by flash chromatography. This gave 44 mg (22% of theory) of the desired product as an orange foam.

LCMS (Method 2): $R_t$=1.33 min; m/z=413 (M+H)$^+$ $^1$H-NMR (300 MHz, CDCl$_3$): δ=0.93 (d, 3H), 2.82 (dd, 1H), 2.88 (d, 3H), 2.81 (dd, 1H), 2.97-3.00 (m, 4H), 3.07 (dd, 1H), 3.78-3.81 (m, 4H), 5.35-5.45 (m, 1H), 6.44 (q, br, 1H), 6.58 (d, 1H), 6.89 (dd, 1H), 7.12 (d, 1H), 7.36 (d, 2H), 7.44 (d, 2H).

Enantiomer Separation

By chiral preparative HPLC, 14 mg of (±)-1-(4-chlorophenyl)-N,4-dimethyl-8-(morpholin-4-yl)-4,5-dihydro-3H-2,3-benzodiazepine-3-carboxamide (Example 11) were separated into the enantiomers under the following conditions:

System: Dionex: Pump P 580, Gilson: Liquid Handler 215, Knauer: UV detector K-2501; column: Chiralpak IC 5 µm 250×20 mm; mobile phase: ethanol/methanol 50:50 (v/v); flow rate: 15 ml/min; temperature: RT; solution: 14 mg/1.2 ml of EtOH/MeOH; injection: 1×1.2 ml; detection: UV 254 nm.

Example 11.1: (4S)-1-(4-Chlorophenyl)-N,4-dimethyl-8-(morpholin-4-yl)-4,5-dihydro-3H-2,3-benzodiazepine-3-carboxamide 6 mg, colourless solid, HPLC (Method E): $R_t$=2.88 min, purity 99.9%

Example 11.2: (4R)-1-(4-Chlorophenyl)-N,4-dimethyl-8-(morpholin-4-yl)-4,5-dihydro-3H-2,3-benzodiazepine-3-carboxamide 6 mg, colourless solid, HPLC (Method E): $R_t$=3.22 min, purity 97.1%

Example 12

(±)-1-(4-Chlorophenyl)-N,4-dimethyl-8-(4-methylpiperazin-1-yl)-4,5-dihydro-3H-2,3-benzodiazepine-3-carboxamide

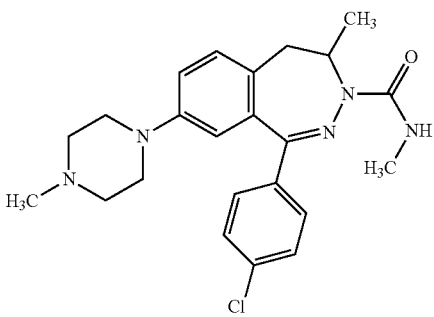 [SMILES: CNC(=O)N1N=C(c2ccc(Cl)cc2)c2cc(N3CCN(C)CC3)ccc2CC1C]

100 mg (246 µmol) of 8-bromo-1-(4-chlorophenyl)-N,4-dimethyl-4,5-dihydro-3H-2,3-benzodiazepine-3-carboxamide (Example 52A) were dissolved in 2 ml of 1,4-dioxane, and 30 mg (295 µmol) of 1-methylpiperazine (CAS [109-01-3]), 33 mg (34 µmol) of sodium tert-butoxide, 11 mg (12 µmol) of tris(dibenzylideneacetone)dipalladium(0) (CAS [51364-51-3]) and 6 mg (12 µmol) of Xphos (=2-(dicyclohexylphosphino)-2',4',6'-triisopropylbiphenyl, CAS [564483-18-7]) were added. The mixture was irratiated in a microwave reactor (150 W) at 130° C. for 15 min Sat. sodium bicarbonate solution was added, and the mixture was extracted with ethyl acetate. The combined organic phases were washed with water and sat. sodium chloride solution and dried with sodium sulphate. The solvents were removed on a rotary evaporator and the residue was purified by preparative HPLC. This gave 7 mg (7% of theory) of the desired product as a slightly yellow solid.

LCMS (Method 3): $R_t$=0.91 min; m/z=426 (M+H)$^+$

¹H-NMR (300 MHz, CDCl₃): δ=0.94 (d, 3H), 2.32 (s, 3H), 2.50-2.53 (m, 4H), 2.81 (dd, 1H), 2.88 (d, 3H), 3.00-3.09 (m, 5H), 5.33-5.45 (m, 1H), 6.38-6.46 (m, 1H), 6.60 (d, 1H), 6.90 (dd, 1H), 7.11 (d, 1H), 7.36 (d, 2H), 7.45 (d, 2H).

¹H-NMR (300 MHz, CDCl₃): δ=0.90 (d, 3H), 2.90 (d, 3H), 2.91 (dd, 1H), 3.14 (dd, 1H), 3.69 (s, 3H), 5.47-5.53 (m, 1H), 6.51-6.60 (m, 1H), 6.60 (d, 1H), 6.89 (dd, 1H), 7.15 (d, 1H), 7.29-7.33 (m, 1H), 7.71-7.75 (m, 1H), 8.62 (dd, 2H), 8.77 (d, 1H).

The following exemplary compound was prepared analogously to Example 12 from Example 52A and the appropriate commercially available amine:

| No | Structure | Name | Analytical data |
|---|---|---|---|
| 13 | 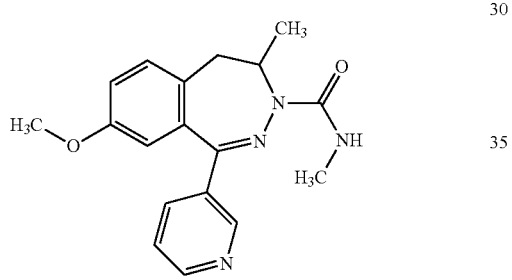 | (±)-1-(4-chlorophenyl)-N,4-dimethyl-8-(piperidin-1-yl)-4,5-dihydro-3H-2,3-benzodiazepine-3-carboxamide | LCMS (Method 2): R_t = 1.35 min; m/z = 411 (M + H)⁺<br>¹H-NMR (300 MHz, CDCl₃): δ = 0.94 (d, 3H), 1.55-1.69 (m, 5H), 2.79 (dd, 1H), 2.88 (d, 3H), 2.96-3.00 (m, 4H), 3.05 (dd, 1H), 5.33-5.43 (m, 1H), 6.38-6.45 (m, 1H), 6.60 (d, 1H), 6.92 (dd, 1H), 7.09 (d, 1H), 7.36 (d, 2H), 7.45 (d, 2H). |

Example 14

(±)-8-Methoxy-N,4-dimethyl-1-(pyridin-3-yl)-4,5-dihydro-3H-2,3-benzodiazepine-3-carboxamide The following exemplary compound was prepared analogously to Example 49A from the appropriate 4,5-dihydro-3H-2,3-benzodiazepine:

| No | Structure | Name | Analytical data |
|---|---|---|---|
| 15 | 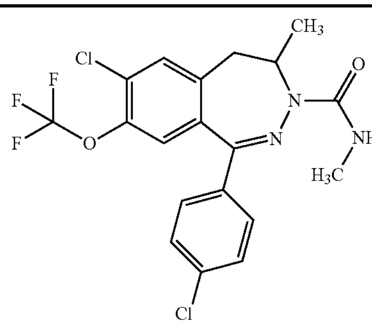 | (±)-7-chloro-1-(4-chlorophenyl)-N,4-dimethyl-8-(trifluoromethoxy)-4,5-dihydro-3H-2,3-benzodiazepine-3-carboxamide | ¹H-NMR (300 MHz, DMSO-d₆): δ = 0.86 (d, 3H), 2.65 (d, 3H), 2.87 (dd, 1H), 3.04 (dd, 1H), 5.11-5.21 (m, 1H), 6.81 (q, 1H), 7.06 (s, 1H), 7.45 (d, 2H), 7.60 (d, 2H), 7.75 (s, 1H). LCMS (Method 1): R_t = 1.57 min; m/z = 446; 448 (Cl isotope pattern, M + H)⁺ |

The compound was prepared analogously to Example 49A from 155 mg (0.48 mmol) of crude 8-methoxy-4-methyl-1-(pyridin-3-yl)-4,5-dihydro-3H-2,3-benzodiazepine (Example 37A), 230 mg (1.16 mmol) of 4-nitrophenyl chloroformate and 3.0 ml of 2M methylamine solution in 8 ml of THF. This gave 26 mg (about 13% of theory) of product as an orange foam.

UPLC/MS (Method 3): R_t=0.97 min; m/z=325 (M+H)⁺

Enantiomer Separation

Preparative HPLC According to Method IV

Example 15.1: 7-Chloro-1-(4-chlorophenyl)-N,4-dimethyl-8-(trifluoromethoxy)-4,5-dihydro-3H-2,3-benzodiazepine-3-carboxamide, enantiomer 1

HPLC (Method F): R_t=2.86 min, purity>99%

Enantiomer 2: 7-Chloro-1-(4-chlorophenyl)-N,4-dimethyl-8-(trifluoromethoxy)-4,5-dihydro-3H-2,3-benzodiazepine-3-carboxamide, enantiomer 2

HPLC (Method F): $R_t$=3.70 min, purity>99%

Example 16

(4S)-1-[4-(3,5-Dimethyl-1H-pyrazol-1-yl)phenyl]-8-methoxy-N,4-dimethyl-4,5-dihydro-3H-2,3-benzodiazepine-3-carboxamide

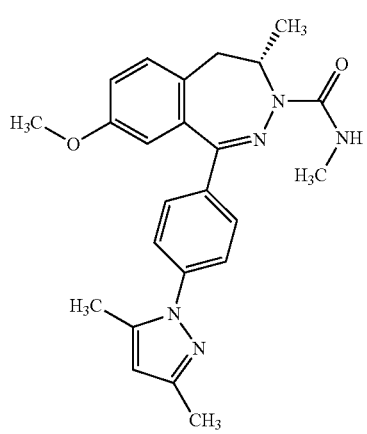 [SMILES: CNC(=O)N1N=C(c2ccc(-n3nc(C)cc3C)cc2)c2cc(OC)ccc2C[C@@H]1C]

Under argon, 100 mg (0.30 mmol) of (4S)-1-(4-aminophenyl)-8-methoxy-N,4-dimethyl-4,5-dihydro-3H-2,3-benzodiazepine-3-carboxamide (Example 53.2A) were dissolved in 5 ml of concentrated hydrochloric acid, and the solution was cooled to 0° C. Over a period of 25 min, a solution of 24.5 mg sodium nitrite in 1 ml of water was metered in, and the mixture was stirred at this temperature for 30 min. A solution of 140 mg of tin(II) chloride in 1 ml of concentrated hydrochloric acid was then slowly added dropwise over a period of 30 min. The ice bath was removed and the mixture was stirred at RT for 45 min. 60.7 µl (0.59 mmol) of 2,4-pentanedione were then added, and the mixture was stirred for 30 min Finally, 2 ml of acetonitrile were added, and the mixture was stirred at RT for 1 h. The reaction was poured into ice-water, the pH was adjusted to 10 using aqueous sodium hydroxide solution and the mixture was extracted three times with ethyl acetate. The solvent was removed on a rotary evaporator and the residue was purified by flash chromatography. This gave 79 mg (63% of theory) of the desired product.

UPLC/MS (Method 2): $R_t$=1.32 min; m/z=418 (M+H)$^+$ $^1$H-NMR (300 MHz, CDCl$_3$): δ=0.95 (d, 3H), 2.32 (s, 3H), 2.37 (s, 3H), 2.86 (dd, 1H), 2.90 (d, 3H), 3.11 (dd, 1H), 3.69 (s, 3H), 5.39-5.48 (m, 1H), 6.03 (s, 1H), 6.46-6.54 (m, 1H), 6.66 (d, 1H), 6.89 (dd, 1H), 7.14 (d, 1H), 7.48 (d, 2H), 7.57 (d, 2H).

Example 17

(4S)-8-Methoxy-N,4-dimethyl-1-[4-(morpholin-4-yl)phenyl]-4,5-dihydro-3H-2,3-benzodiazepine-3-carboxamide

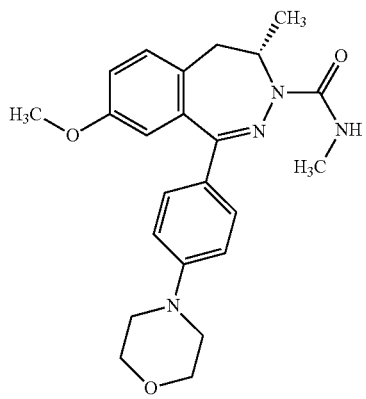 [SMILES: CNC(=O)N1N=C(c2ccc(N3CCOCC3)cc2)c2cc(OC)ccc2C[C@@H]1C]

Under argon, 100 mg (0.30 mmol) of (4S)-1-(4-aminophenyl)-8-methoxy-N,4-dimethyl-4,5-dihydro-3H-2,3-benzodiazepine-3-carboxamide (Example 53.2A) were dissolved in 4 ml of N,N-dimethylacetamide, and 103 mg (0.44 mmol) of 1-bromo-2-(2-bromoethoxy)ethane and 0.1 ml (0.59 mmol) of diisopropylethylamine were added. The mixture was stirred at 120° C. for three days. The reaction was added to water and extracted three times with ethyl acetate. The solvent was removed on a rotary evaporator and the residue was purified by flash chromatography. This gave 95 mg (79% of theory) of the desired product.

UPLC/MS (Method 2): $R_t$=1.18 min; m/z=409 (M+H)$^+$ $^1$H-NMR (300 MHz, CDCl$_3$): δ=1.07 (d, 3H), 2.72 (dd, 1H), 2.86 (d, 3H), 2.95 (dd, 1H), 3.25 (m 4H), 3.71 (s, 3H), 3.89 (m, 4H), 5.19-5.30 (m, 1H), 6.12 (m, 1H), 6.67 (d, 1H), 6.89 (dd, 1H), 6.92 (d, 2H), 7.15 (d, 1H), 7.51 (d, 2H).

Example 18

(4S)-1-[4-(4-Isoxazolyl)phenyl]-8-methoxy-N,4-dimethyl-4,5-dihydro-3H-2,3-benzodiazepine-3-carboxamide

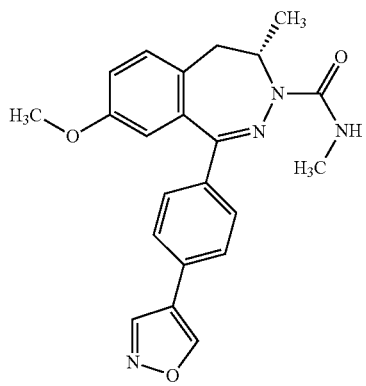 [SMILES: CNC(=O)N1N=C(c2ccc(-c3cnoc3)cc2)c2cc(OC)ccc2C[C@@H]1C]

The reaction was carried out analogously to Example 3 using 100 mg (249 µmol) of (4S)-1-(4-bromophenyl)-8- methoxy-N,4-dimethyl-4,5-dihydro-3H-2,3-benzodiazepine-3-carboxamide (Example 54A), 3.6 ml of 1,4-dioxane, 56 mg (497 μmol) of isoxazole-4-boronic acid (CAS [1008139-25-0]), 0.25 ml of 2 M aqueous potassium carbonate solution and 4 1 mg (50 μmol) of dichloro[1,1'-bis(diphenylphosphino)ferrocene]palladium(II) (complex with CH$_2$Cl$_2$, CAS [95464-05-4]). This gave 6 mg (6% of theory) of the title compound.

UPLC/MS (Method 3): R$_t$=1.17 min; m/z=391 (M+H)$^+$ $^1$H-NMR (300 MHz, CDCl$_3$): δ=0.94 (d, 3H), 2.87 (dd, 1H), 2.89 (d, 3H), 3.11 (dd, 1H), 3.69 (s, 3H), 5.43 (m, 1H), 6.51 (m, 1H), 6.65 (d, 1H), 6.89 (dd, 1H), 7.14 (d, 1H), 7.51 (d, 2H), 7.55 (d, 2H), 8.60 (s, 1H), 8.73 (s, 1H).

The following exemplary compounds were prepared analogously to Example 3 using the appropriate, commercially available boronic acids, from the compound obtained in Example 54A:

| No | Structure | Name | Analytical data |
|---|---|---|---|
| 19 | 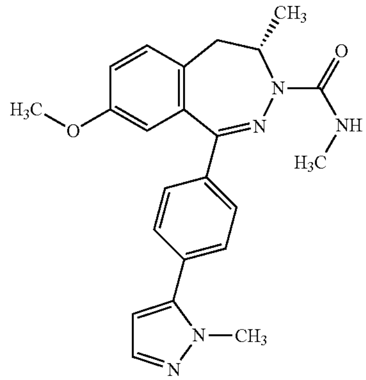 [SMILES: CNC(=O)N1N=C(c2ccc(-c3ccnn3C)cc2)c2cc(OC)ccc2C[C@@H]1C] | (4S)-8-methoxy-N,4-dimethyl-1-[4-(1-methyl-1H-pyrazol-5-yl)phenyl]-4,5-dihydro-3H-2,3-benzodiazepine-3-carboxamide | $^1$H-NMR (300 MHz, CDCl$_3$): δ = 0.95 (d, 3H), 2.87 (dd, 1H), 2.90 (d, 3H), 3.11 (dd, 1H), 3.71 (s, 3H), 3.95 (s, 3H), 5.44 (m, 1H), 6.36 (d, 1H), 6.52 (m, 1H), 6.68 (d, 1H), 6.90 (dd, 1H), 7.15 (d, 1H), 7.45 (d, 2H), 7.54 (d, 1H), 7.58 (d, 2H). UPLC/MS (Method 3): R$_t$ = 1.16 min; m/z = 404 (M + H)$^+$ |
| 20 | 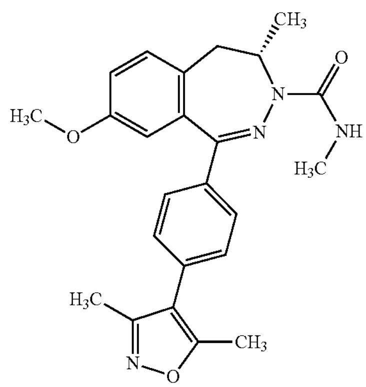 [SMILES: CNC(=O)N1N=C(c2ccc(-c3c(C)noc3C)cc2)c2cc(OC)ccc2C[C@@H]1C] | (4S)-1-[4-(3,5-dimethyl-4-isoxazolyl)phenyl]-8-methoxy-N,4-dimethyl-4,5-dihydro-3H-2,3-benzodiazepine-3-carboxamide | $^1$H-NMR (300 MHz, CDCl$_3$): δ = 0.97 (d, 3H), 2.33 (s, 3H), 2.46 (s, 3H), 2.86 (dd, 1H), 2.90 (d, 3H), 3.11 (dd, 1H), 3.72 (s, 3H), 5.42 (m, 1H), 6.48 (m, 1H), 6.70 (d, 1H), 6.90 (dd, 1H), 7.16 (d, 1H), 7.28 (d, 2H), 7.57 (d, 2H). UPLC/MS (Method 3): R$_t$ = 1.25 min; m/z = 419 (M + H)$^+$ |
| 21 | 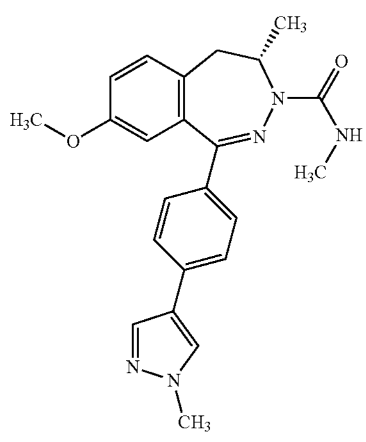 [SMILES: CNC(=O)N1N=C(c2ccc(-c3cnn(C)c3)cc2)c2cc(OC)ccc2C[C@@H]1C] | (4S)-8-methoxy-N,4-dimethyl-1-[4-(1-methyl-1H-pyrazol-4-yl)phenyl]-4,5-dihydro-3H-2,3-benzodiazepine-3-carboxamide | $^1$H-NMR (300 MHz, CDCl$_3$): δ = 0.99 (d, 3H), 2.82 (dd, 1H), 2.89 (d, 3H), 3.06 (dd, 1H), 3.69 (s, 3H), 3.97 (s, 3H), 5.38 (m, 1H), 6.42 (m, 1H), 6.68 (d, 1H), 6.89 (dd, 1H), 7.14 (d, 1H), 7.48 (d, 2H), 7.51 (d, 2H), 7.66 (s, 1H), 7.80 (s, 1H). UPLC/MS (Method 3): R$_t$ = 1.08 min; m/z = 404 (M + H)$^+$ |

-continued

| No | Structure | Name | Analytical data |
|---|---|---|---|
| 22 | 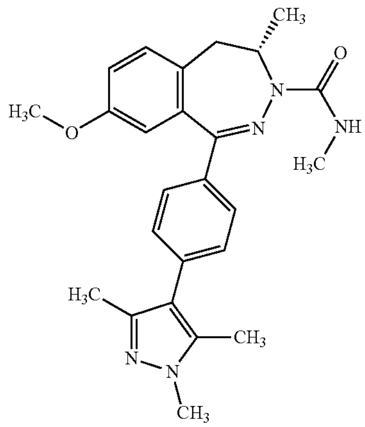 [SMILES: CNC(=O)N1N=C(c2ccc(-c3c(C)nn(C)c3C)cc2)c2cc(OC)ccc2C[C@@H]1C] | (4S)-8-methoxy-N,4-dimethyl-1-[4-(1,3,5-trimethyl-1H-pyrazol-4-yl)phenyl]-4,5-dihydro-3H-2,3-benzodiazepine-3-carboxamide | $^1$H-NMR (300 MHz, CDCl$_3$): δ = 1.00 (d, 3H), 2.29 (s, 6H), 2.82 (dd, 1H), 2.90 (d, 3H), 3.07 (dd, 1H), 3.72 (s, 3H), 3.80 (s, 3H), 5.38 (m, 1H), 6.41 (m, 1H), 6.73 (d, 1H), 6.90 (dd, 1H), 7.16 (d, 1H), 7.27 (d, 2H), 7.56 (d, 2H). UPLC/MS (Method 3): R$_t$ = 1.16 min; m/z = 432 (M + H)$^+$ |
| 23 | 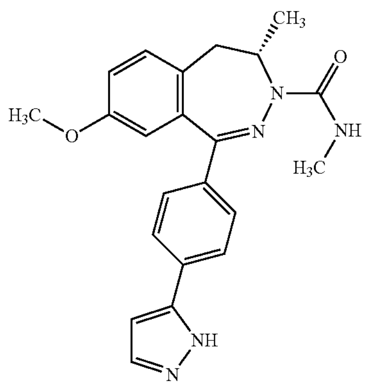 [SMILES: CNC(=O)N1N=C(c2ccc(-c3ccn[nH]3)cc2)c2cc(OC)ccc2C[C@@H]1C] | (4S)-8-methoxy-N,4-dimethyl-1-[4-(1H-pyrazol-5-yl)phenyl]-4,5-dihydro-3H-2,3-benzodiazepine-3-carboxamide | $^1$H-NMR (300 MHz, CDCl$_3$): δ = 0.97 (d, 3H), 2.85 (dd, 1H), 2.90 (d, 3H), 3.09 (dd, 1H), 3.68 (s, 3H), 5.41 (m, 1H), 6.49 (m, 1H), 6.68 (d, 1H), 6.68 (sbr, 1H), 6.89 (dd, 1H), 7.14 (d, 1H), 7.57 (d, 2H), 7.81 (d, 2H), 7.66 (sbr, 1H). UPLC/MS (Method 3): R$_t$ = 1.04 min; m/z = 390 (M + H)$^+$ |

The following exemplary compound was prepared analogously to Example 16 starting with the aniline derivative 53.2A by reaction with the appropriate, commercially available diketones. The use of asymmetrical diketones results in each case in the formation of regioisomers which can be separated by preparative HPLC.

| No | Structure | Name | Analytical data |
|---|---|---|---|
| 24 | 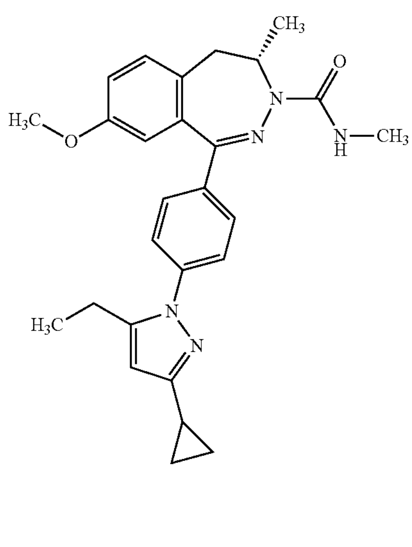 | (4S)-8-methoxy-N,4-dimethyl-1-[4-(1-methyl-1H-pyrazol-5-yl)phenyl]-4,5-dihydro-3H-2,3-benzodiazepine-3-carboxamide | UPLC/MS (Method 2): R$_t$ = 1.46 min; m/z = 458 (M + H)$^+$. $^1$H-NMR (500 MHz, CDCl$_3$): δ = 0.79-0.84 (m, 2H), 0.95 (d, 3H), 0.97-1.01 (m, 2H), 1.24 (t, 3H), 2.02-2.07 (m, 1H), 2.69 (q, 2H), 2.83-2.93 (m, 4H), 3.11 (dd, 1H), 3.69 (s, 3H), 5.39-5.47 (m, 1H), 5.92 (s, 1H), 6.50 (m, 1H), 6.66 (d, 1H), 6.89 (dd, 1H), 7.14 (d, 1H), 7.46 (d, 2H), 7.58 (d, 2H). |

| No | Structure | Name | Analytical data |
|---|---|---|---|
| 25 | 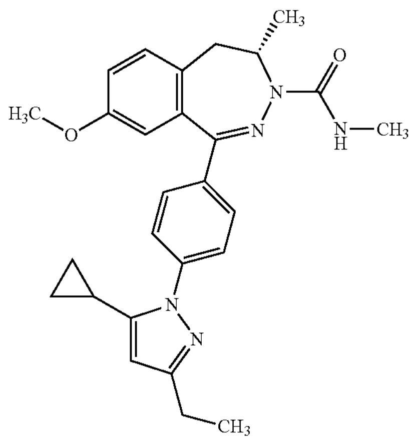 | (4S)-1-[4-(5-cyclopropyl-3-ethyl-1H-pyrazol-1-yl)phenyl]-8-methoxy-N,4-dimethyl-4,5-dihydro-3H-2,3-benzodiazepine-3-carboxamide | UPLC/MS (Method 2): $R_t$ = 1.47 min; m/z = 458 (M + H)$^+$.<br>$^1$H-NMR (300 MHz, CDCl$_3$): δ = 0.79-0.84 (m, 2H), 0.95 (d, 3H), 1.0-1.06 (m, 2H), 1.28 (t, 3H), 1.8-1.9 (m, 1H), 2.71 (q, 2H), 2.84-2.95 (m, 4H), 3.07-3.14 (m, 1H), 3.69 (s, 3H), 5.37-5.47 (m, 1H), 5.84 (s, 1H), 6.45-6.54 (m, 1H), 6.66 (d, 1H), 6.89 (dd, 1H), 7.14 (d, 1H), 7.59 (d, 2H), 7.67 (d, 2H). |
| 26 | 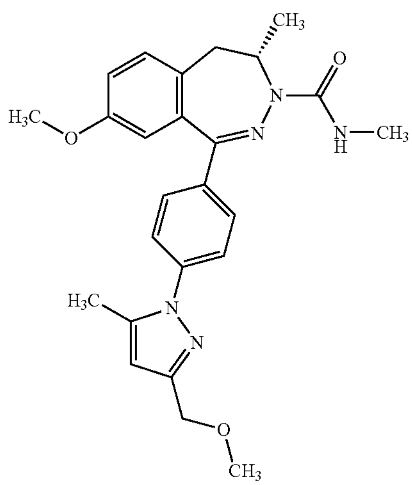 | (4S)-8-methoxy-1-{4-[3-(methoxymethyl)-5-methyl-1H-pyrazol-1-yl]phenyl}-N,4-dimethyl-4,5-dihydro-3H-2,3-benzodiazepine-3-carboxamide | UPLC/MS (Method 2): $R_t$ = 1.25 min; m/z = 448 (M + H)$^+$.<br>$^1$H-NMR (500 MHz, CDCl$_3$): δ = 0.94 (d, 3H), 2.40 (s, 3H), 2.84-2.93 (m, 4H), 3.12 (dd, 1H), 3.45 (s, 3H), 3.69 (s, 3H), 4.52 (s, 2H), 5.44 (m, 1H), 6.28 (s, 1H), 6.51 (m, 1H), 6.66 (d, 1H), 6.89 (dd, 1H), 7.14 (d, 1H), 7.48 (d, 2H), 7.59 (d, 2H). |
| 27 | 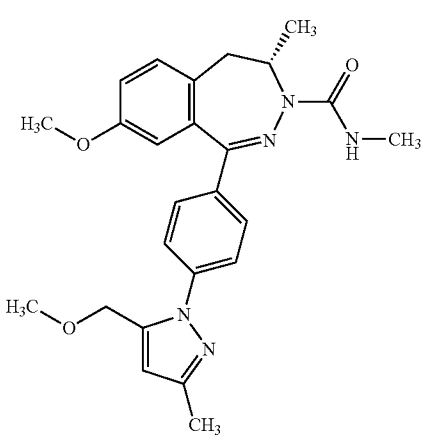 | (4S)-8-methoxy-1-{4-[5-(methoxymethyl)-3-methyl-1H-pyrazol-1-yl]phenyl}-N,4-dimethyl-4,5-dihydro-3H-2,3-benzodiazepine-3-carboxamide | UPLC/MS (Method 2): $R_t$ = 1.28 min; m/z = 448 (M + H)$^+$.<br>$^1$H-NMR (300 MHz, CDCl$_3$): δ = 0.95 (d, 3H), 2.36 (s, 3H), 2.82-2.93 (m, 4H), 3.10 (dd, 1H), 3.41 (s, 3H), 3.68 (s, 3H), 4.42 (dd, 2H), 5.37-5.48 (m, 1H), 6.29 (s, 1H), 6.49 (m, 1H), 6.67 (d, 1H), 6.89 (dd, 1H), 7.14 (d, 1H), 7.58 (d, 2H), 7.64 (d, 2H). |

| No | Structure | Name | Analytical data |
|---|---|---|---|
| 28 | 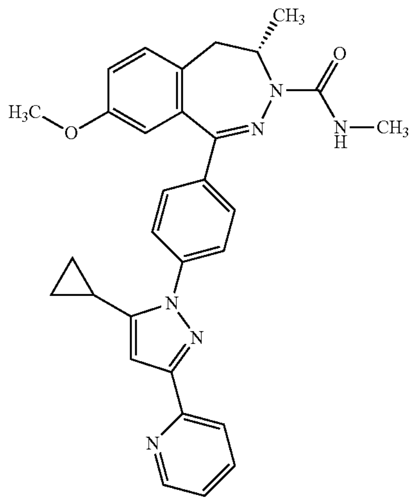 | (4S)-1-{4-[5-cyclopropyl-3-(pyridin-2-yl)-1H-pyrazol-1-yl]phenyl}-8-methoxy-N,4-dimethyl-4,5-dihydro-3H-2,3-benzodiazepine-3-carboxamide | UPLC/MS (Method 2): $R_t$ = 1.24 min; m/z = 507 (M + H)$^+$. $^1$H-NMR (500 MHz, CDCl$_3$): δ = 0.88-0.92 (m, 2H), 0.96 (d, 3H), 1.08-1.13 (m, 2H), 1.90-1.96 (m, 1H), 2.85-2.94 (m, 4H), 3.13 (dd, 1H), 3.71 (s, 3H), 5.45 (m, 1H), 6.38 (s, 1H), 6.53 (m, 1H), 6.70 (d, 1H), 6.91 (dd, 1H), 7.16 (d, 1H), 7.47 (br. s., 1H), 7.64 (d, 2H), 7.74 (d, 2H), 8.32 (d, 1H), 8.59 (br s, 1H), 9.10 (br s, 1H). |
| 29 | 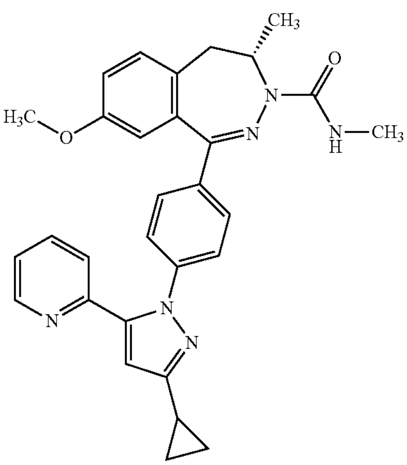 [SMILES: CNC(=O)N1N=C(c2ccc(-n3nc(C4CC4)cc3-c3ccccn3)cc2)c2cc(OC)ccc2C[C@@H]1C] | (4S)-1-{4-[3-cyclopropyl-5-(pyridin-2-yl)-1H-pyrazol-1-yl]phenyl}-8-methoxy-N,4-dimethyl-4,5-dihydro-3H-2,3-benzodiazepine-3-carboxamide | UPLC/MS (Method 2): $R_t$ = 1.32 min; m/z = 507 (M + H)$^+$. $^1$H-NMR (500 MHz, CDCl$_3$): δ = 0.85-0.89 (m, 2H), 0.93 (d, 3H), 1.00-1.06 (m, 2H), 2.07 (tt, 2H), 2.82-2.91 (m, 4H), 3.08 (dd, 1H), 3.68 (s, 3H), 5.38-5.45 (m, 1H), 6.30 (s, 1H), 6.45 (m, 1H), 6.59 (d, 1H), 6.87 (dd, 1H), 7.12 (d, 1H), 7.28 (d, 2H), 7.32-7.44 (m, 1H), 7.49 (d, 2H), 7.66 (d, 1H), 8.59 (br s, 1H). |

Example 30

(4S)-8-Methoxy-N,4-dimethyl-1-[4-(1H-tetrazol-1-yl)phenyl]-4,5-dihydro-3H-2,3-benzodiazepine-3-carboxamide

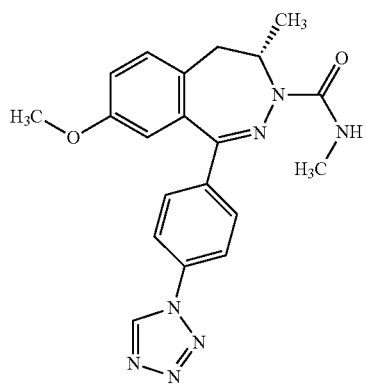 [SMILES: CNC(=O)N1N=C(c2ccc(-n3cnnn3)cc2)c2cc(OC)ccc2C[C@@H]1C]

Under argon, 100 mg (0.30 mmol) of (4S)-1-(4-aminophenyl)-8-methoxy-N,4-dimethyl-4,5-dihydro-3H-2,3-benzodiazepine-3-carboxamide (Example 53.2A) were stirred with 157 ml (0.95 mmol) of triethyl orthoformate, 271 ml (4.73 mmol) of acetic acid and 24 mg (0.37 mmol) of sodium azide at 80° C. for 3 hours. The reaction was poured into saturated aqueous sodium bicarbonate solution and extracted three times with ethyl acetate. The solvent was removed on a rotary evaporator and the residue was purified by flash chromatography. This gave 74 mg (63% of theory) of the desired product.

UPLC/MS (Method 3): $R_t$=1.04 min; m/z=392 (M+H)$^+$ $^1$H-NMR (300 MHz, CDCl$_3$): δ=0.91 (d, 3H), 2.92 (dd, 1H), 2.90 (d, 3H), 3.15 (dd, 1H), 3.70 (s, 3H), 5.50 (m, 1H), 6.55 (m, 1H), 6.61 (d, 1H), 6.90 (dd, 1H), 7.16 (d, 1H), 7.69 (d, 2H), 7.74 (d, 2H), 9.05 (s, 1H).

Example 31

(±)-1-[3-(3,5-Dimethylisoxazol-4-yl)phenyl]-7,8-dimethoxy-N,4-dimethyl-4,5-dihydro-3H-2,3-benzodiazepine-3-carboxamide

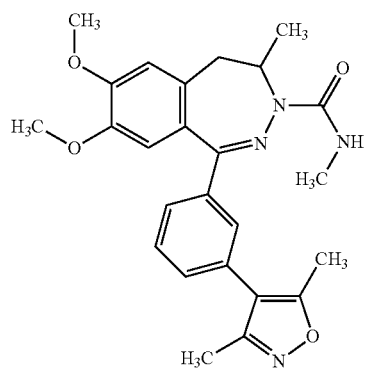 [SMILES: CNC(=O)N1N=C(c2cccc(-c3c(C)noc3C)c2)c2cc(OC)c(OC)cc2CC1C]

The reaction was carried out analogously to Example 2 using 170 mg (393 µmol) of (±)-1-(3-bromophenyl)-7,8-dimethoxy-N,4-dimethyl-4,5-dihydro-3H-2,3-benzodiazepine-3-carboxamide (Example 51A), 4 ml of 1,4-dioxane, 111 mg (768 µmol) of 3,5-dimethylisoxazole-4-boronic acid (CAS [16114-47-9]), 0.39 ml of 2 M aqueous potassium carbonate solution and 64 mg (79 µmol) of dichloro[1,1'-bis(diphenylphosphino)ferrocene]palladium(II) (complex with $CH_2Cl_2$, CAS [95464-05-4]). This gave 97 mg (54% of theory) of the title compound.

UPLC/MS (Method 3): $R_t$=1.16 min; m/z=449 (M+H)$^+$ $^1$H-NMR (300 MHz, CDCl$_3$): δ=0.98 (d, 3H), 2.27 (s, 3H), 2.41 (s, 3H), 2.86 (dd, 1H), 2.89 (d, 3H), 3.13 (dd, 1H), 3.66 (s, 3H), 3.94 (s, 3H), 5.46 (m, 1H), 6.52 (m, 1H), 6.61 (s, 1H), 6.73 (s, 1H), 7.29 (m, 1H), 7.33 (sbr, 1H), 7.47 (m, 1H), 7.51 (m, 1H).

Example 32

(±)-1-(4-Chlorophenyl)-N,4-dimethyl-8-[2-(morpholin-4-yl)ethoxy]-4,5-dihydro-3H-2,3-benzodiazepine-3-carboxamide

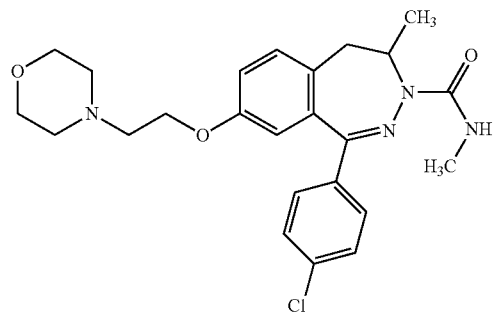 [SMILES: CNC(=O)N1N=C(c2ccc(Cl)cc2)c2cc(OCCN3CCOCC3)ccc2CC1C]

272 mg of caesium carbonate were added to a solution of 57.4 mg (167 µmol) of (±)-1-(4-chlorophenyl)-N,4-dimethyl-8-hydroxy-4,5-dihydro-3H-2,3-benzodiazepine-3-carboxamide (Example 55A) in 5 ml of N,N-dimethylformamide, and the mixture was stirred at room temperature for 1 hour. 77.7 mg (417 µmol) of 4-(2-chloroethyl)morpholine were then added. The mixture was stirred at 60° C. for 16 hours. For work-up, the reaction mixture was concentrated, water was added and the mixture was extracted three times with ethyl acetate. The organic phase was dried over sodium sulphate, filtered and concentrated. Flash chromatography afforded 26 mg (33% of theory) of the title compound.

UPLC/MS (Method 3): $R_t$=0.88 min; m/z=457; 459 (M+H, Cl isotope pattern)$^+$ $^1$H-NMR (300 MHz, CDCl$_3$): δ=0.92 (d, 3H), 2.53 (m, 4H), 2.73 (m, 2H), 2.85 (dd, 1H), 2.88 (d, 3H), 3.08 (dd, 1H), 3.72 (m, 4H), 3.97 (m, 2H), 5.42 (m, 1H), 6.60 (d, 1H), 6.88 (dd, 1H), 7.12 (d, 1H), 7.36 (d, 2H), 7.41 (d, 2H).

The following exemplary compound was prepared analogously to Example 32 using the appropriate, commercially available heterocyclylchloroalkane:

| No | Structure | Name | Analytical data |
|---|---|---|---|
| 33 | 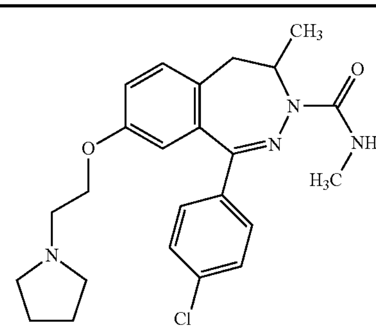 | (±)-1-(4-chlorophenyl)-N,4-dimethyl-8-[2-(pyrrolidin-1-yl)ethoxy]-4,5-dihydro-3H-2,3-benzodiazepine-3-carboxamide | $^1$H-NMR (300 MHz, CDCl$_3$): δ = 0.92 (d, 3H), 1.81 (m, 4H), 2.63 (m, 4H), 2.85 (dd, 1H), 2.87 (m, 2H), 2.88 (d, 3H), 3.08 (dd, 1H), 4.00 (m, 2H), 5.42 (m, 1H), 6.45 (m, 1H), 6.61 (d, 1H), 6.90 (dd, 1H), 7.11 (d, 1H), 7.36 (d, 2H), 7.41 (d, 2H). UPLC/MS (Method 3): $R_t$ = 0.88 min; m/z = 457; 459 (M + H, Cl isotope pattern)$^+$ |

Example 34

(±)-7,8-Dimethoxy-N,4-dimethyl-1-[4-(2-oxooxazolidin-3-yl)phenyl]-4,5-dihydro-3H-2,3-benzodiazepine-3-carboxamide

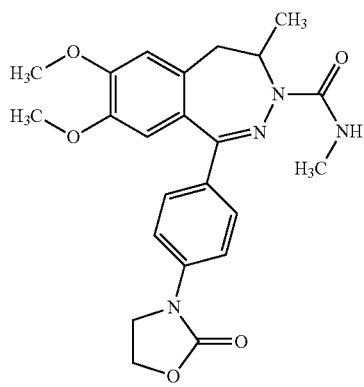 [SMILES: CNC(=O)N1N=C(c2ccc(N3CCOC3=O)cc2)c2cc(OC)c(OC)cc2CC1C]

Under argon, 100 mg (0.231 mmol) of (±)-1-(4-bromophenyl)-7,8-dimethoxy-N,4-dimethyl-4,5-dihydro-3H-2,3-benzodiazepine-3-carboxamide (Example 49A), 22 mg (0.254 mmol) of oxazolidin-2-one, 98 mg (0.46 mmol) of potassium phosphate and 88 mg (0.46 mmol) of copper(I) iodide were initially charged in 4 ml of degassed dioxane. Under argon, 82 mg (0.93 mmol) of N,N-dimethylethylenediamine were then added, and the mixture was degassed again and heated at 130° C. for 3 hours. After cooling, ethyl acetate and saturated aqueous ammonium chloride solution were added to the mixture. The aqueous phase was extracted three times with ethyl acetate, and the combined organic phases dried with sodium sulphate. The solvent was removed on a rotary evaporator and the residue was purified by preparative HPLC. This gave 50 mg (49% of theory) of the desired product as a solid.

LCMS (Method 2): $R_t$=1.0 min; m/z=439 (M+H)$^+$ $^1$H-NMR (400 MHz, CDCl$_3$): δ=1.03 (d, 3H), 2.82 (dd, 1H), 2.88 (s, br, 3H), 3.08 (dd, 1H), 3.67 (s, 3H), 3.94 (s, 3H), 4.09-4.16 (m, 2H), 4.53 (t, 2H), 5.37-5.47 (m, 1H), 6.41 (m, 1H), 6.59 (s, 1H), 6.74 (s, 1H), 7.55 (d, 2H), 7.60 (d, 2H).

Example 34.1

(4S)-7,8-Dimethoxy-N,4-dimethyl-1-[4-(2-oxooxazolidin-3-yl)phenyl]-4,5-dihydro-3H-2,3-benzodiazepine-3-carboxamide Analogously to the preparation of Example 34, 100 mg (0.231 mmol) of (4S)-1-(4-bromophenyl)-7,8-dimethoxy-N,4-dimethyl-4,5-dihydro-3H-2,3-benzodiazepine-3-carboxamide (Example 49.2A) gave, by reaction with 22 mg (0.254 mmol) of oxazolidin-2-one, after purification by preparative HPLC, 84 mg (82% of theory) of the desired product as a solid.

LCMS (Method 2): $R_t$=1.0 min; m/z=439 (M+H)$^+$ $[α]_D^{20}$=237.1° (c=1.00; methanol)

The following exemplary compounds were prepared analogously to Example 34 from Example 49A or Example 49.2A and the appropriate commercially available lactams or cyclic carbamates:

| No | Structure | Name | Analytical data |
|---|---|---|---|
| 35 | 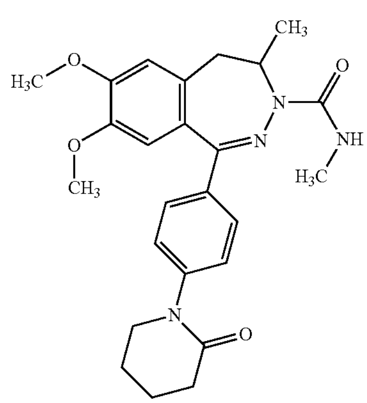 [SMILES: CNC(=O)N1N=C(c2ccc(N3CCCCC3=O)cc2)c2cc(OC)c(OC)cc2CC1C] | (±)-7,8-dimethoxy-N,4-dimethyl-1-[4-(2-oxopiperidin-1-yl)phenyl]-4,5-dihydro-3H-2,3-benzodiazepine-3-carboxamide | $^1$H-NMR (300 MHz, CDCl$_3$): δ = 1.00 (d, 3H), 1.92-2.02 (m, 2H), 2.54-2.65 (m, 2H), 2.80 (dd, 1H), 2.88 (s, br, 3H), 3.06 (d, 1H), 3.67 (s, 3H), 3.68-3.75 (m, 2H), 3.93 (s, 3H), 5.41 (q, 1H), 6.44 (m, 1H), 6.63 (s, 3H), 6.72 (s, 1H), 7.30 (d, 2H), 7.53 (d, 2H). LCMS (Method 2): $R_t$ = 1.04 min; m/z = 451 (M + H)$^+$ |

| No | Structure | Name | Analytical data |
|---|---|---|---|
| 36 | 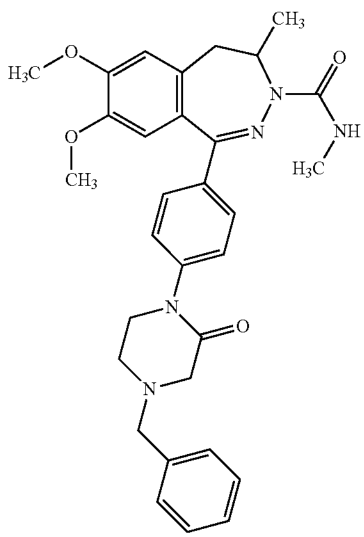 [SMILES: CNC(=O)N1N=C(c2ccc(N3CCN(Cc4ccccc4)CC3=O)cc2)c2cc(OC)c(OC)cc2CC1C] | (±)-1-[4-(4-benzyl-2-oxopiperazin-1-yl)phenyl]-7,8-dimethoxy-N,4-dimethyl-4,5-dihydro-3H-2,3-benzodiazepine-3-carboxamide | $^1$H-NMR (400 MHz, CDCl$_3$): δ = 0.99 (d, 3H), 2.78-2.87 (m, 3H), 2.89 (d, 3H), 3.08 (dd, 1H), 3.37 (s, 2H), 3.65 (s, 2H), 3.67 (s, 3H), 3.69-3.77 (m, 2H), 3.93 (s, 3H), 5.38-5.47 (m, 1H), 6.45 (m, 1H), 6.62 (s, 1H), 6.72 (s, 1H), 7.30-7.39 (m, 7H) 7.53 (d, 2H). LCMS (Method 2): R$_t$ = 1.06 min; m/z = 542 (M + H)$^+$ |
| 37 | 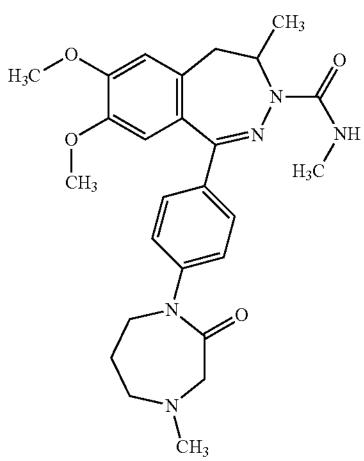 [SMILES: CNC(=O)N1N=C(c2ccc(N3CCCN(C)CC3=O)cc2)c2cc(OC)c(OC)cc2CC1C] | (±)-7,8-dimethoxy-N,4-dimethyl-1-[4-(4-methyl-2-oxo-1,4-diazepan-1-yl)phenyl]-4,5-dihydro-3H-2,3-benzodiazepine-3-carboxamide | $^1$H-NMR (300 MHz, CDCl$_3$): δ = 0.98 (d, 3H), 2.06-2.20 (m, 2H), 2.70 (s, 3H), 2.82 (dd, 1H), 2.88 (d, 3H), 3.08 (dd, 1H), 3.18 (m, 2H), 3.68 (s, 3H), 3.82 (s, br, 2H), 3.90-4.01 (m, 2H), 3.93 (s, 3H), 5.43 (m, 1H), 6.46 (q, 1H), 6.62 (s, 1H), 6.72 (s, 1H), 7.28 (d, 2H) 7.53 (d, 2H). LCMS (Method 2): R$_t$ = 0.70 min; m/z = 480 (M + H)$^+$ |
| 38 | 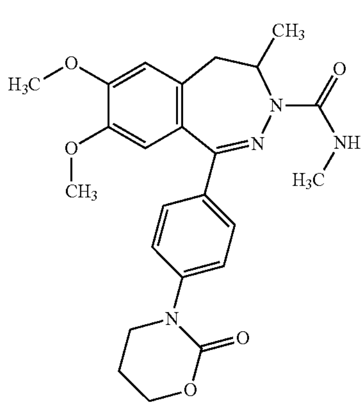 [SMILES: CNC(=O)N1N=C(c2ccc(N3CCCOC3=O)cc2)c2cc(OC)c(OC)cc2CC1C] | (±)-7,8-dimethoxy-N,4-dimethyl-1-[4-(2-oxo-1,3-oxazinan-3-yl)phenyl]-4,5-dihydro-3H-2,3-benzodiazepine-3-carboxamide | $^1$H-NMR (400 MHz, CDCl$_3$): δ = 1.00 (d, 3H), 2.20-2.30 (m, 2H), 2.82 (dd, 1H), 2.88 (d, 3H), 3.08 (dd, 1H), 3.67 (s, 3H), 3.78 (t, 2H), 3.93 (s, 3H), 4.45 (t, 2H), 5.37-5.48 (m, 1H), 6.45 (m, 1H), 6.62 (s, 1H), 6.72 (s, 1H), 7.38 (d, 2H), 7.54 (d, 2H). LCMS (Method 2): R$_t$ = 0.96 min; m/z = 453 (M + H)$^+$ |

| No | Structure | Name | Analytical data |
|---|---|---|---|
| 39 | 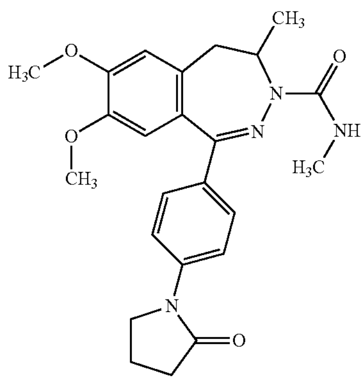 [SMILES: CNC(=O)N1N=C(c2ccc(N3CCCC3=O)cc2)c2cc(OC)c(OC)cc2CC1C] | (±)-7,8-dimethoxy-N,4-dimethyl-1-[4-(2-oxopyrrolidin-1-yl)phenyl]-4,5-dihydro-3H-2,3-benzodiazepine-3-carboxamide | $^1$H-NMR (400 MHz, CDCl$_3$): δ = 1.03 (d, 3H), 2.16-2.25 (m, 2H), 2.65 (t, 2H), 2.80 (dd, 1H), 2.88 (d, 3H), 3.07 (dd, 1H), 3.66 (s, 3H), 3.88-3.93 (m, 2H), 3.93 (s, 3H), 5.35-5.45 (m, 1H), 6.40 (s, br, 1H), 6.60 (s, 1H), 6.73 (s, 1H), 7.53 (d, 2H), 7.68 (d, 2H). LCMS (Method 2): R$_t$ = 1.04 min; m/z = 437 (M + H)$^+$ |
| 40 | 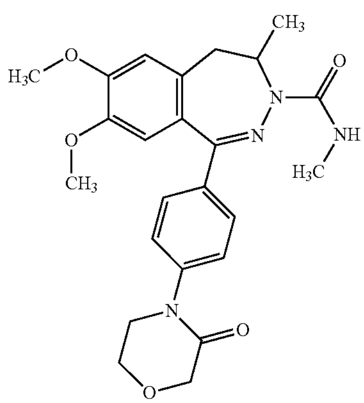 [SMILES: CNC(=O)N1N=C(c2ccc(N3CCOCC3=O)cc2)c2cc(OC)c(OC)cc2CC1C] | (±)-7,8-dimethoxy-N,4-dimethyl-1-[4-(3-oxomorpholin-4-yl)phenyl]-4,5-dihydro-3H-2,3-benzodiazepine-3-carboxamide | $^1$H-NMR (400 MHz, CDCl$_3$): δ = 1.01 (d, 3H), 2.82 (dd, 1H), 2.89 (d, 3H), 3.08 (dd, 1H), 3.68 (s, 3H), 3.80-3.86 (m, 2H), 3.94 (s, 3H), 4.07 (t, 2H), 4.37 (s, 2H), 5.39-5.49 (m, 1H), 6.46 (s, br, 1H), 6.62 (s, 1H), 6.73 (s, 1H), 7.40 (d, 2H), 7.57 (d, 2H). LCMS (Method 2): R$_t$ = 0.95 min; m/z = 453 (M + H)$^+$ |
| 40.1 | 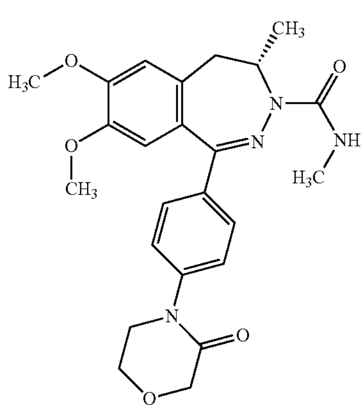 [SMILES: CNC(=O)N1N=C(c2ccc(N3CCOCC3=O)cc2)c2cc(OC)c(OC)cc2C[C@@H]1C] | (4S)-7,8-dimethoxy-N,4-dimethyl-1-[4-(3-oxomorpholin-4-yl)phenyl]-4,5-dihydro-3H-2,3-benzodiazepine-3-carboxamide | $^1$H-NMR (400 MHz, CDCl$_3$): δ = 0.99 (d, 3H), 2.83 (dd, 1H), 2.89 (s, br, 3H), 3.09 (dd, 1H), 3.67 (s, 3H), 3.80-3.86 (m, 2H), 3.94 (s, 3H), 4.06 (t, 2H), 4.37 (s, 2H), 5.39-5.49 (m, 1H), 6.47 (s, br, 1H), 6.62 (s, 1H), 6.72 (s, 1H), 7.40 (d, 2H), 7.56 (d, 2H). LCMS (Method 2): R$_t$ = 0.95 min; m/z = 453 (M + H)$^+$. [α]$_D^{20}$ = 135.4° (c = 1.00; methanol) |

| No | Structure | Name | Analytical data |
|---|---|---|---|
| 41 | 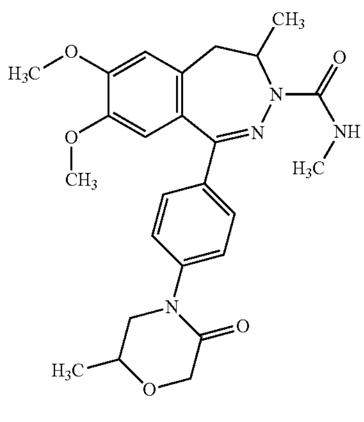 [SMILES: CNC(=O)N1N=C(c2ccc(N3CC(C)OCC3=O)cc2)c2cc(OC)c(OC)cc2CC1C] | (±)-7,8-dimethoxy-N,4-dimethyl-1-[4-(2-methyl-5-oxomorpholin-4-yl)phenyl]-4,5-dihydro-3H-2,3-benzodiazepine-3-carboxamide (stereoisomer mixture) | ¹H-NMR (400 MHz, CDCl₃): δ = 1.01 (d, 3H), 1.36 (d, 3H), 2.82 (dd, 1H), 2.89 (s, br, 3H), 3.09 (d, 1H), 3.54-3.62 (s, 1H), 3.68 (s, 3H), 3.69-3.77 (m, 1H), 3.94 (s, 3H), 4.05-4.16 (m, 1H), 4.35 (d, 1H), 4.43 (d, 1H), 5.44 (m, 1H), 6.45 (s, br, 1H), 6.62 (s, 1H), 6.73 (s, 1H), 7.39 (d, 2H), 7.56 (d, 2H).<br>LCMS (Method 2): R$_t$ = 1.03 min; m/z = 467 (M + H)⁺ |
| 42 | 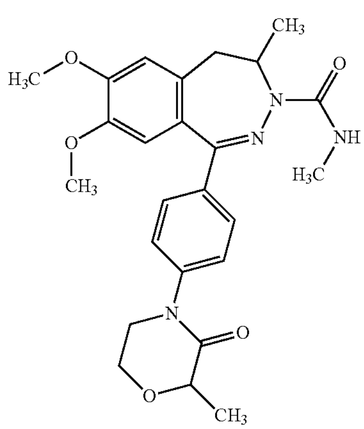 [SMILES: CNC(=O)N1N=C(c2ccc(N3CCOC(C)C3=O)cc2)c2cc(OC)c(OC)cc2CC1C] | (±)-7,8-dimethoxy-N,4-dimethyl-1-[4-(2-methyl-3-oxomorpholin-4-yl)phenyl]-4,5-dihydro-3H-2,3-benzodiazepine-3-carboxamide (stereoisomer mixture) | ¹H-NMR (400 MHz, CDCl₃): δ = 1.01 (d, 3H), 1.57 (dd, 3H), 2.82 (dd, 1H), 2.88 (s, br, 3H), 3.09 (d, 1H), 3.61-3.66 (m, 1H), 3.67/3.68 (s, 3H), 3.94 (s, 3H), 3.98-4.08 (m, 2H), 4.11-4.18 (m, 1H), 4.38-4.46 (m, 1H), 5.39-5.49 (m, 1H), 6.45 (s, br, 1H), 6.63 (s, 1H), 6.73 (s, 1H), 7.38 (d, 2H), 7.56 (d, 2H).<br>LCMS (Method 2): R$_t$ = 1.02 min; m/z = 467 (M + H)⁺ |
| 43 | 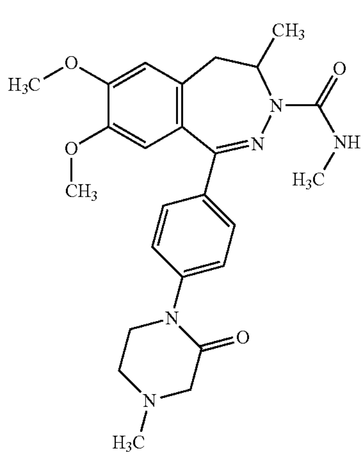 [SMILES: CNC(=O)N1N=C(c2ccc(N3CCN(C)CC3=O)cc2)c2cc(OC)c(OC)cc2CC1C] | (±)-7,8-dimethoxy-N,4-dimethyl-1-[4-(4-methyl-2-oxopiperazin-1-yl)phenyl]-4,5-dihydro-3H-2,3-benzodiazepine-3-carboxamide | ¹H-NMR (500 MHz, CDCl₃): δ = 0.97 (d, 3H), 2.84 (dd, 1H), 2.89 (s, 3H), 2.99 (s, 3H), 3.11 (dd, 1H), 3.37 (br. s., 1H), 3.64 (br. s., 1H), 3.67 (s, 3H), 3.77 (br. s., 2H), 3.94 (s, 3H), 4.27 (br. s., 1H), 4.83 (br. s., 1H), 5.46 (td, 1H), 6.49 (br. s., 1H), 6.59 (s, 1H), 6.72 (s, 1H), 7.38 (d, 2H), 7.56 (d, 2H).<br>LCMS (Method 2): R$_t$ = 0.70 min; m/z = 466 (M + H)⁺. |

| No | Structure | Name | Analytical data |
|---|---|---|---|
| 43.1 | 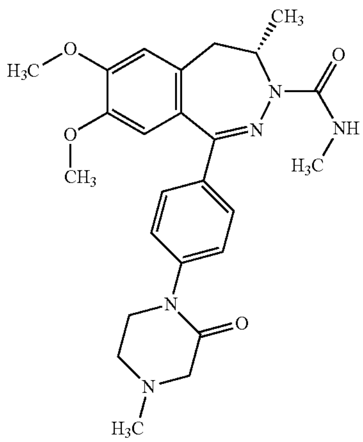 [SMILES: CNC(=O)N1N=C(c2ccc(N3CCN(C)CC3=O)cc2)c2cc(OC)c(OC)cc2C[C@@H]1C] | (4S)-7,8-dimethoxy-N,4-dimethyl-1-[4-(4-methyl-2-oxopiperazin-1-yl)phenyl]-4,5-dihydro-3H-2,3-benzodiazepine-3-carboxamide | prep. HPLC: Method XIV analyt. HPLC (Method S): $R_t$ = 8.73 min LCMS (Method 2): $R_t$ = 0.70 min; m/z = 466 (M + H)$^+$. $[\alpha]_D^{20}$ = 107.0° (c = 1.00; methanol) |
| 43.2 | 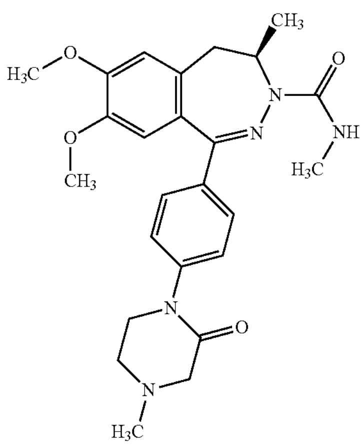 [SMILES: CNC(=O)N1N=C(c2ccc(N3CCN(C)CC3=O)cc2)c2cc(OC)c(OC)cc2C[C@H]1C] | (4R)-7,8-dimethoxy-N,4-dimethyl-1-[4-(4-methyl-2-oxopiperazin-1-yl)phenyl]-4,5-dihydro-3H-2,3-benzodiazepine-3-carboxamide | prep. HPLC: Method XIV analyt. HPLC (Method S): $R_t$ = 5.90 min LCMS (Method 2): $R_t$ = 0.70 min; m/z = 466 (M + H)$^+$. $[\alpha]_D^{20}$ = −119.4° (c = 1.00; methanol) |

Example 44

(±)-7,8-Dimethoxy-N,4-dimethyl-1-[4-(2-oxopiperazin-1-yl)phenyl]-4,5-dihydro-3H-2,3-benzodiazepine-3-carboxamide

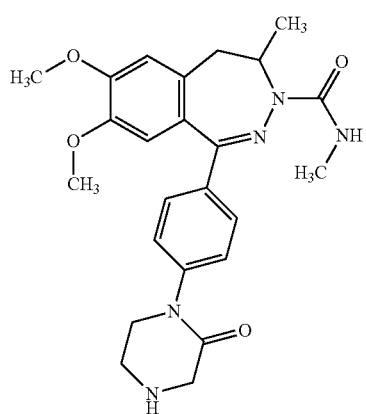 [SMILES: CNC(=O)N1N=C(c2ccc(N3CCNCC3=O)cc2)c2cc(OC)c(OC)cc2CC1C]

Under argon, 87 mg (0.161 mmol) of (±)-1-[4-(4-benzyl-2-oxopiperazin-1-yl)phenyl]-7,8-dimethoxy-N,4-dimethyl-4,5-dihydro-3H-2,3-benzodiazepine-3-carboxamide (Example 36) were initially charged in 1 ml of ethanol, and 17 mg of palladium on carbon (10%) were added. The mixture was hydrogenated with hydrogen in a fitted balloon for 16 h. As the conversion was still incomplete, another spatula tip of catalyst was added and the mixture was hydrogenated with hydrogen for a further 16 h. The crude mixture was freed from the catalyst using a PTFE filter, the catalyst washed with ethyl acetate and the solvent was then removed on a rotary evaporator. The residue was purified by preparative HPLC. This gave 20 mg (20% of theory) of the desired product as a solid.

LCMS (Method 2): $R_t$=0.67 min; m/z=452 (M+H)$^+$ $^1$H-NMR (300 MHz, CDCl$_3$): δ=0.98 (d, 3H), 2.78-2.87 (m, 1H), 2.88 (d, 3H), 3.09 (dd, 1H), 3.49 (m, 2H), 3.67 (s, 3H), 3.74-3.79 (m, 1H), 3.86-3.91 (m, 1H), 3.93 (s, 3H), 3.95-4.01 (m, 2H), 4.22 (s, br 1H), 5.39-5.49 (m, 1H), 6.44-6.51 (m, 1H), 6.60 (s, 1H), 6.72 (s, 1H), 7.35 (d, 2H), 7.55 (d, 2H).

The following exemplary compounds were prepared analogously to Example 2 from Example 49A or Example 49.2A and the appropriate commercially available boronic acid derivatives:

| No. | Structure | Name | Analytical data |
|---|---|---|---|
| 45 | 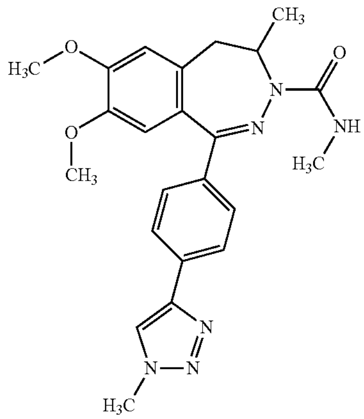 [SMILES: CNC(=O)N1N=C(c2ccc(-c3cn(C)nn3)cc2)c2cc(OC)c(OC)cc2CC1C] | (±)-7,8-dimethoxy-N,4-dimethyl-1-[4-(1-methyl-1H-1,2,3-triazol-4-yl)phenyl]-4,5-dihydro-3H-2,3-benzodiazepine-3-carboxamide | $^1$H-NMR (400 MHz, CDCl$_3$): δ = 1.01 (d, 3H), 2.84 (dd, 1H), 2.90 (d, 3H), 3.12 (dd, 1H), 3.66 (s, 3H), 3.94 (s, 3H), 4.18 (s, 3H), 5.40-5.50 (m, 1H), 6.46-6.53 (m, 1H), 6.63 (s, 1H), 6.73 (s, 1H), 7.57 (d, 2H), 7.80 (s, 1H), 7.86 (d, 2H).<br>LCMS (Method 2): R$_t$ = 1.01 min; m/z = 435 (M + H)$^+$ |
| 45.1 | 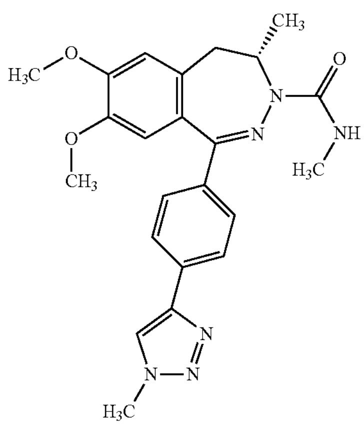 [SMILES: CNC(=O)N1N=C(c2ccc(-c3cn(C)nn3)cc2)c2cc(OC)c(OC)cc2C[C@@H]1C] | (4S)-7,8-dimethoxy-N,4-dimethyl-1-[4-(1-methyl-1H-1,2,3-triazol-4-yl)phenyl]-4,5-dihydro-3H-2,3-benzodiazepine-3-carboxamide | LCMS (Method 2): R$_t$ = 1.00 min; m/z = 435 (M + H)$^+$<br>[α]$_D^{20}$ = −71.3° (c = 1.00; chloroform) |
| 46 | 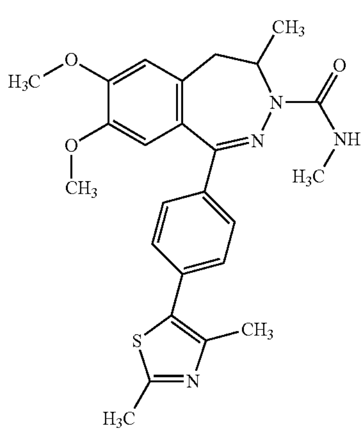 [SMILES: CNC(=O)N1N=C(c2ccc(-c3sc(C)nc3C)cc2)c2cc(OC)c(OC)cc2CC1C] | (±)-1-[4-(2,4-dimethylthiazol-5-yl)phenyl]-7,8-dimethoxy-N,4-dimethyl-4,5-dihydro-3H-2,3-benzodiazepine-3-carboxamide | $^1$H-NMR (300 MHz, CDCl$_3$): δ = 1.01 (d, 3H), 2.51 (s, 3H), 2.71 (s, 3H), 2.84 (dd, 1H), 2.90 (d, 3H), 3.12 (dd, 1H), 3.68 (s, 3H), 3.94 (s, 3H), 5.44 (m, 1H), 6.48 (q, 1H), 6.63 (s, 1H), 6.73 (s, 1H), 7.44 (d, 2H), 7.55 (d, 2H).<br>LCMS (Method 2): R$_t$ = 1.24 min; m/z = 465 (M + H)$^+$ |

| No. | Structure | Name | Analytical data |
|---|---|---|---|
| 46.1 | 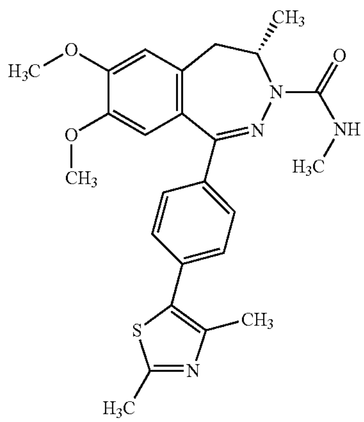 [SMILES: CNC(=O)N1N=C(c2ccc(-c3sc(C)nc3C)cc2)c2cc(OC)c(OC)cc2C[C@@H]1C] | (4S)-1-[4-(2,4-dimethylthiazol-5-yl)phenyl]-7,8-dimethoxy-N,4-dimethyl-4,5-dihydro-3H-2,3-benzodiazepine-3-carboxamide enantiomer 1 of Ex. 46 separation HPLC Method VIII | HPLC (Method L): $R_t$ = 5.9 min |
| 46.2 | 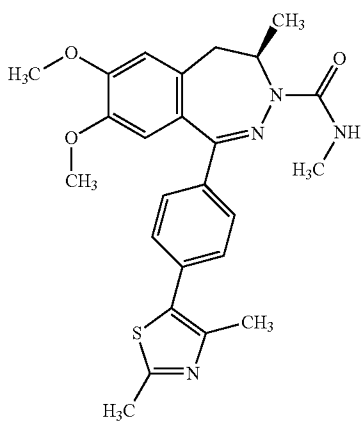 [SMILES: CNC(=O)N1N=C(c2ccc(-c3sc(C)nc3C)cc2)c2cc(OC)c(OC)cc2C[C@H]1C] | (4R)-1-[4-(2,4-dimethylthiazol-5-yl)phenyl]-7,8-dimethoxy-N,4-dimethyl-4,5-dihydro-3H-2,3-benzodiazepine-3-carboxamide enantiomer 2 of Ex. 46 separation HPLC Method VIII | HPLC (Method L): $R_t$ = 8.9 min<br>$[\alpha]_D^{20}$ = −127.2° (c = 1.00; methanol) |
| 47 | 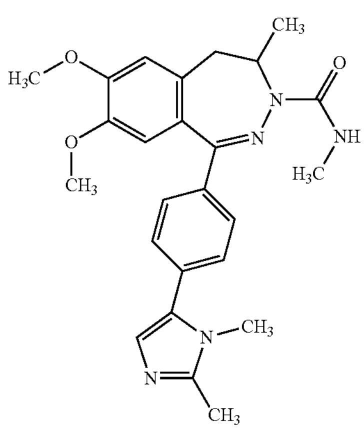 [SMILES: CNC(=O)N1N=C(c2ccc(-c3cnc(C)n3C)cc2)c2cc(OC)c(OC)cc2CC1C] | (±)-1-[4-(1,2-dimethyl-1H-imidazol-5-yl)phenyl]-7,8-dimethoxy-N-dimethyl-4,5-dihydro-3H-2,3-benzodiazepine-3-carboxamide | $^1$H-NMR (300 MHz, CDCl$_3$): δ = 1.01 (d, 3H), 2.46 (s, 3H), 2.83 (dd, 1H), 2.89 (d, 3H), 3.10 (dd, 1H), 3.58 (s, 3H), 3.68 (s, 3H), 3.94 (s, 3H), 5.43 (m, 1H), 6.47 (q, 1H), 6.63 (s, 1H), 6.73 (s, 1H), 7.03 (s, 1H), 7.39 (d, 2H), 7.57 (d, 2H).<br>LCMS (Method 2): $R_t$ = 0.75 min; m/z = 448 (M + H)$^+$ |

| No. | Structure | Name | Analytical data |
|---|---|---|---|
| 48 | 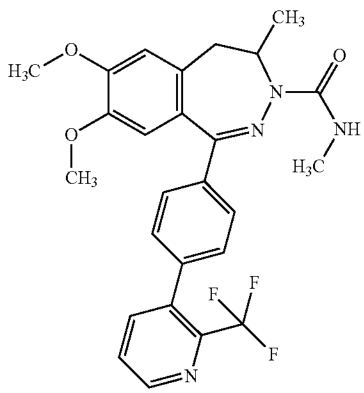 [SMILES: CNC(=O)N1N=C(c2ccc(-c3cccnc3C(F)(F)F)cc2)c2cc(OC)c(OC)cc2CC1C] | (±)-7,8-dimethoxy-N,4-dimethyl-1-{4-[2-(trifluoromethyl)pyridin-3-yl]phenyl}-4,5-dihydro-3H-2,3-benzodiazepine-3-carboxamide | $^1$H-NMR (300 MHz, CDCl$_3$): δ = 1.01 (d, 3H), 2.87 (dd, 1H), 2.92 (d, 3H), 3.17 (dd, 1H), 3.67 (s, 3H), 3.94 (s, 3H), 5.50 (m, 1H), 6.56 (q, 1H), 6.59 (s, 1H), 6.73 (s, 1H), 7.37 (d, 2H), 7.54-7.61 (m, 3H), 7.79 (dd, 1H), 8.76 (dd, 1H).<br>LCMS (Method 2): R$_t$ = 1.28 min; m/z = 499 (M + H)$^+$ |
| 49 | 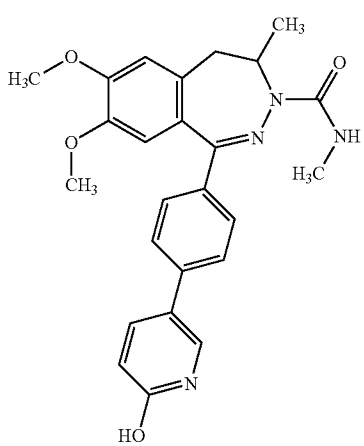 [SMILES: CNC(=O)N1N=C(c2ccc(-c3ccc(O)nc3)cc2)c2cc(OC)c(OC)cc2CC1C] | (±)-1-[4-(6-hydroxypyridin-3-yl)phenyl]-7,8-dimethoxy-N,4-dimethyl-4,5-dihydro-3H-2,3-benzodiazepine-3-carboxamide | $^1$H-NMR (300 MHz, CDCl$_3$): δ = 1.01 (d, 3H), 2.84 (dd, 1H), 2.91 (d, 3H), 3.12 (dd, 1H), 3.68 (s, 3H), 3.95 (s, 3H), 5.45 (m, 1H), 6.48 (q, 1H), 6.62 (s, 1H), 6.69-6.80 (s, br 1H), 6.74 (s, 1H), 7.46 (s, br, 2H), 7.58 (d, 2H), 7.73 (s, br, 1H), 7.86 (s, br, 1H).<br>LCMS (Method 2): R$_t$ = 0.94 min; m/z = 447 (M + H)$^+$ |
| 49.1 | 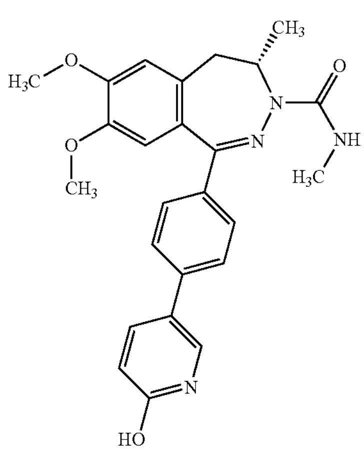 [SMILES: CNC(=O)N1N=C(c2ccc(-c3ccc(O)nc3)cc2)c2cc(OC)c(OC)cc2C[C@@H]1C] | (4S)-1-[4-(6-hydroxypyridin-3-yl)phenyl]-7,8-dimethoxy-N,4-dimethyl-4,5-dihydro-3H-2,3-benzodiazepine-3-carboxamide | LCMS (Method 2): R$_t$ = 0.97 min; m/z = 447 (M + H)$^+$<br>[α]$_D^{20}$ = −102.3° (c = 1.00; CHCl$_3$) |

| No. | Structure | Name | Analytical data |
|---|---|---|---|
| 50 | 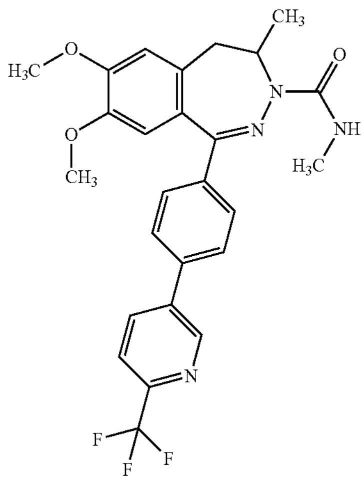 [SMILES: CNC(=O)N1N=C(c2ccc(-c3ccc(C(F)(F)F)nc3)cc2)c2cc(OC)c(OC)cc2CC1C] | (±)-7,8-dimethoxy-N,4-dimethyl-1-{4-[6-(trifluoromethyl)pyridin-3-yl]phenyl}-4,5-dihydro-3H-2,3-benzodiazepine-3-carboxamide | $^1$H-NMR (300 MHz, CDCl$_3$): δ = 0.99 (d, 3H), 2.86 (dd, 1H), 2.91 (d, 3H), 3.15 (dd, 1H), 3.68 (s, 3H), 3.95 (s, 3H), 5.49 (m, 1H), 6.54 (m, 1H), 6.62 (s, 1H), 6.74 (s, 1H), 7.65 (s, br, 4H), 7.79 (d, 1H), 8.10 (dd, 1H), 9.0 (s, br, 1H).<br>LCMS (Method 2): R$_t$ = 1.35 min; m/z = 499 (M + H)$^+$ |
| 50.1 | 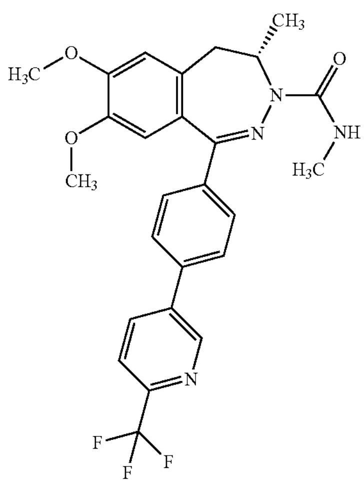 [SMILES: CNC(=O)N1N=C(c2ccc(-c3ccc(C(F)(F)F)nc3)cc2)c2cc(OC)c(OC)cc2C[C@@H]1C] | (4S)-7,8-dimethoxy-N,4-dimethyl-1-{4-[6-(trifluoromethyl)pyridin-3-yl]phenyl}-4,5-dihydro-3H-2,3-benzodiazepine-3-carboxamide | prep. HPLC: Method IIIa<br>analyt. HPLC (Method K1):<br>R$_t$ = 3.24 min<br>[α]$_D^{20}$ = 109.2° (c = 1.00; MeOH)<br>LCMS (Method 1): R$_t$ = 1.36 min; m/z = 499 (M + H)$^+$ |
| 50.2 | 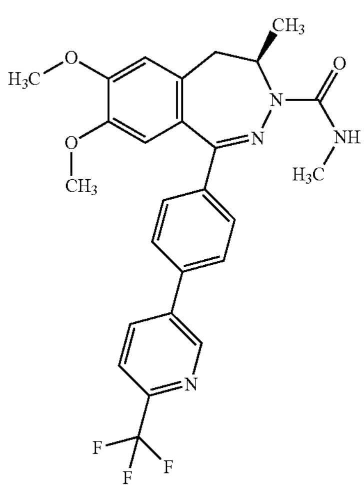 [SMILES: CNC(=O)N1N=C(c2ccc(-c3ccc(C(F)(F)F)nc3)cc2)c2cc(OC)c(OC)cc2C[C@H]1C] | (4R)-7,8-dimethoxy-N,4-dimethyl-1-{4-[6-(trifluoromethyl)pyridin-3-yl]phenyl}-4,5-dihydro-3H-2,3-benzodiazepine-3-carboxamide | prep. HPLC: Method IIIa<br>analyt. HPLC (Method K1):<br>R$_t$ = 2.54 min<br>[α]$_D^{20}$ = -113.2° (c = 1.00; MeOH)<br>LCMS (Method 1): R$_t$ = 1.36 min; m/z = 499 (M + H)$^+$ |

| No. | Structure | Name | Analytical data |
|---|---|---|---|
| 51 | 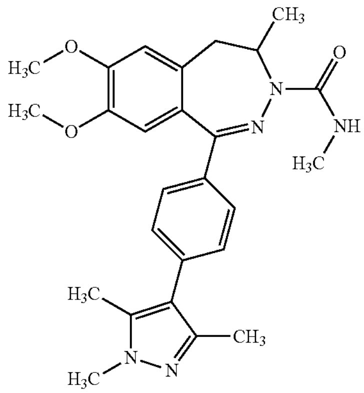 [SMILES: CNC(=O)N1N=C(c2ccc(-c3c(C)nn(C)c3C)cc2)c2cc(OC)c(OC)cc2CC1C] | (±)-7,8-dimethoxy-N,4-dimethyl-1-[4-(1,3,5-trimethyl-1H-pyrazol-4-yl)phenyl]-4,5-dihydro-3H-2,3-benzodiazepine-3-carboxamide | $^1$H-NMR (400 MHz, CDCl$_3$): δ = 1.05 (d, 3H), 2.29 (s, 6H), 2.82 (dd, 1H), 2.90 (d, 3H), 3.08 (dd, 1H), 3.69 (s, 3H), 3.81 (s, 3H), 3.95 (s, 3H), 5.41 (m, 1H), 6.42 (qbr, 1H), 6.67 (s, 1H), 6.75 (s, 1H), 7.28 (d, 2H), 7.56 (d, 2H).<br>LCMS (Method 3): R$_t$ = 1.11 min; m/z = 462 (M + H)$^+$ |
| 51.1 | 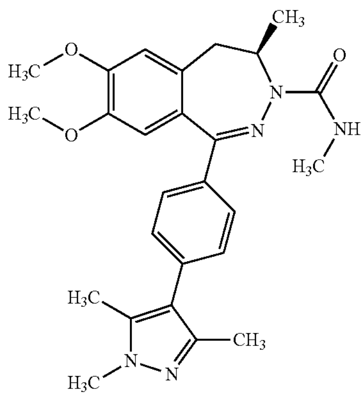 [SMILES: CNC(=O)N1N=C(c2ccc(-c3c(C)nn(C)c3C)cc2)c2cc(OC)c(OC)cc2C[C@H]1C] | (4R)-7,8-dimethoxy-N,4-dimethyl-1-[4-(1,3,5-trimethyl-1H-pyrazol-4-yl)phenyl]-4,5-dihydro-3H-2,3-benzodiazepine-3-carboxamide | prep. HPLC: Method XVI<br>analyt. HPLC (Method U):<br>R$_t$ = 7.78 min<br>$[α]_D^{20}$ = −199.0° (c = 1.00; MeOH) |
| 51.2 | 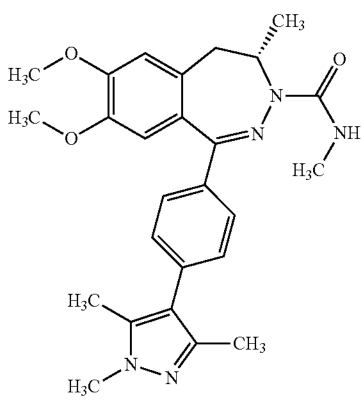 [SMILES: CNC(=O)N1N=C(c2ccc(-c3c(C)nn(C)c3C)cc2)c2cc(OC)c(OC)cc2C[C@@H]1C] | (4S)-7,8-dimethoxy-N,4-dimethyl-1-[4-(1,3,5-trimethyl-1H-pyrazol-4-yl)phenyl]-4,5-dihydro-3H-2,3-benzodiazepine-3-carboxamide | prep. HPLC: Method XVI<br>analyt. HPLC (Method U):<br>R$_t$ = 10.16 min<br>$[α]_D^{20}$ = +183.3° (c = 1.00; MeOH) |
| 52 | 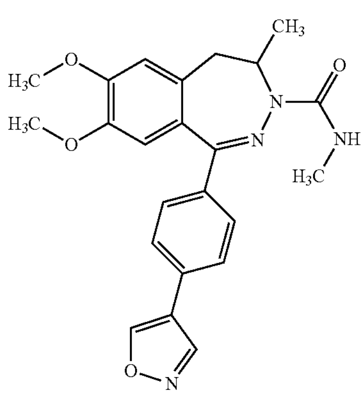 [SMILES: CNC(=O)N1N=C(c2ccc(-c3cnoc3)cc2)c2cc(OC)c(OC)cc2CC1C] | (±)-1-[4-(isoxazol-4-yl)phenyl]-7,8-dimethoxy-N,4-dimethyl-4,5-dihydro-3H-2,3-benzodiazepine-3-carboxamide | $^1$H-NMR (400 MHz, CDCl$_3$): δ = 0.99 (d, 3H), 2.85 (dd, 1H), 2.90 (d, 3H), 3.12 (dd, 1H), 3.66 (s, 3H), 3.94 (s, 3H), 5.46 (m, 1H), 6.50 (m, 1H), 6.60 (s, 1H), 6.73 (s, 1H), 7.51 (d, 2H), 7.56 (d, 2H), 8.61 (s, 1H), 8.74 (s, 1H).<br>LCMS (Method 3): R$_t$ = 1.12 min; m/z = 421 (M + H)$^+$ |

The following exemplary compounds were prepared analogously to Example 2 from Example 51A and the appropriate commercially available boronic acid derivatives:

| No | Structure | Name | Analytical data |
|----|-----------|------|-----------------|
| 53 | 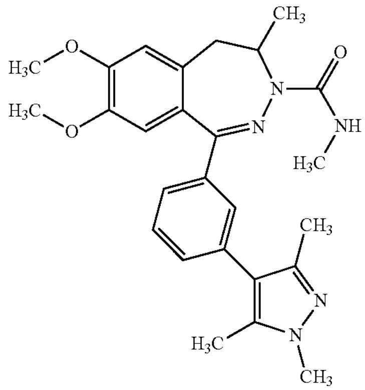 [SMILES: CNC(=O)N1N=C(c2cccc(-c3c(C)nn(C)c3C)c2)c2cc(OC)c(OC)cc2CC1C] | (±)-7,8-dimethoxy-N,4-dimethyl-1-[3-(1,3,5-trimethyl-1H-pyrazol-4-yl)phenyl]-4,5-dihydro-3H-2,3-benzodiazepine-3-carboxamide | $^1$H-NMR (400 MHz, CDCl$_3$): δ = 1.01 (d, 3H), 2.24 (s, 3H), 2.25 (s, 3H), 2.83 (dd, 1H), 2.88 (d, 3H), 3.11 (dd, 1H), 3.67 (s, 3H), 3.78 (s, 3H), 3.93 (s, 3H), 5.44 (m, 1H), 6.51 (qbr, 1H), 6.65 (s, 1H), 6.72 (s, 1H), 7.26 (m, 1H), 7.31 (m, 1H), 7.44 (m, 2H). LCMS (Method 3): R$_t$ = 1.12 min; m/z = 462 (M + H)$^+$ |
| 54 | 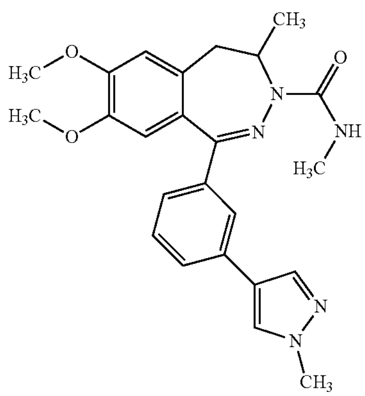 [SMILES: CNC(=O)N1N=C(c2cccc(-c3cnn(C)c3)c2)c2cc(OC)c(OC)cc2CC1C] | (±)-7,8-dimethoxy-N,4-dimethyl-1-[3-(1-methyl-1H-pyrazol-4-yl)phenyl]-4,5-dihydro-3H-2,3-benzodiazepine-3-carboxamide | $^1$H-NMR (300 MHz, CDCl$_3$): δ = 1.00 (d, 3H), 2.86 (dd, 1H), 2.88 (d, 3H), 3.13 (dd, 1H), 3.63 (s, 3H), 3.94 (s, 3H), 3.95 (s, 3H), 5.48 (m, 1H), 6.51 (m, 1H), 6.61 (s, 1H), 6.73 (s, 1H), 7.36 (m, 1H), 7.39 (dd, 1H), 7.50 (m, 1H), 7.55 (m, 1H), 7.61 (s, 1H), 7.76 (s, 1H). LCMS (Method 3): R$_t$ = 1.04 min; m/z = 434 (M + H)$^+$ |
| 55 | 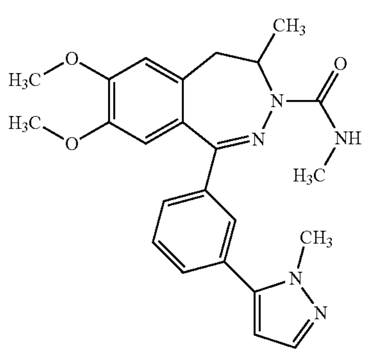 [SMILES: CNC(=O)N1N=C(c2cccc(-c3ccnn3C)c2)c2cc(OC)c(OC)cc2CC1C] | (±)-7,8-dimethoxy-N,4-dimethyl-1-[3-(1-methyl-1H-pyrazol-5-yl)phenyl]-4,5-dihydro-3H-2,3-benzodiazepine-3-carboxamide | $^1$H-NMR (400 MHz, CDCl$_3$): δ = 0.98 (d, 3H), 2.87 (dd, 1H), 2.89 (d, 3H), 3.14 (dd, 1H), 3.65 (s, 3H), 3.93 (s, 3H), 3.94 (s, 3H), 5.48 (m, 1H), 6.33 (d, 1H), 6.50 (qbr, 1H), 6.59 (s, 1H), 6.73 (s, 1H), 7.42-7.58 (m, 4H), 7.54 (d, 1H). LCMS (Method 3): R$_t$ = 1.07 min; m/z = 434 (M + H)$^+$ |

The following exemplary compounds were prepared analogously to Example 2 from Example 60A and the appropriate commercially available boronic acid derivatives:

| No | Structure | Name | Analytical data |
|---|---|---|---|
| 56 | 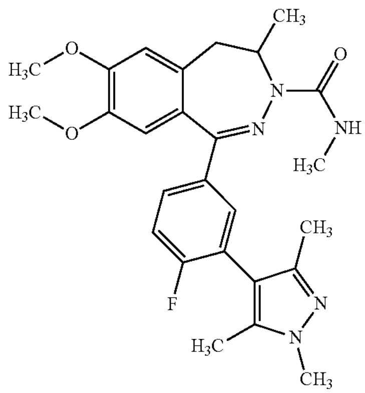 [SMILES: CNC(=O)N1N=C(c2ccc(F)c(-c3c(C)nn(C)c3C)c2)c2cc(OC)c(OC)cc2CC1C] | (±)-1-[4-fluoro-3-(1,3,5-trimethyl-1H-pyrazol-4-yl)phenyl]-7,8-dimethoxy-N,4-dimethyl-4,5-dihydro-3H-2,3-benzodiazepine-3-carboxamide | $^1$H-NMR (400 MHz, CDCl$_3$): δ = 0.99 (d, 3H), 2.18 (s, 6H), 2.83 (dd, 1H), 2.88 (d, 3H), 3.09 (dd, 1H), 3.68 (s, 3H), 3.78 (s, 3H), 3.93 (s, 3H), 5.43 (m, 1H), 6.44 (qbr, 1H), 6.62 (s, 1H), 6.72 (s, 1H), 7.17 (dd, 1H), 7.28 (dd, 1H), 7.46 (ddd, 1H). LCMS (Method 3): R$_t$ = 1.15 min; m/z = 480 (M + H)$^+$ |
| 57 | 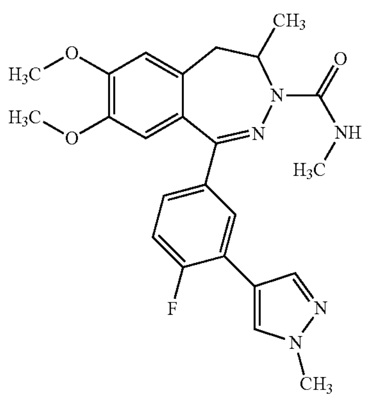 [SMILES: CNC(=O)N1N=C(c2ccc(F)c(-c3cnn(C)c3)c2)c2cc(OC)c(OC)cc2CC1C] | (±)-1-[4-fluoro-3-(1-methyl-1H-pyrazol-4-yl)phenyl]-7,8-dimethoxy-N,4-dimethyl-4,5-dihydro-3H-2,3-benzodiazepine-3-carboxamide | $^1$H-NMR (400 MHz, CDCl$_3$): δ = 0.99 (d, 3H), 2.85 (m, 1H), 2.89 (d, 3H), 3.12 (dd, 1H), 3.64 (s, 3H), 3.95 (s, 3H), 3.97 (s, 3H), 5.47 (m, 1H), 6.46 (m, 1H), 6.59 (s, 1H), 6.73 (s, 1H), 7.14 (dd, 1H), 7.31 (m, 1H), 7.64 (dd, 1H), 7.79 (s, 1H), 7.83 (s, 1H). LCMS (Method 3): R$_t$ = 1.14 min; m/z = 452 (M + H)$^+$ |
| 58 | 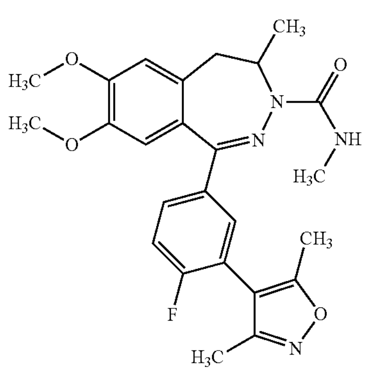 [SMILES: CNC(=O)N1N=C(c2ccc(F)c(-c3c(C)noc3C)c2)c2cc(OC)c(OC)cc2CC1C] | (±)-1-[3-(3,5-dimethylisoxazol-4-yl)-4-fluoroophenyl]-7,8-dimethoxy-N,4-dimethyl-4,5-dihydro-3H-2,3-benzodiazepine-3-carboxamide | $^1$H-NMR (400 MHz, CDCl$_3$): δ = 0.98 (d, 3H), 2.23 (s, 3H), 2.36 (s, 3H), 2.86 (dd, 1H), 2.89 (d, 3H), 3.11 (dd, 1H), 3.68 (s, 3H), 3.94 (s, 3H), 5.46 (m, 1H), 6.45 (qbr, 1H), 6.58 (s, 1H), 6.72 (s, 1H), 7.21 (dd, 1H), 7.30 (dd, 1H), 7.53 (ddd, 1H). LCMS (Method 3): R$_t$ = 1.25 min; m/z = 467 (M + H)$^+$ |

The following exemplary compounds were prepared analogously to Example 2 from Example 49A and the appropriate commercially available boronic acid derivatives:

| No | Structure | Name | LCMS data (Method 4) | |
|---|---|---|---|---|
| | | | R$_t$ [min] | [M + H]$^+$ |
| 59 | 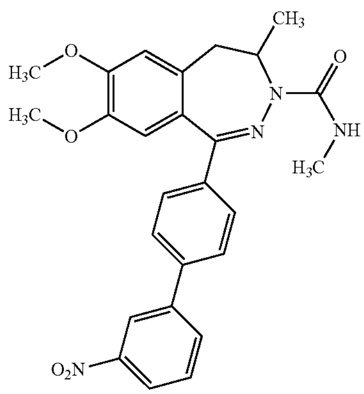 [SMILES: CNC(=O)N1N=C(c2ccc(-c3cccc([N+](=O)[O-])c3)cc2)c2cc(OC)c(OC)cc2CC1C] | (±)-7,8-dimethoxy-N,4-dimethyl-1-(3'-nitrobiphenyl-4-yl)-4,5-dihydro-3H-2,3-benzodiazepine-3-carboxamide | 1.34 | 475 |
| 60 | 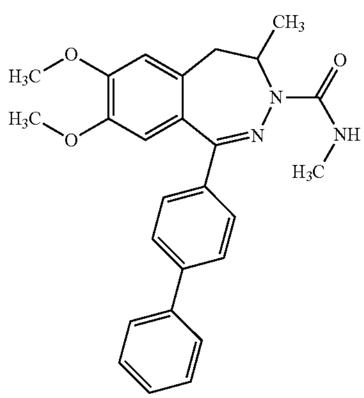 [SMILES: CNC(=O)N1N=C(c2ccc(-c3ccccc3)cc2)c2cc(OC)c(OC)cc2CC1C] | (±)-1-(biphenyl-4-yl)-7,8-dimethoxy-N,4-dimethyl-4,5-dihydro-3H-2,3-benzodiazepine-3-carboxamide | 1.39 | 430 |
| 61 | 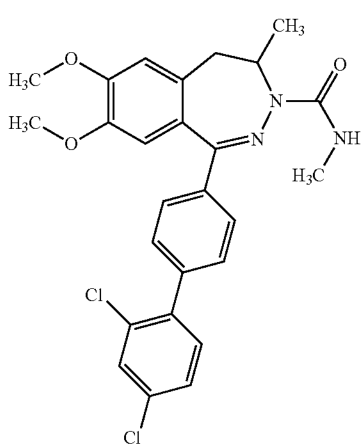 [SMILES: CNC(=O)N1N=C(c2ccc(-c3ccc(Cl)cc3Cl)cc2)c2cc(OC)c(OC)cc2CC1C] | (±)-1-(2',4'-dichlorobiphenyl-4-yl)-7,8-dimethoxy-N,4-dimethyl-4,5-dihydro-3H-2,3-benzodiazepine-3-carboxamide | 1.57 | 498 |

-continued

| No | Structure | Name | LCMS data (Method 4) | |
|---|---|---|---|---|
| | | | R$_t$ [min] | [M + H]$^+$ |
| 62 | 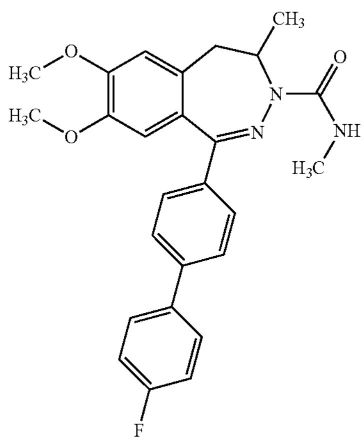 [SMILES: CNC(=O)N1N=C(c2ccc(-c3ccc(F)cc3)cc2)c2cc(OC)c(OC)cc2CC1C] | (±)-1-(4'-fluorobiphenyl-4-yl)-7,8-dimethoxy-N,4-dimethyl-4,5-dihydro-3H-2,3-benzodiazepine-3-carboxamide | 1.39 | 448 |
| 63 | 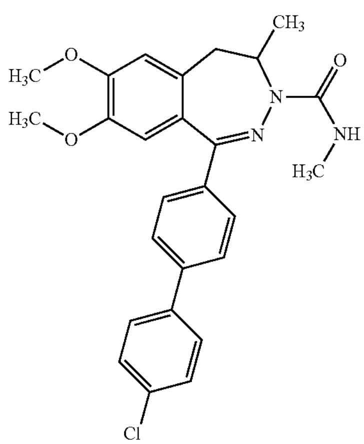 [SMILES: CNC(=O)N1N=C(c2ccc(-c3ccc(Cl)cc3)cc2)c2cc(OC)c(OC)cc2CC1C] | (±)-1-(4'-chlorobiphenyl-4-yl)-7,8-dimethoxy-N,4-dimethyl-4,5-dihydro-3H-2,3-benzodiazepine-3-carboxamide | 1.49 | 464 |
| 64 | 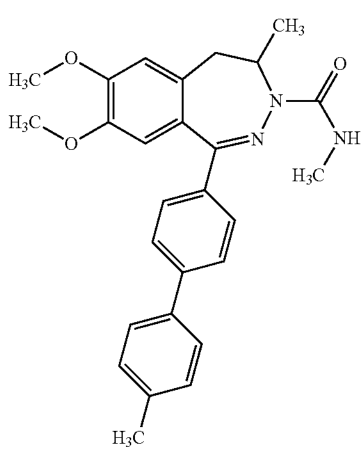 | (±)-7,8-dimethoxy-N,4-dimethyl-1-(4'-methylbiphenyl-4-yl)-4,5-dihydro-3H-2,3-benzodiazepine-3-carboxamide | 1.47 | 444 |

-continued

| No | Structure | Name | LCMS data (Method 4) | |
|---|---|---|---|---|
| | | | R$_t$ [min] | [M + H]$^+$ |
| 65 | 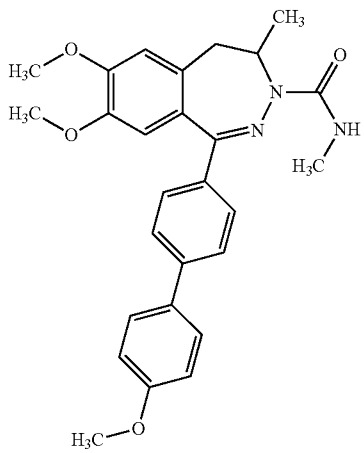 [SMILES: CNC(=O)N1N=C(c2ccc(-c3ccc(OC)cc3)cc2)c2cc(OC)c(OC)cc2CC1C] | (±)-7,8-dimethoxy-1-(4'-methoxybiphenyl-4-yl)-N,4-dimethyl-4,5-dihydro-3H-2,3-benzodiazepine-3-carboxamide | 1.35 | 460 |
| 66 | 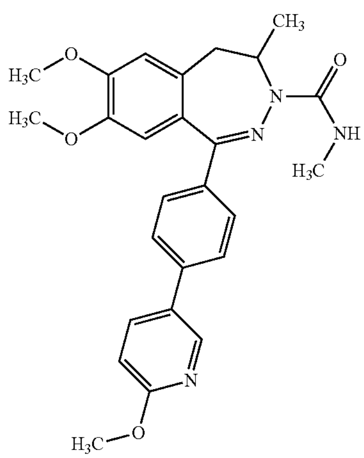 [SMILES: CNC(=O)N1N=C(c2ccc(-c3ccc(OC)nc3)cc2)c2cc(OC)c(OC)cc2CC1C] | (±)-7,8-dimethoxy-1-[4-(6-methoxypyridin-3-yl)phenyl]-N,4-dimethyl-4,5-dihydro-3H-2,3-benzodiazepine-3-carboxamide | 1.27 | 461 |
| 67 | 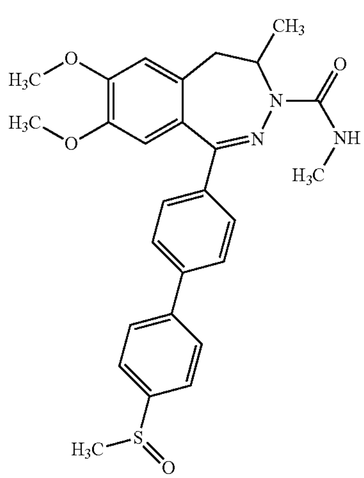 [SMILES: CNC(=O)N1N=C(c2ccc(-c3ccc(S(C)=O)cc3)cc2)c2cc(OC)c(OC)cc2CC1C] | (±)-7,8-dimethoxy-N,4-dimethyl-1-[4'-(methylsulphinyl)biphenyl-4-yl]-4,5-dihydro-3H-2,3-benzodiazepine-3-carboxamide | 1.05 | 492 |

-continued

| No | Structure | Name | LCMS data (Method 4) | |
|---|---|---|---|---|
| | | | R_t [min] | [M + H]+ |
| 68 | 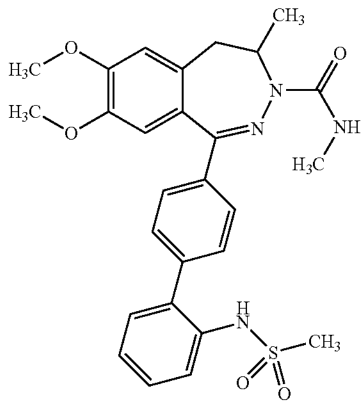 [SMILES: CNC(=O)N1N=C(c2ccc(-c3ccccc3NS(C)(=O)=O)cc2)c2cc(OC)c(OC)cc2CC1C] | (±)-7,8-dimethoxy-N,4-dimethyl-1-{2'-[(methylsulphonyl)amino]-biphenyl-4-yl}-4,5-dihydro-3H-2,3-benzodiazepine-3-carboxamide | 1.16 | 523 |
| 69 | 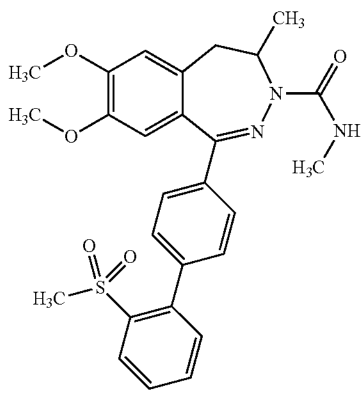 [SMILES: CNC(=O)N1N=C(c2ccc(-c3ccccc3S(C)(=O)=O)cc2)c2cc(OC)c(OC)cc2CC1C] | (±)-7,8-dimethoxy-N,4-dimethyl-1-[2'-(methylsulphonyl)biphenyl-4-yl]-4,5-dihydro-3H-2,3-benzodiazepine-3-carboxamide | 1.16 | 508 |
| 70 | 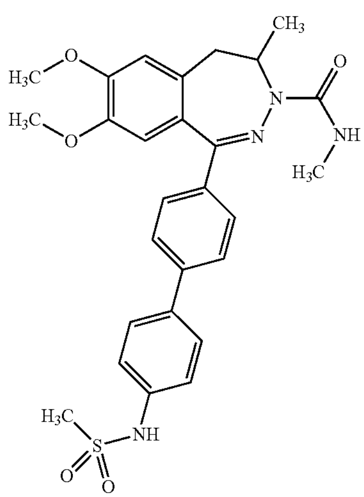 [SMILES: CNC(=O)N1N=C(c2ccc(-c3ccc(NS(C)(=O)=O)cc3)cc2)c2cc(OC)c(OC)cc2CC1C] | (±)-7,8-dimethoxy-N,4-dimethyl-1-{4'-[(methylsulphonyl)amino]biphenyl-4-yl}-4,5-dihydro-3H-2,3-benzodiazepine-3-carboxamide | 1.10 | 523 |

| No | Structure | Name | LCMS data (Method 4) | |
|---|---|---|---|---|
| | | | R$_t$ [min] | [M + H]$^+$ |
| 71 | 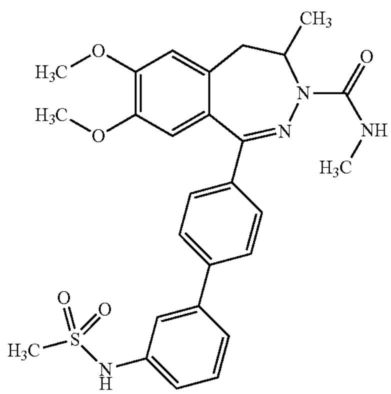 [SMILES: CNC(=O)N1N=C(c2ccc(-c3cccc(NS(C)(=O)=O)c3)cc2)c2cc(OC)c(OC)cc2CC1C] | (±)-7,8-dimethoxy-N,4-dimethyl-1-{3'-[(methylsulphonyl)amino]biphenyl-4-yl}-4,5-dihydro-3H-2,3-benzodiazepine-3-carboxamide | 1.13 | 523 |
| 72 | 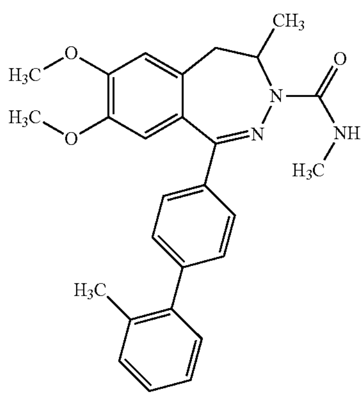 [SMILES: CNC(=O)N1N=C(c2ccc(-c3ccccc3C)cc2)c2cc(OC)c(OC)cc2CC1C] | (±)-7,8-dimethoxy-N,4-dimethyl-1-(2'-methylbiphenyl-4-yl)-4,5-dihydro-3H-2,3-benzodiazepine-3-carboxamide | 1.45 | 444 |
| 73 | 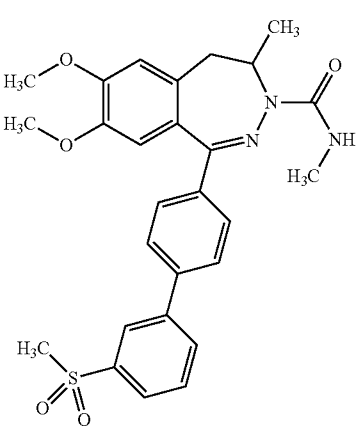 [SMILES: CNC(=O)N1N=C(c2ccc(-c3cccc(S(C)(=O)=O)c3)cc2)c2cc(OC)c(OC)cc2CC1C] | (±)-7,8-dimethoxy-N,4-dimethyl-1-[3'-(methylsulphonyl)biphenyl-4-yl]-4,5-dihydro-3H-2,3-benzodiazepine-3-carboxamide | 1.14 | 508 |

-continued

| No | Structure | Name | LCMS data (Method 4) | |
|---|---|---|---|---|
| | | | R_t [min] | [M + H]+ |
| 74 | 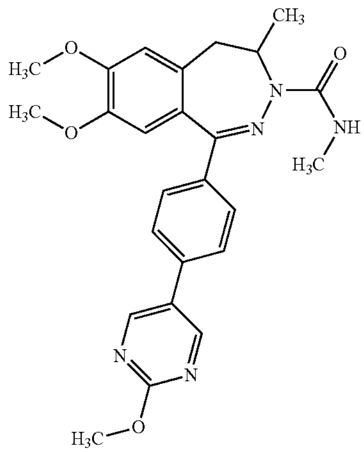 [SMILES: CNC(=O)N1N=C(c2ccc(-c3cnc(OC)nc3)cc2)c2cc(OC)c(OC)cc2CC1C] | (±)-7,8-dimethoxy-1-[4-(2-methoxypyrimidin-5-yl)phenyl]-N,4-dimethyl-4,5-dihydro-3H-2,3-benzodiazepine-3-carboxamide | 1.12 | 462 |
| 75 | 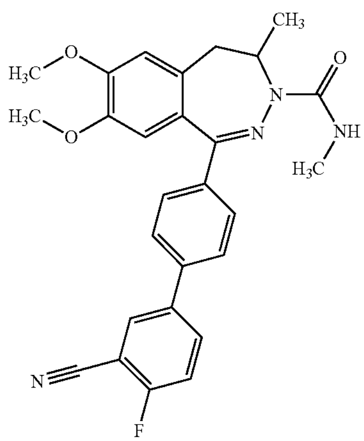 [SMILES: CNC(=O)N1N=C(c2ccc(-c3ccc(F)c(C#N)c3)cc2)c2cc(OC)c(OC)cc2CC1C] | (±)-1-(3'-cyano-4'-fluorobiphenyl-4-yl)-7,8-dimethoxy-N,4-dimethyl-4,5-dihydro-3H-2,3-benzodiazepine-3-carboxamide | 1.31 | 473 |
| 76 | 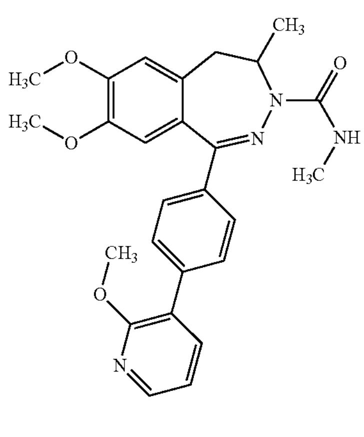 [SMILES: CNC(=O)N1N=C(c2ccc(-c3cccnc3OC)cc2)c2cc(OC)c(OC)cc2CC1C] | (±)-7,8-dimethoxy-1-[4-(2-methoxypyridin-3-yl)phenyl]-N,4-dimethyl-4,5-dihydro-3H-2,3-benzodiazepine-3-carboxamide | 1.27 | 461 |

-continued

| No | Structure | Name | LCMS data (Method 4) | |
|---|---|---|---|---|
| | | | R$_t$ [min] | [M + H]$^+$ |
| 77 | 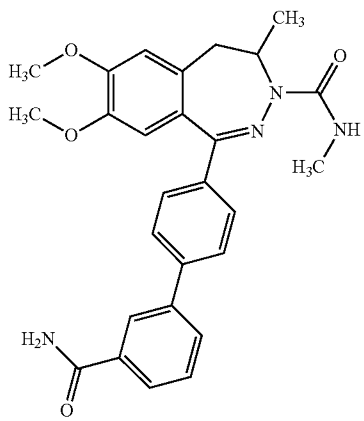 [SMILES: CNC(=O)N1N=C(c2ccc(-c3cccc(C(N)=O)c3)cc2)c2cc(OC)c(OC)cc2CC1C] | (±)-1-(3'-carbamoylbiphenyl-4-yl)-7,8-dimethoxy-N,4-dimethyl-4,5-dihydro-3H-2,3-benzodiazepine-3-carboxamide | 1.03 | 473 |
| 78 | 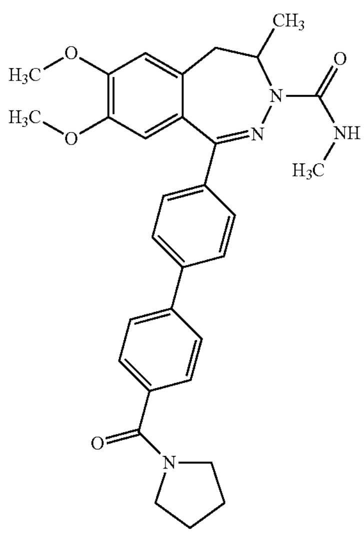 [SMILES: CNC(=O)N1N=C(c2ccc(-c3ccc(C(=O)N4CCCC4)cc3)cc2)c2cc(OC)c(OC)cc2CC1C] | (±)-7,8-dimethoxy-N,4-dimethyl-1-[4'-(pyrrolidin-1-ylcarbonyl)biphenyl-4-yl]-4,5-dihydro-3H-2,3-benzodiazepine-3-carboxamide | 1.19 | 527 |
| 79 | 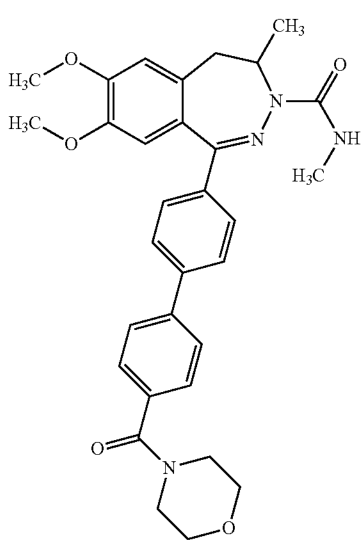 [SMILES: CNC(=O)N1N=C(c2ccc(-c3ccc(C(=O)N4CCOCC4)cc3)cc2)c2cc(OC)c(OC)cc2CC1C] | (±)-7,8-dimethoxy-N,4-dimethyl-1-[4'-(morpholin-4-ylcarbonyl)biphenyl-4-yl]-4,5-dihydro-3H-2,3-benzodiazepine-3-carboxamide | 1.10 | 543 |

-continued

| No | Structure | Name | LCMS data (Method 4) | |
|---|---|---|---|---|
| | | | R$_t$ [min] | [M + H]$^+$ |
| 80 | 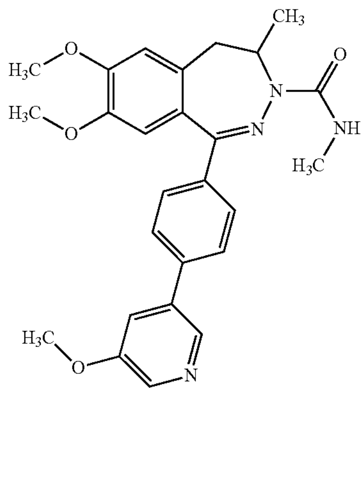 | (±)-7,8-dimethoxy-1-[4-(5-methoxypyridin-3-yl)phenyl]-N,4-dimethyl-4,5-dihydro-3H-2,3-benzodiazepine-3-carboxamide | 1.06 | 461 |
| 81 | 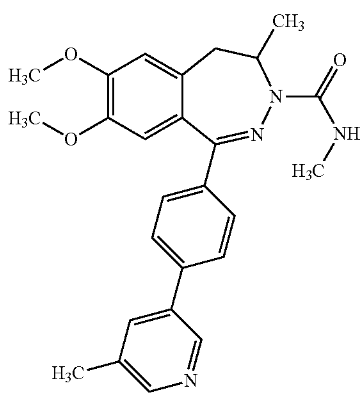 [SMILES: CNC(=O)N1N=C(c2ccc(-c3cncc(C)c3)cc2)c2cc(OC)c(OC)cc2CC1C] | (±)-7,8-dimethoxy-N,4-dimethyl-1-[4-(5-methylpyridin-3-yl)phenyl]-4,5-dihydro-3H-2,3-benzodiazepine-3-carboxamide | 0.94 | 445 |
| 82 | 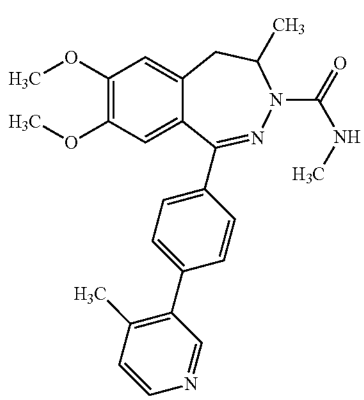 [SMILES: CNC(=O)N1N=C(c2ccc(-c3cnccc3C)cc2)c2cc(OC)c(OC)cc2CC1C] | (±)-7,8-dimethoxy-N,4-dimethyl-1-[4-(4-methylpyridin-3-yl)phenyl]-4,5-dihydro-3H-2,3-benzodiazepine-3-carboxamide | 0.85 | 445 |

-continued
| No | Structure | Name | LCMS data (Method 4) | |
|---|---|---|---|---|
| | | | R$_t$ [min] | [M + H]$^+$ |
| 83 | 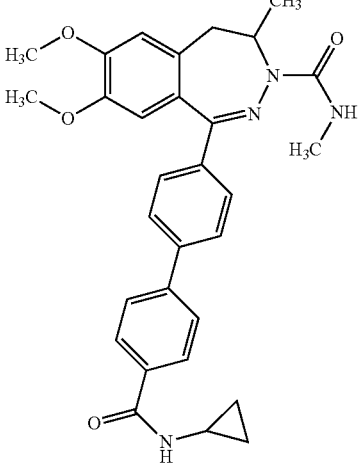 | (±)-1-[4'-(cyclopropylcarbamoyl)biphenyl-4-yl]-7,8-dimethoxy-N,4-dimethyl-4,5-dihydro-3H-2,3-benzodiazepine-3-carboxamide | 1.13 | 513 |
| 84 | 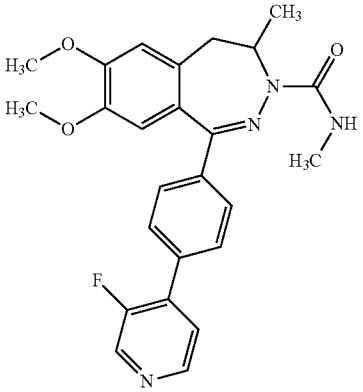 [SMILES: CNC(=O)N1N=C(c2ccc(-c3ccncc3F)cc2)c2cc(OC)c(OC)cc2CC1C] | (±)-1-[4-(3-fluoropyridin-4-yl)phenyl]-7,8-dimethoxy-N,4-dimethyl-4,5-dihydro-3H-2,3-benzodiazepine-3-carboxamide | 1.15 | 449 |
| 85 | 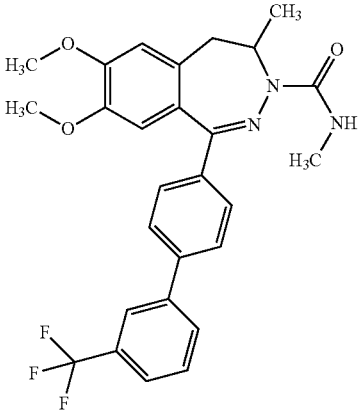 [SMILES: CNC(=O)N1N=C(c2ccc(-c3cccc(C(F)(F)F)c3)cc2)c2cc(OC)c(OC)cc2CC1C] | (±)-7,8-dimethoxy-N,4-dimethyl-1-[3'-(trifluoromethyl)biphenyl-4-yl]-4,5-dihydro-3H-2,3-benzodiazepine-3-carboxamide | 1.48 | 498 |

-continued
| No | Structure | Name | LCMS data (Method 4) | |
|---|---|---|---|---|
| | | | R$_t$ [min] | [M + H]$^+$ |
| 86 | 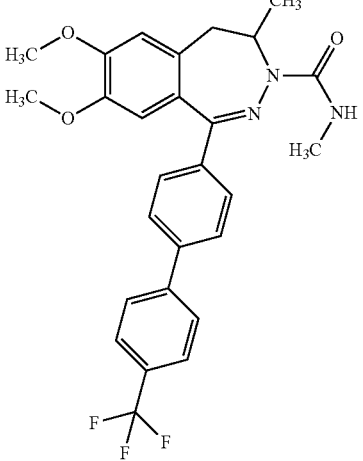 | (±)-7,8-dimethoxy-N,4-dimethyl-1-[4'-(trifluoromethyl)biphenyl-4-yl]-4,5-dihydro-3H-2,3-benzodiazepine-3-carboxamide | 1.49 | 498 |
| 87 | 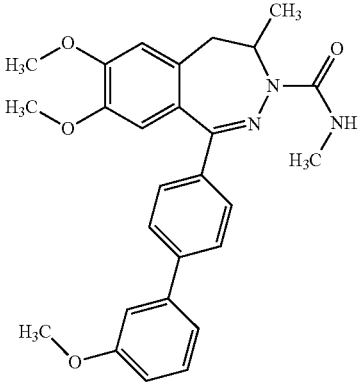 [SMILES: CNC(=O)N1N=C(c2ccc(-c3cccc(OC)c3)cc2)c2cc(OC)c(OC)cc2CC1C] | (±)-7,8-dimethoxy-1-(3'-methoxybiphenyl-4-yl)-N,4-dimethyl-4,5-dihydro-3H-2,3-benzodiazepine-3-carboxamide | 1.36 | 460 |
| 88 | 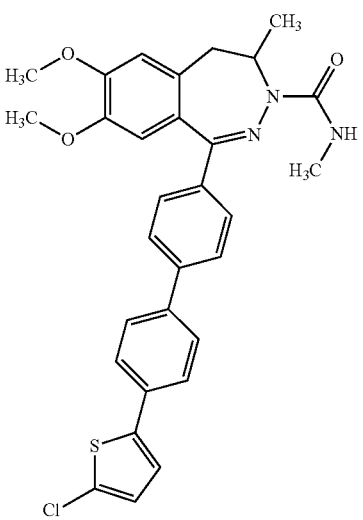 [SMILES: CNC(=O)N1N=C(c2ccc(-c3ccc(-c4ccc(Cl)s4)cc3)cc2)c2cc(OC)c(OC)cc2CC1C] | (±)-1-[4'-(5-chlorothien-2-yl)biphenyl-4-yl]-7,8-dimethoxy-N,4-dimethyl-4,5-dihydro-3H-2,3-benzodiazepine-3-carboxamide | 1.52 | 470 |

| No | Structure | Name | R$_t$ [min] | [M + H]$^+$ |
|---|---|---|---|---|
| | | | LCMS data (Method 4) | |
| 89 | 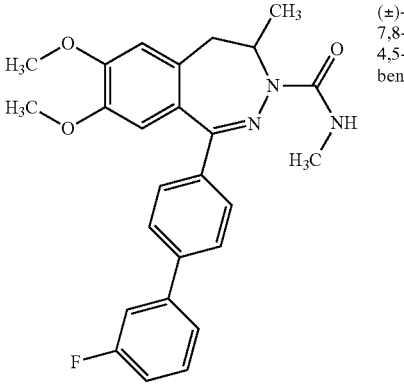 | (±)-1-(3'-fluorobiphenyl-4-yl)-7,8-dimethoxy-N,4-dimethyl-4,5-dihydro-3H-2,3-benzodiazepine-3-carboxamide | 1.40 | 448 |
| 90 | 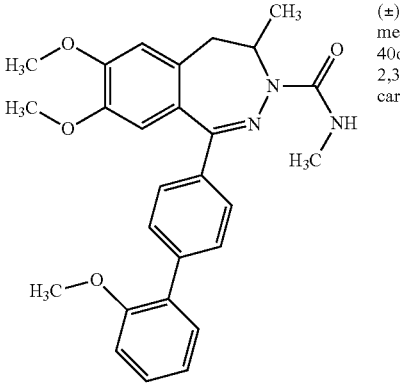 | (±)-7,8-dimethoxy-1-(2'-methoxybiphenyl-4-yl)-N,4-40dimethyl-4,5-dihydro-3H-2,3-benzodiazepine-3-carboxamide | 1.37 | 460 |
| 91 | 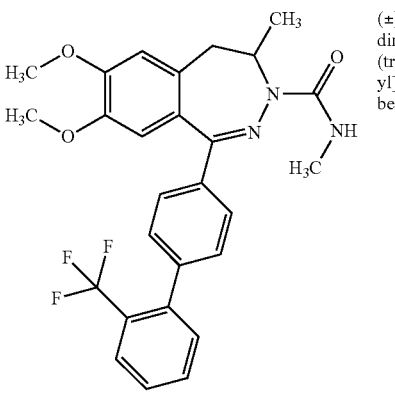 | (±)-7,8-dimethoxy-N,4-dimethyl-1-[2'-(trifluoromethyl)biphenyl-4-yl]-4,5-dihydro-3H-2,3-benzodiazepine-3-carboxamide | 1.45 | 498 |
| 92 | 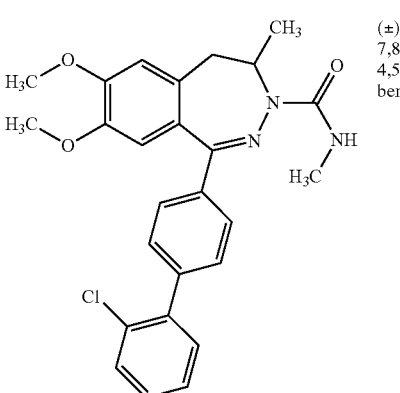 | (±)-1-(2'-chlorobiphenyl-4-yl)-7,8-dimethoxy-N,4-dimethyl-4,5-dihydro-3H-2,3-benzodiazepine-3-carboxamide | 1.44 | 464 |

-continued

| No | Structure | Name | LCMS data (Method 4) | |
|----|-----------|------|------|------|
| | | | $R_t$ [min] | $[M + H]^+$ |
| 93 | 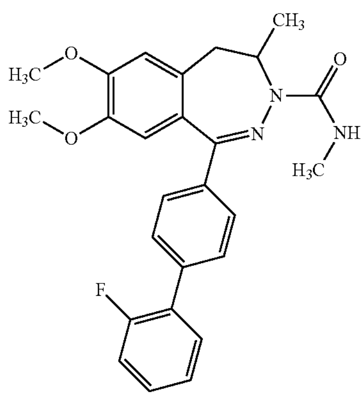 [SMILES: CNC(=O)N1N=C(c2ccc(-c3ccccc3F)cc2)c2cc(OC)c(OC)cc2CC1C] | (±)-1-(2'-fluorobiphenyl-4-yl)-7,8-dimethoxy-N,4-dimethyl-4,5-dihydro-3H-2,3-benzodiazepine-3-carboxamide | 1.38 | 448 |
| 94 | 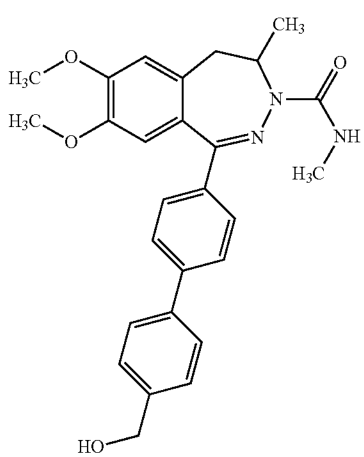 [SMILES: CNC(=O)N1N=C(c2ccc(-c3ccc(CO)cc3)cc2)c2cc(OC)c(OC)cc2CC1C] | (±)-1-[4'-(hydroxymethyl)biphenyl-4-yl]-7,8-dimethoxy-N,4-dimethyl-4,5-dihydro-3H-2,3-benzodiazepine-3-carboxamide | 1.10 | 460 |
| 95 | 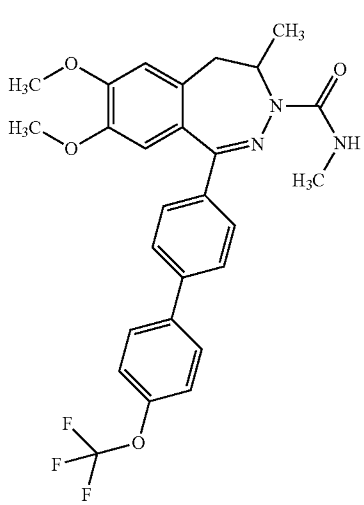 [SMILES: CNC(=O)N1N=C(c2ccc(-c3ccc(OC(F)(F)F)cc3)cc2)c2cc(OC)c(OC)cc2CC1C] | (±)-7,8-dimethoxy-N,4-dimethyl-1-[4'-(trifluoromethoxy)biphenyl-4-yl]-4,5-dihydro-3H-2,3-benzodiazepine-3-carboxamide | 1.51 | 514 |

| No | Structure | Name | LCMS data (Method 4) | |
|---|---|---|---|---|
| | | | R_t [min] | [M + H]+ |
| 96 | 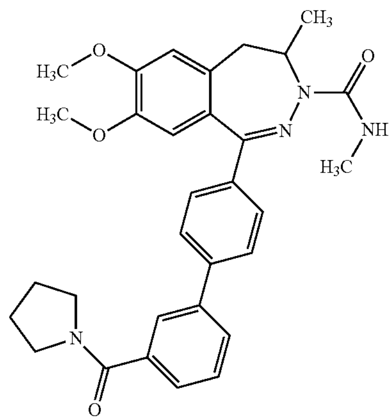 [SMILES: CNC(=O)N1N=C(c2ccc(-c3cccc(C(=O)N4CCCC4)c3)cc2)c2cc(OC)c(OC)cc2CC1C] | (±)-7,8-dimethoxy-N,4-dimethyl-1-[3'-(pyrrolidin-1-ylcarbonyl)biphenyl-4-yl]-4,5-dihydro-3H-2,3-benzodiazepine-3-carboxamide | 1.20 | 527 |
| 97 | 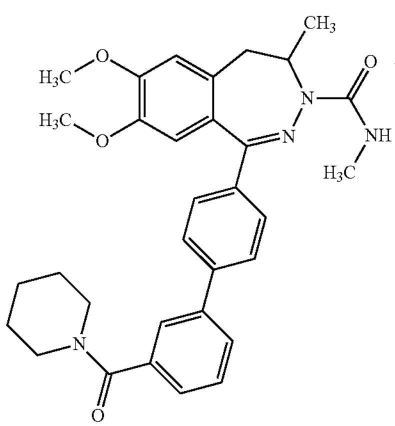 [SMILES: CNC(=O)N1N=C(c2ccc(-c3cccc(C(=O)N4CCCCC4)c3)cc2)c2cc(OC)c(OC)cc2CC1C] | (±)-7,8-dimethoxy-N,4-dimethyl-1-[3'-(piperidin-1-ylcarbonyl)biphenyl-4-yl]-4,5-dihydro-3H-2,3-benzodiazepine-3-carboxamide | 1.29 | 541 |
| 98 | 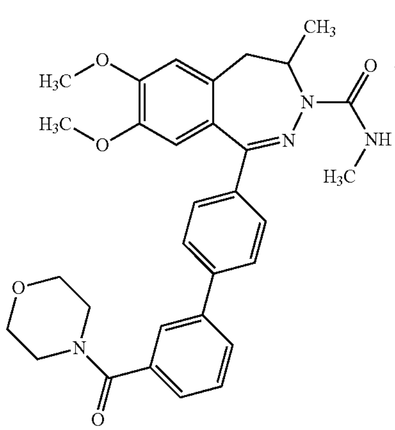 [SMILES: CNC(=O)N1N=C(c2ccc(-c3cccc(C(=O)N4CCOCC4)c3)cc2)c2cc(OC)c(OC)cc2CC1C] | (±)-7,8-dimethoxy-N,4-dimethyl-1-[3'-(morpholin-4-ylcarbonyl)biphenyl-4-yl]-4,5-dihydro-3H-2,3-benzodiazepine-3-carboxamide | 1.12 | 543 |

| No | Structure | Name | LCMS data (Method 4) | |
|---|---|---|---|---|
| | | | R<sub>t</sub> [min] | [M + H]<sup>+</sup> |
| 99 | 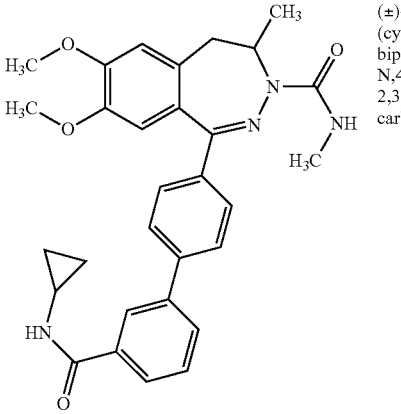 | (±)-1-[3'-(cyclopropylcarbamoyl)-biphenyl-4-yl]-7,8-dimethoxy-N,4-dimethyl-4,5-dihydro-3H-2,3-benzodiazepine-3-carboxamide | 1.15 | 513 |
| 100 | 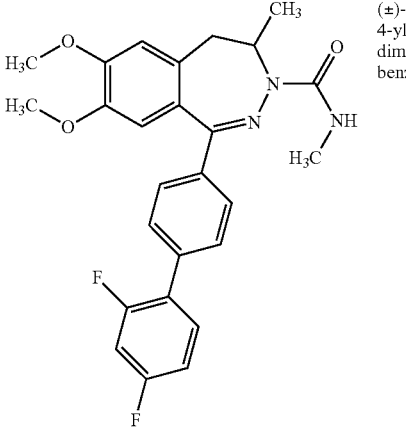 | (±)-1-(2,4'-difluorobiphenyl-4-yl)-7,8-dimethoxy-N,4-dimethyl-4,5-dihydro-3H-2,3-benzodiazepine-3-carboxamide | 1.41 | 466 |
| 101 | 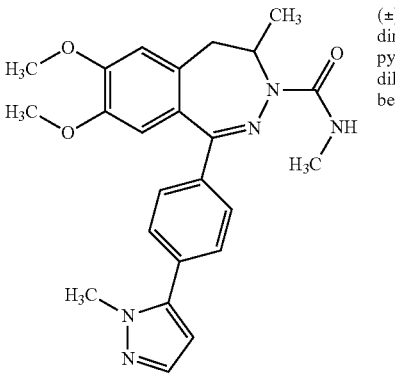 | (±)-7,8-dimethoxy-N,4-dimethyl-1-[4-(1-methyl-1H-pyrazol-5-yl)phenyl]-4,5-dihydro-3H-2,3-benzodiazepine-3-carboxamide | 1.09 | 434 |

-continued

| No | Structure | Name | LCMS data (Method 4) | |
|---|---|---|---|---|
| | | | R_t [min] | [M + H]+ |
| 102 | 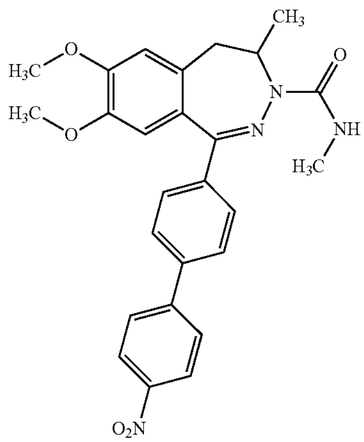 | (±)-7,8-dimethoxy-N,4-dimethyl-1-(4'-nitrobiphenyl-4-yl)-4,5-dihydro-3H-2,3-benzodiazepine-3-carboxamide | 1.34 | 475 |
| 103 | 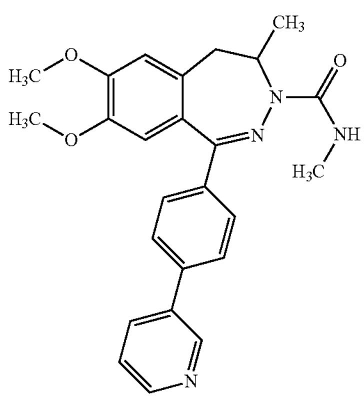 [SMILES: CNC(=O)N1N=C(c2ccc(-c3cccnc3)cc2)c2cc(OC)c(OC)cc2CC1C] | (±)-7,8-dimethoxy-N,4-dimethyl-1-[4-(pyridin-3-yl)phenyl]-4,5-dihydro-3H-2,3-benzodiazepine-3-carboxamide | 0.93 | 431 |
| 104 | 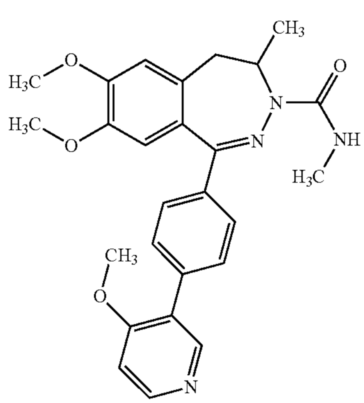 [SMILES: CNC(=O)N1N=C(c2ccc(-c3cnccc3OC)cc2)c2cc(OC)c(OC)cc2CC1C] | (±)-7,8-dimethoxy-1-[4-(4-methoxypyridin-3-yl)phenyl]-N,4-dimethyl-4,5-dihydro-3H-2,3-benzodiazepine-3-carboxamide | 0.77 | 461 |

-continued

| No | Structure | Name | LCMS data (Method 4) | |
|---|---|---|---|---|
| | | | R$_t$ [min] | [M + H]$^+$ |
| 105 | 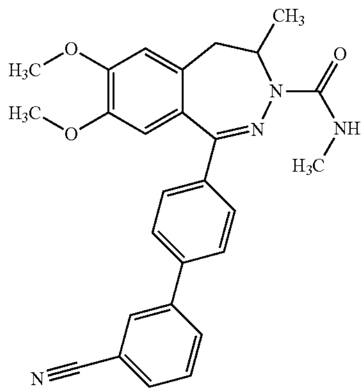 | (±)-1-(3'-cyanobiphenyl-4-yl)-7,8-dimethoxy-N,4-dimethyl-4,5-dihydro-3H-2,3-benzodiazepine-3-carboxamide | 1.28 | 455 |
| 106 | 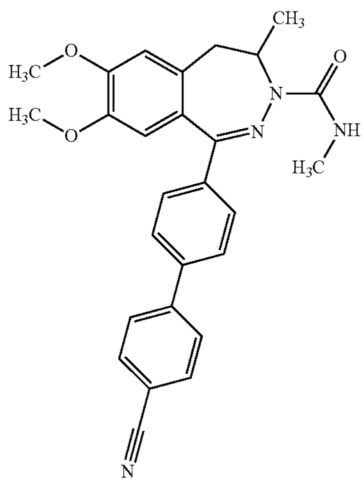 [SMILES: CNC(=O)N1N=C(c2ccc(-c3ccc(C#N)cc3)cc2)c2cc(OC)c(OC)cc2CC1C] | (±)-1-(4'-cyanobiphenyl-4-yl)-7,8-dimethoxy-N,4-dimethyl-4,5-dihydro-3H-2,3-benzodiazepine-3-carboxamide | 1.27 | 455 |
| 107 | 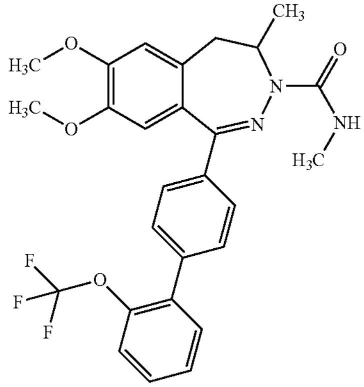 [SMILES: CNC(=O)N1N=C(c2ccc(-c3ccccc3OC(F)(F)F)cc2)c2cc(OC)c(OC)cc2CC1C] | (±)-7,8-dimethoxy-N,4-dimethyl-1-[2'-(trifluoromethoxy)biphenyl-4-yl]-4,5-dihydro-3H-2,3-benzodiazepine-3-carboxamide | 1.48 | 514 |

-continued

| No | Structure | Name | LCMS data (Method 4) | |
|---|---|---|---|---|
| | | | R$_t$ [min] | [M + H]$^+$ |
| 108 | 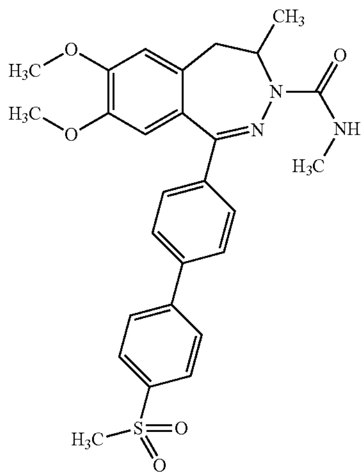 [SMILES: CNC(=O)N1N=C(c2ccc(-c3ccc(S(C)(=O)=O)cc3)cc2)c2cc(OC)c(OC)cc2CC1C] | (±)-7,8-dimethoxy-N,4-dimethyl-1-[4'-(methylsulphonyl)biphenyl-4-yl]-4,5-dihydro-3H-2,3-benzodiazepine-3-carboxamide | 1.12 | 508 |
| 109 | 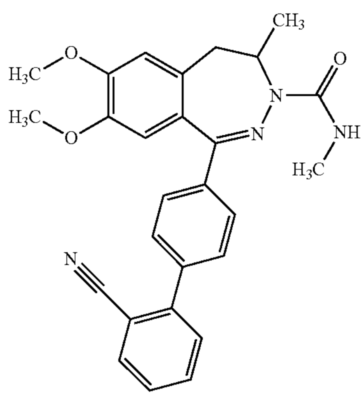 [SMILES: CNC(=O)N1N=C(c2ccc(-c3ccccc3C#N)cc2)c2cc(OC)c(OC)cc2CC1C] | (±)-1-(2'-cyanobiphenyl-4-yl)-7,8-dimethoxy-N,4-dimethyl-4,5-dihydro-3H-2,3-benzodiazepine-3-carboxamide | 1.27 | 455 |
| 110 | 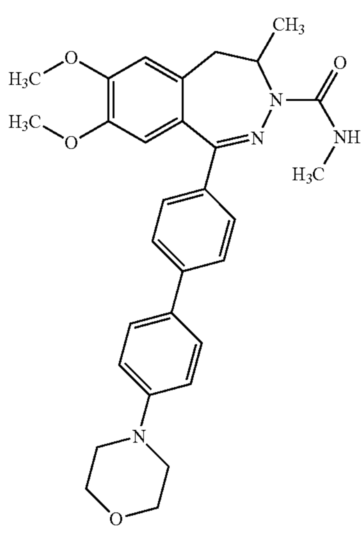 [SMILES: CNC(=O)N1N=C(c2ccc(-c3ccc(N4CCOCC4)cc3)cc2)c2cc(OC)c(OC)cc2CC1C] | (±)-7,8-dimethoxy-N,4-dimethyl-1-[4'-(morpholin-4-yl)biphenyl-4-yl]-4,5-dihydro-3H-2,3-benzodiazepine-3-carboxamide | 1.29 | 515 |

| No | Structure | Name | LCMS data (Method 4) | |
|---|---|---|---|---|
| | | | R$_t$ [min] | [M + H]$^+$ |
| 111 | 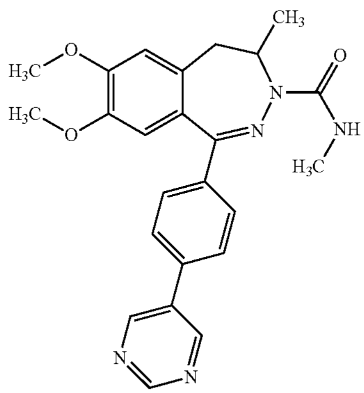 [SMILES: CNC(=O)N1N=C(c2ccc(-c3cncnc3)cc2)c2cc(OC)c(OC)cc2CC1C] | (±)-7,8-dimethoxy-N,4-dimethyl-1-[4-(pyrimidin-5-yl)phenyl]-4,5-dihydro-3H-2,3-benzodiazepine-3-carboxamide | 1.01 | 432 |
| 112 | 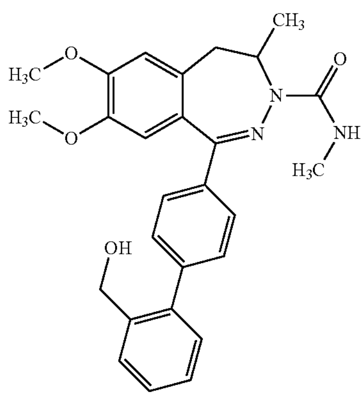 [SMILES: CNC(=O)N1N=C(c2ccc(-c3ccccc3CO)cc2)c2cc(OC)c(OC)cc2CC1C] | (±)-1-[2'-(hydroxymethyl)biphenyl-4-yl]-7,8-dimethoxy-N,4-dimethyl-4,5-dihydro-3H-2,3-benzodiazepine-3-carboxamide | 1.17 | 460 |
| 113 | 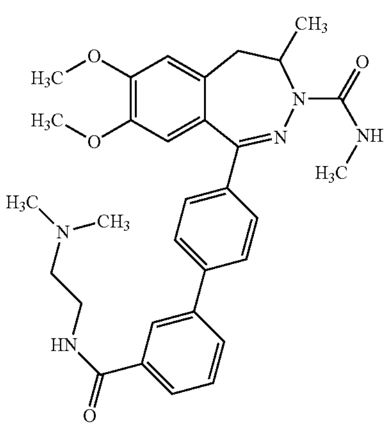 [SMILES: CNC(=O)N1N=C(c2ccc(-c3cccc(C(=O)NCCN(C)C)c3)cc2)c2cc(OC)c(OC)cc2CC1C] | (±)-1-(3'-{[2-(dimethylamino)ethyl]carbamoyl}biphenyl-4-yl)-7,8-dimethoxy-N,4-dimethyl-4,5-dihydro-3H-2,3-benzodiazepine-3-carboxamide | 0.84 | 544 |

-continued

| No | Structure | Name | LCMS data (Method 4) | |
|---|---|---|---|---|
| | | | R$_t$ [min] | [M + H]$^+$ |
| 114 | 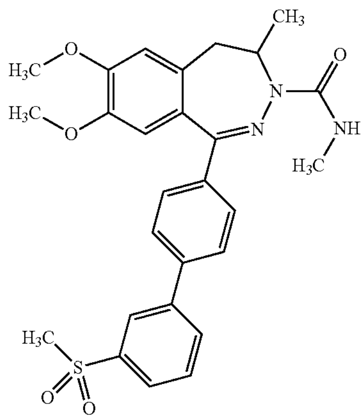 [SMILES: CNC(=O)N1N=C(c2ccc(-c3cccc(S(C)(=O)=O)c3)cc2)c2cc(OC)c(OC)cc2CC1C] | (±)-7,8-dimethoxy-N,4-dimethyl-1-(3'-sulphamoylbiphenyl-4-yl)-4,5-dihydro-3H-2,3-benzodiazepine-3-carboxamide | 1.06 | 509 |
| 115 | 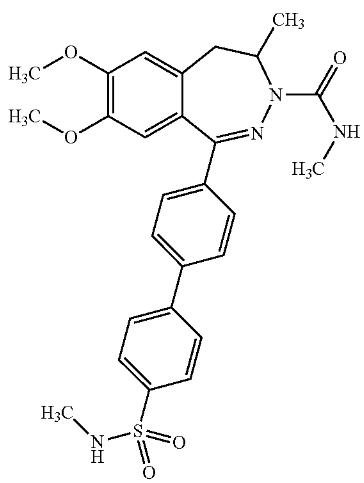 [SMILES: CNC(=O)N1N=C(c2ccc(-c3ccc(S(=O)(=O)NC)cc3)cc2)c2cc(OC)c(OC)cc2CC1C] | (±)-7,8-dimethoxy-N,4-dimethyl-1-[4'-(methylsulphamoyl)biphenyl-4-yl]-4,5-dihydro-3H-2,3-benzodiazepine-3-carboxamide | 1.13 | 523 |
| 116 | 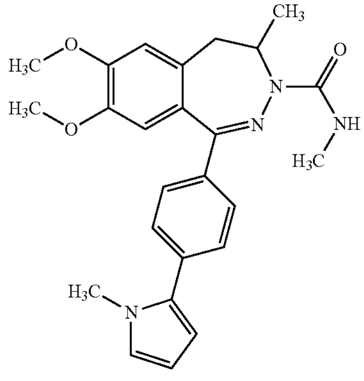 [SMILES: CNC(=O)N1N=C(c2ccc(-c3cccn3C)cc2)c2cc(OC)c(OC)cc2CC1C] | (±)-7,8-dimethoxy-N,4-dimethyl-1-[4-(1-methyl-1H-pyrrol-2-yl)phenyl]-4,5-dihydro-3H-2,3-benzodiazepine-3-carboxamide | 1.28 | 433 |

-continued

| No | Structure | Name | LCMS data (Method 4) | |
|---|---|---|---|---|
| | | | R$_t$ [min] | [M + H]$^+$ |
| 117 | 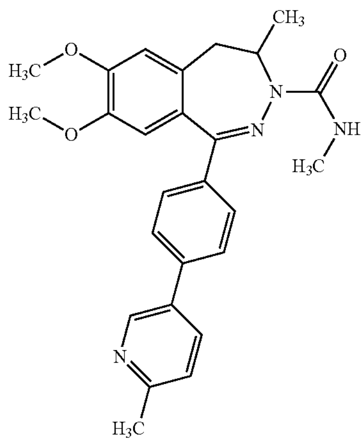 [SMILES: CNC(=O)N1N=C(c2ccc(-c3ccc(C)nc3)cc2)c2cc(OC)c(OC)cc2CC1C] | (±)-7,8-dimethoxy-N,4-dimethyl-1-[4-(6-methylpyridin-3-yl)phenyl]-4,5-dihydro-3H-2,3-benzodiazepine-3-carboxamide | 0.87 | 445 |
| 118 | 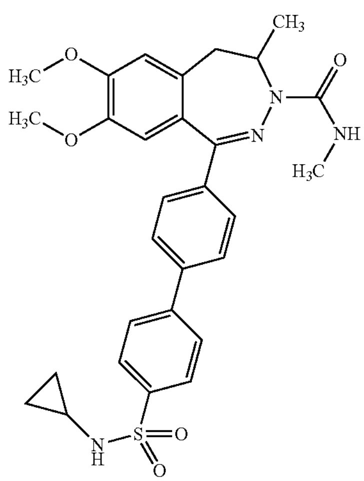 [SMILES: CNC(=O)N1N=C(c2ccc(-c3ccc(S(=O)(=O)NC4CC4)cc3)cc2)c2cc(OC)c(OC)cc2CC1C] | (±)-1-[4'-(cyclopropylsulphamoyl)-biphenyl-4-yl]-7,8-dimethoxy-N,4-dimethyl-4,5-dihydro-3H-2,3-benzodiazepine-3-carboxamide | 1.20 | 549 |
| 119 | 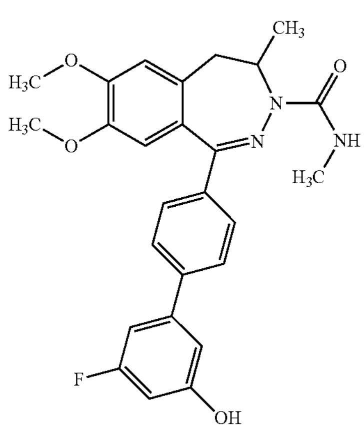 [SMILES: CNC(=O)N1N=C(c2ccc(-c3cc(O)cc(F)c3)cc2)c2cc(OC)c(OC)cc2CC1C] | (±)-1-(3'-fluoro-5'-hydroxybiphenyl-4-yl)-7,8-dimethoxy-N,4-dimethyl-4,5-dihydro-3H-2,3-benzodiazepine-3-carboxamide | 1.20 | 464 |

-continued

| No | Structure | Name | LCMS data (Method 4) | |
|---|---|---|---|---|
| | | | R$_t$ [min] | [M + H]$^+$ |
| 120 | 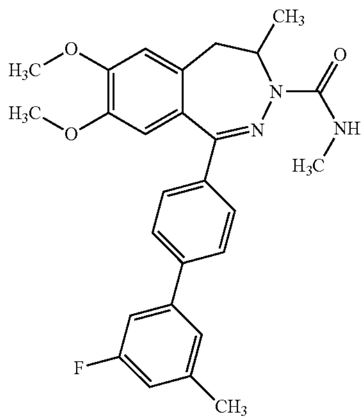 [SMILES: CNC(=O)N1N=C(c2ccc(-c3cc(C)cc(F)c3)cc2)c2cc(OC)c(OC)cc2CC1C] | (±)-1-(3'-fluoro-5'-methylbiphenyl-4-yl)-7,8-dimethoxy-N,4-dimethyl-4,5-dihydro-3H-2,3-benzodiazepine-3-carboxamide | 1.48 | 462 |
| 121 | 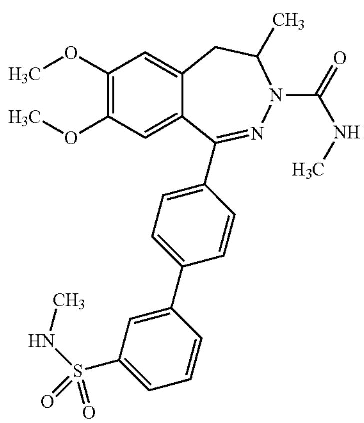 [SMILES: CNC(=O)N1N=C(c2ccc(-c3cccc(S(=O)(=O)NC)c3)cc2)c2cc(OC)c(OC)cc2CC1C] | (±)-7,8-dimethoxy-N,4-dimethyl-1-[3'-(methylsulphamoyl)biphenyl-4-yl]-4,5-dihydro-3H-2,3-benzodiazepine-3-carboxamide | 1.15 | 523 |
| 122 | 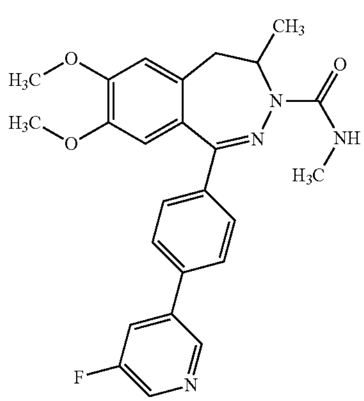 [SMILES: CNC(=O)N1N=C(c2ccc(-c3cncc(F)c3)cc2)c2cc(OC)c(OC)cc2CC1C] | (±)-1-[4-(5-fluoropyridin-3-yl)phenyl]-7,8-dimethoxy-N,4-dimethyl-4,5-dihydro-3H-2,3-benzodiazepine-3-carboxamide | 1.18 | 449 |

-continued

| No | Structure | Name | LCMS data (Method 4) | |
|---|---|---|---|---|
| | | | R$_t$ [min] | [M + H]$^+$ |
| 123 | 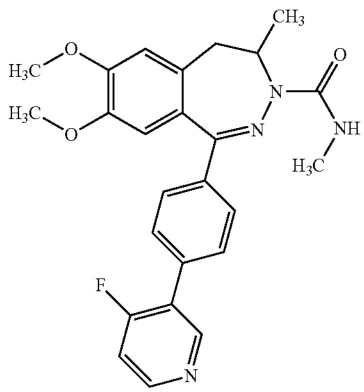 [SMILES: CNC(=O)N1N=C(c2ccc(-c3cnccc3F)cc2)c2cc(OC)c(OC)cc2CC1C] | (±)-1-[4-(4-fluoropyridin-3-yl)phenyl]-7,8-dimethoxy-N,4-dimethyl-4,5-dihydro-3H-2,3-benzodiazepine-3-carboxamide | 1.11 | 449 |
| 124 | 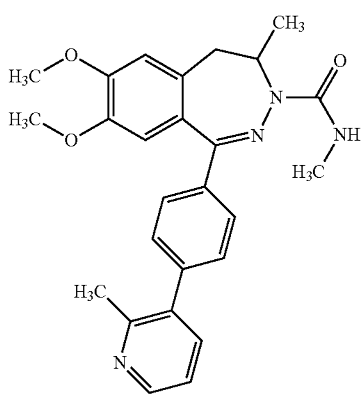 [SMILES: CNC(=O)N1N=C(c2ccc(-c3cccnc3C)cc2)c2cc(OC)c(OC)cc2CC1C] | (±)-7,8-dimethoxy-N,4-dimethyl-1-[4-(2-methylpyridin-3-yl)phenyl]-4,5-dihydro-3H-2,3-benzodiazepine-3-carboxamide | 0.84 | 445 |
| 125 | 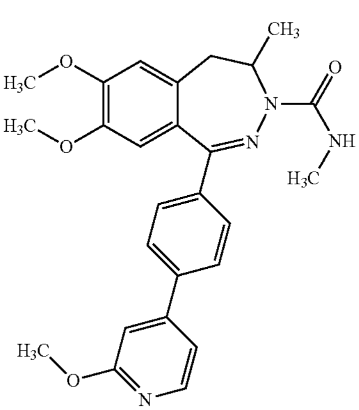 [SMILES: CNC(=O)N1N=C(c2ccc(-c3ccnc(OC)c3)cc2)c2cc(OC)c(OC)cc2CC1C] | (±)-7,8-dimethoxy-1-[4-(2-methoxypyridin-4-yl)phenyl]-N,4-dimethyl-4,5-dihydro-3H-2,3-benzodiazepine-3-carboxamide | 1.26 | 461 |

| No | Structure | Name | LCMS data (Method 4) | |
|---|---|---|---|---|
| | | | R$_t$ [min] | [M + H]$^+$ |
| 126 | 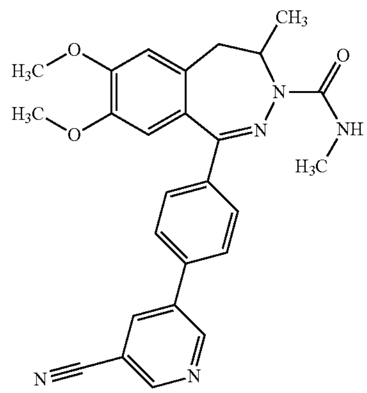 [SMILES: CNC(=O)N1N=C(c2ccc(-c3cncc(C#N)c3)cc2)c2cc(OC)c(OC)cc2CC1C] | (±)-1-[4-(5-cyanopyridin-3-yl)phenyl]-7,8-dimethoxy-N,4-dimethyl-4,5-dihydro-3H-2,3-benzodiazepine-3-carboxamide | 1.14 | 456 |

Alternative Process for Preparing Example 7

(±)-7,8-Dimethoxy-N,4-dimethyl-1-[4-(morpholin-4-yl)phenyl]-4,5-dihydro-3H-2,3-benzodiazepine-3-carboxamide

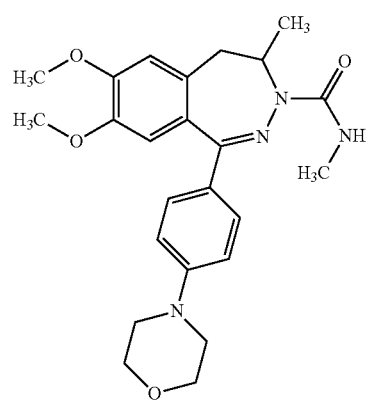 [SMILES: CNC(=O)N1N=C(c2ccc(N3CCOCC3)cc2)c2cc(OC)c(OC)cc2CC1C]

Under argon, 100 mg (231 µmol) of (±)-1-(4-bromophenyl)-7,8-dimethoxy-N,4-dimethyl-4,5-dihydro-3H-2,3-benzodiazepine-3-carboxamide (Example 49A) were initially charged in 5 ml of degassed toluene. 22 µl (22 mg, 254 µmol) of morpholine, 31 mg (324 µmol) of sodium tert-butoxide and 9 mg (12 µmol) of chloro-(2-dicyclohexylphosphino-2,4,6-triisopropyl-1,1-biphenyl) [2-(2-amino-1,1-biphenyl)]palladium(II) (CAS [1310584-14-5]) were added. The mixture was degassed again, saturated with argon and then stirred at 110° C. for 6 hours. After cooling, the mixture was partitioned between 15 ml of sat. sodium bicarbonate solution and 15 ml of ethyl acetate, and the phases were separated. The aqueous phase was extracted with ethyl acetate, and the combined organic phases were washed with water and sat. sodium chloride solution and dried with sodium sulphate. The solvents were removed on a rotary evaporator and the residue (156 mg yellow oil) was purified by flash chromatography (SiO$_2$, hexane/ethyl acetate). This gave 87 mg (86% of theory) of the desired product as a yellow solid.

LCMS (Method 2): R$_t$=1.08 min; m/z=439 (M+H)$^+$ $^1$H-NMR (300 MHz, CDCl$_3$): δ=1.10 (d, 3H), 2.73 (dd, 1H), 2.86 (d, 3H), 2.95 (dd, 1H), 3.25-3.28 (m, 4H), 3.70 (s, 3H), 3.88-3.91 (m, 4H), 3.93 (s, 3H), 5.25-5.35 (m, 1H), 6.14 (q, 1H), 6.63 (s, 1H), 6.75 (s, 1H), 6.93 (d, 2H), 7.51 (d, 2H).

Enantiomer Separation

By chiral preparative HPLC using Method V, 78 mg of (±)-7,8-dimethoxy-N,4-dimethyl-1-[4-(morpholin-4-yl)phenyl]-4,5-dihydro-3H-2,3-benzodiazepine-3-carboxamide (Example 7) were separated into the enantiomers:

Example 7.1: (4R)-7,8-dimethoxy-N,4-dimethyl-1-[4-(morpholin-4-yl)phenyl]-4,5-dihydro-3H-2,3-benzodiazepine-3-carboxamide 20 mg yellowish solid, HPLC (Method G): R$_t$=6.08 min, purity 100%

Example 7.2: (4S)-7,8-dimethoxy-N,4-dimethyl-1-[4-(morpholin-4-yl)phenyl]-4,5-dihydro-3H-2,3-benzodiazepine-3-carboxamide 20 mg yellowish solid, HPLC (Method G): R$_t$=7.42 min, purity 99.3%

Example 127.1

(4S)-7,8-Dimethoxy-N,4-dimethyl-1-[4-(4-methyl-piperazin-1-yl)phenyl]-4,5-dihydro-3H-2,3-benzodi-azepine-3-carboxamide

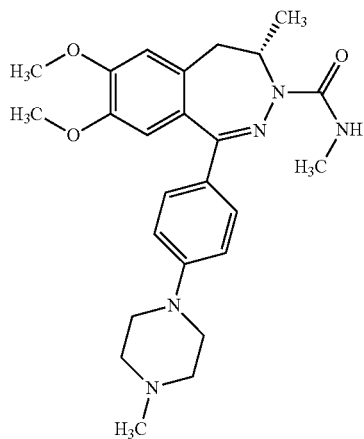 [SMILES: CNC(=O)N1N=C(c2ccc(N3CCN(C)CC3)cc2)c2cc(OC)c(OC)cc2C[C@@H]1C]

Under argon, 1.30 g (3.01 mmol) of (4S)-1-(4-bromophenyl)-7,8-dimethoxy-N,4-dimethyl-4,5-dihydro-3H-2,3-benzodiazepine-3-carboxamide (Example 49.2A) were initially charged in 65 ml of degassed toluene. 0.37 ml (331 mg, 3.31 mmol) of 1-methylpiperazine, 405 mg (4.21 mmol) of sodium tert-butoxide and 118 mg (0.15 mmol) of chloro-(2-dicyclohexylphosphino-2,4,6-triisopropyl-1,1-biphenyl)[2-(2-amino-1,1-biphenyl)]palladium(II) (CAS [1310584-14-5]) were added. The mixture was degassed again, saturated with argon and then stirred at 80° C. for 12 hours. After cooling, the mixture was added to sat. sodium bicarbonate solution and extracted with ethyl acetate. The combined organic phases were washed with sat. sodium chloride solution and dried with sodium sulphate. The solvents were removed on a rotary evaporator and the residue (1.5 g orange foam) was purified by flash chromatography ($SiO_2$, dichloromethane/methanol 0-3-10%). This gave 850 mg (63% of theory) of the desired product as a yellow solid.

LCMS (Method 2): $R_t$=0.69 min; m/z=452 (M+H)$^+$ $^1$H-NMR (400 MHz, DMSO-$d_6$): δ=1.02 (d, 3H), 2.19 (s, 3H), 2.38-2.44 (m, 4H), 2.46-2.51 (m, 1H), 2.60 (d, 3H), 2.80 (dd, 1H), 3.18-3.24 (m, 4H), 3.57 (s, 3H), 3.80 (s, 3H), 4.82-4.90 (m, 1H), 6.25 (q, 1H), 6.51 (s, 1H), 6.91 (d, 2H), 6.99 (s, 1H), 7.55 (d, 2H).

Specific optical rotation: $[α]_D^{20}$=374.4°+/−0.17° (c=1.00; methanol)

The following exemplary compounds were prepared analogously to Example 127.1 from Example 49A or Example 49.2A and the appropriate commercially available amines, where appropriate with subsequent enantiomer separation by chiral preparative HPLC:

| No | Structure | Name | Analytical data |
|---|---|---|---|
| 128 | 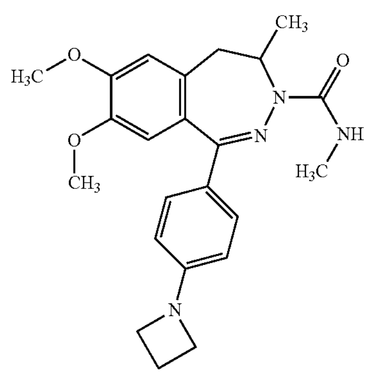 [SMILES: CNC(=O)N1N=C(c2ccc(N3CCC3)cc2)c2cc(OC)c(OC)cc2CC1C] | (±)-1-[4-(azetidin-1-yl)phenyl]-7,8-dimethoxy-N,4-dimethyl-4,5-dihydro-3H-2,3-benzodiazepine-3-carboxamide | $^1$H-NMR (400 MHz, CDCl$_3$): δ = 1.17 (d, 3H), 2.39-2.46 (m, 2H), 2.70 (dd, 1H), 2.85 (d, 3H), 2.89 (dd, 1H), 3.71 (s, 3H), 3.93 (s, 3H), 3.95-3.99 (m, 4H), 5.19-5.27 (m, 1H), 5.96 (q, 1H), 6.42 (d, 2H), 6.64 (s, 1H), 6.76 (s, 1H), 7.49 (d, 2H). LCMS (Method 2): $R_t$ = 1.18 min; m/z = 409 (M + H)$^+$ |
| 128.1 | 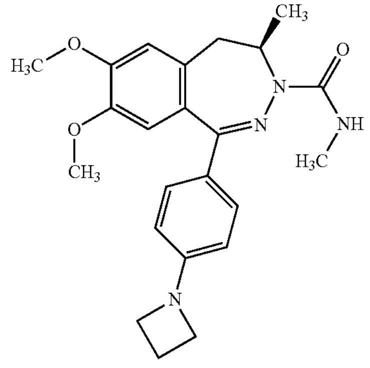 [SMILES: CNC(=O)N1N=C(c2ccc(N3CCC3)cc2)c2cc(OC)c(OC)cc2C[C@H]1C] | (4R)-1-[4-(azetidin-1-yl)phenyl]-7,8-dimethoxy-N,4-dimethyl-4,5-dihydro-3H-2,3-benzodiazepine-3-carboxamide | prep. HPLC: Method VII analyt. HPLC (Method J): $R_t$ = 2.93 min $[α]_D^{20}$ = −415° (c = 1.00; methanol) |

| No | Structure | Name | Analytical data |
|---|---|---|---|
| 128.2 | 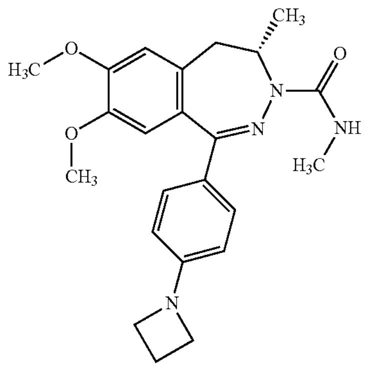 [SMILES: CNC(=O)N1N=C(c2ccc(N3CCC3)cc2)c2cc(OC)c(OC)cc2C[C@@H]1C] | (4S)-1-[4-(azetidin-1-yl)phenyl]-7,8-dimethoxy-N,4-dimethyl-4,5-dihydro-3H-2,3-benzodiazepine-3-carboxamide | prep. HPLC: Method VII<br>analyt. HPLC (Method J):<br>$R_t$ = 3.68 min<br>$[\alpha]_D^{20}$ = 442° (c = 1.00; methanol) |
| 129 | 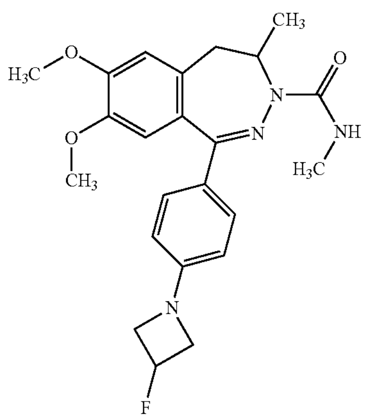 [SMILES: CNC(=O)N1N=C(c2ccc(N3CC(F)C3)cc2)c2cc(OC)c(OC)cc2CC1C] | (±)-1-[4-(3-fluoroazetidin-1-yl)phenyl]-7,8-dimethoxy-N,4-dimethyl-4,5-dihydro-3H-2,3-benzodiazepine-3-carboxamide | $^1$H-NMR (300 MHz, CDCl$_3$): δ = 1.12 (d, 3H), 2.72 (dd, 1H), 2.86 (d, 3H), 2.93 (dd, 1H), 3.70 (s, 3H), 3.93 (s, 3H), 3.98-4.10 (m, 2H), 4.20-4.31 (m, 2H), 5.21-5.31 (m, 1H), 5.32-5.39 and 5.52-5.58 (m, 1H), 6.05 (q, 1H), 6.47 (d, 2H), 6.62 (s, 1H), 6.75 (s, 1H), 7.48 (d, 2H).<br>LCMS (Method 2): $R_t$ = 1.15 min; m/z = 427 (M + H)$^+$ |
| 129.1 | 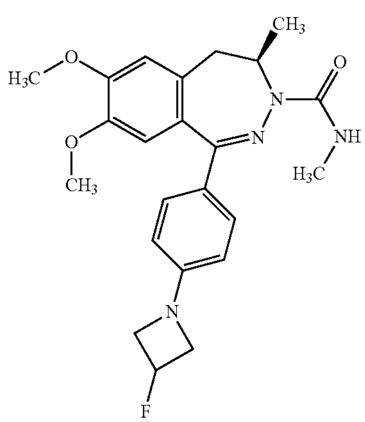 [SMILES: CNC(=O)N1N=C(c2ccc(N3CC(F)C3)cc2)c2cc(OC)c(OC)cc2C[C@H]1C] | (4R)-1-[4-(3-fluoroazetidin-1-yl)phenyl]-7,8-dimethoxy-N,4-dimethyl-4,5-dihydro-3H-2,3-benzodiazepine-3-carboxamide | prep. HPLC: Method VII<br>analyt. HPLC (Method J):<br>$R_t$ = 2.93 min<br>$[\alpha]_D^{20}$ = −340° (c = 1.00; methanol) |
| 129.2 | 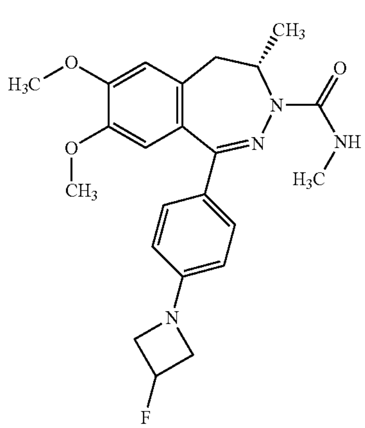 [SMILES: CNC(=O)N1N=C(c2ccc(N3CC(F)C3)cc2)c2cc(OC)c(OC)cc2C[C@@H]1C] | (4S)-1-[4-(3-fluoroazetidin-1-yl)phenyl]-7,8-dimethoxy-N,4-dimethyl-4,5-dihydro-3H-2,3-benzodiazepine-3-carboxamide | prep. HPLC: Method VII<br>analyt. HPLC (Method J):<br>$R_t$ = 3.68 min<br>$[\alpha]_D^{20}$ = 401° (c = 1.00; methanol) |

| No | Name | Analytical data |
|---|---|---|
| 130 | (±)-1-[4-(4-hydroxypiperidin-1-yl)phenyl]-7,8-dimethoxy-N,4-dimethyl-4,5-dihydro-3H-2,3-benzodiazepine-3-carboxamide | $^1$H-NMR (300 MHz, DMSO-d$_6$): δ = 1.02 (d, 3H), 1.35-1.47 (m, 2H), 1.72-1.83 (m, 2H), 2.36-2.50 (m, 1H), 2.59 (d, 3H), 2.79 (dd, 1H), 2.88-3.00 (m, 2H), 3.57 (s, 3H), 3.57-3.67 (m, 3H), 3.80 (s, 3H), 4.65 (d, 1H), 4.78-4.90 (m, 1H), 6.22 (q, 1H), 6.52 (s, 1H), 6.90 (d, 2H), 6.99 (s, 1H), 7.54 (d, 2H). LCMS (Method 2): R$_t$ = 0.93 min; m/z = 453 (M + H)$^+$ |
| 130.1 | (4S)-1-[4-(4-hydroxypiperidin-1-yl)phenyl]-7,8-dimethoxy-N,4-dimethyl-4,5-dihydro-3H-2,3-benzodiazepine-3-carboxamide | [α]$_D^{20}$ = 336° (c = 1.00; methanol) LCMS (Method 2): R$_t$ = 0.93 min; m/z = 453 (M + H)$^+$ |
| 131 | (±)-7,8-dimethoxy-N,4-dimethyl-1-[4-(piperazin-1-yl)phenyl]-4,5-dihydro-3H-2,3-benzodiazepine-3-carboxamide | $^1$H-NMR (300 MHz, DMSO-d$_6$): δ = 1.02 (d, 3H), 2.38-2.49 (m, 1H), 2.59 (d, 3H), 2.80 (dd, 1H), 2.84-2.87 (m, 4H), 3.16-3.19 (m, 4H), 3.56 (s, 3H), 3.80 (s, 3H), 4.80-4.91 (m, 1H), 6.26 (q, 1H), 6.50 (s, 1H), 6.91 (d, 2H), 6.99 (s, 1H), 7.56 (d, 2H). LCMS (Method 2): R$_t$ = 0.69 min; m/z = 438 (M + H)$^+$ |

| No | Structure | Name | Analytical data |
|---|---|---|---|
| 131.1 | 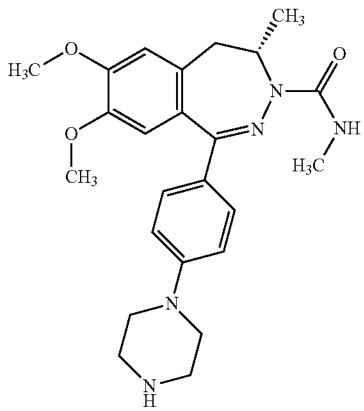 [SMILES: CNC(=O)N1N=C(c2ccc(N3CCNCC3)cc2)c2cc(OC)c(OC)cc2C[C@@H]1C] | (4S)-7,8-dimethoxy-N,4-dimethyl-1-[4-(piperazin-1-yl)phenyl]-4,5-dihydro-3H-2,3-benzodiazepine-3-carboxamide | $[\alpha]_D^{20}$ = +323.7° (c = 1.00; methanol) LCMS (Method 1): $R_t$ = 0.70 min; m/z = 438 (M + H)⁺ |
| 127 | 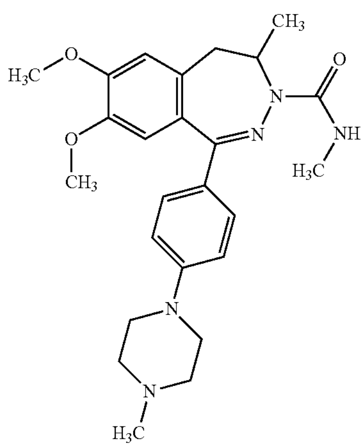 [SMILES: CNC(=O)N1N=C(c2ccc(N3CCN(C)CC3)cc2)c2cc(OC)c(OC)cc2CC1C] | (±)-7,8-dimethoxy-N,4-dimethyl-1-[4-(4-methylpiperazin-1-yl)phenyl]-4,5-dihydro-3H-2,3-benzodiazepine-3-carboxamide | ¹H-NMR (300 MHz, CDCl₃): δ = 1.10 (d, 3H), 2.39 (s, 3H), 2.58-2.66 (m, 4H), 2.72 (dd, 1H), 2.86 (d, 3H), 2.94 (dd, 1H), 3.29-3.37 (m, 4H), 3.70 (s, 3H), 3.93 (s, 3H), 5.24-5.34 (m, 1H), 6.10 (q, 1H), 6.64 (s, 1H), 6.74 (s, 1H), 6.92 (d, 2H), 7.49 (d, 2H). LCMS (Method 1): $R_t$ = 0.73 min; m/z = 452 (M + H)⁺ |
| 132 | 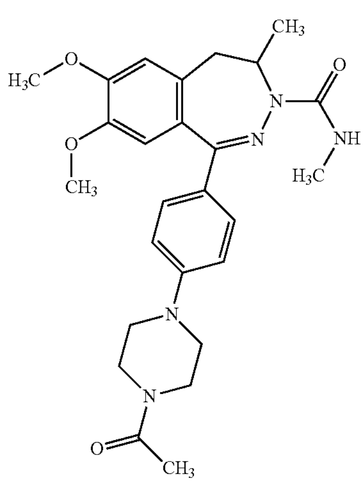 [SMILES: CNC(=O)N1N=C(c2ccc(N3CCN(C(C)=O)CC3)cc2)c2cc(OC)c(OC)cc2CC1C] | (±)-1-[4-(4-acetylpiperazin-1-yl)phenyl]-7,8-dimethoxy-N,4-dimethyl-4,5-dihydro-3H-2,3-benzodiazepine-3-carboxamide | ¹H-NMR (300 MHz, DMSO-d₆): δ = 1.01 (d, 3H), 2.01 (s, 3H), 2.39-2.50 (m, 1H), 2.59 (d, 3H), 2.81 (dd, 1H), 3.16-3.31 (m, 4H), 3.51-3.59 (m, 4H), 3.56 (s, 3H), 3.80 (s, 3H), 4.80-4.92 (m, 1H), 6.28 (q, 1H), 6.50 (s, 1H), 6.94 (d, 2H), 6.99 (s, 1H), 7.58 (d, 2H). LCMS (Method 2): $R_t$ = 0.97 min; m/z = 480 (M + H)⁺ |

| No | Structure | Name | Analytical data |
|---|---|---|---|
| 132.1 | 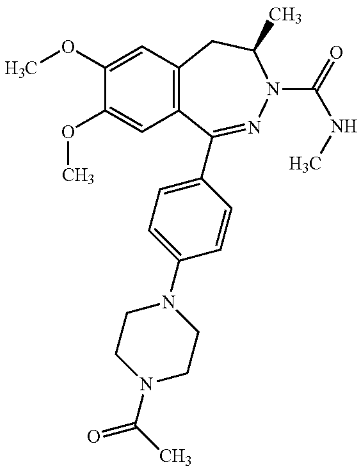 [SMILES: CNC(=O)N1N=C(c2ccc(N3CCN(C(C)=O)CC3)cc2)c2cc(OC)c(OC)cc2C[C@H]1C] | (4R)-1-[4-(4-acetylpiperazin-1-yl)phenyl]-7,8-dimethoxy-N,4-dimethyl-4,5-dihydro-3H-2,3-benzodiazepine-3-carboxamide | prep. HPLC: Method XI analyt. HPLC (Method L): $R_t$ = 7.27 min |
| 132.2 | 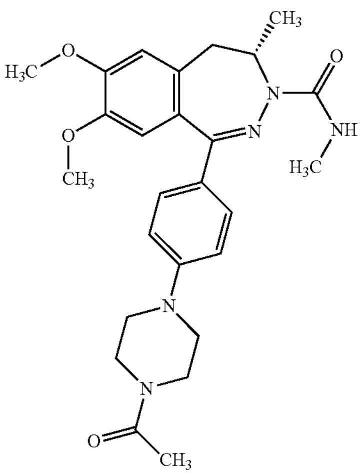 [SMILES: CNC(=O)N1N=C(c2ccc(N3CCN(C(C)=O)CC3)cc2)c2cc(OC)c(OC)cc2C[C@@H]1C] | (4S)-1-[4-(4-acetylpiperazin-1-yl)phenyl]-7,8-dimethoxy-N,4-dimethyl-4,5-dihydro-3H-2,3-benzodiazepine-3-carboxamide | prep. HPLC: Method XI analyt. HPLC (Method L): $R_t$ = 8.98 min |
| 133 | 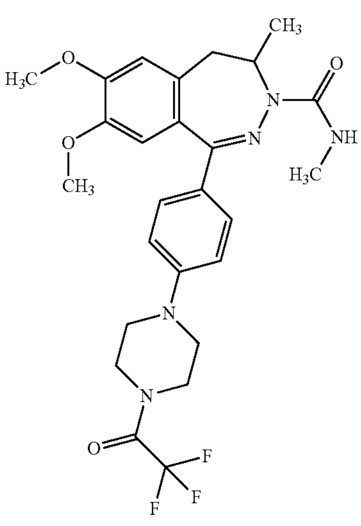 [SMILES: CNC(=O)N1N=C(c2ccc(N3CCN(C(=O)C(F)(F)F)CC3)cc2)c2cc(OC)c(OC)cc2CC1C] | (±)-7,8-dimethoxy-N,4-dimethyl-1-{4-[4-(trifluoroacetyl)piperazin-1-yl]phenyl}-4,5-dihydro-3H-2,3-benzodiazepine-3-carboxamide | $^1$H-NMR (300 MHz, DMSO-d$_6$): δ = 1.01 (d, 3H), 2.40-2.49 (m, 1H), 2.60 (d, 3H), 2.81 (dd, 1H), 3.31-3.40 (m, 4H), 3.56 (s, 3H), 3.65-3.75 (m, 4H), 3.80 (s, 3H), 4.82-4.94 (m, 1H), 6.29 (q, 1H), 6.50 (s, 1H), 6.95 (d, 2H), 6.99 (s, 1H), 7.59 (d, 2H). LCMS (Method 2): $R_t$ = 1.22 min; m/z = 534 (M + H)$^+$ |

| No | Structure | Name | Analytical data |
|---|---|---|---|
| 134 | 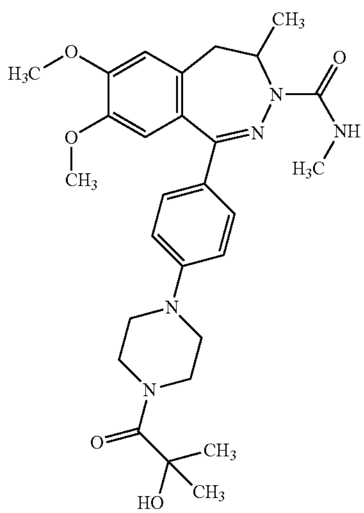 [SMILES: CNC(=O)N1N=C(c2ccc(N3CCN(C(=O)C(C)(C)O)CC3)cc2)c2cc(OC)c(OC)cc2CC1C] | (±)-1-{4-[4-(2-hydroxy-2-methylpropanoyl)-piperazin-1-yl]phenyl}-7,8-dimethoxy-N,4-dimethyl-4,5-dihydro-3H-2,3-benzodiazepine-3-carboxamide | $^1$H-NMR (300 MHz, CDCl$_3$): δ = 1.08 (d, 3H), 1.54 (s, 6H), 2.74 (dd, 1H), 2.87 (d, 3H), 2.97 (dd, 1H), 3.27-3.34 (m, 4H), 3.69 (s, 3H), 3.65-3.92 (m, 4H), 3.93 (s, 3H), 4.07 (s, 1H), 6.25-6.37 (m, 1H), 6.17 (q, 1H), 6.62 (s, 1H), 6.74 (s, 1H), 6.92 (d, 2H), 7.50 (d, 2H).<br>LCMS (Method 1): R$_t$ = 1.02 min; m/z = 524 (M + H)$^+$ |
| 134.1 | 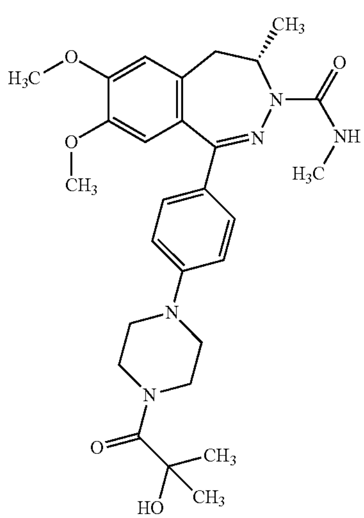 [SMILES: CNC(=O)N1N=C(c2ccc(N3CCN(C(=O)C(C)(C)O)CC3)cc2)c2cc(OC)c(OC)cc2C[C@@H]1C] | (4S)-1-{4-[4-(2-hydroxy-2-methylpropanoyl)piper-azin-1-yl]phenyl}-7,8-dimethoxy-N,4-dimethyl-4,5-dihydro-3H-2,3-benzodiazepine-3-carboxamide | [α]$_D^{20}$ = +291.8° (c = 1.00; methanol)<br>LCMS (Method 1): R$_t$ = 1.01 min; m/z = 524 (M + H)$^+$ |
| 135 | 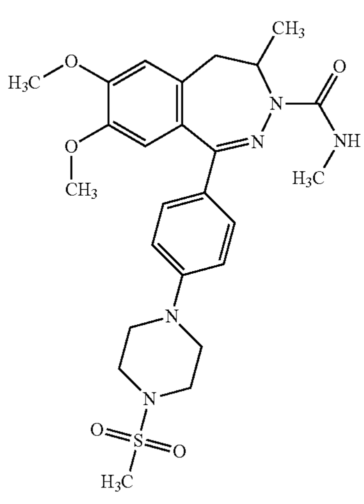 [SMILES: CNC(=O)N1N=C(c2ccc(N3CCN(S(C)(=O)=O)CC3)cc2)c2cc(OC)c(OC)cc2CC1C] | (±)-7,8-dimethoxy-N,4-dimethyl-1-{4-[4-(methylsulphonyl)piper-azin-1-yl]phenyl}-4,5-dihydro-3H-2,3-benzodiazepine-3-carboxamide | $^1$H-NMR (300 MHz, DMSO-d$_6$): δ = 1.01 (d, 3H), 2.38-2.49 (m, 1H), 2.60 (d, 3H), 2.81 (dd, 1H), 2.89 (s, 3H), 3.17-3.26 (m, 4H), 3.30-3.38 (m, 4H), 3.56 (s, 3H), 3.80 (s, 3H), 4.82-4.94 (m, 1H), 6.29 (q, 1H), 6.51 (s, 1H), 6.97 (d, 2H), 6.99 (s, 1H), 7.58 (d, 2H).<br>LCMS (Method 2): R$_t$ = 1.04 min; m/z = 516 (M + H)$^+$ |

| No | Structure | Name | Analytical data |
|---|---|---|---|
| 135.1 | 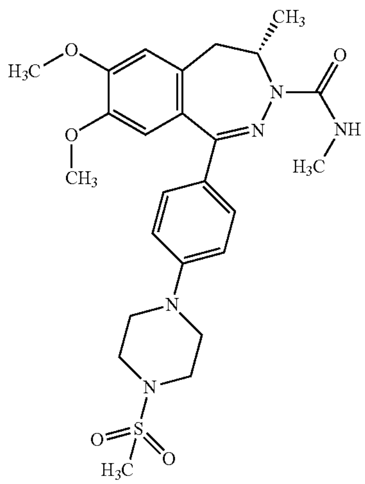 [SMILES: CNC(=O)N1N=C(c2ccc(N3CCN(S(C)(=O)=O)CC3)cc2)c2cc(OC)c(OC)cc2C[C@@H]1C] | (4S)-7,8-dimethoxy-N,4-dimethyl-1-{4-[4-(methylsulphonyl)piper-azin-1-yl]phenyl}-4,5-dihydro-3H-2,3-benzodiazepine-3-carboxamide | $[\alpha]_D^{20}$ = +314.3° (c = 1.00; methanol) LCMS (Method 1): $R_t$ = 1.08 min; m/z = 516 (M + H)$^+$ |
| 136 | 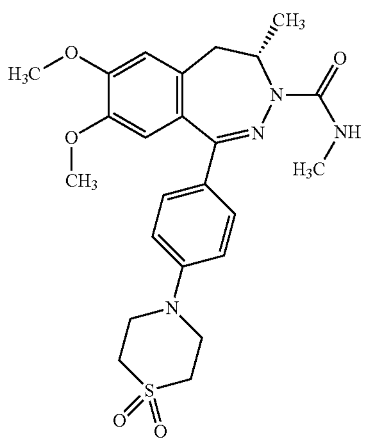 [SMILES: CNC(=O)N1N=C(c2ccc(N3CCS(=O)(=O)CC3)cc2)c2cc(OC)c(OC)cc2C[C@@H]1C] | (4S)-1-[4-(1,1-dioxidothiomorpholin-4-yl)phenyl]-7,8-dimethoxy-N,4-dimethyl-4,5-dihydro-3H-2,3-benzodiazepine-3-carboxamide | $^1$H-NMR (300 MHz, DMSO-d$_6$): δ = 1.01 (d, 3H), 2.40-2.50 (m, 1H), 2.60 (d, 3H), 2.81 (dd, 1H), 3.06-3.15 (m, 4H), 3.57 (s, 3H), 3.80 (s, 3H), 3.82-3.98 (m, 4H), 4.82-4.94 (m, 1H), 6.29 (q, 1H), 6.52 (s, 1H), 7.00 (s, 1H), 7.01 (d, 2H), 7.59 (d, 2H). LCMS (Method 2): $R_t$ = 0.96 min; m/z = 487 (M + H)$^+$ $[\alpha]_D^{20}$ = +309.1° (c = 1.00; methanol) |
| 137 | 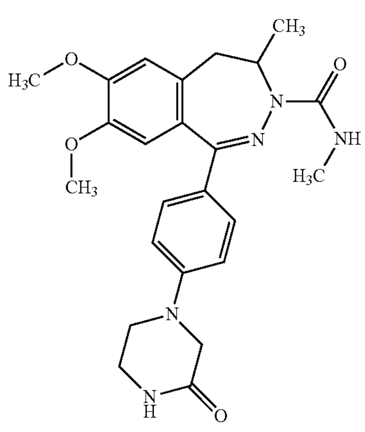 [SMILES: CNC(=O)N1N=C(c2ccc(N3CCNC(=O)C3)cc2)c2cc(OC)c(OC)cc2CC1C] | (±)-7,8-dimethoxy-N,4-dimethyl-1-[4-(3-oxopiperazin-1-yl)phenyl]-4,5-dihydro-3H-2,3-benzodiazepine-3-carboxamide | $^1$H-NMR (300 MHz, DMSO-d$_6$): δ = 1.02 (d, 3H), 2.38-2.51 (m, 1H), 2.60 (d, 3H), 2.81 (dd, 1H), 3.26-3.33 (m, 2H), 3.44-3.50 (m, 2H), 3.56 (s, 3H), 3.76-3.79 (m, 2H), 3.80 (s, 3H), 4.80-4.93 (m, 1H), 6.27 (q, 1H), 6.50 (s, 1H), 6.89 (d, 2H), 6.99 (s, 1H), 7.58 (d, 2H), 8.08 (s, 1H). LCMS (Method 2): $R_t$ = 0.88 min; m/z = 452 (M + H)$^+$ |

| No | Name | Analytical data |
|---|---|---|
| 138 | (±)-7,8-dimethoxy-N,4-dimethyl-1-[4-(4-methyl-3-oxopiperazin-1-yl)phenyl]-4,5-dihydro-3H-2,3-benzodiazepine-3-carboxamide | $^1$H-NMR (300 MHz, CDCl$_3$): δ = 1.09 (d, 3H), 2.73 (dd, 1H), 2.87 (d, 3H), 2.96 (dd, 1H), 3.06 (s, 3H), 3.49-3.54 (m, 2H), 3.55-3.61 (m, 2H), 3.69 (s, 3H), 3.93 (s, 3H), 3.96 (s, 2H), 5.26-5.35 (m, 1H), 6.15 (q, 1H), 6.62 (s, 1H), 6.74 (s, 1H), 6.86 (d, 2H), 7.51 (d, 2H). LCMS (Method 2): R$_t$ = 0.96 min; m/z = 466 (M + H)$^+$ |
| 138.1 | (4S)-7,8-dimethoxy-N,4-dimethyl-1-[4-(4-methyl-3-oxopiperazin-1-yl)phenyl]-4,5-dihydro-3H-2,3-benzodiazepine-3-carboxamide | [α]$_D^{20}$ = +327.3° (c = 1.00; methanol) LCMS (Method 1): R$_t$ = 0.95 min; m/z = 466 (M + H)$^+$ |
| 139 | (±)-7,8-dimethoxy-N,4-dimethyl-1-[4-(piperidin-1-yl)phenyl]-4,5-dihydro-3H-2,3-benzodiazepine-3-carboxamide | $^1$H-NMR (300 MHz, CDCl$_3$): δ = 1.13 (d, 3H), 1.56-1.76 (m, 6H), 2.71 (dd, 1H), 2.86 (d, 3H), 2.91 (dd, 1H), 3.24-3.32 (m, 4H), 3.70 (s, 3H), 3.93 (s, 3H), 5.20-5.30 (m, 1H), 6.03 (q, 1H), 6.65 (s, 1H), 6.75 (s, 1H), 6.91 (d, 2H), 7.49 (d, 2H). LCMS (Method 2): R$_t$ = 1.24 min; m/z = 437 (M + H)$^+$ |

The following exemplary compounds were prepared analogously to Example 7 (alternative method) from Example 51A and the appropriate commercially available amines.

| No | Structure | Name | Analytical data |
|---|---|---|---|
| 140 | 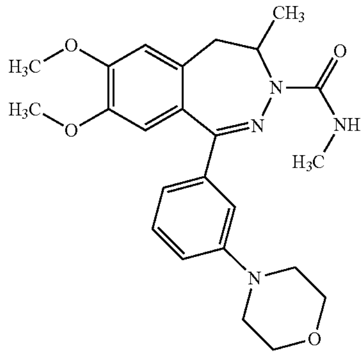 [SMILES: CNC(=O)N1N=C(c2cccc(N3CCOCC3)c2)c2cc(OC)c(OC)cc2CC1C] | (±)-7,8-dimethoxy-N,4-dimethyl-1-[3-(morpholin-4-yl)phenyl]-4,5-dihydro-3H-2,3-benzodiazepine-3-carboxamide | $^1$H-NMR (300 MHz, CDCl$_3$): δ = 1.00 (d, 3H), 2.83 (dd, 1H), 2.87 (d, 3H), 3.10 (dd, 1H), 3.16 (m, 4H), 3.65 (s, 3H), 3.86 (m, 4H), 3.93 (s, 3H), 5.45 (m, 1H), 6.47 (qbr, 1H), 6.61 (s, 1H), 6.71 (s, 1H), 6.96 (dbr, 1H), 7.00 (sbr, 1H), 7.03 (dbr, 1H), 7.31 (dd, 1H). LCMS (Method 3): R$_t$ = 1.11 min; m/z = 439 (M + H)$^+$ |
| 141 | 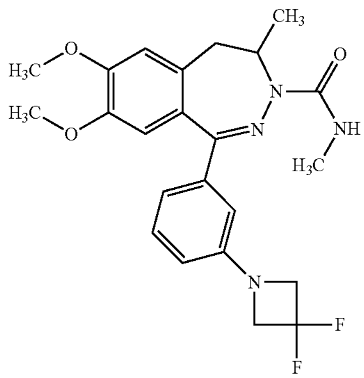 [SMILES: CNC(=O)N1N=C(c2cccc(N3CC(F)(F)C3)c2)c2cc(OC)c(OC)cc2CC1C] | (±)-1-[3-(3,3-difluoroazetidin-1-yl)phenyl]-7,8-dimethoxy-N,4-dimethyl-4,5-dihydro-3H-2,3-benzodiazepine-3-carboxamide | $^1$H-NMR (400 MHz, CDCl$_3$): δ = 0.99 (d, 3H), 2.84 (dd, 1H), 2.87 (d, 3H), 3.11 (dd, 1H), 3.66 (s, 3H), 3.93 (s, 3H), 4.23 (m, 4H), 5.46 (m, 1H), 6.48 (m, 1H), 6.55 (dbr, 1H), 6.59 (m, 2H), 6.71 (s, 1H), 6.96 (dbr, 1H), 7.28 (dd, 1H). LCMS (Method 3): R$_t$ = 1.22 min; m/z = 445 (M + H)$^+$ |
| 142 | 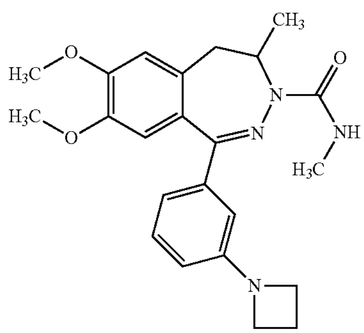 [SMILES: CNC(=O)N1N=C(c2cccc(N3CCC3)c2)c2cc(OC)c(OC)cc2CC1C] | (±)-1-[3-(azetidin-1-yl)phenyl]-7,8-dimethoxy-N,4-dimethyl-4,5-dihydro-3H-2,3-benzodiazepine-3-carboxamide | $^1$H-NMR (300 MHz, CDCl$_3$): δ = 1.00 (d, 3H), 2.40 (m, 2H), 2.82 (dd, 1H), 2.87 (d, 3H), 3.09 (dd, 1H), 3.67 (s, 3H), 3.91 (m, 4H), 3.93 (s, 3H), 5.43 (m, 1H), 6.48 (m, 1H), 6.57 (m, 2H), 6.62 (s, 1H), 6.71 (s, 1H), 6.89 (m, 1H), 7.24 (dd, 1H). LCMS (Method 3): R$_t$ = 1.22 min; m/z = 409 (M + H)$^+$ |
| 143 | 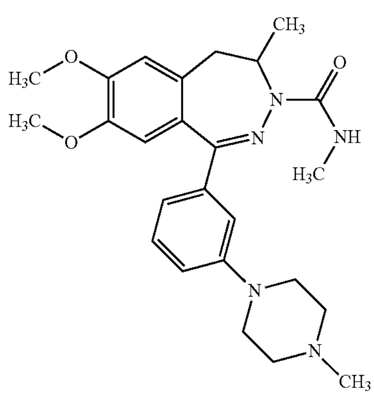 | (±)-7,8-dimethoxy-N,4-dimethyl-1-[3-(4-methylpiperazin-1-yl)phenyl]-4,5-dihydro 3H-2,3-benzodiazepine-3-carboxamide | $^1$H-NMR (400 MHz, CDCl$_3$): δ = 0.99 (d, 3H), 2.36 (s, 3H), 2.59 (m, 4H), 2.83 (dd, 1H), 2.86 (d, 3H), 3.09 (dd, 1H), 3.22 (m, 4H), 3.64 (s, 3H), 3.93 (s, 3H), 5.43 (m, 1H), 6.47 (qbr, 1H), 6.61 (s, 1H), 6.71 (s, 1H), 6.99 (m, 2H), 7.01 (sbr, 1H), 7.28 (dd, 1H). LCMS (Method 3): R$_t$ = 0.76 min; m/z = 452 (M + H)$^+$ |

The following exemplary compounds were prepared analogously to Example 7 (alternative method) from Example 60A and the appropriate commercially available amines.

| No | Structure | Name | Analytical data |
|---|---|---|---|
| 144 | 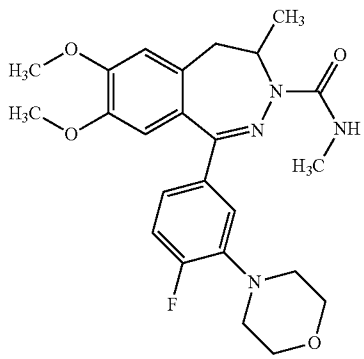 [SMILES: CNC(=O)N1N=C(c2ccc(F)c(N3CCOCC3)c2)c2cc(OC)c(OC)cc2CC1C] | (±)-1-[4-fluoro-3-(morpholin-4-yl)phenyl]-7,8-dimethoxy-N,4-dimethyl-4,5-dihydro-3H-2,3-benzodiazepine-3-carboxamide | $^1$H-NMR (300 MHz, CDCl$_3$): δ = 0.99 (d, 3H), 2.85 (dd, 1H), 2.88 (d, 3H), 3.08 (m, 1H), 3.09 (m, 4H), 3.66 (s, 3H), 3.88 (m, 4H), 3.94 (s, 3H), 5.45 (m, 1H), 6.43 (qbr, 1H), 6.56 (s, 1H), 6.72 (s, 1H), 7.02-7.18 (m, 3H). LCMS (Method 3): R$_t$ = 0.96 min; m/z = 457 (M + H)$^+$ |
| 145 | 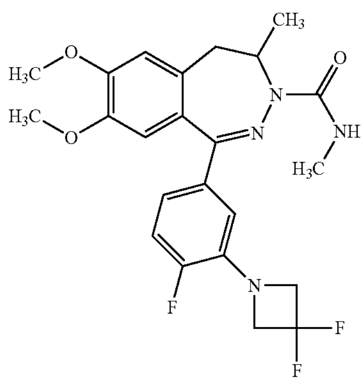 [SMILES: CNC(=O)N1N=C(c2ccc(F)c(N3CC(F)(F)C3)c2)c2cc(OC)c(OC)cc2CC1C] | (±)-1-[3-(3,3-difluoroazetidin-1-yl)-4-fluorophenyl]-7,8-dimethoxy-N,4-dimethyl-4,5-dihydro-3H-2,3-benzodiazepine-3-carboxamide | $^1$H-NMR (400 MHz, CDCl$_3$): δ = 0.99 (d, 3H), 2.83 (dd, 1H), 2.88 (d, 3H), 3.09 (dd, 1H), 3.68 (s, 3H), 3.94 (s, 3H), 4.32 (m, 4H), 5.45 (m, 1H), 6.41 (m, 1H), 6.56 (d, 1H), 6.63 (dd, 1H), 6.72 (s, 1H), 6.91 (ddd, 1H), 7.02 (dd, 1H). LCMS (Method 3): R$_t$ = 1.31 min; m/z = 463 (M + H)$^+$ |
| 146 | 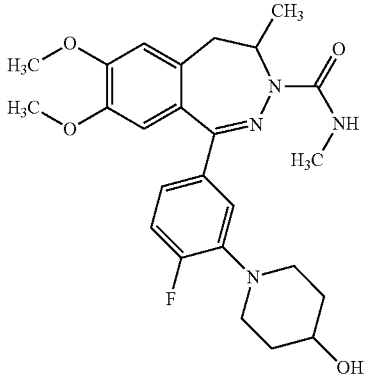 [SMILES: CNC(=O)N1N=C(c2ccc(F)c(N3CCC(O)CC3)c2)c2cc(OC)c(OC)cc2CC1C] | (±)-1-[4-fluoro-3-(4-hydroxypiperidin-1-yl)phenyl]-7,8-dimethoxy-N,4-dimethyl-4,5-dihydro-3H-2,3-benzodiazepine-3-carboxamide | $^1$H-NMR (400 MHz, CDCl$_3$): δ = 1.00 (d, 3H), 1.76 (m, 2H), 2.03 (m, 2H), 2.82 (dd, 1H), 2.85 (m, 2H), 2.88 (d, 3H), 3.07 (m, 1H), 3.34 (m, 2H), 3.66 (s, 3H), 3.85 (m, 1H), 3.94 (s, 3H), 5.42 (m, 1H), 6.40 (m, 1H), 6.56 (s, 1H), 6.72 (s, 1H), 7.00-7.14 (m, 3H). LCMS (Method 3): R$_t$ = 1.03 min; m/z = 471 (M + H)$^+$ |

Example 147

(±)-7,8-Dimethoxy-N,4-dimethyl-1-[4-(5-methyl-3-phenyl-1H-pyrazol-1-yl)phenyl]-4,5-dihydro-3H-2,3-benzodiazepine-3-carboxamide

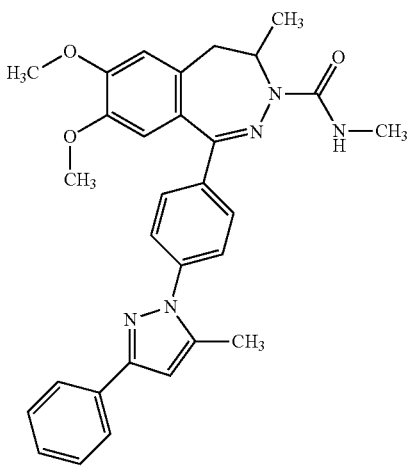 [SMILES: CNC(=O)N1N=C(c2ccc(-n3nc(-c4ccccc4)cc3C)cc2)c2cc(OC)c(OC)cc2CC1C]

Under argon, 100 mg (0.231 mmol) of (±)-1-(4-bromophenyl)-7,8-dimethoxy-N,4-dimethyl-4,5-dihydro-3H-2,3-benzodiazepine-3-carboxamide (Example 49A), 44 mg (0.28 mmol) of 5-methyl-3-phenyl-1H-pyrazole, 67 mg (0.49 mmol) of potassium carbonate and 4.4 mg (0.023 mmol) of copper(I) iodide were initially charged in 2 ml of degassed toluene. Under argon, 13.2 mg (0.093 mmol) of (±)-(trans)-N,N'-dimethylcyclohexane-1,2-diamine were then added, and the mixture was degassed again and heated at 140° C. for 16 hours. After cooling, the mixture was filtered off and the filter cake washed with ethyl acetate and dried under reduced pressure. The residue was purified by preparative HPLC. This gave 17 mg (14% of theory) of the desired product as a solid.

LCMS (Method 2): $R_t$=1.44 min; m/z=510 (M+H)$^+$ $^1$H-NMR (300 MHz, CDCl$_3$): δ=1.01 (d, 3H), 2.45 (s, 3H), 2.87 (dd, 1H), 2.92 (d, 3H), 3.14 (dd, 1H), 3.70 (s, 3H), 3.95 (s, 3H), 5.43-5.52 (m, 1H), 6.48-6.56 (m, 1H), 6.58 (s, 1H), 6.65 (s, 1H), 6.74 (s, 1H), 7.34 (t, 1H), 7.39-7.47 (m, 2H), 7.58 (d, 2H), 7.63 (d, 2H), 7.89 (d, 2H).

The following exemplary compounds were prepared analogously to Example 147 starting with the bromo derivative 49A by reaction with the appropriate, commercially available pyrazoles. Using the enantiomerically pure bromide 49.2A, it was possible to obtain the corresponding enantiomerically pure products directly.

| No | Structure | Name | Analytical data |
|---|---|---|---|
| 147.1 | 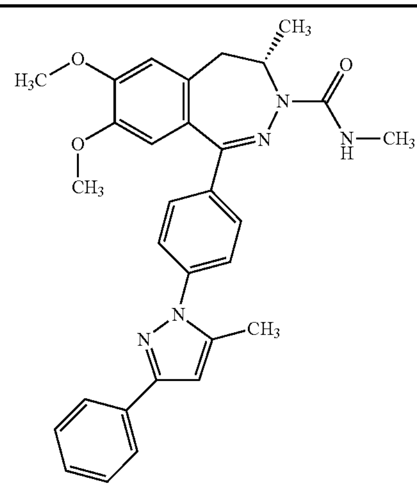 | (4S)-7,8-dimethoxy-N,4-dimethyl-1-[4-(5-methyl-3-phenyl-1H-pyrazol-1-yl)phenyl]-4,5-dihydro-3H-2,3-benzodiazepine-3-carboxamide | LCMS (Method 2): $R_t$ = 1.44 min; m/z = 510 (M + H)$^+$. $[α]_D^{20}$ = 68.8° (c = 1.00; methanol) |
| 148 | 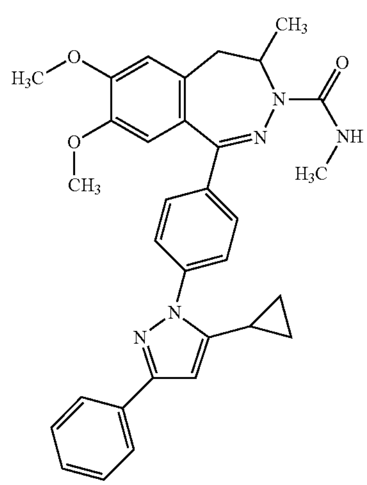 [SMILES: CNC(=O)N1N=C(c2ccc(-n3nc(-c4ccccc4)cc3C3CC3)cc2)c2cc(OC)c(OC)cc2CC1C] | (±)-1-[4-(5-cyclopropyl-3-phenyl-1H-pyrazol-1-yl)phenyl]-7,8-dimethoxy-N,4-dimethyl-4,5-dihydro-3H-2,3-benzodiazepine-3-carboxamide | $^1$H-NMR (300 MHz, CDCl$_3$): δ = 0.89 (d, 2H), 1.01 (d, 3H), 1.07 (d, 2H), 1.84-1.98 (m, 1H), 2.86 (dd, 1H), 2.92 (d, 3H), 3.14 (d, 1H), 3.70 (s, 3H), 3.95 (s, 3H), 5.40-5.53 (m, 1H), 6.35 (s, 1H), 6.52 (s, br, 1H), 6.65 (s, 1H), 6.74 (s, 1H), 7.34 (d, 1H), 7.42 (t, 2H), 7.64 (d, 2H), 7.77 (d, 2H), 7.88 (d, 2H). LCMS (Method 2): $R_t$ = 1.52 min; m/z = 536 (M + H)$^+$. |

-continued

| No | Structure | Name | Analytical data |
|---|---|---|---|
| 148.1 | 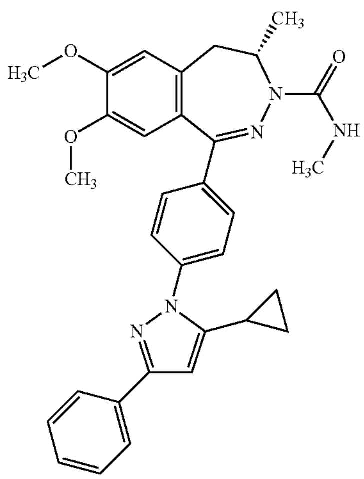 [SMILES: CNC(=O)N1N=C(c2ccc(-n3nc(-c4ccccc4)cc3C3CC3)cc2)c2cc(OC)c(OC)cc2C[C@@H]1C] | (4S)-1-[4-(5-cyclopropyl-3-phenyl-1H-pyrazol-1-yl)phenyl]-7,8-dimethoxy-N,4-dimethyl-4,5-dihydro-3H-2,3-benzodiazepine-3-carboxamide | LCMS (Method 2): $R_t$ = 1.52 min; m/z = 536 (M + H)$^+$. $[\alpha]_D^{20}$ = 103.9° (c = 1.00; methanol) |
| 149 | 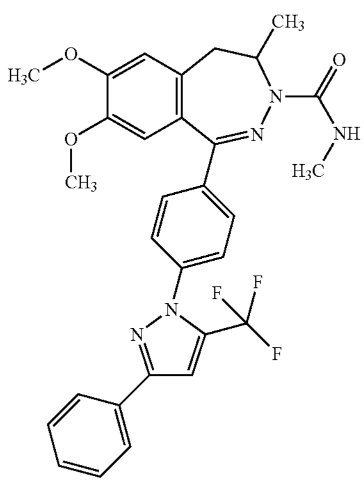 [SMILES: CNC(=O)N1N=C(c2ccc(-n3nc(-c4ccccc4)cc3C(F)(F)F)cc2)c2cc(OC)c(OC)cc2CC1C] | (±)-7,8-dimethoxy-N,4-dimethyl-1-{4-[3-phenyl-5-(trifluoromethyl)-1H-pyrazol-1-yl]phenyl}-4,5-dihydro-3H-2,3-benzodiazepine-3-carboxamide | $^1$H-NMR (400 MHz, CDCl$_3$): δ = 0.98 (d, 3H), 2.79-2.88 (m, 1H), 2.90 (s, br., 3H), 3.12 (d, 1H), 3.65 (s, 3H), 3.93 (s, 3H), 5.41-5.53 (m, 1H), 6.42-6.52 (m, 1H), 6.53 (s, 1H), 6.70 (s, 1H), 6.78 (s, 1H), 7.26-7.31 (m, 2H), 7.31-7.41 (m, 5H), 7.49 (d, 2H). LCMS (Method 2): $R_t$ = 1.52 min; m/z = 564 (M + H)$^+$. |
| 150 | 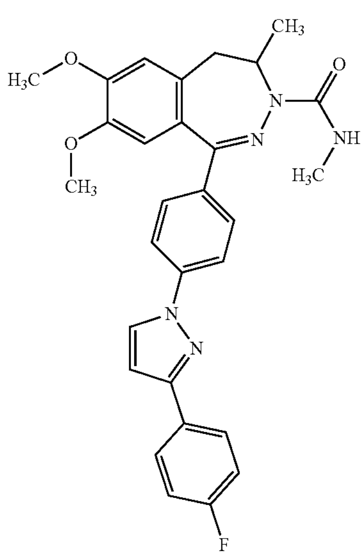 [SMILES: CNC(=O)N1N=C(c2ccc(-n3ccc(-c4ccc(F)cc4)n3)cc2)c2cc(OC)c(OC)cc2CC1C] | (±)-1-{4-[3-(4-fluorophenyl)-1H-pyrazol-1-yl]phenyl}-7,8-dimethoxy-N,4-dimethyl-4,5-dihydro-3H-2,3-benzodiazepine-3-carboxamide | $^1$H-NMR (400 MHz, CDCl$_3$): δ = 1.02 (d, 3H), 2.86 (dd, 1H), 2.91 (s, 3H), 3.13 (d, 1H), 3.67 (s, 3H), 3.95 (s, 3H), 5.46 (m, 1H), 6.49 (m, 1H), 6.63 (s, 1H), 6.72-6.81 (m, 2H), 7.09-7.19 (m, 2H), 7.62 (d, 2H), 7.81 (d, 2H), 7.87-7.95 (m, 2H), 7.99-8.04 (m, 1H). LCMS (Method 2): $R_t$ = 1.46 min; m/z = 514 (M + H)$^+$. |

| No | Structure | Name | Analytical data |
|---|---|---|---|
| 150.1 | 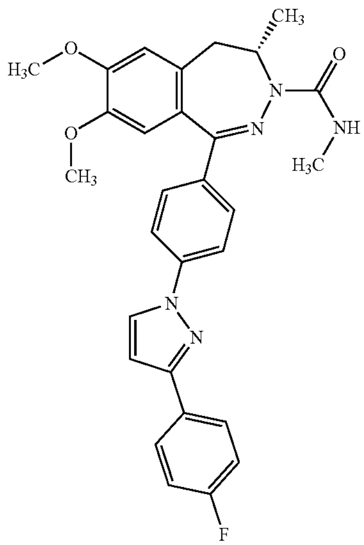 [SMILES: CNC(=O)N1N=C(c2ccc(-n3ccc(-c4ccc(F)cc4)n3)cc2)c2cc(OC)c(OC)cc2C[C@@H]1C] | (4S)-1-{4-[3-(4-fluorophenyl)-1H-pyrazol-1-yl]phenyl}-7,8-dimethoxy-N,4-dimethyl-4,5-dihydro-3H-2,3-benzodiazepine-3-carboxamide | prep. HPLC: Method V<br>analyt. HPLC (Method F): $R_t$ = 12.1 min<br>LCMS (Method 2): $R_t$ = 1.46 min; m/z = 514 (M + H)$^+$.<br>$[\alpha]_D^{20}$ = 142.0° (c = 1.00; methanol) |
| 150.2 | 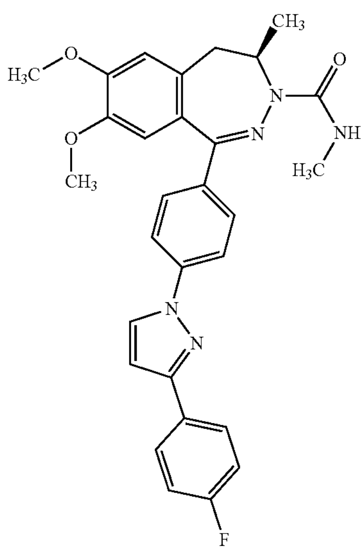 [SMILES: CNC(=O)N1N=C(c2ccc(-n3ccc(-c4ccc(F)cc4)n3)cc2)c2cc(OC)c(OC)cc2C[C@H]1C] | (4R)-1-{4-[3-(4-fluorophenyl)-1H-pyrazol-1-yl]phenyl}-7,8-dimethoxy-N,4-dimethyl-4,5-dihydro-3H-2,3-benzodiazepine-3-carboxamide | prep. HPLC: Method V<br>analyt. HPLC (Method F): $R_t$ = 7.6 min<br>LCMS (Method 2): $R_t$ = 1.46 min; m/z = 514 (M + H)$^+$.<br>$[\alpha]_D$20 = −137.3° (c = 1.00; methanol) |
| 151 | 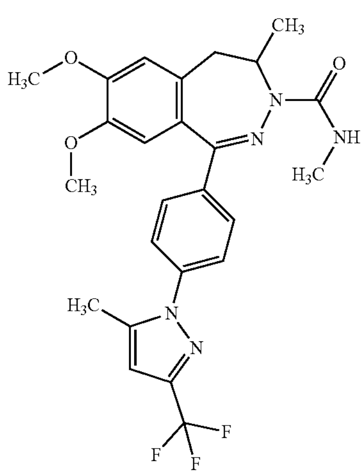 [SMILES: CNC(=O)N1N=C(c2ccc(-n3nc(C(F)(F)F)cc3C)cc2)c2cc(OC)c(OC)cc2CC1C] | (±)-7,8-dimethoxy-N,4-dimethyl-1-{4-[5-methyl-3-(trifluoromethyl)-1H-pyrazol-1-yl]phenyl}-4,5-dihydro-3H-2,3-benzodiazepine-3-carboxamide | $^1$H-NMR (500 MHz, CDCl$_3$): δ = 0.98 (d, 3H), 2.41 (s, 3H), 2.84-2.95 (m, 4H), 3.15 (dd, 1H), 3.67 (s, 3H), 3.94 (s, 3H), 5.46-5.53 (m, 1H), 6.50 (s, 1H), 6.51-6.55 (m, 1H), 6.60 (s, 1H), 6.73 (s, 1H), 7.49 (d, 2H), 7.60-7.65 (m, 2H).<br>LCMS (Method 2): $R_t$ = 1.38 min; m/z = 502 (M + H)$^+$. |

Example 152

(±)-7,8-Dimethoxy-N,4-dimethyl-1-[4-(1H-1,2,4-triazol-1-yl)phenyl]-4,5-dihydro-3H-2,3-benzodiazepine-3-carboxamide

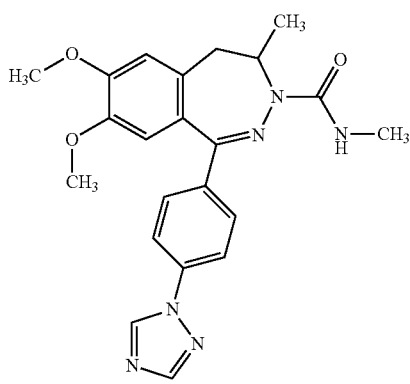

Under argon, 100 mg (0.231 mmol) of (±)-1-(4-bromophenyl)-7,8-dimethoxy-N,4-dimethyl-4,5-dihydro-3H-2,3-benzodiazepine-3-carboxamide (Example 49A), 19 mg (0.28 mmol) of 1H-1,2,4-triazole, 98 mg (0.46 mmol) of potassium phosphate, 2.2 mg (0.012 mmol) of copper(I) iodide and 3.3 mg (0.023 mmol) of (±)-(trans)-N,N'-dimethylcyclohexane-1,2-diamine were initially charged in 2 ml of DMF, the solution was degassed and the mixture was heated at 110° C. for 16 hours. As the conversion was poor, a further 2 mg of copper(I) iodide were added, and the mixture was degassed again and heated at 140° C. for a further 10 h. After cooling, sat. aqueous ammonium chloride solution was added, the mixture was extracted three times with ethyl acetate and the combined organic phases were dried under reduced pressure. The residue was purified by preparative HPLC. This gave 15 mg (2% of theory) of the desired product as a solid.

LCMS (Method 2): $R_t$=1.01 min; m/z=421 (M+H)$^+$ $^1$H-NMR (500 MHz, DMSO-d$_6$): δ=0.98 (d, 3H), 2.70 (d, 3H), 2.73 (dd, 1H), 2.97 (dd, 1H), 3.57 (s, 3H), 3.85 (s, 3H), 5.09-5.17 (m, 1H), 6.55 (s, 1H), 6.67 (q, 1H), 7.03 (s, 1H), 7.80-7.85 (m, 2H), 7.89-7.94 (m, 2H), 8.26 (s, 1H), 9.39 (s, 1H).

The following exemplary compounds were prepared analogously to Example 152 from the bromo derivative 49A by reaction with the appropriate, commercially available triazoles.

| No | Structure | Name | Analytical data |
|---|---|---|---|
| 153 | 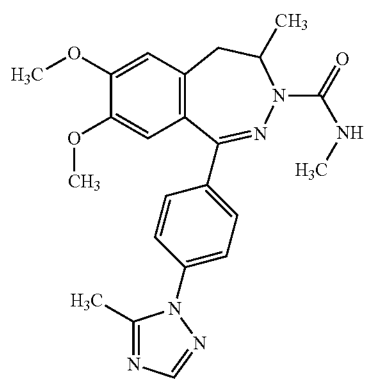 [SMILES: CNC(=O)N1N=C(c2ccc(-n3ncnc3C)cc2)c2cc(OC)c(OC)cc2CC1C] | (±)-7,8-dimethoxy-N,4-dimethyl-1-[4-(5-methyl-1H-1,2,4-triazol-1-yl)phenyl]-4,5-dihydro-3H-2,3-benzodiazepine-3-carboxamide | $^1$H-NMR (400 MHz, CDCl$_3$): δ = 0.98 (d, 3H), 2.51 (s, 3H), 2.87-2.95 (dd, 1H), 2.90 (d, 3H), 3.14 (dd, 1H), 3.65 (s, 3H), 3.94 (s, 3H), 5.43-5.53 (m, 1H), 6.51 (q, 1H), 6.58 (s, 1H), 6.73 (s, 1H), 7.61 (d, 2H), 7.68 (d, 2H), 8.51 (s, br, 1H). LCMS (Method 2): $R_t$ = 1.04 min; m/z = 435 (M + H)+. |
| 154 | 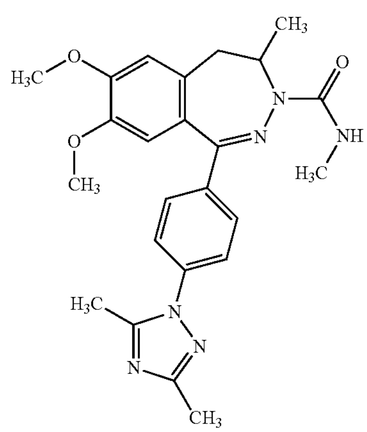 [SMILES: CNC(=O)N1N=C(c2ccc(-n3nc(C)nc3C)cc2)c2cc(OC)c(OC)cc2CC1C] | (±)-1-[4-(3,5-dimethyl-1H-1,2,4-triazol-1-yl)phenyl]-7,8-dimethoxy-N,4-dimethyl-4,5-dihydro-3H-2,3-benzodiazepine-3-carboxamide | $^1$H-NMR (300 MHz, CDCl$_3$): δ = 0.97 (d, 3H), 2.50 (s, 3H), 2.64 (s, br, 3H), 2.88 (dd, 1H), 2.91 (d, 3H), 3.15 (d, 1H), 3.66 (s, 3H), 3.94 (s, 3H), 5.43-5.55 (m, 1H), 6.53 (q, 1H), 6.57 (s, 1H), 6.73 (s, 1H), 7.48 (d, 2H), 7.61-7.70 (m, 2H). LCMS (Method 2): $R_t$ = 1.01 min; m/z = 449 (M + H)$^+$. |

Example 155

(±)-8-tert-Butyl-1-[4-(3,5-dimethylisoxazol-4-yl)phenyl]-N,4-dimethyl-4,5-dihydro-3H-2,3-benzodiazepine-3-carboxamide

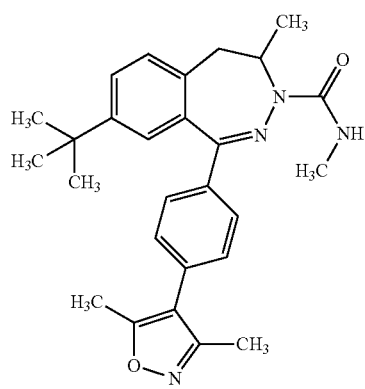 [SMILES: CNC(=O)N1N=C(c2ccc(-c3c(C)noc3C)cc2)c2cc(C(C)(C)C)ccc2CC1C]

150 mg (0.391 mmol) of (±)-8-tert-butyl-1-(4-chlorophenyl)-N,4-dimethyl-4,5-dihydro-3H-2,3-benzodiazepine-3-carboxamide (Example 83A) were dissolved in 7.3 ml of a 1:0.1 mixture of THF and water and degassed with argon. 113.5 mg (1.95 mmol) of potassium fluoride, 57.3 mg (0.41 mmol) of (3,5-dimethylisoxazol-4-yl)boronic acid and 15.4 mg (0.02 mmol) of chloro-(2-dicyclohexylphosphino-2',4',6'-triisopropyl-1,1'-biphenyl) [2-(2'-amino-1,1'-biphenyl)]palladium(II) (CAS [1310584-14-5]) were then added, and the reaction mixture was once more degassed carefully with argon. The mixture was heated at 80° C. for 5 h. After cooling, saturated aqueous sodium bicarbonate solution was added and the mixture was extracted three times with ethyl acetate. The combined organic phases were dried and evaporated to dryness on a rotary evaporator. The residue was purified by preparative HPLC. This gave 43 mg (25% of theory) of the desired product as a solid.

LCMS (Method 2): $R_t$=1.50 min; m/z=445 (M+H)+

$^1$H-NMR (300 MHz, CDCl$_3$): δ=0.99 (d, 3H), 1.22 (s, 9H), 2.33 (s, 3H), 2.46 (s, 3H), 2.87 (dd, 1H), 2.90 (d, 3H), 3.10 (dd, 1H), 5.36-5.49 (m, 1H), 6.45 (q, 1H), 7.14 (d, 1H), 7.18 (d, 1H), 7.30 (d, 2H), 7.37 (dd, 1H), 7.59 (d, 2H).

Example 156

(±)-7-Chloro-1-[4-(3,5-dimethylisoxazol-4-yl)phenyl]-N,4-dimethyl-8-(trifluoromethoxy)-4,5-dihydro-3H-2,3-benzodiazepine-3-carboxamide

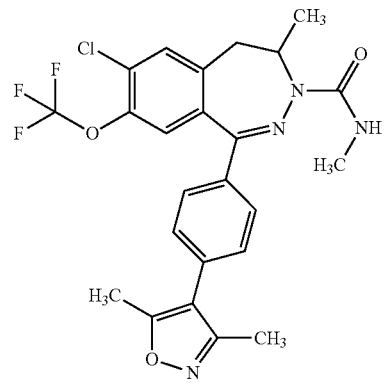 [SMILES: CNC(=O)N1N=C(c2ccc(-c3c(C)noc3C)cc2)c2cc(OC(F)(F)F)c(Cl)cc2CC1C]

The preparation was carried out analogously to the process for the preparation of Example 155 using Example 15 as starting material. This gave a mixture of the desired compound with the regioisomeric (±)-1-(4-chlorophenyl)-7-(3,5-dimethylisoxazol-4-yl)-N,4-dimethyl-8-(trifluoromethoxy)-4,5-dihydro-3H-2,3-benzodiazepine-3-carboxamide. The regioisomers were separated by preparative HPLC (method: system: Waters AutoPurification System: Pump 254, Sample Manager 2767, CFO, DAD 2996, SQD 3100, Prep FC; column: XBrigde C18 5 µm 100×30 mm; mobile phase: A=H$_2$O+0.1% HCOOH (99%), B=acetonitrile; gradient: 0-8 min 60-80% B flow rate: 50 ml/min; temperature: RT; detection: DAD scan range 210-400 nm). 100 mg of Example 15 gave, in addition to 14.7 mg of the regioisomer (LCMS (Method 2): $R_t$=1.54 min; m/z=507 (M+H)$^+$; $^1$H-NMR (400 MHz, CDCl$_3$): δ=0.97 (d, 3H), 2.20 (s, 3H), 2.34 (s, 3H), 2.92 (d, 3H), 2.98 (dd, 1H), 3.18 (dd, 1H), 5.53-5.59 (m, 1H), 6.52 (q, 1H), 7.10 (s, 1H), 7.13 (s, 1H), 7.40-7.46 (m, 4H).), 5 mg of the desired compound.

LCMS (Method 2): $R_t$=1.51 min; m/z=507 (M+H)$^+$ $^1$H-NMR (400 MHz, CDCl$_3$): δ=0.90 (d, 3H), 2.26 (s, 3H), 2.40 (s, 3H), 2.85 (d, 3H), 2.88 (dd, 1H), 3.08 (dd, 1H), 5.44-5.52 (m, 1H), 6.48 (q, 1H), 7.05 (d, 1H), 7.24 (s, 1H), 7.28 (d, 2H), 7.45 (d, 2H)

Enantiomer Separation 35 mg of (±)-7-chloro-1-[4-(3,5-dimethylisoxazol-4-yl)phenyl]-N,4-dimethyl-8-(trifluoromethoxy)-4,5-dihydro-3H-2,3-benzodiazepine-3-carboxamide (Example 165) were separated into the enantiomers by chiral preparative HPLC using Method XVIII:

Example 156.1: (4S)-7-Chloro-1-[4-(3,5-dimethylisoxazol-4-yl)phenyl]-N,4-dimethyl-8-(trifluoromethoxy)-4,5-dihydro-3H-2,3-benzodiazepine-3-carboxamide 15 mg yellowish solid, HPLC (Method W): $R_t$=1.91 min, purity 98%

Example 156.2: (4R)-7-Chloro-1-[4-(3,5-dimethyl-isoxazol-4-yl)phenyl]-N,4-dimethyl-8-(trifluoromethoxy)-4,5-dihydro-3H-2,3-benzodiazepine-3-carboxamide 10 mg yellowish solid, HPLC (Method W): $R_t$=2.86 min, purity 96%

The following compounds were prepared from the appropriate chlorophenyl precursors using the process for the preparation of Example 155:

| No | Structure | Name | Analytical data |
|---|---|---|---|
| 157 | 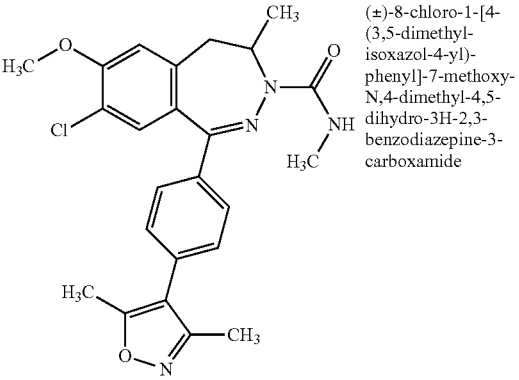 | (±)-8-chloro-1-[4-(3,5-dimethyl-isoxazol-4-yl)-phenyl]-7-methoxy-N,4-dimethyl-4,5-dihydro-3H-2,3-benzodiazepine-3-carboxamide | $^1$H-NMR (300 MHz, CDCl$_3$): δ = 1.00 (d, 3H), 2.34 (s, 3H), 2.47 (s, 3H), 2.84-2.97 (m, 4H), 3.14 (dd, 1H), 3.97 (s, 3H), 5.43-5.55 (m, 1H), 6.43-6.55 (m, 1H), 6.80 (s, 1H), 7.17 (s, 1H), 7.30 (d, 2H), 7.53 (d, 2H). LCMS (Method 2): $R_t$ = 1.35 min; m/z = 453 (M + H)$^+$. |
| 157.1 | 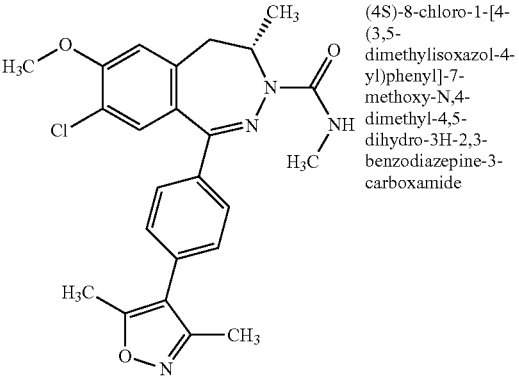 | (4S)-8-chloro-1-[4-(3,5-dimethylisoxazol-4-yl)phenyl]-7-methoxy-N,4-dimethyl-4,5-dihydro-3H-2,3-benzodiazepine-3-carboxamide | LCMS (Method 2): $R_t$ = 1.35 min; m/z = 453 (M + H)$^+$ HPLC (Method N): $R_t$ = 2.82 min [α]$_D^{20}$ = 131.8° (c = 1.00; chloroform) |
| 157.2 | 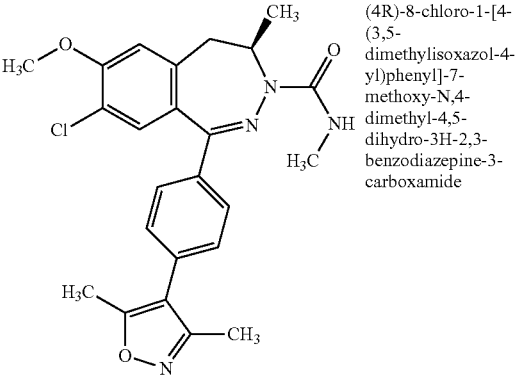 | (4R)-8-chloro-1-[4-(3,5-dimethylisoxazol-4-yl)phenyl]-7-methoxy-N,4-dimethyl-4,5-dihydro-3H-2,3-benzodiazepine-3-carboxamide | LCMS (Method 2): $R_t$ = 1.35 min; m/z = 453 (M + H)$^+$ HPLC (Method N): $R_t$ = 4.27 min |

| No | Structure | Name | Analytical data |
|---|---|---|---|
| 158 | 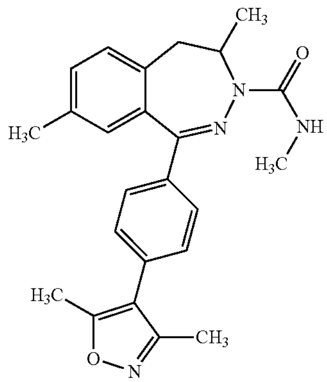 [SMILES: CNC(=O)N1N=C(c2ccc(-c3c(C)noc3C)cc2)c2cc(C)ccc2CC1C] | (±)-1-[4-(3,5-dimethylisoxazol-4-yl)phenyl]-N,4,8-trimethyl-4,5-dihydro-3H-2,3-benzodiazepine-3-carboxamide | $^1$H-NMR (600 MHz, CDCl$_3$): δ = 0.98 (d, 3H), 2.28 (s, 3H), 2.34 (s, 3H), 2.47 (s, 3H), 2.87 (dd, 1H), 2.90 (d, 3H), 3.10 (dd, 1H), 5.39-5.44 (m, 1H), 6.45 (q, 1H), 6.96 (s, 1H), 7.12-7.17 (m, 2H), 7.30 (d, 2H), 7.57 (d, 2H). LCMS (Method 2): R$_t$ = 1.35 min; m/z = 403 (M + H)$^+$. |

Example 160

(±)-7,8-Bis(difluoromethoxy)-1-[4-(3,5-dimethyl-isoxazol-4-yl)phenyl]-N,4-dimethyl-4,5-dihydro-3H-2,3-benzodiazepine-3-carboxamide

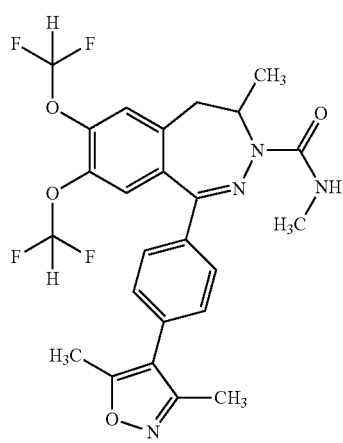 [SMILES: CNC(=O)N1N=C(c2ccc(-c3c(C)noc3C)cc2)c2cc(OC(F)F)c(OC(F)F)cc2CC1C]

286 mg (7.17 mmol) of (±)-1-(4-bromophenyl)-7,8-bis(difluoromethoxy)-N,4-dimethyl-4,5-dihydro-3H-2,3-benzodiazepine-3-carboxamide (Example 92A) were reacted analogously to Example 155, and the crude product was purified by preparative HPLC. This gave 22 mg (19% of theory) of the desired product.

LCMS (Method 2): R$_t$=1.35 min; m/z=521 (M+H)$^+$ $^1$H-NMR (300 MHz, DMSO-d$_6$): δ=0.96 (d, 3H), 2.24 (s, 3H), 2.42 (s, 3H), 2.65 (d, 3H), 2.74 (dd, 1H), 3.02 (dd, 1H), 5.02-5.12 (m, 1H), 6.67 (q, 1H), 6.97 (s, 1H), 7.08 (t, J=74 Hz, 1H), 7.27 (t, J=74 Hz, 1H), 7.41 (s, 1H), 7.43 (d, 2H), 7.74 (d, 2H).

Example 161

(±)-1-[4-(3,5-Dimethylisoxazol-4-yl)phenyl]-7,8-diethoxy-N,4-dimethyl-4,5-dihydro-3H-2,3-benzodiazepine-3-carboxamide

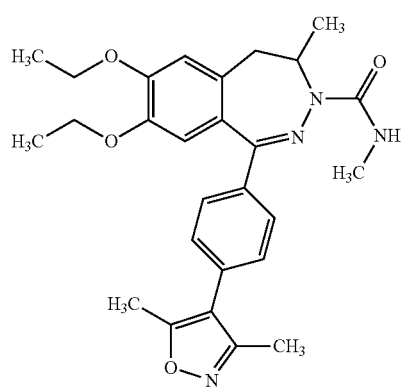 [SMILES: CCOc1cc2c(cc1OCC)C(c1ccc(-c3c(C)noc3C)cc1)=NN(C(=O)NC)C(C)C2]

The preparation was carried out analogously to Example 160 using Example 93A as starting material.

LCMS (Method 1): R$_t$=1.35 min; m/z=477 (M+H)$^+$ $^1$H-NMR (300 MHz, DMSO-d$_6$): δ=0.95 (d, 3H), 1.20 (t, 3H), 1.32 (t, 3H), 2.24 (s, 3H), 2.42 (s, 3H), 2.59-2.69 (m, 1H), 2.64 (d, 3H), 2.90 (dd, 1H), 3.79 (q, 2H), 4.08 (q, 2H), 4.97-5.09 (m, 1H), 6.51 (s, 1H), 6.59 (q, 1H), 6.99 (s, 1H), 7.41 (d, 2H), 7.72 (d, 2H).

The following exemplary compounds were prepared from Example 97A and the appropriate commercially available boronic acid using the process for the preparation of Example 155:

| No | Structure | Name | Analytical data |
|---|---|---|---|
| 162 | 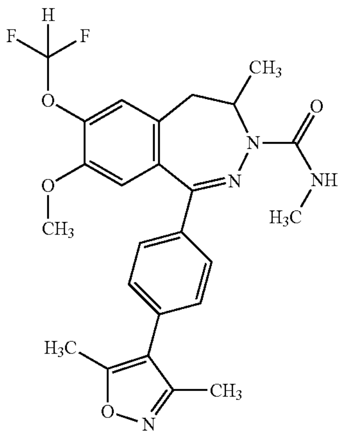 [SMILES: CNC(=O)N1N=C(c2ccc(-c3c(C)noc3C)cc2)c2cc(OC)c(OC(F)F)cc2CC1C] | (±)-7-(difluoromethoxy)-1-[4-(3,5-dimethyl-isoxazol-4-yl)phenyl]-8-methoxy-N,4-dimethyl-4,5-dihydro-3H-2,3-benzodiazepine-3-carboxamide | $^1$H-NMR (300 MHz, DMSO-d$_6$): δ = 0.96 (d, 3H), 2.24 (s, 3H), 2.42 (s, 3H), 2.58-2.65 (m, 1H), 2.65 (d, 3H), 2.93 (dd, 1H), 3.64 (s, 3H), 4.94-5.05 (m, 1H), 6.60 (q, 1H), 6.73 (s, 1H), 7.14 (t, J = 75 Hz, 1H), 7.23 (s, 1H), 7.42 (d, 2H), 7.76 (d, 2H). LCMS (Method 2): R$_t$ = 1.32 min; m/z = 485 (M + H)$^+$ |
| 162.1 | 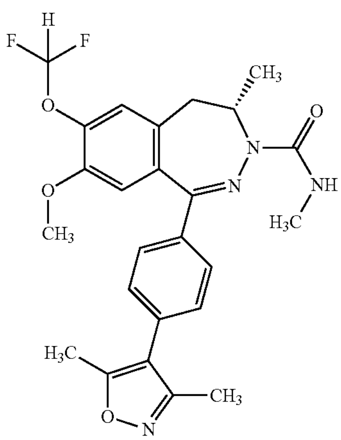 [SMILES: CNC(=O)N1N=C(c2ccc(-c3c(C)noc3C)cc2)c2cc(OC)c(OC(F)F)cc2C[C@@H]1C] | (4S)-7-(difluoromethoxy)-1-[4-(3,5-dimethyl-isoxazol-4-yl)phenyl]-8-methoxy-N,4-dimethyl-4,5-dihydro-3H-2,3-benzodiazepine-3-carboxamide | prep. HPLC: Method XII analyt. HPLC (Method Q): R$_t$ = 8.39 min |
| 162.2 | 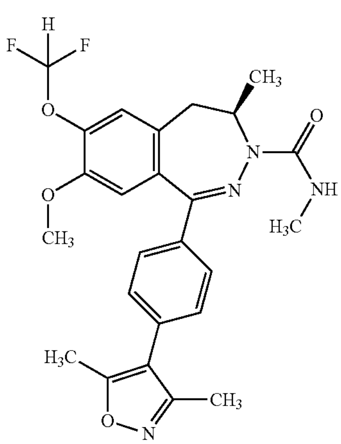 [SMILES: CNC(=O)N1N=C(c2ccc(-c3c(C)noc3C)cc2)c2cc(OC)c(OC(F)F)cc2C[C@H]1C] | (4R)-7-(difluoromethoxy)-1-[4-(3,5-dimethyl-isoxazol-4-yl)phenyl]-8-methoxy-N,4-dimethyl-4,5-dihydro-3H-2,3-benzodiazepine-3-carboxamide | prep. HPLC: Method XII analyt. HPLC (Method Q): R$_t$ = 10.53 min |

The following exemplary compounds were prepared analogously to Example 127.1 from Example 97A and the appropriate commercially available amines:

| No | Structure | Name | Analytical data |
|---|---|---|---|
| 163 | 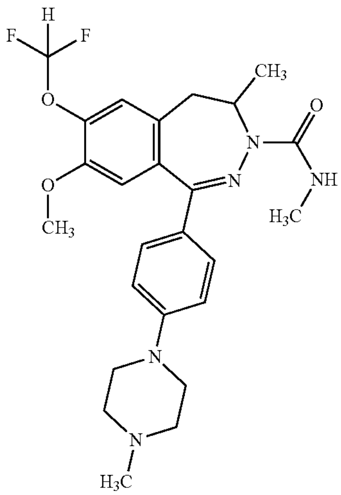 [SMILES: CNC(=O)N1N=C(c2ccc(N3CCN(C)CC3)cc2)c2cc(OC)c(OC(F)F)cc2CC1C] | (±)-7-(difluoromethoxy)-8-methoxy-N,4-dimethyl-1-[4-(4-methylpiperazin-1-yl)phenyl]-4,5-dihydro-3H-2,3-benzodiazepine-3-carboxamide | $^1$H-NMR (400 MHz, DMSO-$d_6$): δ = 1.02 (d, 3H), 2.20 (s, 3H), 2.37-2.44 (m, 5H), 2.60 (d, 3H), 2.84 (dd, 1H), 3.19-3.25 (m, 4H), 3.65 (s, 3H), 4.77-4.86 (m, 1H), 6.30 (q, 1H), 6.70 (s, 1H), 6.93 (d, 2H), 7.13 (t, 1H), 7.21 (s, 1H), 7.58 (d, 2H). LCMS (Method 2): $R_t$ = 0.80 min; m/z = 488 (M + H)$^+$ |
| 163.1 | 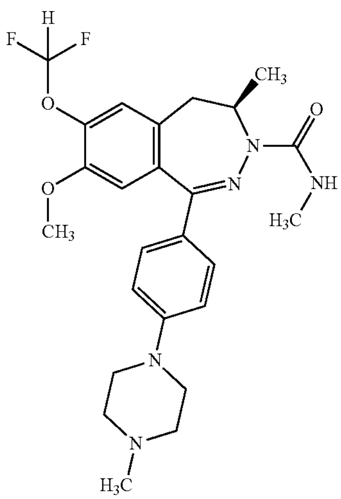 [SMILES: CNC(=O)N1N=C(c2ccc(N3CCN(C)CC3)cc2)c2cc(OC)c(OC(F)F)cc2C[C@H]1C] | (4R)-7-(difluoromethoxy)-8-methoxy-N,4-dimethyl-1-[4-(4-methylpiperazin-1-yl)phenyl]-4,5-dihydro-3H-2,3-benzodiazepine-3-carboxamide | prep. HPLC: Method XII analyt. HPLC (Method Q): $R_t$ = 5.01 min |
| 163.2 | 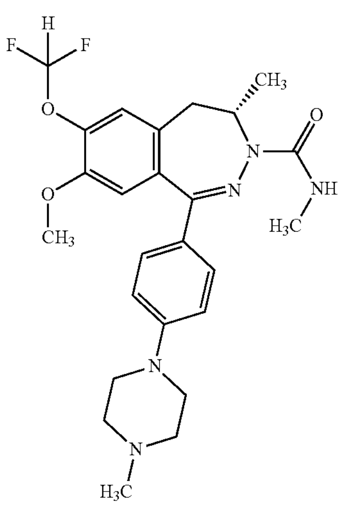 [SMILES: CNC(=O)N1N=C(c2ccc(N3CCN(C)CC3)cc2)c2cc(OC)c(OC(F)F)cc2C[C@@H]1C] | (4S)-7-(difluoromethoxy)-8-methoxy-N,4-dimethyl-1-[4-(4-methylpiperazin-1-yl)phenyl]-4,5-dihydro-3H-2,3-benzodiazepine-3-carboxamide | prep. HPLC: Method XII analyt. HPLC (Method Q): $R_t$ = 7.00 min |

The following exemplary compounds were prepared analogously to Example 32 using the appropriate commercially available heterocyclylchloroalkanes or heteroarylchloroalkanes:

| No | Structure | Name | Analytical data |
|---|---|---|---|
| 164 | 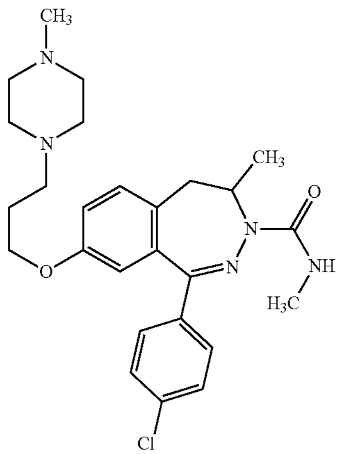 [SMILES: CNC(=O)N1N=C(c2ccc(Cl)cc2)c2cc(OCCCN3CCN(C)CC3)ccc2CC1C] | (±)-1-(4-chlorophenyl)-N,4-dimethyl-8-[3-(4-methylpiperazin-1-yl)propoxy]-4,5-dihydro-3H-2,3-benzodiazepine-3-carboxamide | $^1$H-NMR (300 MHz, CDCl$_3$): δ = 0.92 (d, 3H), 1.89 (m, 2H), 2.28 (s, 3H), 2.46 (m, 10H), 2.84 (dd, 1H), 2.88 (d, 3H), 3.08 (dd, 1H), 3.87 (m, 2H), 5.42 (m, 1H), 6.45 (qbr, 1H), 6.58 (d, 1H), 6.87 (dd, 1H), 7.11 (d, 1H), 7.36 (d, 2H), 7.42 (d, 2H). LC/MS (Method 3): R$_t$ = 0.89 min; m/z = 484; 486 (M + H, Cl isotope pattern)$^+$ |
| 164.1 | 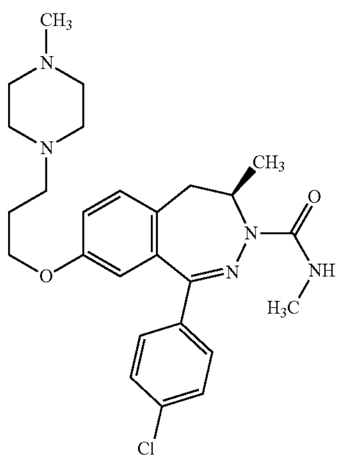 [SMILES: CNC(=O)N1N=C(c2ccc(Cl)cc2)c2cc(OCCCN3CCN(C)CC3)ccc2C[C@H]1C] | (4R)-1-(4-chlorophenyl)-N,4-dimethyl-8-[3-(4-methylpiperazin-1-yl)propoxy]-4,5-dihydro-3H-2,3-benzodiazepine-3-carboxamide (Comparative Example) | prep. HPLC: Method XVII analyt. HPLC (Method K): R$_t$ = 1.88 min [α]$_D^{20}$ = −124.2° (c = 1.00; MeOH) |
| 164.2 | 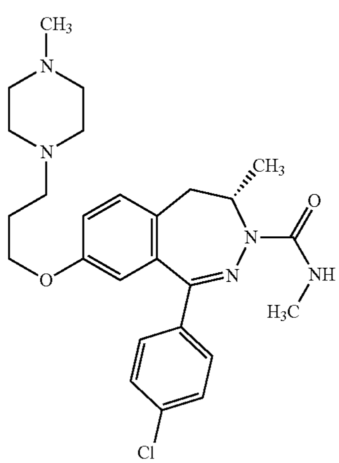 [SMILES: CNC(=O)N1N=C(c2ccc(Cl)cc2)c2cc(OCCCN3CCN(C)CC3)ccc2C[C@@H]1C] | (4S)-1-(4-chlorophenyl)-N,4-dimethyl-8-[3-(4-methylpiperazin-1-yl)propoxy]-4,5-dihydro-3H-2,3-benzodiazepine-3-carboxamide | prep. HPLC: Method XVII analyt. HPLC (Method K): R$_t$ = 2.41 min [α]$_D^{20}$ = +114.2° (c = 1.00; MeOH) |

| No | Structure | Name | Analytical data |
|---|---|---|---|
| 165 | 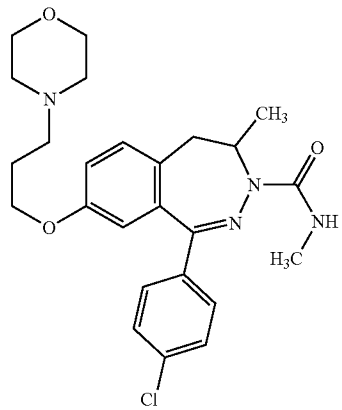 [SMILES: CNC(=O)N1N=C(c2ccc(Cl)cc2)c2cc(OCCCN3CCOCC3)ccc2CC1C] | (±)-1-(4-chlorophenyl)-N,4-dimethyl-8-[3-(morpholin-4-yl)propoxy]-4,5-dihydro-3H-2,3-benzodiazepine-3-carboxamide | $^1$H-NMR (300 MHz, CDCl$_3$): δ = 0.92 (d, 3H), 1.93 (m, 2H), 2.49 (m, 4H), 2.51 (m, 2H), 2.84 (dd, 1H), 2.89 (d, 3H), 3.08 (dd, 1H), 3.73 (m, 4H), 3.88 (m, 2H), 5.42 (m, 1H), 6.45 (qbr, 1H), 6.58 (d, 1H), 6.87 (dd, 1H), 7.11 (d, 1H), 7.36 (d, 2H), 7.42 (d, 2H).<br>LC/MS (Method 3): R$_t$ = 0.89 min; m/z = 471; 473 (M + H, Cl isotope pattern)$^+$ |
| 166 | 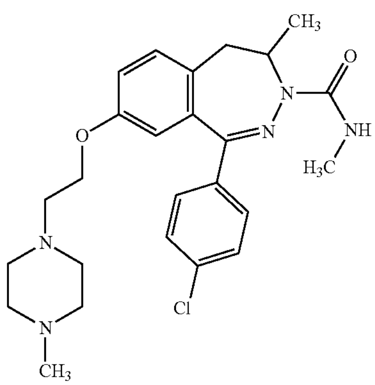 [SMILES: CNC(=O)N1N=C(c2ccc(Cl)cc2)c2cc(OCCN3CCN(C)CC3)ccc2CC1C] | (±)-1-(4-chlorophenyl)-N,4-dimethyl-8-[2-(4-methylpiperazin-1-yl)ethoxy]-4,5-dihydro-3H-2,3-benzodiazepine-3-carboxamide | $^1$H-NMR (300 MHz, CDCl$_3$): δ = 0.92 (d, 3H), 2.42 (s, 3H), 2.69 (m, 8H), 2.78 (tbr, 2H), 2.85 (m, 1H), 2.88 (d, 3H), 3.08 (dd, 1H), 3.95 (tbr, 2H), 5.42 (m, 1H), 6.45 (qbr, 1H), 6.58 (d, 1H), 6.87 (dd, 1H), 7.12 (d, 1H), 7.36 (d, 2H), 7.41 (d, 2H).<br>LC/MS (Method 3): R$_t$ = 0.94 min; m/z = 470; 472 (M + H, Cl isotope pattern)$^+$ |
| 167 | 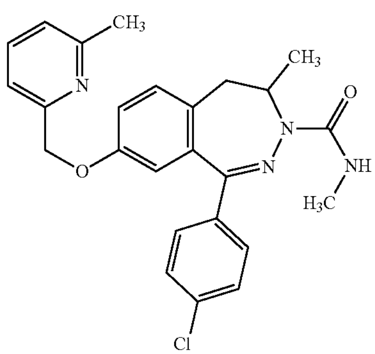 [SMILES: CNC(=O)N1N=C(c2ccc(Cl)cc2)c2cc(OCc3cccc(C)n3)ccc2CC1C] | (±)-1-(4-chlorophenyl)-N,4-dimethyl-8-[(6-methylpiperazin-2-yl)methoxy]-4,5-dihydro-3H-2,3-benzodiazepine-3-carboxamide | $^1$H-NMR (300 MHz, CDCl$_3$): δ = 0.92 (d, 3H), 2.53 (s, 3H), 2.85 (dd, 1H), 2.88 (d, 3H), 3.07 (dd, 1H), 4.99 (d, 1H), 5.04 (d, 1H), 5.43 (m, 1H), 6.47 (qbr, 1H), 6.64 (d, 1H), 6.98 (dd, 1H), 7.08 (d, 1H), 7.13 (d, 1H), 7.23 (d, 1H), 7.29 (d, 2H), 7.33 (d, 2H), 7.58 (dd, 1H).<br>LC/MS (Method 3): R$_t$ = 1.31 min; m/z = 449; 451 (M + H, Cl isotope pattern)$^+$ |

Example 168

(±)-1-[4-(3,5-Dimethylisoxazol-4-yl)phenyl]-8-hydroxy-N,4-dimethyl-4,5-dihydro-3H-2,3-benzodiazepine-3-carboxamide

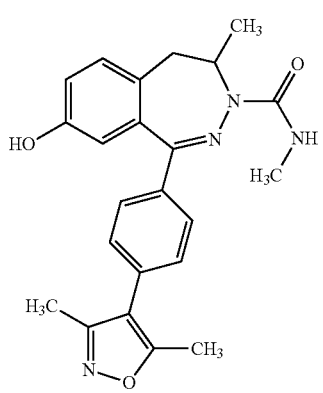 [SMILES: CNC(=O)N1N=C(c2ccc(-c3c(C)noc3C)cc2)c2cc(O)ccc2CC1C]

The title compound was prepared analogously to Example 55A from the racemate of the compound described in Example 20.

LCMS (Method 3): $R_t$=1.06 min; m/z=405 (M+H)$^+$ $^1$H-NMR (400 MHz, DMSO-d$_6$): δ=0.95 (d, 3H), 2.24 (s, 3H), 2.42 (s, 3H), 2.57 (dd, 1H), 2.65 (d, 3H), 2.88 (dd, 1H), 4.95 (m, 1H), 6.44 (d, 1H), 6.58 (qbr, 1H), 6.81 (dd, 1H), 7.18 (d, 1H), 7.43 (d, 2H), 7.73 (d, 2H), 9.63 (sbr, 1H).

Example 169

(±)-1-[4-(3,5-Dimethylisoxazol-4-yl)phenyl]-N,4-dimethyl-8-[3-(morpholin-4-yl)propoxy]-4,5-dihydro-3H-2,3-benzodiazepine-3-carboxamide

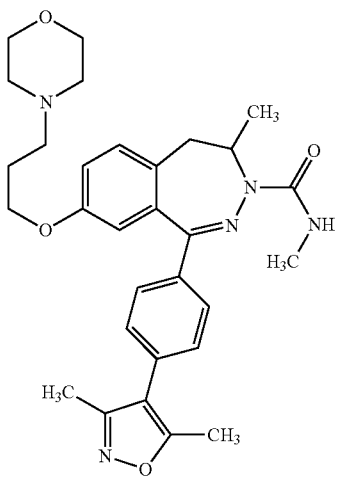 [SMILES: CNC(=O)N1N=C(c2ccc(-c3c(C)noc3C)cc2)c2cc(OCCCN3CCOCC3)ccc2CC1C]

The preparation was carried out analogously to Example 32.

LCMS (Method 3): $R_t$=0.88 min; m/z=532 (M+H)$^+$ $^1$H-NMR (400 MHz, CDCl$_3$): δ=0.98 (d, 3H), 1.96 (m, 2H), 2.33 (s, 3H), 2.47 (s, 3H), 2.51 (m, 4H), 2.54 (m, 2H), 2.84 (dd, 1H), 2.90 (d, 3H), 3.08 (dd, 1H), 3.73 (m, 4H), 3.93 (m, 2H), 5.40 (m, 1H), 6.44 (qbr, 1H), 6.69 (d, 1H), 6.90 (dd, 1H), 7.14 (d, 1H), 7.29 (d, 2H), 7.58 (d, 2H).

Example 170

(±)-7-Cyano-1-[4-(3,5-dimethylisoxazol-4-yl)phenyl]-8-methoxy-N,4-dimethyl-4,5-dihydro-3H-2,3-benzodiazepine-3-carboxamide

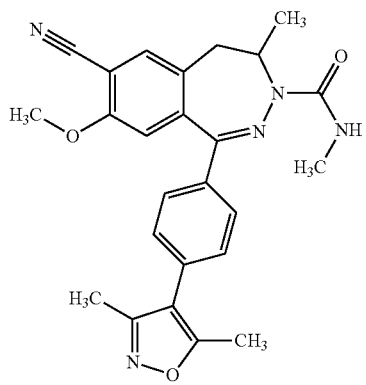 [SMILES: CNC(=O)N1N=C(c2ccc(-c3c(C)noc3C)cc2)c2cc(OC)c(C#N)cc2CC1C]

The preparation was carried out analogously to Example 155.

LCMS (Method 3): $R_t$=1.19 min; m/z=444 (M+H)$^+$ $^1$H-NMR (400 MHz, CDCl$_3$): δ=0.94 (d, 3H), 2.33 (s, 3H), 2.47 (s, 3H), 2.90 (dd, 1H), 2.92 (d, 3H), 3.11 (dd, 1H), 3.73 (s, 3H), 5.50 (m, 1H), 6.54 (qbr, 1H), 6.74 (s, 1H), 7.33 (d, 2H), 7.42 (s, 1H), 7.54 (d, 2H).

Example 171

(±)-8-Acetamido-N,4-dimethyl-1-[4-(morpholin-4-yl)phenyl]-4,5-dihydro-3H-2,3-benzodiazepine-3-carboxamide

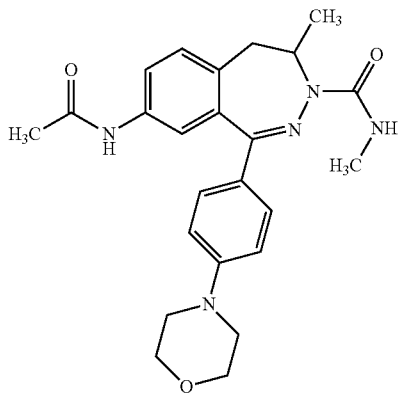 [SMILES: CNC(=O)N1N=C(c2ccc(N3CCOCC3)cc2)c2cc(NC(C)=O)ccc2CC1C]

Under argon, 200 mg (520 µmol) of (±)-8-acetamido-1-(4-chlorophenyl)-N,4-dimethyl-4,5-dihydro-3H-2,3-benzodiazepine-3-carboxamide (Example 89A) were initially charged in 8 ml of degassed toluene. 47 µl (47 mg, 540 µmol) of morpholine, 70 mg (728 µmol) of sodium tert-butoxide and 20 mg (26 µmol) of chloro-(2-dicyclohexylphosphino-2,4,6-triisopropyl-1,1-biphenyl) [2-(2-amino-1,1-biphenyl)]palladium(II) [CAS 1310584-14-5] were added.

353

The mixture was degassed again, saturated with argon and then stirred at 110° C. for 5 hours. A further 25 mg of morpholine, 35 mg of sodium tert-butoxide and 10 mg of catalyst were added, and the mixture was stirred at 110° C. for a further 7 h. After cooling, the mixture was partitioned between sat. sodium bicarbonate solution and ethyl acetate and the phases were separated. The aqueous phase was extracted with ethyl acetate, and the combined organic phases were washed with water and sat. sodium chloride solution and dried with sodium sulphate. The solvents were removed on a rotary evaporator and the residue was purified by preparative HPLC. This gave 9.8 mg (4.2% of theory) of the desired product.

LCMS (Method 2): $R_t$=0.98 min; m/z=436 (M+H)$^+$ $^1$H-NMR (300 MHz, DMSO-d$_6$): δ=1.00 (d, 3H), 1.94 (s, 3H), 2.34-2.40 (m, 1H), 2.59 (d, 3H), 2.82 (dd, 1H), 3.14-3.22 (m, 4H), 3.66-3.77 (m, 4H), 4.76-4.89 (m, 1H), 6.31 (q, 1H), 6.94 (d, 2H), 7.25 (d, 1H), 7.31 (d, 1H), 7.52-7.60 (m, 3H), 9.90 (s, 1H).

Example 172

(±)-8-Acetamido-N,4-dimethyl-1-[4-(4-methylpiperazin-1-yl)phenyl]-4,5-dihydro-3H-2,3-benzodiazepine-3-carboxamide

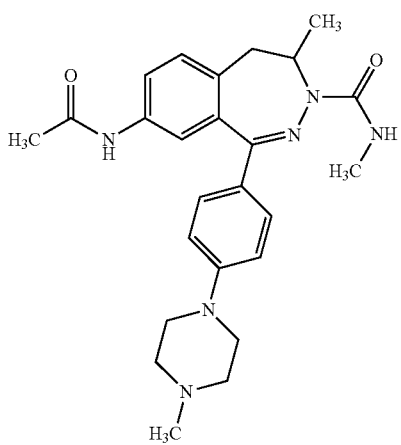 [SMILES: CNC(=O)N1N=C(c2ccc(N3CCN(C)CC3)cc2)c2cc(NC(C)=O)ccc2CC1C]

The compound was prepared analogously to Example 127.1.

LCMS (Method 2): $R_t$=0.65 min; m/z=449 (M+H)$^+$ $^1$H-NMR (300 MHz, DMSO-d$_6$): δ=1.01 (d, 3H), 1.94 (s, 3H), 2.19 (s, 3H), 2.34-2.53 (m, 5H), 2.59 (d, 3H), 2.82 (dd, 1H), 3.20-3.24 (m, 4H), 4.75-4.86 (m, 1H), 6.28 (q, 1H), 6.92 (d, 2H), 7.25 (d, 1H), 7.31 (d, 1H), 7.54 (d, 2H), 7.52-7.57 (m, 1H), 9.90 (s, 1H).

Example 173

(±)-8-Acetamido-1-[4-(3,5-dimethylisoxazol-4-yl)phenyl]-N,4-dimethyl-4,5-dihydro-3H-2,3-benzodiazepine-3-carboxamide

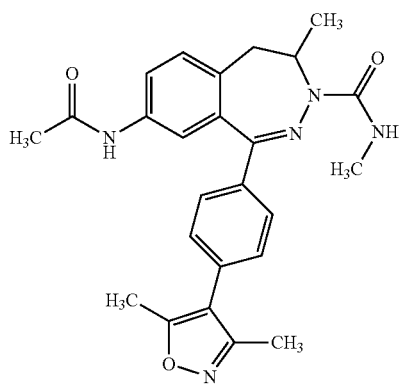 [SMILES: CNC(=O)N1N=C(c2ccc(-c3c(C)noc3C)cc2)c2cc(NC(C)=O)ccc2CC1C]

200 mg (520 μmol) of (±)-8-acetamido-1-(4-chlorophenyl)-N,4-dimethyl-4,5-dihydro-3H-2,3-benzodiazepine-3-carboxamide were dissolved in 8 ml of degassed THF/water 10:1, and 76 mg (540 μmol) of 3,5-dimethylisoxazole-4-boronic acid, 150 mg (260 μmol) of potassium fluoride and 20 mg (26 μmol) of chloro-(2-dicyclohexylphosphino-2,4,6-triisopropyl-1,1-biphenyl)[2-(2-amino-1,1-biphenyl)]palladium(II) were added. The reaction mixture was degassed again and stirred under an atmosphere of argon at 80° C. for 7 hours. The mixture was then partitioned between sat. sodium bicarbonate solution and ethyl acetate, and the phases were separated. The aqueous phase was extracted with ethyl acetate, and the combined organic phases were washed with water and sat. sodium chloride solution and dried with sodium sulphate. The solvents were removed on a rotary evaporator and the residue was purified by preparative HPLC. This gave 24.4 mg (11% of theory) of the desired product.

LCMS (Method 2): $R_t$=1.09 min; m/z=446 (M+H)$^+$ $^1$H-NMR (300 MHz, DMSO-d$_6$): δ=0.94 (d, 3H), 1.93 (s, 3H), 2.24 (s, 3H), 2.42 (s, 3H), 2.59-2.68 (m, 1H), 2.64 (d, 3H), 2.92 (dd, 1H), 4.93-5.05 (m, 1H), 6.58 (q, 1H), 7.28 (d, 1H), 7.29 (s, 1H), 7.43 (d, 1H), 7.64 (dd, 1H), 7.74 (d, 2H), 9.92 (s, 1H).

Example 174

(±)-1-(4-Chlorophenyl)-8-(3,5-dimethyl-1H-pyrazol-1-yl)-N,4-dimethyl-4,5-dihydro-3H-2,3-benzodiazepine-3-carboxamide

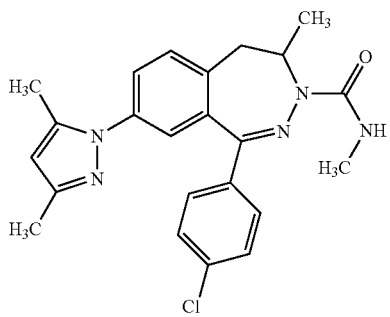 [SMILES: CNC(=O)N1N=C(c2ccc(Cl)cc2)c2cc(-n3nc(C)cc3C)ccc2CC1C]

The compound was prepared analogously to Example 16 in a yield of 87%.

LCMS (Method 1): R$_t$=1.38 min; m/z=422 (M+H)$^+$ $^1$H-NMR (300 MHz, DMSO-d$_6$): δ=0.91 (d, 3H), 2.07 (s, 3H), 2.17 (s, 3H), 2.65 (d, 3H), 2.83 (dd, 1H), 3.05 (dd, 1H), 5.10-5.18 (m, 1H), 5.98 (s, 1H), 6.71 (q, 1H), 7.02 (d, 1H), 7.45 (d, 2H), 7.43-7.53 (m, 2H), 7.64 (d, 2H).

Example 175

(±)-1-[4-(3,5-Dimethylisoxazol-4-yl)phenyl]-8-(3,5-dimethyl-1H-pyrazol-1-yl)-N,4-dimethyl-4,5-dihydro-3H-2,3-benzodiazepine-3-carboxamide

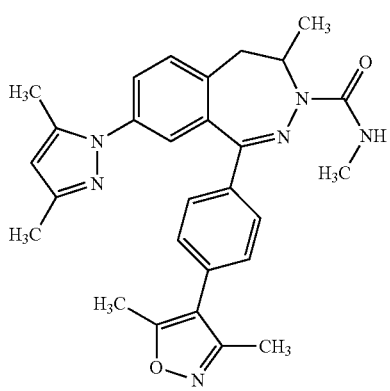 [SMILES: CNC(=O)N1N=C(c2ccc(-c3c(C)noc3C)cc2)c2cc(-n3nc(C)cc3C)ccc2CC1C]

The compound was prepared analogously to Example 155 in a yield of 24%.

LCMS (Method 1): R$_t$=1.31 min; m/z=483 (M+H)$^+$ $^1$H-NMR (300 MHz, DMSO-d$_6$): δ=0.95 (d, 3H), 2.07 (s, 3H), 2.19 (s, 3H), 2.23 (s, 3H), 2.41 (s, 3H), 2.65 (d, 3H), 2.80 (dd, 1H), 3.05 (dd, 1H), 5.05-5.15 (m, 1H), 5.99 (s, 1H), 6.69 (q, 1H), 7.08 (d, 1H), 7.43 (d, 2H), 7.44-7.55 (m, 2H), 7.75 (d, 2H).

Example 176

(±)-1-[4-(3,5-Dimethylisoxazol-4-yl)phenyl]-N,4-dimethyl-8-(morpholin-4-yl)-4,5-dihydro-3H-2,3-benzodiazepine-3-carboxamide

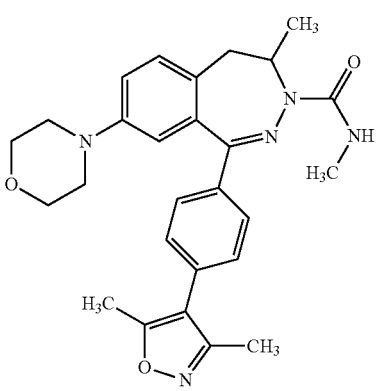 [SMILES: CNC(=O)N1N=C(c2ccc(-c3c(C)noc3C)cc2)c2cc(N3CCOCC3)ccc2CC1C]

The compound was prepared analogously to Example 155 from (±)-1-(4-chlorophenyl)-N,4-dimethyl-8-(morpholin-4-yl)-4,5-dihydro-3H-2,3-benzodiazepine-3-carboxamide (Example 11).

LCMS (Method 2): R$_t$=1.24 min; m/z=474 (M+H)$^+$ $^1$H-NMR (400 MHz, DMSO-d$_6$): δ=0.96 (d, 3H), 2.24 (s, 3H), 2.42 (s, 3H), 2.56 (dd, 1H), 2.64 (d, 3H), 2.87 (dd, 1H), 2.92-2.98 (m, 4H), 3.61-3.67 (m, 4H), 4.89-4.97 (m, 1H), 6.52-6.56 (m, 2H), 7.02 (dd, 1H), 7.23 (d, 1H), 7.42 (d, 2H), 7.76 (d, 2H).

Enantiomer Separation 90 mg of (±)-1-[4-(3,5-dimethylisoxazol-4-yl)phenyl]-N,4-dimethyl-8-(morpholin-4-yl)-4,5-dihydro-3H-2,3-benzodiazepine-3-carboxamide (Example 185) were separated into the enantiomers by chiral preparative HPLC using Method XIII:

Example 176.1: (4R)-1-[4-(3,5-Dimethylisoxazol-4-yl)phenyl]-N,4-dimethyl-8-(morpholin-4-yl)-4,5-dihydro-3H-2,3-benzodiazepine-3-carboxamide 27 mg of a solid, HPLC (Method R): R$_t$=2.58 min, purity 98.2%/100% ee Example 176.2: (4S)-1-[4-(3,5-Dimethylisoxazol-4-yl)phenyl]-N,4-dimethyl-8-(morpholin-4-yl)-4,5-dihydro-3H-2,3-benzodiazepine-3-carboxamide 23 mg of a solid, HPLC (Method R): R$_t$=3.06 min, purity 96.3%/92.7% ee

Example 177

(4S)-8-Methoxy-N,4-dimethyl-1-[4-(3-oxomorpholin-4-yl)phenyl]-4,5-dihydro-3H-2,3-benzodiazepine-3-carboxamide

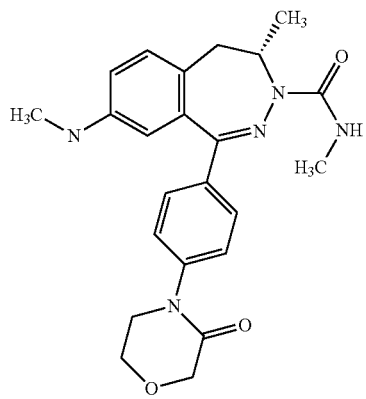 [SMILES: CNC(=O)N1N=C(c2ccc(N3CCOCC3=O)cc2)c2cc(NC)ccc2C[C@@H]1C]

112 mg (0.244 mmol) of (4S)-1-(4-{[(2-chloroethoxy)acetyl]amino}phenyl)-8-methoxy-N,4-dimethyl-4,5-dihydro-3H-2,3-benzodiazepine-3-carboxamide (Example 94A) were dissolved in 1.1 ml of acetonitrile, and 71 mg (0.512 mmol) of potassium carbonate were added. After addition of a catalytic amount of sodium iodide, the mixture was heated at reflux for 5 h. The reaction was filtered, the filter cake washed with acetonitrile and the solvent was removed on a rotary evaporator. The residue was purified by preparative HPLC. This gave 16 mg (15% of theory) of the desired product as a solid.

UPLC/MS (Method 1): $R_t$=1.0 min; m/z=423 (M+H)$^+$

The following exemplary compounds were prepared analogously to Example 127.1 from Example 49A or Example 49.2A and the appropriate commercially available amines:

| No. | Structure | Name | Analytical data |
|---|---|---|---|
| 178 | 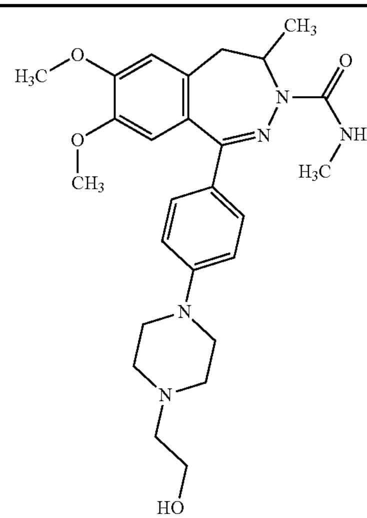 | (±)-1-{4-[4-(2-hydroxyethyl)piperazin-1-yl]phenyl}-7,8-dimethoxy-N,4-dimethyl-4,5-dihydro-3H-2,3-benzodiazepine-3-carboxamide | $^1$H-NMR (500 MHz, CDCl$_3$): δ = 1.11 (d, 3H), 2.61-2.64 (m, 2H), 2.69-2.71 (m, 4H), 2.73 (dd, 1H), 2.87 (d, 3H), 2.94 (dd, 1H), 3.30-3.32 (m, 4H), 3.65-3.69 (m, 2H), 3.70 (s, 3H), 3.93 (s, 3H), 5.24-5.33 (m, 1H), 6.12 (q, 1H), 6.64 (s, 1H), 6.75 (s, 1H), 6.91 (d, 2H), 7.49 (d, 2H). LCMS (Method 1): $R_t$ = 0.72 min; m/z = 482 (M + H)$^+$ |
| 179 | 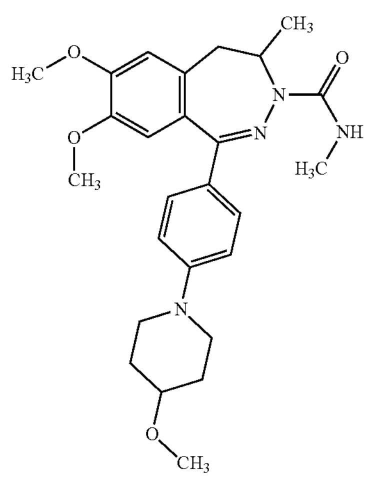 [SMILES: CNC(=O)N1N=C(c2ccc(N3CCC(OC)CC3)cc2)c2cc(OC)c(OC)cc2CC1C] | (±)-7,8-dimethoxy-1-[4-(4-methoxypiperidin-1-yl)phenyl]-N,4-dimethyl-4,5-dihydro-3H-2,3-benzodiazepine-3-carboxamide | $^1$H-NMR (500 MHz, CDCl$_3$): δ = 1.12 (d, 3H), 1.68-1.75 (m, 2H), 1.99-2.05 (m, 2H), 2.72 (dd, 1H), 2.86 (d, 3H), 2.92 (dd, 1H), 3.04-3.09 (m, 2H), 3.39 (s, 3H), 3.60-3.64 (m, 2H), 3.70 (s, 3H), 3.93 (s, 3H), 5.24-5.30 (m, 1H), 6.07 (q, 1H), 6.64 (s, 1H), 6.75 (s, 1H), 6.91 (d, 2H), 7.48 (d, 2H). LCMS (Method 1): $R_t$ = 1.13 min; m/z = 467 (M + H)$^+$ |

| No. | Structure | Name | Analytical data |
|---|---|---|---|
| 179.1 | 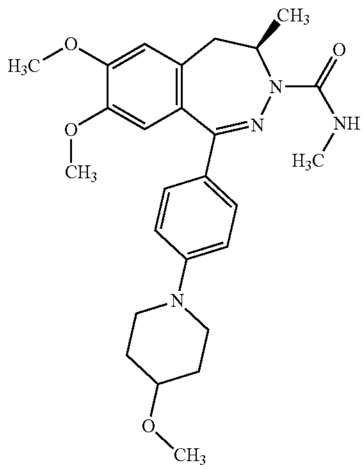 [SMILES: CNC(=O)N1N=C(c2ccc(N3CCC(OC)CC3)cc2)c2cc(OC)c(OC)cc2C[C@H]1C] | (4R)-7,8-dimethoxy-1-[4-(4-methoxypiperidin-1-yl)phenyl]-N,4-dimethyl-4,5-dihydro-3H-2,3-benzodiazepine-3-carboxamide | Prep. HPLC: Method XX Analyt. HPLC (Method L): $R_t$ = 7.77 min |
| 179.2 | 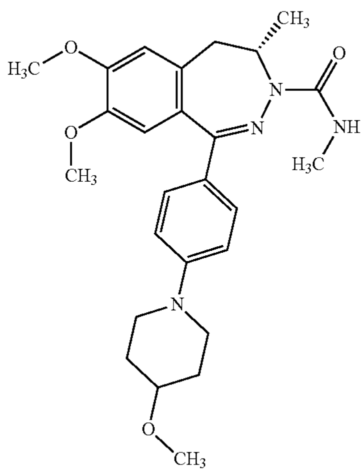 [SMILES: CNC(=O)N1N=C(c2ccc(N3CCC(OC)CC3)cc2)c2cc(OC)c(OC)cc2C[C@@H]1C] | (4S)-7,8-dimethoxy-1-[4-(4-methoxypiperidin-1-yl)phenyl]-N,4-dimethyl-4,5-dihydro-3H-2,3-benzodiazepine-3-carboxamide | Prep. HPLC: Method XX Analyt. HPLC (Method L): $R_t$ = 12.0 min |
| 180 | 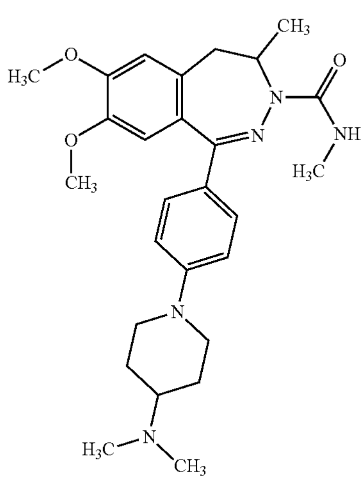 [SMILES: CNC(=O)N1N=C(c2ccc(N3CCC(N(C)C)CC3)cc2)c2cc(OC)c(OC)cc2CC1C] | (±)-1-{4-[4-(dimethylamino)piperidin-1-yl]phenyl}-7,8-dimethoxy-N,4-dimethyl-4,5-dihydro-3H-2,3-benzodiazepine-3-carboxamide | $^1$H-NMR (500 MHz, CDCl$_3$): δ = 1.05 (d, 3H), 1.52-1.62 (m, 3H), 1.85-1.91 (m, 2H), 2.25 (s, 6H), 2.65 (dd, 1H), 2.72-2.78 (m, 2H), 2.79 (d, 3H), 2.85 (dd, 1H), 3.63 (s, 3H), 3.76-3.82 (m, 2H), 3.86 (s, 3H), 5.17-5.23 (m, 1H), 6.00 (q, 1H), 6.58 (s, 1H), 6.68 (s, 1H), 6.84 (d, 2H), 7.41 (d, 2H). LCMS (Method 1): $R_t$ = 0.76 min; m/z = 480 (M + H)$^+$ |

| No. | Structure | Name | Analytical data |
|---|---|---|---|
| 180.1 | 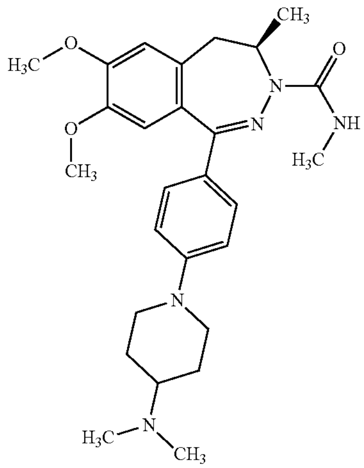 [SMILES: CNC(=O)N1N=C(c2ccc(N3CCC(N(C)C)CC3)cc2)c2cc(OC)c(OC)cc2C[C@H]1C] | (4R)-1-{4-[4-(dimethylamino)piperidin-1-yl]phenyl}-7,8-dimethoxy-N,4-dimethyl-4,5-dihydro-3H-2,3-benzodiazepine-3-carboxamide | Prep. HPLC: Method XX Analyt. HPLC (Method L): R$_t$ = 9.20 min |
| 180.2 | 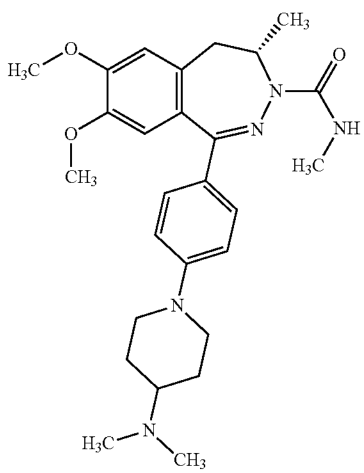 | (4S)-1-{4-[4-(dimethylamino)piperidin-1-yl]phenyl}-7,8-dimethoxy-N,4-dimethyl-4,5-dihydro-3H-2,3-benzodiazepine-3-carboxamide | Prep. HPLC: Method XX Analyt. HPLC (Method L): R$_t$ = 14.3 min |
| 181 | 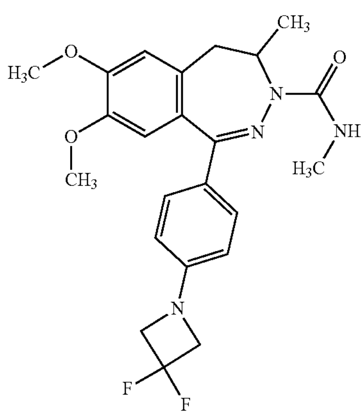 [SMILES: CNC(=O)N1N=C(c2ccc(N3CC(F)(F)C3)cc2)c2cc(OC)c(OC)cc2CC1C] | (±)-1-[4-(3,3-difluoroazetidin-1-yl)phenyl]-7,8-dimethoxy-N,4-dimethyl-4,5-dihydro-3H-2,3-benzodiazepine-3-carboxamide | $^1$H-NMR (500 MHz, CDCl$_3$): δ = 1.10 (d, 3H), 2.74 (dd, 1H), 2.87 (d, 3H), 2.96 (dd, 1H), 3.70 (s, 3H), 3.94 (s, 3H), 4.29 (t, 4H), 5.27-5.34 (m, 1H), 6.14 (q, 1H), 6.50 (d, 2H), 6.61 (s, 1H), 6.75 (s, 1H), 7.49 (d, 2H). LCMS (Method 1): R$_t$ = 1.21 min; m/z = 445 (M + H)$^+$ |

| No. | Structure | Name | Analytical data |
|---|---|---|---|
| 182 | 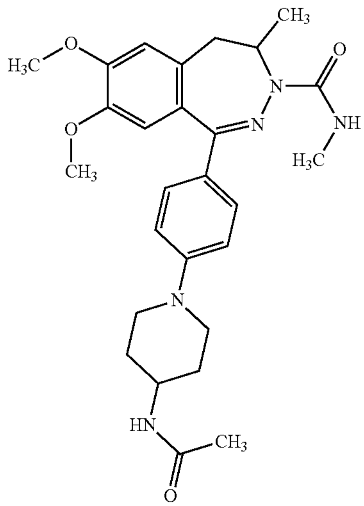 [SMILES: CNC(=O)N1N=C(c2ccc(N3CCC(NC(C)=O)CC3)cc2)c2cc(OC)c(OC)cc2CC1C] | (±)-1-[4-(4-acetamidopiperidin-1-yl)phenyl]-7,8-dimethoxy-N,4-dimethyl-4,5-dihydro-3H-2,3-benzodiazepine-3-carboxamide | $^1$H-NMR (500 MHz, CDCl$_3$): δ = 1.11 (d, 3H), 1.50-1.58 (m, 2H), 1.99 (s, 3H), 2.04 -2.10 (m, 2H), 2.72 (dd, 1H), 2.86 (d, 3H), 2.92-2.98 (m, 3H), 3.70 (s, 3H), 3.73-3.80 (m, 2H), 3.93 (s, 3H), 3.95-4.03 (m, 1H), 5.25-5.32 (m, 1H), 5.34 (d, 1H), 6.10 (q, 1H), 6.64 (s, 1H), 6.75 (s, 1H), 6.91 (d, 2H), 7.48 (d, 2H).<br>LCMS (Method 1): R$_t$ = 0.94 min; m/z = 494 (M + H)$^+$ |
| 183 | 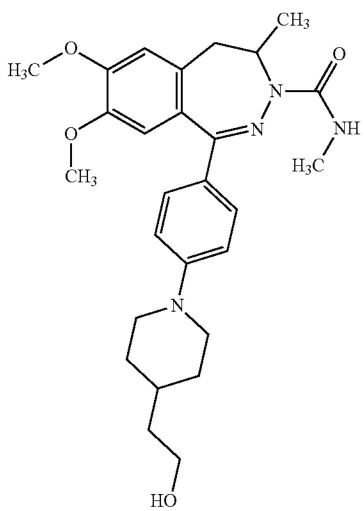 [SMILES: CNC(=O)N1N=C(c2ccc(N3CCC(CCO)CC3)cc2)c2cc(OC)c(OC)cc2CC1C] | (±)-1-{4-[4-(2-hydroxyethyl)piperidin-1-yl]phenyl}-7,8-dimethoxy-N,4-dimethyl-4,5-dihydro-3H-2,3-benzodiazepine-3-carboxamide | $^1$H-NMR (500 MHz, CDCl$_3$): δ = 1.13 (d, 3H), 1.35-1.43 (m, 2H), 1.56-1.60 (m, 2H), 1.63-1.71 (m, 1H), 1.81-1.87 (m, 2H), 2.71 (dd, 1H), 2.78-2.84 (m, 2H), 2.86 (d, 3H), 2.91 (dd, 1H), 3.70 (s, 3H), 3.74-3.77 (m, 2H), 3.78-3.83 (m, 2H), 3.93 (s, 3H), 5.23-5.29 (m, 1H), 6.05 (q, 1H), 6.65 (s, 1H), 6.75 (s, 1H), 6.92 (d, 2H), 7.48 (d, 2H).<br>LCMS (Method 1): R$_t$ = 0.96 min; m/z = 481 (M + H)$^+$ |
| 184 | 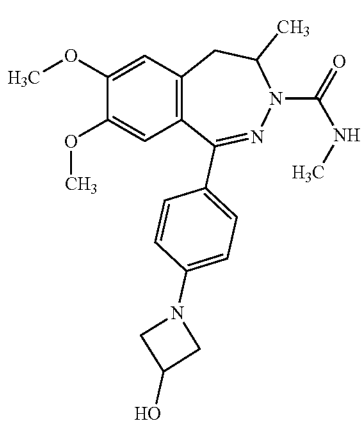 [SMILES: CNC(=O)N1N=C(c2ccc(N3CC(O)C3)cc2)c2cc(OC)c(OC)cc2CC1C] | (±)-1-[4-(3-hydroxyazetidin-1-yl)phenyl]-7,8-dimethoxy-N,4-dimethyl-4,5-dihydro-3H-2,3-benzodiazepine-3-carboxamide | $^1$H-NMR (400 MHz, CDCl$_3$): δ = 1.16 (d, 3H), 2.21 (d, 1H), 2.73 (dd, 1H), 2.88 (d, 3H), 2.92 (dd, 1H), 3.73 (s, 3H), 3.80 (dd, 2H), 3.96 (s, 3H), 4.27 (t, 2H), 4.80-4.87 (m, 1H), 5.22-5.31 (m, 1H), 6.02 (q, 1H), 6.47 (d, 2H), 6.65 (s, 1H), 6.76 (s, 1H), 7.50 (d, 2H).<br>LCMS (Method 1): R$_t$ = 0.91 min; m/z = 425 (M + H)$^+$ |

| No. | Structure | Name | Analytical data |
|---|---|---|---|
| 185 | 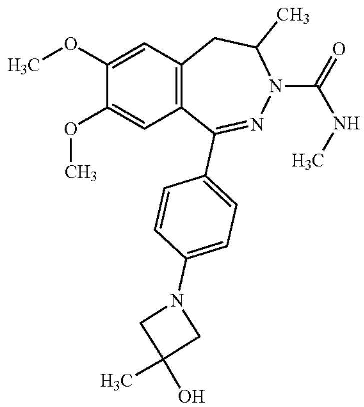 [SMILES: CNC(=O)N1N=C(c2ccc(N3CC(C)(O)C3)cc2)c2cc(OC)c(OC)cc2CC1C] | (±)-1-[4-(3-hydroxy-3-methylazetidin-1-yl)phenyl]-7,8-dimethoxy-N,4-dimethyl-4,5-dihydro-3H-2,3-benzodiazepine-3-carboxamide | $^1$H-NMR (400 MHz, CDCl$_3$): δ = 1.16 (d, 3H), 1.66 (s, 3H), 2.10 (s, br, 1H), 2.73 (dd, 1H), 2.88 (d, 3H), 2.92 (dd, 1H), 3.73 (s, 3H), 3.86 (d, 2H), 3.95 (d, 2H), 3.96 (s, 3H), 5.22-5.30 (m, 1H), 6.02 (q, 1H), 6.48 (d, 2H), 6.65 (s, 1H), 6.76 (s, 1H), 7.50 (d, 2H). LCMS (Method 1): R$_t$ = 0.97 min; m/z = 439 (M + H)$^+$ |
| 185.1 | 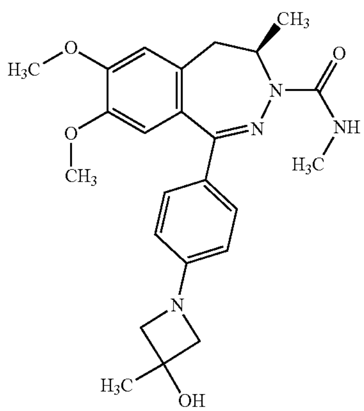 [SMILES: CNC(=O)N1N=C(c2ccc(N3CC(C)(O)C3)cc2)c2cc(OC)c(OC)cc2C[C@H]1C] | (4R)-1-[4-(3-hydroxy-3-methylazetidin-1-yl)phenyl]-7,8-dimethoxy-N,4-dimethyl-4,5-dihydro-3H-2,3-benzodiazepine-3-carboxamide | Prep. HPLC: Method XXI Analyt. HPLC (Method Y): R$_t$ = 2.35 min |
| 185.2 | 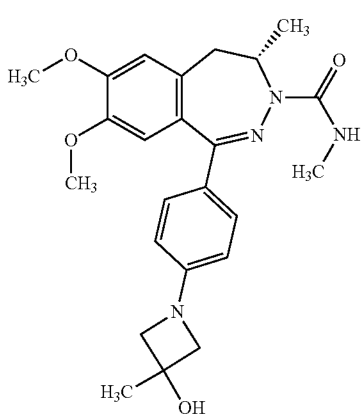 [SMILES: CNC(=O)N1N=C(c2ccc(N3CC(C)(O)C3)cc2)c2cc(OC)c(OC)cc2C[C@@H]1C] | (4S)-1-[4-(3-hydroxy-3-methylazetidin-1-yl)phenyl]-7,8-dimethoxy-N,4-dimethyl-4,5-dihydro-3H-2,3-benzodiazepine-3-carboxamide | Prep. HPLC: Method XXI Analyt. HPLC (Method Y): R$_t$ = 3.13 min |

| No. | Structure | Name | Analytical data |
|---|---|---|---|
| 186 | 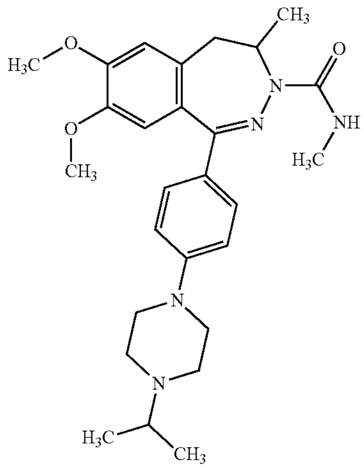 [SMILES: CNC(=O)N1N=C(c2ccc(N3CCN(C(C)C)CC3)cc2)c2cc(OC)c(OC)cc2CC1C] | (±)-1-[4-(4-Isopropylpiperazin-1-yl)phenyl]-7,8-dimethoxy-N,4-dimethyl-4,5-dihydro-3H-2,3-benzodiazepine-3-carboxamide | $^1$H-NMR (400 MHz, CDCl$_3$): δ = 1.12-1.14 (m, 9H), 2.71-2.79 (m, 6H), 2.89 (d, 3H), 2.96 (dd, 1H), 3.32-3.35 (m, 4H), 3.72 (s, 3H), 3.96 (s, 3H), 5.26-5.34 (m, 1H), 6.11 (q, 1H), 6.67 (s, 1H), 6.77 (s, 1H), 6.94 (d, 2H), 7.52 (d, 2H). LCMS (Method 1): R$_t$ = 0.76 min; m/z = 480 (M + H)$^+$ |
| 187 | 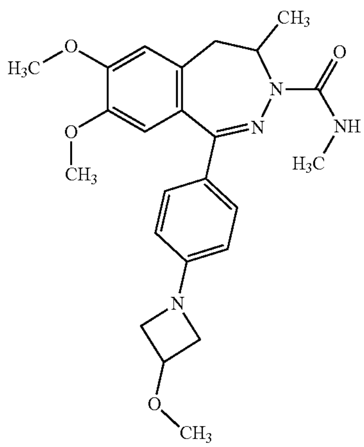 [SMILES: CNC(=O)N1N=C(c2ccc(N3CC(OC)C3)cc2)c2cc(OC)c(OC)cc2CC1C] | (±)-7,8-dimethoxy-1-[4-(3-methoxyazetidin-1-yl)phenyl]-N,4-dimethyl-4,5-dihydro-3H-2,3-benzodiazepine-3-carboxamide | $^1$H-NMR (300 MHz, CDCl$_3$): δ = 1.16 (d, 3H), 2.73 (dd, 1H), 2.88 (d, 3H), 2.93 (dd, 1H), 3.38 (s, 3H), 3.73 (s, 3H), 3.80-3.84 (m, 2H), 3.96 (s, 3H), 4.17-4.22 (m, 2H), 4.37-4.43, 5.22-5.32 (m, 1H), 6.02 (q, 1H), 6.47 (d, 2H), 6.65 (s, 1H), 6.78 (s, 1H), 7.50 (d, 2H). LCMS (Method 1): R$_t$ = 1.11 min; m/z = 439 (M + H)$^+$ |
| 188 | 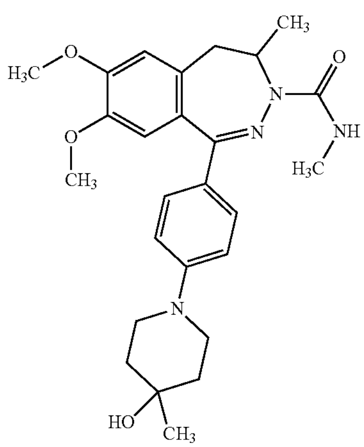 | (±)-1-[4-(4-hydroxy-4-methylpiperidin-1-yl)phenyl]-7,8-dimethoxy-N,4-dimethyl-4,5-dihydro-3H-2,3-benzodiazepine-3-carboxamide | $^1$H-NMR (400 MHz, CDCl$_3$): δ = 1.15 (d, 3H), 1.34 (s, 3H), 1.71-1.84 (m, 4H), 2.74 (dd, 1H), 2.89 (d, 3H), 2.95 (dd, 1H), 3.29-3.35 (m, 2H), 3.49-3.54 (m, 2H), 3.73 (s, 3H), 3.96 (s, 3H), 5.24-5.33 (m, 1H), 6.08 (q, 1H), 6.68 (s, 1H), 6.78 (s, 1H), 6.95 (d, 2H), 7.51 (d, 2H). LCMS (Method 1): R$_t$ = 0.96 min; m/z = 467 (M + H)$^+$ |

| No. | Structure | Name | Analytical data |
|---|---|---|---|
| 188.1 | 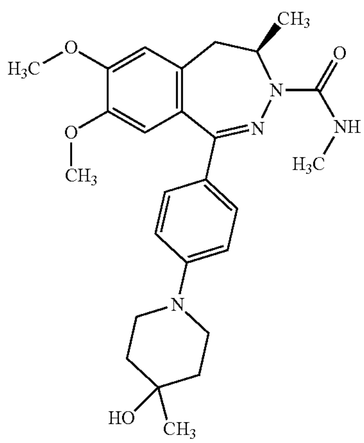 [SMILES: CNC(=O)N1N=C(c2ccc(N3CCC(C)(O)CC3)cc2)c2cc(OC)c(OC)cc2C[C@H]1C] | (4R)-1-[4-(4-hydroxy-4-methylpiperidin-1-yl)phenyl]-7,8-dimethoxy-N,4-dimethyl-4,5-dihydro-3H-2,3-benzodiazepine-3-carboxamide | Prep. HPLC: Method XX<br>Analyt. HPLC (Method L): $R_t$ = 5.45 min |
| 188.2 | 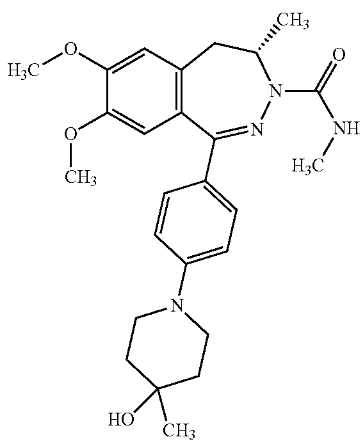 [SMILES: CNC(=O)N1N=C(c2ccc(N3CCC(C)(O)CC3)cc2)c2cc(OC)c(OC)cc2C[C@@H]1C] | (4S)-1-[4-(4-hydroxy-4-methylpiperidin-1-yl)phenyl]-7,8-dimethoxy-N,4-dimethyl-4,5-dihydro-3H-2,3-benzodiazepine-3-carboxamide | Prep. HPLC: Method XX<br>Analyt. HPLC (Method L): $R_t$ = 8.05 min |
| 189 | 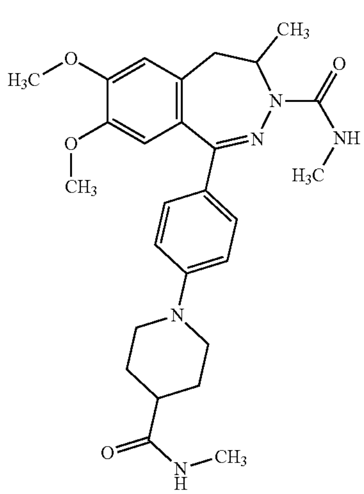 | (±)-7,8-dimethoxy-N,4-dimethyl-1-{4-[4-(methylcarbamoyl)piperidin-1-yl]phenyl}-4,5-dihydro-3H-2,3-benzodiazepine-3-carboxamide | $^1$H-NMR (300 MHz, CDCl$_3$): δ = 1.14 (d, 3H), 1.82-2.06 (m, 4H), 2.24-2.38 (m, 1H), 2.72 (dd, 1H), 2.81-3.02 (m, 9H), 3.73 (s, 3H), 3.89 (d, 2H), 3.96 (s, 3H), 5.29 (m, 1H), 5.55 (m, 1H), 6.10 (m, 1H), 6.67 (s, 1H), 6.77 (s, 1H), 6.93 (d, 2H), 7.51 (d, 2H).<br>LCMS (Method 1): $R_t$ = 0.93 min; m/z = 494 (M + H)$^+$ |

| No. | Structure | Name | Analytical data |
|---|---|---|---|
| 189.1 | 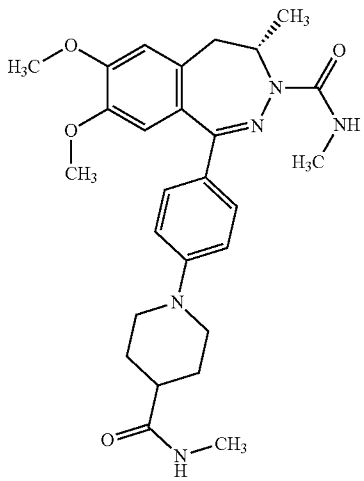 [SMILES: CNC(=O)C1CCN(c2ccc(C3=NN(C(=O)NC)[C@@H](C)Cc4cc(OC)c(OC)cc43)cc2)CC1] | (4S)-7,8-dimethoxy-N,4-dimethyl-1-{4-[4-(methylcarbamoyl)piperidin-1-yl]phenyl}-4,5-dihydro-3H-2,3-benzodiazepine-3-carboxamide | Prep. HPLC: Method XIX<br>Analyt. HPLC (Method V):<br>$R_t$ = 7.35 min<br>$[\alpha]_D^{20}$ = 292.7° (c = 1.00; MeOH) |
| 189.2 | 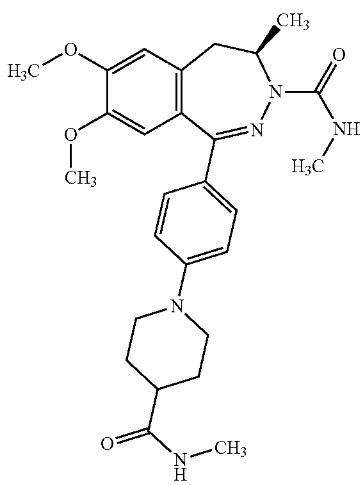 [SMILES: CNC(=O)C1CCN(c2ccc(C3=NN(C(=O)NC)[C@H](C)Cc4cc(OC)c(OC)cc43)cc2)CC1] | (4R)-7,8-dimethoxy-N,4-dimethyl-1-{4-[4-(methylcarbamoyl)piperidin-1-yl]phenyl}-4,5-dihydro-3H-2,3-benzodiazepine-3-carboxamide | Prep. HPLC: Method XIX<br>Analyt. HPLC (Method V):<br>$R_t$ = 6.23 min<br>$[\alpha]_D^{20}$ = −311.5° (c = 1.00; MeOH) |
| 190 | 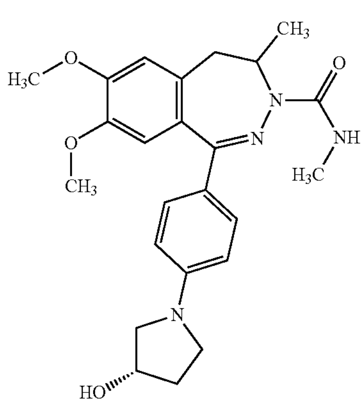 [SMILES: CNC(=O)N1N=C(c2ccc(N3CC[C@H](O)C3)cc2)c2cc(OC)c(OC)cc2CC1C] | (±)-1-{4-[(3S)-3-hydroxypyrrolidin-1-yl]phenyl}-7,8-dimethoxy-N,4-dimethyl-4,5-dihydro-3H-2,3-benzodiazepine-3-carboxamide | LCMS (Method 2): $R_t$ = 0.80 min; m/z = 439 (M + H)⁺ |

-continued

| No. | Structure | Name | Analytical data |
|---|---|---|---|
| 190.1 | 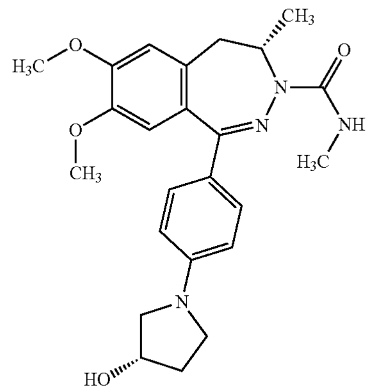 [SMILES: CNC(=O)N1N=C(c2ccc(N3CC[C@H](O)C3)cc2)c2cc(OC)c(OC)cc2C[C@@H]1C] | (4S)-1-{4-[(3S)-3-hydroxypyrrolidin-1-yl]phenyl}-7,8-dimethoxy-N,4-dimethyl-4,5-dihydro-3H-2,3-benzodiazepine-3-carboxamide | $^1$H-NMR (300 MHz, CDCl$_3$): δ = 1.20 (d, 3H), 1.74 (s, br, 1H), 2.07-2.30 (m, 2H), 2.71 (dd, 1H), 2.88 (d, 3H), 2.90 (dd, 1H), 3.37 (d, 1H), 3.47 (dt, 1H), 3.57-3.65 (m, 2H), 3.74 (s, 3H), 3.96 (s, 3H), 4.68 (m, 1H), 5.17-5.30 (m, 1H), 5.94 (q, 1H), 6.59 (d, 2H), 6.68 (s, 1H), 6.79 (s, 1H), 7.54 (d, 2H). LCMS (Method 1): R$_t$ = 0.92 min; m/z = 439 (M + H)$^+$ |
| 191 | 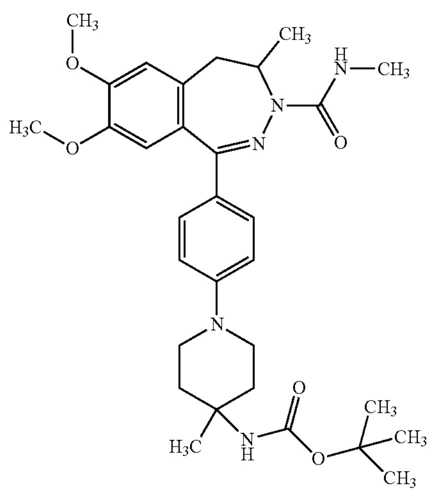 [SMILES: CNC(=O)N1N=C(c2ccc(N3CCC(C)(NC(=O)OC(C)(C)C)CC3)cc2)c2cc(OC)c(OC)cc2CC1C] | (±)-tert-butyl (1-{4-[7,8-dimethoxy-4-methyl-3-(methylcarbamoyl)-4,5-dihydro-3H-2,3-benzodiazepin-1-yl]phenyl}-4-methylpiperidin-4-yl)carbamate | $^1$H-NMR (300 MHz, CDCl$_3$): δ = 1.14 (d, 3H), 1.43 (s, 3H), 1.47 (s, 9H), 1.77 (dt, 2H), 2.16 (d, br, 2H), 2.74 (dd, 1H), 2.88 (d, 3H), 2.95 (dd, 1H), 3.16 (dt, 2H), 3.43-3.54 (m, 2H), 3.73 (s, 3H), 3.96 (s, 3H), 4.41 (s, br, 1H), 5.23-5.37 (m, 1H), 6.10 (q, 1H), 6.67 (s, 1H), 6.77 (s, 1H), 6.94 (d, 2H), 7.51 (d, 2H). LCMS (Method 2): R$_t$ = 1.29 min; m/z = 566 (M + H)$^+$ |
| 192 | 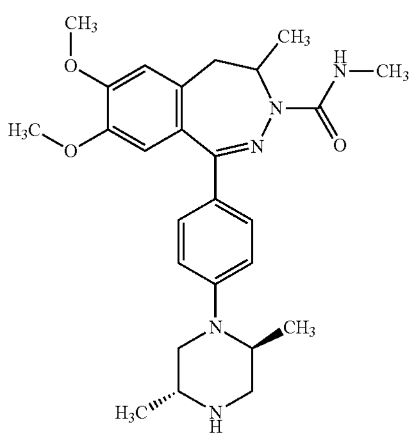 | (±)-1-{4-[(2S,5R)-2,5-dimethylpiperazin-1-yl]phenyl}-7,8-dimethoxy-N,4-dimethyl-4,5-dihydro-3H-2,3-benzodiazepine-3-carboxamide | $^1$H-NMR (300 MHz, CDCl$_3$): δ = 1.05 (d, 3H), 1.10 (dd, 3H), 1.15 (d, 3H), 2.65 (dd, 1H), 2.73-2.84 (m, 2H), 2.90 (d, 3H), 3.02 (dt, 1H), 3.10-3.29 (m, 4H), 3.71 (s, 3H), 3.96 (s, 3H), 5.30-5.42 (m, 1H), 6.21-6.31 (m, 1H), 6.65 (s, 1H), 6.76 (s, 1H), 7.09 (d, 2H), 7.51 (d, 2H). LCMS (Method 2): R$_t$ = 0.64 min; m/z = 466 (M + H)$^+$ |

| No. | Structure | Name | Analytical data |
|---|---|---|---|
| 193 | 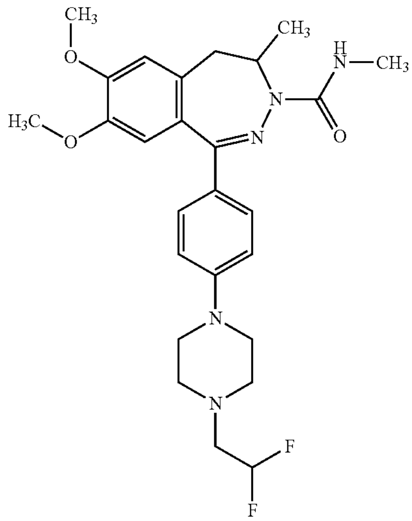 | (±)-1-{4-[4-(2,2-difluoroethyl)piperazin-1-yl]phenyl}-7,8-dimethoxy-N,4-dimethyl-4,5-dihydro-3H-2,3-benzodiazepine-3-carboxamide | ¹H-NMR (600 MHz, DMSO-d₆): δ = 1.05 (d, 3H), 2.44-2.49 (m, 1H), 2.63 (d, 3H), 2.66-2.69 (m, 4H), 2.76-2.87 (m, 3H), 3.23-3.28 (m, 4H), 3.60 (s, 3H), 3.84 (s, 3H), 4.90 (dquin, 1H), 6.07-6.33 (m, 2H), 6.55 (s, 1H), 6.95 (d, 2H), 7.02 (s, 1H), 7.59 (d, 2H). LCMS (Method 2): R_t = 0.90 min; m/z = 502 (M + H)⁺ |
| 194 | 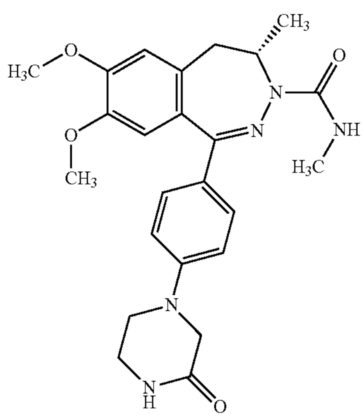 [SMILES: CNC(=O)N1N=C(c2ccc(N3CCNC(=O)C3)cc2)c2cc(OC)c(OC)cc2C[C@@H]1C] | (4S)-7,8-dimethoxy-N,4-dimethyl-1-[4-(3-oxopiperazin-1-yl)phenyl]-4,5-dihydro-3H-2,3-benzodiazepine-3-carboxamide | ¹H-NMR (300 MHz, CDCl₃): δ = 1.00 (d, 3H), 2.59-2.69 (m, 5H), 2.92 (dd, 1H), 3.03 (t, 2H), 3.41 (s, 2H), 3.59 (s, 3H), 3.63-3.68 (m, 2H), 3.84 (s, 3H), 4.97-5.10 (m, 1H), 6.50-6.56 (m, 2H), 7.03 (s, 1H), 7.40 (d, 2H), 7.70 (d, 2H). LCMS (Method 1): R_t = 0.69 min; m/z = 452 (M + H)⁺ |
| 195 | 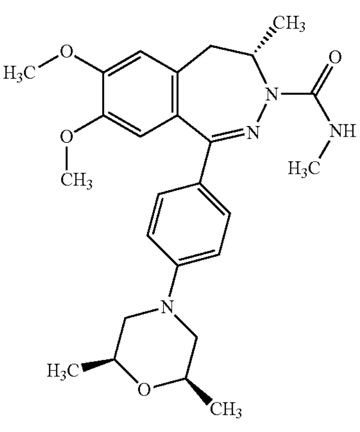 [SMILES: CNC(=O)N1N=C(c2ccc(N3C[C@@H](C)O[C@@H](C)C3)cc2)c2cc(OC)c(OC)cc2C[C@@H]1C] | (4S)-1-{4-[(2R,6S)-2,6-dimethylmorpholin-4-yl]phenyl}-7,8-dimethoxy-N,4-dimethyl-4,5-dihydro-3H-2,3-benzodiazepine-3-carboxamide | ¹H-NMR (300 MHz, CDCl₃): δ = 1.13 (d, 3H), 1.31 (d, 6H), 2.52 (dd, 2H), 2.75 (dd, 1H), 2.89 (d, 3H), 2.98 (dd, 1H), 3.58 (d, 2H), 3.72 (s, 3H), 3.78-3.90 (m, 2H), 3.96 (s, 3H), 5.25-5.39 (m, 1H), 6.15 (q, 1H), 6.66 (s, 1H), 6.77 (s, 1H), 6.92 (d, 2H), 7.52 (d, 2H). LCMS (Method 1): R_t = 1.23 min; m/z = 467 (M + H)⁺ |

| No. | Structure | Name | Analytical data |
|---|---|---|---|
| 196 | 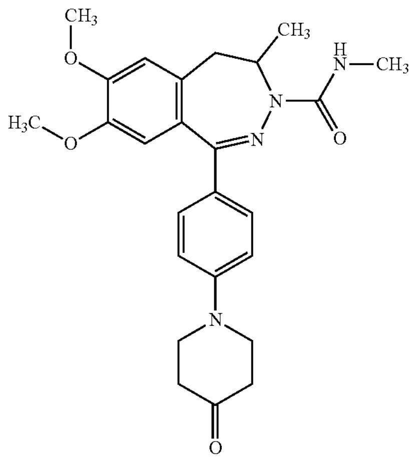 | (±)-7,8-dimethoxy-N,4-dimethyl-1-[4-(4-oxopiperidin-1-yl)phenyl]-4,5-dihydro-3H-2,3-benzodiazepine-3-carboxamide | $^1$H-NMR (300 MHz, CDCl$_3$): δ = 1.13 (d, 3H), 2.62 (t, 4H), 2.76 (dd, 1H), 2.89 (d, 3H), 2.98 (dd, 1H), 3.73 (s, 3H), 3.71-3.79 (m, 4H), 3.97 (s, 3H), 5.27-5.39 (m, 1H), 6.12-6.20 (m, 1H), 6.68 (s, 1H), 6.78 (s, 1H), 6.99 (d, 2H), 7.56 (d, 2H).<br>LCMS (Method 5): R$_t$ = 0.92 min; m/z = 451 (M + H)$^+$ |
| 197 | 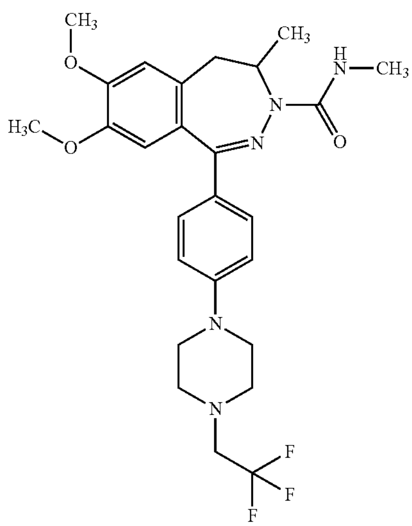 | (±)-7,8-dimethoxy-N,4-dimethyl-1-{4-[4-(2,2,2-trifluoroethyl)piperazin-1-yl]phenyl}-4,5-dihydro-3H-2,3-benzodiazepine-3-carboxamide | $^1$H-NMR (300 MHz, CDCl$_3$): δ = 1.12 (d, 3H), 2.75 (dd, 1H), 2.85-2.92 (m, 4H), 2.88 (d, 3H), 2.97 (dd, 1H), 3.08 (q, 2H), 3.31-3.39 (m, 4H), 3.72 (s, 3H), 3.96 (s, 3H), 5.27-5.37 (m, 1H), 6.12-6.19 (m, 1H), 6.66 (s, 1H), 6.77 (s, 1H), 6.94 (d, 2H), 7.52 (d, 2H).<br>LCMS (Method 5): R$_t$ = 1.22 min; m/z = 520 (M + H)$^+$ |
| 198 | 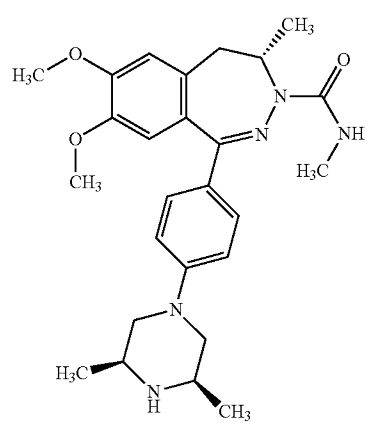 [SMILES: CNC(=O)N1N=C(c2ccc(N3C[C@@H](C)N[C@@H](C)C3)cc2)c2cc(OC)c(OC)cc2C[C@@H]1C] | (4S)-1-{4-[(3R,5S)-3,5-dimethylpiperazin-1-yl]phenyl}-7,8-dimethoxy-N,4-dimethyl-4,5-dihydro-3H-2,3-benzodiazepine-3-carboxamide | $^1$H-NMR (300 MHz, CDCl$_3$): δ = 1.14 (d, 3H), 1.19 (d, 6H), 2.40 (t, 2H), 2.74 (dd, 1H), 2.88 (d, 3H), 2.96 (dd, 1H), 3.01-3.13 (m, 2H), 3.66 (dd, 2H), 3.73 (s, 3H), 3.96 (s, 3H), 5.24-5.37 (m, 1H), 6.11 (q, 1H), 6.67 (s, 1H), 6.77 (s, 1H), 6.93 (d, 2H), 7.51 (d, 2H).<br>LCMS (Method 1): R$_t$ = 0.77 min; m/z = 466 (M + H)$^+$ |

Example 199

(±)-7,8-Dihydroxy-N,4-dimethyl-1-[4-(4-methylpiperazin-1-yl)phenyl]-4,5-dihydro-3H-2,3-benzodiazepine-3-carboxamide

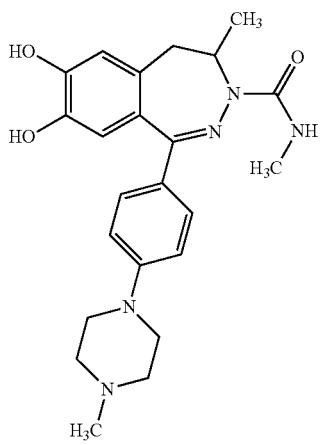 [SMILES: CNC(=O)N1N=C(c2ccc(N3CCN(C)CC3)cc2)c2cc(O)c(O)cc2CC1C]

The compound was prepared analogously to Example 91A from Example 127.

LCMS (Method 1): $R_t$=1.01 min; m/z=424 (M+H)$^+$ $^1$H-NMR (300 MHz, DMSO-d$_6$): δ=0.97 (d, 3H), 2.50 (m, 1H), 2.60 (d, 3H), 3.11 (s, 3H), 3.22-3.53 (m, 5H), 3.77-3.94 (m, 4H), 4.80-4.90 (m, 1H), 6.26-6.32 (m, 1H), 6.36 (s, 1H), 6.69 (s, 1H), 6.99 (d, 2H), 7.57 (d, 2H), 8.91 (s, br, 1H), 9.36 (s, br, 1H).

Example 200

(±)-7,8-Diethoxy-N,4-dimethyl-1-[4-(4-methylpiperazin-1-yl)phenyl]-4,5-dihydro-3H-2,3-benzodiazepine-3-carboxamide

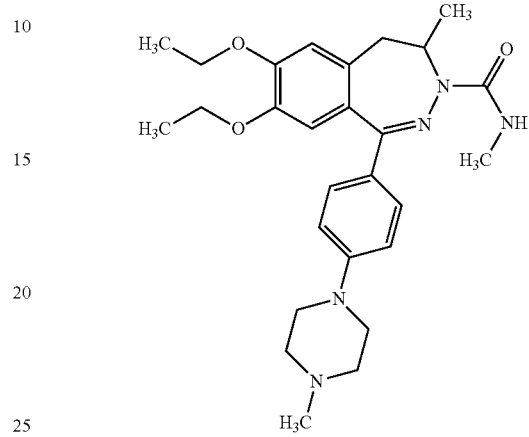

The compound was prepared analogously to Example 93A from Example 199.

LCMS (Method 1): $R_t$=1.48 min; m/z=480 (M+H)$^+$ $^1$H-NMR (600 MHz, DMSO-d$_6$): δ=1.03 (d, 3H), 1.22 (t, 3H), 1.35 (t, 3H), 2.51 (m, 1H), 2.64 (d, 3H), 2.84 (dd, 1H), 3.14 (s, 3H), 3.30-3.37 (m, 2H), 3.51 (d, 2H), 3.77-3.88 (m, 4H), 3.92 (d, 2H), 4.11 (q, 2H), 4.90-4.96 (m, 1H), 6.37 (q, 1H), 6.50 (s, 1H), 7.00 (s, 1H), 7.02 (d, 2H), 7.62 (d, 2H).

The following exemplary compounds were prepared analogously to Example 127.1 from Example 127A and the appropriate commercially available amines:

| No. | Structure | Name | Analytical data |
|---|---|---|---|
| 201 | 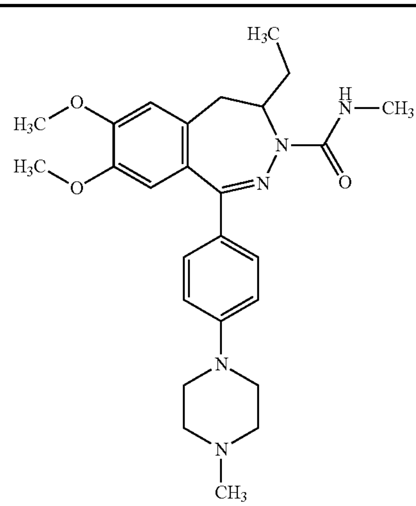 | (±)-4-ethyl-7,8-dimethoxy-N-methyl-1-[4-(4-methylpiperazin-1-yl)phenyl]-4,5-dihydro-3H-2,3-benzodiazepine-3-carboxamide | $^1$H-NMR (300 MHz, CDCl$_3$): δ = 0.90 (t, 3H), 1.21-1.37 (m, 1H), 1.50-1.61 (m, 1H), 2.40 (s, 3H), 2.56-2.69 (m, 4H), 2.84 (dd, 1H), 2.88 (d, 3H), 2.99 (dd, 1H), 3.29-3.39 (m, 4H), 3.71 (s, 3H), 3.96 (s, 3H), 5.12-5.24 (m, 1H), 6.22-6.32 (m, 1H), 6.68 (s, 1H), 6.76 (s, 1H), 6.94 (d, 2H), 7.49 (d, 2H). LCMS (Method 1): $R_t$ = 0.65 min; m/z = 466 (M + H)$^+$ |

| No. | Structure | Name | Analytical data |
|---|---|---|---|
| 201.1 | 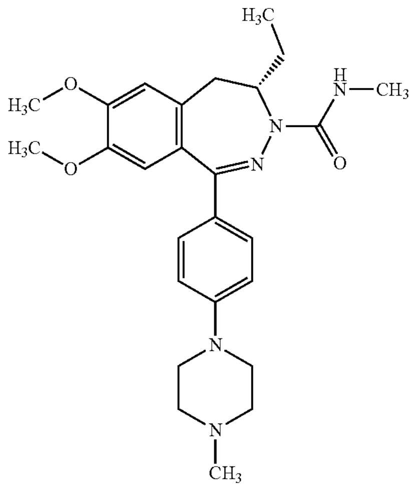 | (4S)-4-ethyl-7,8-dimethoxy-N-methyl-1-[4-(4-methylpiperazin-1-yl)phenyl]-4,5-dihydro-3H-2,3-benzodiazepine-3-carboxamide | Prep. HPLC: Method XIIa<br>Analyt. HPLC (Method Q):<br>$R_t$ = 10.90 min<br>$[\alpha]_D^{20}$ = 100.8° (c = 1.00; CHCl$_3$)<br>LCMS (Method 5): $R_t$ = 0.64 min;<br>m/z = 466 (M + H)$^+$ |
| 202 | 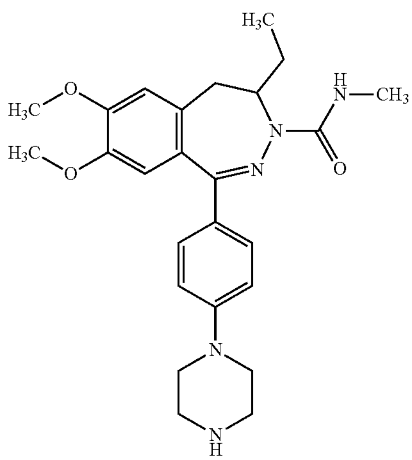 | (±)-4-ethyl-7,8-dimethoxy-N-methyl-1-[4-(piperazin-1-yl)phenyl]-4,5-dihydro-3H-2,3-benzodiazepine-3-carboxamide | $^1$H-NMR (300 MHz, CDCl$_3$): δ = 0.90 (t, 3H), 1.23-1.38 (m, 1H), 1.52-1.61 (m, 1H), 2.85 (dd, 1H), 2.88 (d, 3H), 2.99 (dd, 1H), 3.04-3.11 (m, 4H), 3.23-3.31 (m, 4H), 3.71 (s, 3H), 3.96 (s, 3H), 5.13-5.22 (m, 1H), 6.26 (q, 1H), 6.69 (s, 1H), 6.77 (s, 1H), 6.93 (d, 2H), 7.49 (d, 2H).<br>LCMS (Method 1): $R_t$ = 0.65 min;<br>m/z = 452 (M + H)$^+$ |
| 202.1 | 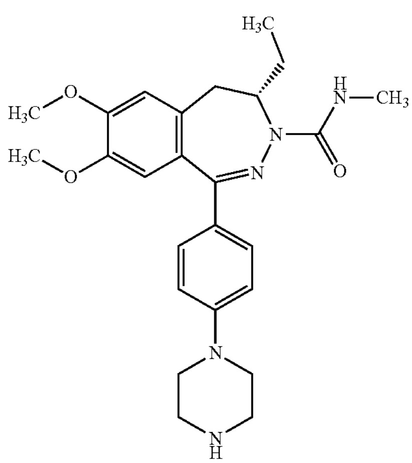 | (4S)-4-ethyl-7,8-dimethoxy-N-methyl-1-[4-(piperazin-1-yl)phenyl]-4,5-dihydro-3H-2,3-benzodiazepine-3-carboxamide | Prep. HPLC: Method XXa<br>Analyt. HPLC (Method L1):<br>$R_t$ = 4.10 min<br>$[\alpha]_D^{20}$ = 86.2° (c = 1.00; CHCl$_3$)<br>LCMS (Method 5): $R_t$ = 0.63 min;<br>m/z = 452 (M + H)$^+$ |

| No. | Name | Analytical data |
|---|---|---|
| 202.2 | (4R)-4-ethyl-7,8-dimethoxy-N-methyl-1-[4-(piperazin-1-yl)phenyl]-4,5-dihydro-3H-2,3-benzodiazepine-3-carboxamide | Prep. HPLC: Method XXa<br>Analyt. HPLC (Method L1):<br>$R_t$ = 5.50 min<br>$[\alpha]_D^{20}$ = −103.4° (c = 1.00; CHCl$_3$)<br>LCMS (Method 5): $R_t$ = 0.63 min;<br>m/z = 452 (M + H)$^+$ |
| 203 | (±)-4-ethyl-7,8-dimethoxy-N-methyl-1-{4-[4-(methylsulphonyl)piperazin-1-yl]phenyl}-4,5-dihydro-3H-2,3-benzodiazepine-3-carboxamide | $^1$H-NMR (300 MHz, CDCl$_3$): δ = 0.89 (t, 3H), 1.18-1.33 (m, 1H), 1.46-1.59 (m, 1H), 2.87 (s, 3H), 2.81-2.88 (m, 1H), 2.89 (d, 3H), 3.01 (dd, 1H), 3.35-3.47 (m, 8H), 3.70 (s, 3H), 3.96 (s, 3H), 5.15-5.25 (m, 1H), 6.30-6.38 (m, 1H), 6.66 (s, 1H), 6.76 (s, 1H), 6.95 (d, 2H), 7.49 (d, 2H).<br>LCMS (Method 1): $R_t$ = 1.01 min;<br>m/z = 530 (M + H)$^+$ |
| 203.1 | (4S)-4-ethyl-7,8-dimethoxy-N-methyl-1-{4-[4-(methylsulphonyl)piperazin-1-yl]phenyl}-4,5-dihydro-3H-2,3-benzodiazepine-3-carboxamide | Prep. HPLC: Method IVa<br>Analyt. HPLC (Method Fa):<br>$R_t$ = 6.22 min<br>$[\alpha]_D^{20}$ = 252.5° (c = 1.00; MeOH)<br>LCMS (Method 5): $R_t$ = 1.0 min;<br>m/z = 530 (M + H)$^+$ |

| No. | Structure | Name | Analytical data |
|---|---|---|---|
| 203.2 | 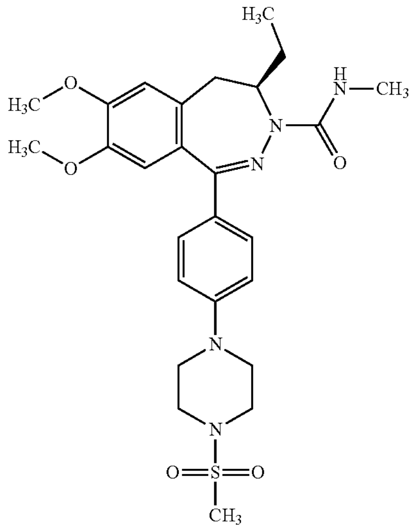 | (4R)-4-ethyl-7,8-dimethoxy-N-methyl-1-{4-[4-(methylsulphonyl)piperazin-1-yl]phenyl}-4,5-dihydro-3H-2,3-benzodiazepine-3-carboxamide | Prep. HPLC: Method IVa Analyt. HPLC (Method Fa): $R_t$ = 4.37 min $[\alpha]_D^{20}$ = −257.4° (c = 1.00; MeOH) LCMS (Method 5): $R_t$ = 1.0 min; m/z = 530 (M + H)$^+$ |
| 204 | 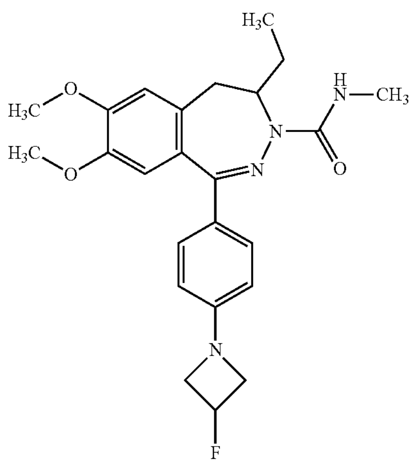 | (±)-4-ethyl-1-[4-(3-fluoroazetidin-1-yl)phenyl]-7,8-dimethoxy-N-methyl-4,5-dihydro-3H-2,3-benzodiazepine-3-carboxamide | $^1$H-NMR (300 MHz, CDCl$_3$): δ = 0.92 (t, 3H), 1.26-1.46 (m, 1H), 1.53-1.71 (m, 1H), 2.83 (m, 1H), 2.87 (d, 3H), 2.98 (dd, 1H), 3.72 (s, 3H), 3.96 (s, 3H), 4.0-4.15 (m, 2H), 4.23-4.37 (m, 2H), 5.10-5.23 (m, 1H), 5.49 (d, 1H), 6.20 (q, 1H), 6.49 (d, 2H), 6.67 (s, 1H), 6.78 (s, 1H), 7.52 (s, br, 2H). LCMS (Method 5): $R_t$ = 1.13 min; m/z = 441 (M + H)$^+$ |
| 205 | 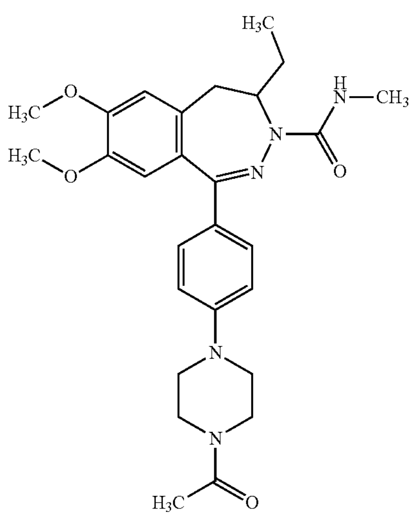 | (±)-1-[4-(4-acetylpiperazin-1-yl)phenyl]-4-ethyl-7,8-dimethoxy-N-methyl-4,5-dihydro-3H-2,3-benzodiazepine-3-carboxamide | $^1$H-NMR (300 MHz, CDCl$_3$): δ = 0.90 (t, 3H), 1.19-1.36 (m, 1H), 1.47-1.62 (m, 1H), 2.18 (s, 3H), 2.83-2.93 (m, 1H), 2.88 (d, 3H), 3.01 (dd, 1H), 3.26-3.38 (m, 4H), 3.66-3.73 (m, 2H), 3.70 (s, 3H), 3.80-3.88 (m, 2H), 3.96 (s, 3H), 5.14-5.26 (m, 1H), 6.29-6.38 (m, 1H), 6.66 (s, 1H), 7.77 (s, 1H), 6.96 (d, 2H), 7.51 (d, 2H). LCMS (Method 5): $R_t$ = 0.92 min; m/z = 494 (M + H)$^+$ |

| No. | Structure | Name | Analytical data |
|---|---|---|---|
| 206 | 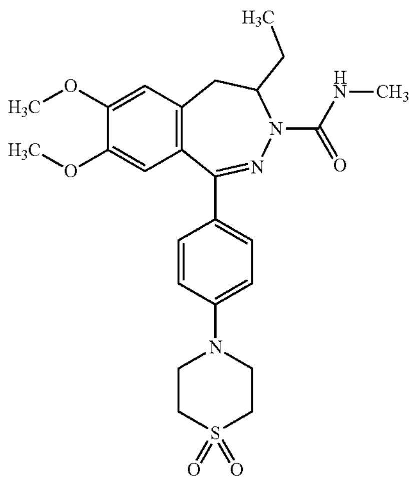 | (±)-1-[4-(1,1-dioxidothiomorpholin-4-yl)phenyl]-4-ethyl-7,8-dimethoxy-N-methyl-4,5-dihydro-3H-2,3-benzodiazepine-3-carboxamide | $^1$H-NMR (300 MHz, CDCl$_3$): δ = 0.90 (t, 3H), 1.17-1.34 (m, 1H), 1.45-1.59 (m, 1H), 2.85-2.95 (m, 1H), 2.89 (d, 3H), 3.02 (dd, 1H), 3.12-3.20 (m, 4H), 3.72 (s, 3H), 3.97 (s, 3H), 3.96-4.03 (m, 4H), 5.17-5.28 (m, 1H), 6.34-6.43 (m, 1H), 6.66 (s, 1H), 6.77 (s, 1H), 6.94 (d, 2H), 7.53 (d, 2H). LCMS (Method 5): R$_t$ = 0.92 min; m/z = 501 (M + H)$^+$ |
| 207 | 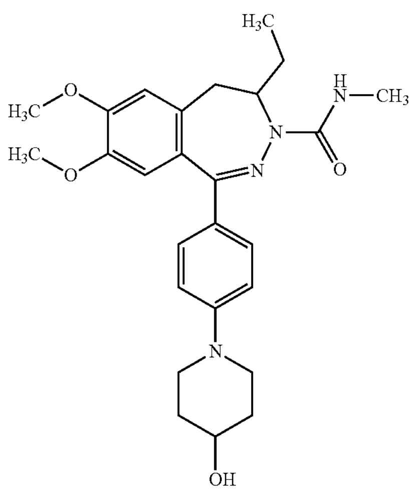 | (±)-4-ethyl-1-[4-(4-hydroxypiperidin-1-yl)phenyl]-7,8-dimethoxy-N-methyl-4,5-dihydro-3H-2,3-benzodiazepine-3-carboxamide | $^1$H-NMR (400 MHz, CDCl$_3$): δ = 0.90 (t, 3H), 1.25-1.38 (m, 1H), 1.51-1.64 (m, 2H), 1.67-1.78 (m, 2H), 2.01-2.10 (m, 2H), 2.84 (dd, 1H), 2.88 (d, 3H), 2.98 (dd, 1H), 3.07 (dt, 2H), 3.66-3.71 (m, 2H), 3.71 (s, 3H), 3.89-3.95 (m, 1H), 3.96 (s, 3H), 5.12-5.21 (m, 1H), 6.20-6.26 (m, 1H), 6.69 (s, 1H), 6.77 (s, 1H), 6.94 (d, 2H), 7.48 (d, 2H). LCMS (Method 5): R$_t$ = 0.87 min; m/z = 467 (M + H)$^+$ |
| 208 | 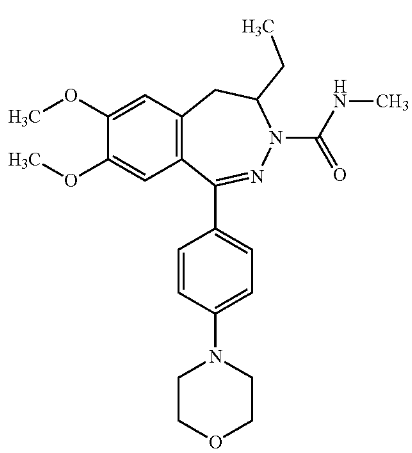 | (±)-4-ethyl-7,8-dimethoxy-N-methyl-1-[4-(morpholin-4-yl)phenyl]-4,5-dihydro-3H-2,3-benzodiazepine-3-carboxamide | $^1$H-NMR (300 MHz, CDCl$_3$): δ = 0.90 (t, 3H), 1.20-1.36 (m, 1H), 1.50-1.65 (m, 1H), 2.86 (dd, 1H), 2.88 (d, 3H), 3.00 (dd, 1H), 3.24-3.31 (m, 4H), 3.71 (s, 3H), 3.87-3.94 (m, 4H), 3.96 (s, 3H), 5.13-5.24 (m, 1H), 6.30 (q, 1H), 6.68 (s, 1H), 6.76 (s, 1H), 6.93 (d, 2H), 7.50 (d, 2H). LCMS (Method 5): R$_t$ = 1.06 min; m/z = 453 (M + H)$^+$ |

| No. | Structure | Name | Analytical data |
|---|---|---|---|
| 209 | 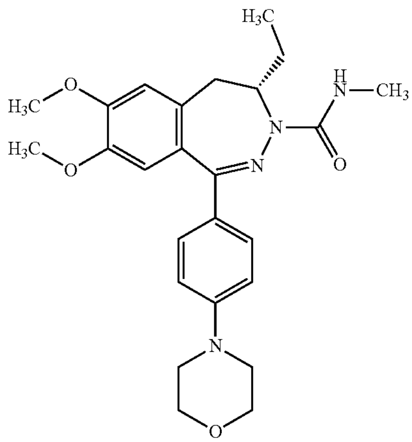 | (4S)-4-ethyl-7,8-dimethoxy-N-methyl-1-[4-(morpholin-4-yl)phenyl]-4,5-dihydro-3H-2,3-benzodiazepine-3-carboxamide | Prep. HPLC: Method XIIa<br>Analyt. HPLC (Method V):<br>$R_t$ = 12.46 min<br>$[\alpha]_D^{20}$ = 75.1° (c = 1.00; CHCl$_3$)<br>LCMS (Method 5): $R_t$ = 1.06 min;<br>m/z = 453 (M + H)$^+$ |

The following exemplary compounds were prepared analogously to Example 127.1 from Example 130A and the appropriate commercially available amines. In many cases, under the reaction conditions, mixtures of mono- and di-aminated products, and also mono-dehalogenated coupling products, were obtained, and were separated by chromatography.

| No. | Structure | Name | Analytical data |
|---|---|---|---|
| 210 | 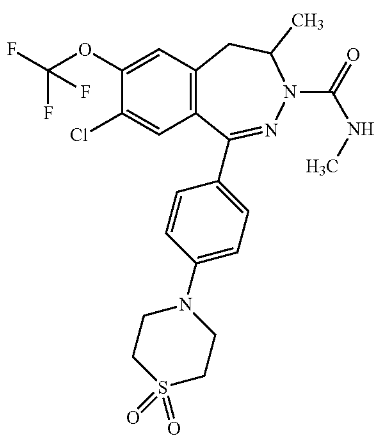 [SMILES: CNC(=O)N1N=C(c2ccc(N3CCS(=O)(=O)CC3)cc2)c2cc(Cl)c(OC(F)(F)F)cc2CC1C] | (±)-8-chloro-1-[4-(1,1-dioxidothiomorpholin-4-yl)phenyl]-N,4-dimethyl-7-(trifluoromethoxy)-4,5-dihydro-3H-2,3-benzodiazepine-3-carboxamide | $^1$H-NMR (400 MHz, CDCl$_3$): δ = 1.02 (d, 3H), 2.79-2.92 (m, 4H), 3.06 (dd, 1H), 3.11-3.18 (m, 4H), 3.92-4.01 (m, 4H), 5.35-5.48 (m, 1H), 6.27 (br. s., 1H), 6.95 (d, 2H), 7.21 (d, 1H), 7.26 (s, 1H), 7.46 (d, 2H).<br>LCMS (Method 1): $R_t$ = 1.28 min; m/z = 545 (M + H)$^+$ |
| 211 | 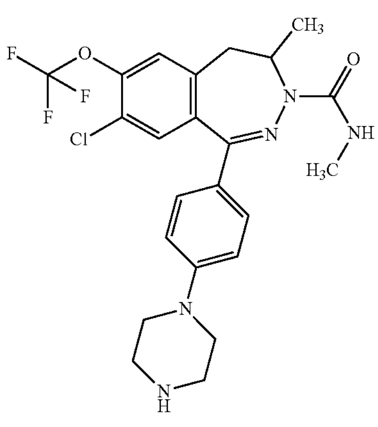 [SMILES: CNC(=O)N1N=C(c2ccc(N3CCNCC3)cc2)c2cc(Cl)c(OC(F)(F)F)cc2CC1C] | (±)-8-chloro-N,4-dimethyl-1-[4-(piperazin-1-yl)phenyl]-7-(trifluoromethoxy)-4,5-dihydro-3H-2,3-benzodiazepine-3-carboxamide | $^1$H-NMR (400 MHz, CDCl$_3$): δ = 1.07 (d, 3H), 2.79 (dd, 1H), 2.86 (d, 3H), 3.00 (dd, 1H), 3.05-3.11 (m, 4H), 3.26-3.35 (m, 4H), 5.27-5.37 (m, 1H), 6.12 (q, 1H), 6.92 (d, 2H), 7.21 (s, br, 1H), 7.28 (s, 1H), 7.44 (d, 2H).<br>LCMS (Method 1): $R_t$ = 0.93 min; m/z = 496 (M + H)$^+$ |

| No. | Structure | Name | Analytical data |
|---|---|---|---|
| 212 | 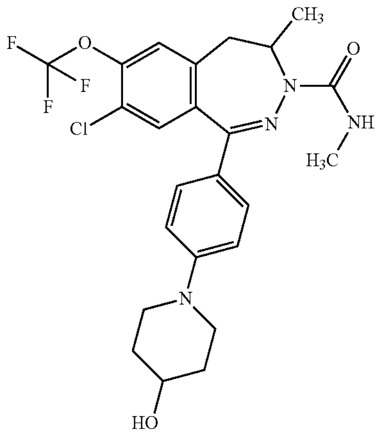 [SMILES: CNC(=O)N1N=C(c2ccc(N3CCC(O)CC3)cc2)c2cc(Cl)c(OC(F)(F)F)cc2CC1C] | (±)-8-chloro-1-[4-(4-hydroxypiperidin-1-yl)phenyl]-N,4-dimethyl-7-(trifluoromethoxy)-4,5-dihydro-3H-2,3-benzodiazepine-3-carboxamide | $^1$H-NMR (300 MHz, CDCl$_3$): δ = 1.11 (d, 3H), 1.72-1.86 (m, 2H), 1.99-2.11 (m, 2H), 2.78 (dd, 1H), 2.88 (d, 3H), 3.00 (dd, 1H), 3.04-3.16 (m, 2H), 3.66-3.78 (m, 2H), 3.88-4.01 (m, 1H), 5.25-5.38 (m, 1H), 6.05-6.15 (m, 1H), 6.95 (d, 2H), 7.23 (s, 1H), 7.29 (s, 1H), 7.46 (d, 2H).<br>LCMS (Method 1): R$_t$ = 1.26 min; m/z = 511 (M + H)$^+$ |
| 213 | 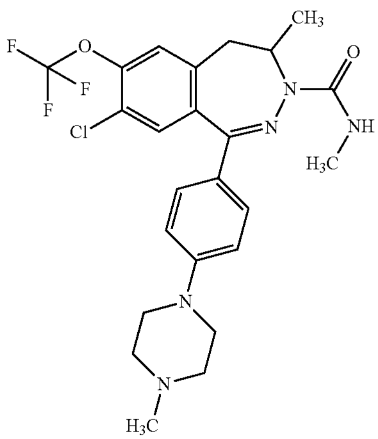 [SMILES: CNC(=O)N1N=C(c2ccc(N3CCN(C)CC3)cc2)c2cc(Cl)c(OC(F)(F)F)cc2CC1C] | (±)-8-chloro-N,4-dimethyl-1-[4-(4-methylpiperazin-1-yl)phenyl]-7-(trifluoromethoxy)-4,5-dihydro-3H-2,3-benzodiazepine-3-carboxamide | $^1$H-NMR (400 MHz, CDCl$_3$): δ = 1.04 (d, 3H), 2.61 (br. s., 3H), 2.73-2.93 (m, 7H), 3.03 (dd, 2H), 3.51 (d, 4H), 5.37 (br. s., 1H), 6.20 (br. s., 1H), 6.93 (d, 2H), 7.20 (s, 1H), 7.25 (s, 1H), 7.43 (d, 2H).<br>LCMS (Method 1): R$_t$ = 0.95 min; m/z = 510 (M + H)$^+$ |
| 214 | 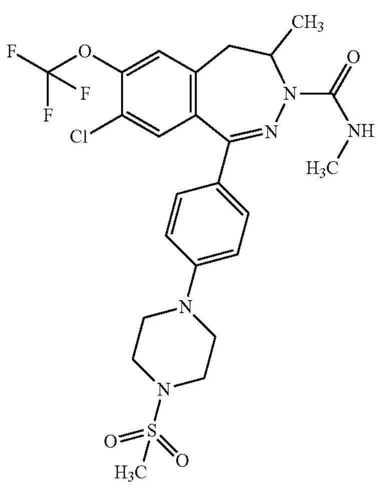 [SMILES: CNC(=O)N1N=C(c2ccc(N3CCN(S(C)(=O)=O)CC3)cc2)c2cc(Cl)c(OC(F)(F)F)cc2CC1C] | (±)-8-chloro-N,4-dimethyl-1-{4-[4-(methylsulphonyl)piperazin-1-yl]phenyl}-7-(trifluoromethoxy)-4,5-dihydro-3H-2,3-benzodiazepine-3-carboxamide | $^1$H-NMR (300 MHz, CDCl$_3$): δ = 1.06 (d, 3H), 2.85 (dd, 1H), 2.87 (s, 3H), 2.90 (d, 3H), 3.06 (d, 1H), 3.39-3.51 (br. s., 8H), 5.34-5.46 (m, 1H), 6.25 (q, 1H), 6.97 (d, 2H), 7.23 (s, 1H), 7.28 (s, 1H), 7.47 (d, 2H).<br>LCMS (Method 1): R$_t$ = 1.35 min; m/z = 574 (M + H)$^+$ |

| No. | Structure | Name | Analytical data |
|---|---|---|---|
| 215 | 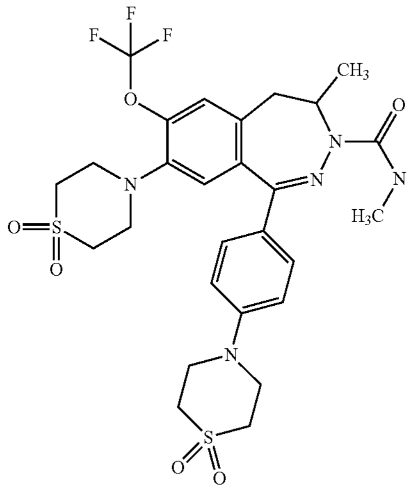 [SMILES: CNC(=O)N1N=C(c2ccc(N3CCS(=O)(=O)CC3)cc2)c2cc(N3CCS(=O)(=O)CC3)c(OC(F)(F)F)cc2CC1C] | (±)-8-(1,1-dioxidothiomorpholin-4-yl)-1-[4-(1,1-dioxidothiomorpholin-4-yl)phenyl]-N,4-dimethyl-7-(trifluoromethoxy)-4,5-dihydro-3H-2,3-benzodiazepine-3-carboxamide | $^1$H-NMR (400 MHz, CDCl$_3$): δ = 1.08 (d, 3H), 2.80 (dd, 1H), 2.90 (s, 3H), 3.01 (dd, 1H), 3.15-3.20 (m, 8H), 3.42-3.48 (m, 4H), 3.98-4.03 (m, 4H), 5.31-5.41 (m, 1H), 6.12-6.26 (m, 1H), 6.86 (s, 1H), 6.97 (d, 2H), 7.16 (d, 1H), 7.51 (d, 2H). LCMS (Method 1): R$_t$ = 1.11 min; m/z = 644 (M + H)$^+$ |
| 216 | 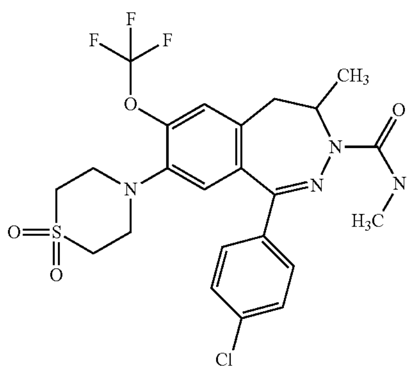 | (±)-1-(4-chlorophenyl)-8-(1,1-dioxidothiomorpholin-4-yl)-N,4-dimethyl-7-(trifluoromethoxy)-4,5-dihydro-3H-2,3-benzodiazepine-3-carboxamide | $^1$H-NMR (400 MHz, DMSO-d$_6$): δ = 0.95 (d, 3H), 2.68 (d, 3H), 2.75 (dd, 1H), 2.91 (s, 3H), 2.92-3.05 (m, 5H), 3.16-3.23 (m, 4H), 5.02-5.13 (m, 1H), 6.70 (q, 1H), 6.76 (s, 1H), 7.39 (d, 1H), 7.49 (d, 2H), 7.69 (d, 2H). LCMS (Method 5): R$_t$ = 1.33 min; m/z = 574 (M + H)$^+$ |
| 217 | 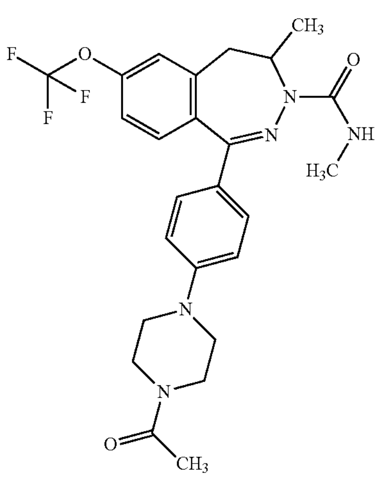 [SMILES: CNC(=O)N1N=C(c2ccc(N3CCN(C(C)=O)CC3)cc2)c2ccc(OC(F)(F)F)cc2CC1C] | (±)-1-[4-(4-acetylpiperazin-1-yl)phenyl]-N,4-dimethyl-7-(trifluoromethoxy)-4,5-dihydro-3H-2,3-benzodiazepine-3-carboxamide | $^1$H-NMR (400 MHz, CDCl$_3$): δ = 1.09 (d, 3H), 2.18 (s, 3H), 2.84 (dd, 1H), 2.89 (d, 3H), 3.06 (dd, 1H), 3.26-3.36 (m, 4H), 3.68 (t, 2H), 3.82 (t, 2H), 5.33-5.42 (m, 1H), 6.19 (q, 1H), 6.94 (d, 2H), 7.08 (d, 1H), 7.13 (s, br, 1H), 7.20 (d, 1H), 7.48 (d, 2H). LCMS (Method 1): R$_t$ = 1.21 min; m/z = 504 (M + H)$^+$ |

| No. | Structure | Name | Analytical data |
|---|---|---|---|
| 218 | 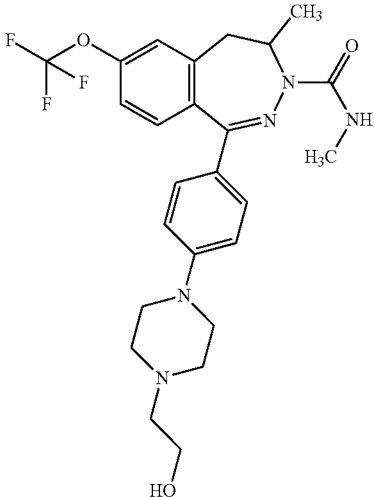 [SMILES: CNC(=O)N1N=C(c2ccc(N3CCN(CCO)CC3)cc2)c2ccc(OC(F)(F)F)cc2CC1C] | (±)-1-{4-[4-(2-hydroxyethyl)piperazin-1-yl]phenyl}-N,4-dimethyl-7-(trifluoromethoxy)-4,5-dihydro-3H-2,3-benzodiazepine-3-carboxamide | $^1$H-NMR (400 MHz, CDCl$_3$): δ = 1.07 (d, 3H), 2.83 (d, 1H), 2.90 (d, 3H), 2.93 (d, 1H), 2.94-3.01 (m, 2H), 3.04-3.17 (m, 5H), 3.52-3.61 (m, 4H), 3.89-3.96 (m, 2H), 5.32-5.44 (m, 1H), 6.18-6.25 (m, 1H), 6.95 (d, 2H), 7.08 (d, 1H), 7.13 (s, br, 1H), 7.19 (d, 1H), 7.48 (d, 2H). LCMS (Method 1): R$_t$ = 1.03 min; m/z = 506 (M + H)$^+$ |
| 219 | 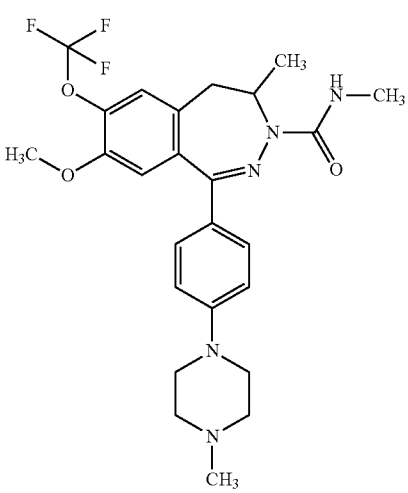 [SMILES: CNC(=O)N1N=C(c2ccc(N3CCN(C)CC3)cc2)c2cc(OC)c(OC(F)(F)F)cc2CC1C] | (±)-8-methoxy-N,4-dimethyl-1-[4-(4-methylpiperazin-1-yl)phenyl]-7-(trifluoromethoxy)-4,5-dihydro-3H-2,3-benzodiazepine-3-carboxamide | $^1$H-NMR (300 MHz, CDCl$_3$): δ = 1.11 (d, 3H), 2.40 (s, 3H), 2.58-2.65 (m, 4H), 2.73 (dd, 1H), 2.89 (d, 3H), 2.96 (dd, 1H), 3.32-3.39 (m, 4H), 3.73 (s, 3H), 5.24-5.34 (m, 1H), 6.12 (q, 1H), 6.79 (s, 1H), 6.95 (d, 2H), 7.14 (s, br, 1H), 7.51 (d, 2H). LCMS (Method 5): R$_t$ = 0.80 min; m/z = 506 (M + H)$^+$ |

The following exemplary compounds were prepared analogously to Example 2 from Example 127A or Example 128A and the appropriate commercially available boronic acid derivatives:

| No. | Structure | Name | Analytical data |
|---|---|---|---|
| 220 | 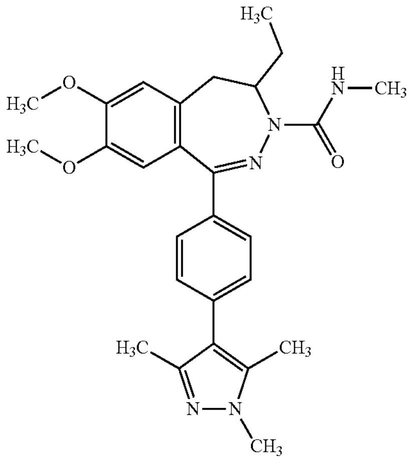 | (±)-4-ethyl-7,8-dimethoxy-N-methyl-1-[4-(1,3,5-trimethyl-1H-pyrazol-4-yl)phenyl]-4,5-dihydro-3H-2,3-benzodiazepine-3-carboxamide | $^1$H-NMR (400 MHz, CDCl$_3$): δ = 0.90 (t, 3H), 1.13-1.26 (m, 1H), 1.42-1.56 (m, 1H), 2.32 (s, 6H), 2.92 (d, 3H), 2.98 (dd, 1H), 3.08 (dd, 1H), 3.70 (s, 3H), 3.83 (s, 3H), 3.97 (s, 3H), 5.24-5.32 (m, 1H), 6.57 (q, 1H), 6.71 (s, 1H), 6.76 (s, 1H), 7.30 (d, 2H), 7.56 (d, 2H). LCMS (Method 5): R$_t$ = 1.10 min; m/z = 476 (M + H)$^+$ |
| 221 | 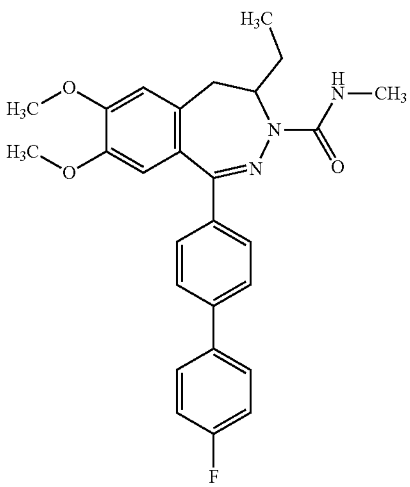 | (±)-4-ethyl-1-(4'-fluorobiphenyl-4-yl)-7,8-dimethoxy-N-methyl-4,5-dihydro-3H-2,3-benzodiazepine-3-carboxamide | $^1$H-NMR (400 MHz, CDCl$_3$): δ = 0.89 (t, 3H), 1.11-1.23 (m, 1H), 1.39-1.51 (m, 1H), 2.92 (d, 3H), 3.01 (dd, 1H), 3.10 (dd, 1H), 3.69 (s, 3H), 3.97 (s, 3H), 5.27-5.35 (m, 1H), 6.63 (q, 1H), 6.69 (s, 1H), 6.76 (s, 1H), 7.18 (dd, 2H), 7.55-7.66 (m, 6H). LCMS (Method 5): R$_t$ = 1.42 min; m/z = 462 (M + H)$^+$ |
| 222 | 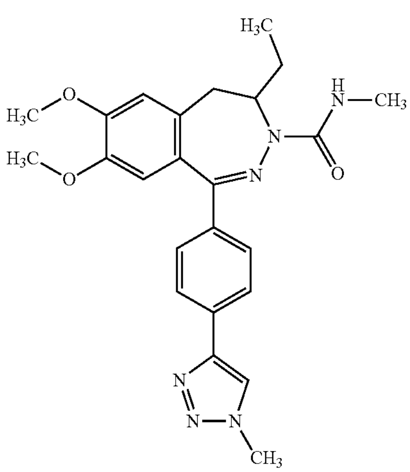 | (±)-4-ethyl-7,8-dimethoxy-N-methyl-1-[4-(1-methyl-1H-1,2,3-triazol-4-yl)phenyl]-4,5-dihydro-3H-2,3-benzodiazepine-3-carboxamide | $^1$H-NMR (400 MHz, CDCl$_3$): δ = 0.88 (t, 3H), 1.08-1.22 (m, 1H), 1.37-1.49 (m, 1H), 2.92 (d, 3H), 3.01 (dd, 1H), 3.10 (dd, 1H), 3.67 (s, 3H), 3.96 (s, 3H), 4.20 (s, 3H), 5.27-5.37 (m, 1H), 6.63 (q, 1H), 6.67 (s, 1H), 6.75 (s, 1H), 7.57 (d, 2H), 7.82 (s, 1H), 7.88 (d, 2H). LCMS (Method 5): R$_t$ = 0.97 min; m/z = 449 (M + H)$^+$ |

| No. | Structure | Name | Analytical data |
|---|---|---|---|
| 223 | 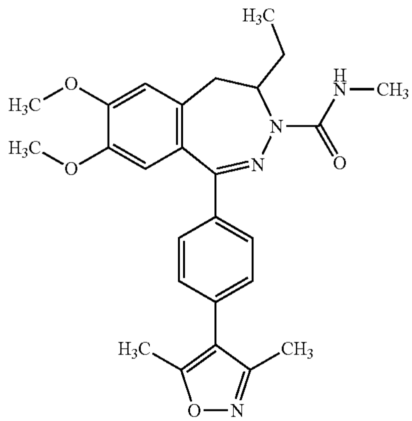 | (±)-1-[4-(3,5-dimethyl-1,2-oxazol-4-yl)phenyl]-4-ethyl-7,8-dimethoxy-N-methyl-4,5-dihydro-3H-2,3-benzodiazepine-3-carboxamide | ¹H-NMR (300 MHz, CDCl₃): δ = 0.89 (t, 3H), 1.07-1.23 (m, 1H), 1.36-1.52 (m, 1H), 2.35 (s, 3H), 2.49 (s, 3H), 2.92 (d, 3H), 3.01 (dd, 1H), 3.10 (dd, 1H), 3.70 (s, 3H), 3.97 (s, 3H), 5.26-5.37 (m, 1H), 6.62 (q, 1H), 6.67 (s, 1H), 6.76 (s, 1H), 7.32 (d, 2H), 7.59 (d, 2H). LCMS (Method 5): R$_t$ = 1.21 min; m/z = 463 (M + H)⁺ |
| 224 | 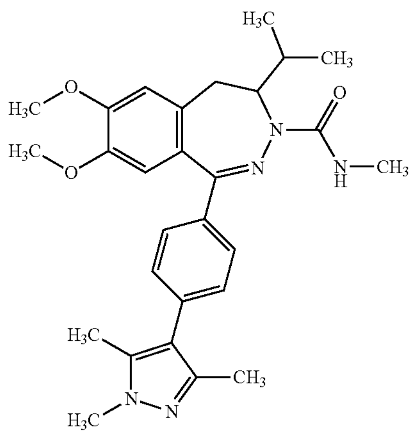 | (±)-4-isopropyl-7,8-dimethoxy-N-methyl-1-[4-(1,3,5-trimethyl-1H-pyrazol-4-yl)phenyl]-4,5-dihydro-3H-2,3-benzodiazepine-3-carboxamide | ¹H-NMR (300 MHz, CDCl₃): δ = 0.87 (d, 3H), 0.89 (d, 3H), 1.32-1.46 (m, 1H), 2.32 (s, 6H), 2.90 (d, 3H), 3.0 (dd, 1H), 3.13 (dd, 1H), 3.69 (s, 3H), 3.83 (s, 3H), 3.96 (s, 3H), 5.14-5.24 (m, 1H), 6.64 (q, 1H), 6.73 (s, 1H), 6.77 (s, 1H), 7.30 (d, 2H), 7.55 (d, 2H). LCMS (Method 5): R$_t$ = 1.17 min; m/z = 490 (M + H)⁺ |

The following exemplary compounds were prepared analogously to Example 34 from Example 127A and the appropriate commercially available lactams or cyclic carbamates:

| No. | Structure | Name | Analytical data |
|---|---|---|---|
| 225 | 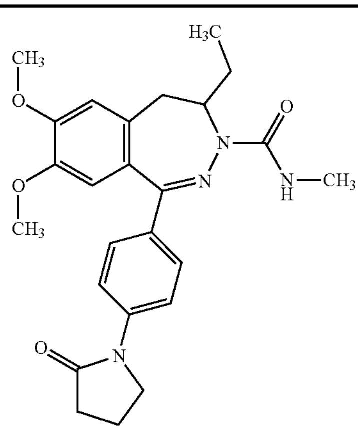 | (±)-4-ethyl-7,8-dimethoxy-N-methyl-1-[4-(2-oxopyrrolidin-1-yl)phenyl]-4,5-dihydro-3H-2,3-benzodiazepine-3-carboxamide | ¹H-NMR (400 MHz, CDCl₃): δ = 0.88 (t, 3H), 1.10-1.22 (m, 1H), 1.38-1.50 (m, 1H), 2.22 (pent, 2H), 2.67 (dd, 2H), 2.91 (d, 3H), 2.97 (dd, 1H), 3.07 (dd, 1H), 3.68 (s, 3H), 3.93 (dd, 2H), 3.95 (s, 3H), 5.23-5.31 (m, 1H), 6.56 (q, 1H), 6.64 (s, 1H), 6.75 (s, 1H), 7.52 (d, 2H), 7.68 (d, 2H). LCMS (Method 1): R$_t$ = 1.11 min; m/z = 452 (M + H)⁺ |

| No. | Structure | Name | Analytical data |
|---|---|---|---|
| 226 | 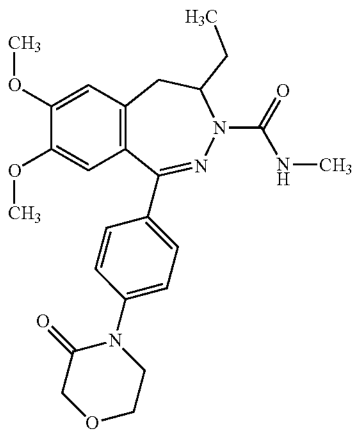 [SMILES: CCC1Cc2cc(OC)c(OC)cc2C(c2ccc(N3CCOCC3=O)cc2)=NN1C(=O)NC] | (±)-4-ethyl-7,8-dimethoxy-N-methyl-1-[4-(3-oxomorpholin-4-yl)phenyl]-4,5-dihydro-3H-2,3-benzodiazepine-3-carboxamide | $^1$H-NMR (400 MHz, CDCl$_3$): δ = 0.87 (t, 3H), 1.07-1.19 (m, 1H), 1.34-1.47 (m, 1H), 2.91 (d, 3H), 2.99 (dd, 1H), 3.07 (dd, 1H), 3.69 (s, 3H), 3.81-3.90 (m, 2H), 3.96 (s, 3H), 4.09 (t, 2H), 4.39 (s, 2H), 5.26-5.34 (m, 1H), 6.61 (q, 1H), 6.66 (s, 1H), 6.74 (s, 1H), 7.41 (d, 2H), 7.55 (d, 2H). LCMS (Method 5): R$_t$ = 0.91 min; m/z = 467 (M + H)$^+$ |
| 227 | 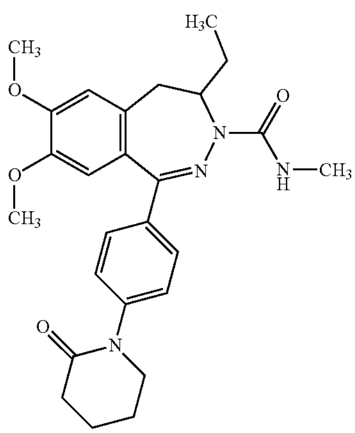 [SMILES: CCC1Cc2cc(OC)c(OC)cc2C(c2ccc(N3CCCCC3=O)cc2)=NN1C(=O)NC] | (±)-4-ethyl-7,8-dimethoxy-N-methyl-1-[4-(2-oxopiperidin-1-yl)phenyl]-4,5-dihydro-3H-2,3-benzodiazepine-3-carboxamide | $^1$H-NMR (400 MHz, CDCl$_3$): δ = 0.88 (t, 3H), 1.08-1.21 (m, 1H), 1.36-1.48 (m, 1H), 1.94-2.06 (m, 4H), 2.62 (t, 2H), 2.90 (d, 3H), 2.98 (dd, 1H), 3.06 (dd, 1H), 3.69 (s, 3H), 3.73 (t, 2H), 3.95 (s, 3H), 5.24-5.33 (m, 1H), 6.59 (q, 1H), 6.68 (s, 1H), 6.74 (s, 1H), 7.32 (d, 2H), 7.53 (d, 2H). LCMS (Method 5): R$_t$ = 1.01 min; m/z = 465 (M + H)$^+$ |
| 228 | 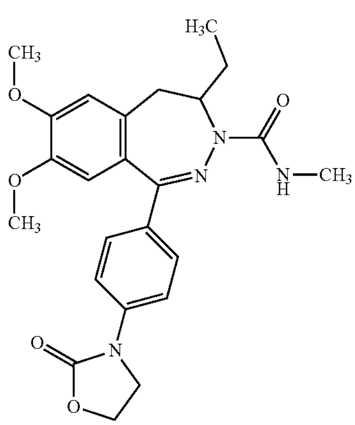 [SMILES: CCC1Cc2cc(OC)c(OC)cc2C(c2ccc(N3CCOC3=O)cc2)=NN1C(=O)NC] | (±)-4-ethyl-7,8-dimethoxy-N-methyl-1-[4-(2-oxo-1,3-oxazolidin-3-yl)phenyl]-4,5-dihydro-3H-2,3-benzodiazepine-3-carboxamide | $^1$H-NMR (300 MHz, CDCl$_3$): δ = 0.88 (t, 3H), 1.07-1.24 (m, 1H), 1.35-1.51 (m, 1H), 2.91 (d, 3H), 2.98 (dd, 1H), 3.08 (dd, 1H), 3.68 (s, 3H), 3.96 (s, 3H), 4.15 (dd, 2H), 4.56 (t, 2H), 5.23-5.34 (m, 1H), 6.56 (q, 1H), 6.63 (s, 1H), 6.75 (s, 1H), 7.53 (d, 2H), 7.61 (d, 2H). LCMS (Method 5): R$_t$ = 0.97 min; m/z = 453 (M + H)$^+$ |

The following exemplary compounds were prepared analogously to Example 34 from Example 49.2A and the appropriate commercially available lactams or cyclic carbamates:

| No. | Structure | Name | Analytical data |
|---|---|---|---|
| 229 | 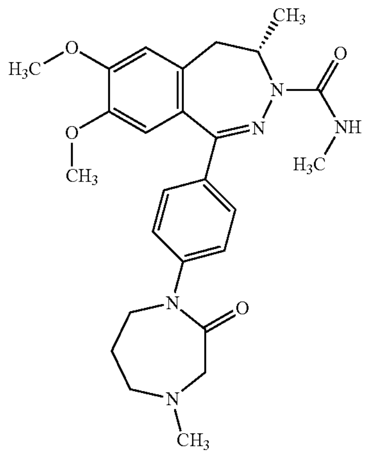 [SMILES: CNC(=O)N1N=C(c2ccc(N3CCCN(C)CC3=O)cc2)c2cc(OC)c(OC)cc2C[C@@H]1C] | (4S)-7,8-dimethoxy-N,4-dimethyl-1-[4-(4-methyl-2-oxo-1,4-diazepan-1-yl)phenyl]-4,5-dihydro-3H-2,3-benzodiazepine-3-carboxamide | $^1$H-NMR (300 MHz, CDCl$_3$): δ = 0.98 (d, 3H), 2.08 (m, 2H), 2.64 (s, 3H), 2.81 (dd, 1H), 2.88 (d, 3H), 3.03-3.16 (m, 3H), 3.68 (s, 3H), 3.75 (s, br, 2H), 3.87-3.92 (m, 2H), 3.93 (s, 3H), 5.36-5.49 (m, 1H), 6.45 (q, 1H), 6.62 (s, 1H), 6.72 (s, 1H), 7.27 (d, 2H), 7.52 (d, 2H).<br>LCMS (Method 1): R$_t$ = 0.72 min; m/z = 480 (M + H)$^+$ |

The following exemplary compounds were prepared analogously to Example 34 from Example 129A and the appropriate commercially available lactams or cyclic carbamates.

| No. | Structure | Name | Analytical data |
|---|---|---|---|
| 230 | 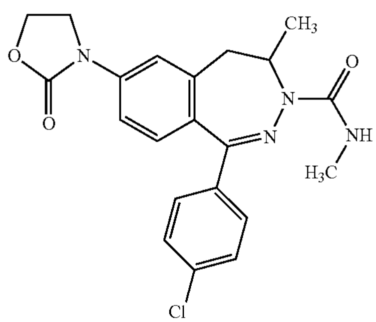 [SMILES: CNC(=O)N1N=C(c2ccc(Cl)cc2)c2ccc(N3CCOC3=O)cc2CC1C] | (±)-1-(4-chlorophenyl)-N,4-dimethyl-7-(2-oxo-1,3-oxazolidin-3-yl)-4,5-dihydro-3H-2,3-benzodiazepine-3-carboxamide | $^1$H-NMR (400 MHz, CDCl$_3$): δ = 0.97 (d, 3H), 2.92 (d, 3H), 2.99 (dd, 1H), 3.20 (d, 1H), 4.07-4.20 (m, 2H), 4.54 (t, 2H), 5.48-5.59 (m, 1H), 6.47-6.57 (m, 1H), 7.12 (d, 1H), 7.34-7.46 (m, 5H), 7.53 (d, 1H).<br>LCMS (Method 1): R$_t$ = 1.23 min; m/z = 413 (M + H)$^+$ |
| 230.1 | 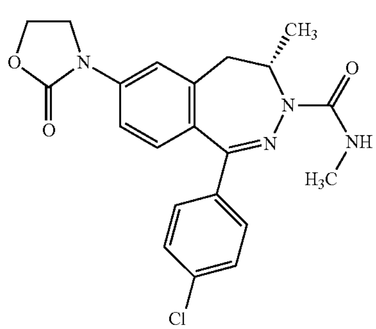 | (4S)-1-(4-chlorophenyl)-N,4-dimethyl-7-(2-oxo-1,3-oxazolidin-3-yl)-4,5-dihydro-3H-2,3-benzodiazepine-3-carboxamide | Prep. HPLC: Method XXIa<br>Analyt. HPLC (Method Y1):<br>R$_t$ = 3.93 min<br>[α]$_D^{20}$ = 108.1° (c = 1.00; MeOH)<br>LCMS (Method 1): R$_t$ = 1.36 min; m/z = 499 (M + H)$^+$ |

-continued

| No. | Structure | Name | Analytical data |
|---|---|---|---|
| 231 | 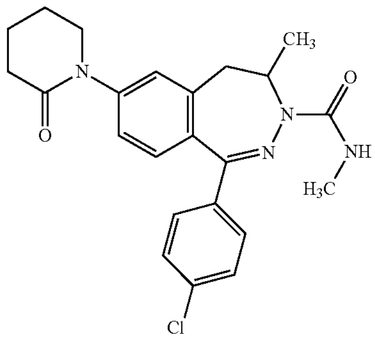 [SMILES: CNC(=O)N1N=C(c2ccc(Cl)cc2)c2ccc(N3CCCCC3=O)cc2CC1C] | (±)-1-(4-chlorophenyl)-N,4-dimethyl-7-(2-oxopiperidin-1-yl)-4,5-dihydro-3H-2,3-benzodiazepine-3-carboxamide | $^1$H-NMR (400 MHz, CDCl$_3$): δ = 0.99 (d, 3H), 1.93-2.05 (m, 4H), 2.61 (t, 2H), 2.88-2.95 (m, 1H), 2.91 (d, 3H), 3.15 (dd, 1H), 3.65-3.76 (m, 2H), 5.43-5.53 (m, 1H), 6.42-6.50 (m, 1H), 7.09-7.17 (m, 2H), 7.21 (d, 1H), 7.39 (d, 2H), 7.46 (d, 2H). LCMS (Method 1): R$_t$ = 1.22 min; m/z = 425 (M + H)$^+$ |
| 232 | 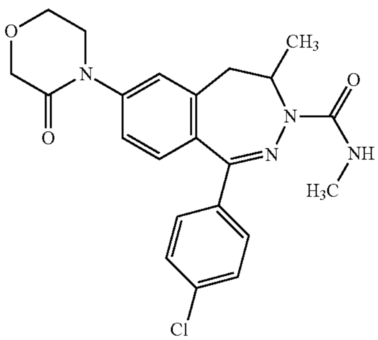 [SMILES: CNC(=O)N1N=C(c2ccc(Cl)cc2)c2ccc(N3CCOCC3=O)cc2CC1C] | (±)-1-(4-chlorophenyl)-N,4-dimethyl-7-(3-oxomorpholin-4-yl)-4,5-dihydro-3H-2,3-benzodiazepine-3-carboxamide | $^1$H-NMR (400 MHz, CDCl$_3$): δ = 0.99 (d, 3H), 2.91 (d, 3H), 2.94 (dd, 1H), 3.17 (dd, 1H), 3.77-3.89 (m, 2H), 4.08 (t, 2H), 4.38 (s, 2H), 5.46-5.56 (m, 1H), 6.42-6.50 (m, 1H), 7.15 (d, 1H), 7.24 (dd, 1H), 7.31 (d, 1H), 7.39 (d, 2H), 7.45 (d, 2H). LCMS (Method 1): R$_t$ = 1.15 min; m/z = 427 (M + H)$^+$ |

The following exemplary compounds were prepared analogously to Example 127.1 from Example 129A and the appropriate commercially available amines. In many cases, under the reaction conditions, mixtures of mono- and di-aminated products were obtained, and were separated by chromatography.

| No. | Structure | Name | Analytical data |
|---|---|---|---|
| 233 | 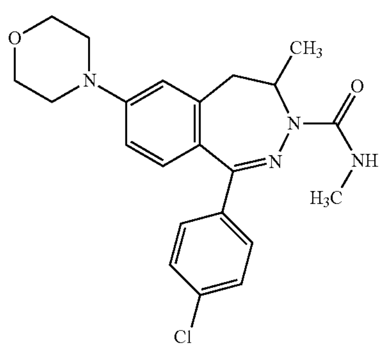 [SMILES: CNC(=O)N1N=C(c2ccc(Cl)cc2)c2ccc(N3CCOCC3)cc2CC1C] | (±)-1-(4-chlorophenyl)-N,4-dimethyl-7-(morpholin-4-yl)-4,5-dihydro-3H-2,3-benzodiazepine-3-carboxamide | $^1$H-NMR (300 MHz, CDCl$_3$): δ = 1.00 (d, 3H), 2.88 (dd, 1H), 2.90 (d, 3H), 3.16 (dd, 1H), 3.24-3.33 (m, 4H), 3.86-3.95 (m, 4H), 5.44-5.57 (m, 1H), 6.49 (q, 1H), 6.67-6.79 (m, 2H), 6.99 (d, 1H), 7.37 (d, 2H), 7.43 (d, 2H). LCMS (Method 1): R$_t$ = 1.34 min; m/z = 413 (M + H)$^+$ |
| 234 | 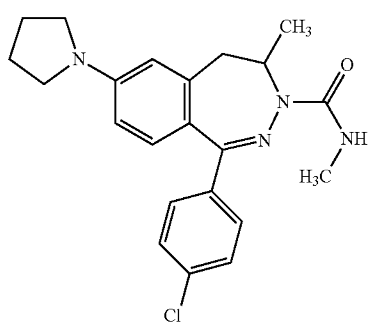 [SMILES: CNC(=O)N1N=C(c2ccc(Cl)cc2)c2ccc(N3CCCC3)cc2CC1C] | (±)-1-(4-chlorophenyl)-N,4-dimethyl-7-(pyrrolidin-1-yl)-4,5-dihydro-3H-2,3-benzodiazepine-3-carboxamide | $^1$H-NMR (400 MHz, CDCl$_3$): δ = 1.04 (d, 3H), 2.00-2.11 (m, 4H), 2.88 (dd, 1H), 2.89 (d, 3H), 3.15 (dd, 1H), 3.36 (m, 4H), 5.44-5.55 (m, 1H), 6.35 (dd, 1H), 6.40 (d, 1H), 6.48 (q, 1H), 6.91 (d, 1H), 7.36 (d, 2H), 7.44 (d, 2H). LCMS (Method 1): R$_t$ = 1.56 min; m/z = 397 (M + H)$^+$ |

| No. | Name | Analytical data |
|---|---|---|
| 235 | (±)-1-(4-chlorophenyl)-7-(1,1-dioxidothiomorpholin-4-yl)-N,4-dimethyl-4,5-dihydro-3H-2,3-benzodiazepine-3-carboxamide | $^1$H-NMR (300 MHz, CDCl$_3$): δ = 0.99 (d, 3H), 2.80-3.00 (m, 1H), 2.89 (d, 3H), 3.13 (s, br, 5H), 3.97 (s, br, 4H), 5.43-5.60 (m, 1H), 6.42-6.54 (m, 1H), 6.64-6.79 (m, 2H), 7.02 (d, 1H), 7.33-7.50 (m, 4H).<br>LCMS (Method 1): R$_t$ = 1.21 min; m/z = 461 (M + H)$^+$ |
| 236 | (±)-1-(4-chlorophenyl)-N,4-dimethyl-7-(4-methylpiperazin-1-yl)-4,5-dihydro-3H-2,3-benzodiazepine-3-carboxamide | $^1$H-NMR (400 MHz, CDCl$_3$): δ = 1.00 (d, 3H), 2.43 (s, 3H), 2.66 (t, 4H), 2.87 (dd, 1H), 2.90 (d, 3H), 3.15 (dd, 1H), 3.37 (t, 4H), 5.44-5.54 (m, 1H), 6.48 (q, 1H), 6.69 (dd, 1H), 6.73 (d, 1H), 6.96 (d, 1H), 7.37 (d, 2H), 7.43 (d, 2H).<br>LCMS (Method 1): R$_t$ = 0.91 min; m/z = 426 (M + H)$^+$ |
| 237 | (±)-N,4-dimethyl-7-(4-methylpiperazin-1-yl)-1-[4-(4-methylpiperazin-1-yl)phenyl]-4,5-dihydro-3H-2,3-benzodiazepine-3-carboxamide | $^1$H-NMR (400 MHz, CDCl$_3$): δ = 1.12 (d, 3H), 2.42 (s, 3H), 2.43 (s, 3H), 2.63-2.71 (m, 8H), 2.77 (dd, 1H), 2.87 (d, 3H), 2.98 (dd, 1H), 3.36 (t, 8H), 5.27-5.37 (m, 1H), 6.13 (q, 1H), 6.71 (dd, 1H), 6.76 (d, 1H), 6.92 (d, 2H), 7.03 (d, 1H), 7.49 (d, 2H).<br>LCMS (Method 1): R$_t$ = 0.55 min; m/z = 490 (M + H)$^+$ |

| No. | Structure | Name | Analytical data |
|---|---|---|---|
| 238 | 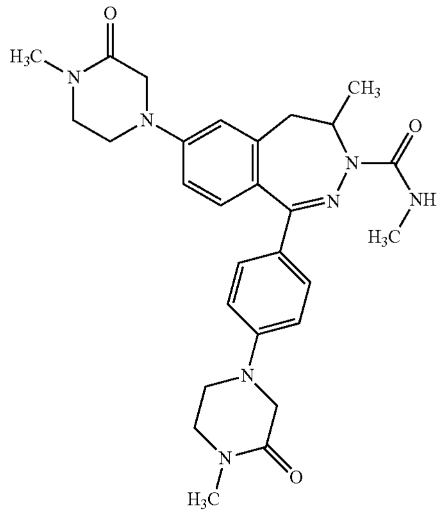 [SMILES: CNC(=O)N1N=C(c2ccc(N3CCN(C)C(=O)C3)cc2)c2ccc(N3CCN(C)C(=O)C3)cc2CC1C] | (±)-N,4-dimethyl-7-(4-methyl-3-oxopiperazin-1-yl)-1-[4-(4-methyl-3-oxopiperazin-1-yl)phenyl]-4,5-dihydro-3H-2,3-benzodiazepine-3-carboxamide | $^1$H-NMR (400 MHz, CDCl$_3$): δ = 1.17 (d, 3H), 2.79 (dd, 1H), 2.86 (d, 3H), 2.98 (dd, 1H), 3.08 (s, 6H), 3.50-3.57 (m, 4H), 3.59-3.67 (m, 4H), 4.00 (s, br, 4H), 5.29-5.39 (m, 1H), 6.15 (q, 1H), 6.67 (dd, 1H), 6.72 (d, 1H), 6.89 (d, 2H), 7.07 (d, 1H), 7.59 (d, 2H). LCMS (Method 1): R$_t$ = 0.87 min; m/z = 518 (M + H)$^+$ |

The following exemplary compounds were prepared analogously to Example 2 from Example 129A and the appropriate commercially available boronic acid derivatives:

| No. | Structure | Name | Analytical data |
|---|---|---|---|
| 239 | 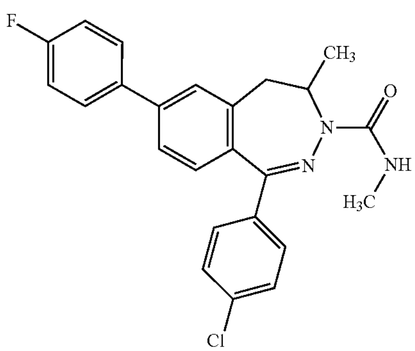 [SMILES: CNC(=O)N1N=C(c2ccc(Cl)cc2)c2ccc(-c3ccc(F)cc3)cc2CC1C] | (±)-1-(4-chlorophenyl)-7-(4-fluorophenyl)-N,4-dimethyl-4,5-dihydro-3H-2,3-benzodiazepine-3-carboxamide | $^1$H-NMR (300 MHz, CDCl$_3$): δ = 1.00 (d, 3H), 2.93 (s, br, 3H), 3.02 (d, 1H), 3.24 (d, 1H), 5.49-5.65 (m, 1H), 6.46-6.62 (m, 1H), 7.13-7.23 (m, 3H), 7.36-7.51 (m, 6H), 7.59 (d, 1H), 7.62 (d, 1H). LCMS (Method 1): R$_t$ = 1.60 min; m/z = 422 (M + H)$^+$ |
| 240 | 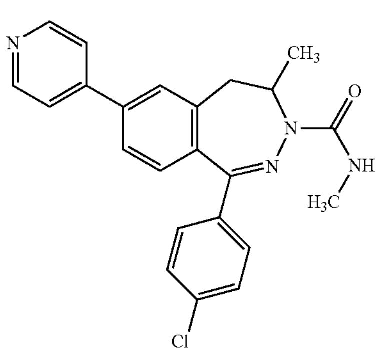 [SMILES: CNC(=O)N1N=C(c2ccc(Cl)cc2)c2ccc(-c3ccncc3)cc2CC1C] | (±)-1-(4-chlorophenyl)-N,4-dimethyl-7-(pyridin-4-yl)-4,5-dihydro-3H-2,3-benzodiazepine-3-carboxamide | $^1$H-NMR (400 MHz, MeOD): δ = 1.06 (d, 3H), 2.82 (s, br, 3H), 3.03 (dd, 1H), 3.22 (dd, 1H), 5.27-5.38 (m, 1H), 7.29 (d, 1H), 7.46 (d, 2H), 7.60-7.68 (m, 3H), 7.81 (d, 1H), 7.91 (s, 1H), 8.17 (s, br, 2H), 8.78 (s, br, 2H). LCMS (Method 1): R$_t$ = 1.07 min; m/z = 405 (M + H)$^+$ |

| No. | Structure | Name | Analytical data |
|---|---|---|---|
| 241 | 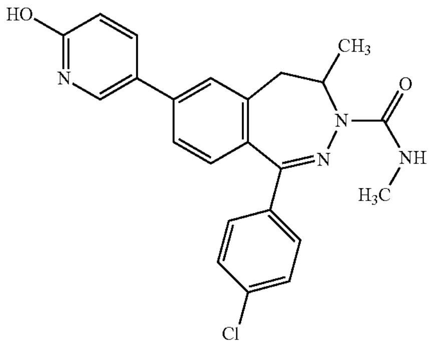 [SMILES: CNC(=O)N1N=C(c2ccc(Cl)cc2)c2ccc(-c3ccc(O)nc3)cc2CC1C] | (±)-1-(4-chlorophenyl)-7-(6-hydroxypyridin-3-yl)-N,4-dimethyl-4,5-dihydro-3H-2,3-benzodiazepine-3-carboxamide | $^1$H-NMR (400 MHz, MeOD): δ = 1.06 (d, 3H), 2.81 (s, br, 3H), 2.93 (dd, 1H), 3.13 (d, 1H), 5.21-5.33 (m, 1H), 6.63-6.74 (m, 1H), 7.13 (d, 1H), 7.40-7.49 (m, 3H), 7.53-7.67 (m, 4H), 7.84 (s, br, 1H), 8.05 (s, br, 1H). LCMS (Method 1): R$_t$ = 1.15 min; m/z = 421 (M + H)$^+$ |
| 242 | 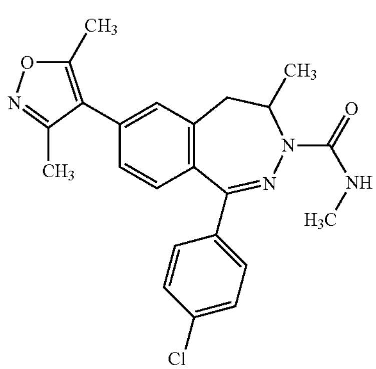 [SMILES: CNC(=O)N1N=C(c2ccc(Cl)cc2)c2ccc(-c3c(C)noc3C)cc2CC1C] | (±)-1-(4-chlorophenyl)-7-(3,5-dimethyl-1,2-oxazol-4-yl)-N,4-dimethyl-4,5-dihydro-3H-2,3-benzodiazepine-3-carboxamide | $^1$H-NMR (300 MHz, CDCl$_3$): δ = 0.99 (d, 3H), 2.33 (s, 3H), 2.47 (s, 3H), 2.94 (s, br, 3H), 3.01 (d, 1H), 3.22 (d, 1H), 5.49-5.63 (m, 1H), 6.46-6.58 (m, 1H), 7.09-7.22 (m, 3H), 7.41 (d, 2H), 7.48 (d, 2H). LCMS (Method 1): R$_t$ = 1.42 min; m/z = 423 (M + H)$^+$ |

| No. | Structure | Name | Analytical data |
|---|---|---|---|
| 243 | 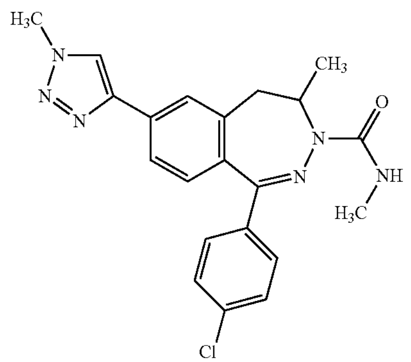 [SMILES: CNC(=O)N1N=C(c2ccc(Cl)cc2)c2ccc(-c3cn(C)nn3)cc2CC1C] | (±)-1-(4-chlorophenyl)-N,4-dimethyl-7-(1-methyl-1H-1,2,3-triazol-4-yl)-4,5-dihydro-3H-2,3-benzodiazepine-3-carboxamide | $^1$H-NMR (300 MHz, CDCl$_3$): δ = 0.98 (d, 3H), 2.92 (d, 3H), 3.03 (dd, 1H), 3.22 (dd, 1H), 4.20 (s, 3H), 5.48-5.63 (m, 1H), 6.50-6.60 (m, 1H), 7.17 (d, 1H), 7.40 (d, 2H), 7.45 (d, 2H), 7.64 (d, 1H), 7.77 (s, 1H), 7.82 (s, 1H). LCMS (Method 1): R$_t$ = 1.22 min; m/z = 409 (M + H)$^+$ |

Example 130.2

(4R)-1-[4-(4-Hydroxypiperidin-1-yl)phenyl]-7,8-dimethoxy-N,4-dimethyl-4,5-dihydro-3H-2,3-benzodiazepine-3-carboxamide

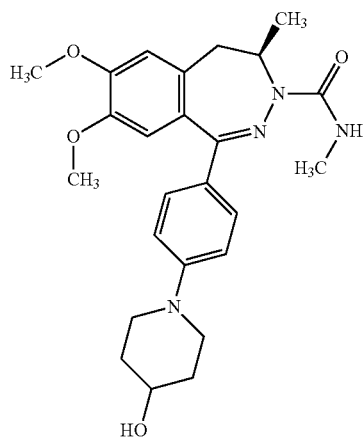 [SMILES: CNC(=O)N1N=C(c2ccc(N3CCC(O)CC3)cc2)c2cc(OC)c(OC)cc2C[C@H]1C]

Under argon, 1.0 g (2.3 mmol) of (4R)-1-(4-bromophenyl)-7,8-dimethoxy-N,4-dimethyl-4,5-dihydro-3H-2,3-benzodiazepine-3-carboxamide (Example 49.1A) were charged in 25 ml of THF. 63.5 mg (0.069 mmol) of tris(dibenzylideneacetone)dipalladium (CAS [51364-51-3]) and 91 mg (0.231 mmol) of 2-'(dicyclohexylphosphino)-N,N-dimethyl-biphenyl-2-amine (CAS [213697-53-1]) were added and the mixture was briefly degassed with argon. Then 311 mg (3.24 mmol) of sodium tert-butoxide and thereafter 936 mg (9.25 mmol) of piperidin-4-ol were added, degassing was carried out again, and the mixture was stirred at 70° C. oil bath temperature for 1 h. After cooling, the batch was admixed with diatomaceous earth, the solvent was removed on a rotary evaporator and the residue was purified by flash chromatography (amino phase). This gave 590 mg (55% of theory) of the desired product as a solid.

LCMS (Method 5): R$_t$=0.80 min; m/z=453 (M+H)$^+$ $^1$H-NMR (300 MHz, DMSO-d$_6$): δ=1.05 (d, 3H), 1.36-1.51 (m, 2H), 1.74-1.87 (m, 2H), 2.42 (d, 1H), 2.61 (d, 3H), 2.82 (dd, 1H), 2.96 (t, 2H), 3.59 (s, 3H), 3.61-3.72 (m, 3H), 3.82 (s, 3H), 4.70 (d, 1H), 4.80-4.94 (m, 1H), 6.25 (q, 1H), 6.54 (s, 1H), 6.93 (d, 2H), 7.02 (s, 1H), 7.57 (d, 2H).

Specific optical rotation: [α]D$^{20}$=−385.5°+/−0.18° (c=1.00; methanol)

The following exemplary compounds were prepared analogously to Example 130.2 from Example 49.1A and methylpiperazine:

| No. | Structure | Name | Analytical data |
|---|---|---|---|
| 127.2 | 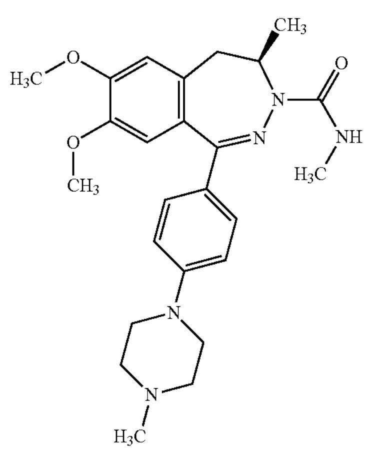 [SMILES: CNC(=O)N1N=C(c2ccc(N3CCN(C)CC3)cc2)c2cc(OC)c(OC)cc2C[C@H]1C] | (4R)-7,8-dimethoxy-N,4-dimethyl-1-[4-(4-methylpiperazin-1-yl)phenyl]-4,5-dihydro-3H-2,3-benzodiazepine-3-carboxamide | [α]$_D^{20}$ = −361.8° (c = 1.00; MeOH) LCMS (Method 5): R$_t$ = 0.56 min; m/z = 452 (M + H)$^+$ |

Example 244

(±)-1-[4-(1,1-Dioxido-1,2-thiazolidin-2-yl)phenyl]-7,8-dimethoxy-N,4-dimethyl-4,5-dihydro-3H-2,3-benzodiazepine-3-carboxamide

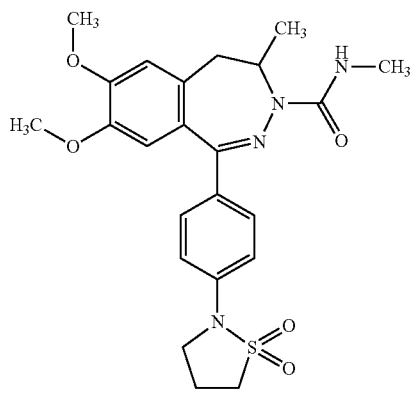

100 mg (0.231 mmol) of (±)-1-(4-bromophenyl)-7,8-dimethoxy-N,4-dimethyl-4,5-dihydro-3H-2,3-benzodiazepine-3-carboxamide (Example 49A), 33.6 mg (0.278 mmol) of 1,2-thiazolidine 1,1-dioxide (CAS [5908-62-3]), 64 mg (0.46 mmol) of potassium carbonate and 13 mg (0.023 mmol) of allylchloropalladium dimer (CAS [12012-95-2]) are charged in 3 ml of 2-methyltetrahydrofuran and the suspension is degassed with argon for 10 min. Then 39 mg (0.093 mmol) of di-tert-butyl(2',4',6'-triisopropylbiphenyl-2-yl)phosphane (CAS [564483-19-8]) are added, degassing with argon is carried out again, and the mixture is heated at 80° C. for 16 h. The crude mixture is filtered, and then the solvent is removed and the residue obtained is purified by preparative HPLC. This gave 32 mg (29% of theory) of the desired product as a solid.

LCMS (Method 5): $R_t$=0.90 min; m/z=473 (M+H)$^+$ $^1$H-NMR (300 MHz, CDCl$_3$): δ=1.04 (d, 3H), 2.61 (pent, 2H), 2.83 (dd, 1H), 2.91 (d, 3H), 3.09 (dd, 1H), 3.46 (t, 2H), 3.70 (s, 3H), 3.87 (t, 2H), 3.96 (s, 3H), 5.37-5.50 (m, 1H), 6.42 (q, 1H), 6.62 (s, 1H), 6.75 (s, 1H), 7.30 (d, 2H), 7.55 (d, 2H).

Example 245

(±)-1-{7,8-Dimethoxy-4-methyl-1-[4-(4-methylpiperazin-1-yl)phenyl]-4,5-dihydro-3H-2,3-benzodiazepin-3-yl}ethanone

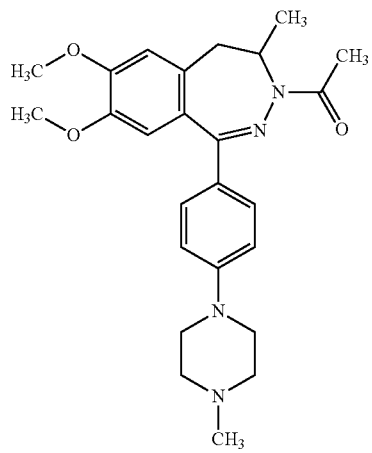 [SMILES: COc1cc2c(cc1OC)C(c1ccc(N3CCN(C)CC3)cc1)=NN(C(C)=O)C(C)C2]

Making analogous use of the process for preparing Example 127.1, the desired compound was obtained from (±)-1-[1-(4-bromophenyl)-7,8-dimethoxy-4-methyl-4,5-dihydro-3H-2,3-benzodiazepin-3-yl]ethanone (Example 133A).

LCMS (Method 1): $R_t$=0.70 min; m/z=437 (M+H)$^+$ $^1$H-NMR (300 MHz, CDCl$_3$): δ=1.33 (d, 3H), 2.07 (s, 3H), 2.39 (s, 3H), 2.59-2.62 (m, 4H), 2.65-2.82 (m, 2H), 3.35-3.38 (m, 4H), 3.77 (s, 3H), 3.96 (s, 3H), 5.23-5.36 (m, 1H), 6.65 (s, 1H), 6.82 (s, 1H), 6.96 (d, 2H), 7.64 (d, 2H).

Enantiomer Separation

Preparative HPLC by Method VIa

Example 245.1: 1-{(4S)-7,8-Dimethoxy-4-methyl-1-[4-(4-methylpiperazin-1-yl)phenyl]-4,5-dihydro-3H-2,3-benzodiazepin-3-yl}ethanone (enantiomer 1)

HPLC (Method Ea): $R_t$=5.38 min, purity>99%

Specific optical rotation: $[\alpha]_D^{20}$=225.3°+/−0.33° (c=1.00; methanol)

Enantiomer 2: 1-{(4R)-7,8-Dimethoxy-4-methyl-1-[4-(4-methylpiperazin-1-yl)phenyl]-4,5-dihydro-3H-2,3-benzodiazepin-3-yl}ethanone HPLC (Method Ea): $R_t$=4.13 min, purity>99%

Specific optical rotation: $[\alpha]_D^{20}$=−201.4°+/−0.27° (c=1.00; methanol)

The following exemplary compound was prepared analogously to Example 2 from Example 133A and the appropriate commercially available boronic acid derivative:

| 246 | 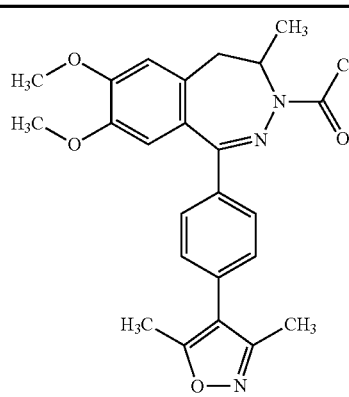 | (±)-1-{1-[4-(3,5-dimethyl-1,2-oxazol-4-yl)phenyl]-7,8-dimethoxy-4-methyl-4,5-dihydro-3H-2,3-benzodiazepin-3-yl}ethanone | $^1$H-NMR (300 MHz, CDCl$_3$): δ = 1.24 (d, 3H), 2.23 (s, 3H), 2.35 (s, 3H), 2.49 (s, 3H), 2.78 (dd, 1H), 2.94 (dd, 1H), 3.77 (s, 3H), 3.98 (s, 2H), 5.32-5.44 (m, 1H), 6.66 (s, 1H), 6.83 (s, 1H), 7.36 (d, 2H), 7.77 (d, 2H). LCMS (Method 1): R$_t$ = 1.19 min; m/z = 434 (M + H)$^+$ |
|---|---|---|---|

Example 247

(±)-7,8-Dimethoxy-N,4-dimethyl-1-[4-(5-methyl-1,3,4-oxadiazol-2-yl)phenyl]-4,5-dihydro-3H-2,3-benzodiazepine-3-carboxamide

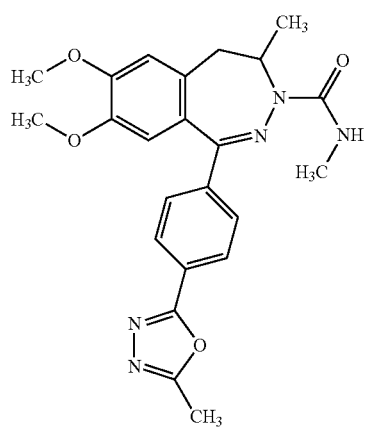 [SMILES: CNC(=O)N1N=C(c2ccc(-c3nnc(C)o3)cc2)c2cc(OC)c(OC)cc2CC1C]

Added at 0° C. to a solution of 163 mg (410 µmol) of (±)-4-[7,8-dimethoxy-4-methyl-3-[(methylamino)carbonyl]-4,5-dihydro-3H-2,3-benzodiazepin-1-yl]benzoic acid (Example 134A) in 10 ml of N,N-dimethylformamide were 69.9 mg (431 µmol) of N,N'-carbonyldiimidazole. After 4.5 hours 46 mg (616 µmol) of acetic hydrazide were added, and the mixture was stirred at 80° C. overnight. It was worked up by addition of water and extraction three times with ethyl acetate. The organic phase washed with saturated aqueous sodium chloride solution and with water, dried using sodium sulphate, and the solvent was removed on a rotary evaporator. The crude product was then dissolved in 10 ml of dichloromethane and admixed at 0° C. with 23 mg (331 µmol) of 1H-imidazole, 76 mg (291 µmol) of triphenylphosphine and 97 mg (291 µmol) of carbon tetrabromide. This mixture was stirred at room temperature overnight. It was worked up by adding water and carrying out extraction three times with ethyl acetate. The organic phase washed with saturated aqueous sodium chloride solution and dried using sodium sulphate, and the solvent was removed on a rotary evaporator. Chromatography gave 10 mg of the title compound as a yellow film.

LCMS (Method 3): R$_t$=1.01 min; m/z=436 (M+H)$^+$ $^1$H-NMR (400 MHz, CDCl$_3$): δ=0.96 (d, 3H), 2.64 (s, 3H), 2.88 (dd, 1H), 2.91 (d, 3H), 3.16 (dd, 1H), 3.64 (s, 3H), 3.94 (s, 3H), 5.50 (m, 1H), 6.55 (s, 1H), 6.58 (sbr, 1H), 6.72 (s, 1H), 7.62 (d, 2H), 8.05 (d, 2H).

Example 248

(±)-7,8-Dimethoxy-N,4-dimethyl-1-[4-(3-methyl-1,2,4-oxadiazol-5-yl)phenyl]-4,5-dihydro-3H-2,3-benzodiazepine-3-carboxamide

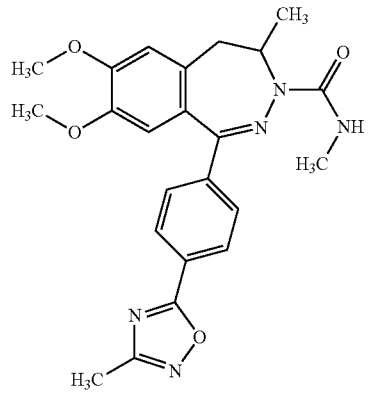 [SMILES: CNC(=O)N1N=C(c2ccc(-c3nc(C)no3)cc2)c2cc(OC)c(OC)cc2CC1C]

A solution of 175 mg (440 µmol) of (±)-4-[7,8-dimethoxy-4-methyl-3-[(methylamino)carbonyl]-4,5-dihydro-3H-2,3-benzodiazepin-1-yl]benzoic acid (Example 134A), 49 mg (661 µmol) of N-hydroxyethanimideamide (CAS [22059-22-9]), 184 ml (1.32 mmol) of triethylamine and 643 µl (1.10 mmol) of 1-propanephosphonic cyclo-anhydride (CAS [68957-94-8]) in 20 ml of ethyl acetate was heated at 80° C. for 48 hours. It was worked up by addition of saturated aqueous sodium hydrogen carbonate solution and extraction three times with ethyl acetate. The organic phase was washed with saturated aqueous sodium hydrogen carbonate solution and dried using sodium sulphate, and the solvent was removed on a rotary evaporator. Chromatography gave 26 mg (13% of theory) of the title compound as a yellow foam.

LCMS (Method 3): R$_t$=1.21 min; m/z=436 (M+H)$^+$ $^1$H-NMR (400 MHz, CDCl$_3$): δ=0.96 (d, 3H), 2.50 (s, 3H), 2.89 (dd, 1H), 2.91 (d, 3H), 3.17 (dd, 1H), 3.64 (s, 3H), 3.94 (s, 3H), 5.52 (m, 1H), 6.55 (s, 1H), 6.57 (q, 1H), 6.72 (s, 1H), 7.63 (d, 2H), 8.14 (d, 2H).

Using the process for preparing Example 155, Example 249 was prepared from Example 1. This was followed by separation into the enantiomers by preparative chiral HPLC.

| No. | Structure | Name | Analytical data |
|---|---|---|---|
| 249 | 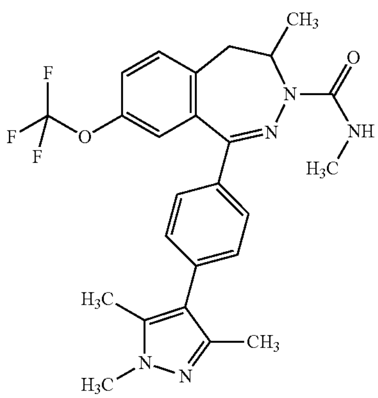 [SMILES: CNC(=O)N1N=C(c2ccc(-c3c(C)nn(C)c3C)cc2)c2cc(OC(F)(F)F)ccc2CC1C] | (±)-N,4-dimethyl-8-(trifluoromethoxy)-1-[4-(1,3,5-trimethyl-1H-pyrazol-4-yl)phenyl]-4,5-dihydro-3H-2,3-benzodiazepine-3-carboxamide | $^1$H-NMR (400 MHz, CDCl$_3$): δ = 0.99 (d, 3H), 2.30 (s, 6H), 2.91 (d, 3H), 2.92 (dd, 1H), 3.13 (dd, 1H), 3.80 (s, 3H), 5.46 (m, 1H), 6.47 (q, 1H), 7.06 (d, 1H), 7.21 (dd, 1H), 7.29 (d, 1H), 7.29 (d, 2H), 7.51 (d, 2H). LCMS (Method 3): R$_t$ = 1.34 min; m/z = 486 (M + H)$^+$. |
| 249.1 | 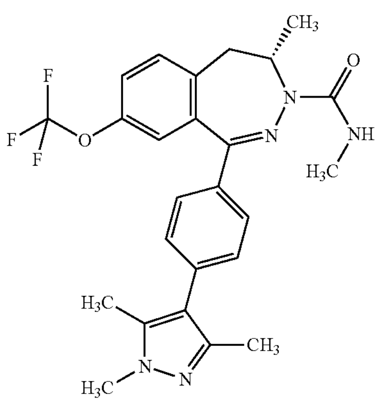 [SMILES: CNC(=O)N1N=C(c2ccc(-c3c(C)nn(C)c3C)cc2)c2cc(OC(F)(F)F)ccc2C[C@@H]1C] | (4S)-N,4-dimethyl-8-(trifluoromethoxy)-1-[4-(1,3,5-trimethyl-1H-pyrazol-4-yl)phenyl]-4,5-dihydro-3H-2,3-benzodiazepine-3-carboxamide | Prep. HPLC: Method XVIa<br>Analyt. HPLC (Method Ca):<br>R$_t$ = 4.77 min<br>[α]$_D^{20}$ = 198.1° (c = 1.00; MeOH) |
| 249.2 | 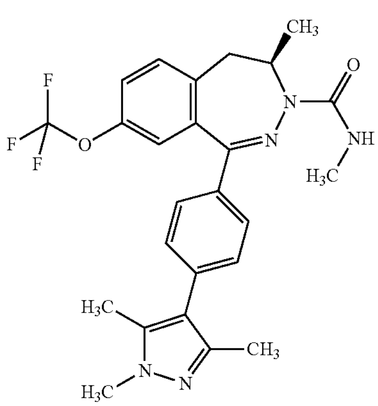 [SMILES: CNC(=O)N1N=C(c2ccc(-c3c(C)nn(C)c3C)cc2)c2cc(OC(F)(F)F)ccc2C[C@H]1C] | (4R)-N,4-dimethyl-8-(trifluoromethoxy)-1-[4-(1,3,5-trimethyl-1H-pyrazol-4-yl)phenyl]-4,5-dihydro-3H-2,3-benzodiazepine-3-carboxamide | Prep. HPLC: Method XVIa<br>Analyt. HPLC (Method Ca):<br>R$_t$ = 7.21 min<br>[α]$_D^{20}$ = −189.7° (c = 1.00; MeOH) |

Using the process for preparing Example 171, optionally with subsequent enantiomer separation by chiral preparative HPLC, the following compounds were prepared from Example 1:

| No. | Structure | Name | Analytical data |
|---|---|---|---|
| 250 | 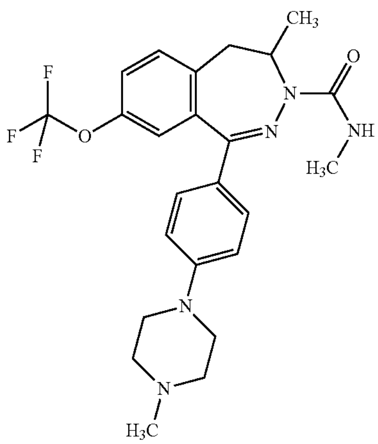 [SMILES: CNC(=O)N1N=C(c2ccc(N3CCN(C)CC3)cc2)c2cc(OC(F)(F)F)ccc2CC1C] | (±)-N,4-dimethyl-1-[4-(4-methyl-1-piperazinyl)phenyl]-8-(trifluoromethoxy)-4,5-dihydro-3H-2,3-benzodiazepine-3-carboxamide | $^1$H-NMR (300 MHz, CDCl$_3$): δ = 1.07 (d, 3H), 2.37 (s, 3H), 2.58 (m, 4H), 2.79 (dd, 1H), 2.87 (d, 3H), 3.00 (dd, 1H), 3.32 (m, 4H), 5.30 (m, 1H), 6.12 (q, 1H), 6.91 (d, 2H), 7.02 (d, 1H), 7.19 (dd, 1H), 7.26 (d, 1H), 7.45 (d, 2H). LCMS (Method 3): R$_t$ = 0.88 min; m/z = 476 (M + H)$^+$. |
| 250.1 | 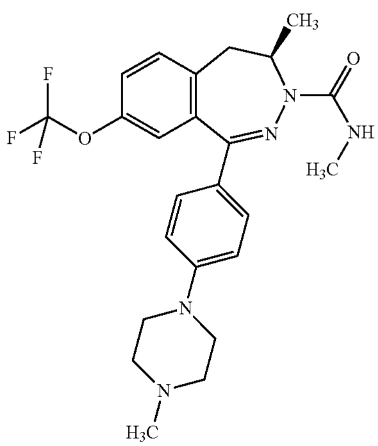 [SMILES: CNC(=O)N1N=C(c2ccc(N3CCN(C)CC3)cc2)c2cc(OC(F)(F)F)ccc2C[C@H]1C] | (4R)-N,4-dimethyl-1-[4-(4-methyl-1-piperazinyl)phenyl]-8-(trifluoromethoxy)-4,5-dihydro-3H-2,3-benzodiazepine-3-carboxamide | Prep. HPLC: Method XXb Analyt. HPLC (Method Ra): R$_t$ = 1.88 min [α]$_D^{20}$ = −442.8 (c = 1.00; MeOH) |
| 250.2 | 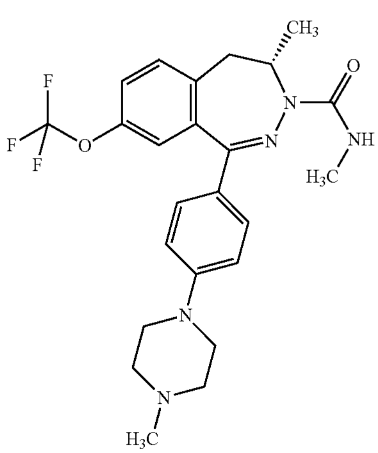 [SMILES: CNC(=O)N1N=C(c2ccc(N3CCN(C)CC3)cc2)c2cc(OC(F)(F)F)ccc2C[C@@H]1C] | (4S)-N,4-dimethyl-1-[4-(4-methyl-1-piperazinyl)phenyl]-8-(trifluoromethoxy)-4,5-dihydro-3H-2,3-benzodiazepine-3-carboxamide | Prep. HPLC: Method XXb Analyt. HPLC (Method Ra): R$_t$ = 2.32 min [α]$_D^{20}$ = 428.6° (c = 1.00; MeOH) |

-continued

| No. | Structure | Name | Analytical data |
|---|---|---|---|
| 251 | 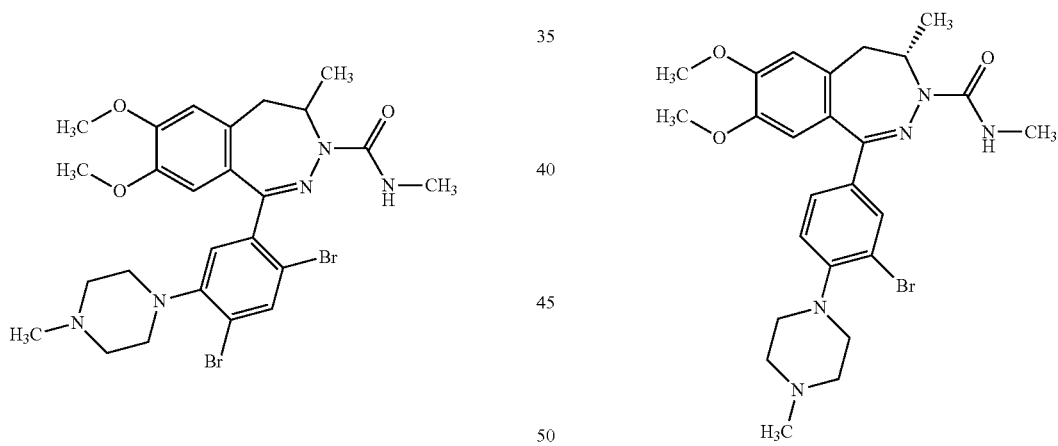 | (±)-1-[4-(4-hydroxy-1-piperidinyl)phenyl]-N,4-dimethyl-8-(trifluoromethoxy)-4,5-dihydro-3H-2,3-benzodiazepine-3-carboxamide | $^1$H-NMR (300 MHz, CDCl$_3$): δ = 1.08 (d, 3H), 1.69 (m, 2H), 2.02 (m, 2H), 2.78 (dd, 1H), 2.86 (d, 3H), 2.99 (dd, 1H), 3.06 (m, 2H), 3.69 (m, 2H), 3.92 (m, 1H), 5.28 (m, 1H), 6.08 (q, 1H), 6.92 (d, 2H), 7.02 (d, 1H), 7.19 (dd, 1H), 7.27 (d, 1H), 7.45 (d, 2H). LCMS (Method 3): R$_t$ = 0.88 min; m/z = 476 (M + H)$^+$. |

Example 252

(±)-1-[2,4-Dibromo-5-(4-methylpiperazin-1-yl)phenyl]-7,8-dimethoxy-N,4-dimethyl-4,5-dihydro-3H-2,3-benzodiazepine-3-carboxamide The compound was prepared analogously to Example 95A from (±)-7,8-dimethoxy-N,4-dimethyl-1-[3-(4-methylpiperazin-1-yl)phenyl]-4,5-dihydro-3H-2,3-benzodiazepine-3-carboxamide (Example 143).

LCMS (Method 3): R$_t$=0.94 min; m/z=608, 610, 612 (Br$_2$ isotope pattern, M+H)

$^1$H-NMR (300 MHz, CDCl$_3$): δ=0.96 (d, 3H), 2.85 (d, 3H), 2.96 (s, 3H), 2.97 (dd, 1H), 3.22 (dd, 1H), 3.45 (mbr, 8H), 3.61 (s, 3H), 3.92 (s, 3H), 5.63 (m, 1H), 6.25 (s, 1H), 6.52 (q, 1H), 6.71 (s, 1H), 7.08 (s, 1H), 7.85 (s, 1H).

Example 253

(4S)-1-[3-Bromo-4-(4-methylpiperazin-1-yl)phenyl]-7,8-dimethoxy-N,4-dimethyl-4,5-dihydro-3H-2,3-benzodiazepine-3-carboxamide The compound was prepared analogously to Example 95A from (4S)-7,8-dimethoxy-N,4-dimethyl-1-[4-(4-methylpiperazin-1-yl)phenyl]-4,5-dihydro-3H-2,3-benzodiazepine-3-carboxamide (Example 127.1).

LCMS (Method 3): R$_t$=0.78 min; m/z=529, 532 (Br isotope pattern, M+H)

$^1$H-NMR (300 MHz, CDCl$_3$): δ=1.02 (d, 3H), 2.42 (s, 3H), 2.60-2.76 (m, 4H), 2.82 (dd, 1H), 2.91 (d, 3H), 3.07 (dd, 1H), 3.12-3.26 (m, 4H), 3.71 (s, 3H), 3.96 (s, 3H), 5.36-5.49 (m, 1H), 6.38 (q, 1H), 6.62 (s, 1H), 6.75 (s, 1H), 7.08 (d, 1H), 7.43 (dd, 1H), 7.76 (d, 1H).

Example 254

(4S)-1-[3-Cyano-4-(4-methylpiperazin-1-yl)phenyl]-7,8-dimethoxy-N,4-dimethyl-4,5-dihydro-3H-2,3-benzodiazepine-3-carboxamide

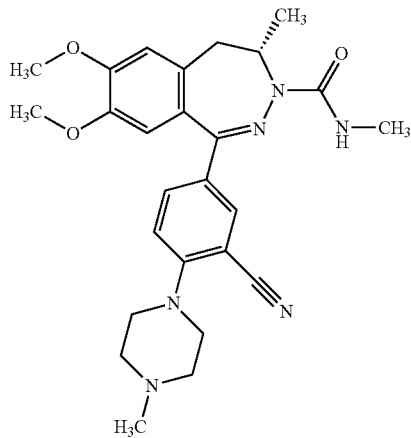

The compound was prepared analogously to Example 96A from (4S)-1-[3-bromo-4-(4-methylpiperazin-1-yl)phenyl]-7,8-dimethoxy-N,4-dimethyl-4,5-dihydro-3H-2,3-benzodiazepine-3-carboxamide (Example 253).

LCMS (Method 3): $R_t$=0.72 min; m/z=477 (M+H)$^+$.

$^1$H-NMR (400 MHz, CDCl$_3$): δ=1.01 (d, 3H), 2.41 (s, 3H), 2.68 (t, 4H), 2.83 (dd, 1H), 2.92 (d, 3H), 3.09 (dd, 1H), 3.32-3.42 (m, 4H), 3.72 (s, 3H), 3.96 (s, 3H), 5.40-5.50 (m, 1H), 6.37 (q, 1H), 6.56 (s, 1H), 6.75 (s, 1H), 7.02 (d, 1H), 7.61 (dd, 1H), 7.76 (d, 1H).

Specific optical rotation: $[α]_D^{20}$=154.6°+/−0.28° (c=1.00; methanol)

Using the process for preparing Example 88A, the following compounds were prepared from Example 136A

| No. | Structure | Name | Analytical data |
|---|---|---|---|
| 255 | 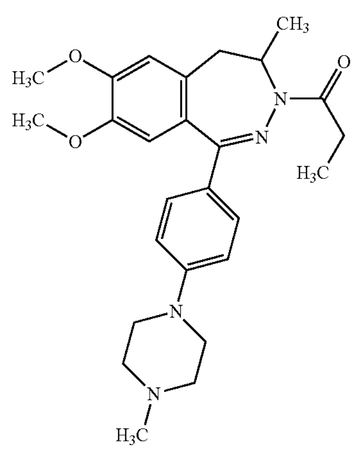 | (±)-7,8-dimethoxy-4-methyl-1-[4-(4-methylpiperazin-1-yl)phenyl]-3-(1-oxopropyl)-4,5-dihydro-3H-2,3-benzodiazepine | $^1$H-NMR (400 MHz, DMSO-d$_6$): δ = 0.89 (t, 3H), 1.15 (d, 3H), 2.13 (m, 1H), 2.22 (s, 3H), 2.34 (m, 1H), 2.44 (m, 4H), 2.49 (m, 1H), 2.84 (dd, 1H), 3.27 (m, 4H), 3.62 (s, 3H), 3.84 (s, 3H), 5.00 (m, 1H), 6.60 (s, 1H), 6.99 (d, 2H), 7.05 (s, 1H), 7.51 (d, 2H). LCMS (Method 3): $R_t$ = 0.75 min; m/z = 451 (M + H)$^+$. |
| 256 | 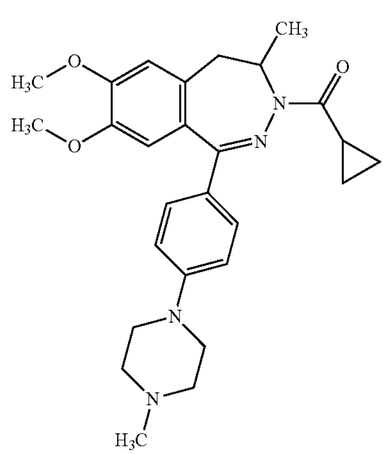 [SMILES: COc1cc2c(cc1OC)C(c1ccc(N3CCN(C)CC3)cc1)=NN(C(=O)C1CC1)C(C)C2] | (±)-3-(cyclopropylcarbonyl)-7,8-dimethoxy-4-methyl-1-[4-(4-methylpiperazin-1-yl)phenyl]-4,5-dihydro-3H-2,3-benzodiazepine | $^1$H-NMR (400 MHz, DMSO-d$_6$): δ = 0.57 (m, 1H), 0.65 (m, 1H), 0.74 (m, 2H), 1.15 (d, 3H), 2.22 (s, 3H), 2.44 (m, 4H), 2.50 (m, 1H), 2.84 (dd, 1H), 3.27 (m, 4H), 3.63 (s, 3H), 3.84 (s, 3H), 5.01 (m, 1H), 6.62 (s, 1H), 6.99 (d, 2H), 7.05 (s, 1H), 7.54 (d, 2H). LCMS (Method 3): $R_t$ = 0.74 min; m/z = 463 (M + H)$^+$. |

Using the process for preparing Example 49A, the following compound from Example 136A was prepared with cyclopropylamine:

| No. | Structure | Name | Analytical data |
|---|---|---|---|
| 257 | 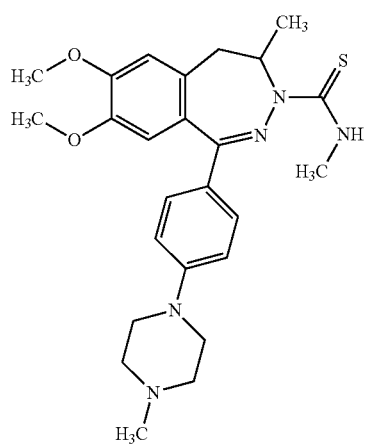 | (±)-N-cyclopropyl-7,8-dimethoxy-4-methyl-1-[4-(4-methylpiperazin-1-yl)phenyl]-4,5-dihydro-3H-2,3-benzodiazepine | $^1$H-NMR (300 MHz, DMSO-$d_6$): δ = 0.45 (m, 2H), 0.56 (m, 2H), 1.05 (d, 3H), 2.22 (s, 3H), 2.39 (m, 1H), 2.44 (m, 4H), 2.47 (m, 1H), 2.85 (dd, 1H), 3.24 (m, 4H), 3.69 (s, 3H), 3.83 (s, 3H), 4.90 (m, 1H), 6.29 (d, 1H), 6.56 (s, 1H), 6.95 (d, 2H), 7.02 (s, 1H), 7.51 (d, 2H). LCMS (Method 3): $R_t$ = 1.12 min; m/z = 478 (M + H)$^+$. |

Example 258

(±)-7,8-Dimethoxy-N,4-dimethyl-1-[4-(4-methylpiperazin-1-yl)phenyl]-4,5-dihydro-3H-2,3-benzodiazepine-3-carbothioamide

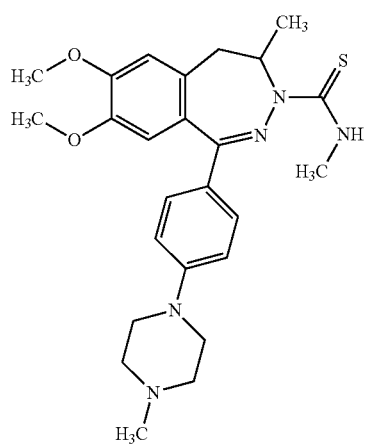 [SMILES: CNC(=S)N1N=C(c2ccc(N3CCN(C)CC3)cc2)c2cc(OC)c(OC)cc2CC1C]

A solution of 100 mg (215 μmol) of (±)-7,8-dimethoxy-4-methyl-1-[4-(4-methylpiperazin-1-yl)phenyl]-4,5-dihydro-3H-2,3-benzodiazepine (Example 136A), 79 mg (1077 μmol) of methyl isothiocyanate and 37.5 μl (215 μmol) of triethylamine in 2.5 ml of tetrahydrofuran was heated at reflux overnight. It was worked up by addition of saturated aqueous ammonium carbonate solution and extraction three times with ethyl acetate. The organic phase washed with saturated aqueous ammonium carbonate solution and with water and dried using sodium sulphate, and the solvent was removed on a rotary evaporator. Chromatography gave 77 mg (69% of theory) of the title compound as a yellow foam.

LCMS (Method 3): $R_t$=0.85 min; m/z=468 (M+H)$^+$ $^1$H-NMR (400 MHz, DMSO-$d_6$): δ=1.24 (d, 3H), 2.22 (s, 3H), 2.44 (m, 4H), 2.47 (m, 1H), 2.86 (m, 1H), 2.89 (d, 3H), 3.29 (m, 4H), 3.63 (s, 3H), 3.84 (s, 3H), 5.73 (m, 1H), 6.58 (s, 1H), 6.97 (d, 2H), 7.09 (s, 1H), 7.18 (q, 1H), 7.68 (d, 2H).

Example 259

Methyl(±)-7,8-dimethoxy-4-methyl-1-[4-(4-methylpiperazin-1-yl)phenyl]-4,5-dihydro-3H-2,3-benzodiazepine-3-carboxylate

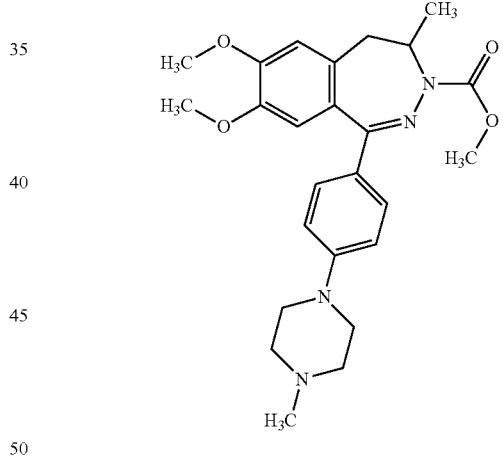

A solution of 100 mg (215 μmol) of (±)-7,8-dimethoxy-4-methyl-1-[4-(4-methylpiperazin-1-yl)phenyl]-4,5-dihydro-3H-2,3-benzodiazepine (Example 136A) and 50 μl (646 μmol) of methyl chloroformate in 4 ml of dichloromethane was heated at 40° C. for an hour. It was worked up by addition of saturated aqueous sodium hydrogen carbonate solution and extraction three times with dichloromethane. The organic phase washed with saturated aqueous sodium hydrogen carbonate solution and with water and dried using sodium sulphate, and the solvent was removed on a rotary evaporator. Chromatography gave 53 mg (52% of theory) of the title compound as a yellow foam.

LCMS (Method 3): $R_t$=0.78 min; m/z=453 (M+H)$^+$ $^1$H-NMR (300 MHz, DMSO-$d_6$): δ=1.21 (d, 3H), 2.22 (s, 3H), 2.44 (m, 4H), 2.39 (m, 1H), 2.82 (dd, 1H), 3.55 (s, 3H), 3.26 (m, 4H), 3.63 (s, 3H), 3.84 (s, 3H), 4.69 (m, 1H), 6.58 (s, 1H), 6.98 (d, 2H), 7.06 (s, 1H), 7.50 (d, 2H).

The following compound was prepared analogously to Example 259 from Example 136A with ethyl chloroformate:

| No. | Structure | Name | Analytical data |
|---|---|---|---|
| 260 | 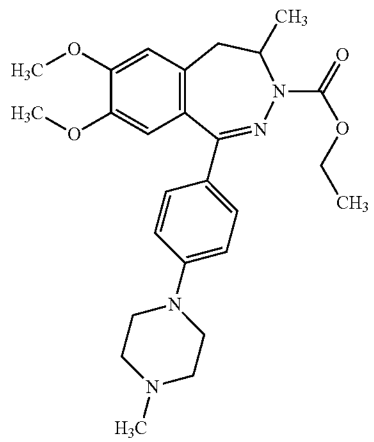 [SMILES: CCOC(=O)N1N=C(c2ccc(N3CCN(C)CC3)cc2)c2cc(OC)c(OC)cc2CC1C] | Ethyl (±)-7,8-dimethoxy-4-methyl-1-[4-(4-methylpiperazin-1-yl)phenyl]-4,5-dihydro-3H-2,3-benzodiazepine-3-carboxylate | $^1$H-NMR (300 MHz, DMSO-$d_6$): δ = 1.15 (t, 3H), 1.21 (d, 3H), 2.22 (s, 3H), 2.44 (m, 4H), 2.40 (m, 1H), 2.82 (dd, 1H), 3.26 (m, 4H), 3.63 (s, 3H), 3.84 (s, 3H), 3.99 (q, 2H), 4.69 (m, 1H), 6.58 (s, 1H), 6.98 (d, 2H), 7.06 (s, 1H), 7.50 (d, 2H). LCMS (Method 3): $R_t$ = 0.85 min; m/z = 467 (M + H)$^+$. |

Example 261

(±)-N-Ethyl-7,8-dimethoxy-4-methyl-1-[4-(4-methylpiperazin-1-yl)phenyl]-4,5-dihydro-3H-2,3-benzodiazepine-3-carboxamide

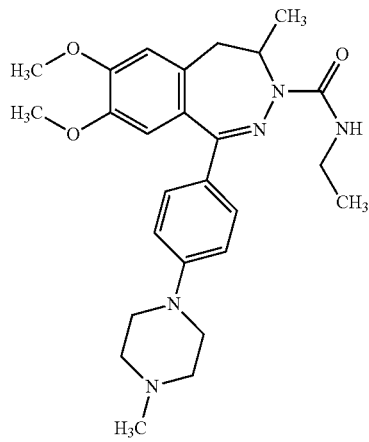 [SMILES: CCNC(=O)N1N=C(c2ccc(N3CCN(C)CC3)cc2)c2cc(OC)c(OC)cc2CC1C]

Using the process for preparing Example 127.1, Example 261 was prepared from the intermediate 137A.

LCMS (Method 5): $R_t$=0.62 min; m/z=466 (M+H)$^+$ $^1$H-NMR (400 MHz, CDCl$_3$): δ=1.13 (d, 3H), 1.20 (t, 3H), 2.39 (s, 3H), 2.58-2.64 (m, 4H), 2.74 (dd, 1H), 2.97 (dd, 1H), 3.27-3.40 (m, 6H), 3.73 (s, 3H), 3.96 (s, 3H), 5.25-5.35 (m, 1H), 6.20 (t, 1H), 6.68 (s, 1H), 6.77 (s, 1H), 6.94 (d, 2H), 7.51 (d, 2H).

Enantiomer Separation 56 mg of (±)-N-ethyl-7,8-dimethoxy-4-methyl-1-[4-(4-methylpiperazin-1-yl)phenyl]-4,5-dihydro-3H-2,3-benzodiazepine-3-carboxamide (Example X) was separated into the enantiomers by means of chiral preparative HPLC using Method Va. The following working example was obtained:

Example 261.1: (4S)—N-Ethyl-7,8-dimethoxy-4-methyl-1-[4-(4-methylpiperazin-1-yl)phenyl]-4,5-dihydro-3H-2,3-benzodiazepine-3-carboxamide 22 mg of solid, analyt. HPLC (Method Ua): $R_t$=7.53 min, purity 99%

$[α]_D^{20}$=384.1° (c=1.00; MeOH)

Biological Activity of the Compounds According to the Invention

1. Assays 1.1 Protein-Protein Interaction Assay

Binding Assay BRD4/Acetylated Peptide H4 ("PRO")

To assess the BRD4 binding of the substances described in the present application, their ability to inhibit the interaction between BRD4 (BD1) and acetylated histone H4 in a dose-dependent manner was quantified (Filippakopoulos et al., Cell, 2012, 149: 214-231).

For this purpose, use was made of a time-resolved fluorescence resonance energy transfer (TR-FRET) assay which measured binding between N-terminally His$_6$-tagged BRD4 (BD1) (amino acids 67-152, with relatively long constructs also being possible, preferably amino acids 44-168) and a synthetic acetylated histone H4 (Ac—H4) peptide having the sequence GRGK(Ac)GGK(Ac)GLGK(Ac)GGAK(Ac)RHGSGSK-biotin. The recombinant BRD4 protein-produced according to Filippakopoulos et al., Cell, 2012, 149: 214-231—was expressed in E. coli and purified by (Ni-NTA) affinity and (Sephadex G-75) size exclusion chromatography. The Ac—H4 peptide is commercially available, for example from Biosyntan (Berlin, Germany). In a typical assay, 11 different concentrations of each substance (0.1 nM, 0.33 nM, 1.1 nM, 3.8 nM, 13 nM, 44 nM, 0.15 µM, 0.51 µM, 1.7 µM, 5.9 µM and 20 µM) were measured in duplicate on the same microtitre plate. To this end, 100-fold concentrated solutions in DMSO were prepared by serial dilution (1:3.4) of a 2 mM stock solution in a clear 384-well microtitre platte (Greiner Bio-One, Frickenhausen, Germany) 50 nl of these were transferred into a black test plate (Greiner Bio-One, Frickenhausen, Germany). The test was started by addition of 2 µl of a 2.5-fold concentrated BRD4 solution (final concentration usually 10 nM in the 5 ml of the reaction volume) in aqueous assay buffer [50 mM HEPES pH 7.5. 50 mM sodium chloride (NaCl), 0.25 mM CHAPS and 0.05% serum albumin (BSA)] to the substances in the test plate. This was followed by a 10-minute incubation step at 22° C. to pre-equilibrate putative complexes between BRD4 and the substances. This was followed by the addition of 3 μl of a 1.67-fold concentrated solution (in the assay buffer) consisting of Ac—H4 peptide (83.5 nM) and TR-FRET detection reagents [16.7 nM anti-6His-XL665 and 3.34 nM streptavidin cryptate (both from Cisbio Bioassays, Codolet, France), and 668 mM potassium fluoride (KF)].

The mixture was then incubated in the dark for one hour at 22° C. and then for at least 3 hours and at most overnight at 4° C. Formation of BRD4/Ac—H4 complexes was determined by measuring the resonance energy transfer from the streptavidin-Eu cryptate to the anti-6His-XL665 antibody in the reaction. To this end, the fluorescence emission was measured at 620 nm and 665 nm after excitation at 330-350 nm in a TR-FRET measuring device, for example a Rubystar or Pherastar (both from BMG Lab Technologies, Offenburg, Germany) or a Viewlux (Perkin-Elmer). The ratio of the emission at 665 nm and at 622 nm was used as an indicator for the amount of BRD4/Ac—H4 complexes formed.

The data obtained (ratios) were normalized, with 0% inhibition corresponding to the mean of the measured values of a set of controls (usually 32 data points) comprising all reagents. Here, 50 nl of DMSO (100%) were used instead of test substances. An inhibition of 100% corresponded to the mean of the measured values of a set of controls (usually 32 data points) comprising all reagents except for BRD4. The $IC_{50}$ was determined by regression analysis based on a 4-parameter equation (minimum, maximum, $IC_{50}$, Hill; $Y=Max+(Min-Max)/(1+(X/IC\ 50)^{Hill})$).

1.2 Cell Assays
Cell Proliferation Assays

In accordance with the invention, the capability of the substances to inhibit cell proliferation was determined Cell viability was determined using the alamarBlue® reagent (Invitrogen) in a Victor X3 Multilabel Reader (Perkin Elmer). The excitation wavelength was 530 nm and the emission wavelenth 590 nM.

The MOLM-13 cells (DSMZ, ACC 554) were sown at a concentration of 4000 cells/well in 100 μl growth medium (RPMI1640, 10% FCS) on 96-well microtitre plates.

The MV4-11 cells (ATCC, CRL 9591) were sown at a concentration of 5000 cells/well in 100 μl growth medium (RPMI1640, 10% FCS) on 96-well microtitre plates.

The B16F10 cells (ATCC, CRL-6475) were sown at a concentration of 300-500 cells/well in 100 μl growth medium (DMEM with phenol red, 10% FCS) on 96-well microtitre plates.

The LOX-IMVI cells (NCI-60) were sown at a concentration of 1000 cells/well in 100 μl growth medium (RPMI1640, 10% FCS) on 96-well microtitre plates.

The MOLP-8 cells (DSMZ, ACC 569) were sown at a concentration of 4000 cells/well in 100 μl growth medium (RPMI1640, 20% FCS) on 96-well microtitre plates.

The KMS-12-PE cells (DSMZ, ACC 606) were sown at a concentration of 4000 cells/well in 100 μl growth medium (RPMI1640, 20% FCS) on 96-well microtitre plates.

The LAPC-4 cells (ATCC, PTA-1441TM) were sown at a concentration of 4000 cells/well in 100 μl growth medium (RPMI1640, 2 mM L-glutamine, 10% cFCS) on 96-well microtitre plates. A day later, the LAPC-4 cells were treated with 1 nM methyltrienolone and various substance dilutions.

The MDA-MB-231 cells (DSMZ, ACC 732) were sown at a concentration of 4000 cells/well in 100 μl growth medium (DMEM/Ham's F12 medium, 10% FCS) on 96-well microtitre plates. The Caov-3 cells (ATCC, HTB-75) were sown at a concentration of 2000 cells/well in 100 μl growth medium (MEM Earle's medium, 10% FCS) on 96-well microtitre plates.

After an overnight incubation at 37° C., the fluorescence values (CI values) were determined. The plates were then treated with various substance dilutions (1E-5 M, 3E-6 M, 1E-6M, 3E-7 M, 1E-7 M, 3E-8 M, 1E-8 M) and incubated at 37° C. for 72 (MV4-11-, LOX-IMVI cells), 96 (MOLM-13-, B16F10-, MDA-MB-431-, Caov-3 cells), 120 (MOLP-8-, KMS-12-PE cells) or 168 (LAPC-4 cells) hours. The fluorescence values (CO values) were then determined. For the data analysis, the CI values were subtracted from the CO values and the results were compared between cells treated with different dilutions of the substance or with buffer solution only. These were used to calculate the IC 50 values (substance concentration required for 50% inhibition of cell proliferation).

The substances were tested in the cell lines of Table 1 which represent, in an exemplary manner, the given indications:

TABLE 1

| Cell line | Source | Indication |
| --- | --- | --- |
| MOLM-13 | DSMZ | acute myeloid leukaemia |
| MV4-11 | ATCC | acute myeloid leukaemia |
| B16F10 | ATCC | melanoma (BRAF wild-type) |
| LOX IMVI | NCI-60 | melanoma (BRAF mutated) |
| MOLP-8 | DSMZ | multiple myeloma |
| KMS-12-PE | DSMZ | multiple myeloma |
| LAPC-4 | ATCC | prostate cancer |
| MDA-MB-231 | DSMZ | breast carcinoma |
| Caov-3 | ATCC | ovarian carcinoma |

2. Results:
2.1 Binding Assay

Table 2 shows the results from the BRD4 (BD1) binding assay.

TABLE 2

| Example | $IC_{50}$ (BRD4) (μmol/l) |
| --- | --- |
| 1 | 0.19 |
| 1.1 | 0.06 |
| 1.2 | 2.50 |
| 2 | 0.08 |
| 2.1 | 0.25 |
| 2.2 | 0.06 |
| 3 | 0.05 |
| 4 | 0.08 |
| 4.1 | 0.78 |
| 4.2 | 0.06 |
| 5 | 0.03 |
| 6 | 0.91 |
| 7 | 0.03 |
| 7.1 | 3.19 |
| 7.2 | 0.03 |
| 8 | 0.09 |
| 9 | 0.12 |
| 10 | 0.16 |
| 11 | 0.31 |
| 11.1 | 0.08 |
| 11.2 | 2.51 |
| 12 | 0.54 |
| 13 | 0.21 |
| 14 | 0.59 |
| 15 | 0.87 |
| 15.1 | 0.45 |
| 16 | 0.05 |
| 17 | 0.04 |
| 18 | 0.16 |

TABLE 2-continued

| Example | IC$_{50}$ (BRD4) (μmol/l) |
|---|---|
| 19 | 0.04 |
| 20 | 0.07 |
| 21 | 0.13 |
| 22 | 0.03 |
| 23 | 0.09 |
| 24 | 0.25 |
| 25 | 0.16 |
| 26 | 0.04 |
| 27 | 0.03 |
| 28 | 0.01 |
| 29 | 0.13 |
| 30 | 0.23 |
| 31 | 0.18 |
| 32 | 0.38 |
| 33 | 0.77 |
| 34 | 0.05 |
| 34.1 | 0.04 |
| 35 | 0.22 |
| 36 | 0.26 |
| 37 | 0.12 |
| 38 | 0.12 |
| 39 | 0.08 |
| 40 | 0.28 |
| 40.1 | 0.12 |
| 41 | 0.26 |
| 42 | 0.20 |
| 43 | 0.30 |
| 43.1 | 0.17 |
| 43.2 | 4.52 |
| 44 | 0.05 |
| 45 | 0.04 |
| 45.1 | 0.07 |
| 46 | 0.03 |
| 46.1 | 0.96 |
| 46.2 | 1.16 |
| 47 | 0.11 |
| 48 | 0.11 |
| 49 | 0.04 |
| 49.1 | 0.02 |
| 50 | 0.15 |
| 50.1 | 0.11 |
| 50.2 | 18.90 |
| 51 | 0.03 |
| 51.1 | 1.86 |
| 51.2 | 0.03 |
| 52 | 0.05 |
| 53 | 0.04 |
| 54 | 0.05 |
| 55 | 0.12 |
| 56 | 0.18 |
| 57 | 0.09 |
| 58 | 0.25 |
| 59 | 0.07 |
| 60 | 0.08 |
| 61 | 0.57 |
| 62 | 0.06 |
| 63 | 0.17 |
| 64 | 0.11 |
| 65 | 0.10 |
| 66 | 0.07 |
| 67 | 0.04 |
| 68 | 0.07 |
| 69 | 0.13 |
| 70 | 0.04 |
| 71 | 0.04 |
| 72 | 0.21 |
| 73 | 0.03 |
| 74 | 0.08 |
| 75 | 0.13 |
| 76 | 0.05 |
| 77 | 0.04 |
| 78 | 0.04 |
| 79 | 0.05 |
| 80 | 0.05 |
| 81 | 0.05 |
| 82 | 0.08 |
| 83 | 0.03 |

TABLE 2-continued

| Example | IC$_{50}$ (BRD4) (μmol/l) |
|---|---|
| 84 | 0.06 |
| 85 | 0.29 |
| 86 | 0.39 |
| 87 | 0.11 |
| 88 | 0.29 |
| 89 | 0.14 |
| 90 | 0.07 |
| 91 | 0.34 |
| 92 | 0.18 |
| 93 | 0.12 |
| 94 | 0.04 |
| 95 | 0.63 |
| 96 | 0.04 |
| 97 | 0.05 |
| 98 | 0.03 |
| 99 | 0.03 |
| 100 | 0.11 |
| 101 | 0.06 |
| 102 | 0.09 |
| 103 | 0.04 |
| 104 | 0.03 |
| 105 | 0.08 |
| 106 | 0.09 |
| 107 | 0.26 |
| 108 | 0.06 |
| 109 | 0.05 |
| 110 | 0.06 |
| 111 | 0.08 |
| 112 | 0.08 |
| 113 | 0.04 |
| 114 | 0.04 |
| 115 | 0.05 |
| 116 | 0.07 |
| 117 | 0.05 |
| 118 | 0.07 |
| 119 | 0.09 |
| 120 | 0.19 |
| 121 | 0.04 |
| 122 | 0.06 |
| 123 | 0.05 |
| 124 | 0.09 |
| 125 | 0.07 |
| 126 | 0.09 |
| 127 | 0.08 |
| 127.1 | 0.05 |
| 127.2 | 8.80 |
| 128 | 0.03 |
| 128.1 | 3.98 |
| 128.2 | 0.02 |
| 129 | 0.05 |
| 129.1 | 6.62 |
| 129.2 | 0.02 |
| 130 | 0.03 |
| 130.1 | 0.02 |
| 130.2 | 9.87 |
| 131 | 0.05 |
| 131.1 | 0.07 |
| 132 | 0.03 |
| 132.1 | 4.08 |
| 132.2 | 0.02 |
| 133 | 0.05 |
| 134 | 0.05 |
| 134.1 | 0.03 |
| 135 | 0.05 |
| 135.1 | 0.04 |
| 136 | 0.02 |
| 137 | 0.06 |
| 138 | 0.03 |
| 138.1 | 0.04 |
| 139 | 0.04 |
| 140 | 0.06 |
| 141 | 0.07 |
| 142 | 0.10 |
| 143 | 0.17 |
| 144 | 0.19 |
| 145 | 0.11 |
| 146 | 0.47 |

TABLE 2-continued

| Example | IC$_{50}$ (BRD4) (µmol/l) |
|---|---|
| 147 | 0.03 |
| 147.1 | 0.03 |
| 148 | 0.04 |
| 148.1 | 0.03 |
| 149 | 1.62 |
| 150 | 0.08 |
| 150.1 | 0.11 |
| 150.2 | 12.300 |
| 151 | 0.02 |
| 152 | 0.07 |
| 153 | 0.11 |
| 154 | 0.17 |
| 155 | 0.04 |
| 156 | 0.23 |
| 156.1 | 0.33 |
| 156.2 | 2.24 |
| 157 | 0.21 |
| 157.1 | 0.13 |
| 157.2 | 0.47 |
| 158 | 0.06 |
| 160 | 0.26 |
| 161 | 0.11 |
| 162 | 0.13 |
| 162.1 | 0.10 |
| 162.2 | 0.56 |
| 163 | 0.06 |
| 163.1 | 8.94 |
| 163.2 | 0.03 |
| 164 | 0.06 |
| 164.1 (Comparative Example) | >20.0 |
| 164.2 | 0.06 |
| 165 | 0.13 |
| 166 | 0.27 |
| 167 | 0.31 |
| 168 | 0.11 |
| 169 | 0.03 |
| 170 | 0.07 |
| 171 | 0.12 |
| 172 | 0.13 |
| 173 | 0.18 |
| 174 | 0.25 |
| 175 | 0.19 |
| 176 | 0.04 |
| 176.1 | 0.73 |
| 176.2 | 0.04 |
| 177 | 0.07 |
| 178 | 0.07 |
| 179 | 0.07 |
| 179.1 | 3.77 |
| 179.2 | 0.04 |
| 180 | 0.07 |
| 180.1 | 0.39 |
| 180.2 | 0.06 |
| 181 | 0.07 |
| 182 | 0.05 |
| 183 | 0.04 |
| 184 | 0.06 |
| 185 | 0.07 |
| 185.1 | 1.49 |
| 185.2 | 0.03 |
| 186 | 0.13 |
| 187 | 0.08 |
| 188 | 0.05 |
| 188.1 | 0.27 |
| 188.2 | 0.03 |
| 189 | 0.06 |
| 189.1 | 0.04 |
| 189.2 | 17.40 |
| 190 | 0.09 |
| 190.1 | 0.03 |
| 191 | 0.07 |
| 192 | 0.09 |
| 193 | 0.09 |
| 194 | 0.48 |
| 195 | 0.69 |
| 196 | 0.09 |
| 197 | 0.08 |
| 198 | 5.30 |
| 199 | 1.02 |
| 200 | 0.50 |
| 201 | 1.37 |
| 201.1 | 0.71 |
| 202 | 1.23 |
| 202.1 | 0.64 |
| 202.2 | 6.54 |
| 203 | 0.84 |
| 203.1 | 0.26 |
| 203.2 | 11.20 |
| 204 | 1.22 |
| 205 | 1.08 |
| 206 | 0.93 |
| 207 | 1.22 |
| 208 | 1.10 |
| 209 | 0.37 |
| 210 | 0.25 |
| 211 | 0.30 |
| 212 | 0.31 |
| 213 | 0.36 |
| 214 | 1.23 |
| 215 | 0.38 |
| 216 | 0.52 |
| 217 | 1.73 |
| 218 | 0.88 |
| 219 | 0.37 |
| 220 | 0.49 |
| 221 | 1.98 |
| 222 | 0.96 |
| 223 | 0.32 |
| 224 | 7.69 |
| 225 | 1.72 |
| 226 | 8.76 |
| 227 | 6.28 |
| 228 | 1.69 |
| 229 | 0.07 |
| 230 | 0.24 |
| 230.1 | 0.33 |
| 231 | 3.37 |
| 232 | 2.84 |
| 233 | 3.45 |
| 234 | 3.83 |
| 235 | 5.02 |
| 236 | 2.20 |
| 237 | 1.07 |
| 238 | 0.13 |
| 239 | 11.40 |
| 240 | 4.50 |
| 241 | 2.56 |
| 242 | 2.69 |
| 243 | 0.32 |
| 244 | 0.03 |
| 245 | 0.62 |
| 245.1 | 0.39 |
| 246 | 0.33 |
| 247 | 0.19 |
| 248 | 0.19 |
| 249 | 0.03 |
| 249.1 | 0.02 |
| 249.2 | 2.34 |
| 250 | 0.04 |
| 250.1 | 9.89 |
| 250.2 | 0.02 |
| 251 | 0.03 |
| 252 | 5.29 |
| 253 | 0.04 |
| 254 | 0.11 |
| 255 | 0.24 |
| 256 | 0.61 |
| 257 | 2.00 |
| 258 | 0.19 |
| 259 | 0.52 |

TABLE 2-continued

| Example | IC$_{50}$ (BRD4) (μmol/l) |
|---|---|
| 260 | 6.49 |
| 261 | 1.49 |
| 261.1 | 1.22 |

2.2 Cell Assays

Tables 3A and 3B show results from various cell proliferation assays. The indications corresponding to the respective cell lines can be found in Table 1.

TABLE 3A

| Example | MOLM-13 IC$_{50}$ (μmol/l) | MV4-11 IC$_{50}$ (μmol/l) | B16F10 IC$_{50}$ (μmol/l) | LOX IMVI IC$_{50}$ (μmol/l) | MOLP-8 IC$_{50}$ (μmol/l) | KMS-12-PE IC$_{50}$ (μmol/l) |
|---|---|---|---|---|---|---|
| 1 | 1.26 | | 0.69 | | | |
| 1.1 | 0.39 | | 0.39 | | 0.51 | |
| 1.2 | >10 | | >10 | | | |
| 2 | 0.17 | 0.11 | 0.18 | 0.43 | 0.12 | 0.09 |
| 2.1 | 1.51 | | 1.05 | | | |
| 2.2 | 0.13 | 0.10 | 0.11 | 0.33 | 0.12 | 0.11 |
| 3 | 0.24 | 0.26 | 0.11 | 0.95 | 0.28 | 0.23 |
| 4 | 0.19 | 0.12 | 0.11 | 0.45 | 0.17 | 0.11 |
| 4.1 | | | | | | |
| 4.2 | | | | | | |
| 5 | 0.82 | | 0.69 | | | |
| 7 | 0.20 | 0.17 | 0.14 | 0.57 | 0.12 | 0.09 |
| 7.1 | >10 | | | | | |
| 7.2 | 0.10 | 0.06 | | 0.19 | 0.05 | 0.05 |
| 8 | 0.38 | | 0.19 | | | |
| 9 | 0.65 | | 0.54 | | | |
| 10 | 0.31 | | 0.27 | | | |
| 11 | 1.91 | | 1.12 | | | |
| 11.1 | 0.57 | | | | | |
| 11.2 | 7.74 | | | | | |
| 12 | 1.61 | | 1.32 | | | |
| 13 | 1.44 | | 0.92 | | | |
| 14 | 3.07 | | 2.63 | | | |
| 15 | 3.45 | | | | | |
| 15.1 | 3.05 | | | | | |
| 16 | 0.22 | 0.27 | | 0.64 | 0.29 | 0.25 |
| 17 | 0.17 | 0.13 | | 0.30 | 0.11 | 0.11 |
| 18 | 0.25 | 0.30 | | 0.76 | 0.34 | 0.35 |
| 19 | 0.17 | 0.27 | | 0.65 | 0.27 | 0.27 |
| 20 | 0.19 | 0.14 | | 0.33 | 0.12 | 0.11 |
| 21 | 0.56 | | | | | |
| 22 | 0.08 | 0.88 | 0.10 | 0.24 | 0.09 | 0.11 |
| 23 | 0.27 | | | | | |
| 24 | 1.17 | | | | | |
| 25 | 0.74 | | | | | |
| 26 | 0.43 | | | | | |
| 27 | 0.63 | | | | | |
| 28 | 0.04 | 0.03 | | 0.04 | 0.02 | 0.03 |
| 29 | 0.36 | | | | | |
| 30 | 0.79 | | | | | |
| 31 | 0.27 | | | | | |
| 32 | 1.18 | | | | | |
| 33 | 3.31 | | | | | |
| 34 | 0.35 | | | | | |
| 34.1 | 0.24 | 0.12 | | 0.44 | 0.08 | 0.08 |
| 35 | 1.47 | | | | | |
| 36 | 1.16 | | | | | |
| 37 | 1.13 | | | | | |
| 38 | 0.73 | | | | | |
| 39 | 0.70 | | | | | |
| 40 | 1.47 | | | | | |
| 40.1 | 0.96 | 0.76 | 0.79 | 0.33 | 0.59 | 0.08 |
| 41 | 1.35 | | | | | |
| 42 | 1.29 | | | | | |
| 43 | 0.84 | | | | | |
| 43.1 | 0.81 | | | | | |
| 43.2 | 9.85 | | | | | |
| 44 | 0.21 | | | | | |
| 45 | 0.23 | 0.14 | | 0.35 | 0.13 | 0.13 |
| 45.1 | 0.22 | | | | | |
| 46 | 0.19 | 0.11 | | 0.37 | 0.16 | 0.12 |
| 46.1 | 5.14 | | | | | |
| 46.2 | >10 | | | | 9.47 | |
| 47 | 0.53 | | | | | |
| 48 | 0.19 | 0.22 | | 0.65 | 0.25 | 0.26 |
| 49 | 0.42 | | | | | |
| 49.1 | 0.23 | | | | | |
| 50 | 0.56 | | | | | |
| 50.1 | 0.37 | | | | | |
| 51 | 0.21 | 0.12 | | 0.35 | 0.12 | 0.09 |
| 51.1 | >10 | | | | | |
| 51.2 | 0.11 | 0.05 | | 0.17 | 0.05 | 0.04 |
| 52 | 0.24 | 0.14 | | 0.45 | 0.15 | 0.13 |
| 53 | 0.35 | | | | | |
| 54 | 0.44 | | | | | |
| 55 | 0.90 | | | | | |
| 56 | 0.90 | | | | | |
| 57 | 0.79 | | | | | |
| 58 | 0.99 | | | | | |
| 59 | 0.62 | | | | | |
| 60 | 0.48 | | | | | |
| 61 | 2.11 | | | | | |
| 62 | 0.65 | | | | | |
| 63 | 0.77 | | | | | |
| 64 | 0.88 | | | | | |
| 65 | 0.63 | | | | | |
| 66 | 0.63 | | | | | |
| 67 | 0.47 | | | | | |
| 68 | 1.17 | | | | | |
| 69 | 1.21 | | | | | |
| 70 | 0.30 | | | | | |
| 71 | 0.25 | 0.05 | | 0.15 | 0.09 | 0.08 |
| 72 | 0.66 | | | | | |
| 73 | 0.30 | | | | | |
| 74 | 0.55 | | | | | |
| 75 | 0.66 | | | | | |
| 76 | 0.75 | | | | | |
| 77 | 0.49 | | | | | |
| 78 | 0.37 | | | | | |
| 79 | 0.46 | | | | | |
| 80 | 0.56 | | | | | |
| 81 | 0.30 | | | | | |
| 82 | 0.55 | | | | | |
| 83 | 0.45 | | | | | |
| 84 | 0.34 | | | | | |
| 85 | 1.08 | | | | | |
| 86 | 1.43 | | | | | |
| 87 | 0.56 | | | | | |
| 88 | 0.67 | | | | | |
| 89 | 0.38 | | | | | |
| 90 | 0.46 | | | | | |
| 91 | 0.55 | | | | | |
| 92 | 0.85 | | | | | |
| 93 | 0.46 | | | | | |
| 94 | 0.38 | | | | | |
| 95 | 2.76 | | | | | |
| 96 | 0.25 | 0.07 | | 0.22 | 0.09 | 0.07 |
| 97 | 0.45 | | | | | |
| 98 | 0.27 | | | | | |
| 99 | 0.27 | | | | | |
| 100 | 0.53 | | | | | |
| 101 | 0.65 | | | | | |
| 102 | 0.96 | | | | | |
| 103 | 0.35 | | | | | |
| 104 | 0.26 | | | | | |
| 105 | 0.67 | | | | | |
| 106 | 2.55 | | | | | |
| 107 | 0.63 | | | | | |
| 108 | 1.56 | | | | | |
| 109 | 1.16 | | | | | |
| 110 | 0.36 | | | | | |
| 111 | 0.81 | | | | | |
| 112 | 0.63 | | | | | |

TABLE 3A-continued

| Example | MOLM-13 IC$_{50}$ (µmol/l) | MV4-11 IC$_{50}$ (µmol/l) | B16F10 IC$_{50}$ (µmol/l) | LOX IMVI IC$_{50}$ (µmol/l) | MOLP-8 IC$_{50}$ (µmol/l) | KMS-12-PE IC$_{50}$ (µmol/l) |
|---|---|---|---|---|---|---|
| 113 | 1.42 | | | | | |
| 114 | 0.30 | | | | | |
| 115 | 0.46 | | | | | |
| 116 | 0.49 | | | | | |
| 117 | 0.38 | | | | | |
| 118 | 0.50 | | | | | |
| 119 | 0.41 | | | | | |
| 120 | 0.80 | | | | | |
| 121 | 0.27 | | | | | |
| 122 | 0.66 | | | | | |
| 123 | 0.63 | | | | | |
| 124 | 1.07 | | | | | |
| 125 | 1.16 | | | | | |
| 126 | 0.74 | | | | | |
| 127 | 0.18 | 0.12 | | 0.25 | 0.09 | 0.09 |
| 127.1 | 0.11 | 0.07 | 0.10 | 0.29 | 0.06 | 0.09 |
| 127.2 | >10 | | | | | |
| 128 | 0.23 | | | 0.39 | 0.10 | 0.10 |
| 128.1 | >10 | | | | | |
| 128.2 | 0.15 | 0.07 | | 0.19 | 0.05 | 0.05 |
| 129 | 0.22 | 0.18 | | 0.58 | 0.15 | 0.12 |
| 129.1 | >10 | | | | | |
| 129.2 | 0.15 | | | 0.08 | | |
| 130 | 0.17 | | | | | |
| 130.1 | 0.07 | 0.05 | 0.10 | 0.19 | 0.05 | 0.07 |
| 131 | 0.11 | 0.04 | | 0.07 | 0.03 | 0.03 |
| 131.1 | 0.11 | | 0.06 | | | |
| 132 | 0.20 | 0.13 | | 0.42 | 0.12 | 0.11 |
| 132.1 | 7.56 | | | | | |
| 132.2 | 0.23 | | | | | |
| 133 | 0.18 | 0.08 | | 0.17 | 0.07 | 0.08 |
| 134 | 0.36 | | | | | |
| 134.1 | 0.08 | | | | | |
| 135 | 0.20 | 0.12 | | 0.36 | 0.13 | 0.12 |
| 135.1 | 0.15 | | 0.08 | | | |
| 136 | 0.20 | | | | | |
| 137 | 0.49 | | | | | |
| 138 | 0.28 | | | | | |
| 138.1 | 0.18 | | | | | |
| 139 | 0.21 | 0.13 | | 0.38 | 0.13 | 0.11 |
| 140 | 0.47 | | | | | |
| 141 | 0.55 | | | | | |
| 142 | 0.68 | | | | | |
| 143 | 0.84 | | | | | |
| 144 | 0.96 | | | | | |
| 145 | 0.83 | | | | | |
| 146 | 1.15 | | | | | |
| 147 | 0.07 | 0.05 | | 0.18 | 0.08 | 0.06 |
| 147.1 | 0.06 | 0.02 | | 0.51 | 0.02 | 0.03 |
| 148 | 0.08 | 0.07 | | 0.25 | 0.09 | 0.08 |
| 148.1 | 0.08 | 0.05 | | 0.09 | 0.05 | 0.05 |
| 149 | 3.00 | | | | | |
| 150 | 0.48 | | | | | |
| 150.1 | 0.23 | 0.13 | | 0.34 | 0.23 | 0.18 |
| 150.2 | 9.87 | | | | | |
| 151 | 1.31 | | | | | |
| 152 | 0.43 | | | | | |
| 153 | 0.48 | | | | | |
| 154 | 2.08 | | | | | |
| 155 | 0.38 | | | | | |
| 156 | 0.79 | | | | | |
| 156.1 | 0.56 | | | | | |
| 156.2 | >10 | | | | | |
| 157 | 0.09 | 0.19 | | 0.58 | 0.12 | 0.24 |
| 157.1 | 0.12 | | | | | |
| 157.2 | 2.19 | | | | | |
| 158 | 0.43 | | | | | |
| 160 | 0.40 | | | | | |
| 161 | 0.28 | | | | | |
| 162 | 0.38 | | | | | |
| 162.1 | 0.21 | | | | | |
| 162.2 | 1.68 | | | | | |
| 163 | 0.21 | | | | | |
| 163.1 | 7.08 | | | | | |
| 163.2 | 0.26 | | | | | |
| 164 | 0.58 | | | | | |
| 164.2 | 0.42 | | | | | |
| 165 | 0.88 | | | | | |
| 166 | 0.67 | | | | | |
| 167 | 3.24 | | | | 2.95 | |
| 168 | 0.39 | 0.22 | | | | |
| 169 | 0.24 | | | 0.41 | 0.12 | 0.12 |
| 170 | 0.52 | | | | | |
| 171 | 1.91 | | | | | |
| 172 | 1.91 | | | | | |
| 173 | 1.21 | | | | | |
| 174 | 2.34 | | | | 2.03 | |
| 175 | 0.44 | | | | | |
| 176 | 0.52 | | | | | |
| 176.1 | 2.19 | | | | | |
| 176.2 | 0.25 | | | | | |
| 177 | 0.49 | | | | | |
| 178 | 0.18 | | | | | |
| 179 | 0.29 | | | | | |
| 179.2 | 0.08 | | | | | |
| 180 | 0.37 | | | | | |
| 180.1 | 2.70 | | | | | |
| 180.2 | 0.05 | | | | | |
| 181 | 0.30 | | | 0.17 | | |
| 182 | 0.40 | | | | | |
| 184 | 0.30 | | 0.13 | | | |
| 185 | 0.28 | | 0.16 | | | |
| 185.2 | 0.10 | | | | | |
| 186 | 0.33 | | 0.24 | | | |
| 187 | 0.33 | | 0.17 | | | |
| 188 | 0.20 | | 0.10 | | | |
| 188.1 | 1.13 | | | | | |
| 188.2 | 0.07 | | | | | |
| 189 | 0.44 | | 0.21 | | | |
| 189.1 | 0.21 | | 0.10 | | 0.08 | |
| 190 | 0.08 | | | | | |
| 191 | 0.17 | | | | | |
| 192 | 0.27 | | | | | |
| 193 | 0.11 | | | | | |
| 200 | 0.18 | | | | | |
| 201.1 | 1.99 | | | | | |
| 202.1 | 0.58 | | | | | |
| 203 | 3.31 | | | | | |
| 203.1 | 1.27 | | | | | |
| 209 | 0.19 | | | | | |
| 210 | 0.17 | | | | | |
| 212 | 0.82 | | | | | |
| 213 | 0.86 | | | | | |
| 215 | 2.27 | | | | | |
| 216 | 1.03 | | | | | |
| 218 | 0.30 | | | | | |
| 219 | 0.57 | | | | | |
| 220 | 2.40 | | | | | |
| 222 | 2.12 | | | | | |
| 229 | 0.14 | | | | | |
| 230 | 0.23 | | | | | |
| 243 | 0.34 | | | | | |
| 245 | 0.86 | | | | | |
| 246 | 2.06 | | | | | |
| 247 | 0.57 | | | | | |
| 248 | 0.14 | | | | | |
| 249.1 | 0.06 | | | | | |
| 250 | 0.14 | | 0.10 | | | |
| 250.2 | 0.05 | | 0.04 | | | |
| 251 | 0.10 | | | | | |
| 253 | 0.06 | | | | | |
| 254 | 0.17 | | | | | |

TABLE 3B

| Example | LAPC-4 IC$_{50}$ (µmol/l) | MDA-MB-231 IC$_{50}$ (µmol/l) | Caov-3 IC$_{50}$ (µmol/l) |
| --- | --- | --- | --- |
| 1 | 0.60 | 0.90 | |
| 1.1 | 0.60 | 0.53 | |
| 1.2 | 5.17 | >10.00 | |
| 2 | 0.24 | 0.31 | 0.31 |
| 2.1 | 0.71 | 1.39 | |
| 2.2 | 0.09 | 0.20 | 0.25 |
| 3 | 0.11 | 0.21 | 0.55 |
| 4 | 0.09 | 0.17 | 0.32 |
| 5 | 0.27 | 1.35 | |
| 7 | 0.09 | 0.25 | 0.40 |
| 8 | 0.18 | 0.28 | |
| 9 | 0.43 | 0.73 | |
| 10 | 0.12 | 0.26 | |
| 11 | 0.45 | 2.58 | |
| 11.1 | 0.31 | 1.11 | |
| 11.2 | | 10.00 | |
| 12 | 0.87 | 1.85 | |
| 13 | 0.90 | 1.30 | |
| 14 | 1.65 | 3.64 | |
| 15 | | 6.23 | |
| 16 | 0.11 | 0.47 | 0.37 |
| 17 | 0.10 | 0.21 | 0.22 |
| 18 | | 0.28 | 0.48 |
| 19 | 0.11 | | 0.41 |
| 20 | 0.12 | 0.22 | 0.24 |
| 21 | | | |
| 22 | 0.06 | 0.15 | 0.11 |
| 23 | 0.19 | | |
| 26 | 0.13 | | |
| 27 | 0.18 | | |
| 28 | 0.02 | | 0.04 |
| 34.1 | | | 0.31 |
| 40.1 | 0.29 | 1.28 | |
| 45 | | | 0.24 |
| 46 | | | 0.28 |
| 48 | | | 0.47 |
| 51 | | | 0.28 |
| 51.2 | | | 0.13 |
| 52 | | | 0.35 |
| 71 | | | 0.15 |
| 96 | | | 0.17 |
| 127 | | | 0.24 |
| 127.1 | 0.04 | 0.13 | 0.17 |
| 128 | | | 0.32 |
| 128.2 | | | 0.16 |
| 129 | | | 0.42 |
| 130.1 | 0.05 | 0.14 | 0.003 |
| 131 | | | 0.05 |
| 132 | | | 0.32 |
| 133 | | | 0.18 |
| 135 | | | 0.30 |
| 139 | | | 0.31 |
| 147 | | | 0.18 |
| 147.1 | | | 0.08 |
| 148 | | | 0.30 |
| 148.1 | | | 0.13 |
| 150.1 | | | 0.34 |
| 157 | | | 0.42 |
| 169 | | | 0.37 |

The invention claimed is:

1. A compound of formula I

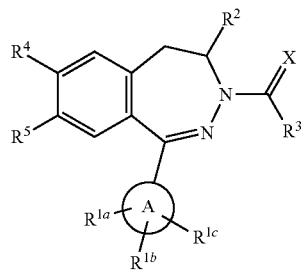

in which

X represents an oxygen or sulphur atom, and

A represents a monocyclic heteroaryl ring which has 5 or 6 ring atoms or represents a phenyl ring, and $R^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, or represents a monocyclic heterocyclyl radical which has 3 to 8 ring atoms and may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl, —$NR^6C(=O)$—$R^9$, —$C(=O)$—$NR^6R^7$, —$C(=O)$—$R^8$, —$S(=O)_2$—$NR^6R^7$, —$S(=O)$—$R^9$, —$S(=O)_2$—$R^9$, —NH—$S(=O)_2$—$R^9$, and/or a monocyclic heterocyclyl radical which has 3 to 8 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —$C(=O)$—$NR^6R^7$, —$C(=O)$—$R^8$, —$S(=O)_2$—$NR^6R^7$, —$S(=O)$—$R^9$, —$S(=O)_2$—$R^9$, —NH—$S(=O)_2$—$R^9$, and/or by a monocyclic heterocyclyl radical which has 3 to 8 ring atoms, and/or by a monocyclic heteroaryl radical which has 5 or 6 ring atoms, and/or by a phenyl radical which for its part may optionally be mono- or polysubstituted by halogen, $C_1$-$C_3$-alkyl and/or $C_1$-$C_3$-alkoxy, or represents a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$- alkylamino, amino-$C_1$-$C_6$-alkyl, $C_1$-$C_6$-alkylamino-$C_1$-$C_6$-alkyl, —C(=O)NR$^6$R$^7$, —C(=O)R$^8$, $C_1$-$C_3$-alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl, and/or a monocyclic heterocyclyl radical which has 3 to 8 ring atoms, and/or a monocyclic heteroaryl radical which has 5 or 6 ring atoms and which for its part may optionally be mono- or polysubstituted by identical or different substituents from the group consisting of halogen, $C_1$-$C_3$-alkyl and $C_1$-$C_3$-alkoxy, and $R^{1b}$ and $R^{1c}$ independently of one another represent hydrogen, halogen, hydroxy, cyano, nitro and/or represent a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl radical and/or a monocyclic heterocyclyl radical which has 3 to 8 ring atoms, and $R^2$ represents a $C_1$-$C_3$-alkyl or trifluoromethyl or a $C_3$- or $C_4$-cycloalkyl radical, and $R^3$ represents cyclopropyl, $C_1$-$C_3$-alkyl, $C_1$-$C_3$-alkoxy, amino, cyclopropylamino or $C_1$-$C_3$-alkylamino, and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, monocyclic heterocyclyl which has 3 to 8 ring atoms and/or monocyclic heteroaryl which has 5 or 6 ring atoms, where the monocyclic heterocyclyl and heteroaryl radicals mentioned for their part may optionally be monosubstituted by $C_1$-$C_3$-alkyl, or represent $C_3$-$C_{10}$-cycloalkyl which may optionally be mono- or polysubstituted by identical or different substituents from the group consisting of halogen, amino, hydroxy, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical which has 3 to 8 ring atoms, or represent monocyclic heteroaryl which has 5 or 6 ring atoms and which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —C(=O)R$^8$, —S(=O)$_2$R$^9$, —NR$^6$R$^7$, and/or a monocyclic heterocyclyl radical which has 3 to 8 ring atoms, or represent monocyclic heterocyclyl which has 3 to 8 ring atoms and which may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-Cycloalkyl, —C(=O)R$^8$, —S(=O)$_2$R$^9$, —NR$^6$R$^7$, and/or a monocyclic heterocyclyl radical which has 3 to 8 ring atoms, or represent phenyl which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-Cycloalkyl and/or a monocyclic heterocyclyl radical which has 3 to 8 ring atoms, and $R^6$ and $R^7$ independently of one another represent hydrogen, $C_1$-$C_3$-alkyl, cyclopropyl, di-$C_1$-$C_3$-alkyl-amino-$C_1$-$C_3$-alkyl or fluoropyridyl, and $R^8$ represents hydroxy, $C_1$-$C_6$-alkyl, halo-$C_1$-$C_3$-alkyl, hydroxy-$C_1$-$C_3$-alkyl, $C_1$-$C_3$-alkoxy-$C_1$-$C_3$-alkyl, $C_3$-$C_8$-cycloalkyl, phenyl, monocyclic heterocyclyl which has 3 to 8 ring atoms or monocyclic heteroaryl which has 5 or 6 ring atoms, where phenyl, heteroaryl and heterocyclyl may optionally be mono- or disubstituted by halogen, $C_1$-$C_3$-alkoxy or $C_1$-$C_3$-alkyl, and $R^9$ represents hydrogen, $C_1$-$C_6$-alkyl or $C_1$-$C_4$-alkoxy, or an enantiomer, diastereomer, racemate, tautomer, or physiologically acceptable salt thereof, with the proviso that, if A represents a phenyl ring and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylamino-carbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, monocyclic heterocyclyl which has 3 to 8 ring atoms and/or monocyclic heteroaryl which has 5 or 6 ring atoms, where the monocyclic heterocyclyl and heteroaryl radicals mentioned for their part may optionally be monosubstituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, except that the proviso does not encompass those compounds of the formula (I) in which A is phenyl and $R^4$ is hydrogen, fluorine, chlorine or bromine and $R^5$ is $C_1$-$C_6$-alkoxy which is substituted one or more times by identical or different halogens, and $R^{1a}$ is halogen, and also not encompass those compounds of the formula (I) in which A is phenyl and $R^4$ is hydrogen and $R^5$ is $C_1$-$C_6$-alkoxy which is substituted one or more times by identical or different monocyclic heterocyclyl radicals having 3 to 8 ring atoms and/or monocyclic heteroaryl radicals having 5 or 6 ring atoms, it being possible for the stated monocyclic heterocyclyl and heteroaryl radicals in turn to be optionally monosubstituted by $C_1$-$C_3$-alkyl, and $R^{1a}$ is halogen.

2. A compound of formula (I) according to claim 1 in which

X represents an oxygen atom, and

A represents a phenyl or pyridyl ring, and $R^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, or represents a monocyclic heterocyclyl radical which has 4 to 7 ring atoms and may optionally be mono- or polysubstituted by identical or different substituents from the group consisting of halogen, cyano, nitro, hydroxy, amino, oxo, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, phenyl, halophenyl, phenyl-$C_1$-$C_6$-alkyl, pyridinyl, —$NR^6C(=O)R^9$, —$C(=O)$—$NR^6R^7$, —$C(=O)$—$R^8$, —$S(=O)_2$—$NR^6R^7$, —$S(=O)$—$R^9$, —$S(=O)_2$—$R^9$, —NH—$S(=O)_2$—$R^9$, and/or by a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —$C(=O)$—$NR^6R^7$, —$C(=O)$—$R^8$, —$S(=O)_2$—$NR^6R^7$, —$S(=O)$—$R^9$, —$S(=O)_2$—$R^9$, —NH—$S(=O)_2$—$R^9$, and/or by a monocyclic heterocyclyl radical which has 4 to 7 ring atoms and/or by a monocyclic heteroaryl radical which has 5 or 6 ring atoms and/or by a phenyl radical which for its part may optionally be mono- or polysubstituted by halogen, $C_1$-$C_3$-alkyl and/or $C_1$-$C_3$-alkoxy, or represents a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, —$C(=O)NR^6R^7$, $C(=O)R^8$, $C_1$-$C_3$-alkylsulphinyl, $C_1$-$C_3$-alkylsulphonyl, —$S(=O)_2NH_2$, $C_1$-$C_3$-alkylsulphonylamino, $C_1$-$C_3$-alkylaminosulphonyl, $C_3$-$C_6$-cycloalkylaminosulphonyl, halo-$C_1$-$C_6$-alkyl, halo-$C_1$-$C_6$-alkoxy, hydroxy-$C_1$-$C_6$-alkyl, $C_3$-$C_{10}$-cycloalkyl, and/or a monocyclic heterocyclyl radical which has 4 to 7 ring atoms and/or monocyclic heteroaryl radical which has 5 or 6 ring atoms and which for its part may be mono- or polysubstituted by identical or different substituents from the group consisting of halogen, $C_1$-$C_3$-alkyl and $C_1$-$C_3$-alkoxy, and $R^{1b}$ and $R^{1c}$ independently of one another represent hydrogen, halogen, hydroxy, cyano, nitro or represent a $C_1$-$C_6$-alkyl, $C_1$-$C_6$-alkoxy, $C_1$-$C_6$-alkoxy-$C_1$-$C_6$-alkyl, halo-$C_1$-$C_6$-alkyl, halo-$C_1$-$C_6$-alkoxy, $C_3$-$C_{10}$-cycloalkyl radical, and/or a monocyclic heterocyclyl radical which has 4 to 7 ring atoms, and $R^2$ represents methyl, ethyl or isopropyl, and $R^3$ represents cyclopropyl, $C_1$-$C_3$-alkyl, $C_1$-$C_3$-alkoxy, amino, cyclopropylamino or $C_1$-$C_3$-alkylamino, and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, monocyclic heterocyclyl which has 4 to 7 ring atoms, and/or monocyclic heteroaryl which has 5 or 6 ring atoms, where the monocyclic heterocyclyl and heteroaryl radicals mentioned for their part may optionally be monosubstituted by $C_1$-$C_3$-alkyl, or represent a $C_3$-$C_{10}$-cycloalkyl radical which may optionally be mono- or polysubstituted by identical or different substituents from the group consisting of halogen, amino, hydroxy, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, and/or a monocyclic heterocyclyl radical which has 4 to 7 ring atoms, or represent monocyclic heteroaryl which has 5 or 6 ring atoms and which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, hydroxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, halo-$C_1$-$C_6$-alkyl, halo-$C_1$-$C_6$-alkoxy, $C_3$-$C_{10}$-cycloalkyl, —$C(=O)R^8$, —$S(=O)_2R^9$, —$NR^6R^7$, and/or a monocyclic heterocyclyl radical which has 4 to 7 ring atoms, or represent monocyclic heterocyclyl which has 4 to 7 ring atoms and which may optionally be mono- or polysubstituted by identical or different substituents from the group consisting of halogen, amino, hydroxy, cyano, oxo, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, —$C(=O)R^8$, —$S(=O)_2R^9$, —$NR^6R^7$ and/or a monocyclic heterocyclyl radical which has 4 to 7 ring atoms, or represent a phenyl radical which may optionally be mono- or polysubstituted by identical or different substituents from the group consisting of halogen, amino, hydroxy, cyano, nitro, carboxyl, $C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, $C_1$-$C_6$-alkylaminocarbonyl, $C_1$-$C_6$-alkylaminosulphonyl, $C_1$-$C_6$-alkylamino-$C_1$-$C_6$-alkyl, hydroxy-$C_1$-$C_6$-alkyl, halo-$C_1$-$C_6$-alkyl, halo-$C_1$-$C_6$-alkoxy, $C_3$-$C_{10}$-cycloalkyl, and/or a monocyclic heterocyclyl radical which has 4 to 7 ring atoms, and $R^6$ and $R^7$ independently of one another represent hydrogen, $C_1$-$C_3$-alkyl, cyclopropyl, di-$C_1$-$C_3$-alkyl-amino-$C_1$-$C_3$-alkyl or fluoropyridyl, and $R^8$ represents hydroxy, $C_1$-$C_6$-alkyl, halo-$C_1$-$C_3$-alkyl, hydroxy-$C_1$-$C_3$-alkyl, $C_1$-$C_3$-alkoxy-$C_1$-$C_3$-alkyl, $C_3$-$C_5$-cycloalkyl, phenyl, monocyclic heterocyclyl having 5 or 6 ring atoms, and $R^9$ represents hydrogen, $C_1$-$C_6$-alkyl or $C_1$-$C_4$-alkoxy, or an enantiomer, diastereomer, racemate, tautomer, or physiologically acceptable salt thereof, with the proviso that, if A represents a phenyl ring and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl which may optionally be mono- or polysubstituted by identical or different substituents from the group consisting of halogen, amino, hydroxy, carboxyl, hydroxy-$C_1$-$C_6$-alkyl, $C_1$-$C_6$-alkoxy, $C_1$-$C_6$-alkoxy-$C_1$-$C_6$-alkyl, $C_1$-$C_6$-alkylamino, amino-$C_1$-$C_6$-alkyl, monocyclic heterocyclyl which has 4 to 7 ring atoms and/or monocyclic heteroaryl which has 5 or 6 ring atoms, where the monocyclic heterocyclyl and heteroaryl radicals mentioned for their part may optionally be monosubstituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_6$-alkylamino, $C_1$-$C_6$-alkylcarbonylamino, $C_1$-$C_6$-alkylamino-$C_1$-$C_6$-alkyl, N-(heterocyclyl)-$C_1$-$C_6$-alkyl, N-(heterocyclyl)-$C_1$-$C_6$-alkoxy, hydroxy-$C_1$-$C_6$-alkyl, hydroxy-$C_1$-$C_6$-alkoxy, halo-$C_1$-$C_6$-alkyl, halo-$C_1$-$C_6$-alkoxy, $C_1$-$C_6$-alkylcarbonyl or $C_1$-$C_6$-alkoxycarbonyl radical, and where the proviso does not embrace those compounds of the formula (I) in which A is phenyl and $R^4$ is hydrogen, fluorine, chlorine or bromine and $R^5$ is $C_1$-$C_6$-alkoxy which is substituted one or more times by identical or different halogens, and $R^{1a}$ is halogen, and also not those compounds of the formula (I) in which A is phenyl and $R^4$ is hydrogen and $R^5$ is $C_1$-$C_6$-alkoxy which is substituted one or more times by identical or different monocyclic heterocyclyl radicals having 4 to 7 ring atoms and/or monocyclic heteroaryl radicals having 5 or 6 ring atoms, it being possible for the stated monocyclic heterocyclyl and heteroaryl radicals in turn to be optionally monosubstituted by $C_1$-$C_3$-alkyl, and $R^{1a}$ is halogen.

3. A compound of formula (I) according to claim 1 in which

X represents an oxygen atom, and

A represents a phenyl or pyridyl ring, and $R^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_3$-alkylamino, $C_1$-$C_3$-alkylcarbonylamino, $C_1$-$C_3$-alkylamino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_1$-$C_3$-alkylcarbonyl or $C_1$-$C_4$-alkoxycarbonyl radical, or represents a monocyclic heterocyclyl radical which has 4 to 7 ring atoms and may optionally be mono- or polysubstituted by identical or different substituents from the group consisting of halogen, cyano, nitro, hydroxy, amino, oxo, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, phenyl, halophenyl, phenyl-$C_1$-$C_3$-alkyl, pyridinyl, —NR$^6$C(=O)—R$^9$, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical which has 4 to 7 ring atoms, and/or by a monocyclic heteroaryl radical which has 5 or 6 ring atoms, and/or by a phenyl radical which for its part may be mono- or polysubstituted by identical or different substituents from the group consisting of fluorine, chlorine, bromine, methyl and/or methoxy, or represents a phenyl radical which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, —C(=O)NR$^6$R$^7$, C(=O)R$^8$, $C_1$-$C_3$-alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, fluoro-$C_1$-$C_3$-alkyl, fluoro-$C_1$-$C_3$-alkoxy, hydroxy-$C_1$-$C_3$-alkyl, $C_3$-$C_6$-cycloalkyl and/or a monocyclic heterocyclyl radical which has 4 to 7 ring atoms, and/or a monocyclic heteroaryl radical which has 5 or 6 ring atoms and which for its part may optionally be mono- or polysubstituted by identical or different substituents from the group consisting of fluorine, chlorine, bromine, methyl and/or methoxy, and $R^{1b}$ represents hydrogen, halogen, hydroxy, cyano, nitro or represents a $C_1$-$C_3$-alkyl, $C_1$-$C_3$-alkoxy, fluoro-$C_1$-$C_3$-alkyl or fluoro-$C_1$-$C_3$-alkoxy radical, and $R^{1c}$ represents hydrogen, fluorine, chlorine, bromine or cyano, and $R^2$ represents methyl, ethyl or isopropyl, and $R^3$ represents cyclopropyl, $C_1$-$C_3$-alkyl, $C_1$-$C_3$-alkoxy, cyclopropylamino or $C_1$-$C_3$-alkylamino, and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_3$-alkyl, $C_1$-$C_3$-alkoxy, $C_1$-$C_3$-alkylamino which may be mono- or polysubstituted by identical or different substituents from the group consisting of halogen, amino, hydroxy, carboxyl, hydroxy-$C_1$-$C_3$-alkyl, $C_1$-$C_3$-alkoxy, $C_1$-$C_3$-alkylamino, amino-$C_1$-$C_3$-alkyl, monocyclic heterocyclyl which has 4 to 7 ring atoms, and/or monocyclic heteroaryl which has 5 or 6 ring atoms, where the monocyclic heterocyclyl and heteroaryl radicals mentioned for their part may optionally be monosubstituted by $C_1$-$C_3$-alkyl, or represent a $C_3$-$C_7$-cycloalkyl radical which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical which has 4 to 7 ring atoms, or represent monocyclic heteroaryl which has 5 or 6 ring atoms and which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)$R^8$, —S(=O)$_2R^9$, —$NR^6R^7$, and/or a monocyclic heterocyclyl radical which has 4 to 7 ring atoms, or represent monocyclic heterocyclyl which has 4 to 7 ring atoms and which may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O)$R^8$, —S(=O)$_2R^9$, —$NR^6R^7$, and/or a monocyclic heterocyclyl radical which has 4 to 7 ring atoms, or represent a phenyl radical which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical which has 4 to 7 ring atoms, and $R^6$ and $R^7$ independently of one another represent hydrogen, $C_1$-$C_3$-alkyl, cyclopropyl, di-$C_1$-$C_3$-alkyl-amino-$C_1$-$C_3$-alkyl or fluoropyridyl, and $R^8$ represents hydroxy, $C_1$-$C_6$-alkyl, hydroxy-$C_1$-$C_3$-alkyl, fluoro-$C_1$-$C_3$-alkyl, $C_1$-$C_3$-alkoxy-$C_1$-$C_3$-alkyl, $C_3$-$C_8$-cycloalkyl or monocyclic heterocyclyl which has 5 or 6 ring atoms, and $R^9$ represents hydrogen, $C_1$-$C_6$-alkyl or $C_1$-$C_4$-alkoxy, or an enantiomer, diastereomer, racemate, tautomer, or physiologically acceptable salt thereof, with the proviso that, if A represents a phenyl ring and $R^4$ and $R^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_3$-alkyl, $C_1$-$C_3$-alkoxy, $C_1$-$C_3$-alkylamino, which may optionally be mono- or polysubstituted by identical or different substituents from the group consisting of halogen, amino, hydroxy, carboxyl, hydroxy-$C_1$-$C_3$-alkyl, $C_1$-$C_3$-alkoxy, $C_1$-$C_3$-alkylamino, amino-$C_1$-$C_3$-alkyl, monocyclic heterocyclyl which has 4 to 7 ring atoms and/or monocyclic heteroaryl which has 5 or 6 ring atoms, where the monocyclic heterocyclyl and heteroaryl radicals mentioned for their part may optionally be monosubstituted by $C_1$-$C_3$-alkyl, $R^{1a}$ does not represent hydrogen, halogen, cyano, carboxyl, amino or aminosulphonyl, or represent a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_3$-alkylamino, $C_1$-$C_3$-alkylcarbonylamino, $C_1$-$C_3$-alkylamino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_1$-$C_3$-alkylcarbonyl or $C_1$-$C_4$-alkoxycarbonyl radical, and where the proviso does not embrace those compounds of the formula (I) in which A is phenyl and $R^4$ is hydrogen, fluorine, chlorine or bromine and $R^5$ is $C_1$-$C_3$-alkoxy which is substituted one or more times by identical or different halogens, and $R^{1a}$ is halogen, and also not those compounds of the formula (I) in which A is phenyl and $R^4$ is hydrogen and $R^5$ is $C_1$-$C_3$-alkoxy which is substituted one or more times by identical or different monocyclic heterocyclyl radicals having 4 to 7 ring atoms and/or monocyclic heteroaryl radicals having 5 or 6 ring atoms, it being possible for the stated monocyclic heterocyclyl and heteroaryl radicals in turn to be optionally monosubstituted by $C_1$-$C_3$-alkyl, and $R^{1a}$ is halogen.

4. A compound of formula (I) according to claim 1 in which

X represents an oxygen atom, and

A represents a phenyl or pyridyl ring, and $R^{1a}$ represents a monocyclic heterocyclyl radical which has 4 to 7 ring atoms and may optionally be mono- or polysubstituted by identical or different substituents from the group consisting of halogen, cyano, nitro, hydroxy, amino, oxo, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, phenyl, halophenyl, phenyl-$C_1$-$C_3$-alkyl, pyridinyl, —$NR^6C$(=O)—$R^9$, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or by a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)—$NR^6R^7$, —C(=O)—$R^8$, —S(=O)$_2$—$NR^6R^7$, —S(=O)—$R^9$, —S(=O)$_2$—$R^9$, —NH—S(=O)$_2$—$R^9$, and/or by a monocyclic heterocyclyl radical which has 4 to 7 ring atoms, and/or by a monocyclic heteroaryl radical which has 5 or 6 ring atoms, and/or by a phenyl radical which for its part may be mono- or polysubstituted by identical or different substituents from the group consisting of fluorine, chlorine, bromine, methyl and/or methoxy, or represents a phenyl radical which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, —C(=O)NR$^6$R$^7$, C(=O)R$^8$, $C_1$-$C_3$-alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, fluoro-$C_1$-$C_3$-alkyl, fluoro-$C_1$-$C_3$-alkoxy, hydroxy-$C_1$-$C_3$-alkyl, $C_3$-$C_6$-cycloalkyl and/or a monocyclic heterocyclyl radical which has 4 to 7 ring atoms, and/or a monocyclic heteroaryl radical which has 5 or 6 ring atoms which for its part may optionally be mono- or polysubstituted by identical or different substituents from the group consisting of fluorine, chlorine, bromine, methyl or methoxy, and R$^{1b}$ represents hydrogen, halogen, hydroxy, cyano, nitro or represents a $C_1$-$C_3$-alkyl, $C_1$-$C_3$-alkoxy, fluoro-$C_1$-$C_3$-alkyl or fluoro-$C_1$-$C_3$-alkoxy radical, and R$^{1c}$ represents hydrogen, fluorine, chlorine, bromine or cyano, and R$^2$ represents methyl, ethyl or isopropyl, and R$^3$ represents cyclopropyl, $C_1$-$C_3$-alkyl, $C_1$-$C_3$-alkoxy, cyclopropylamino or $C_1$-$C_3$-alkylamino, and R$^4$ and R$^5$ independently of one another represent hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, or represent $C_1$-$C_3$-alkyl, $C_1$-$C_3$-alkoxy, $C_1$-$C_3$-alkylamino which may be mono- or polysubstituted by identical or different substituents from the group consisting of halogen, amino, hydroxy, carboxyl, hydroxy-$C_1$-$C_3$-alkyl, $C_1$-$C_3$-alkoxy, $C_1$-$C_3$-alkylamino, amino-$C_1$-$C_3$-alkyl, monocyclic heterocyclyl which has 4 to 7 ring atoms, and/or monocyclic heteroaryl which has 5 or 6 ring atoms, where the monocyclic heterocyclyl and heteroaryl radicals mentioned for their part may optionally be mono-substituted by $C_1$-$C_3$-alkyl, or represent a $C_3$-$C_7$-cycloalkyl radical which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical which has 4 to 7 ring atoms, or represent monocyclic heteroaryl which has 5 or 6 ring atoms and may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)R$^8$, —S(=O)$_2$R$^9$, —NR$^6$R$^7$, and/or a monocyclic heterocyclyl radical which has 4 to 7 ring atoms, or represent monocyclic heterocyclyl which has 4 to 7 ring atoms and may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O)R$^8$, —S(=O)$_2$R$^9$, —NR$^6$R$^7$, and/or a monocyclic heterocyclyl radical which has 4 to 7 ring atoms, or represent a phenyl radical which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical which has 4 to 7 ring atoms, and R$^6$ and R$^7$ independently of one another represent hydrogen, $C_1$-$C_3$-alkyl, cyclopropyl, di-$C_1$-$C_3$-alkyl-amino-$C_1$-$C_3$-alkyl or fluoropyridyl, and R$^8$ represents hydroxy, $C_1$-$C_6$-alkyl, hydroxy-$C_1$-$C_3$-alkyl, fluoro-$C_1$-$C_3$-alkyl, $C_1$-$C_3$-alkoxy-$C_1$-$C_3$-alkyl, $C_3$-$C_5$-cycloalkyl or monocyclic heterocyclyl which has 5 or 6 ring atoms, and R$^9$ represents hydrogen, $C_1$-$C_6$-alkyl or $C_1$-$C_4$-alkoxy, or an enantiomer, diastereomer, racemate, tautomer, or physiologically acceptable salt thereof.

5. A compound of formula (I) according to claim 1 in which

X represents an oxygen atom, and

A represents a phenyl or pyridyl ring, and

R$^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_3$-alkylamino, $C_1$-$C_3$-alkylcarbonylamino, $C_1$-$C_3$-alkylamino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_1$-$C_3$-alkylcarbonyl or $C_1$-$C_4$-alkoxycarbonyl radical, or represents a monocyclic heterocyclyl radical which has 4 to 7 ring atoms and may optionally be mono- or polysubstituted by identical or different substituents from the group consisting of halogen, cyano, nitro, hydroxy, amino, oxo, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, phenyl, halophenyl, phenyl-$C_1$-$C_3$-alkyl, pyridinyl, —NR$^6$C(=O)—R$^9$, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical which has 4 to 7 ring atoms, and/or by a monocyclic heteroaryl radical which has 5 or 6 ring atoms, and/or by a phenyl radical which for its part may be mono- or polysubstituted by identical or different substituents from the group consisting of fluorine, chlorine, bromine, methyl and/or methoxy, or represents a phenyl radical which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, —C(=O)NR$^6$R$^7$, C(=O)R$^8$, $C_1$-$C_3$-alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, fluoro-$C_1$-$C_3$-alkyl, fluoro-$C_1$-$C_3$-alkoxy, hydroxy-$C_1$-$C_3$-alkyl, $C_3$-$C_6$-cycloalkyl and/or a monocyclic heterocyclyl radical which has 4 to 7 ring atoms, and/or a monocyclic heteroaryl radical which has 5 or 6 ring atoms which for its part may optionally be mono- or polysubstituted by identical or different substituents from the group consisting of fluorine, chlorine, bromine, methyl and/or methoxy, and R$^{1b}$ represents hydrogen, halogen, hydroxy, cyano, nitro or represents a $C_1$-$C_3$-alkyl, $C_1$-$C_3$-alkoxy, fluoro-$C_1$-$C_3$-alkyl, fluoro-$C_1$-$C_3$-alkoxy radical, and R$^{1c}$ represents hydrogen, fluorine, chlorine, bromine or cyano, and R$^2$ represents methyl, ethyl or isopropyl, and R$^3$ represents cyclopropyl, $C_1$-$C_3$-alkyl, $C_1$-$C_3$-alkoxy, cyclopropylamino or $C_1$-$C_3$-alkylamino, and R$^4$ represents a $C_3$-$C_7$-cycloalkyl radical which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical which has 4 to 7 ring atoms, or represents monocyclic heteroaryl which has 5 or 6 ring atoms and may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)R$^8$, —S(=O)$_2$R$^9$, —NR$^6$R$^7$, and/or a monocyclic heterocyclyl radical which has 4 to 7 ring atoms, or represents monocyclic heterocyclyl which has 4 to 7 ring atoms and may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, —C(=O)R$^8$, —S(=O)$_2$R$^9$, —NR$^6$R$^7$, and/or a monocyclic heterocyclyl radical which has 4 to 7 ring atoms, or represents a phenyl radical which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical which has 4 to 7 ring atoms, R$^5$ represents hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkylaminosulphonyl, and R$^6$ and R$^7$ independently of one another represent hydrogen, $C_1$-$C_3$-alkyl, cyclopropyl, di-$C_1$-$C_3$-alkyl-amino-$C_1$-$C_3$-alkyl or fluoropyridyl, and R$^8$ represents hydroxy, $C_1$-$C_6$-alkyl, hydroxy-$C_1$-$C_3$-alkyl, fluoro-$C_1$-$C_3$-alkyl, $C_1$-$C_3$-alkoxy-$C_1$-$C_3$-alkyl, $C_3$-$C_8$-cycloalkyl or monocyclic heterocyclyl which has 5 or 6 ring atoms, and R$^9$ represents hydrogen, $C_1$-$C_6$-alkyl or $C_1$-$C_4$-alkoxy, or an enantiomer, diastereomer, racemate, tautomer, or physiologically acceptable salt thereof.

6. A compound of formula (I) according to claim 1 in which

X represents an oxygen atom, and

A represents a phenyl or pyridyl ring, and

R$^{1a}$ represents hydrogen, halogen, cyano, carboxyl, amino or aminosulphonyl, or represents a $C_1$-$C_6$-alkoxy, $C_1$-$C_3$-alkoxy-$C_1$-$C_3$-alkyl, $C_1$-$C_3$-alkoxy-$C_2$-$C_3$-alkoxy, $C_1$-$C_3$-alkylamino, $C_1$-$C_3$-alkylcarbonylamino, $C_1$-$C_3$-alkylamino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_1$-$C_3$-alkylcarbonyl or $C_1$-$C_4$-alkoxycarbonyl radical, or represents a monocyclic heterocyclyl radical which has 4 to 7 ring atoms and may optionally be mono- or polysubstituted by identical or different substituents from the group consisting of halogen, cyano, nitro, hydroxy, amino, oxo, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, phenyl, halophenyl, phenyl-$C_1$-$C_3$-alkyl, pyridinyl, —NR$^6$C(=O)—R$^9$, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical which has 4 to 7 ring atoms, or represents a monocyclic heteroaryl radical which has 5 or 6 ring atoms and may optionally be mono- or polysubstituted by identical or different substituents from the group consisting of halogen, hydroxy, amino, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, —C(=O)—NR$^6$R$^7$, —C(=O)—R$^8$, —S(=O)$_2$—NR$^6$R$^7$, —S(=O)—R$^9$, —S(=O)$_2$—R$^9$, —NH—S(=O)$_2$—R$^9$, and/or by a monocyclic heterocyclyl radical which has 4 to 7 ring atoms, and/or by a monocyclic heteroaryl radical which has 5 or 6 ring atoms, and/or by a phenyl radical which for its part may be mono- or polysubstituted by identical or different substituents from the group consisting of fluorine, chlorine, bromine, methyl and/or methoxy, or represents a phenyl radical which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, —C(=O)NR$^6$R$^7$, —C(=O)R$^8$, $C_1$-$C_3$-alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, fluoro-$C_1$-$C_3$-alkyl, fluoro-$C_1$-$C_3$-alkoxy, hydroxy-$C_1$-$C_3$-alkyl, $C_3$-$C_6$- cycloalkyl and/or a monocyclic heterocyclyl radical which has 4 to 7 ring atoms, and/or a monocyclic heteroaryl radical which has 5 or 6 ring atoms which for its part may optionally be mono- or polysubstituted by identical or different substituents from the group consisting of fluorine, chlorine, bromine, methyl and/or methoxy, and $R^{1b}$ represents hydrogen, halogen, hydroxy, cyano, nitro or represents a $C_1$-$C_3$-alkyl, $C_1$-$C_3$-alkoxy, fluoro-$C_1$-$C_3$-alkyl or fluoro-$C_1$-$C_3$-alkoxy radical, and $R^{1c}$ represents hydrogen, fluorine, chlorine, bromine or cyano, and $R^2$ represents methyl, ethyl or isopropyl, and $R^3$ represents cyclopropyl, $C_1$-$C_3$-alkyl, $C_1$-$C_3$-alkoxy, cyclopropylamino or $C_1$-$C_3$-alkylamino, and $R^4$ represents hydrogen, hydroxy, cyano, nitro, amino, aminocarbonyl, fluorine, chlorine, bromine, $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl or $C_1$-$C_6$-alkyl-aminosulphonyl, and $R^5$ represents a $C_3$-$C_7$-cycloalkyl radical which may optionally be mono- or polysubstituted by identical or different substituents from the group consisting of halogen, amino, hydroxy, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, and/or a monocyclic heterocyclyl radical which has 4 to 7 ring atoms, or represents monocyclic heteroaryl which has 5 or 6 ring atoms and may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, $C_1$-$C_3$-alkylamino, amino-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical which has 4 to 7 ring atoms, or represents monocyclic heterocyclyl which has 4 to 7 ring atoms and may optionally be mono- or polysubstituted by identical or different substituents from the group consisting of halogen, amino, hydroxy, cyano, oxo, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical which has 4 to 7 ring atoms, or represents a phenyl radical which may optionally be mono- or polysubstituted by identical or different substituents from the group consisting of halogen, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, $C_1$-$C_3$-alkylamino, amino-$C_1$-$C_3$-alkyl, $C_1$-$C_3$-alkylaminocarbonyl, $C_1$-$C_3$-alkylaminosulphonyl, hydroxy-$C_1$-$C_3$-alkyl, fluoro-$C_1$-$C_3$-alkyl, fluoro-$C_1$-$C_3$-alkoxy, $C_3$-$C_6$-cycloalkyl, and/or a monocyclic heterocyclyl radical which has 4 to 7 ring atoms, and $R^6$ and $R^7$ independently of one another represent hydrogen, $C_1$-$C_3$-alkyl, cyclopropyl, di-$C_1$-$C_3$-alkyl-amino-$C_1$-$C_3$-alkyl or fluoropyridyl, and $R^8$ represents hydroxy, $C_1$-$C_6$-alkyl, hydroxy-$C_1$-$C_3$-alkyl, fluoro-$C_1$-$C_3$-alkyl, $C_1$-$C_3$-alkoxy-$C_1$-$C_3$-alkyl, $C_3$-$C_5$-cycloalkyl or monocyclic heterocyclyl which has 5 or 6 ring atoms, and $R^9$ represents hydrogen, $C_1$-$C_6$-alkyl or $C_1$-$C_4$-alkoxy, or an enantiomer, diastereomer, racemate, tautomer, or physiologically acceptable salt thereof.

7. A compound of formula (I) according to claim 1 in which

X represents an oxygen atom, and

A represents a phenyl or 3-pyridyl ring, and $R^{1a}$ represents hydrogen or chlorine, or represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, chlorine, cyano, nitro, hydroxy, oxo, $C_1$-$C_3$-alkyl, $C_1$-$C_3$-alkoxy, $C_1$-$C_2$-alkoxy-$C_1$-$C_2$-alkyl, hydroxy-$C_1$-$C_3$-alkyl, dimethylamino, trifluoromethyl, difluoroethyl, trifluoroethyl, trifluoromethoxy, cyclopropyl, phenyl, fluorophenyl, phenyl-$C_1$-$C_3$-alkyl, pyridinyl, —NR$^6$C(=O)—R$^9$, —C(=O)—NR$^6$R$^7$, —C(=O)—R$^8$, —S(=O)$_2$—NR$^6$R$^7$, —S(=O)—R$^9$, —S(=O)$_2$—R$^9$ and/or —NH—S(=O)$_2$—R$^9$, or represents tetrazolyl, or represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, amino, cyano, nitro, $C_1$-$C_3$-alkyl, $C_1$-$C_3$-alkoxy, $C_1$-$C_2$-alkoxy-$C_1$-$C_2$-alkyl, dimethylamino, trifluoromethyl, difluoroethyl, trifluoroethyl, trifluoromethoxy, cyclopropyl, pyridinyl, phenyl, fluorophenyl, —C(=O)—NR$^6$R$^7$, —C(=O)—R$^8$, —S(=O)$_2$—NR$^6$R$^7$, —S(=O)—R$^9$, —S(=O)$_2$—R$^9$, and/or —NH—S(=O)$_2$—R$^9$, or represents a phenyl radical which may optionally be mono- or polysubstituted by identical or different substituents from the group consisting of fluorine, chlorine, amino, hydroxy, cyano, nitro, carboxyl, $C_1$-$C_3$-alkyl, $C_1$-$C_3$-alkoxy, $C_1$-$C_2$-alkoxy-$C_1$-$C_2$-alkyl, dimethylamino, —C(=O)NR$^6$R$^7$, —C(=O)R$^8$, $C_1$-$C_3$-alkylsulphinyl, $C_1$-$C_3$-alkylsulphonyl, —S(=O)$_2$NH$_2$, $C_1$-$C_3$-alkylsulphonylamino, $C_1$-$C_3$-alkylaminosulphonyl, $C_3$-$C_6$-cycloalkylaminosulphonyl, trifluoromethyl, difluoroethyl, trifluoroethyl, trifluoromethoxy, hydroxy-$C_1$-$C_3$-alkyl, cyclopropyl, chlorothienyl, morpholino and/or pyridinyl, and $R^{1b}$ represents hydrogen, fluorine, bromine or cyano, and $R^{1c}$ represents hydrogen or bromine, and $R^2$ represents methyl, ethyl or isopropyl, and $R^3$ represents cyclopropyl, methyl, ethyl, methoxy, ethoxy, cyclopropylamino, methylamino or ethylamino, and $R^4$ and $R^5$ independently of one another represent hydrogen, hydroxy, cyano, amino, chlorine, $C_1$-$C_6$-alkyl, methoxy, ethoxy or $C_1$-$C_3$-alkylcarbonylamino, or represent difluoromethoxy or trifluoromethoxy, or represent $C_1$-$C_3$-alkoxy which may be substituted by pyridinyl, morpholinyl, pyrrolidinyl or piperazinyl, in which pyridinyl and piperazinyl in turn may be optionally substituted by $C_1$-$C_3$-alkyl, or represents cyclopropyl, or represents pyridinyl, pyrazolyl, triazolyl or isoxazolyl, which may be optionally mono- or polysubstituted by identical or different substituents from the group consting of hydroxy and/or methyl, or represents pyrrolidinyl, morpholinyl, piperidinyl, piperazinyl, oxazolidinyl, thiomorpholinyl, which may optionally be mono- or polysubstituted by oxo, methyl and/or —S(=O)$_2$R$^9$, or represents phenyl optionally substituted by C$_1$-C$_3$-alkylaminosulphonyl or fluorine, and R$^6$ and R$^7$ independently of one another represent hydrogen, C$_1$-C$_3$-alkyl, cyclopropyl, di-C$_1$-C$_3$-alkyl-amino-C$_1$-C$_3$-alkyl or fluoropyridyl, and R$^8$ represents hydroxy, C$_1$-C$_3$-alkyl, hydroxy-C$_1$-C$_3$-alkyl, trifluoromethyl, pyrrolidinyl, morpholinyl or piperidinyl, and R$^9$ represents C$_1$-C$_4$-alkyl or C$_1$-C$_4$-alkoxy, or an enantiomer, diastereomer, racemate, tautomer, or physiologically acceptable salt thereof, with the proviso that, if A represents a phenyl ring and R$^4$ and R$^5$ independently of one another represent hydrogen, hydroxy, cyano, amino, chlorine, C$_1$-C$_6$-alkyl, methoxy, ethoxy or C$_1$-C$_3$-alkylcarbonylamino, or represent difluoromethoxy or trifluoromethoxy, or represent C$_1$-C$_3$-alkoxy which may be substituted by pyridinyl, morpholinyl, pyrrolidinyl or piperazinyl, in which pyridinyl and piperazinyl in turn may be optionally substituted by C$_1$-C$_3$-alkyl, R$^{1a}$ does not represent hydrogen or chlorine, and where the proviso does not encompass those compounds of the formula (I) in which A represents phenyl and R$^4$ represents hydrogen or chlorine and R$^5$ represents trifluoromethoxy, and R$^{1a}$ represents chlorine, and also not those compounds of the formula (I) in which A represents phenyl and R$^4$ represents hydrogen and R$^5$ represents C$_1$-C$_3$-alkoxy which is substituted by morpholinyl, pyrrolidinyl, piperazinyl or pyridyl, in which the piperazinyl and pyridinyl itself may be substituted by C$_1$-C$_3$-alkyl, and R$^{1a}$ represents chlorine.

8. A compound of formula (I) according to claim 1 in which

X represents an oxygen atom, and

A represents a phenyl or 3-pyridyl ring, and

R$^{1a}$ represents hydrogen or chlorine, or represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, hydroxy, oxo, C$_1$-C$_3$-alkyl, methoxy, hydroxy-C$_1$-C$_3$-alkyl, dimethylamino, difluoroethyl, trifluoroethyl, benzyl, —NR$^6$C(=O)—R$^9$, —C(=O)—NR$^6$R$^7$, —C(=O)—R$^8$, and/or —S(=O)$_2$—R$^9$, or represents tetrazolyl, or represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, cyano, C$_1$-C$_2$-alkyl, methoxy, methoxymethyl, trifluoromethyl, cyclopropyl, pyridinyl, phenyl, fluorophenyl and/or —C(=O)—R$^8$, or represents a phenyl radical which may optionally be mono- or polysubstituted by identical or different substituents from the group consisting of fluorine, chlorine, hydroxy, cyano, nitro, carboxyl, C$_1$-C$_3$-alkyl, methoxy, —C(=O)NR$^6$R$^7$, —C(=O)R$^8$, C$_1$-C$_3$-alkylsulphinyl, C$_1$-C$_3$-alkylsulphonyl, —S(=O)$_2$NH$_2$, C$_1$-C$_3$-alkylsulphonylamino, C$_1$-C$_3$-alkylaminosulphonyl, C$_3$-C$_6$-cycloalkylaminosulphonyl, trifluoromethyl, trifluoromethoxy, hydroxy-C$_1$-C$_3$-alkyl, cyclopropyl, chlorotheinyl and/or morpholino, and R$^{1b}$ represents hydrogen, fluorine, bromine or cyano, and R$^{1c}$ represents hydrogen or bromine, and R$^2$ represents methyl, ethyl or isopropyl, and R$^3$ represents cyclopropyl, methyl, ethyl, methoxy, ethoxy, cyclopropylamino, methylamino or ethylamino, and R$^4$ and R$^5$ independently of one another represent hydrogen, hydroxy, cyano, amino, chlorine, C$_1$-C$_6$-alkyl, methoxy, ethoxy or C$_1$-C$_3$-alkylcarbonylamino, or represent difluoromethoxy or trifluoromethoxy, or represent C$_1$-C$_3$-alkoxy which may be substituted by pyridinyl, morpholinyl, pyrrolidinyl or piperazinyl, in which the pyridinyl and piperazinyl may in turn optionally be substituted by C$_1$-C$_3$-alkyl, or represent cyclopropyl, or represent pyridinyl, pyrazolyl, triazolyl or isoxazolyl, which may optionally be mono- or polysubstituted by identical or different substituents from the group consisting of hydroxy and/or methyl, or represent pyrrolidinyl, morpholinyl, piperidinyl, piperazinyl, oxazolidinyl, thiomorpholinyl, which may optionally be mono- or polysubstituted by methyl, oxo, and/or —S(=O)$_2$R$^9$, or represent phenyl optionally substituted by C$_1$-C$_3$-alkylaminosulphonyl or fluorine, and R$^6$ and R$^7$ independently of one another represent hydrogen, C$_1$-C$_3$-alkyl, cyclopropyl, di-C$_1$-C$_3$-alkyl-amino-C$_1$-C$_3$-alkyl or fluoropyridyl, and R$^8$ represents hydroxy, C$_1$-C$_3$-alkyl, hydroxy-C$_1$-C$_3$-alkyl, trifluoromethyl, pyrrolidinyl, morpholinyl or piperidinyl, and R$^9$ represents C$_1$-C$_4$-alkyl or C$_1$-C$_4$-alkoxy, or an enantiomer, diastereomer, racemate, tautomer, or physiologically acceptable salt thereof, with the proviso that, if A represents a phenyl ring and R$^4$ and R$^5$ independently of one another represent hydrogen, hydroxy, cyano, amino, chlorine, C$_1$-C$_6$-alkyl, methoxy, ethoxy or C$_1$-C$_3$-alkylcarbonylamino, or represent difluoromethoxy or trifluoromethoxy, or represent C$_1$-C$_3$-alkoxy which may be substituted by pyridinyl, morpholinyl, pyrrolidinyl or piperazinyl, in which the pyridinyl and piperazinyl may in turn optionally be substituted by C$_1$-C$_3$-alkyl, R$^{1a}$ does not represent hydrogen or chlorine, and where the proviso does not encompass those compounds of the formula (I) in which A represents phenyl and R$^4$ represents hydrogen or chlorine and R$^5$ represents trifluoromethoxy, and R$^{1a}$ represents chlorine, and also not those compounds of the formula (I) in which A represents phenyl and R$^4$ represents hydrogen and R$^5$ represents C$_1$-C$_3$-alkoxy which is substituted by morpholinyl, pyrrolidinyl, piperazinyl or pyridyl, in which the piperazinyl and pyridinyl itself may be substituted by C$_1$-C$_3$-alkyl, and R$^{1a}$ represents chlorine.

9. Compounds of formula (I) according to claim 1 in which

X represents an oxygen atom, and

A represents a phenyl ring, and

R$^{1a}$ represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, hydroxy, oxo, $C_1$-$C_3$-alkyl, methoxy, hydroxy-$C_1$-$C_3$-alkyl, dimethylamino, difluoroethyl, trifluoroethyl, benzyl, —$NR^6C(=O)$—$R^9$, —$C(=O)$—$NR^6R^7$, —$C(=O)$—$R^8$, and/or —$S(=O)_2$—$R^9$, or represents tetrazolyl, or represents isoxazolyl, pyrazolyl, thienyl, thiazolyl, imidazolyl, triazolyl, pyrrolyl, oxadiazolyl, pyridinyl or pyrimidinyl, which may optionally be mono- or polysubstituted by identical or different substituents from the group consisting of fluorine, chlorine, hydroxy, cyano, $C_1$-$C_2$-alkyl, methoxy, methoxymethyl, trifluoromethyl, cyclopropyl, pyridinyl, phenyl, fluorophenyl and/or —$C(=O)$—$R^8$, or represents a phenyl radical, which may optionally be mono- or polysubstituted by identical or different substituents from the group consisting of fluorine, chlorine, hydroxy, cyano, nitro, carboxyl, $C_1$-$C_3$-alkyl, methoxy, —$C(=O)NR^6R^7$, $C(=O)R^8$, $C_1$-$C_3$-alkylsulphinyl, $C_1$-$C_3$-alkylsulphonyl, —$S(=O)_2NH_2$, $C_1$-$C_3$-alkylsulphonylamino, $C_1$-$C_3$-alkylaminosulphonyl, $C_3$-$C_6$-cycloalkylaminosulphonyl, trifluoromethyl, trifluoromethoxy, hydroxy-$C_1$-$C_3$-alkyl, cyclopropyl, chlorothienyl and/or morpholino, $R^{1b}$ represents hydrogen, fluorine, bromine or cyano, and $R^{1c}$ represents hydrogen, and $R^2$ represents methyl or ethyl, and $R^3$ represents methylamino, and $R^4$ and $R^5$ independently of one another represent hydrogen, hydroxy, cyano, chlorine, $C_1$-$C_6$-alkyl, methoxy, ethoxy or $C_1$-$C_3$-alkylcarbonylamino, or difluoromethoxy or trifluoromethoxy, and $R^6$ and $R^7$ independently of one another represent hydrogen, $C_1$-$C_3$-alkyl, cyclopropyl or di-$C_1$-$C_3$-alkyl-amino-$C_1$-$C_3$-alkyl, and $R^8$ represents hydroxy, $C_1$-$C_3$-alkyl, hydroxy-$C_1$-$C_3$-alkyl, trifluoromethyl, pyrrolidinyl, morpholinyl or piperidinyl, and $R^9$ represents $C_1$-$C_4$-alkyl or $C_1$-$C_4$-alkoxy, or a tautomer or physiologically acceptable salt thereof, and where the stereocentre, which is represented by the carbon atom of the benzodiazepine skeleton which is bound to $R^2$, is present either in racemic form or predominantly or completely in the (S) configuration.

10. A compound of formula (I) according to claim 1 in which

X represents an oxygen atom, and

A represents a phenyl ring, and $R^{1a}$ represents hydrogen or chlorine, and $R^{1b}$ represents hydrogen, fluorine, bromine or cyano, and $R^{1c}$ represents hydrogen, and $R^2$ represents methyl or ethyl, and $R^3$ represents methylamino, and $R^4$ represents cyclopropyl, or represents pyridinyl, pyrazolyl, triazolyl or isoxazolyl, which may optionally be mono- or polysubstituted by identical or different substituents from the group consisting of hydroxy and/or methyl, or represents pyrrolidinyl, morpholinyl, piperidinyl, piperazinyl, oxazolidinyl or thiomorpholinyl, which may optionally be mono- or polysubstituted by methyl, oxo and/or —$S(=O)_2R^9$, or represents phenyl which is optionally substituted by $C_1$-$C_3$-alkylaminosulphonyl or fluorine, and $R^5$ represents hydrogen, hydroxy, cyano, chlorine, $C_1$-$C_6$-alkyl, methoxy, ethoxy or $C_1$-$C_3$-alkylcarbonylamino, or represents difluoromethoxy or trifluoromethoxy, and $R^6$ and $R^7$ independently of one another represent hydrogen, $C_1$-$C_3$-alkyl, cyclopropyl or di-$C_1$-$C_3$-alkyl-amino-$C_1$-$C_3$-alkyl, and $R^8$ represents hydroxy, $C_1$-$C_3$-alkyl, hydroxy-$C_1$-$C_3$-alkyl, trifluoromethyl, pyrrolidinyl, morpholinyl or piperidinyl, and $R^9$ represents $C_1$-$C_4$-alkyl or $C_1$-$C_4$-alkoxy, or a tautomer or physiologically acceptable salt thereof, and where the stereocentre, which is represented by the carbon atom of the benzodiazepine skeleton which is bound to $R^2$, is present either in racemic form or predominantly or completely in the (S) configuration.

11. A compound of formula (I), according to claim 1, in which

X represents an oxygen atom, and

A represents a phenyl ring, and $R^{1a}$ represents hydrogen or chlorine, and $R^{1b}$ represents hydrogen, fluorine, bromine or cyano, and $R^{1c}$ represents hydrogen, and $R^2$ represents methyl or ethyl, and $R^3$ represents methylamino, and $R^4$ represents hydrogen, chlorine, methoxy or ethoxy, or represents difluoromethoxy or trifluoromethoxy, and $R^5$ represents cyclopropyl, or represents pyridinyl or pyrazolyl, which may optionally be substituted one or more times by methyl, or represents morpholinyl, piperidinyl, piperazinyl or thiomorpholinyl, which may optionally be mono- or polysubstituted by methyl, oxo and/or —$S(=O)_2R^9$, or represents phenyl which is substituted by $C_1$-$C_3$-alkylaminosulphonyl, and $R^6$ and $R^7$ independently of one another represent hydrogen, $C_1$-$C_3$-alkyl, cyclopropyl or di-$C_1$-$C_3$-alkylamino-$C_1$-$C_3$-alkyl, and $R^8$ represents hydroxy, $C_1$-$C_3$-alkyl, hydroxy-$C_1$-$C_3$-alkyl, trifluoromethyl, pyrrolidinyl, morpholinyl or piperidinyl, and $R^9$ represents $C_1$-$C_4$-alkyl or $C_1$-$C_4$-alkoxy, or a tautomer or physiologically acceptable salt thereof, and where the stereocentre, which is represented by the carbon atom of the benzodiazepine skeleton which is bound to $R^2$, is present either in racemic form or predominantly or completely in the (S) configuration.

12. A compound of formula (I), according to claim 1, in which

X represents an oxygen atom, and

A represents a phenyl ring, and $R^{1a}$ represents piperazinyl, pyrrolidinyl, piperidinyl, diazepanyl, oxazinanyl, oxazolidinyl, morpholinyl, thiomorpholinyl, thiazolidinyl or azetidinyl, which may optionally be mono- or polysubstituted by identical or different substituents from the group consisting of fluorine, hydroxy, oxo, $C_1$-$C_3$-alkyl, methoxy, hydroxy-$C_1$-$C_3$-alkyl, dimethylamino, difluoroethyl, trifluoroethyl, benzyl, —$NR^6C(=O)$—$R^9$, —$C(=O)$—$NR^6R^7$, —$C(=O)$—$R^8$, and/or —$S(=O)_2$—$R^9$, or represents isoxazolyl or pyrazolyl, which may optionally be substituted one or more times by identical or different $C_1$-$C_2$-alkyls, and $R^{1b}$ represents hydrogen, fluorine, bromine or cyano, and $R^{1c}$ represents hydrogen, and $R^2$ represents methyl, and $R^3$ represents methylamino, and $R^4$ and $R^5$ independently of one another represent hydrogen, hydroxy, cyano, chlorine, $C_1$-$C_6$-alkyl, methoxy, ethoxy or $C_1$-$C_3$-alkylcarbonylamino, or represent difluoromethoxy or trifluoromethoxy, and $R^6$ and $R^7$ independently of one another represent hydrogen, $C_1$-$C_3$-alkyl, cyclopropyl or di-$C_1$-$C_3$-alkylamino-$C_1$-$C_3$-alkyl, and $R^8$ represents hydroxyl, $C_1$-$C_3$-alkyl, hydroxy-$C_1$-$C_3$-alkyl, trifluoromethyl, pyrrolidinyl, morpholinyl or piperidinyl, and $R^9$ represents $C_1$-$C_4$-alkyl or $C_1$-$C_4$-alkoxy, or a tautomer or physiologically acceptable salt thereof, and where the stereocentre, which is represented by the carbon atom of the benzodiazepine skeleton which is bound to $R^2$, is present either in racemic form or predominantly or completely in the (S) configuration.

13. A compound of formula (I), according to claim 1 in which

X represents an oxygen atom, and

A represents a phenyl ring, and $R^{1a}$ represents piperazinyl, pyrrolidinyl, piperidinyl, morpholinyl, thiomorpholinyl or azetidinyl, which may optionally be mono- or polysubstituted by identical or different substituents from the group consisting of hydoxy, oxo, $C_1$-$C_3$-alkyl, methoxy, dimethylamino, difluoroethyl, trifluoroethyl, —$NR^6C(=O)$—$R^9$, —$C(=O)$—$NR^6R^7$, and/or —$C(=O)$—$R^8$, and $R^{1b}$ represents hydrogen, fluorine, bromine or cyano, and $R^{1c}$ represents hydrogen, and $R^2$ represents methyl, and $R^3$ represents methylamino, and $R^4$ and $R^5$ independently of one another represent hydrogen, chlorine, methoxy or ethoxy, or represent difluoromethoxy or trifluoromethoxy, and $R^6$ and $R^7$ independently of one another represent hydrogen or $C_1$-$C_3$-alkyl, and $R^8$ represents methyl, and $R^9$ represents methyl, or a tautomer or physiologically acceptable salt thereof, and where the stereocentre, which is represented by the carbon atom of the benzodiazepine skeleton which is bound to $R^2$, is present either in racemic form or predominantly or completely in the (S) configuration.

14. A compound of formula (I) according to claim 1 in which

A represents a phenyl ring and $R^4$ represents hydrogen or chlorine and $R^5$ represents trifluoromethoxy and $R^{1a}$ represents chlorine, and compounds of the formula (I) in which A represents a phenyl ring and $R^4$ represents hydrogen and $R^5$ represents $C_1$-$C_3$-alkoxy which may be substituted by morpholinyl, pyrrolidinyl, piperazinyl or pyridyl, where the piperazinyl or pyridinyl for its part may be substituted by $C_1$-$C_3$-alkyl, and $R^{1a}$ represents chlorine, or a tautomer or physiologically acceptable salt thereof.

15. A compound of formula (I) according to claim 1, selected from the group consisting of (±)-1-(4-chlorophenyl)-N,4-dimethyl-8-(trifluoromethoxy)-4,5-dihydro-3H-2,3-benzodiazepine-3-carboxamide, (4S)-1-(4-chlorophenyl)-N,4-dimethy-8-(trimethxy)-4,5-dimethyl-8-trifluoromethoxy)-4,5-dihydro-3H-2,3-benzodiazepine-3-carboxamide, (4R)-1-(4-chlorophenyl)-N,4-dimethyl-8-(trifluoromethoxy)-4,5-dihydro-3H-2,3-benzodiazepine-3-carboxamide, (±)-1-[4-(3,5-dimethyl-4-isoxazolyl)phenyl]-7,8-dimethoxy-N,4-dimethyl-4,5-dihydro-3H-2,3-benzodiazepine-3-carboxamide, (4R)-1-[4-(3,5-dimethyl-4-isoxazolyl)phenyl]-7,8-dimethoxy-N,4-dimethyl-4,5-dihydro-3H-2,3-benzodiazepine-3-carboxamide, (4S)-1-[4-(3,5-dimethyl-4-isoxazolyl)phenyl]-7,8-dimethoxy-N,4-dimethyl-4,5-dihydro-3H-2,3-benzodiazepine-3-carboxamide, (±)-7,8-dimethoxy-N,4-dimethyl-1-[4-(1H-pyrazol-3-yl)phenyl]-4,5-dihydro-3H-2,3-benzodiazepine-3-carboxamide, (±)-1-[4-(2-chloropyridin-3-yl)phenyl]-7,8-dimethoxy-N,4-dimethyl-4,5-dihydro-3H-2,3-benzodiazepine-3-carboxamide, (±)-5-(4-{7,8-dimethoxy-4-methyl-3-[(methylamino)carbonyl]-4,5-dihydro-3H-2,3-benzodiazepin-1-yl}phenyl)thiophen-2-carboxylic acid, (±)-4'-{7,8-dimethoxy-4-methyl-3-[(methylamino)carbonyl]-4,5-dihydro-3H-2,3-benzodiazepin-1-yl}biphenyl-2-carboxylic acid, (±)-7,8-dimethoxy-N,4-dimethyl-1-[4-(morpholin-4-yl)phenyl]-4,5-dihydro-3H-2,3-benzodiazepine-3-carboxamide, (±)-1-(4-chlorophenyl)-N,4-dimethyl-8-(pyridin-4-yl)-4,5-dihydro-3H-2,3-benzodiazepine-3-carboxamide, (±)-1-(4-chlorophenyl)-8-cyclopropyl-N,4-dimethyl-4,5-dihydro-3H-2,3-benzodiazepine-3-carboxamide, (±)-1-(4-chlorophenyl)-N,4-dimethyl-8-{4-[(methylamino)sulphonyl]phenyl}-4,5-dihydro-3H-2,3-benzodiazepine-3-carboxamide, (±)-1-(4-chlorophenyl)-N,4-dimethyl-8-(morpholin-4-yl)-4,5-dihydro-3H-2,3-benzodiazepine-3-carboxamide, (4S)-1-(4-chlorophenyl)-N,4-dimethyl-8-(morpholin-4-yl)-4,5-dihydro-3H-2,3-benzodiazepine-3-carboxamide, (4R)-1-(4-chlorophenyl)-N,4-dimethyl-8-(morpholin-4-yl)-4,5-dihydro-3H-2,3-benzodiazepine-3-carboxamide, (±)-1-(4-chlorophenyl)-N,4-dimethyl-8-(4-methylpiperazin-1-yl)-4,5-dihydro-3H-2,3-benzodiazepine-3-carboxamide, (±)-1-(4-chlorophenyl)-N,4-dimethyl-8-(piperidin-1-yl)-4,5-dihydro-3H-2,3-benzodiazepine-3-carboxamide, (±)-8-methoxy-N,4-dimethyl-1-(pyridin-3-yl)-4,5-dihydro-3H-2,3-benzodiazepine-3-carboxamide, (±)-7-chloro-1-(4-chlorophenyl)-N,4-dimethyl-8-(trifluoromethoxy)-4,5-dihydro-3H-2,3-benzodiazepine-3-carboxamide, 7-chloro-1-(4-chlorophenyl)-N,4-dimethyl-8-(trifluoromethoxy)-4,5-dihydro-3H-2,3-benzodiazepine-3-carboxamide, (4S)-1-[4-(3,5-dimethyl-1H-pyrazol-1-yl)phenyl]-8-methoxy-N,4-dimethyl-4,5-dihydro-3H-2,3-benzodiazepine-3-carboxamide, (4S)-8-methoxy-N,4-dimethyl-1-[4-(morpholin-4-yl)phenyl]-4,5-dihydro-3H-2,3-benzodiazepine-3-carboxamide,
(4S)-1-[4-(4-isoxazolyl)phenyl]-8-methoxy-N,4-dimethyl-4,5-dihydro-3H-2,3-benzodiazepine-3-carboxamide,
(4S)-8-methoxy-N,4-dimethyl-1-[4-(1-methyl-1H-pyrazol-5-yl)phenyl]-4,5-dihydro-3H-2,3-benzodiazepine-3-carboxamide,
(4S)-1-[4-(3,5-dimethyl-4-isoxazolyl)phenyl]-8-methoxy-N,4-dimethyl-4,5-dihydro-3H-2,3-benzodiazepine-3-carboxamide,
(4S)-8-methoxy-N,4-dimethyl-1-[4-(1-methyl-H-pyrazol-4-yl)phenyl]-4,5-dihydro-3H-2,3-benzodiazepine-3-carboxamide,
(4S)-8-methoxy-N,4-dimethyl-1-[4-(1,3,5-trimethyl-H-pyrazol-4-yl)phenyl]-4,5-dihydro-3H-2,3-benzodiazepine-3-carboxamide,
(4S)-8-methoxy-N,4-dimethyl-1-[4-(1H-pyrazol-5-yl)phenyl]-4,5-dihydro-3H-2,3-benzodiazepine-3-carboxamide,
(4S)-1-[4-(3-cyclopropyl-5-ethyl-1H-pyrazol-1-yl)phenyl]-8-methoxy-N,4-dimethyl-4,5-dihydro-3H-2,3-benzodiazepine-3-carboxamide,
(4S)-1-[4-(5-cyclopropyl-3-ethyl-1H-pyrazol-1-yl)phenyl]-8-methoxy-N,4-dimethyl-4,5-dihydro-3H-2,3-benzodiazepine-3-carboxamide,
(4S)-8-methoxy-1-{4-[3-(methoxymethyl)-5-methyl-1H-pyrazol-1-yl]phenyl}-N,4-dimethyl-4,5-dihydro-3H-2,3-benzodiazepine-3-carboxamide,
(4S)-8-methoxy-1-{4-[5-(methoxymethyl)-3-methyl-1H-pyrazol-1-yl]phenyl}-N,4-dimethyl-4,5-dihydro-3H-2,3-benzodiazepine-3-carboxamide,
(4S)-1-{4-[5-cyclopropyl-3-(pyridin-2-yl)-1H-pyrazol-1-yl]phenyl}-8-methoxy-N,4-dimethyl-4,5-dihydro-3H-2,3-benzodiazepine-3-carboxamide,
(4S)-1-{4-[3-cyclopropyl-5-(pyridin-2-yl)-1H-pyrazol-1-yl]phenyl}-8-methoxy-N,4-dimethyl-4,5-dihydro-3H-2,3-benzodiazepine-3-carboxamide,
(4S)-8-methoxy-N,4-dimethyl-1-[4-(1H-tetrazol-1-yl)phenyl]-4,5-dihydro-3H-2,3-benzodiazepine-3-carboxamide,
(±)-1-[3-(3,5-dimethylisoxazol-4-yl)phenyl]-7,8-dimethoxy-N,4-dimethyl-4,5-dihydro-3H-2,3-benzodiazepine-3-carboxamide,
(±)-1-(4-chlorophenyl)-N,4-dimethyl-8-[2-(morpholin-4-yl)ethoxy]-4,5-dihydro-3H-2,3-benzodiazepine-3-carboxamide,
(±)-1-(4-chlorophenyl)-N,4-dimethyl-8-[2-(pyrrolidin-1-yl)ethoxy]-4,5-dihydro-3H-2,3-benzodiazepine-3-carboxamide,
(±)-7,8-dimethoxy-N,4-dimethyl-1-[4-(2-oxooxazolidin-3-yl)phenyl]-4,5-dihydro-3H-2,3-benzodiazepine-3-carboxamide,
(4S)-7,8-dimethoxy-N,4-dimethyl-1-[4-(2-oxooxazolidin-3-yl)phenyl]-4,5-dihydro-3H-2,3-benzodiazepine-3-carboxamide,
(±)-7,8-dimethoxy-N,4-dimethyl-1-[4-(2-oxopiperidin-1-yl)phenyl]-4,5-dihydro-3H-2,3-benzodiazepine-3-carboxamide,
(±)-1-[4-(4-benzyl-2-oxopiperazin-1-yl)phenyl]-7,8-dimethoxy-N,4-dimethyl-4,5-dihydro-3H-2,3-benzodiazepine-3-carboxamide,
(±)-7,8-dimethoxy-N,4-dimethyl-1-[4-(4-methyl-2-oxo-1,4-diazepan-1-yl)phenyl]-4,5-dihydro-3H-2,3-benzodiazepine-3-carboxamide,
(±)-7,8-dimethoxy-N,4-dimethyl-1-[4-(2-oxo-1,3-oxazinan-3-yl)phenyl]-4,5-dihydro-3H-2,3-benzodiazepine-3-carboxamide,
(±)-7,8-dimethoxy-N,4-dimethyl-1-[4-(2-oxopyrrolidin-1-yl)phenyl]-4,5-dihydro-3H-2,3-benzodiazepine-3-carboxamide,
(±)-7,8-dimethoxy-N,4-dimethyl-1-[4-(3-oxomorpholin-4-yl)phenyl]-4,5-dihydro-3H-2,3-benzodiazepine-3-carboxamide,
(4S)-7,8-dimethoxy-N,4-dimethyl-1-[4-(3-oxomorpholin-4-yl)phenyl]-4,5-dihydro-3H-2,3-benzodiazepine-3-carboxamide,
(±)-7,8-dimethoxy-N,4-dimethyl-1-[4-(2-methyl-5-oxomorpholin-4-yl)phenyl]-4,5-dihydro-3H-2,3-benzodiazepine-3-carboxamide (stereoisomer mixture),
(±)-7,8-dimethoxy-N,4-dimethyl-1-[4-(2-methyl-3-oxomorpholin-4-yl)phenyl]-4,5-dihydro-3H-2,3-benzodiazepine-3-carboxamide (stereoisomer mixture),
(±)-7,8-dimethoxy-N,4-dimethyl-1-[4-(4-methyl-2-oxopiperazin-1-yl)phenyl]-4,5-dihydro-3H-2,3-benzodiazepine-3-carboxamide,
(4S)-7,8-dimethoxy-N,4-dimethyl-1-[4-(4-methyl-2-oxopiperazin-1-yl)phenyl]-4,5-dihydro-3H-2,3-benzodiazepine-3-carboxamide,
(4R)-7,8-dimethoxy-N,4-dimethyl-1-[4-(4-methyl-2-oxopiperazin-1-yl)phenyl]-4,5-dihydro-3H-2,3-benzodiazepine-3-carboxamide,
(±)-7,8-dimethoxy-N,4-dimethyl-1-[4-(2-oxopiperazin-1-yl)phenyl]-4,5-dihydro-3H-2,3-benzodiazepine-3-carboxamide,
(±)-7,8-dimethoxy-N,4-dimethyl-1-[4-(1-methyl-1H-1,2,3-triazol-4-yl)phenyl]-4,5-dihydro-3H-2,3-benzodiazepine-3-carboxamide,
(4S)-7,8-dimethoxy-N,4-dimethyl-1-[4-(1-methyl-H-1,2,3-triazol-4-yl)phenyl]-4,5-dihydro-3H-2,3-benzodiazepine-3-carboxamide,
(±)-1-[4-(2,4-dimethylthiazol-5-yl)phenyl]-7,8-dimethoxy-N,4-dimethyl-4,5-dihydro-3H-2,3-benzodiazepine-3-carboxamide,
(4S)-1-[4-(2,4-dimethylthiazol-5-yl)phenyl]-7,8-dimethoxy-N,4-dimethyl-4,5-dihydro-3H-2,3-benzodiazepine-3-carboxamide,
(4R)-1-[4-(2,4-dimethylthiazol-5-yl)phenyl]-7,8-dimethoxy-N,4-dimethyl-4,5-dihydro-3H-2,3-benzodiazepine-3-carboxamide,
(±)-1-[4-(1,2-dimethyl-H-imidazol-5-yl)phenyl]-7,8-dimethoxy-N,4-dimethyl-4,5-dihydro-3H-2,3-benzodiazepine-3-carboxamide,
(±)-7,8-dimethoxy-N,4-dimethyl-1-{4-[2-(trifluoromethyl)pyridin-3-yl]phenyl}-4,5-dihydro-3H-2,3-benzodiazepine-3-carboxamide,
(±)-1-[4-(6-hydroxypyridin-3-yl)phenyl]-7,8-dimethoxy-N,4-dimethyl-4,5-dihydro-3H-2,3-benzodiazepine-3-carboxamide,
(4S)-1-[4-(6-hydroxypyridin-3-yl)phenyl]-7,8-dimethoxy-N,4-dimethyl-4,5-dihydro-3H-2,3-benzodiazepine-3-carboxamide,
(±)-7,8-dimethoxy-N,4-dimethyl-1-{4-[6-(trifluoromethyl)pyridin-3-yl]phenyl}-4,5-dihydro-3H-2,3-benzodiazepine-3-carboxamide,
(±)-7,8-dimethoxy-N,4-dimethyl-1-[4-(1,3,5-trimethyl-H-pyrazol-4-yl)phenyl]-4,5-dihydro-3H-2,3-benzodiazepine-3-carboxamide,
(4R)-7,8-dimethoxy-N,4-dimethyl-1-[4-(1,3,5-trimethyl-1H-pyrazol-4-yl)phenyl]-4,5-dihydro-3H-2,3-benzodiazepine-3-carboxamide, (4S)-7,8-dimethoxy-N,4-dimethyl-1-[4-(1,3,5-trimethyl-1H-pyrazol-4-yl)phenyl]-4,5-dihydro-3H-2,3-benzodiazepine-3-carboxamide, (±)-1-[4-(isoxazol-4-yl)phenyl]-7,8-dimethoxy-N,4-dimethyl-4,5-dihydro-3H-2,3-benzodiazepine-3-carboxamide, (±)-7,8-dimethoxy-N,4-dimethyl-1-[3-(1,3,5-trimethyl-H-pyrazol-4-yl)phenyl]-4,5-dihydro-3H-2,3-benzodiazepine-3-carboxamide, (±)-7,8-dimethoxy-N,4-dimethyl-1-[3-(1-methyl-H-pyrazol-4-yl)phenyl]-4,5-dihydro-3H-2,3-benzodiazepine-3-carboxamide, (±)-7,8-dimethoxy-N,4-dimethyl-1-[3-(1-methyl-1H-pyrazol-5-yl)phenyl]-4,5-dihydro-3H-2,3-benzodiazepine-3-carboxamide, (±)-1-[4-fluoro-3-(1,3,5-trimethyl-1H-pyrazol-4-yl)phenyl]-7,8-dimethoxy-N,4-dimethyl-4,5-dihydro-3H-2,3-benzodiazepine-3-carboxamide, (±)-1-[4-fluoro-3-(1-methyl-1H-pyrazol-4-yl)phenyl]-7,8-dimethoxy-N,4-dimethyl-4,5-dihydro-3H-2,3-benzodiazepine-3-carboxamide, (±)-1-[3-(3,5-dimethylisoxazol-4-yl)-4-fluorophenyl]-7,8-dimethoxy-N,4-dimethyl-4,5-dihydro-3H-2,3-benzodiazepine-3-carboxamide, (±)-7,8-dimethoxy-N,4-dimethyl-1-(3'-nitrobiphenyl-4-yl)-4,5-dihydro-3H-2,3-benzodiazepine-3-carboxamide, (±)-1-(biphenyl-4-yl)-7,8-dimethoxy-N,4-dimethyl-4,5-dihydro-3H-2,3-benzodiazepine-3-carboxamide, (±)-1-(2',4'-dichlorobiphenyl-4-yl)-7,8-dimethoxy-N,4-dimethyl-4,5-dihydro-3H-2,3-benzodiazepine-3-carboxamide, (±)-1-(4'-fluorobiphenyl-4-yl)-7, 8-dimethoxy-N,4-dimethyl-4,5-dihydro-3H-2,3-benzodiazepine-3-carboxamide, (±)-1-(4'-Chlorbiphenyl-4-yl)-7,8-dimethoxy-N,4-dimethyl-4,5-dihydro-3H-2,3-benzodiazepine-3-carboxamide, (±)-7,8-dimethoxy-N,4-dimethyl-1-(4'-methylbiphenyl-4-yl)-4,5-dihydro-3H-2,3-benzodiazepine-3-carboxamide, (±)-7,8-dimethoxy-1-(4'-methoxybiphenyl-4-yl)-N,4-dimethyl-4,5-dihydro-3H-2,3-benzodiazepine-3-carboxamide, (±)-7,8-dimethoxy-1-[4-(6-methoxypyridin-3-yl)phenyl]-N,4-dimethyl-4,5-dihydro-3H-2,3-benzodiazepine-3-carboxamide, (±)-7,8-dimethoxy-N,4-dimethyl-1-[4'-(methylsulphinyl)biphenyl-4-yl]-4,5-dihydro-3H-2,3-benzodiazepine-3-carboxamide, (±)-7,8-dimethoxy-N,4-dimethyl-1-{2'-[(methylsulphonyl)amino]biphenyl-4-yl}-4,5-dihydro-3H-2,3-benzodiazepine-3-carboxamide, (±)-7,8-dimethoxy-N,4-dimethyl-1-[2'-(methylsulphonyl)biphenyl-4-yl]-4,5-dihydro-3H-2,3-benzodiazepine-3-carboxamide, (±)-7,8-dimethoxy-N,4-dimethyl-1-{4'-[(methylsulphonyl)amino]biphenyl-4-yl}-4,5-dihydro-3H-2,3-benzodiazepine-3-carboxamide, (±)-7,8-dimethoxy-N,4-dimethyl-1-{3'-[(methylsulphonyl)amino]biphenyl-4-yl}-4,5-dihydro-3H-2,3-benzodiazepine-3-carboxamide, (±)-7,8-dimethoxy-N,4-dimethyl-1-(2'-methylbiphenyl-4-yl)-4,5-dihydro-3H-2,3-benzodiazepine-3-carboxamide, (±)-7,8-dimethoxy-N,4-dimethyl-1-[3'-(methylsulphonyl)biphenyl-4-yl]-4,5-dihydro-3H-2,3-benzodiazepine-3-carboxamide, (±)-7,8-dimethoxy-1-[4-(2-methoxypyrimidin-5-yl)phenyl]-N,4-dimethyl-4,5-dihydro-3H-2,3-benzodiazepine-3-carboxamide, (±)-1-(3'-cyano-4'-fluorobiphenyl-4-yl)-7,8-dimethoxy-N,4-dimethyl-4,5-dihydro-3H-2,3-benzodiazepine-3-carboxamide, (±)-7,8-dimethoxy-1-[4-(2-methoxypyridin-3-yl)phenyl]-N,4-dimethyl-4,5-dihydro-3H-2,3-benzodiazepine-3-carboxamide, (±)-1-(3'-carbamoylbiphenyl-4-yl)-7, 8-dimethoxy-N,4-dimethyl-4,5-dihydro-3H-2,3-benzodiazepine-3-carboxamide, (±)-7,8-dimethoxy-N,4-dimethyl-1-[4'-(pyrrolidin-1-ylcarbonyl)biphenyl-4-yl]-4,5-dihydro-3H-2,3-benzodiazepine-3-carboxamide, (±)-7,8-dimethoxy-N,4-dimethyl-1-[4'-(morpholin-4-ylcarbonyl)biphenyl-4-yl]-4,5-dihydro-3H-2,3-benzodiazepine-3-carboxamide, (±)-7,8-dimethoxy-1-[4-(5-methoxypyridin-3-yl)phenyl]-N,4-dimethyl-4,5-dihydro-3H-2,3-benzodiazepine-3-carboxamide, (±)-7,8-dimethoxy-N,4-dimethyl-1-[4-(5-methylpyridin-3-yl)phenyl]-4,5-dihydro-3H-2,3-benzodiazepine-3-carboxamide, (±)-7,8-dimethoxy-N,4-dimethyl-1-[4-(4-methylpyridin-3-yl)phenyl]-4,5-dihydro-3H-2,3-benzodiazepine-3-carboxamide, (±)-1-[4'-(cyclopropylcarbamoyl)biphenyl-4-yl]-7,8-dimethoxy-N,4-dimethyl-4,5-dihydro-3H-2,3-benzodiazepine-3-carboxamide, (±)-1-[4-(3-fluoropyridin-4-yl)phenyl]-7,8-dimethoxy-N,4-dimethyl-4,5-dihydro-3H-2,3-benzodiazepine-3-carboxamide, (±)-7,8-dimethoxy-N,4-dimethyl-1-[3'-(trifluoromethyl)biphenyl-4-yl]-4,5-dihydro-3H-2,3-benzodiazepine-3-carboxamide, (±)-7,8-dimethoxy-N,4-dimethyl-1-[4'-(trifluoromethyl)biphenyl-4-yl]-4,5-dihydro-3H-2,3-benzodiazepine-3-carboxamide, (±)-7,8-dimethoxy-1-(3'-methoxybiphenyl-4-yl)-N,4-dimethyl-4,5-dihydro-3H-2,3-benzodiazepine-3-carboxamide, (±)-1-[4'-(5-chlorothien-2-yl)biphenyl-4-yl]-7,8-dimethoxy-N,4-dimethyl-4,5-dihydro-3H-2,3-benzodiazepine-3-carboxamide, (±)-1-(3'-fluorobiphenyl-4-yl)-7, 8-dimethoxy-N,4-dimethyl-4,5-dihydro-3H-2,3-benzodiazepine-3-carboxamide, (±)-7,8-dimethoxy-1-(2'-methoxybiphenyl-4-yl)-N,4-dimethyl-4,5-dihydro-3H-2,3-benzodiazepine-3-carboxamide, (±)-7,8-dimethoxy-N,4-dimethyl-1-[2'-(trifluoromethyl)biphenyl-4-yl]-4,5-dihydro-3H-2,3-benzodiazepine-3-carboxamide, (±)-1-(2'-chlorobiphenyl-4-yl)-7,8-dimethoxy-N,4-dimethyl-4,5-dihydro-3H-2,3-benzodiazepine-3-carboxamide, (±)-1-(2'-fluorobiphenyl-4-yl)-7, 8-dimethoxy-N,4-dimethyl-4,5-dihydro-3H-2,3-benzodiazepine-3-carboxamide, (±)-1-[4'-(hydroxymethyl)biphenyl-4-yl]-7, 8-dimethoxy-N,4-dimethyl-4,5-dihydro-3H-2,3-benzodiazepine-3-carboxamide, (±)-7,8-dimethoxy-N,4-dimethyl-1-[4'-(trifluoromethoxy)biphenyl-4-yl]-4,5-dihydro-3H-2,3-benzodiazepine-3-carboxamide, (±)-7,8-dimethoxy-N,4-dimethyl-1-[3'-(pyrrolidin-1-ylcarbonyl)biphenyl-4-yl]-4,5-dihydro-3H-2,3-benzodiazepine-3-carboxamide, (±)-7,8-dimethoxy-N,4-dimethyl-1-[3'-(piperidin-1-ylcarbonyl)biphenyl-4-yl]-4,5-dihydro-3H-2,3-benzodiazepine-3-carboxamide, (±)-7,8-dimethoxy-N,4-dimethyl-1-[3'-(morpholin-4-ylcarbonyl)biphenyl-4-yl]-4,5-dihydro-3H-2,3-benzodiazepine-3-carboxamide, (±)-1-[3'-(cyclopropylcarbamoyl)biphenyl-4-yl]-7,8-dimethoxy-N,4-dimethyl-4,5-dihydro-3H-2,3-benzodiazepine-3-carboxamide, (±)-1-(2',4'-difluorobiphenyl-4-yl)-7,8-dimethoxy-N,4-dimethyl-4,5-dihydro-3H-2,3-benzodiazepine-3-carboxamide, (±)-7,8-dimethoxy-N,4-dimethyl-1-[4-(1-methyl-1H-pyrazol-5-yl)phenyl]-4,5-dihydro-3H-2,3-benzodiazepine-3-carboxamide, (±)-7,8-dimethoxy-N,4-dimethyl-1-(4'-nitrobiphenyl-4-yl)-4,5-dihydro-3H-2,3-benzodiazepine-3-carboxamide, (±)-7,8-dimethoxy-N,4-dimethyl-1-[4-(pyridin-3-yl)phenyl]-4,5-dihydro-3H-2,3-benzodiazepine-3-carboxamide, (±)-7,8-dimethoxy-1-[4-(4-methoxypyridin-3-yl)phenyl]-N,4-dimethyl-4,5-dihydro-3H-2,3-benzodiazepine-3-carboxamide, (±)-1-(3'-cyanobiphenyl-4-yl)-7,8-dimethoxy-N,4-dimethyl-4,5-dihydro-3H-2,3-benzodiazepine-3-carboxamide, (±)-1-(4'-cyanobiphenyl-4-yl)-7,8-dimethoxy-N,4-dimethyl-4,5-dihydro-3H-2,3-benzodiazepine-3-carboxamide, (±)-7,8-dimethoxy-N,4-dimethyl-1-[2'-(trifluoromethoxy)biphenyl-4-yl]-4,5-dihydro-3H-2,3-benzodiazepine-3-carboxamide, (±)-7,8-dimethoxy-N,4-dimethyl-1-[4'-(methylsulphonyl)biphenyl-4-yl]-4,5-dihydro-3H-2,3-benzodiazepine-3-carboxamide, (±)-1-(2'-cyanobiphenyl-4-yl)-7,8-dimethoxy-N,4-dimethyl-4,5-dihydro-3H-2,3-benzodiazepine-3-carboxamide, (±)-7,8-dimethoxy-N,4-dimethyl-1-[4'-(morpholin-4-yl)biphenyl-4-yl]-4,5-dihydro-3H-2,3-benzodiazepine-3-carboxamide, (±)-7,8-dimethoxy-N,4-dimethyl-1-[4-(pyrimidin-5-yl)phenyl]-4,5-dihydro-3H-2,3-benzodiazepine-3-carboxamide, (±)-1-[2'-(hydroxymethyl)biphenyl-4-yl]-7,8-dimethoxy-N,4-dimethyl-4,5-dihydro-3H-2,3-benzodiazepine-3-carboxamide, (±)-1-(3'-{[2-(dimethylamino)ethyl]carbamoyl}biphenyl-4-yl)-7,8-dimethoxy-N,4-dimethyl-4,5-dihydro-3H-2,3-benzodiazepine-3-carboxamide, (±)-7,8-dimethoxy-N,4-dimethyl-1-(3'-sulphamoylbiphenyl-4-yl)-4,5-dihydro-3H-2,3-benzodiazepine-3-carboxamide, (±)-7,8-dimethoxy-N,4-dimethyl-1-[4'-(methylsulphamoyl)biphenyl-4-yl]-4,5-dihydro-3H-2,3-benzodiazepine-3-carboxamide, (±)-7,8-dimethoxy-N,4-dimethyl-1-[4-(1-methyl-1H-pyrrol-2-yl)phenyl]-4,5-dihydro-3H-2,3-benzodiazepine-3-carboxamide, (±)-7,8-dimethoxy-N,4-dimethyl-1-[4-(6-methylpyridin-3-yl)phenyl]-4,5-dihydro-3H-2,3-benzodiazepine-3-carboxamide, (±)-1-[4'-(cyclopropylsulphamoyl)biphenyl-4-yl]-7,8-dimethoxy-N,4-dimethyl-4,5-dihydro-3H-2,3-benzodiazepine-3-carboxamide, (±)-1-(3'-fluoro-5'-hydroxybiphenyl-4-yl)-7,8-dimethoxy-N,4-dimethyl-4,5-dihydro-3H-2,3-benzodiazepine-3-carboxamide, (±)-1-(3'-fluoro-5'-methylbiphenyl-4-yl)-7,8-dimethoxy-N,4-dimethy-4,5-dihydro-3H-2,3-benzodiazepine-3-carboxamide, (±)-7,8-dimethoxy-N,4-dimethyl-1-[3'-(methylsulphamoyl)biphenyl-4-yl]-4,5-dihydro-3H-2,3-benzodiazepine-3-carboxamide, (±)-1-[4-(5-fluoropyridin-3-yl)phenyl]-7,8-dimethoxy-N,4-dimethyl-4,5-dihydro-3H-2,3-benzodiazepine-3-carboxamide, (±)-1-[4-(4-fluoropyridin-3-yl)phenyl]-7,8-dimethoxy-N,4-dimethyl-4,5-dihydro-3H-2,3-benzodiazepine-3-carboxamide, (±)-7,8-dimethoxy-N,4-dimethyl-1-[4-(2-methylpyridin-3-yl)phenyl]-4,5-dihydro-3H-2,3-benzodiazepine-3-carboxamide, (±)-7,8-dimethoxy-1-[4-(2-methoxypyridin-4-yl)phenyl]-N,4-dimethyl-4,5-dihydro-3H-2,3-benzodiazepine-3-carboxamide, (±)-1-[4-(5-cyanopyridin-3-yl)phenyl]-7,8-dimethoxy-N,4-dimethyl-4,5-dihydro-3H-2,3-benzodiazepine-3-carboxamide, (4R)-7,8-dimethoxy-N,4-dimethyl-1-[4-(morpholin-4-yl)phenyl]-4,5-dihydro-3H-2,3-benzodiazepine-3-carboxamide, (4S)-7,8-dimethoxy-N,4-dimethyl-1-[4-(morpholin-4-yl)phenyl]-4,5-dihydro-3H-2,3-benzodiazepine-3-carboxamide, (4S)-7,8-dimethoxy-N,4-dimethyl-1-[4-(4-methylpiperazin-1-yl)phenyl]-4,5-dihydro-3H-2,3-benzodiazepine-3-carboxamide, (±)-1-[4-(azetidin-1-yl)phenyl]-7,8-dimethoxy-N,4-dimethyl-4,5-dihydro-3H-2,3-benzodiazepine-3-carboxamide, (4R)-1-[4-(azetidin-1-yl)phenyl]-7,8-dimethoxy-N,4-dimethyl-4,5-dihydro-3H-2,3-benzodiazepine-3-carboxamide, (4S)-1-[4-(azetidin-1-yl)phenyl]-7,8-dimethoxy-N,4-dimethyl-4,5-dihydro-3H-2,3-benzodiazepine-3-carboxamide, (±)-1-[4-(3-fluoroazetidin-1-yl)phenyl]-7,8-dimethoxy-N,4-dimethyl-4,5-dihydro-3H-2,3-benzodiazepine-3-carboxamide, (4R)-1-[4-(3-fluoroazetidin-1-yl)phenyl]-7,8-dimethoxy-N,4-dimethyl-4,5-dihydro-3H-2,3-benzodiazepine-3-carboxamide, (4S)-1-[4-(3-fluoroazetidin-1-yl)phenyl]-7,8-dimethoxy-N,4-dimethyl-4,5-dihydro-3H-2,3-benzodiazepine-3-carboxamide, (±)-1-[4-(4-hydroxypiperidin-1-yl)phenyl]-7,8-dimethoxy-N,4-dimethyl-4,5-dihydro-3H-2,3-benzodiazepine-3-carboxamide, (4S)-1-[4-(4-hydroxypiperidin-1-yl)phenyl]-7,8-dimethoxy-N,4-dimethyl-4,5-dihydro-3H-2,3-benzodiazepine-3-carboxamide, (±)-7,8-dimethoxy-N,4-dimethyl-1-[4-(piperazin-1-yl)phenyl]-4,5-dihydro-3H-2,3-benzodiazepine-3-carboxamide, (4S)-7,8-dimethoxy-N,4-dimethyl-1-[4-(piperazin-1-yl)phenyl]-4,5-dihydro-3H-2,3-benzodiazepine-3-carboxamide, (±)-7,8-dimethoxy-N,4-dimethyl-1-[4-(4-methylpiperazin-1-yl)phenyl]-4,5-dihydro-3H-2,3-benzodiazepine-3-carboxamide, (±)-1-[4-(4-acetylpiperazin-1-yl)phenyl]-7,8-dimethoxy-N,4-dimethyl-4,5-dihydro-3H-2,3-benzodiazepine-3-carboxamide, (4R)-1-[4-(4-acetylpiperazin-1-yl)phenyl]-7,8-dimethoxy-N,4-dimethyl-4,5-dihydro-3H-2,3-benzodiazepine-3-carboxamide, (4S)-1-[4-(4-acetylpiperazin-1-yl)phenyl]-7,8-dimethoxy-N,4-dimethyl-4,5-dihydro-3H-2,3-benzodiazepine-3-carboxamide, (±)-7,8-dimethoxy-N,4-dimethyl-1-{4-[4-(trifluoracetyl)piperazin-1-yl]phenyl}-4,5-dihydro-3H-2,3-benzodiazepine-3-carboxamide, (±)-1-{4-[4-(2-hydroxy-2-methylpropanoyl)piperazin-1-yl]phenyl}-7,8-dimethoxy-N,4-dimethyl-4,5-dihydro-3H-2,3-benzodiazepine-3-carboxamide, (±)-7,8-dimethoxy-N,4-dimethyl-1-{4-[4-(methylsulphonyl)piperazin-1-yl]phenyl}-4,5-dihydro-3H-2,3-benzodiazepine-3-carboxamide, (4S)-1-[4-(1,1-dioxidothiomorpholin-4-yl)phenyl]-7,8-dimethoxy-N,4-dimethyl-4,5-dihydro-3H-2,3-benzodiazepine-3-carboxamide, (±)-7,8-dimethoxy-N,4-dimethyl-1-[4-(3-oxopiperazin-1-yl)phenyl]-4,5-dihydro-3H-2,3-benzodiazepine-3-carboxamide, (±)-7,8-dimethoxy-N,4-dimethyl-1-[4-(4-methyl-3-oxopiperazin-1-yl)phenyl]-4,5-dihydro-3H-2,3-benzodiazepine-3-carboxamide, (±)-7,8-dimethoxy-N,4-dimethyl-1-[4-(piperidin-1-yl)phenyl]-4,5-dihydro-3H-2,3-benzodiazepine-3-carboxamide, (±)-7,8-dimethoxy-N,4-dimethyl-1-[3-(morpholin-4-yl)phenyl]-4,5-dihydro-3H-2,3-benzodiazepine-3-carboxamide, (±)-1-[3-(3,3-difluoroazetidin-1-yl)phenyl]-7,8-dimethoxy-N,4-dimethyl-4,5-dihydro-3H-2,3-benzodiazepine-3-carboxamide, (±)-1-[3-(azetidin-1-yl)phenyl]-7,8-dimethoxy-N,4-dimethyl-4,5-dihydro-3H-2,3-benzodiazepine-3-carboxamide, (±)-7,8-dimethoxy-N,4-dimethyl-1-[3-(4-methylpiperazin-1-yl)phenyl]-4,5-dihydro-3H-2,3-benzodiazepine-3-carboxamide, (±)-1-[4-fluoro-3-(morpholin-4-yl)phenyl]-7,8-dimethoxy-N,4-dimethy-4,5-dihydro-3H-2,3-benzodiazepine-3-carboxamide, (±)-1-[3-(3,3-difluoroazetidin-1-yl)-4-fluorophenyl]-7,8-dimethoxy-N,4-dimethyl-4,5-dihydro-3H-2,3-benzodiazepine-3-carboxamide, (±)-1-[4-fluoro-3-(4-hydroxypiperidin-1-yl)phenyl]-7,8-dimethoxy-N,4-dimethyl-4,5-dihydro-3H-2,3-benzodiazepine-3-carboxamide, (±)-7,8-dimethoxy-N,4-dimethyl-1-[4-(5-methyl-3-phenyl-1H-pyrazol-1-yl)phenyl]-4,5-dihydro-3H-2,3-benzodiazepine-3-carboxamide, (4S)-7,8-dimethoxy-N,4-dimethyl-1-[4-(5-methyl-3-phenyl-1H-pyrazol-1-yl)phenyl]-4,5-dihydro-3H-2,3-benzodiazepine-3-carboxamide, (±)-1-[4-(5-cyclopropyl-3-phenyl-1H-pyrazol-1-yl)phenyl]-7,8-dimethoxy-N,4-dimethyl-4,5-dihydro-3H-2,3-benzodiazepine-3-carboxamide, (4S)-1-[4-(5-cyclopropyl-3-phenyl-1H-pyrazol-1-yl)phenyl]-7,8-dimethoxy-N,4-dimethyl-4,5-dihydro-3H-2,3-benzodiazepine-3-carboxamide, (±)-7,8-dimethoxy-N,4-dimethyl-1-{4-[3-phenyl-5-(trifluoromethyl)-1H-pyrazol-1-yl]phenyl}-4,5-dihydro-3H-2,3-benzodiazepine-3-carboxamide, (±)-1-{4-[3-(4-fluorophenyl)-1H-pyrazol-1-yl]phenyl}-7,8-dimethoxy-N,4-dimethyl-4,5-dihydro-3H-2,3-benzodiazepine-3-carboxamide, (4S)-1-{4-[3-(4-fluorophenyl)-1H-pyrazol-1-yl]phenyl}-7,8-dimethoxy-N,4-dimethyl-4,5-dihydro-3H-2,3-benzodiazepine-3-carboxamide, (4R)-1-{4-[3-(4-fluorophenyl)-1H-pyrazol-1-yl]phenyl}-7,8-dimethoxy-N,4-dimethyl-4,5-dihydro-3H-2,3-benzodiazepine-3-carboxamide, (±)-7,8-dimethoxy-N,4-dimethyl-1-{4-[5-methyl-3-(trifluoromethyl)-1H-pyrazol-1-yl]phenyl}-4,5-dihydro-3H-2,3-benzodiazepine-3-carboxamide, (±)-7,8-dimethoxy-N,4-dimethyl-1-[4-(1H-1,2,4-triazol-1-yl)phenyl]-4,5-dihydro-3H-2,3-benzodiazepine-3-carboxamide, (±)-7,8-dimethoxy-N,4-dimethyl-1-[4-(5-methyl-1H-1,2,4-triazol-1-yl)phenyl]-4,5-dihydro-3H-2,3-benzodiazepine-3-carboxamide, (±)-1-[4-(3,5-dimethyl-1H-1,2,4-triazol-1-yl)phenyl]-7,8-dimethoxy-N,4-dimethyl-4,5-dihydro-3H-2,3-benzodiazepine-3-carboxamide, (±)-8-tert-butyl-1-[4-(3,5-dimethylisoxazol-4-yl)phenyl]-N,4-dimethyl-4,5-dihydro-3H-2,3-benzodiazepine-3-carboxamide, (±)-7-chloro-1-[4-(3,5-dimethylisoxazol-4-yl)phenyl]-N,4-dimethyl-8-(trifluoromethoxy)-4,5-dihydro-3H-2,3-benzodiazepine-3-carboxamide, (4S)-7-chloro-1-[4-(3,5-dimethylisoxazol-4-yl)phenyl]-N,4-dimethyl-8-(trifluoromethoxy)-4,5-dihydro-3H-2,3-benzodiazepine-3-carboxamide, (4R)-7-chloro-1-[4-(3,5-dimethylisoxazol-4-yl)phenyl]-N,4-dimethyl-8-(trifluoromethoxy)-4,5-dihydro-3H-2,3-benzodiazepine-3-carboxamide, (±)-8-chloro-1-[4-(3,5-dimethylisoxazol-4-yl)phenyl]-7-methoxy-N,4-dimethyl-4,5-dihydro-3H-2,3-benzodiazepine-3-carboxamide, (4S)-8-chloro-1-[4-(3,5-dimethylisoxazol-4-yl)phenyl]-7-methoxy-N,4-dimethyl-4,5-dihydro-3H-2,3-benzodiazepine-3-carboxamide, (4R)-8-chloro-1-[4-(3,5-dimethylisoxazol-4-yl)phenyl]-7-methoxy-N,4-dimethyl-4,5-dihydro-3H-2,3-benzodiazepine-3-carboxamide, (±)-1-[4-(3,5-dimethylisoxazol-4-yl)phenyl]-N,4,8-trimethyl-4,5-dihydro-3H-2,3-benzodiazepine-3-carboxamide, (±)-7,8-bis(difluoromethoxy)-1-[4-(3,5-dimethylisoxazol-4-yl)phenyl]-N,4-dimethyl-4,5-dihydro-3H-2,3-benzodiazepine-3-carboxamide, (±)-1-[4-(3,5-dimethylisoxazol-4-yl)phenyl]-7,8-diethoxy-N,4-dimethyl-4,5-dihydro-3H-2,3-benzodiazepine-3-carboxamide, (±)-7-(difluoromethoxy)-1-[4-(3,5-dimethyl-4,5-dihydro-3H-2,3-benzodiazepine-3-carboxamide, (4S)-7-(difluoromethoxy)-1-[4-(3,5-dimethylisoxazol-4-yl)phenyl]-8-methoxy-N,4-dimethyl-4,5-dihydro-3H-2,3-benzodiazepine-3-carboxamide, (4R)-7-(difluoromethoxy)-1-[4-(3,5-dimethylisoxazol-4-yl)phenyl]-8-methoxy-N,4-dimethyl-4,5-dihydro-3H-2,3-benzodiazepine-3-carboxamide, (±)-7-(difluoromethoxy)-8-methoxy-N,4-dimethyl-1-[4-(4-methylpiperazin-1-yl)phenyl]-4,5-dihydro-3H-2,3-benzodiazepine-3-carboxamide, (4R)-7-(difluoromethoxy)-8-methoxy-N,4-dimethyl-1-[4-(4-methylpiperazin-1-yl)phenyl]-4,5-dihydro-3H-2,3-benzodiazepine-3-carboxamide, (4S)-7-(difluoromethoxy)-8-methoxy-N,4-dimethyl-1-[4-(4-methylpiperazin-1-yl)phenyl]-4,5-dihydro-3H-2,3-benzodiazepine-3-carboxamide, (±)-1-(4-chlorophenyl)-N,4-dimethyl-8-[3-(4-methylpiperazin-1-yl)propoxy]-4,5-dihydro-3H-2,3-benzodiazepine-3-carboxamide, (4S)-1-(4-chlorophenyl)-N,4-dimethyl-8-[3-(4-methylpiperazin-1-yl)propoxy]-4,5-dihydro-3H-2,3-benzodiazepine-3-carboxamide, (±)-1-(4-chlorophenyl)-N,4-dimethyl-8-[3-(morpholin-4-yl)propoxy]-4,5-dihydro-3H-2,3-benzodiazepine-3-carboxamide, (±)-1-(4-chlorophenyl)-N,4-dimethyl-8-[2-(4-methylpiperazin-1-yl)ethoxy]-4,5-dihydro-3H-2,3-benzodiazepine-3-carboxamide, (±)-1-(4-chlorophenyl)-N,4-dimethyl-8-[(6-methylpyridin-2-yl)methoxy]-4,5-dihydro-3H-2,3-benzodiazepine-3-carboxamide, (±)-1-[4-(3,5-dimethylisoxazol-4-yl)phenyl]-8-hydroxy-N,4-dimethyl-4,5-dihydro-3H-2,3-benzodiazepine-3-carboxamide, (±)-1-[4-(3,5-dimethylisoxazol-4-yl)phenyl]-N,4-dimethyl-8-[3-(morpholin-4-yl)propoxy]-4,5-dihydro-3H-2,3-benzodiazepine-3-carboxamide, (±)-7-cyano-1-[4-(3,5-dimethylisoxazol-4-yl)phenyl]-8-methoxy-N,4-dimethyl-4,5-dihydro-3H-2,3-benzodiazepine-3-carboxamide, (±)-8-acetamido-N,4-dimethyl-1-[4-(morpholin-4-yl)phenyl]-4,5-dihydro-3H-2,3-benzodiazepine-3-carboxamide, (±)-8-acetamido-N,4-dimethyl-1-[4-(4-methylpiperazin-1-yl)phenyl]-4,5-dihydro-3H-2,3-benzodiazepine-3-carboxamide, (±)-8-acetamido-1-[4-(3,5-dimethylisoxazol-4-yl)phenyl]-N,4-dimethyl-4,5-dihydro-3H-2,3-benzodiazepine-3-carboxamide, (±)-1-(4-chlorophenyl)-8-(3,5-dimethyl-1H-pyrazol-1-yl)-N,4-dimethyl-4,5-dihydro-3H-2,3-benzodiazepine-3-carboxamide, (±)-1-[4-(3,5-dimethylisoxazol-4-yl)phenyl]-8-(3,5-dimethyl-1H-pyrazol-1-yl)-N,4-dimethyl-4,5-dihydro-3H-2,3-benzodiazepine-3-carboxamide, (±)-1-[4-(3,5-dimethylisoxazol-4-yl)phenyl]-N,4-dimethyl-8-(morpholin-4-yl)-4,5-dihydro-3H-2,3-benzodiazepine-3-carboxamide, (4R)-1-[4-(3,5-dimethylisoxazol-4-yl)phenyl]-N,4-dimethyl-8-(morphin-4-yl)-4,5-dihydro-3H-2,3-benzodiazepine-3-carboxamide, (4S)-1-[4-(3,5-dimethylisoxazol-4-yl)phenyl]-N,4-dimethyl-8-(morpholin-4-yl)-4,5-dihydro-3H-2,3-benzodiazepine-3-carboxamide, (4S)-8-methoxy-N,4-dimethyl-1-[4-(3-oxomorphin-4-yl)phenyl]-4,5-dihydro-3H-2,3-benzodiazepine-3-carboxamide, (±)-1-{4-[4-(2-hydroxyethyl)piperazin-1-yl]phenyl}-7,8-dimethoxy-N,4-dimethyl-4,5-dihydro-3H-2,3-benzodiazepine-3-carboxamide, (±)-7,8-dimethoxy-1-[4-(4-methoxypiperidin-1-yl)phenyl]-N,4-dimethyl-4,5-dihydro-3H-2,3-benzodiazepine-3-carboxamide, (4R)-7,8-dimethoxy-1-[4-(4-methoxypiperidin-1-yl)phenyl]-N,4-dimethyl-4,5-dihydro-3H-2,3-benzodiazepine-3-carboxamide, (4S)-7,8-dimethoxy-1-[4-(4-methoxypiperidin-1-yl)phenyl]-N,4-dimethyl-4,5-dihydro-3H-2,3-benzodiazepine-3-carboxamide, (±)-1-{4-[4-(dimethylamino)piperidin-1-yl]phenyl}-7,8-dimethoxy-N,4-dimethyl-4,5-dihydro-3H-2,3-benzodiazepine-3-carboxamide, (4R)-1-{4-[4-(dimethylamino)piperidin-1-yl]phenyl}-7,8-dimethoxy-N,4-dimethyl-4,5-dihydro-3H-2,3-benzodiazepine-3-carboxamide, (4S)-1-{4-[4-(dimethylamino)piperidin-1-yl]phenyl}-7,8-dimethoxy-N,4-dimethyl-4,5-dihydro-3H-2,3-benzodiazepine-3-carboxamide, (±)-1-[4-(3,3-difluoroazetidin-1-yl)phenyl]-7,8-dimethoxy-N,4-dimethyl-4,5-dihydro-3H-2,3-benzodiazepine-3-carboxamide, (±)-1-[4-(4-acetamidopiperidin-1-yl)phenyl]-7,8-dimethoxy-N,4-dimethyl-4,5-dihydro-3H-2,3-benzodiazepine-3-carboxamide, (±)-1-{4-[4-(2-hydroxyethyl)piperidin-1-yl]phenyl}-7,8-dimethoxy-N,4-dimethyl-4,5-dihydro-3H-2,3-benzodiazepine-3-carboxamide, (±)-1-[4-(3-hydroxyazetidin-1-yl)phenyl]-7,8-dimethoxy-N,4-dimethyl-4,5-dihydro-3H-2,3-benzodiazepine-3-carboxamide, (±)-1-[4-(3-hydroxy-3-methylazetidin-1-yl)phenyl]-7,8-dimethoxy-N,4-dimethyl-4,5-dihydro-3H-2,3-benzodiazepine-3-carboxamide, (4R)-1-[4-(3-hydroxy-3-methylazetidin-1-yl)phenyl]-7,8-dimethoxy-N,4-dimethyl-4,5-dihydro-3H-2,3-benzodiazepine-3-carboxamide, (4S)-1-[4-(3-hydroxy-3-methylazetidin-1-yl)phenyl]-7,8-dimethoxy-N,4-dimethyl-4,5-dihydro-3H-2,3-benzodiazepine-3-carboxamide, (±)-1-[4-(4-isopropylpiperazin-1-yl)phenyl]-7,8-dimethoxy-N,4-dimethyl-4,5-dihydro-3H-2,3-benzodiazepine-3-carboxamide, (±)-7,8-dimethoxy-1-[4-(3-methoxyazetidin-1-yl)phenyl]-N,4-dimethyl-4,5-dihydro-3H-2,3-benzodiazepine-3-carboxamide, (±)-1-[4-(4-hydroxy-4-methylpiperidin-1-yl)phenyl]-7,8-dimethoxy-N,4-dimethyl-4,5-dihydro-3H-2,3-benzodiazepine-3-carboxamide, (4R)-1-[4-(4-hydroxy-4-methylpiperidin-1-yl)phenyl]-7,8-dimethoxy-N,4-dimethyl-4,5-dihydro-3H-2,3-benzodiazepine-3-carboxamide, (4S)-1-[4-(4-hydroxy-4-methylpiperidin-1-yl)phenyl]-7,8-dimethoxy-N,4-dimethyl-4,5-dihydro-3H-2,3-benzodiazepine-3-carboxamide, (±)-7,8-dimethoxy-N,4-dimethyl-1-{4-[4-(methylcarbamoyl)piperidin-1-yl]phenyl}-4,5-dihydro-3H-2,3-benzodiazepine-3-carboxamide, (4S)-7,8-dimethoxy-N,4-dimethyl-1-{4-[4-(methylcarbamoyl)piperidin-1-yl]phenyl}-4,5-dihydro-3H-2,3-benzodiazepine-3-carboxamide, (4R)-7,8-dimethoxy-N,4-dimethyl-1-{4-[4-(methylcarbamoyl)piperidin-1-yl]phenyl}-4,5-dihydro-3H-2,3-benzodiazepine-3-carboxamide, (±)-1-{4-[(3S)-3-hydroxypyrrolidin-1-yl]phenyl}-7,8-dimethoxy-N,4-dimethyl-4,5-dihydro-3H-2,3-benzodiazepine-3-carboxamide, (4S)-1-{4-[(3S)-3-hydroxypyrrolidin-1-yl]phenyl}-7,8-dimethoxy-N,4-dimethyl-4,5-dihydro-3H-2,3-benzodiazepine-3-carboxamide, (±)-tert-butyl (1-{4-[7,8-dimethoxy-4-methyl-3-(methylcarbamoyl)-4,5-dihydro-3H-2,3-benzodiazepin-1-yl]phenyl}-4-methylpiperidin-4-yl)carbamate, (±)-1-{4-[(2S,5R)-2,5-dimethylpiperazin-1-yl]phenyl}-7,8-dimethoxy-N,4-dimethyl-4,5-dihydro-3H-2,3-benzodiazepine-3-carboxamide, (±)-1-{4-[4-(2,2-difluoroethyl)piperazin-1-yl]phenyl}-7,8-dimethoxy-N,4-dimethyl-4,5-dihydro-3H-2,3-benzodiazepine-3-carboxamide, (4S)-7,8-dimethoxy-N,4-dimethyl-1-[4-(3-oxopiperazin-1-yl)phenyl]-4,5-dihydro-3H-2,3-benzodiazepine-3-carboxamide, (4S)-1-{4-[(2R,6S)-2,6-dimethylmorpholin-4-yl]phenyl}-7,8-dimethoxy-N,4-dimethyl-4,5-dihydro-3H-2,3-benzodiazepine-3-carboxamide, (±)-7,8-dimethoxy-N,4-dimethyl-1-[4-(4-oxopiperidin-1-yl)phenyl]-4,5-dihydro-3H-2,3-benzodiazepine-3-carboxamide, (±)-7,8-dimethoxy-N,4-dimethyl-1-{4-[4-(2,2,2-trifluoroethyl)piperazin-1-yl]phenyl}-4,5-dihydro-3H-2,3-benzodiazepine-3-carboxamide, (4S)-1-{4-[(3R,5S)-3,5-dimethylpiperazin-1-yl]phenyl}-7,8-dimethoxy-N,4-dimethyl-4,5-dihydro-3H-2,3-benzodiazepine-3-carboxamide, (±)-7,8-dihydroxy-N,4-dimethyl-1-[4-(4-methylpiperazin-1-yl)phenyl]-4,5-dihydro-3H-2,3-benzodiazepine-3-carboxamide, (±)-7,8-diethoxy-N,4-dimethyl-1-[4-(4-methylpiperazin-1-yl)phenyl]-4,5-dihydro-3H-2,3-benzodiazepine-3-carboxamide, (±)-4-ethyl-7,8-dimethoxy-N-methyl-1-[4-(4-methylpiperazin-1-yl)phenyl]-4,5-dihydro-3H-2,3-benzodiazepine-3-carboxamide, (4S)-4-ethyl-7,8-dimethoxy-N-methyl-1-[4-(4-methylpiperazin-1-yl)phenyl]-4,5-dihydro-3H-2,3-benzodiazepine-3-carboxamide, (±)-4-ethyl-7,8-dimethoxy-N-methyl-1-[4-(piperazin-1-yl)phenyl]-4,5-dihydro-3H-2,3-benzodiazepine-3-carboxamide, (4S)-4-ethyl-7,8-dimethoxy-N-methyl-1-[4-(piperazin-1-yl)phenyl]-4,5-dihydro-3H-2,3-benzodiazepine-3-carboxamide, (4R)-4-ethyl-7,8-dimethoxy-N-methyl-1-[4-(piperazin-1-yl)phenyl]-4,5-dihydro-3H-2,3-benzodiazepine-3-carboxamide, (±)-4-ethyl-7,8-dimethoxy-N-methyl-1-{4-[4-(methylsulphonyl)piperazin-1-yl]phenyl}-4,5-dihydro-3H-2,3-benzodiazepine-3-carboxamide, (4S)-4-ethyl-7,8-dimethoxy-N-methyl-1-{4-[4-(methylsulphonyl)piperazin-1-yl]phenyl}-4,5-dihydro-3H-2,3-benzodiazepine-3-carboxamide, (4R)-4-ethyl-7,8-dimethoxy-N-methyl-1-{4-[4-(methylsulphonyl)piperazin-1-yl]phenyl}-4,5-dihydro-3H-2,3-benzodiazepine-3-carboxamide, (±)-4-ethyl-1-[4-(3-fluoroazetidin-1-yl)phenyl]-7,8-dimethoxy-N-methyl-4,5-dihydro-3H-2,3-benzodiazepine-3-carboxamide, (±)-1-[4-(4-acetylpiperazin-1-yl)phenyl]-4-ethyl-7,8-dimethoxy-N-methyl-4,5-dihydro-3H-2,3-benzodiazepine-3-carboxamide, (±)-1-[4-(1,1-dioxidothiomorpholin-4-yl)phenyl]-4-ethyl-7,8-dimethoxy-N-methyl-4,5-dihydro-3H-2,3-benzodiazepine-3-carboxamide, (±)-4-ethyl-1-[4-(4-hydroxypiperidin-1-yl)phenyl]-7,8-dimethoxy-N-methyl-4,5-dihydro-3H-2,3-benzodiazepine-3-carboxamide, (±)-4-ethyl-7,8-dimethoxy-N-methyl-1-[4-(morpholin-4-yl)phenyl]-4,5-dihydro-3H-2,3-benzodiazepine-3-carboxamide, (4S)-4-ethyl-7,8-dimethoxy-N-methyl-1-[4-(morpholin-4-yl)phenyl]-4,5-dihydro-3H-2,3-benzodiazepine-3-carboxamide, (±)-8-chloro-1-[4-(1,1-dioxidothiomorpholin-4-yl)phenyl]-N,4-dimethyl-7-(trifluoromethoxy)-4,5-dihydro-3H-2,3-benzodiazepine-3-carboxamide, (±)-8-chloro-N,4-dimethyl-1-[4-(piperazin-1-yl)phenyl]-7-(trifluoromethoxy)-4,5-dihydro-3H-2,3-benzodiazepine-3-carboxamide, (±)-8-chloro-1-[4-(4-hydroxypiperidin-1-yl)phenyl]-N,4-dimethyl-7-(trifluoromethoxy)-4,5-dihydro-3H-2,3-benzodiazepine-3-carboxamide, (±)-8-chloro-N,4-dimethyl-1-[4-(4-methylpiperazin-1-yl)phenyl]-7-(trifluoromethoxy)-4,5-dihydro-3H-2,3-benzodiazepine-3-carboxamide, (±)-8-chloro-N,4-dimethyl-1-{4-[4-(methylsulphonyl)piperazin-1-yl]phenyl}-7-(trifluoromethoxy)-4,5-dihydro-3H-2,3-benzodiazepine-3-carboxamide, (±)-8-(1,1-dioxidothiomorpholin-4-yl)-1-[4-(1,1-dioxidothiomorpholin-4-yl)phenyl]-N,4-dimethyl-7-(trifluoromethoxy)-4,5-dihydro-3H-2,3-benzodiazepine-3-carboxamide, (±)-1-(4-chlorophenyl)-8-(1,1-dioxidothiomorpholin-4-yl)-N,4-dimethyl-7-(trifluoromethoxy)-4,5-dihydro-3H-2,3-benzodiazepine-3-carboxamide, (±)-1-[4-(4-acetylpiperazin-1-yl)phenyl]-N,4-dimethyl-7-(trifluoromethoxy)-4,5-dihydro-3H-2,3-benzodiazepine-3-carboxamide, (±)-1-{4-[4-(2-hydroxyethyl)piperazin-1-yl]phenyl}-N,4-dimethyl-7-(trifluoromethoxy)-4,5-dihydro-3H-2,3-benzodiazepine-3-carboxamide, (±)-8-methoxy-N,4-dimethyl-1-[4-(4-methylpiperazin-1-yl)phenyl]-7-(trifluoromethoxy)-4,5-dihydro-3H-2,3-benzodiazepine-3-carboxamide, (±)-4-ethyl-7,8-dimethoxy-N-methyl-1-[4-(1,3,5-trimethyl-1H-pyrazol-4-yl)phenyl]-4,5-dihydro-3H-2,3-benzodiazepine-3-carboxamide, (±)-4-ethyl-1-(4'-fluorobiphenyl-4-yl)-7,8-dimethoxy-N-methyl-4,5-dihydro-3H-2,3-benzodiazepine-3-carboxamide, (±)-4-ethyl-7,8-dimethoxy-N-methyl-1-[4-(1-methyl-1H-1,2,3-triazol-4-yl)phenyl]-4,5-dihydro-3H-2,3-benzodiazepine-3-carboxamide, (±)-1-[4-(3,5-dimethyl-1,2-oxazol-4-yl)phenyl]-4-ethyl-7,8-dimethoxy-N-methyl-4,5-dihydro-3H-2,3-benzodiazepine-3-carboxamide, (±)-4-isopropyl-7,8-dimethoxy-N-methyl-1-[4-(1,3,5-trimethyl-1H-pyrazol-4-yl)phenyl]-4,5-dihydro-3H-2,3-benzodiazepine-3-carboxamide, (±)-4-ethyl-7,8-dimethoxy-N-methyl-1-[4-(2-oxopyrrolidin-1-yl)phenyl]-4,5-dihydro-3H-2,3-benzodiazepine-3-carboxamide, (±)-4-ethyl-7,8-dimethoxy-N-methyl-1-[4-(3-oxomorpholin-4-yl)phenyl]-4,5-dihydro-3H-2,3-benzodiazepine-3-carboxamide, (±)-4-ethyl-7,8-dimethoxy-N-methyl-1-[4-(2-oxopiperidin-1-yl)phenyl]-4,5-dihydro-3H-2,3-benzodiazepine-3-carboxamide, (±)-4-ethyl-7,8-dimethoxy-N-methyl-1-[4-(2-oxo-1,3-oxazolidin-3-yl)phenyl]-4,5-dihydro-3H-2,3-benzodiazepine-3-carboxamide, (4S)-7,8-dimethoxy-N,4-dimethyl-1-[4-(4-methyl-2-oxo-1,4-diazepan-1-yl)phenyl]-4,5-dihydro-3H-2,3-benzodiazepine-3-carboxamide, (±)-1-(4-chlorophenyl)-N,4-dimethyl-7-(2-oxo-1,3-oxazolidin-3-yl)-4,5-dihydro-3H-2,3-benzodiazepine-3-carboxamide,
(4S)-1-(4-chlorophenyl)-N,4-dimethyl-7-(2-oxo-1,3-oxazolidin-3-yl)-4,5-dihydro-3H-2,3-benzodiazepine-3-carboxamide,
(±)-1-(4-chlorophenyl)-N,4-dimethyl-7-(2-oxopiperidin-1-yl)-4,5-dihydro-3H-2,3-benzodiazepine-3-carboxamide,
(±)-1-(4-chlorophenyl)-N,4-dimethyl-7-(3-oxomorpholin-4-yl)-4,5-dihydro-3H-2,3-benzodiazepine-3-carboxamide,
(±)-1-(4-chlorophenyl)-N,4-dimethyl-7-(morpholin-4-yl)-4,5-dihydro-3H-2,3-benzodiazepine-3-carboxamide,
(±)-1-(4-chlorophenyl)-N,4-dimethyl-7-(pyrrolidin-1-yl)-4,5-dihydro-3H-2,3-benzodiazepine-3-carboxamide,
(±)-1-(4-chlorophenyl)-7-(1,1-dioxidothiomorpholin-4-yl)-N,4-dimethyl-4,5-dihydro-3H-2,3-benzodiazepine-3-carboxamide,
(±)-1-(4-chlorophenyl)-N,4-dimethyl-7-(4-methylpiperazin-1-yl)-4,5-dihydro-3H-2,3-benzodiazepine-3-carboxamide,
(±)-N,4-dimethyl-7-(4-methylpiperazin-1-yl)-1-[4-(4-methylpiperazin-1-yl)phenyl]-4,5-dihydro-3H-2,3-benzodiazepine-3-carboxamide,
(±)-N,4-dimethyl-7-(4-methyl-3-oxopiperazin-1-yl)-1-[4-(4-methyl-3-oxopiperazin-1-yl)phenyl]-4,5-dihydro-3H-2,3-benzodiazepine-3-carboxamide,
(±)-1-(4-chlorophenyl)-7-(4-fluorophenyl)-N,4-dimethyl-4,5-dihydro-3H-2,3-benzodiazepine-3-carboxamide,
(±)-1-(4-chlorophenyl)-N,4-dimethyl-7-(pyridin-4-yl)-4,5-dihydro-3H-2,3-benzodiazepine-3-carboxamide,
(±)-1-(4-chlorophenyl)-7-(6-hydroxypyridin-3-yl)-N,4-dimethyl-4,5-dihydro-3H-2,3-benzodiazepine-3-carboxamide,
(±)-1-(4-chlorophenyl)-7-(3,5-dimethyl-1,2-oxazol-4-yl)-N,4-dimethyl-4,5-dihydro-3H-2,3-benzodiazepine-3-carboxamide,
(±)-1-(4-chlorophenyl)-N,4-dimethyl-7-(1-methyl-1H-1,2,3-triazol-4-yl)-4,5-dihydro-3H-2,3-benzodiazepine-3-carboxamide,
(4R)-1-[4-(4-hydroxypiperidin-1-yl)phenyl]-7,8-dimethoxy-N,4-dimethyl-4,5-dihydro-3H-2,3-benzodiazepine-3-carboxamide,
(4R)-7,8-dimethoxy-N,4-dimethyl-1-[4-(4-methylpiperazin-1-yl)phenyl]-4,5-dihydro-3H-2,3-benzodiazepine-3-carboxamide,
(±)-1-[4-(1,1-dioxido-1,2-thiazolidin-2-yl)phenyl]-7,8-dimethoxy-N,4-dimethyl-4,5-dihydro-3H-2,3-benzodiazepine-3-carboxamide,
(±)-1-{7,8-dimethoxy-4-methyl-1-[4-(4-methylpiperazin-1-yl)phenyl]-4,5-dihydro-3H-2,3-benzodiazepin-3-yl}ethanone,
1-{(4S)-7,8-dimethoxy-4-methyl-1-[4-(4-methylpiperazin-1-yl)phenyl]-4,5-dihydro-3H-2,3-benzodiazepin-3-yl}ethanone,
(±)-1-{1-[4-(3,5-dimethyl-1,2-oxazol-4-yl)phenyl]-7,8-dimethoxy-4-methyl-4,5-dihydro-3H-2,3-benzodiazepin-3-yl}ethanone,
(±)-7,8-dimethoxy-N,4-dimethyl-1-[4-(5-methyl-1,3,4-oxadiazol-2-yl)phenyl]-4,5-dihydro-3H-2,3-benzodiazepine-3-carboxamide,
(±)-7,8-dimethoxy-N,4-dimethyl-1-[4-(3-methyl-1,2,4-oxadiazol-5-yl)phenyl]-4,5-dihydro-3H-2,3-benzodiazepine-3-carboxamide,
(±)-N,4-dimethyl-8-(trifluoromethoxy)-1-[4-(1,3,5-trimethyl-1H-pyrazol-4-yl)phenyl]-4,5-dihydro-3H-2,3-benzodiazepine-3-carboxamide,
(4S)—N,4-dimethyl-8-(trifluoromethoxy)-1-[4-(1,3,5-trimethyl-1H-pyrazol-4-yl)phenyl]-4,5-dihydro-3H-2,3-benzodiazepine-3-carboxamide,
(4R)—N,4-dimethyl-8-(trifluoromethoxy)-1-[4-(1,3,5-trimethyl-1H-pyrazol-4-yl)phenyl]-4,5-dihydro-3H-2,3-benzodiazepine-3-carboxamide,
(±)-N,4-dimethyl-1-[4-(4-methyl-1-piperazinyl)phenyl]-8-(trifluoromethoxy)-4,5-dihydro-3H-2,3-benzodiazepine-3-carboxamide,
(4R)—N,4-dimethyl-1-[4-(4-methyl-1-piperazinyl)phenyl]-8-(trifluoromethoxy)-4,5-dihydro-3H-2,3-benzodiazepine-3-carboxamide,
(4S)—N,4-dimethyl-1-[4-(4-methyl-1-piperazinyl)phenyl]-8-(trifluoromethoxy)-4,5-dihydro-3H-2,3-benzodiazepine-3-carboxamide,
(±)-1-[4-(4-hydroxy-1-piperidinyl)phenyl]-N,4-dimethyl-8-(trifluoromethoxy)-4,5-dihydro-3H-2,3-benzodiazepine-3-carboxamide,
(±)-1-[2,4-dibromo-5-(4-methylpiperazin-1-yl)phenyl]-7,8-dimethoxy-N,4-dimethyl-4,5-dihydro-3H-2,3-benzodiazepine-3-carboxamide,
(4S)-1-[3-bromo-4-(4-methylpiperazin-1-yl)phenyl]-7,8-dimethoxy-N,4-dimethyl-4,5-dihydro-3H-2,3-benzodiazepine-3-carboxamide,
(4S)-1-[3-cyano-4-(4-methylpiperazin-1-yl)phenyl]-7,8-dimethoxy-N,4-dimethyl-4,5-dihydro-3H-2,3-benzodiazepine-3-carboxamide,
(±)-7,8-dimethoxy-4-methyl-1-[4-(4-methylpiperazin-1-yl)phenyl]-3-(1-oxopropyl)-4,5-dihydro-3H-2,3-benzodiazepine,
(±)-3-(cyclopropylcarbonyl)-7,8-dimethoxy-4-methyl-1-[4-(4-methylpiperazin-1-yl)phenyl]-4,5-dihydro-3H-2,3-benzodiazepine,
(±)-N-cyclopropyl-7,8-dimethoxy-4-methyl-1-[4-(4-methylpiperazin-1-yl)phenyl]-4,5-dihydro-3H-2,3-benzodiazepine,
(±)-7,8-dimethoxy-N,4-dimethyl-1-[4-(4-methylpiperazin-1-yl)phenyl]-4,5-dihydro-3H-2,3-benzodiazepin-3-carbothioamide,
methyl (±)-7,8-dimethoxy-4-methyl-1-[4-(4-methylpiperazin-1-yl)phenyl]-4,5-dihydro-3H-2,3-benzodiazepine-3-carboxylate,
ethyl (±)-7,8-dimethoxy-4-methyl-1-[4-(4-methylpiperazin-1-yl)phenyl]-4,5-dihydro-3H-2,3-benzodiazepine-3-carboxylate,
(±)-N-ethyl-7,8-dimethoxy-4-methyl-1-[4-(4-methylpiperazin-1-yl)phenyl]-4,5-dihydro-3H-2,3-benzodiazepine-3-carboxamide, and
(4S)—N-ethyl-7,8-dimethoxy-4-methyl-1-[4-(4-methylpiperazin-1-yl)phenyl]-4,5-dihydro-3H-2,3-benzodiazepine-3-carboxamide.

16. A method for the control of male fertility comprising administering to a human or mammal in need thereof an effective amount of a compound according to claim 1, or an enantiomer, diastereomer, racemate, tautomer or physiologically acceptable salt thereof.

17. A method for the treatment of a leukaemia, prostate carcinoma, breast carcinoma, melanoma or multiple myeloma responsive to inhibition of BRD4 comprising administering to a human or mammal in need thereof an effective amount of a compound according to claim 1, or an enantiomer, diastereomer, racemate, tautomer or physiologically acceptable salt thereof.

18. A pharmaceutical formulation comprising a compound according to claim 1, or an enantiomer, diastereomer, racemate, tautomer or physiologically acceptable salt thereof, in combination with an antihyperproliferative, cytostatic or cytotoxic substance selected from abiraterone acetate, acolbifene, actinomycin D (dactinomycin), afatinib, aldesleukin, alendronic acid, alitretinoin, allopurinol, altretamine, aminoglutethimide, aminopterin, amifostine, amrubicin, amsacrine, anastrozole, apatinib, arglabin, arsenic trioxide, arzoxifene, asoprisnil, L-asparaginase, atamestane, atrasentan, axitinib, 5-azacytidine, azathioprine, bendamustine, bestatin, betamethasone acetate, betamethasone sodium phosphate, bexarotene, bicalutamide, bleomycin sulphate, broxuridine, bortezomib, bosutinib, busulfan, cabazitaxel, calcitonin, camptothecin, capecitabin, carboplatin, carfilzomib, carmustine, cediranib, celmoleukin, chlorambucil, cisplatin, cladribine, clodronic acid, clofarabine, colaspase, crisnatol, crizotinib, cyclophosphamide, cyproterone acetate, cytarabine, dacarbazine, dactinomycin, dasatinib, daunorubicin, decitabine, degarelix, denileukin diftitox, deslorelin, dexrazoxane, diethylstilbestrol, 2',2'-difluorodeoxycytidine, docetaxel, doxifluridine, doxorubicin, dronabinol, dutasteride, edotecarin, eflornithine, enzalutamide, epirubicin, epoetin-alfa, epothilone, eptaplatin, erlotinib, erythro-hydroxynonyladenine, estradiol, estramustine sodium phosphate, ethynylestradiol, etidronic acid, etoposide, everolimus, exatecan, exemestan, fadrozole, fenretinide, filgrastim, finasteride, floxuridine, fluconazole, fludarabine, 5-fluordeoxyuridine monophosphate, 5-fluorouracil (5-FU), fluoxymesterone, flutamide, formestane, fosteabine, fotemustin, fulvestrant, gefitinib, gemcitabine, gemtuzumab, goserelin, gossypol, granisetron-hydrochloride, hexamethylmelamine, histamine dihydrochloride, histrelin, hydroxyurea, hydroxyprogesterone caproate, ibandronic acid, ibritumomab tiuxetan, idarubicin, ifosfamide, imatinib, iniparib, irinotecan, ixabepilone, keyhole limpet haemocyanin, lanreotide, lapatinib, lasofoxifene, lentinan sulphate, lestaurtinib, letrozole, leucovorin, leuprolide, leuprolide acetate, levamisole, levofolinic acid calcium salt, liposomal MTP-PE, lomustine, lonafarnib, lonidamine, mechlorethamine, mecobalamin, medroxyprogesterone acetate, megestrol acetate, melphalan, 6-mercaptopurine, mesna, methotrexate, miltefosine, minocycline, minodronate, miproxifene, mitomycin C, mitotane, mitoxantrone, nafarelin, nedaplatin, nelarabine, nemorubicin, neratinib, nilotinib, nilutamide, nimustine, nolatrexed, obatoclax, oblimersen, octreotide, olaparib, ondansetron hydrochloride, oxaliplatin, paclitaxel, pamidronate disodium, pazopanib, pegaspargase, pemetrexed, pentostatin, N-phosphonoacetyl-L-aspartate, picibanil, pilocarpine hydrochloride, pirarubicin, plerixafor, plicamycin, porfimer sodium, prednimustine, prednisolone, prednisone, procarbazine, quazepam, raloxifene, raltitrexed, ranpirnase, refametinib, regorafenib, 13-cis-retinoic acid, rhenium-186 etidronate, rituximab, romidepsin, romurtide, ruxolitinib, salinomycin, sargramostim, satraplatin, semaxatinib, semustine, seocalcitol, sipuleucel-T, sizofiran, sobuzoxane, sorafenib, streptozocin, strontium-89 chloride, sunitinib, batabulin, tamoxifen, tamsulosin, tasonermin, testolactone, teceleukin, temozolomide, temsirolimus, teniposide, testosterone propionate, thalidomide, thymosin alpha 1, thioguanine, thiotepa, thyrotropin, tiazofurin, tiludronic acid, tipifarnib, tirapazamine, canfosfamide, toceranib, topotecan, toremifene, tositumomab, tastuzumab, treosulfan, tretinoin, trimethylmelamine, trimetrexate, triptorelin acetate, triptorelin pamoate, trofosfamide, uridine, valrubicin, valspodar, vandetanib, vapreotid, vatalanib, vemurafinib, verteporfin, vesnarinon, vinblastine, vincristine, vindesine, vinflunine, vinorelbine, vismodegib, zinostatin stimalamer, and zoledronic acid.

19. A pharmaceutical formulation comprising a compound according to claim 1, or an enantiomer, diastereomer, racemate, tautomer or physiologically acceptable salt thereof, and a pharmaceutically acceptable excipient.

* * * * *